United States Patent
Wang et al.

(10) Patent No.: US 12,384,753 B2
(45) Date of Patent: Aug. 12, 2025

(54) 17-BETA-HYDROXYSTEROID DEHYDROGENASE TYPE 13 INHIBITORS AND METHODS OF USE THEREOF

(71) Applicant: Enanta Pharmaceuticals, Inc., Watertown, MA (US)

(72) Inventors: Guoqiang Wang, Belmont, MA (US); Jun Ma, Wayland, MA (US); Brett Granger, Sudbury, MA (US); Jiang Long, Wayland, MA (US); Bin Wang, Newton, MA (US); Sourav Ghorai, Waltham, MA (US); Jing He, Somerville, MA (US); Yong He, Lexington, MA (US); Xuechao Xing, Wilmington, MA (US); Ruichao Shen, Belmont, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 17/891,436

(22) Filed: Aug. 19, 2022

(65) Prior Publication Data

US 2023/0143250 A1    May 11, 2023

Related U.S. Application Data

(60) Provisional application No. 63/235,472, filed on Aug. 20, 2021.

(51) Int. Cl.
| | |
|---|---|
| *C07D 265/36* | (2006.01) |
| *C07C 311/29* | (2006.01) |
| *C07D 209/18* | (2006.01) |
| *C07D 209/44* | (2006.01) |
| *C07D 217/20* | (2006.01) |

(Continued)

(52) U.S. Cl.
CPC .......... *C07D 265/36* (2013.01); *C07C 311/29* (2013.01); *C07D 209/18* (2013.01); *C07D 209/44* (2013.01); *C07D 217/20* (2013.01); *C07D 277/36* (2013.01); *C07D 307/81* (2013.01); *C07D 417/04* (2013.01); *C07D 417/12* (2013.01); *C07D 471/04* (2013.01)

(58) Field of Classification Search
CPC .. C07D 277/04; C07D 277/69; C07D 417/12; C07D 513/04; C07D 333/04; C07D 209/44; C07D 487/04; C07D 307/82; C07D 223/16; C07D 265/36; C07D 215/58; C07D 417/10; C07D 231/04; C07D 213/04; C07D 263/04; C07D 317/72; C07D 211/70; C07D 241/04; C07D 209/23; C07D 471/04; C07D 311/21; C07D 209/08; C07D 209/18; C07D 209/30; C07D 217/08; C07D 217/20; C07D 231/12; C07D 231/18; C07D 263/46; C07D 277/22; C07D 277/36; C07D 277/54; C07D 307/79; C07D 307/81; C07D 333/34; C07D 333/62; C07D 417/04; C07D 417/14; A61K 31/426; A61K 31/427; A61K 31/428; A61K 31/4709; A61K 31/4439; A61K 31/415; A61K 31/4418; A61K 31/49; A61K 31/429; A61K 31/4035; A61K 31/451; A61K 31/47; A61K 31/495; A61K 31/4375; A61K 31/506; A61K 31/497; A61K 31/496; A61K 31/438; A61K 31/541; A61K 31/538; A61K 31/421; A61K 31/196; A61K 31/281; A61K 31/357; A61K 31/407; A61K 31/404; A61K 31/55; A61P 1/00; C07C 2601/08; C07C 2601/14; C07C 2601/16; C07C 2602/10; C07C 307/10; C07C 311/21; C07C 311/29

USPC ....................................................... 540/593
See application file for complete search history.

(56) References Cited

U.S. PATENT DOCUMENTS

| | | |
|---|---|---|
| 2006/0287374 A1 | 12/2006 | Barf et al. |
| 2014/0057953 A1 | 2/2014 | Hartmann et al. |
| 2019/0106749 A1 | 4/2019 | Xin et al. |

FOREIGN PATENT DOCUMENTS

| | | |
|---|---|---|
| WO | 2005042513 A1 | 5/2005 |
| WO | 2018136758 A1 | 7/2018 |

(Continued)

OTHER PUBLICATIONS

Kornienko, et. al., Russian Journal of General Chemistry (2014), 84(4), 686-692. (Year: 2014).*

(Continued)

*Primary Examiner* — Jeffrey H Murray
*Assistant Examiner* — Daniel John Burkett
(74) *Attorney, Agent, or Firm* — Edgar W. Harlan; Carolyn S. Elmore; Elmore Patent Law Group, P.C.

(57) ABSTRACT

The present invention provides compounds of Formula (I), (I)

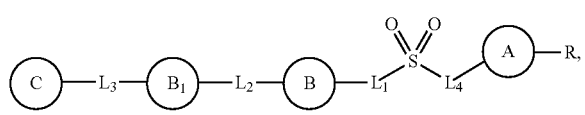

pharmaceutical compositions comprising these compounds and methods of using these compounds to provides a method of modulating a HSD17B13 protein for treatment of metabolic disease or liver condition, The present invention relates generally to compounds and pharmaceutical compositions useful as 17β-HSD13 inhibitors. Specifically, the present (Continued)

invention relates to compounds useful as inhibitors of 17β-HSD13 and methods for their preparation and use.

6 Claims, No Drawings

(51) Int. Cl.
*C07D 277/36* (2006.01)
*C07D 307/81* (2006.01)
*C07D 417/04* (2006.01)
*C07D 417/12* (2006.01)
*C07D 471/04* (2006.01)

(56) References Cited

FOREIGN PATENT DOCUMENTS

| | | | | |
|---|---|---|---|---|
| WO | WO 2019030538 | * | 2/2019 | ........... C07D 333/38 |
| WO | 2019075181 A1 | | 4/2019 | |
| WO | 2019183164 A1 | | 9/2019 | |
| WO | 2019183329 A1 | | 9/2019 | |
| WO | 2020061177 A1 | | 3/2020 | |
| WO | 2020132564 A1 | | 6/2020 | |
| WO | 2021003295 A1 | | 1/2021 | |
| WO | 2021211974 A1 | | 10/2021 | |
| WO | 2021211981 A1 | | 10/2021 | |
| WO | 2022020714 A1 | | 1/2022 | |
| WO | 2022020730 A1 | | 1/2022 | |
| WO | 2021211959 A3 | | 2/2022 | |
| WO | 2023023310 A1 | | 2/2023 | |

OTHER PUBLICATIONS

Diels, et. al., Berichte der Deutschen Chemischen Gesellschaft (1907), 40, 1629-33. (Year: 1907).*
Su et. al.; "Role of HSD17B13 in the liver physiology and pathophysiology"; Mol. Cell. Endocrin. 489, 119-125 (Year: 2019).*
Abul-Husn, N. S. et al., "A Protein-Truncating HSD17B13 Variant and Protection from Chronic Liver Disease", N. Engl. J. Med., 378, DOI: 10.1056/NEJMoa1712191, 2018, 1096-1106.
Day, J. M. et al., "Design and validation of specific inhibitors of 17beta-hydroxysteroid dehydrogenases for therapeutic application in breast and prostate cancer, and in endometriosis", Endocrine-Related Cancer, 15, DOI: 10.1677/ERC-08-0042, 2008, 665-692.
Di Sessa, A. et al., "The rs72613567:TA Variant in the Hydroxysteroid 17-beta Dehydrogenase 13 Gene Reduces Liver Damage in Obese Children", J. Pediatr. Gastroenterol. Nutr., 70 (3), DOI: 10.1097/MPG.0000000000002573, Mar. 2020, 371-374.
Horiguchi, Y. et al., "17beta-Hydroxysteroid dehydrogenase type 13 is a liver-specific lipid droplet-associated protein", Biochem. Biophys. Res. Commun., 370, 2008, 235-238.
Liu, S. et al., "Molecular cloning and expression analysis of a new gene for shortchain dehydrogenase/reductase 9", Acta Biochim. Pol., 54(1), https://doi.org/10.18388/abp.2007_3289, 2007, 213-218.
Pirola, C. J. et al., "Splice variant rs72613567 prevents worst histologic outcomes in patients with nonalcoholic fatty liver disease", J. Lipid Res., 60, 2019, 176-185.
Su, W. et al., "Role of HSD17B13 in the liver physiology and pathophysiology", Mol. Cell. Endocrinol., 489, https://doi.org/10.1016/j.mce.2018.10.014, 2019, 119-125.
PubChem SID 436052844 deposited on Nov. 21, 2020, 1-4.
PubChem SID 441981767 deposited on Jul. 20, 2021, 1-6.

* cited by examiner

17-BETA-HYDROXYSTEROID DEHYDROGENASE TYPE 13 INHIBITORS AND METHODS OF USE THEREOF

RELATED APPLICATIONS

This application claims the benefit of U.S. Provisional Application No. 63/235,472, filed on Aug. 20, 2021. The entire teachings of the above application are incorporated herein by reference.

TECHNICAL FIELD

The present invention relates generally to compounds and pharmaceutical compositions useful as 17β-HSD13 inhibitors. Specifically, the present invention relates to compounds useful as inhibitors of 17β-HSD13 and methods for their preparation and use.

BACKGROUND OF THE INVENTION

17-Beta-hydroxysteroid dehydrogenases (17β-HSDs) are NADP or NAD+ dependent oxidoreductases that catalyze oxidation/reduction reactions of 17β-hydroxysteroids or 17-ketosteroids, respectively. For example, 17β-HSDs can catalyze the interconversion of androstenedione with testosterone, estrone with estradiol, or dehydroepiandrosterone (DHEA) with androstenediol. Of the fifteen 17β-HSDs that have been identified, all but one (17β-HSD type 5) are short-chain dehydrogenases/reductases (SDRs) (J. M. Day, et al., *Endocrine-Related Cancer* 2008, 15, 665-692).

More specifically, 17-Beta-hydroxysteroid dehydrogenase type 13 (17β-HSD13) is encoded by the HSD17B13 gene and is mainly expressed in the liver (S. Liu, et al., *Acta Biochim. Pol.* 2007, 54, 213-218). Moreover, 17β-HSD13 was identified as a lipid droplet associated protein and is up-regulated in mice and patients with nonalcoholic fatty liver disease (NAFLD) (Y. Horiguchi, et al., *Biochem. Biophys. Res. Commun.* 2008, 370, 235-238; W. Su, et al., *Mol. Cell. Endocrinol.* 2019, 489, 119-125). Further studies have shown that a 17β-HSD13 loss-of-function variant has been associated with a significantly reduced risk of NAFLD, cirrhosis associated with nonalcoholic steatohepatitis (NASH), alcoholic liver disease, alcoholic cirrhosis, hepatocellular carcinoma (HCC), NASH disease severity, ballooning degeneration, lobular inflammation, and fibrosis (N. S. Abul-Husn, et al., *N. Engl. J Med.* 2018, 378, 1096-1106; C. J. Pirola, et al., *J. Lipid Res.* 2019, 60, 176-185). This variant has also shown a reduction in liver damage among obese children (A. Di Sessa, et al., *J. Pediatr. Gastroenterol. Nutr.* 2020, 70, 371-374).

Small molecule compounds which act as 17β-HSD13 inhibitors have been disclosed in WO 2021/003295A1. Other agents that act as 17β-HSD13 inhibitors have been disclosed in WO 2020/132564, WO 2020/061177, WO 2019/075181, WO 2019/183164, WO 2019/183329, US 2019/0106749, and WO 2018/136758.

There is a need for the development of 17β-HSD13 inhibitors for the treatment and prevention of disease.

SUMMARY OF THE INVENTION

The present invention relates to compounds which inhibit 17β-HSD13 as well as methods of using these compounds to treat disease.

In one aspect, the invention provides compounds represented by Formula I, and pharmaceutically acceptable salts thereof:

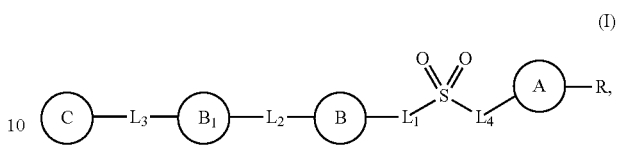

(I)

wherein:
$L_1$ and $L_4$ are each independently absent or $NR_1$;
$R_1$ is hydrogen, optionally substituted methyl, or optionally substituted acetyl;

is absent or selected from the group consisting of optionally substituted aryl, optionally substituted heteroaryl, optionally substituted arylalkyl, optionally substituted heteroarylalkyl, optionally substituted $-C_3$-$C_{12}$ cycloalkyl, optionally substituted 3- to 12-membered heterocycloalkyl, and optionally substituted $-C_3$-$C_{12}$ cycloalkenyl;

Alternatively, $L_1$ is $NR_1$, $R_1$ is connected to

, and $R_1$ and the nitrogen atom to which it is attached form a heterocyclic ring;

$L_2$ is absent or selected from the groups consisting of $-NR_2-$, $-O-$, optionally substituted $-C_1$-$C_6$ alkyl, optionally substituted $-C_2$-$C_6$ alkenyl and optionally substituted $-C_2$-$C_6$ alkynyl;

$R_2$ is hydrogen, optionally substituted $-C_1$-$C_6$ alkyl, optionally substituted $-C_3$-$C_{12}$ cycloalkyl, and optionally substituted 3- to 12-membered heterocycloalkyl;

is absent or selected from the groups consisting of optionally substituted aryl, optionally substituted heteroaryl, optionally substituted $-C_3$-$C_{12}$ cycloalkyl, optionally substituted 3- to 12-membered heterocycloalkyl, and optionally substituted $-C_3$-$C_{12}$ cycloalkenyl;

$L_3$ is absent or selected from the group consisting of optionally substituted $-C_1$-$C_6$ alkyl, optionally substituted $-C_2$-$C_6$ alkenyl, optionally substituted $-C_2$-$C_6$ alkynyl, optional substituted-aliphatic which contains 1-6 carbon atoms and at least one other atom selected from oxygen, nitrogen and sulfur atom, optionally substituted $-C_3$-$C_{12}$ cycloalkyl, optionally substituted 3- to 12-membered heterocycloalkyl, $-O-$, $-NR_2-$, $-C(O)-$, $-OC(O)-$, $-C(O)O-$, $-NR_2C(O)-$, $-C(O)NR_2-$, $-S(O)_2-$, $-S(O)_2NR_2-$, and $-NR_2S(O)_2-$, wherein $R_2$ is as previously defined;

(C)

is absent or selected from the groups consisting of optionally substituted aryl, optionally substituted heteroaryl, optionally substituted arylalkyl, optionally substituted heteroarylalkyl optionally substituted —$C_3$-$C_{12}$ cycloalkyl, optionally substituted 3- to 12-membered heterocycloalkyl, and optionally substituted —$C_3$-$C_{12}$ cycloalkenyl;

(A)

is optionally substituted aryl, optionally substituted heteroaryl, optionally substituted arylalkyl, optionally substituted heteroarylalkyl, optionally substituted —$C_3$-$C_{12}$ cycloalkyl, optionally substituted 3- to 12-membered heterocycloalkyl; or optionally substituted —$C_3$-$C_{12}$ cycloalkenyl;

Alternatively, $L_4$ is $NR_1$, $R_1$ is connected to (A), and $R_1$ and the nitrogen atom to which it is attached form a heterocyclic ring;

R is absent or selected from the group consisting of hydroxy, protected hydroxy, —O-(hydroxy prodrug group), tetrazolyl, 1-methyltetrazolyl, —$CH_2CO_2R_3$, —$CO_2R_3$, —$C(O)N(R_3)O(R_3)$, —$C(O)NR_4R_5$, —$P(O)(OR_6)_2$, —$C(O)NR_7S(O)_2R_8$, —$S(O)_2R_8$, —$CH_2OH$, —$CH_2OC(O)NR_4R_5$, and —$CH_2OC(O)NR_7S(O)_2R_8$;

Each $R_3$ is independently selected from the groups consisting of hydrogen, optionally substituted —$C_1$-$C_8$ alkyl, and optionally substituted —$C_3$-$C_8$ cycloalkyl;

$R_4$ and $R_5$ are each independently selected from the group consisting of hydrogen, optionally substituted —$C_1$-$C_8$ alkyl, and optionally substituted —$C_3$-$C_8$ cycloalkyl; alternatively, $R_4$ and $R_5$ are taken together with the nitrogen atom to which they are attached to form a heterocyclic ring;

$R_6$ is selected from the group consisting of hydrogen, optionally substituted —$C_1$-$C_8$ alkyl, optionally substituted —$C_3$-$C_8$ cycloalkyl, optionally substituted 3- to 8-membered heterocycloalkyl, optionally substituted aryl, and optionally substituted heteroaryl;

$R_7$ is selected from the group consisting of hydrogen, optionally substituted —$C_1$-$C_6$ alkyl, and optionally substituted —$C_3$-$C_6$ cycloalkyl;

$R_8$ is selected from the group consisting of $NR_4R_5$ optionally substituted —$C_1$-$C_8$ alkyl, optionally substituted —$C_3$-$C_8$ cycloalkyl, optionally substituted 3- to 8-membered heterocycloalkyl, optionally substituted aryl, and optionally substituted heteroaryl; provided that at least one of (B), (B$_1$), and (C)

is not absent.

DETAILED DESCRIPTION OF THE INVENTION

In one embodiment, the present invention provides a compound of Formula (I) as described above, or a pharmaceutically acceptable salt thereof.

In certain embodiments, the present invention relates to compounds of Formula (I), and pharmaceutically acceptable salts thereof, wherein $L_1$ is —$NR_1$—.

In certain embodiments, the present invention relates to compounds of Formula (I), and pharmaceutically acceptable salts thereof, wherein $L_1$ is —NH—.

In certain embodiments, the present invention relates to compounds of Formula (I), and pharmaceutically acceptable salts thereof, wherein $L_4$ is —$NR_1$—.

In certain embodiments, the present invention relates to compounds of Formula (I), and pharmaceutically acceptable salts thereof, wherein $L_4$ is —NH—.

In certain embodiments, the present invention relates to compounds of Formula (I), and pharmaceutically acceptable salts thereof, wherein $L_1$ is —NH—, and $L_4$ is absent.

In certain embodiments, the present invention relates to compounds of Formula (I), and pharmaceutically acceptable salts thereof, wherein $L_4$ is —NH—, and $L_1$ is absent.

In certain embodiments, the present invention relates to compounds of Formula (I), and pharmaceutically acceptable salts thereof, wherein $L_1$ is —NH—, and $L_4$ is —NH—.

In certain embodiments, the present invention relates to compounds of Formula (I), and pharmaceutically acceptable salts thereof, wherein (A)

is optionally substituted aryl.

In certain embodiments, the present invention relates to compounds of Formula (I), and pharmaceutically acceptable salts thereof, wherein (A)

is optionally substituted heteroaryl.

In certain embodiments, the present invention relates to compounds of Formula (I), and pharmaceutically acceptable salts thereof, wherein (A)

is optionally substituted phenyl.

In certain embodiments, the present invention relates to compounds of Formula (I), and pharmaceutically acceptable salts thereof, wherein (A)

is

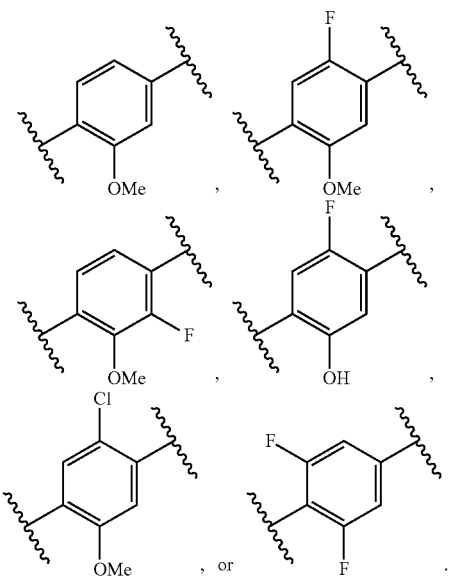

In certain embodiments, the present invention relates to compounds of Formula (I), and pharmaceutically acceptable salts thereof, wherein R is —CO$_2$H.

In certain embodiments, the present invention relates to compounds of Formula (I), and pharmaceutically acceptable salts thereof, wherein R is optionally substituted tetrazolyl, such as 5-tetrazolyl or 1-methyl-5-tetrazolyl.

In certain embodiments, the present invention relates to compounds of Formula (I), and pharmaceutically acceptable salts thereof, wherein R is —CH$_2$OH.

In certain embodiments, the present invention relates to compounds of Formula (I), and pharmaceutically acceptable salts thereof, wherein R is —CH$_2$OC(O)NR$_4$R$_5$, or —CH$_2$OC(O)NR$_7$S(O)$_2$R$_8$, and R$_4$, R$_5$, R$_7$, and R$_8$ are previously defined.

In certain embodiments, the present invention relates to compounds of Formula (I), and pharmaceutically acceptable salts thereof, wherein R is —P(O)(OR$_6$)$_2$ or —C(O)NR$_7$S(O)$_2$R$_8$, and —R$_6$, R$_7$, and R$_8$ are as previously defined.

In certain embodiments, the present invention relates to compounds of Formula (I), and pharmaceutically acceptable salts thereof, wherein

is optionally substituted aryl or optionally substituted heteroaryl.

In certain embodiments, the present invention relates to compounds of Formula (I), and pharmaceutically acceptable salts thereof, wherein

is selected from the groups set forth below by removal of two hydrogen atoms, and

is optionally substituted:

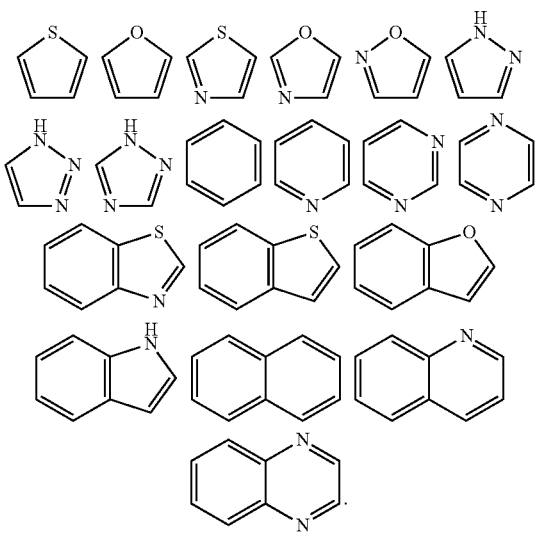

In certain embodiments, the present invention relates to compounds of Formula (I), and pharmaceutically acceptable salts thereof, wherein

is selected from the groups set forth below, and

is optionally substituted:

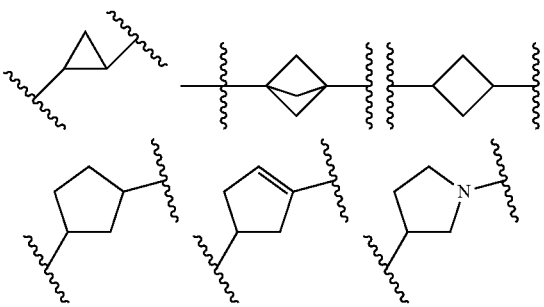

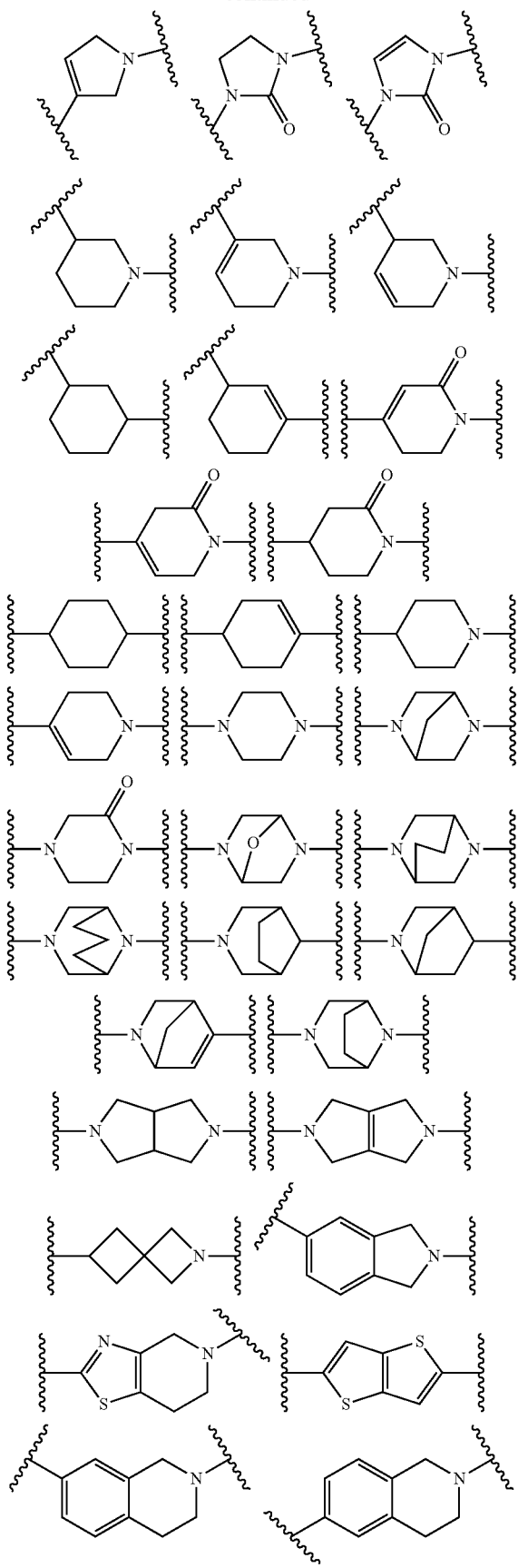
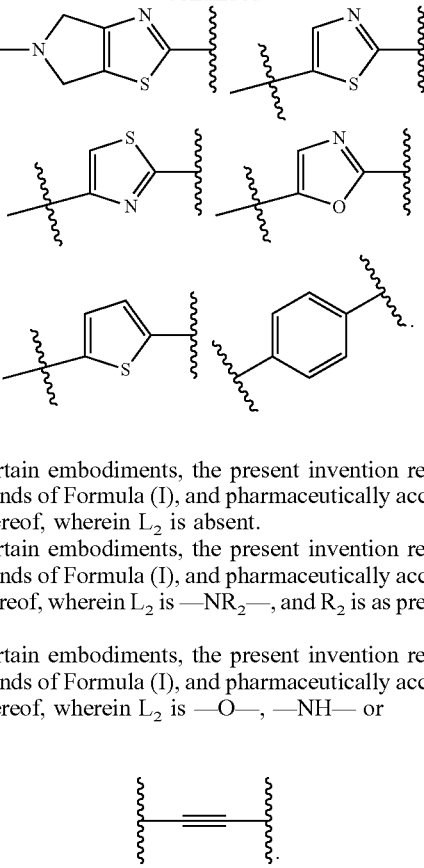

In certain embodiments, the present invention relates to compounds of Formula (I), and pharmaceutically acceptable salts thereof, wherein $L_2$ is absent.

In certain embodiments, the present invention relates to compounds of Formula (I), and pharmaceutically acceptable salts thereof, wherein $L_2$ is —$NR_2$—, and $R_2$ is as previously defined.

In certain embodiments, the present invention relates to compounds of Formula (I), and pharmaceutically acceptable salts thereof, wherein $L_2$ is —O—, —NH— or In certain embodiments, the present invention relates to compounds of Formula (I), and pharmaceutically acceptable salts thereof, wherein $L_2$ is optionally substituted —$C_1$-$C_6$-alkyl.

In certain embodiments, the present invention relates to compounds of Formula (I), and pharmaceutically acceptable salts thereof, wherein $L_2$ is —$C_2$-$C_6$-alkynyl, such as ethynyl.

In certain embodiments, the present invention relates to compounds of Formula (I), and pharmaceutically acceptable salts thereof, wherein $L_3$ is absent.

In certain embodiments, the present invention relates to compounds of Formula (I), and pharmaceutically acceptable salts thereof, wherein $L_3$ is optionally substituted —$C_1$-$C_6$-alkyl.

In certain embodiments, the present invention relates to compounds of Formula (I), and pharmaceutically acceptable salts thereof, wherein $L_3$ is —O— or —$NR_2$—, and $R_2$ is as previously defined.

In certain embodiments, the present invention relates to compounds of Formula (I), and pharmaceutically acceptable salts thereof, wherein $L_3$ is —C(O)—, —OC(O)—, —C(O)O—, —S(O)_2—, —S(O)_2NR_2—, or —$NR_2S(O)_2$—.

In certain embodiments, the present invention relates to compounds of Formula (I), and pharmaceutically acceptable salts thereof, wherein $L_3$ is optionally substituted —$C_1$-$C_6$ alkyl, optionally substituted —$C_2$-$C_5$ heteroalkyl, optionally substituted —$C_1$-$C_6$ alkenyl, or optionally substituted —$C_3$-$C_8$ heteroalkenyl.

In certain embodiments, the present invention relates to compounds of Formula (I), and pharmaceutically acceptable salts thereof, wherein

is absent and $L_3$ is selected from the groups below:

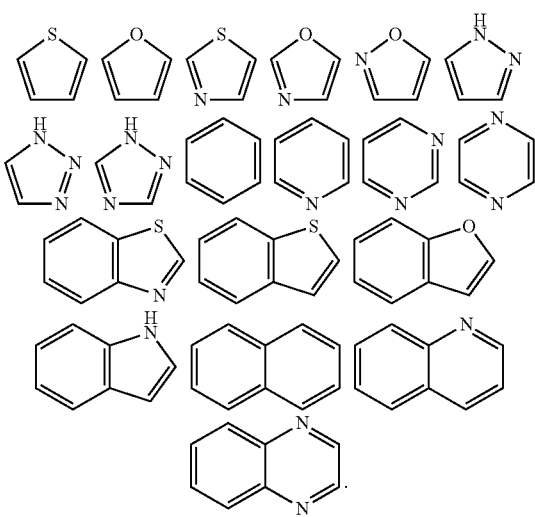

In certain embodiments, the present invention relates to compounds of Formula (I), and pharmaceutically acceptable salts thereof, wherein $L_2$ is absent, and $L_3$ is absent.

In certain embodiments, the present invention relates to compounds of Formula (I), and pharmaceutically acceptable salts thereof, wherein

is selected from the groups set forth below by removal of two hydrogen atoms, and

is optionally substituted:

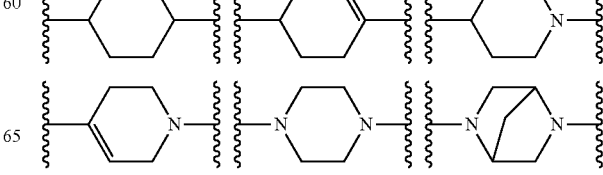

In certain embodiments, the present invention relates to compounds of Formula (I), and pharmaceutically acceptable salts thereof, wherein

is selected from the groups set forth below, and

is optionally substituted:

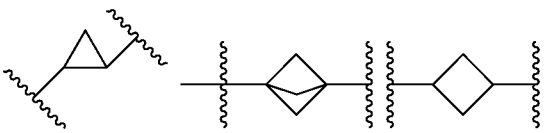

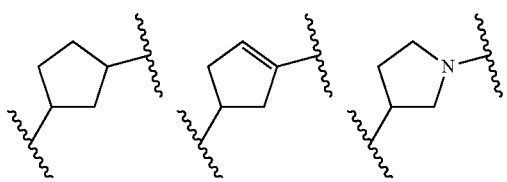

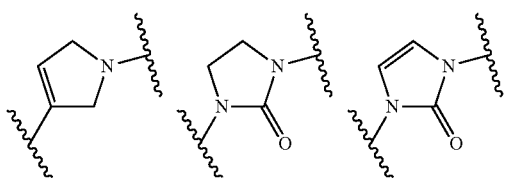

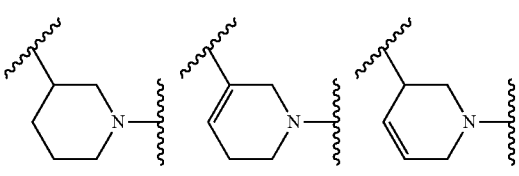

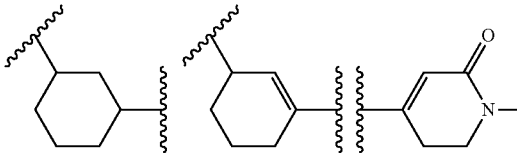

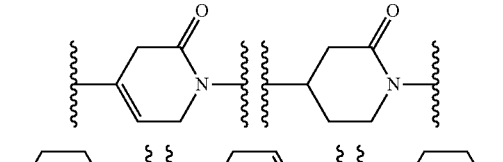

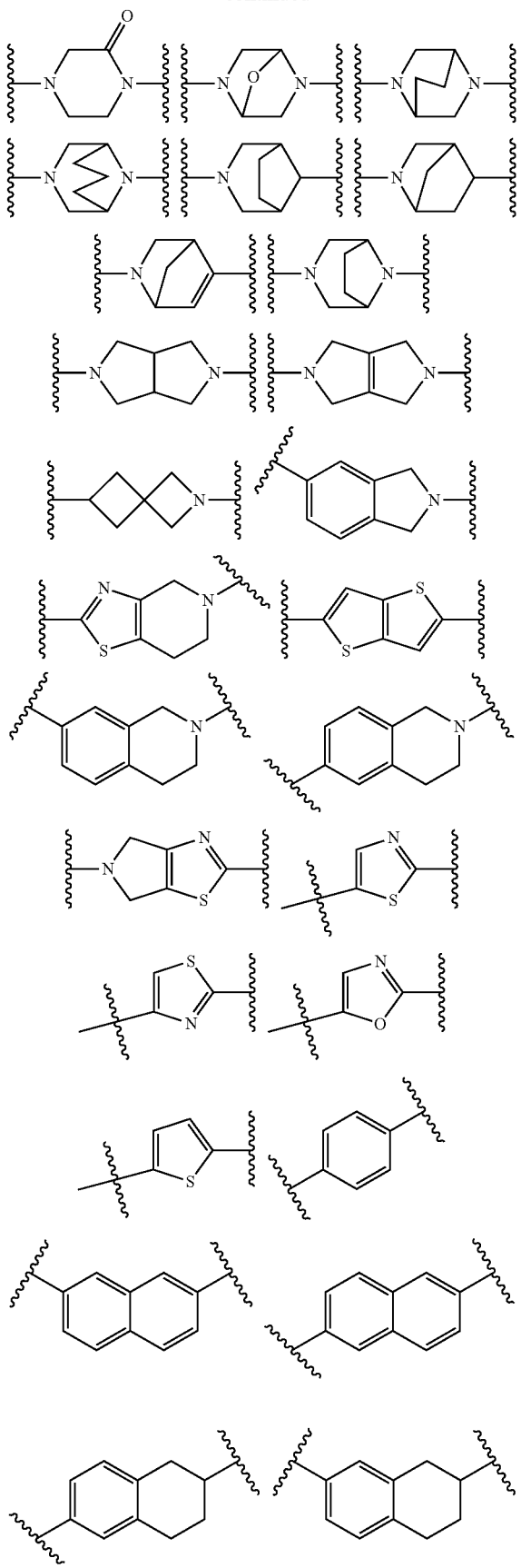

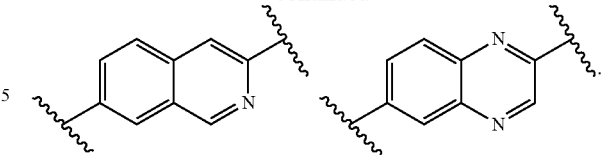

In certain embodiments, the present invention relates to compounds of Formula (I), and pharmaceutically acceptable salts thereof, wherein (C)

is absent.

In certain embodiments, the present invention relates to compounds of Formula (I), and pharmaceutically acceptable salts thereof, wherein (C)

is optionally substituted aryl. Preferably, (C)

is optionally substituted phenyl.

In certain embodiments, the present invention relates to compounds of Formula (I), and pharmaceutically acceptable salts thereof, wherein (C)

is optionally substituted heteroaryl.

In certain embodiments, the present invention relates to compounds of Formula (I), and pharmaceutically acceptable salts thereof, wherein (C)

is optionally substituted —$C_3$-$C_{12}$ cycloalkyl such as but not limited to optionally substituted cyclobutyl, optionally substituted cyclopentyl, optionally substituted cyclohexyl.

In certain embodiments, the present invention relates to compounds of Formula (I), and pharmaceutically acceptable salts thereof, wherein (C)

is optionally substituted —$C_4$-$C_{12}$ cycloalkenyl such as but not limited to optionally substituted cyclopentenyl, optionally substituted cyclohexenyl.

In certain embodiments, the present invention relates to compounds of Formula (I), and pharmaceutically acceptable salts thereof, wherein

is optionally substituted 3 to 12 membered heterocycloalkyl such as but not limited to optionally substituted pyrrolidinyl or optionally substituted piperidinyl.

In certain embodiments, the present invention relates to compounds of Formula (I), and pharmaceutically acceptable salts thereof, wherein

is selected from the groups set forth below by removal of one hydrogen atoms, and

is optionally substituted:

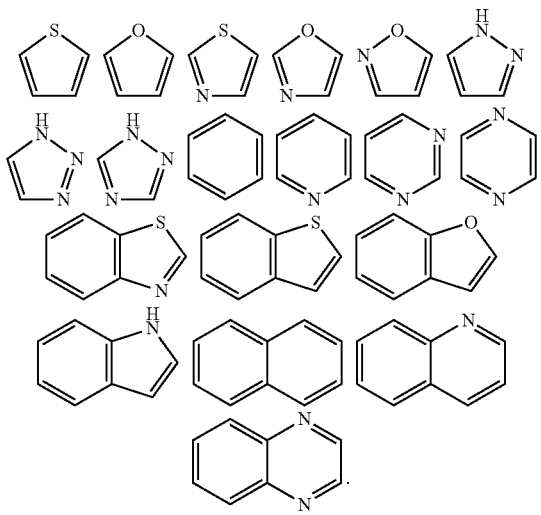

In certain embodiments, the present invention relates to compounds of Formula (I), and pharmaceutically acceptable salts thereof, wherein

is selected from the groups set forth below, and

is optionally substituted:

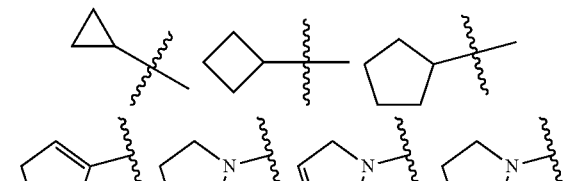
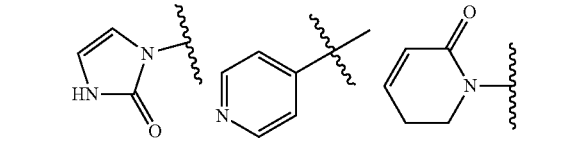
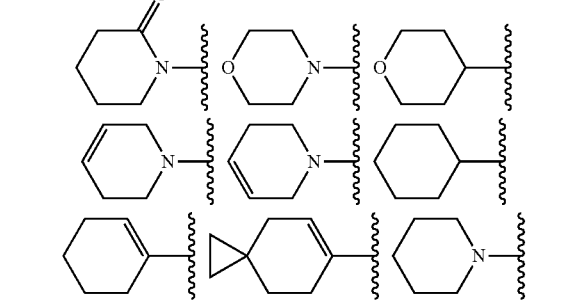
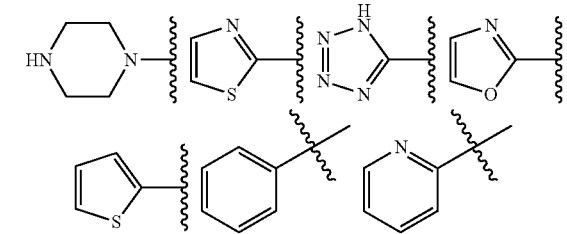
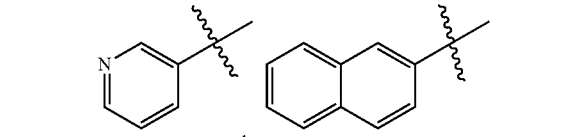
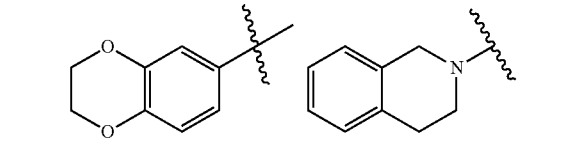
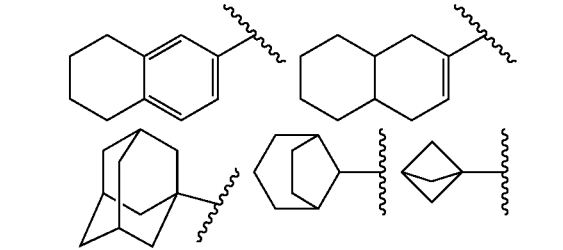

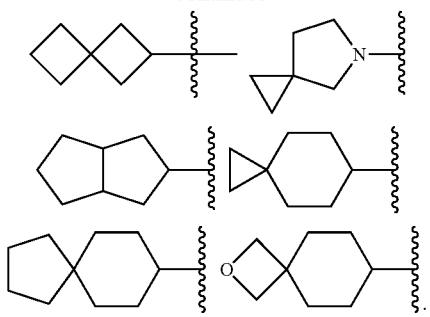

In one embodiment, the compound of Formula (I) is represented by Formula (Ia), or a pharmaceutically acceptable salt thereof:

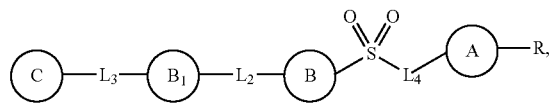

(Ia)

wherein

$L_2$, $L_3$, $L_4$, and R, are as previously defined.

In one embodiment, the compound of Formula (I) is represented by Formula (Ib), or a pharmaceutically acceptable salt thereof:

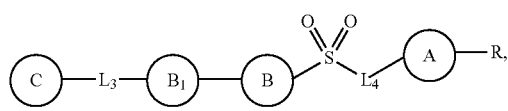

(Ib)

wherein

$L_3$, $L_4$, and R, are as previously defined.

In one embodiment, the compound of Formula (I) is represented by Formula (Ic), or a pharmaceutically acceptable salt thereof:

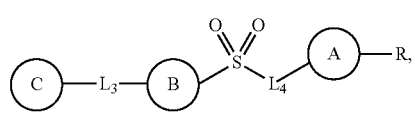

(Ic)

wherein

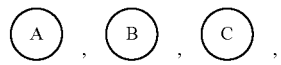

$L_3$, $L_4$, and R, are as previously defined.

In one embodiment, the compound of Formula (I) is represented by Formula (Id), or a pharmaceutically acceptable salt thereof:

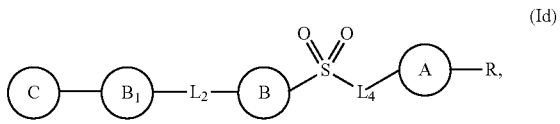

(Id)

wherein

$L_2$, $L_4$, and R, are as previously defined.

In one embodiment, the compound of Formula (I) is represented by Formula (Ie), or a pharmaceutically acceptable salt thereof:

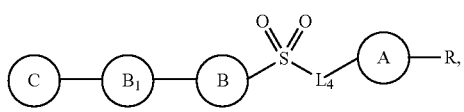

(Ie)

wherein

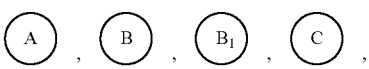

$L_4$, and R, are as previously defined.

In another embodiment, the compound of Formula (I) is represented by one of Formulae (II-1) to (II-6), or a pharmaceutically acceptable salt thereof:

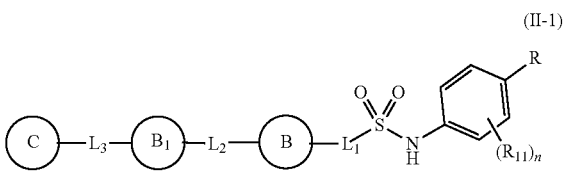

(II-1)

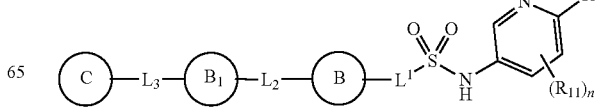

(II-2)

-continued

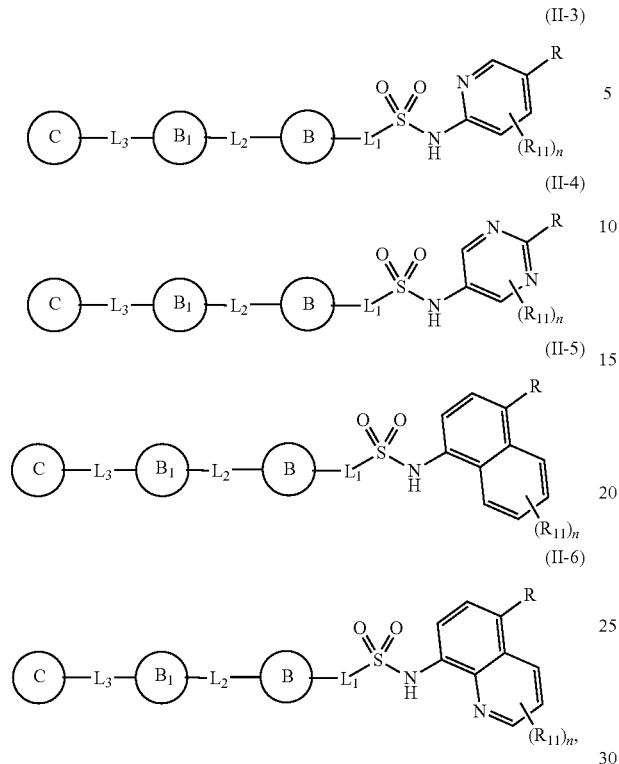

wherein each $R_{11}$ is independently selected from the group consisting of halogen, hydroxy, —$NH_2$, —NHMe, —$NMe_2$, —CN, —$NO_2$, optionally substituted —$C_1$-$C_6$ alkyl, optionally substituted —$C_1$-$C_6$ alkoxyl, optionally substituted $C_3$-$C_6$ cycloalkyl, optionally substituted $C_3$-$C_6$ cycloalkenyl, optionally substituted aryl, and optionally substituted heteroaryl; n is 0, 1, 2, or 3; m is 0, 1 or 2; and

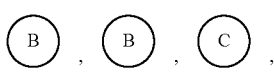

$L_1$, $L_2$, $L_3$, and R are as previously defined.

In another embodiment, the compound of Formula (I) is represented by one of Formulae (III-1) to (III-6), or a pharmaceutically acceptable salt thereof:

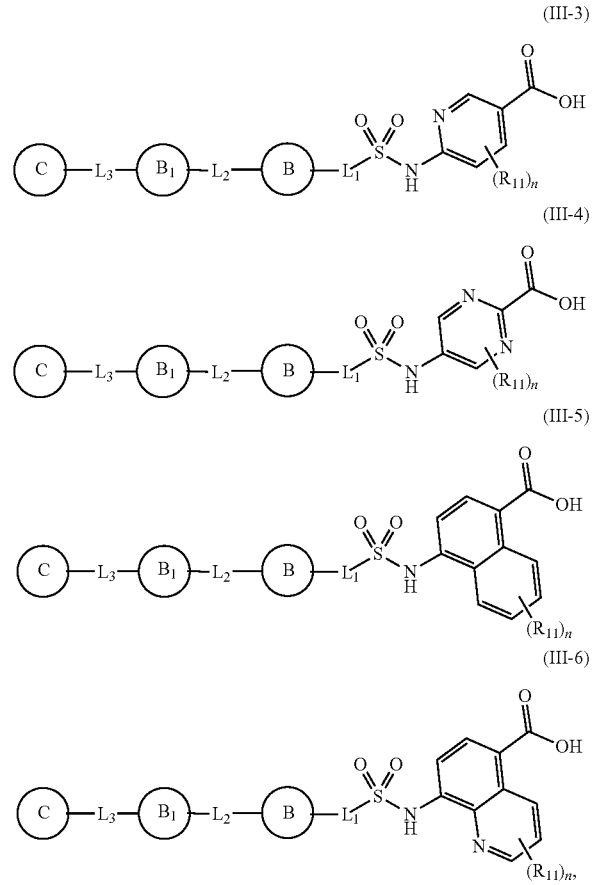

wherein $R_{11}$, m, n,

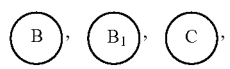

$L_1$, $L_2$, and $L_3$ are as previously defined.

In another embodiment, the compound of Formula (I) is represented by one of Formulae (III-1a) to (III-1f), or a pharmaceutically acceptable salt thereof:

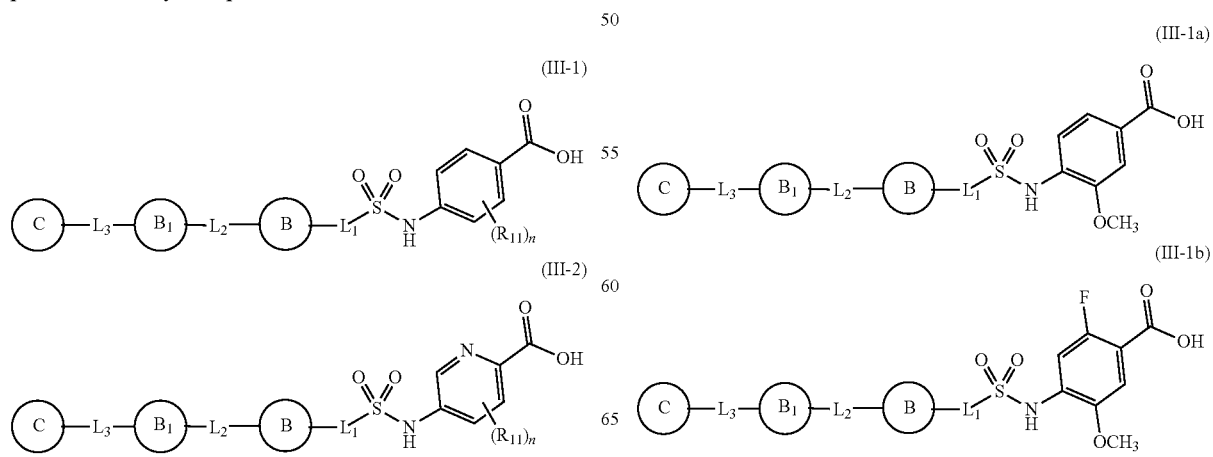

-continued

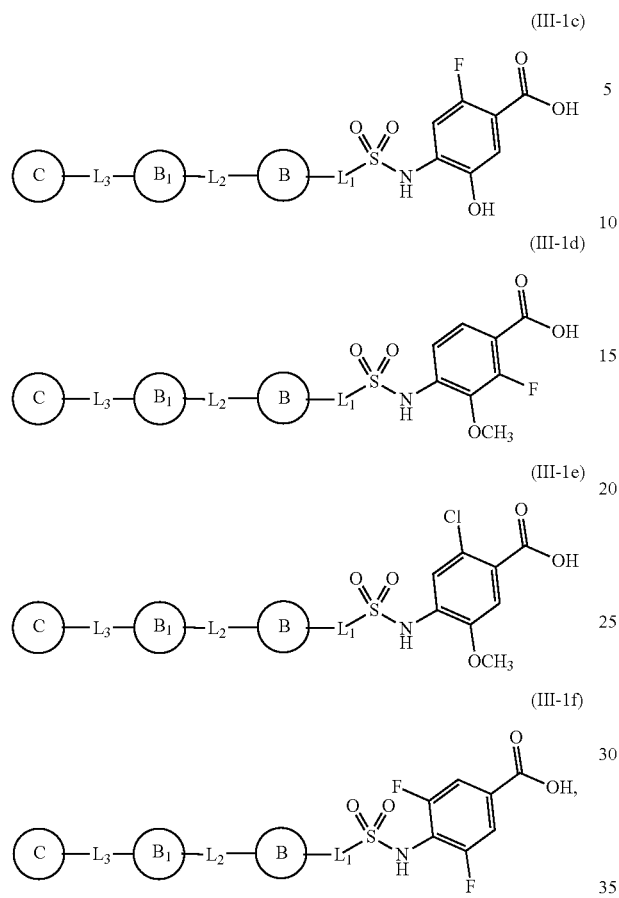

wherein

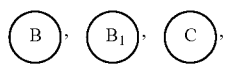

$L_1$, $L_2$, and $L_3$ are as previously defined.

In another embodiment, the compound of Formula (I) is represented by one of Formulae (IV-1) to (IV-6), or a pharmaceutically acceptable salt thereof:

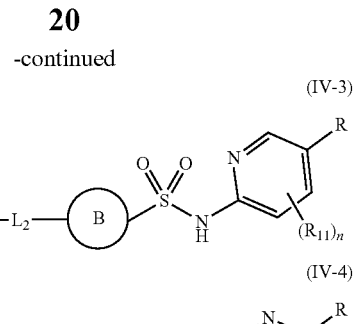

-continued

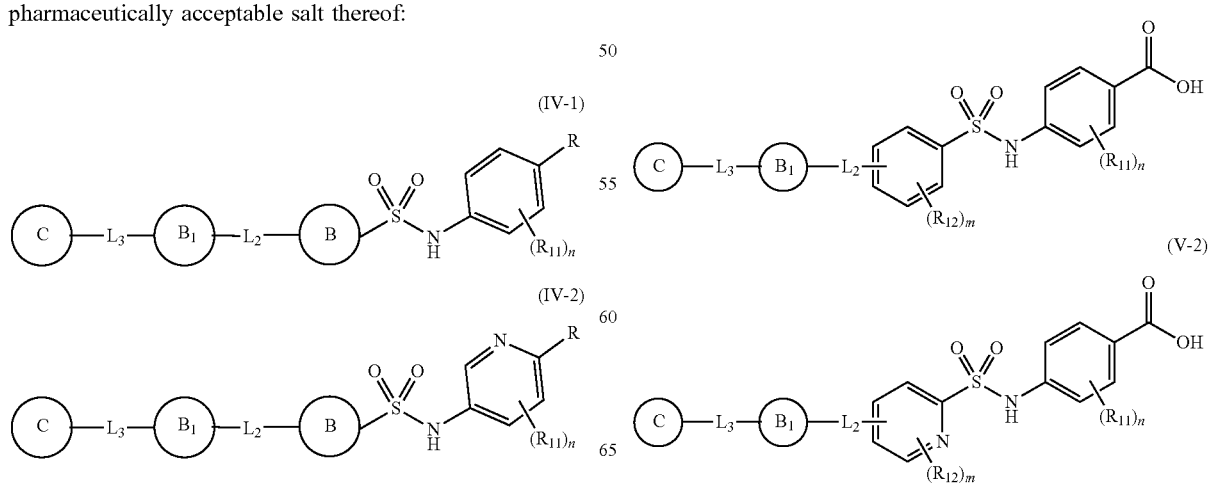

wherein $R_{11}$, m, n,

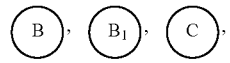

$L_2$, $L_3$, and R are as previously defined.

In another embodiment, the compound of Formula (I) is represented by one of Formulae (V-1) to (V-10), or a pharmaceutically acceptable salt thereof:

(V-3)
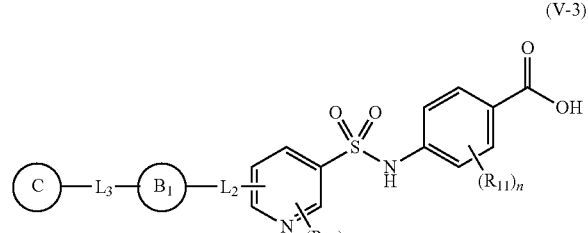

(V-4)
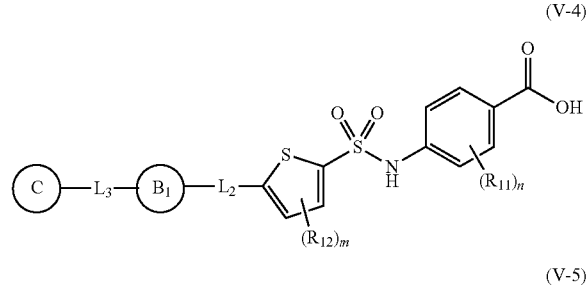

(V-5)
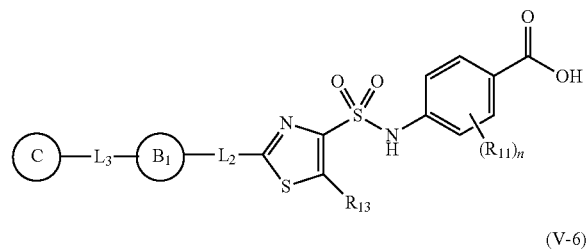

(V-6)
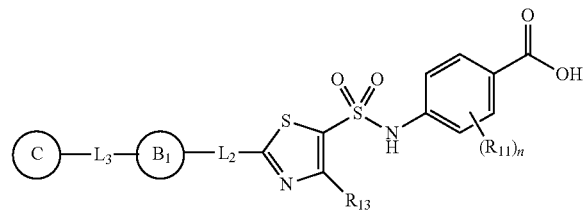

(V-7)
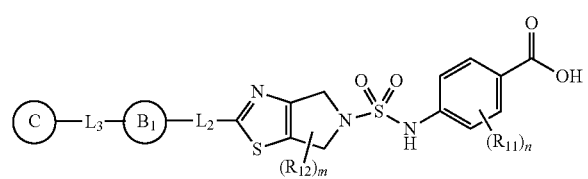

(V-8)
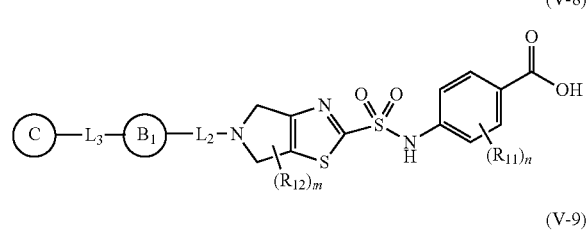

(V-9)
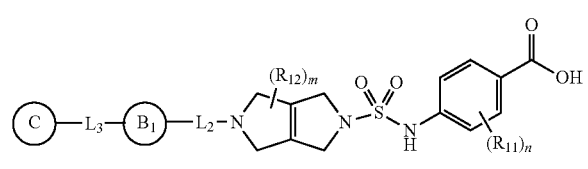

(V-10)
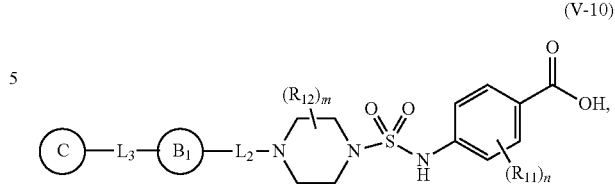

wherein each $R_{12}$ is independently selected from the group consisting of halogen, hydroxy, —NH$_2$, —NHMe, —NMe$_2$, —CN, —NO$_2$, optionally substituted —C$_1$-C$_6$ alkyl, optionally substituted —C$_1$-C$_6$ alkoxyl, optionally substituted C$_3$-C$_6$ cycloalkyl, optionally substituted C$_3$-C$_6$ cycloalkenyl, optionally substituted aryl, and optionally substituted heteroaryl; $R_{13}$ is independently selected from the group consisting of hydrogen, halogen, hydroxy, —NH$_2$, —NHMe, —NMe$_2$, —CN, —NO$_2$, optionally substituted —C$_1$-C$_6$ alkyl, optionally substituted —C$_1$-C$_6$ alkoxyl, optionally substituted C$_3$-C$_6$ cycloalkyl, optionally substituted C$_3$-C$_6$ cycloalkenyl, optionally substituted aryl, and optionally substituted heteroaryl; and $R_{11}$, m, n,

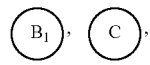

$L_2$, and $L_3$ are as previously defined.

In another embodiment, the compound of Formula (I) is represented by one of Formulae (VI-1) to (VI-6), or a pharmaceutically acceptable salt thereof:

(VI-1)
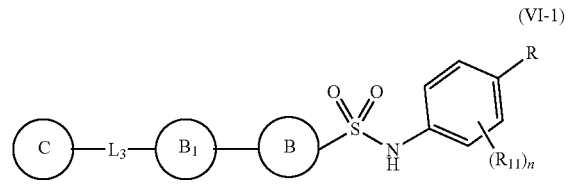

(VI-2)
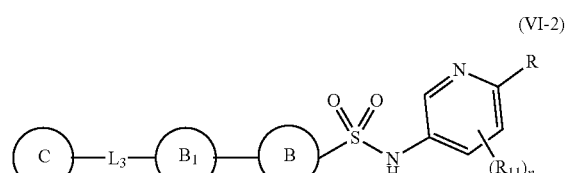

(VI-3)
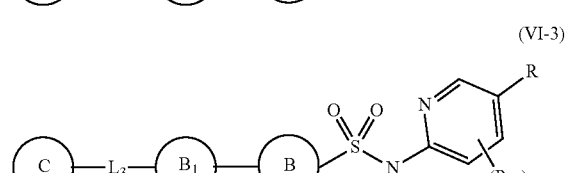

(VI-4)
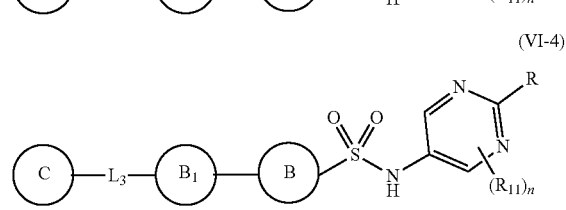

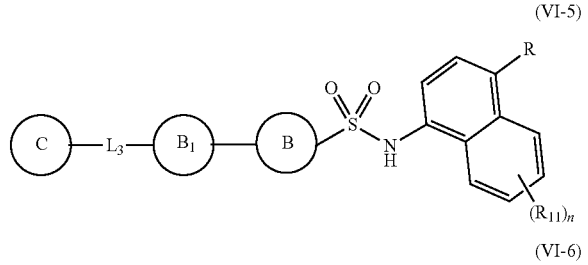
(VI-5)
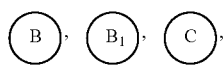
(VI-6)
wherein $R_{11}$, m, n,
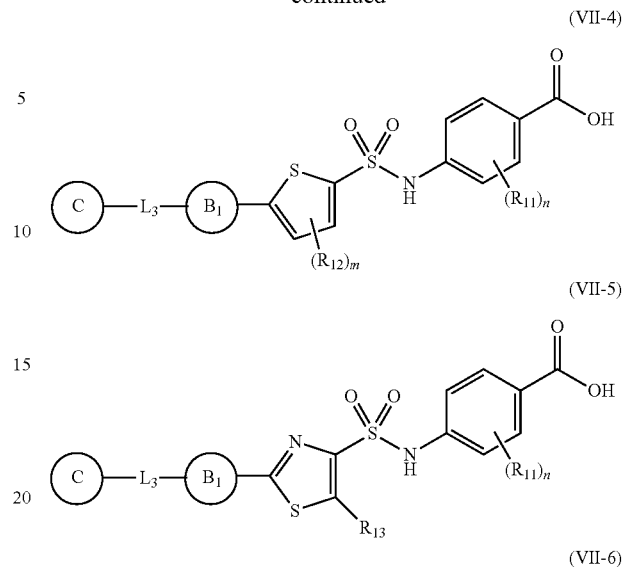
$L_3$, and R are as previously defined.
In another embodiment, the compound of Formula (I) is represented by one of Formulae (VII-1) to (VII-10), or a pharmaceutically acceptable salt thereof:
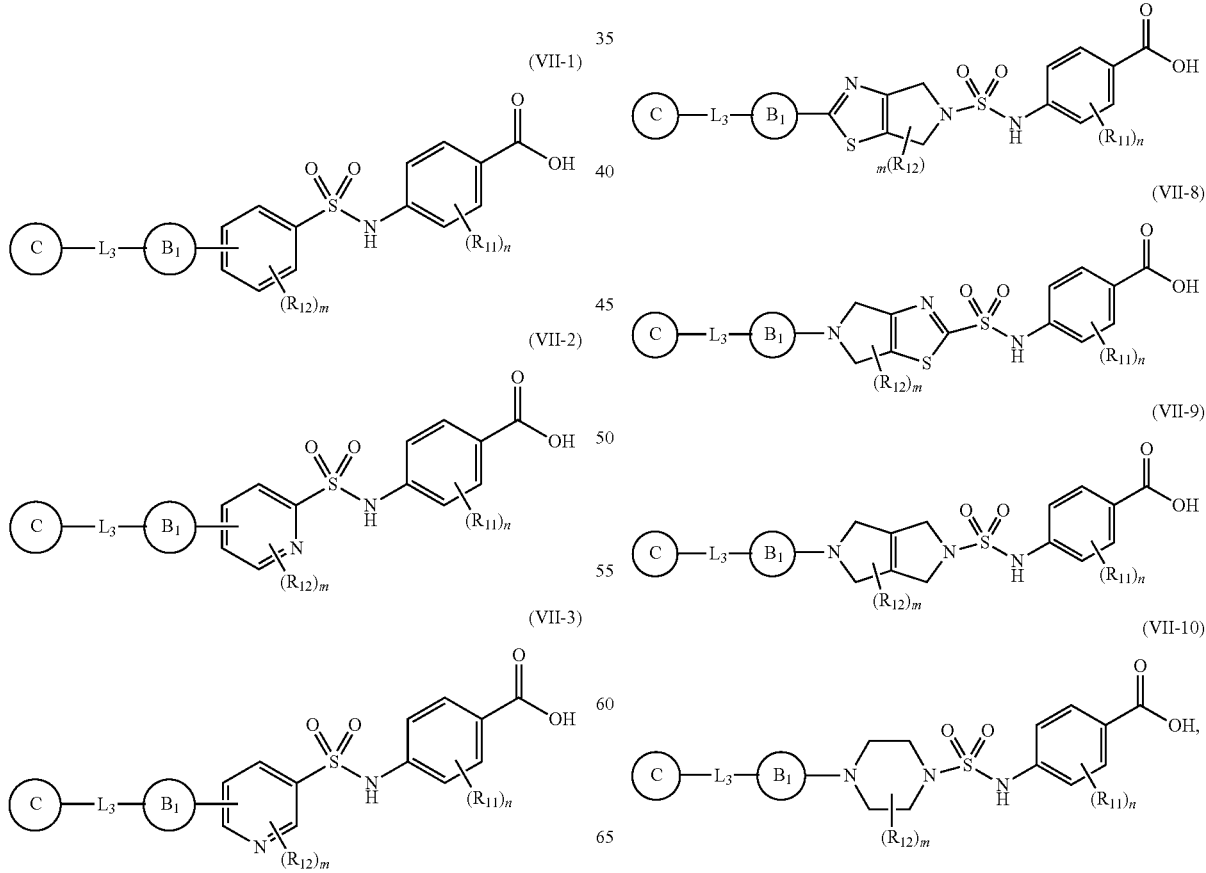

wherein $R_{11}$, $R_{12}$, $R_{13}$, m, n,

and $L_3$ are as previously defined.

In another embodiment, the compound of Formula (I) is represented by one of Formulae (VIII-1) to (VIII-10), or a pharmaceutically acceptable salt thereof:

(VIII-1)

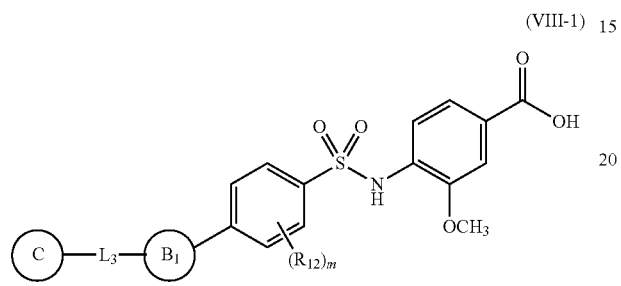

(VIII-2)

(VIII-3)

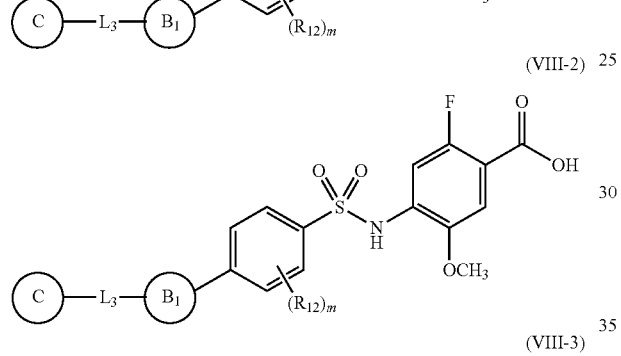

(VIII-4)

(VIII-5)

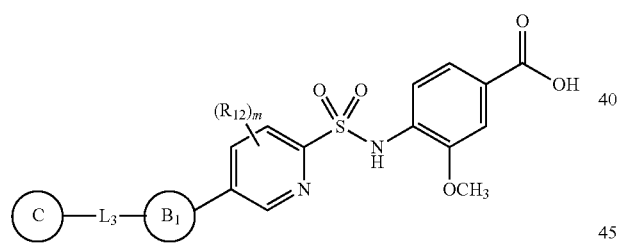

-continued (VIII-6)

(VIII-7)

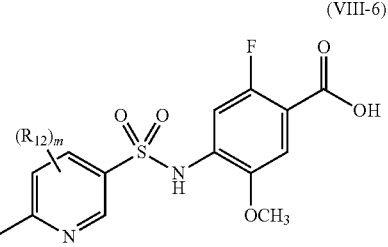

(VIII-8)

(VIII-9)

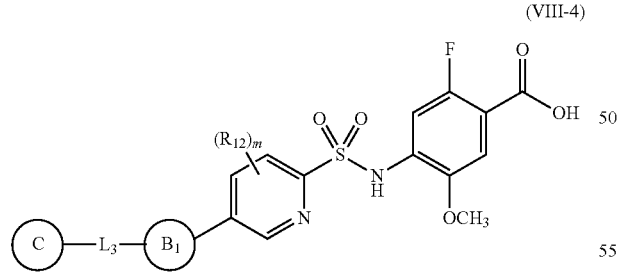

(VIII-10)

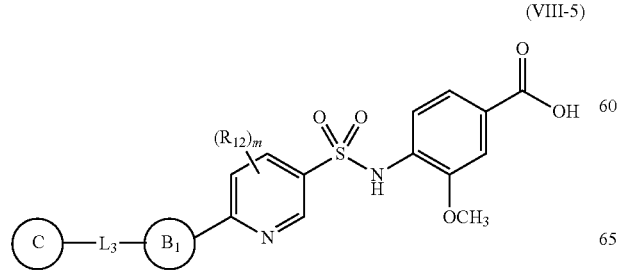

wherein $R_{12}$, $R_{13}$, m,

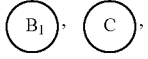

and $L_3$ are as previously defined.

In one embodiment, the compound of Formula (I) is represented by one of Formulae (VIII-1) to (VIII-10), or a pharmaceutically acceptable salt thereof, wherein

is selected from the groups below, and

is optionally substituted.

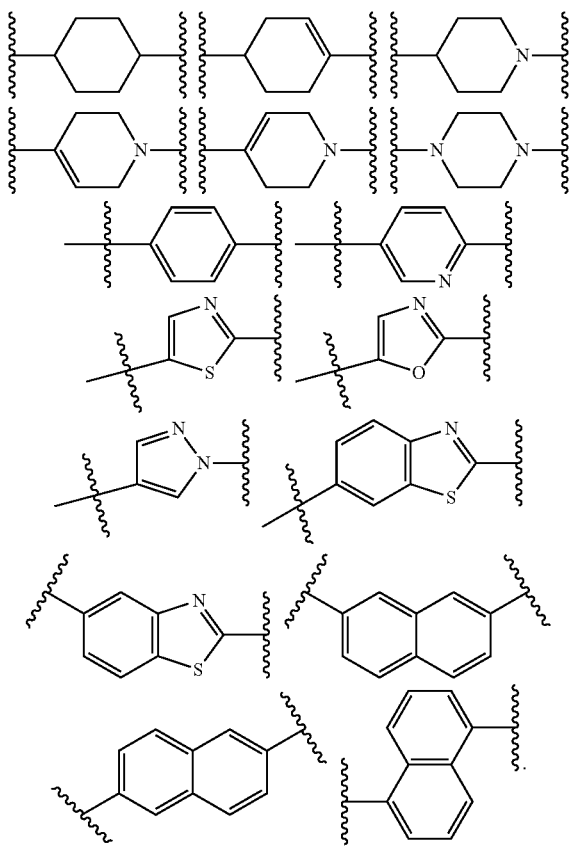

In one embodiment, the compound of Formula (I) is represented by one of Formulae (VIII-1) to (VIII-10), or a pharmaceutically acceptable salt thereof, wherein L₃ is —C(O)—, —OC(O)—, or —C(O)O—,

is selected from the groups below, and

is optionally substituted:

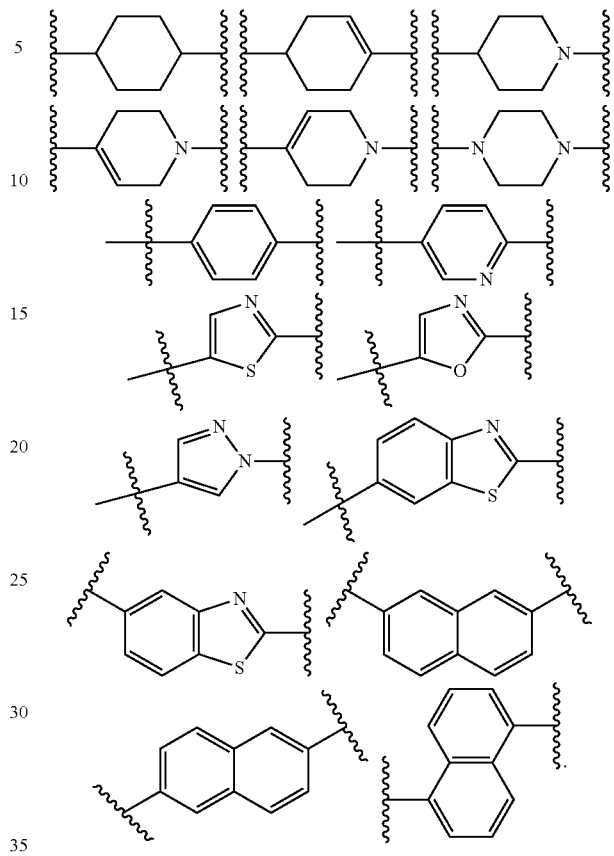

In another embodiment, the compound of Formula (I) is represented by one of Formulae (IX-1) to (IX-6), or a pharmaceutically acceptable salt thereof:

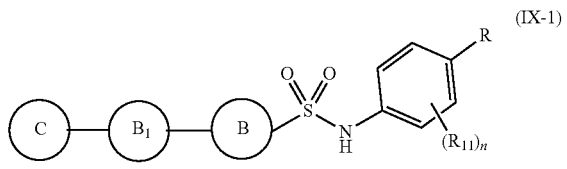

(IX-1)

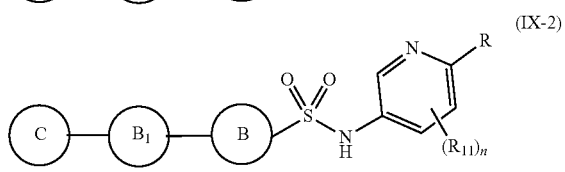

(IX-2)

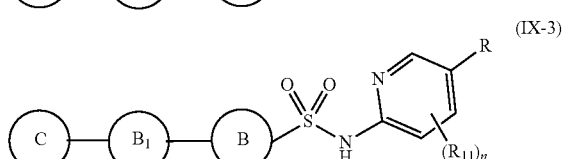

(IX-3)

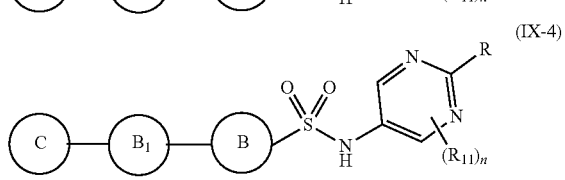

(IX-4)

(IX-5)
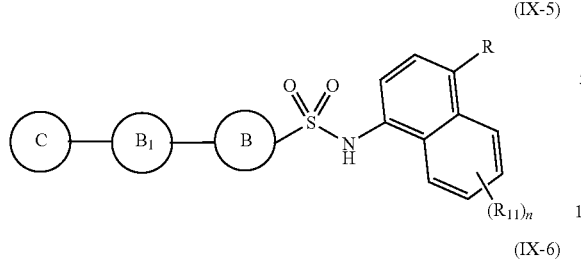
(IX-6)
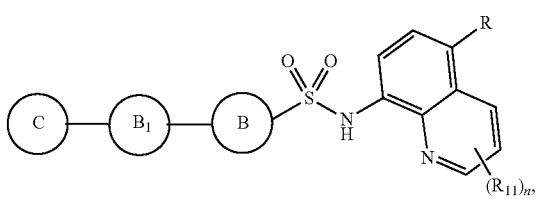
wherein $R_{11}$, m, n
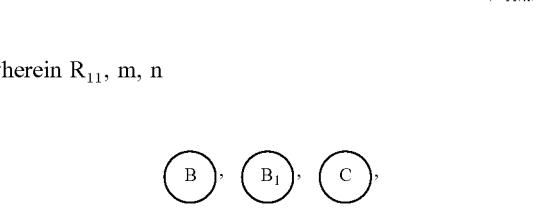
and R are as previously defined.
In another embodiment, the compound of Formula (I) is represented by one of Formulae (X-1) to (X-12), or a pharmaceutically acceptable salt thereof:
(X-1)
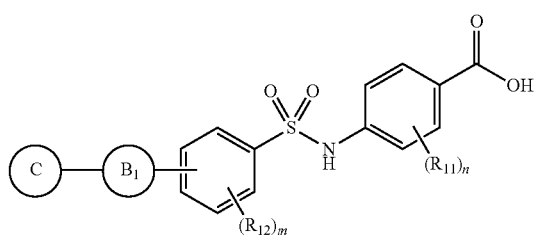
(X-2)
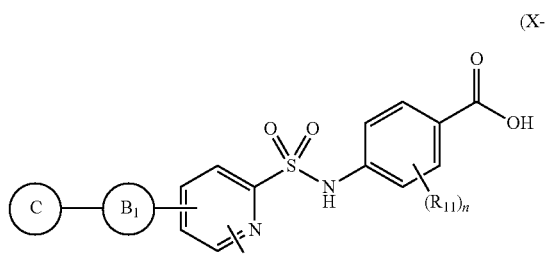
(X-3)
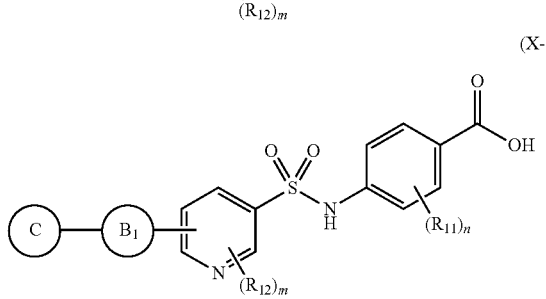
(X-4)
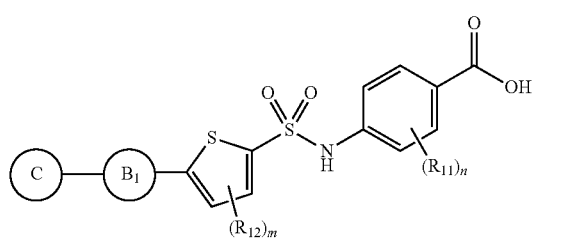
(X-5)
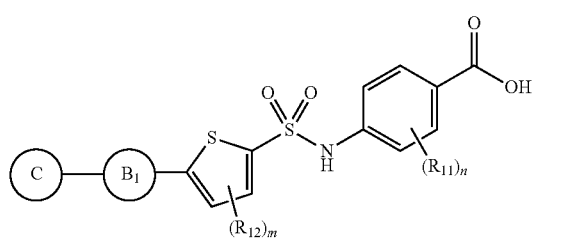
(X-6)
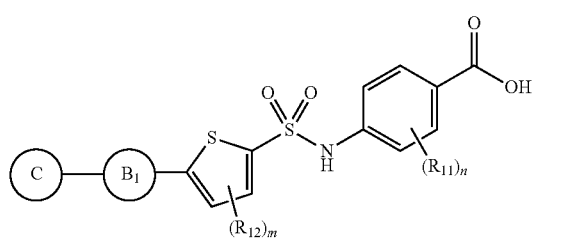
(X-7)
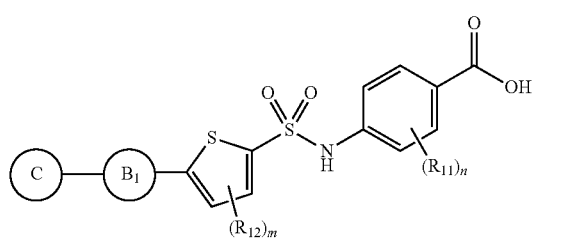
(X-8)
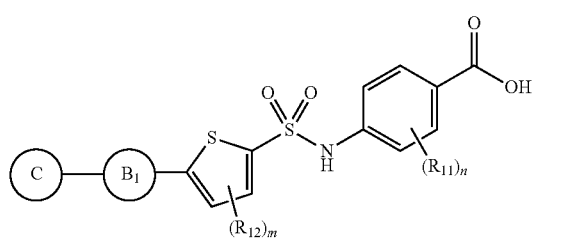
(X-9)
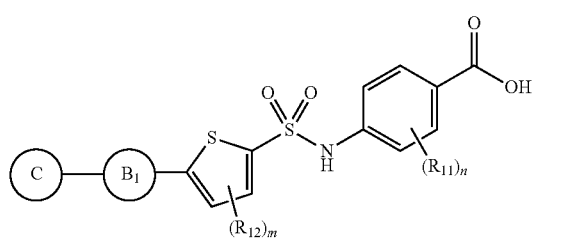

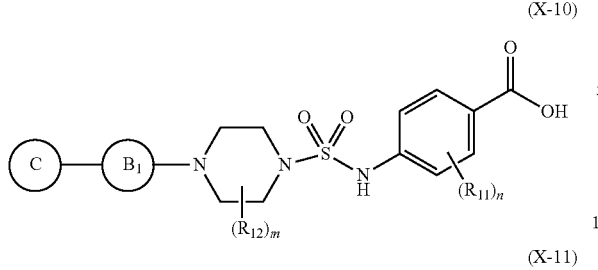
(X-10)
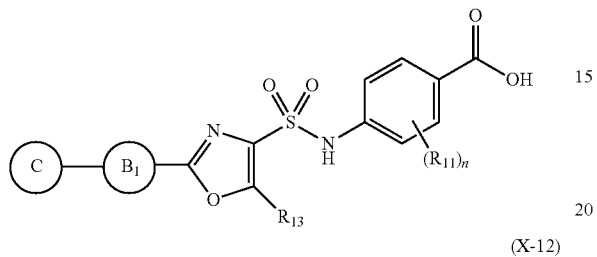
(X-11)
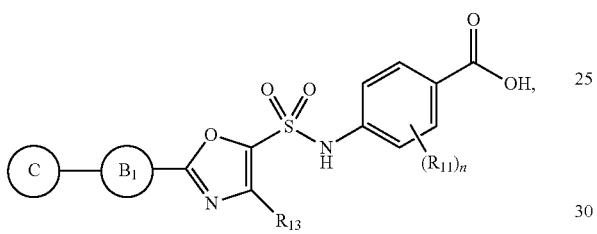
(X-12)
wherein $R_{11}$, $R_{12}$, $R_{13}$ m, n,
(B₁) and (C)
are as previously defined.
In another embodiment, the compound of Formula (I) is represented by one of Formulae (XI-1) to (XI-22), or a pharmaceutically acceptable salt thereof:
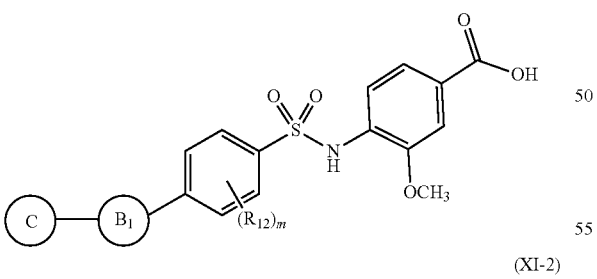
(XI-1)
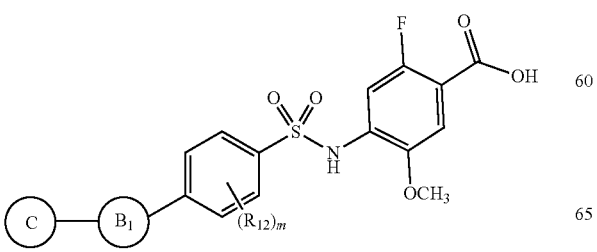
(XI-2)
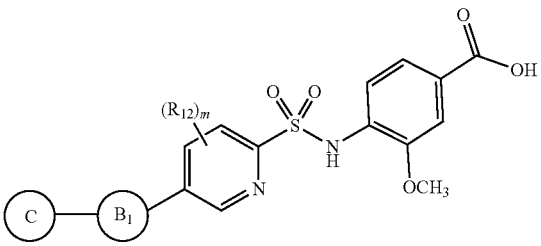
(XI-3)
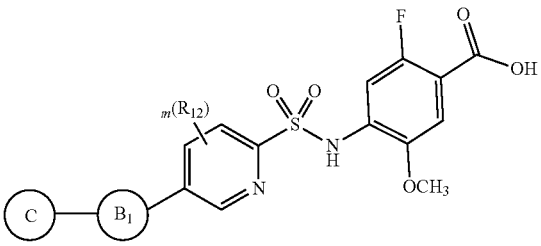
(XI-4)
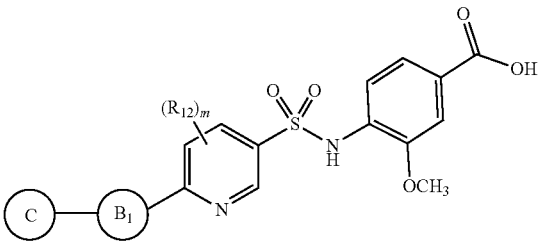
(XI-5)
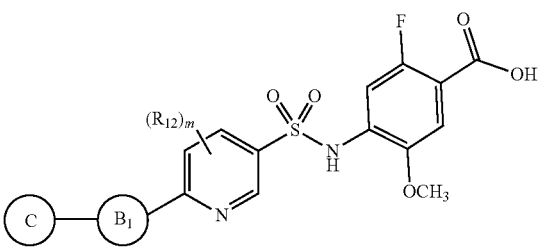
(XI-6)
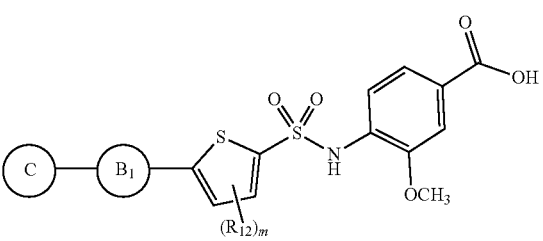
(XI-7)
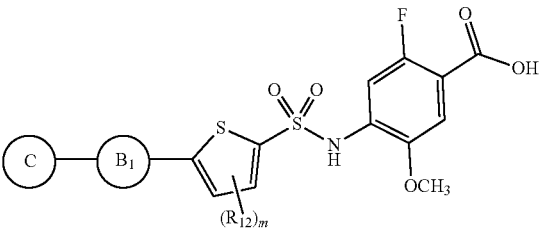
(XI-8)

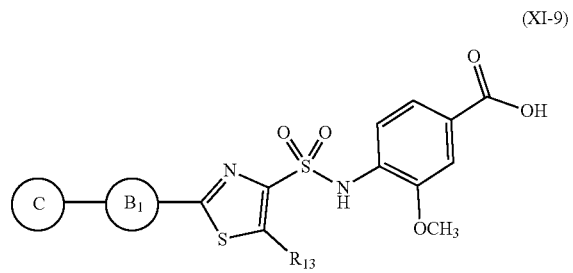
(XI-9)
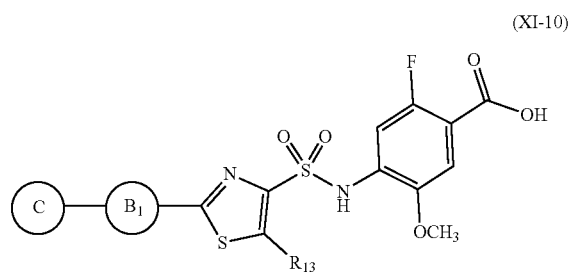
(XI-10)
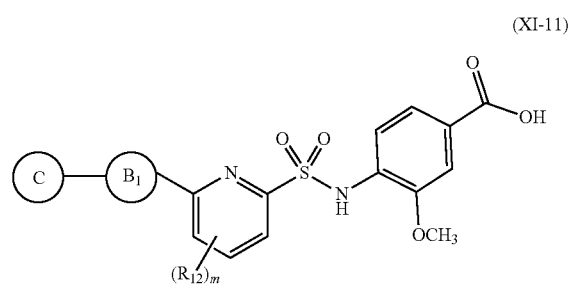
(XI-11)
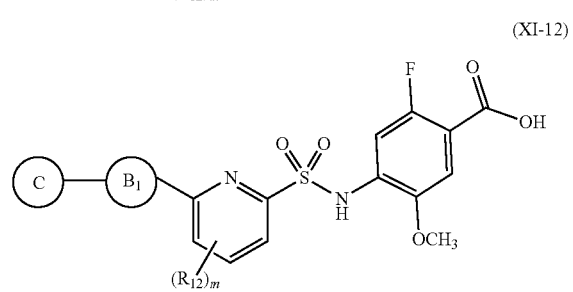
(XI-12)
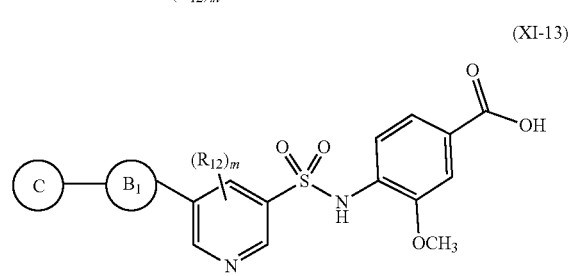
(XI-13)
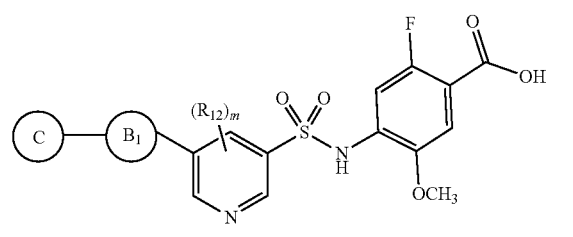
(XI-14)
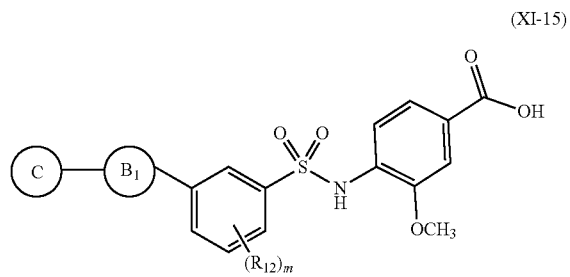
(XI-15)
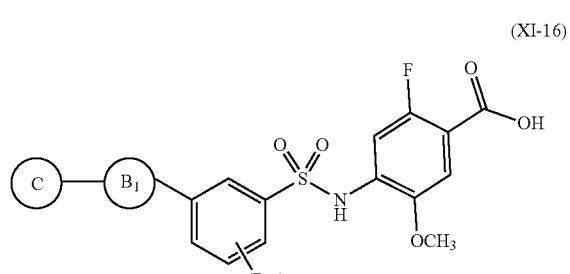
(XI-16)
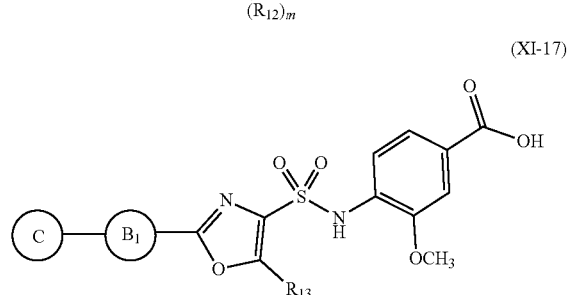
(XI-17)
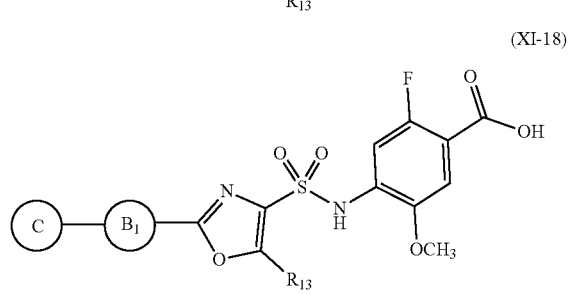
(XI-18)
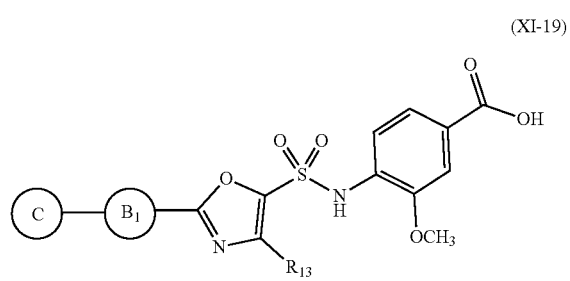
(XI-19)
(XI-20)

-continued

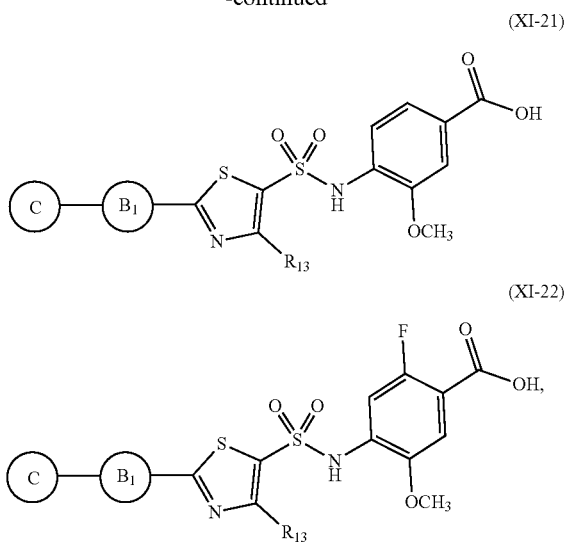

wherein $R_{12}$, $R_{13}$, m,

B₁ and C are as previously defined.

In one embodiment, the compound of Formula (I) is represented by one of Formulae (XI-1) to (XI-22), or a pharmaceutically acceptable salt thereof, where

B₁ is selected from the groups below, and

B₁ is optionally substituted:

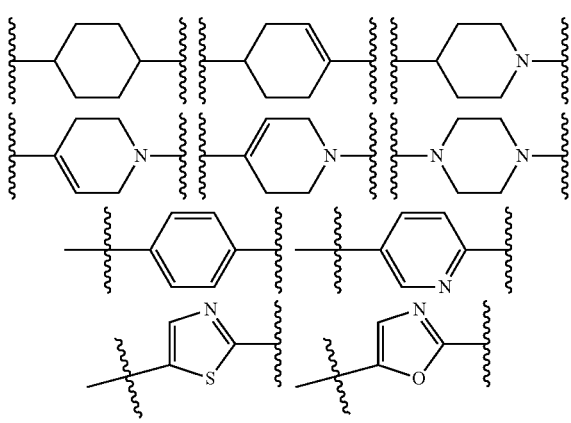

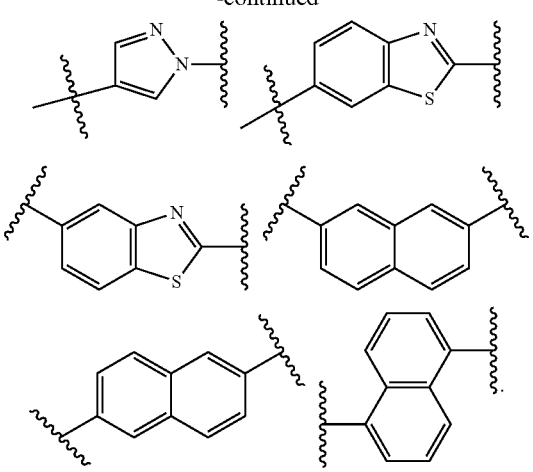

In another embodiment, the compound of Formula (I) is represented by one of Formulae (XII-1) to (XII-6), or a pharmaceutically acceptable salt thereof:

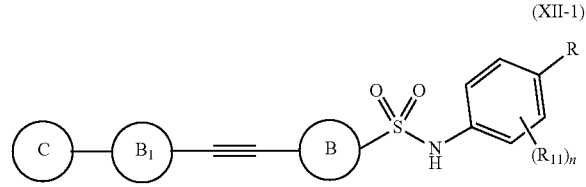

(XII-1)

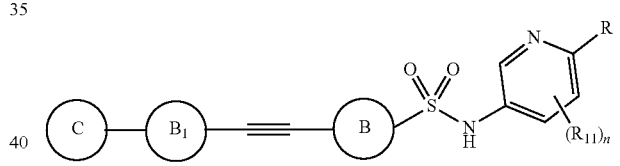

(XII-2)

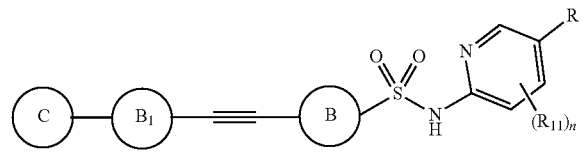

(XII-3)

(XII-4)

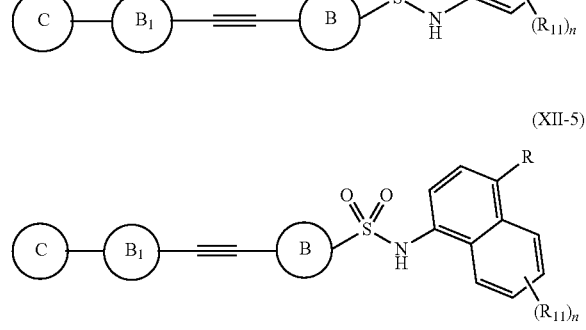

(XII-5)

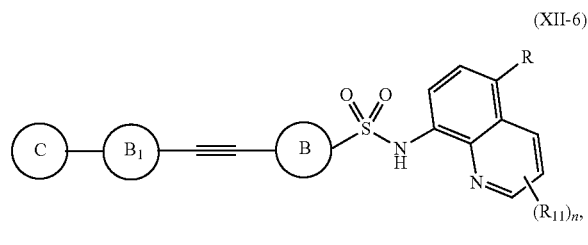

wherein $R_{11}$, m, n,

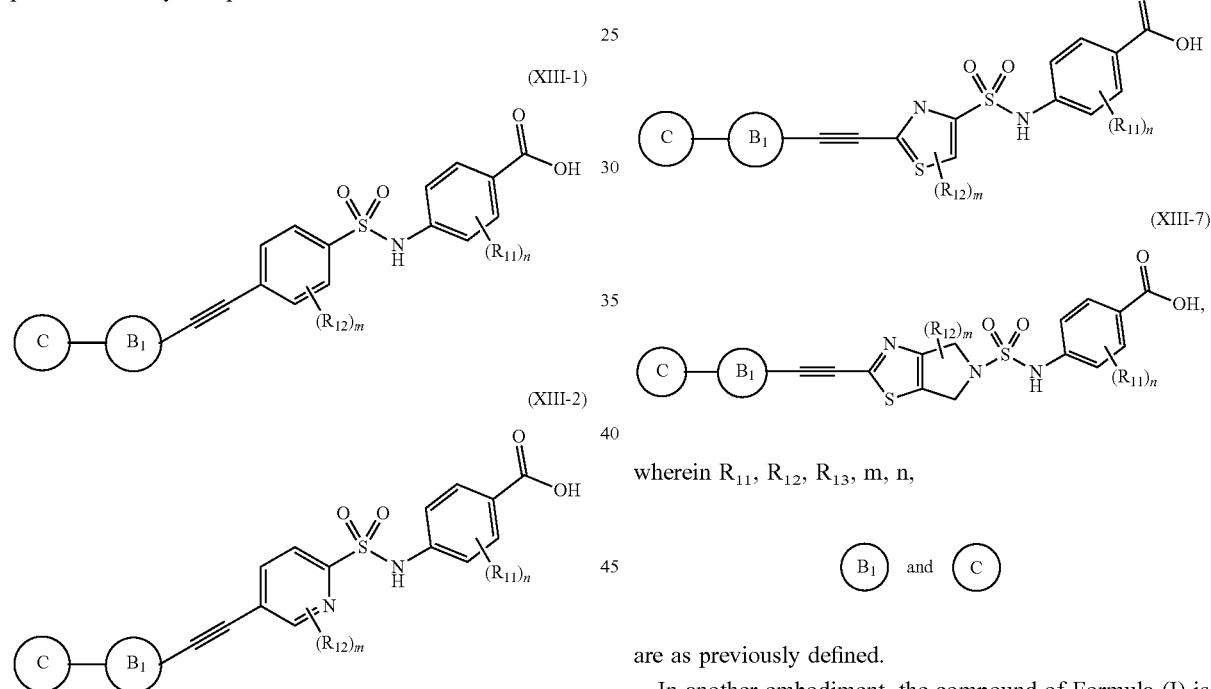

and R are as previously defined.

In another embodiment, the compound of Formula (I) is represented by one of Formulae (XIII-1) to (XIII-7), or a pharmaceutically acceptable salt thereof:

wherein $R_{11}$, $R_{12}$, $R_{13}$, m, n,

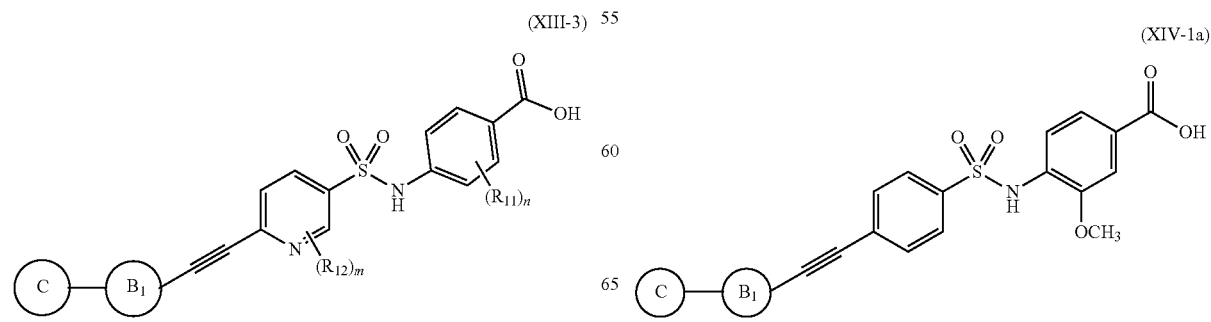

are as previously defined.

In another embodiment, the compound of Formula (I) is represented by one of Formulae (XIV-1a) to (XIV-7a), Formulae (XIV-1b) to (XIV-7b), or a pharmaceutically acceptable salt thereof:

(XIV-1b)
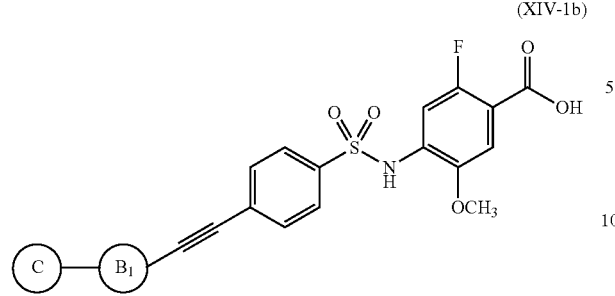
(XIV-2a)
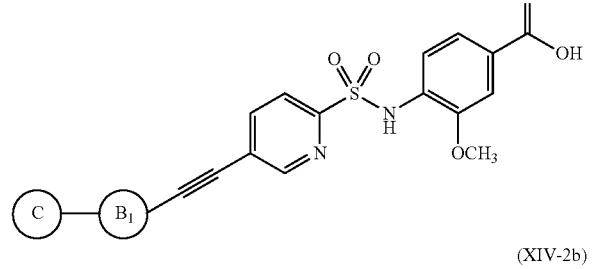
(XIV-2b)
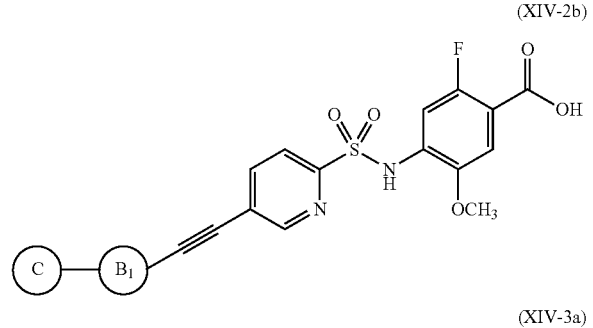
(XIV-3a)
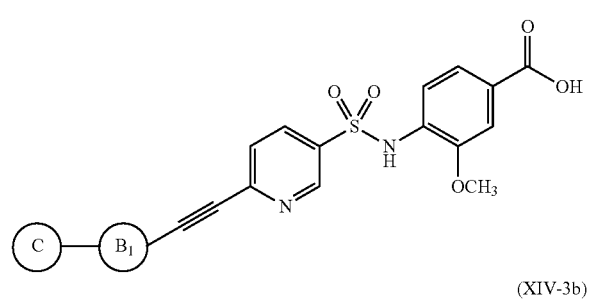
(XIV-3b)
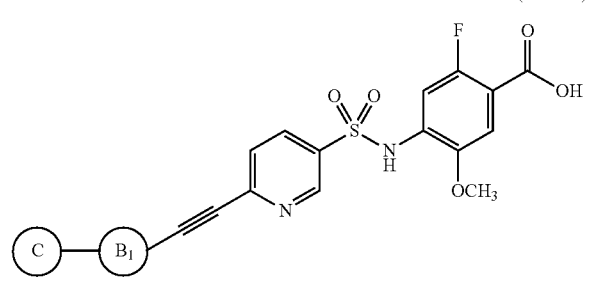
(XIV-4a)
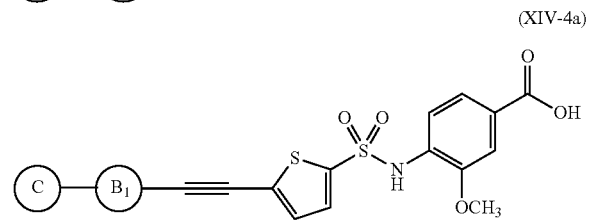
(XIV-4b)
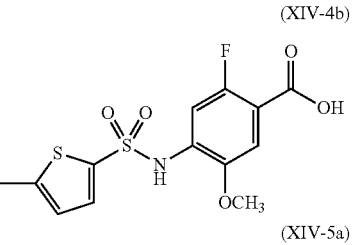
(XIV-5a)
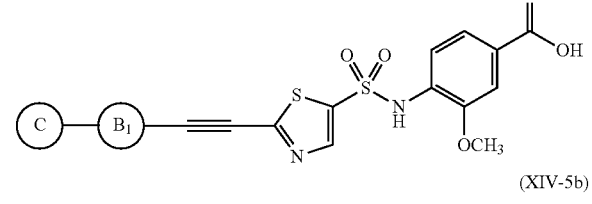
(XIV-5b)
(XIV-6a)
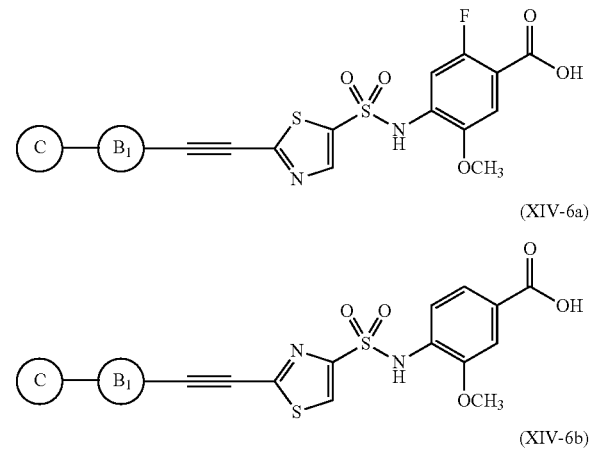
(XIV-6b)
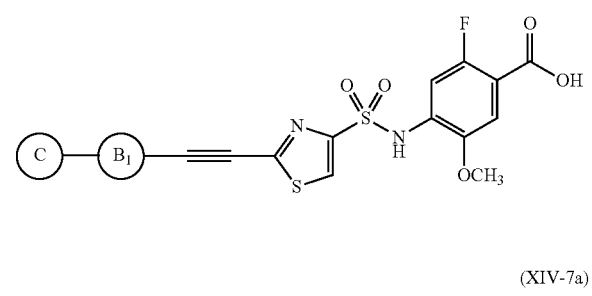
(XIV-7a)
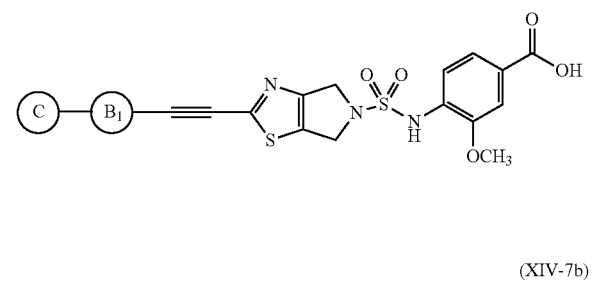
(XIV-7b)
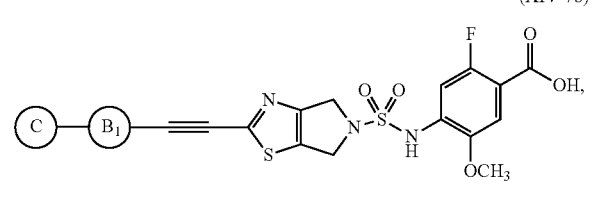

wherein

are as previously defined.

In one embodiment, the compound of Formula (I) is represented by Formulae (XIV-1a) to (XIV-7a), Formulae (XIV-1b) to (XIV-7b), or a pharmaceutically acceptable salt thereof, where

is selected from the groups below, and

is optionally substituted:

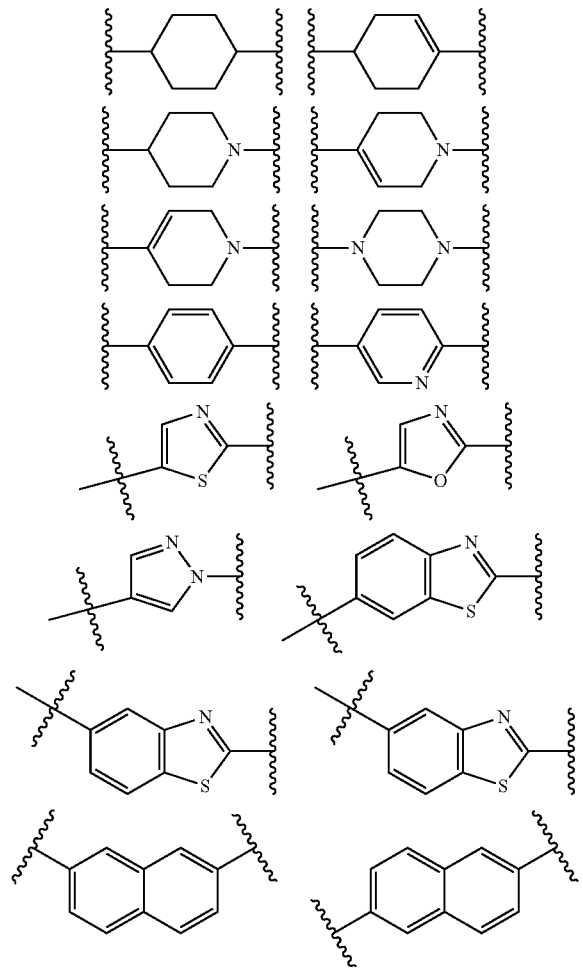

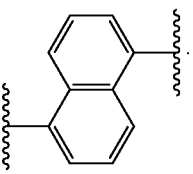

In another embodiment, the compound of Formula (I) is represented by one of Formulae (XV-1) to (XV-4), or a pharmaceutically acceptable salt thereof:

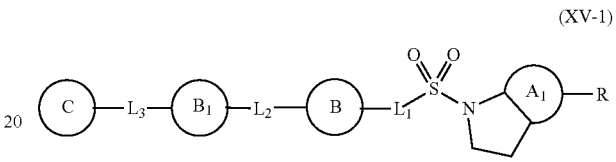
(XV-1)

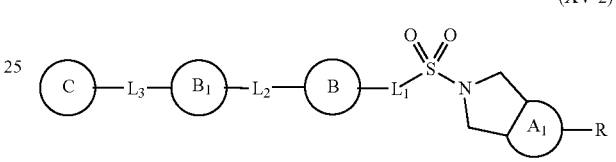
(XV-2)

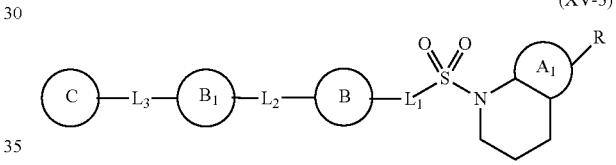
(XV-3)

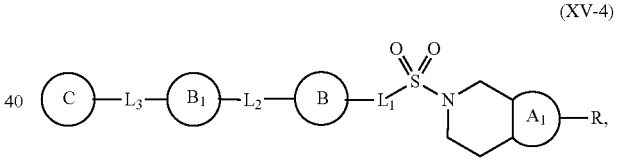
(XV-4)

wherein

is optionally substituted aryl, optionally substituted heteroaryl, optionally substituted —$C_3$-$C_{12}$ cycloalkyl, optionally substituted 3- to 12-membered heterocycloalkyl; or optionally substituted —$C_3$-$C_{12}$ cycloalkenyl; and

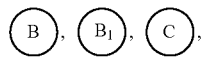

$L_1$, $L_2$, $L_3$, and R are as previously defined.

In another embodiment, the compound of Formula (I) is represented by one of Formulae (XVI-1) to (XVI-8), or a pharmaceutically acceptable salt thereof:

(XVI-1)
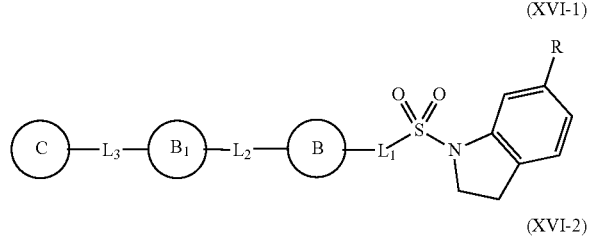
(XVI-2)
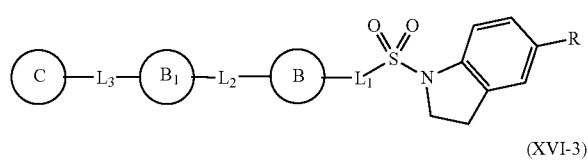
(XVI-3)
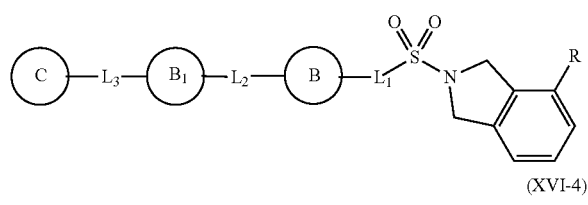
(XVI-4)
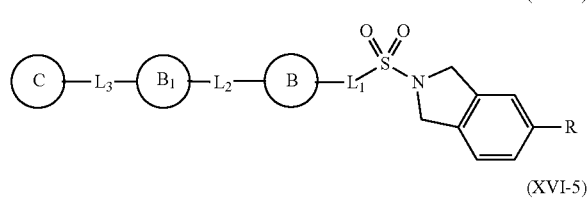
(XVI-5)
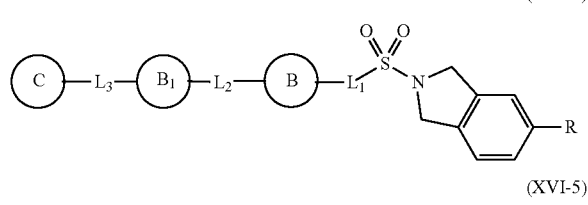
(XVI-6)
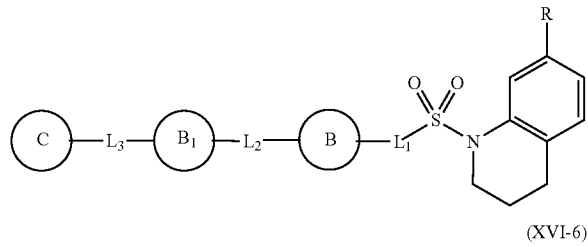
(XVI-7)
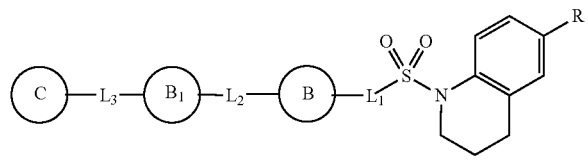
(XVI-8)
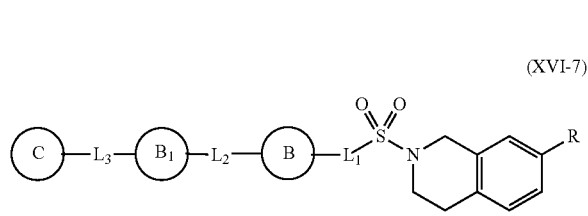
wherein
Ⓑ, Ⓑ₁, Ⓒ,
$L_1$, $L_2$, $L_3$, and R are as previously defined.
In another embodiment, the compound of Formula (I) is represented by one of Formulae (XVII-1) to (XVII-8), or a pharmaceutically acceptable salt thereof.
(XVII-1)
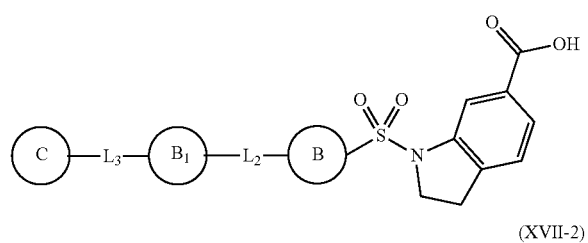
(XVII-2)
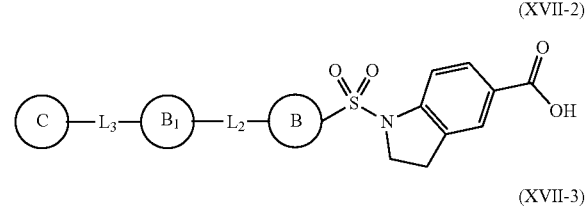
(XVII-3)

(XVII-4)
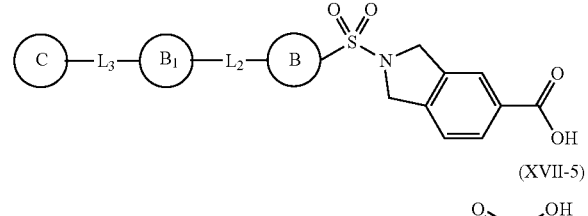
(XVII-5)
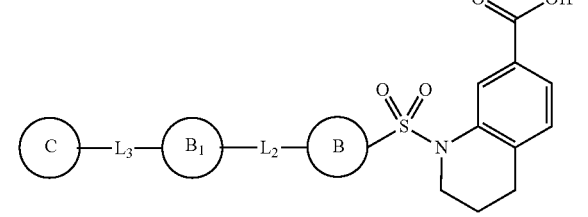
(XVII-6)
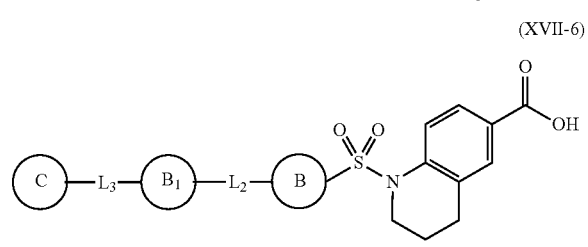

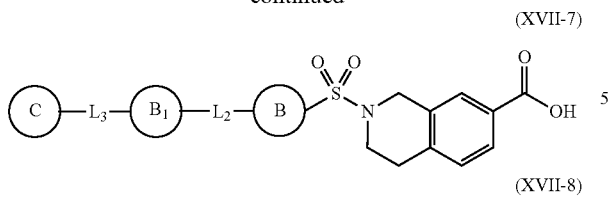 (XVII-7)

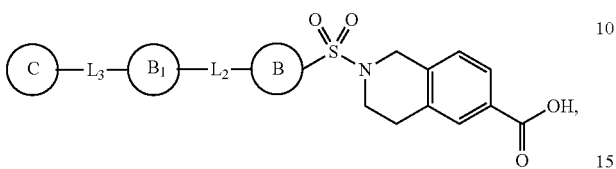 (XVII-8)

wherein

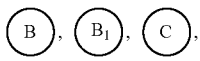

$L_2$, and $L_3$ are as previously defined.

In another embodiment, the compound of Formula (I) is represented by one of Formulae (XVIII-1) to (XVIII-2), or a pharmaceutically acceptable salt thereof:

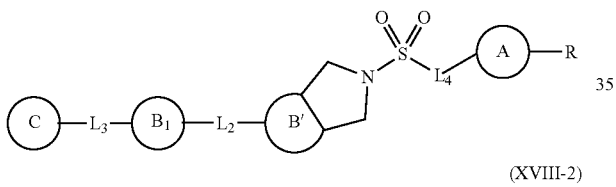 (XVIII-1)

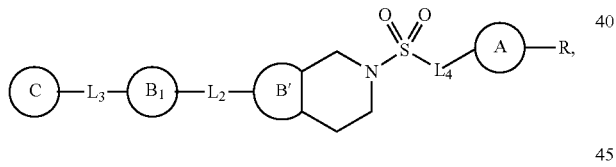 (XVIII-2)

wherein

is optionally substituted aryl, optionally substituted heteroaryl, optionally substituted —$C_3$-$C_{12}$ cycloalkyl, optionally substituted 3- to 12-membered heterocycloalkyl, or optionally substituted —$C_3$-$C_{12}$ cycloalkenyl; and

, , , $L_2$, $L_3$, $L_4$, and R are as previously defined.

In another embodiment, the compound of Formula (I) is represented by one of Formulae (XVIII-1) to (XVIII-2), or a pharmaceutically acceptable salt thereof, wherein

is selected from the groups set forth below, and

is optionally substituted:

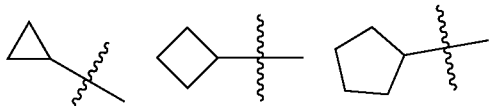

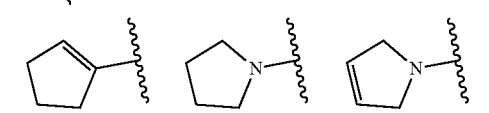

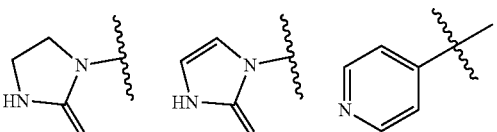

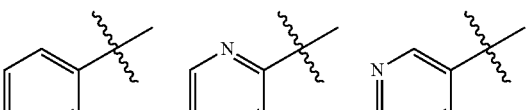

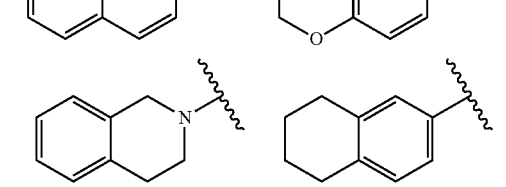

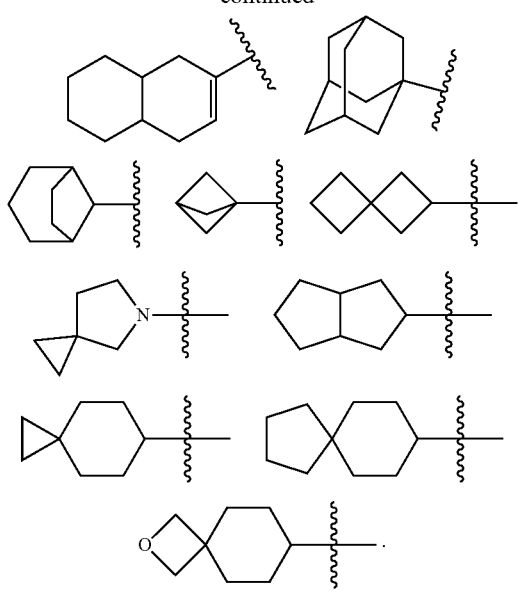
In another embodiment, the compound of Formula (I) is represented by one of Formulae (XIX-1) to (XIX-10), or a pharmaceutically acceptable salt thereof:
(XIX-1)
(XIX-2)
(XIX-3)
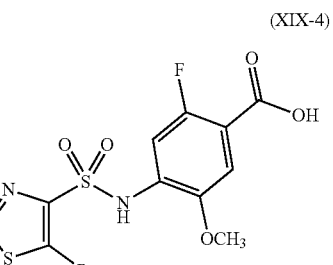
(XIX-4)
(XIX-5)
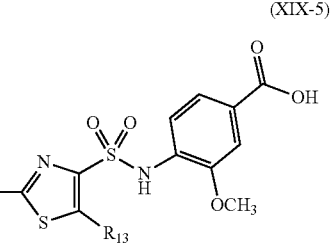
(XIX-6)
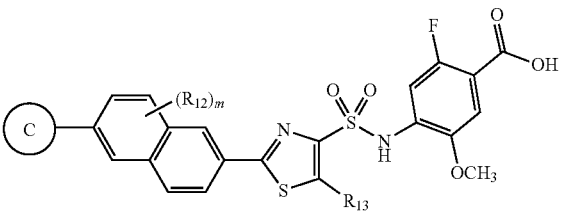
(XIX-7)
(XIX-8)
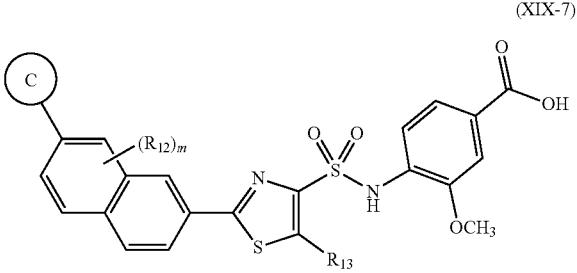
(XIX-9)
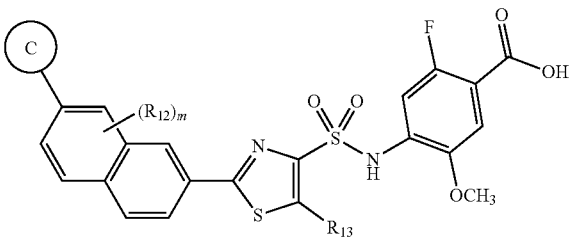
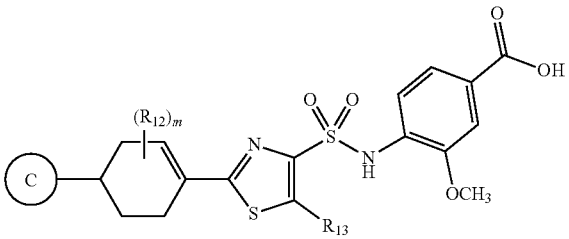

-continued (XIX-10)

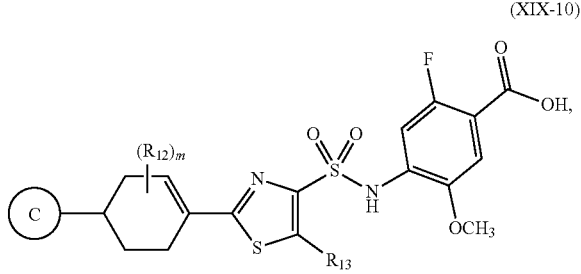

wherein $R_{12}$, $R_{13}$, m, and

are as previously defined, preferably $R_{13}$ is hydrogen.

It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In another embodiment, the present invention provides a pharmaceutical composition comprising a therapeutically effective amount of a compound or combination of compounds of the present invention, or a pharmaceutically acceptable salt form, stereoisomer, solvate, hydrate or combination thereof, in combination with a pharmaceutically acceptable carrier or excipient.

In another embodiment, described herein is a method of treating or preventing a liver disease or condition in a subject, comprising administering to the subject a therapeutically effective amount of one or more of the compounds described herein, or a pharmaceutically acceptable salt or solvate thereof. In some embodiments, the liver disease or condition is an alcoholic or non-alcoholic liver disease.

In another embodiment, described herein is a method of treatment or prevention of a metabolic or liver condition in a mammal comprising administering a therapeutically effective amount of a compound described herein, or a pharmaceutically acceptable salt, or solvate thereof, to the mammal in need thereof.

In another embodiment, the present invention provides a method of modulating a HSD17B13 protein for treatment of metabolic disease or liver condition. The method comprises administering a therapeutically effective amount of a compound of Formula (I).

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_3$ alkyl", "$C_1$-$C_6$ alkyl", "$C_1$-$C_{10}$ alkyl", "$C_2$-$C_4$ alkyl", or "$C_3$-$C_6$ alkyl" refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group. A heteroalkyl group is described herein by the number of carbon atoms in the group. For example, the term "$C_2$-$C_8$-heteroalkyl" refers to a heteroalkyl group having from 2 to 8 carbon atoms and at least one heteroatom selected from oxygen, sulfur and nitrogen at a terminus of such group or between two carbon atoms within the group. Preferably, the number of heteroatoms in such a group is 1 to 4, more preferably 1 or 2, and most preferably 1.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group. A heteroalkenyl group is described herein by the number of carbon atoms in the group. For example, the term "$C_3$-$C_8$-heteroalkenyl" refers to a heteroalkenyl group having from 3 to 8 carbon atoms and at least one heteroatom selected from oxygen, sulfur and nitrogen at a terminus of the group or between two carbon atoms within the group. Preferably, the number of heteroatoms in such a group is 1 to 4, more preferably 1 or 2, and most preferably 1.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)— heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_8$-alkenyl, —OCO$_2$—C$_2$-C$_8$-alkynyl, —OCO$_2$—C$_3$-C$_{12}$-cycloalkyl, —OCO$_2$-aryl, —OCO$_2$-heteroaryl, —OCO$_2$-heterocycloalkyl, —CO$_2$—C$_1$-C$_{12}$ alkyl, —CO$_2$—C$_2$-C$_8$ alkenyl, —CO$_2$—C$_2$-C$_8$ alkynyl, CO$_2$—C$_3$-C$_{12}$-cycloalkyl, —CO$_2$-aryl, CO$_2$-heteroaryl, CO$_2$-heterocyloalkyl, —OCONH$_2$, —OCONH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH-heterocyclo-alkyl, —NHC(O)H, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_8$-alkenyl, —NHCO$_2$—C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH— heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH— heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl, —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S— heterocycloalkyl, or methylthiomethyl. In certain embodiments, the substituents are independently selected from halo, preferably C$_1$ and F; C$_1$-C$_4$-alkyl, preferably methyl and ethyl; C$_2$-C$_4$-alkenyl; halo-C$_1$-C$_4$-alkyl, such as fluoromethyl, difluoromethyl, and trifluoromethyl; halo-C$_2$-C$_4$-alkenyl; C$_3$-C$_6$-cycloalkyl, such as cyclopropyl; —CN; —OH; NH$_2$; C$_1$-C$_4$-alkylamino; di(C$_1$-C$_4$-alkyl)amino; and NO$_2$. In certain embodiments, the substituents are additionally selected from C$_1$-C$_4$-alkoxy, such as methoxy and ethoxy; halo-C$_1$-C$_4$-alkoxy, such as fluoromethoxy, difluoromethoxy, and trifluoromethoxy; and acetyl. It is understood that the substituents, such as the aryls, heteroaryls, alkyls, and the like, are optionally further substituted.

In some cases, each substituent in a substituted moiety is additionally optionally substituted with one or more groups, each group being independently selected from C$_1$-C$_4$-alkyl; CF$_3$, C$_1$-C$_4$-alkoxy; —OCF$_3$, —F, —Cl, —Br, —I, —OH, —NO$_2$, —CN, and —NH$_2$.

It is understood that the aryls, heteroaryls, alkyls, cycloalkyls and the like can be further substituted.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-2*, (Biotechnology: Pharmaceutical Aspects), edited by V. J. Stella, et al, Springer and AAPS Press, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "amino acid" refers to naturally occurring and synthetic α, β, γ, or δ amino acids, and includes but is not limited to, amino acids found in proteins or intermediates in metabolism of amino acids or proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, citrulline, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue selected from the group consisting of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl and β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NR$^u$-G(S$_c$)—C(O)-Q$^1$, wherein Q$^1$ is —SR$^v$, —NR$^v$R$^v$ or alkoxyl, R$^v$ is hydrogen or alkyl, S$_c$ is a side-chain of a naturally occurring or non-naturally occurring amino acid, G is C$_1$-C$_2$ alkyl, and R$^u$ is hydrogen; or R$^u$ and S$_c$ are taken together with the atoms to which they are attached to form a five-membered heterocyclic ring. In an embodiment, an amino acid derivative is provided as a substituent of a compound described herein, wherein the substituent is —O—C(O)-G(S$_c$)—NH-Q$^2$, wherein Q$^2$ is hydrogen or alkoxyl, S$_c$ is a side-chain of a naturally occurring or non-naturally occurring amino acid and G is C$_1$-C$_2$ alkyl. In certain embodiments, Q$^2$ and S$_c$ are taken together with the atoms to which they are attached to form a five-membered heterocyclic ring. In certain embodiments, G is an optionally substituted methylene and S$_c$ is selected from the group consisting of hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl and hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, 2$^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus, a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The present invention also includes pharmaceutically acceptable esters of the compounds of the invention and, in particular, such esters of compounds of Formula (I) wherein R is —C(O)OH or —CH$_2$C(O)OH. As used herein, the term "pharmaceutically acceptable ester" refers to esters which hydrolyze in vivo and include those that break down readily in the human body to leave the parent compound or a salt thereof. Suitable ester groups for drugs including a carboxylic acid group include, for example, those derived from pharmaceutically acceptable alcohols, including aliphatic alcohols, particularly alkyl, alkenyl, and cycloalkyl alcohols, in which each alkyl or alkenyl moiety advantageously has not more than 6 carbon atoms. Examples of particular esters include, but are not limited to, C$_2$-C$_6$-alkyl esters.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
Alloc for allyloxycarbonyl;
Alloc-Cl for allyl chloroformate;
$B_2pin_2$ for Bis(pinacolato)diboron;
Boc for tert-butyloxycarbonyl;
BOP-Cl for bis(2-oxo-3-oxazolidinyl)phosphinic chloride;
Cbz for benzyloxycarbonyl;
Cbz-Cl for benzyl chloroformate;
CDI for carbonyldiimidazole;
$(COCl)_2$ for oxalyl chloride;
CyJohnPhos for (2-Biphenyl)dicyclohexylphosphine, Cyclohexyl JohnPhos, 2-(Dicyclohexylphosphino)biphenyl;
DBU for 1,8-diazabicycloundec-7-ene;
DCC for N,N-dicyclohexylcarbodiimide;
1,2-DCE for 1,2-dichloroethane;
DCM for dichloromethane;
DIC for diisopropylcarbodiimide;
DIPEA or Hunig's base or i-$Pr_2$NEt for N,N-diisopropylethylamine;
DMAc for N,N-dimethylacetamide;
DMAP for N,N-dimethylaminopyridine;
DMF for N,N-dimethyl formamide;
DPPP for 1,3-bis(diphenylphosphino)propane;
EDC for 1-(3-diethylaminopropyl)-3-ethylcarbodiimide hydrochloride;
EGTA for ethylene glycol-bis(2-aminoethylether)-N,N,N',N'-tetraacetic acid;
ESI for electrospray ionization;
$Et_3N$ or TEA for triethylamine;
$Et_2O$ for diethylether;
EtOAc for ethyl acetate;
Ghosez's Reagent for 1-chloro-N,N,2-trimethyl-1-propenylamine;
HATU for 1-[bis(dimethylamino)methylene]-1H-1,2,3-triazolo[4,5-b]pyridinium 3-oxid hexafluorophosphate;
HEPES for 4-(2-Hydroxyethyl)piperazine-1-ethanesulfonic acid, N-(2-Hydroxyethyl)piperazine-N'-(2-ethanesulfonic acid);
Huing's base for N,N-Diisopropylethylamine;
$IC_{50}$ for half maximal inhibitory concentration;
KOt-Bu for potassium tert-butoxide;
LCMS for liquid chromatography-mass spectrometry;
MeCN for acetonitrile;
MTBE for methyl tert-butyl ether;
m/z for mass-to-charge ratio;
NaOt-Bu for sodium tert-butoxide;
NMP for 1-methyl-2-pyrrolidinone;
NMR for nuclear magnetic resonance spectroscopy;
—OMs or mesylate for methanesulfonate;
—OTf or triflate for trifluoromethanesulfonate;
—OTs or tosylate for para-toluenesulfonate;
$Pd_2(dba)_3$ for tris(dibenzylideneacetone)dipalladium(0);
$Pd(PPh_3)_4$ for Tetrakis(triphenylphosphine)palladium(0);
PhMe for toluene;
$P(o-tolyl)_3$ for tri(o-tolyl)phosphine;
PyAOP for 7-azabenzotriazol-1-yloxy)tripyrrolidinophosphonium hexafluorophosphate;
PyBOP for benzotriazol-1-yl-oxytripyrrolidinophosphonium hexafluorophosphate;
TEA for triethylamine;
THF for tetrahydrofuran.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1

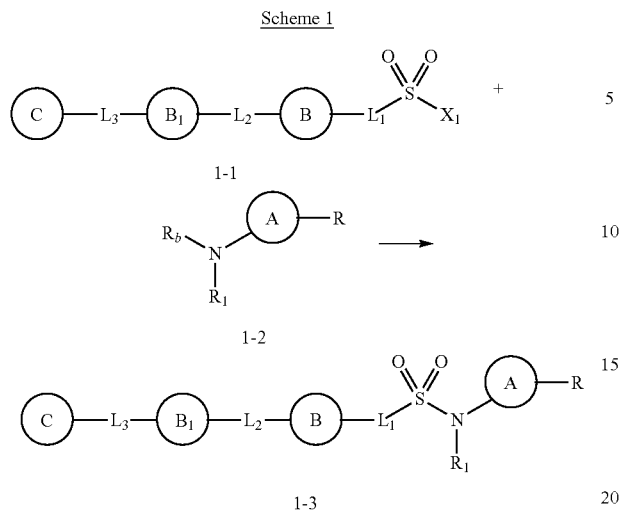

Scheme 1 shows an exemplary synthetic step for the synthesis of compounds provided (e.g., compounds of Formula I-3). Wherein $R_1$, (A), R, $L_1$, (B), $L_2$, ⊙ , $L_3$, (C) are as previously defined and $X_1$ is a leaving group such as Cl, F. The compounds of formula (I-3) can be obtained through the condensation between the compounds of formula 1-1 and compounds of formula 1-2 employing suitable base such as but not limited to pyridine, TEA, DIPEA with or without addition of catalyst such as DMAP in a suitable solvent (e.g., DCM, dioxane, THF, etc.).

Scheme 2

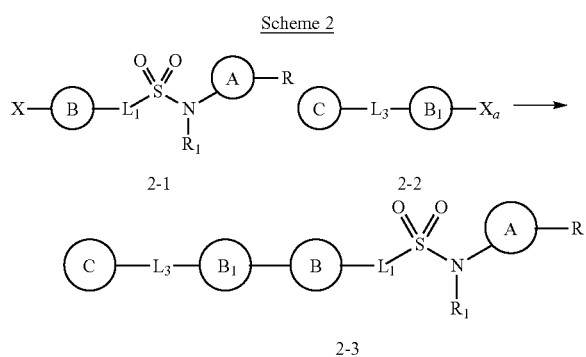

Scheme 2 shows an exemplary synthetic step for the synthesis of compounds provided (e.g., compounds of Formula 2-3). Wherein $R_1$, (A), R, $L_1$, (B), ⊙ , $L_3$, (C) are as previously defined. X is a halogen such as Cl, Br, I or a psudohalide such as —OTf, —OTs, —OMs, —$N_2^+$; $X_a$ is a suitable functional group suitable for metal catalyzed cross couplings such as boronic acid/ester, organic tin, organic zinc species. The compounds of formula 2-1 and compounds of formula 2-2 under standard metal-catalyzed coupling conditions (e.g., using a palladium catalyst) in a suitable solvent (e.g., dioxane, water, etc.), optionally under an inert atmosphere, to provide compounds of formula 2-3. (For metal-catalyzed coupling reactions see: N. Miyaura, S. L. Buchwald, etc. Cross-Coupling Reactions: A Practical Guide (Topics in Current Chemistry, 219), Springer (2002); A. de Meijere, S. Bräse, M. Oestreich, Metal Catalyzed Cross-Coupling Reactions and More, Wiley-VCH (2014); I. D. Kostas, Suzuki-Miyaura Cross-Coupling Reaction and Potential Applications, Mdpi AG (2017)).

Scheme 3

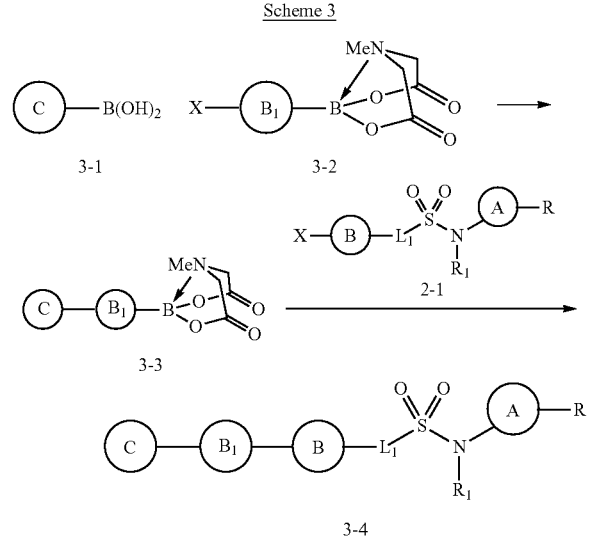

Scheme 3 shows an exemplary synthetic step for the synthesis of compounds provided (e.g., compounds of Formula I-5). Wherein $R_1$, (A), R, $L_1$, (B), ⊙ , (C) are as previously defined. X is a halogen such as Cl, Br, I or a psudohalide such as —OTf, —OTs, —OMs, —$N_2^+$. The boronic acid of formula 3-1 or its corresponding boronic ester and compounds of formula 3-2 under standard metal-catalyzed coupling conditions (e.g., using a palladium catalyst) with or without a suitable ligand (e.g., CyJohnphos) in a suitable solvent (e.g., THF, water, etc.), optionally under an inert atmosphere, to provide compounds of formula 3-3. The masked boronic acid could undergo cross coupling with compounds of formula 2-1 to provide compounds of formula 3-4, alternatively, boronic ester of formula 3-3 be converted into the corresponding boronic acid and then react with compounds of formula 2-1. For these type of iterative Suzuki-Miyaura Cross-Coupling with masked boronic acid see: J. W. B. Fyfe, A. J. B. Watson, *Synlett* 2015, 26, 1139-1144; H. Noguchi, K. Hojo, and M. Suginome *J. AM. CHEM. SOC.* 2007, 129, 758-759; D. M. Knapp, E. P. Gillis, and M. D. Burke, *J. AM. CHEM. SOC.* 2008, 130, 14084; E. P. Gillis, and M. D. Burke, *J. AM. CHEM. SOC.* 2009, 131, 6961-6963.

Scheme 4

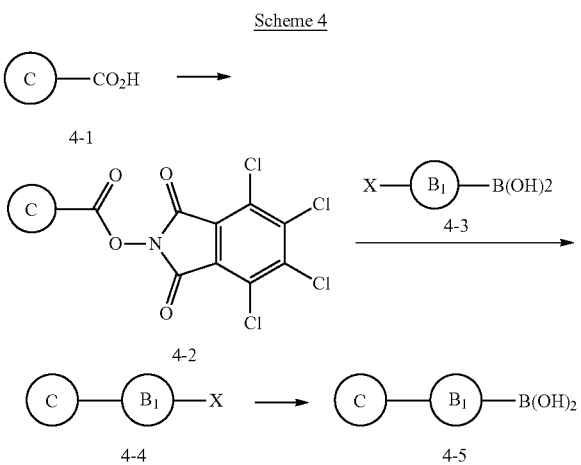

Scheme 4 shows an exemplary synthetic step for the synthesis of boronic acid intermediate provided (e.g., compounds of Formula 4-5). Wherein ⊖, Ⓒ are as previously defined. X is a halogen such as Cl, Br, I or a psudohalide such as —OTf, —OTs, —OMs, —N₂. The acids of formula (4-1) was converted into the active ester of formula (4-2) under esterification condition (and compounds of formula (I-8) under standard metal-catalyzed coupling conditions (e.g., DIC/DMAP in a suitable solvent such as DCM). This intermediate of formula (4-2) and boronic acid of formula (4-3) under Ni-catalyzed coupling conditions in presence of a suitable ligand (e.g., di-tBubipy) and suitable base (e.g., Et₃N) in a suitable solvent(s) (e.g., dioxane/DMF) at a suitable temperature, optionally under an inert atmosphere, to provide compounds of formula 4-4. (For Ni-catalyzed ross-Coupling of Redox-Active Esters with Boronic Acids, see: P. Baran, etc., *Angew. Chem. Int. Ed.* 2016, 55(33), 9676-9679). The compounds of formula (4-4) could be converted into boronic acid of formula 4-5 or the equivalents under metal-catalyzed conditions. (For the synthesis of boronic acid or ester from halides or psudohalids see: T. Ishiyama, M. Murata, and N. Miyaura, *J. Org. Chem.* 1995, 60, 23, 7508-7510; K. L. Billingsley and S. L. Buchwald, *J. Org. Chem.* 2008, 73, 14, 5589-5591; G. A. Molander, L. N. Cavalcanti, and C. Garcia-Garcia, *J. Org. Chem.* 2013, 78, 13, 6427-6439).

Scheme 5

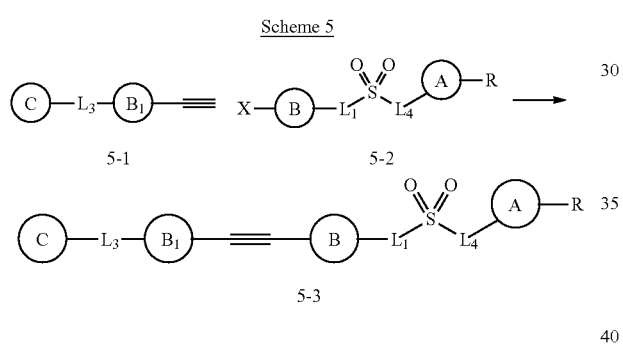

5-1   5-2

5-3

Scheme 5 shows an exemplary synthetic step for the synthesis of compounds provided (e.g., compounds of Formula 5-3). Wherein L₄, Ⓐ, R, L₁, Ⓑ, ⊖, L₃, Ⓒ are as previously defined. X is a halogen such as Cl, Br, I or a psudohalide such as —OTf, —OTs, —OMs, —N₂. The compounds of formula (5-1) and compounds of formula (5-2) under standard Sonogashira coupling conditions (e.g., using a copper catalyst) in a suitable solvent (e.g., dioxane, water, etc.), optionally under an inert atmosphere, to provide compounds of formula 5-3. (For general review on Sonogashira reaction, see: R. Chinchilla and C. Nájera, *Chem. Rev.* 2007, 107, 874-922; For gold catalyzed Sonogashira-Like Coupling Reactions, M. B. Nielsen, *Synthesis*, 2016, 48, 2732-2738).

In the reactions described, reactive functional groups such as hydroxyl, amino, imino, thio or carboxy groups, may be protected to avoid unwanted participation in the reactions. These protecting groups may be removed at suitable steps via solovolysis, reduction, photolysis. The protection and deprotection are common practices in organic synthesis (see P. G. M. Wuts, *Greene's Protective Groups in Organic Synthesis*, 5th. Ed., John Wiley and Sons (2014)).

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or methods of the invention may be made without departing from the spirit of the invention and the scope of the appended claims.

Example 1: Synthesis of 3-ethoxy-4-((2-(4-fluorophenyl)thiazole)-4-sulfonamido)benzoic acid

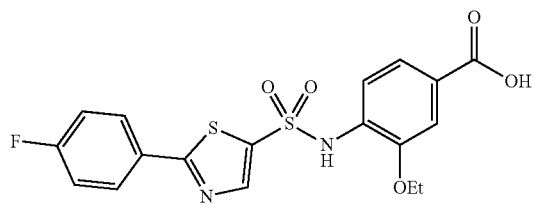

Step 1. Synthesis of ethyl 3-ethoxy-4-((2-(4-fluorophenyl)thiazole)-4-sulfonamido)benzoate Representative Procedure for Sulfonamide Formation.

2-(4-Fluorophenyl)thiazole-5-sulfonyl chloride (40 mg, 0.144 mmol) was added to a solution of ethyl 4-amino-3-ethoxybenzoate (30.1 mg, 0.144 mmol) and DMAP (1.8 mg, 0.014 mmol) in pyridine (0.144 mL) and the reaction was stirred at rt overnight. The reaction was acidified with 1M HCl and diluted with CH₂Cl₂. The layers were separated, and the aqueous layer was extracted with CH₂Cl₂ (2×). The combined organic layers were filtered through a phase separator, rinsing with CH₂Cl₂. The resultant filtrate was concentrated under reduced pressure to afford crude 3-ethoxy-4-((2-(4-fluorophenyl)thiazole)-5-sulfonamido) benzoate as a pink residue that was used directly in the next step: LC-MS (ES, m/z): 451[M+H]⁺.

Step 2. Synthesis of 3-ethoxy-4-((2-(4-fluorophenyl)thiazole)-5-sulfonamido)benzoic acid

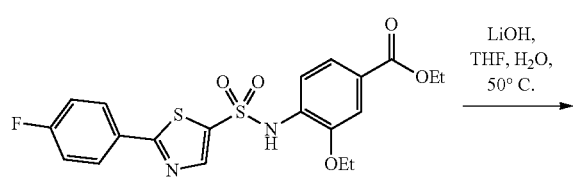

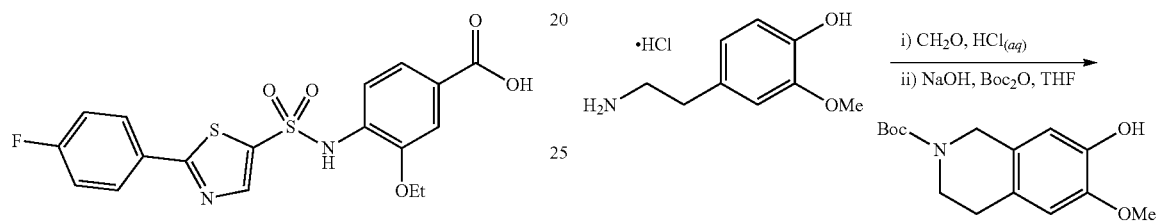

Representative Procedure for Ester Hydrolysis.

LiOH·H$_2$O (0.060 g, 1.440 mmol) was added to a mixture of crude 3-ethoxy-4-((2-(4-fluorophenyl)thiazole)-5-sulfonamido)benzoate (0.065 g, 0.144 mmol) in THF (0.43 mL)/H$_2$O (0.14 mL) and the reaction was heated at 50° C. overnight. The reaction was cooled to rt and acidified with 1M HCl and diluted with brine and EtOAc. The layers were separated, and the aqueous layer was extracted with EtOAc (2×). The combined organic layers were dried (Na$_2$SO$_4$), filtered, and concentrated under reduced pressure. The resultant pink solid was purified by column chromatography eluting with cyclohexane/acetone (0% acetone→50% acetone) to give 3-ethoxy-4-((2-(4-fluorophenyl)thiazole)-5-sulfonamido)benzoic acid (44 mg, 0.104 mmol, 72% yield) as a pale yellow solid: LC-MS (ES, m/z): 423 [M+H]$^+$; $^1$H NMR (400 MHz, DMSO-d$_6$) δ 12.98 (s, 1H), 10.33 (s, 1H), 8.18 (s, 1H), 8.05-8.00 (m, 2H), 7.54 (dd, J=8.2, 1.7 Hz, 1H), 7.44 (d, J=8.2 Hz, 1H), 7.41 (d, J=1.8 Hz, 1H), 7.38 (dd, J=9.9, 7.8 Hz, 2H), 3.91 (q, J=6.9 Hz, 2H), 1.15 (t, J=6.9 Hz, 3H).

Examples 3, 4, 17, 20-23, 26-30, 33, 37, 39, 43-50, 58, and 64-68 were prepared from the corresponding amino methyl or ethyl ester and the corresponding sulfonyl chloride according to the representative procedure for sulfonamide formation, followed by the representative procedure for ester hydrolysis.

Examples 18, 34, 35, 42, 52, and 53 were prepared from the corresponding methyl or ethyl ester and the corresponding sulfonyl chloride according to the representative procedure for sulfonamide formation. Examples 24, and 25 were prepared from the corresponding aniline and the corresponding sulfonyl chloride according to the representative procedure for sulfonamide formation. Examples 19, 51, and 54 were prepared from the corresponding methyl or ethyl ester according to the representative procedure for ester hydrolysis.

Example 5: Synthesis of 2-((4-fluorophenyl)sulfonyl)-6-methoxy-1,2,3,4-tetrahydroisoquinoline-7-carboxylic acid

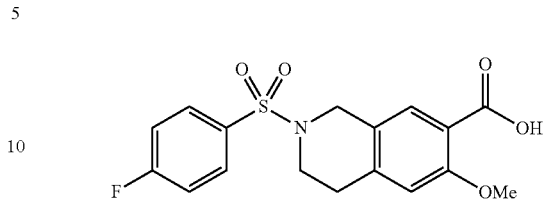

Step 1: Synthesis of tert-butyl 7-hydroxy-6-methoxy-3,4-dihydroisoquinoline-2(1H)-carboxylate Formaldehyde (2.6 mL, 34.4 mmol of a 36% aqueous solution) was added to a solution of 4-(2-aminoethyl)-2-methoxyphenol, hydrochloride (1.0 g, 4.9 mmol) in 1M HCl$_{(aq)}$ (4.9 mL) and the reaction was stirred at 50° C. for 6 h. The reaction was cooled to 0° C. and made basic with 50% aqueous NaOH (0.31 mL, 5.9 mmol). A solution of Boc$_2$O (5.7 mL, 24.55 mmol) in THF (4.9 mL) was added dropwise at 0° C. The cold bath was removed, and the reaction was stirred at rt for 17 h. The reaction was quenched with H$_2$O and diluted with MTBE (30 mL). The layers were separated, and the aqueous layer was extracted with MTBE (2×30 mL). The combined organic layers were washed with brine, dried (MgSO$_4$), filtered, and concentrated under reduced pressure. The resultant orange oil was purified by column chromatography eluting with hexanes/EtOAc (0% EtOAc→40% EtOAc) to afford tert-butyl 7-hydroxy-6-methoxy-3,4-dihydroisoquinoline-2(1H)-carboxylate (570 mg, 2.04 mmol, 41.6% yield) as a colorless gum: $^1$H NMR (400 MHz, Chloroform-d) δ 6.65 (s, 1H), 6.60 (s, 1H), 5.48 (s, 1H), 4.45 (s, 2H), 3.86 (s, 3H), 3.61 (t, J=5.9 Hz, 2H), 2.74 (t, J=5.9 Hz, 2H), 1.48 (s, 9H).

Step 2: Synthesis of tert-butyl 6-methoxy-7-(((trifluoromethyl)sulfonyl)oxy)-3,4-dihydroisoquinoline-2(1H)-carboxylate

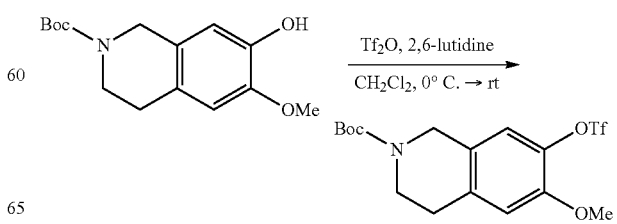

Trifluoromethanesulfonic anhydride (61.2 mL, 61.2 mmol, of a 1.0M solution in CH₂Cl₂) was added dropwise to a solution of tert-butyl 7-hydroxy-6-methoxy-3,4-dihydroisoquinoline-2(1H)-carboxylate (11.4 g, 40.8 mmol) and 2,6-lutidine (14.3 mL, 13.1 g, 122 mmol) in CH₂Cl₂ (204 mL) at 0° C. The cold bath was removed, and the reaction was stirred at rt overnight. The reaction was diluted with CH₂Cl₂ (100 mL) and washed with H₂O (150 mL×2) and brine (150 mL). The organic layer was dried (MgSO₄), filtered, and concentrated under reduced pressure. The resultant yellow gum was purified by column chromatography eluting with hexanes/EtOAc (0% EtOAc→40% EtOAc) to afford tert-butyl 6-methoxy-7-(((trifluoromethyl)sulfonyl)oxy)-3,4-dihydroisoquinoline-2(1H)-carboxylate (12.5 g, 30.4 mmol, 75% yield) as a colorless solid: ¹H NMR (400 MHz, Chloroform-d) δ 6.95 (s, 1H), 6.78 (s, 1H), 4.50 (s, 2H), 3.89 (s, 3H), 3.64 (t, J=5.8 Hz, 3H), 2.82 (t, J=5.9 Hz, 2H), 1.49 (s, 9H).

Step 3: Synthesis of 2-(tert-butyl) 7-methyl 6-methoxy-3,4-dihydroisoquinoline-2,7(1H)-dicarboxylate

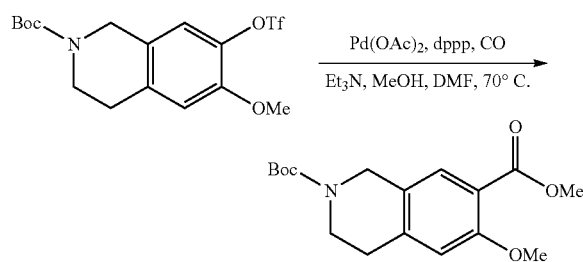

A mixture of 6-methoxy-7-(((trifluoromethyl)sulfonyl)oxy)-3,4-dihydroisoquinoline-2(1H)-carboxylate (6.0 g, 14.6 mmol), Pd(OAc)₂ (0.327 g, 1.46 mmol), 1,3-bis(diphenylphosphino)propane (0.602 g, 1.46 mmol), and Et₃N (6.10 mL, 43.8 mmol) in DMF (58.3 ml)/MeOH (38.9 ml) were stirred under a balloon of CO at 70° C. for 5 h. The reaction was quenched with H₂O/brine (200 m) and diluted with EtOAc (200 mL) and the layers were separated. The organic layer was washed with water/brine (2×100 mL). The organic layer was dried (MgSO₄), filtered, and concentrated under reduced pressure. The resultant brown oil was purified by column chromatography eluting with hexanes/EtOAc (0% EtOAc→40% EtOAc) to afford 2-(tert-butyl) 7-methyl 6-methoxy-3,4-dihydroisoquinoline-2,7(1H)-dicarboxylate (4.3 g, 13.38 mmol, 92% yield) as a colorless solid: ¹H NMR (400 MHz, Chloroform-d) δ 7.57 (s, 1H), 6.72 (s, 1H), 4.51 (s, 2H), 3.88 (s, 3H), 3.87 (s, 3H), 3.63 (t, J=6.1 Hz, 2H), 2.84 (t, J=6.1 Hz, 2H), 1.48 (s, 9H).

Step 4: Synthesis of methyl 6-methoxy-1,2,3,4-tetrahydroisoquinoline-7-carboxylate

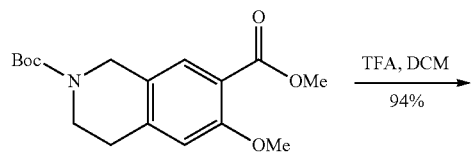

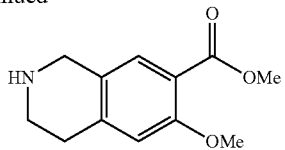

TFA (4.32 mL) was added to a solution of 2-(tert-butyl) 7-methyl 6-methoxy-3,4-dihydroisoquinoline-2,7(1H)-dicarboxylate (1.0 g, 3.11 mmol) in DCM (8.64 mL) at 0° C. The reaction was stirred at 0° C. for 30 min. The cold bath was removed, and the reaction stirred for 4 h. The reaction was concentrated to remove solvents methyl 6-methoxy-1,2,3,4-tetrahydroisoquinoline-7-carboxylate (646 mg, 2.92 mmol, 94% yield) was isolated as a pale-yellow solid.

Step 5: Synthesis of methyl 2-((4-fluorophenyl)sulfonyl)-6-methoxy-1,2,3,4-tetrahydroisoquinoline-7-carboxylate

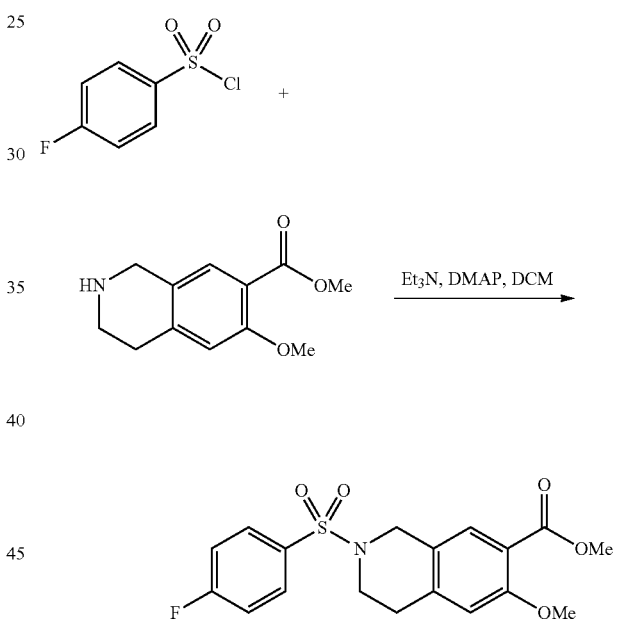

Representative Procedure for Sulfonamide Formation with Triethylamine.

4-Fluorobenzenesulfonyl chloride (30.6 mg, 0.157 mmol) was added to a solution of methyl 6-methoxy-1,2,3,4-tetrahydroisoquinoline-7-carboxylate (50 mg, 0.150 mmol), Et₃N (62.5 μl, 0.449 mmol), and DMAP (1.8 mg, 0.015 mmol) in DCM (1.5 mL) and the reaction was stirred for 1 h at rt. The reaction was acidified with 1M HCl and diluted with CH₂Cl₂. The layers were separated, and the aqueous layer was extracted with CH₂Cl₂ (2×). The combined organic layers were filtered through a phase separator and concentrated to give a yellow gum that was used directly in the next reaction.

Example 5 was prepared from methyl 2-((4-fluorophenyl)sulfonyl)-6-methoxy-1,2,3,4-tetrahydroisoquinoline-7-carboxylate according to the representative procedure for ester hydrolysis.

Example 6: Synthesis of 6-fluoro-2-((4-fluorophenyl)sulfonyl)-1,2,3,4-tetrahydroisoquinoline-7-carboxylic acid

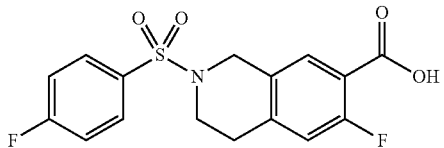 [SMILES: O=C(O)c1cc2c(cc1F)CCN(S(=O)(=O)c1ccc(F)cc1)C2]

Step 1. Synthesis of 7-bromo-6-fluoro-1,2,3,4-tetrahydroisoquinoline

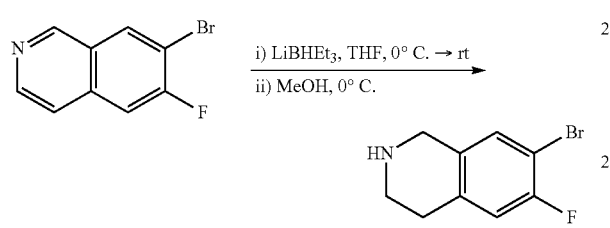

Lithium triethylborohydride (74.0 mL, 74.0 mmol of a 1.0M solution in THF) was added dropwise to a solution of 7-bromo-6-fluoroisoquinoline (7.6 g, 33.6 mmol) in THF (210 mL) at 0° C. The cold bath was removed, and the reaction was stirred at rt overnight.

The reaction was cooled to 0° C. and quenched dropwise with MeOH until gas evolution ceased. The mixture was diluted with 1M HCl and MTBE. The layers were separated, and the organic layer was extracted with 1M HCl (2×). The combined aqueous layers were washed with MTBE (3×). The aqueous layer was made basic (pH 14) with 50% NaOH, then extracted (5×100 mL) with DCM. The combined organic layers were dried ($Na_2SO_4$), filtered, and concentrated under reduced pressure to afford crude 7-bromo-6-fluoro-1,2,3,4-tetrahydroisoquinoline (6.4 g) as a yellow oil: $^1$H NMR (400 MHz, Chloroform-d) δ 7.18 (d, J=6.9 Hz, 1H), 6.85 (d, J=9.3 Hz, 1H), 3.94 (s, 2H), 3.10 (t, J=6.1 Hz, 2H), 2.73 (t, J=6.0 Hz, 2H).

Step 2. Synthesis of tert-butyl 7-bromo-6-fluoro-3,4-dihydroisoquinoline-2(1H)-carboxylate

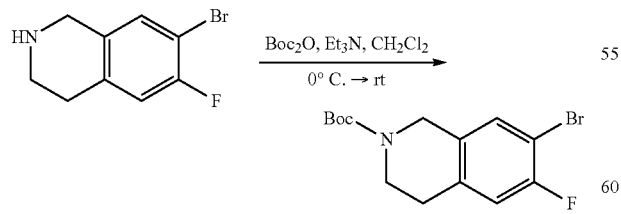

Boc-anhydride (7.75 ml, 33.4 mmol) was added to a solution of crude 7-bromo-6-fluoro-1,2,3,4-tetrahydroisoquinoline (6.4 g, 27.8 mmol) and $Et_3N$ (4.65 ml, 33.4 mmol) in $CH_2Cl_2$ (556 ml) at 0° C. The reaction was stirred for 10 minutes at 0° C. The cold bath removed, and the reaction stirred for 1 h at rt. The reaction was quenched with $H_2O$ and the layers were separated. The organic layer was washed with brine, dried ($MgSO_4$), filtered, and concentrated under reduced pressure. The resultant yellow oil was purified by column chromatography eluting with hexanes/EtOAc (0% EtOAc→15% EtOAc) to afford tert-butyl 7-bromo-6-fluoro-3,4-dihydroisoquinoline-2(1H)-carboxylate (6.4 g, 19.38 mmol, 58% yield over 2 steps) as a colorless solid: $^1$H NMR (400 MHz, Chloroform-d) δ 7.28 (d, J=6.8 Hz, 1H), 6.90 (d, J=9.0 Hz, 1H), 4.51 (s, 2H), 3.62 (t, J=5.8 Hz, 2H), 2.77 (t, J=6.0 Hz, 2H), 1.48 (s, 9H).

Step 3. Synthesis of 2-(tert-butyl) 7-ethyl 6-fluoro-3,4-dihydroisoquinoline-2,7(1H)-dicarboxylate

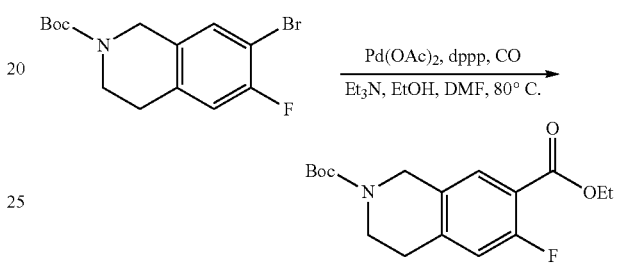

A mixture of tert-butyl 7-bromo-6-fluoro-3,4-dihydroisoquinoline-2(1H)-carboxylate (6.4 g, 19.4 mmol), Pd(OAc)$_2$ (0.435 g, 1.94 mmol), 1,3-bis(diphenylphosphino)propane (1.6 g, 3.88 mmol), and $Et_3N$ (8.10 mL, 5.88 g, 58.1 mmol) in DMF (52.7 mL)/EtOH (26.4 mL) were stirred under a balloon of CO at 80° C. for 24 h. The reaction was cooled to rt, quenched with $H_2O$/brine, and diluted with EtOAc. The layers were separated, and the organic layer was washed with $H_2O$/brine (2×). The organic layer was dried ($MgSO_4$), filtered, and concentrated under reduced pressure. The resultant brown gum was purified by column chromatography eluting with hexanes/EtOAc (0% EtOAc→20% EtOAc) to afford 2-(tert-butyl) 7-ethyl 6-fluoro-3,4-dihydroisoquinoline-2,7(1H)-dicarboxylate (4.5 g, 13.92 mmol, 72% yield) as a colorless solid: $^1$H NMR (400 MHz, Chloroform-d) δ 7.68 (d, J=7.1 Hz, 1H), 6.91 (d, J=11.1 Hz, 1H), 4.56 (s, 2H), 4.38 (q, J=7.1 Hz, 2H), 3.64 (t, J=5.9 Hz, 2H), 2.85 (t, J=5.9 Hz, 2H), 1.49 (s, 9H), 1.39 (t, J=7.1 Hz, 3H).

Example 6 was prepared from 2-(tert-butyl) 7-ethyl 6-fluoro-3,4-dihydroisoquinoline-2,7(1H)-dicarboxylate according to the representative procedure for sulfonamide formation with triethylamine, followed by the representative procedure for ester hydrolysis.

Example 8: Synthesis of 6-((4-fluorophenyl)sulfonyl)-2-methoxy-5,6,7,8-tetrahydro-1,6-naphthyridine-3-carboxylic acid

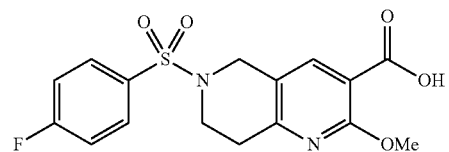 [SMILES: COc1nc2c(cc1C(=O)O)CN(S(=O)(=O)c1ccc(F)cc1)CC2]

Step 1. Synthesis of tert-butyl 3-bromo-2-oxo-1,5,7,8-tetrahydro-1,6-naphthyridine-6(2H)-carboxylate

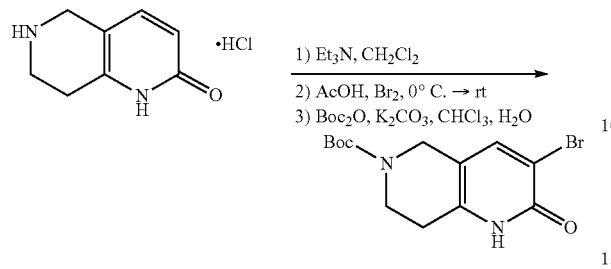

Triethylamine (1.23 mL, 895 mg, 8.84 mmol) was added to a solution of 5,6,7,8-tetrahydro-1,6-naphthyridin-2(1H)-one, Hydrochloride (1.1 g, 5.89 mmol) in CH$_2$Cl$_2$ (5.9 mL)/MeOH (5.9 mL). The reaction was concentrated under reduced pressure. The resultant white solid was taken up in AcOH (11.8 mL) and the mixture was cooled to 0° C. Bromine (0.364 mL, 1.13 g, 7.07 mmol) was added dropwise and the cold bath was removed. The reaction was stirred at rt for 3 h. The reaction concentrated under reduced pressure and azeotroped with CHCl$_3$ (1×) to give a yellow solid. The crude yellow solid was dissolved in CHCl$_3$ (21.0 mL)/H$_2$O (10.7 mL), then Boc$_2$O (2.46 mL, 2.32 g, 10.61 mmol) and K$_2$CO$_3$ (2.44 g, 17.68 mmol) were added. The reaction was stirred overnight. The reaction was quenched with H$_2$O and diluted with CH$_2$Cl$_2$. The layers were separated, and the aqueous layer extracted with CH$_2$Cl$_2$ (2×). The combined organic layers were dried (MgSO$_4$), filtered, and concentrated under reduced pressure. The resultant yellow solid was evaporated from MTBE (1×), suspended in MTBE and filtered, rinsing with MTBE to afford tert-butyl 3-bromo-2-oxo-1,5,7,8-tetrahydro-1,6-naphthyridine-6(2H)-carboxylate (1.15 g, 3.49 mmol, 59.3% yield) as a tan solid: LC-MS (ES, m/z): 331 [M+H]$^+$; $^1$H NMR (500 MHz, Chloroform-d) δ 7.60 (s, 1H), 4.33 (s, 2H), 3.67 (t, J=5.8 Hz, 2H), 2.77 (td, J=5.1, 4.3, 2.8 Hz, 2H), 1.48 (s, 9H).

Step 2. Synthesis of tert-butyl 3-bromo-2-methoxy-7,8-dihydro-1,6-naphthyridine-6(5H)-carboxylate

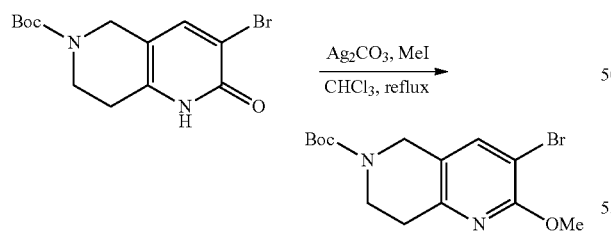

Silver carbonate (4.09 g, 14.82 mmol) and methyl iodide (7.42 mL, 16.8 g, 119 mmol) were added to tert-butyl 3-bromo-2-oxo-1,5,7,8-tetrahydro-1,6-naphthyridine-6(2H)-carboxylate (4.88 g, 14.82 mmol) in CHCl$_3$ (296 mL) and the reaction was heated at reflux in the dark for 2 h. The reaction was cooled to rt then gravity filtered and concentrated under reduced pressure. The resultant yellow oil was purified by column chromatography eluting with cyclohexane/EtOAc (0% EtOAc→20% EtOAc) to give tert-butyl 3-bromo-2-methoxy-7,8-dihydro-1,6-naphthyridine-6(5H)- carboxylate (2.91 g, 8.48 mmol, 57.2% yield) as a colorless solid: $^1$H NMR (400 MHz, Chloroform-d) δ 7.52 (s, 1H), 4.47 (s, 2H), 3.70 (t, J=5.9 Hz, 2H), 2.82 (t, J=6.0 Hz, 2H), 1.48 (s, 9H).

Step 3. Synthesis of 6-(tert-butyl) 3-ethyl 2-methoxy-7,8-dihydro-1,6-naphthyridine-3,6(5H)-dicarboxylate

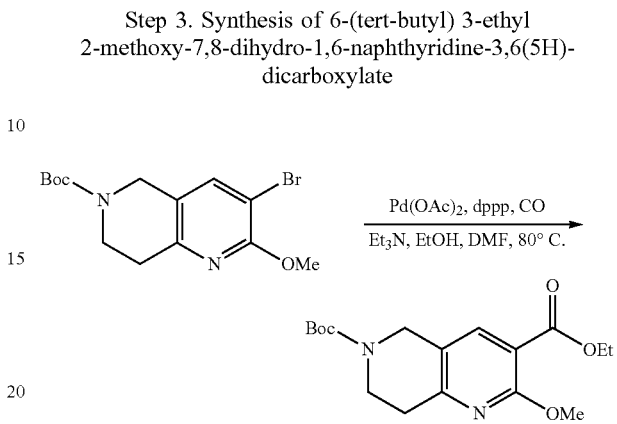

A mixture of tert-butyl 3-bromo-2-methoxy-7,8-dihydro-1,6-naphthyridine-6(5H)-carboxylate (2.91 g, 8.48 mmol), Pd(OAc)$_2$ (0.190 g, 0.848 mmol), 1,3-bis(diphenylphosphino)propane (0.699 g, 1.696 mmol), and Et$_3$N (3.55 mL, 2.57 g, 25.4 mmol) in DMF (23.07 mL)/EtOH (11.54 mL) were stirred under a balloon of CO at 80° C. for 15 h. The reaction was quenched with H$_2$O/brine and diluted with EtOAc. The layers were separated, and the aqueous layer was extracted with EtOAc (1×). The combined organic layers were washed with H$_2$O/brine (2×), dried (MgSO$_4$), filtered, and concentrated under reduced pressure. The resultant brown oil was purified by column chromatography eluting with cyclohexane/EtOAc (0% EtOAc→20% EtOAc) to afford 6-(tert-butyl) 3-ethyl 2-methoxy-7,8-dihydro-1,6-naphthyridine-3,6(5H)-dicarboxylate (2.6 g, 7.73 mmol, 91% yield) as a clear gum: $^1$H NMR (400 MHz, Chloroform-d) δ 7.88 (s, 1H), 4.51 (s, 2H), 4.35 (q, J=7.1 Hz, 2H), 3.72 (t, J=5.9 Hz, 2H), 2.88 (t, J=6.0 Hz, 2H), 1.49 (s, 9H), 1.37 (t, J=7.1 Hz, 3H).

Step 4. Synthesis of 6-(tert-butoxycarbonyl)-2-methoxy-5,6,7,8-tetrahydro-1,6-naphthyridine-3-carboxylic acid

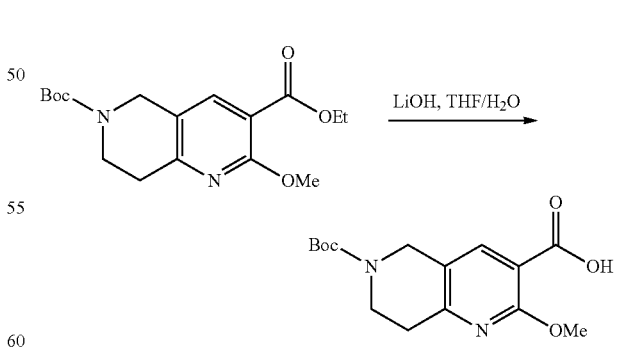

LiOH hydrate (1.62 g, 38.6 mmol) was added to a solution of 6-(tert-butyl) 3-ethyl 2-methoxy-7,8-dihydro-1,6-naphthyridine-3,6(5H)-dicarboxylate (2.6 g, 7.73 mmol) in THF (23.2 mL)/H$_2$O (7.7 mL) and the reaction was stirred at 50° C. overnight. The reaction was cooled to rt then diluted with water and MTBE. The layers were separated, and the aqueous layer was acidified with 10% citric acid and diluted with CH₂Cl₂. The layers were separated, and the aqueous layer was extracted with CH₂Cl₂ (2×). The combined organic layers were dried (MgSO₄), filtered, and concentrated under reduced pressure to afford 1.96 g (2.38 g, 6.36 mmol, 82%) of 6-(tert-butoxycarbonyl)-2-methoxy-5,6,7,8-tetrahydro-1,6-naphthyridine-3-carboxylic acid as a colorless solid: ¹H NMR (400 MHz, Chloroform-d) δ 10.55 (s, 1H), 8.18 (s, 1H), 4.56 (s, 2H), 4.16 (s, 3H), 3.81-3.69 (m, 2H), 2.93 (t, J=5.9 Hz, 2H), 1.49 (s, 9H).

Step 5. Synthesis of 6-(tert-butyl) 3-methyl 2-methoxy-7,8-dihydro-1,6-naphthyridine-3,6(5H)-dicarboxylate

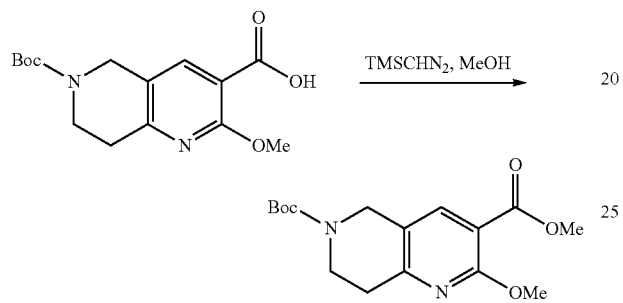

Trimethylsilyldiazomethane (1.78 mL, 3.57 mmol of a 2.0M solution in CH₂Cl₂) was added to a solution of 6-(tert-butoxycarbonyl)-2-methoxy-5,6,7,8-tetrahydro-1,6-naphthyridine-3-carboxylic acid (1.0 g, 3.24 mmol) in MeOH (8.53 mL) and the reaction stirred for 2 h at rt. More trimethylsilyldiazomethane (2.43 mL, 4.86 mmol of a 2.0M solution in CH₂Cl₂) was added dropwise and the reaction stirred overnight at rt. More trimethylsilyldiazomethane (2.432 mL, 4.86 mmol of a 2.0M solution in CH₂Cl₂) was added dropwise and the reaction stirred for 1 h at rt. The reaction was concentrated under reduced pressure to give a yellow gum that was used directly in the next step: LC-MS (ES, m/z): 323 [M+H]⁺.

Step 6. Synthesis of methyl 2-methoxy-5,6,7,8-tetrahydro-1,6-naphthyridine-3-carboxylate hydrochloride

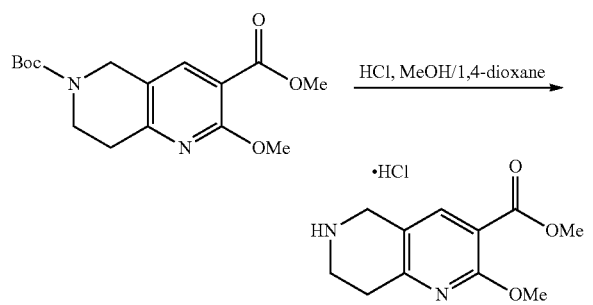

4M HCl in dioxane (8.10 mL) was added to a solution of crude 6-(tert-butyl) 3-methyl 2-methoxy-7,8-dihydro-1,6-naphthyridine-3,6(5H)-dicarboxylate (1.04 g, 3.24 mmol) in MeOH (8.10 mL) and the reaction was stirred at 45° C. for 10 minutes. The reaction was concentrated under reduced pressure to afford methyl 2-methoxy-5,6,7,8-tetrahydro-1,6-naphthyridine-3-carboxylate hydrochloride (757 mg, 2.93 mmol, 90% yield) as an off-white solid: LC-MS (ES, m/z): 323 [M+H]⁺; ¹H NMR (500 MHz, DMSO-d₆) δ 9.54 (s, 2H), 8.07 (s, 1H), 4.25 (s, 2H), 3.91 (s, 3H), 3.81 (s, 3H), 3.46 (t, J=5.8 Hz, 2H), 3.04 (t, J=6.3 Hz, 2H).

Example 8 was prepared from methyl 6-((4-fluorophenyl)sulfonyl)-2-methoxy-5,6,7,8-tetrahydro-1,6-naphthyridine-3-carboxylate according to the representative procedure for sulfonamide formation with triethylamine, followed by the representative procedure for ester hydrolysis.

Example 9: Synthesis of 7-fluoro-4-((4-fluorophenyl)sulfonyl)-3,4-dihydro-2H-benzo[b][1,4]oxazine-6-carboxylic acid

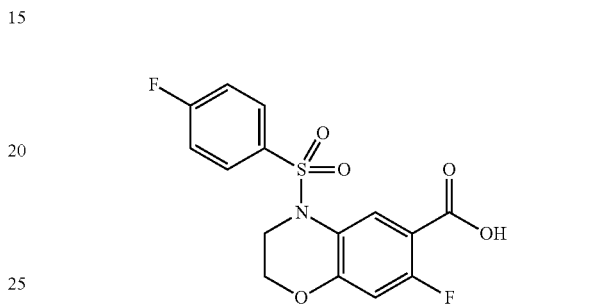

Step 1. Synthesis of benzyl 6-bromo-7-fluoro-2,3-dihydro-4H-benzo[b][1,4]oxazine-4-carboxylate

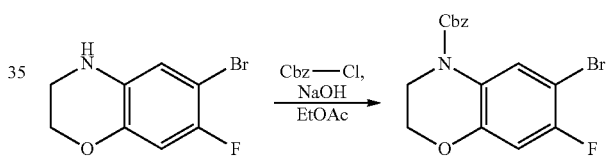

Cbz-Cl (0.638 mL, 762 mg, 4.47 mmol) was added dropwise to a solution of 6-bromo-7-fluoro-3,4-dihydro-2H-benzo[b][1,4]oxazine, Hydrochloride (1.0 g, 3.72 mmol) in EtOAc (10.95 mL) and 10% NaOH (10.95 mL) and the reaction was stirred overnight. The layers were separated, and the organic layer was washed with H₂O (2×) and sat. NaHCO₃ (1×). The organic layer was dried (MgSO₄), filtered, and concentrated under reduced pressure. The resultant yellow oil was purified by column chromatography eluting with hexanes/EtOAc (0% EtOAc→22% EtOAc) to afford 6-bromo-7-fluoro-2,3-dihydro-4H-benzo[b][1,4]oxazine-4-carboxylate (1.24 g, 3.39 mmol, 91% yield) as a pale yellow oil: ¹H NMR (400 MHz, Chloroform-d) δ 7.44-7.32 (comp, 6H), 6.68 (d, J=9.1 Hz, 1H), 5.26 (s, 2H), 4.27-4.22 (m, 2H), 3.95-3.88 (m, 2H).

Step 2. Synthesis of 4-((benzyloxy)carbonyl)-7-fluoro-3,4-dihydro-2H-benzo[b][1,4]oxazine-6-carboxylic acid

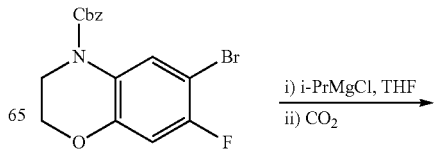

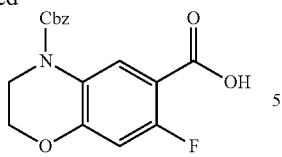
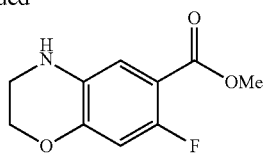

Isopropylmagnesium chloride (1.24 mL, 2.47 mmol of a 2.0M solution in THF) was added dropwise (maintaining internal temperature below 5° C.) to a solution of 6-bromo-7-fluoro-2,3-dihydro-4H-benzo[b][1,4]oxazine-4-carboxylate (647 mg, 1.77 mmol) in THF (7.68 mL) at −10° C. The reaction was stirred for 1 h at −10° C. $CO_{2\ (g)}$ was passed through a drying tube (drierite) and bubbled slowly into the mixture (exothermic) for 15 min. The cold bath was removed, and the reaction was stirred for 1 h at rt. The reaction was quenched with sat. $NH_4Cl$ and diluted with EtOAc. The layers were separated, and aqueous layer was extracted with EtOAc (2×). The combined organic layers were dried ($MgSO_4$), filtered, and concentrated under reduced pressure. The resultant colorless solid was triturated with DCM and filtered to give 4-((benzyloxy)carbonyl)-7-fluoro-3,4-dihydro-2H-benzo[b][1,4]oxazine-6-carboxylic acid (381 mg, 1.15 mmol, 65% yield) as a colorless powder: $^1$H NMR (400 MHz, DMSO-$d_6$) δ 12.96 (s, 1H), 8.46 (s, 1H), 7.48-7.42 (m, 2H), 7.42-7.32 (m, 3H), 6.86 (d, J=11.7 Hz, 1H), 5.23 (s, 2H), 4.34 (dd, J=5.2, 3.8 Hz, 2H), 3.93-3.88 (m, 2H).

Step 3. Synthesis of 4-benzyl 6-methyl 7-fluoro-2,3-dihydro-4H-benzo[b][1,4]oxazine-4,6-dicarboxylate

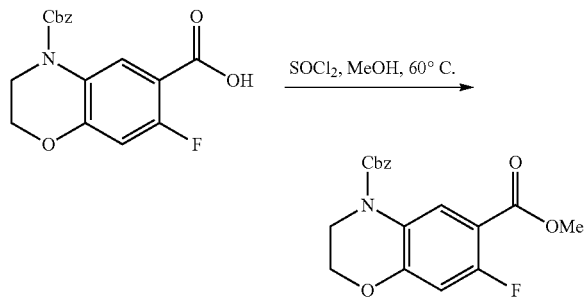

$SOCl_2$ (60.4 μl, 0.827 mmol) was added dropwise to a suspension of 4-((benzyloxy)carbonyl)-7-fluoro-3,4-dihydro-2H-benzo[b][1,4]oxazine-6-carboxylic acid (137 mg, 0.414 mmol) in MeOH (0.414 ml) and the reaction was stirred at 60° C. overnight. The reaction was concentrated under reduced pressure to give a white solid that was used directly in the next step: LC-MS (ES, m/z): 346 [M+H]$^+$.

Step 4. Synthesis of methyl 7-fluoro-3,4-dihydro-2H-benzo[b][1,4]oxazine-6-carboxylate

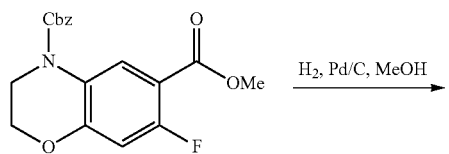

Pd—C (28 mg, 0.263 mmol) was added to a solution of crude 4-benzyl 6-methyl 7-fluoro-2,3-dihydro-4H-benzo[b][1,4]oxazine-4,6-dicarboxylate (143 mg, 0.414 mmol) in MeOH (8.28 mL) and the reaction was evacuated and backfilled with $H_2$ (3×). The reaction was stirred under a balloon of $H_2$ for 2 h. The reaction was filtered and concentrated under reduced pressure to afford methyl 7-fluoro-3,4-dihydro-2H-benzo[b][1,4]oxazine-6-carboxylate (79.3 mg, 0.375 mmol, 91% yield) as a dark yellow solid: LC-MS (ES, m/z): 212 [M+H]$^+$; $^1$H NMR (500 MHz, DMSO-$d_6$) δ 7.15 (d, J=7.3 Hz, 1H), 6.66 (d, J=11.9 Hz, 1H), 4.25-4.20 (m, 2H), 3.77 (s, 3H), 3.31-3.25 (m, 2H).

Step 5. Synthesis of methyl 7-fluoro-4-((4-fluorophenyl)sulfonyl)-3,4-dihydro-2H-benzo[b][1,4]oxazine-6-carboxylate

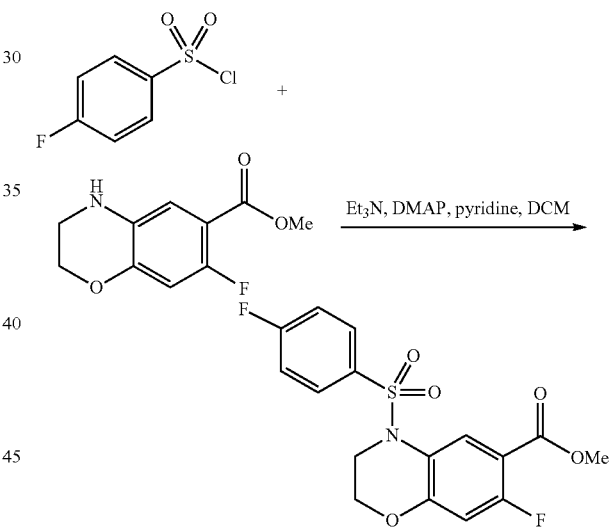

4-Fluorobenzenesulfonyl chloride (48.4 mg, 0.249 mmol) was added to a solution of methyl 7-fluoro-3,4-dihydro-2H-benzo[b][1,4]oxazine-6-carboxylate (50 mg, 0.237 mmol), $Et_3N$ (99 μL, 71.9 mg, 0.710 mmol), and DMAP (2.89 mg, 0.024 mmol) in DCM (2.37 mL) and the reaction was stirred for 3 h at rt. Pyridine (57.4 μL, 56.2 mg, 0.710 mmol) was added, followed by DMAP (2.89 mg, 0.024 mmol) and the reaction was stirred for 2 h at rt. The reaction was quenched with 1M HCl and diluted with $CH_2Cl_2$. The layers were separated, and the aqueous layer was extracted with $CH_2Cl_2$ (2×). The combined organic layers were filtered through a phase separator and concentrated to give a brown oil that was used directly in the next reaction: LC-MS (ES, m/z): 370 [M+H]$^+$.

Example 9 was prepared from methyl 7-fluoro-4-((4-fluorophenyl)sulfonyl)-3,4-dihydro-2H-benzo[b][1,4]oxazine-6-carboxylate according to the representative procedure ester hydrolysis.

Example 10 was prepared from methyl indoline-6-carboxylate and 4-fluorobenzenesulfonyl chloride according to the representative procedure for sulfonamide formation with triethylamine, followed by the representative procedure for ester hydrolysis.

Example 11 was prepared from methyl isoindoline-5-carboxylate, hydrochloride and 4-fluorobenzenesulfonyl chloride according to the representative procedure for sulfonamide formation with triethylamine, followed by the representative procedure for ester hydrolysis.

Example 12 was prepared from methyl indoline-5-carboxylate and 4-fluorobenzenesulfonyl chloride according to the representative procedure for sulfonamide formation with triethylamine, followed by the representative procedure for ester hydrolysis.

Example 13 was prepared from methyl 1-(phenylsulfonyl)indoline-5-carboxylate according to the representative for ester hydrolysis.

Example 14: Synthesis of 7-fluoro-1-((4-fluorophenyl)sulfonyl)-1,2,3,4-tetrahydroquinoline-6-carboxylic acid

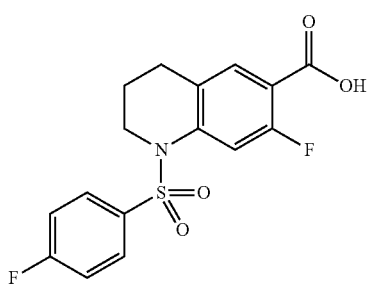 [SMILES: O=C(O)c1cc2c(cc1F)N(S(=O)(=O)c1ccc(F)cc1)CCC2]

Step 1. Synthesis of benzyl 6-bromo-7-fluoro-3,4-dihydroquinoline-1(2H)-carboxylate

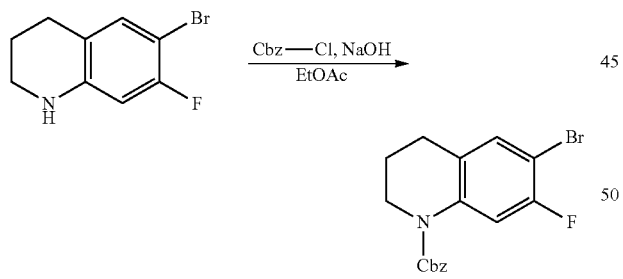

Cbz-Cl (0.372 mL, 445 mg, 2.61 mmol) was added dropwise to a solution of 6-bromo-7-fluoro-1,2,3,4-tetrahydroquinoline (0.5 g, 2.17 mmol) in EtOAc (6.4 mL) and 10% NaOH (6.4 mL) and the reaction was stirred overnight. The layers were separated, and the organic layer was washed with $H_2O$ (2×) and sat. $NaHCO_3$ (1×). The organic layer was dried ($MgSO_4$), filtered, and concentrated under reduced pressure. The resultant clear oil was purified by column chromatography eluting with hexanes/EtOAc (0% EtOAc→22% EtOAc) to afford benzyl 6-bromo-7-fluoro-3,4-dihydroquinoline-1(2H)-carboxylate (741 mg, 2.04 mmol, 94% yield) as a pale yellow oil: $^1$H NMR (400 MHz, Chloroform-d) δ 7.73 (d, J=11.5 Hz, 1H), 7.43-7.32 (comp, 5H), 7.23 (d, J=7.6 Hz, 1H), 5.24 (s, 2H), 3.81-3.75 (m, 2H), 2.71 (t, J=6.5 Hz, 2H), 1.91 (p, J=6.4 Hz, 2H).

Step 2. Synthesis of 1-((benzyloxy)carbonyl)-7-fluoro-1,2,3,4-tetrahydroquinoline-6-carboxylic acid

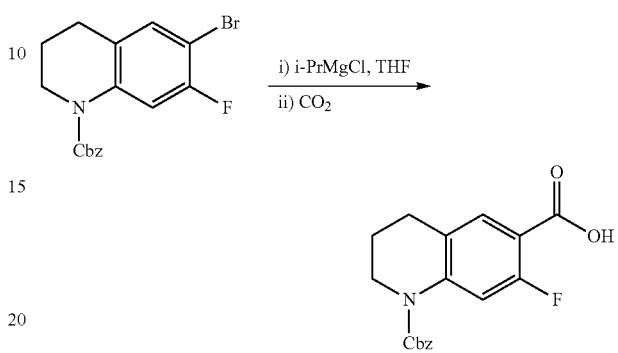

Isopropylmagnesium chloride (0.64 mL, 1.27 mmol of a 2.0M solution in THF) was added dropwise (maintaining internal temperature below 5° C.) to a solution of benzyl 6-bromo-7-fluoro-3,4-dihydroquinoline-1(2H)-carboxylate (331 mg, 0.909 mmol) in THF (3.95 mL) at −10° C. The reaction was stirred for 1 h at −10° C. $CO_2$ $_{(g)}$ was passed through a drying tube (drierite) and bubbled slowly into the mixture (exothermic) for 15 min. The cold bath was removed, and reaction was stirred for 1 h at rt. The reaction was quenched with sat. $NH_4Cl$ and diluted with EtOAc. The layers were separated, and the aqueous layer was extracted with EtOAc (2×). The combined organic layers were dried ($MgSO_4$), filtered, and concentrated under reduced pressure. The resultant colorless solid was purified by column chromatography eluting with $CH_2Cl_2$/MeOH (0% MeOH→8% MeOH) to afford 1-((benzyloxy)carbonyl)-7-fluoro-1,2,3,4-tetrahydroquinoline-6-carboxylic acid (157 mg, 0.477 mmol, 52.5% yield) as a colorless solid: $^1$H NMR (400 MHz, DMSO-$d_6$) δ 12.97 (s, 1H), 7.76 (d, J=14.3 Hz, 1H), 7.63 (d, J=8.5 Hz, 1H), 7.47-7.31 (comp, 5H), 5.23 (s, 2H), 3.81-3.72 (m, 2H), 2.74 (t, J=6.3 Hz, 2H), 1.86 (p, J=6.2 Hz, 2H).

Step 3. Synthesis of 1-benzyl 6-methyl 7-fluoro-3,4-dihydroquinoline-1,6(2H)-dicarboxylate

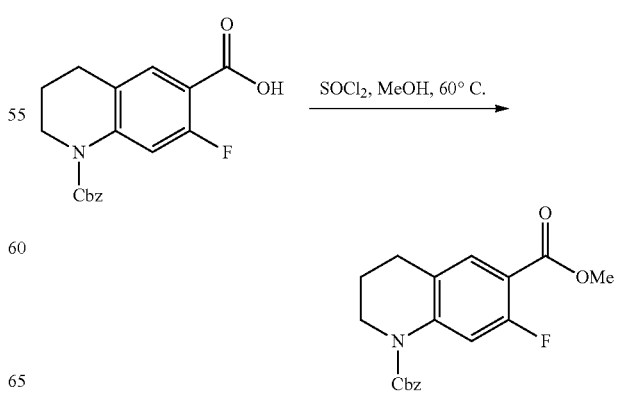

SOCl₂ (16.84 μL, 0.231 mmol) was added dropwise to a solution of 1-((benzyloxy)carbonyl)-7-fluoro-1,2,3,4-tetrahydroquinoline-6-carboxylic acid (38 mg, 0.115 mmol) in MeOH (0.115 mL) and the reaction was stirred at 60° C. overnight. The reaction was concentrated under reduced pressure to give a brown solid that was used directly in the next step: LC-MS (ES, m/z): 344 [M+H]⁺.

Step 4. Synthesis of methyl 7-fluoro-1,2,3,4-tetrahydroquinoline-6-carboxylate hydrochloride

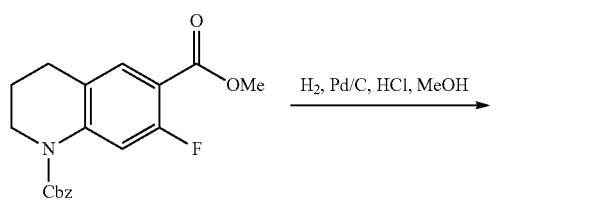

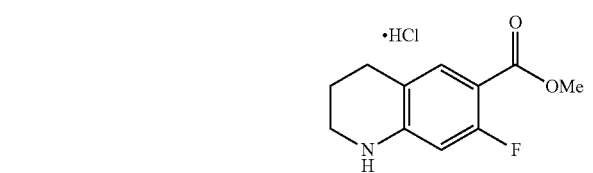

Pd—C (8 mg, 0.075 mmol) was added to a solution of 1-benzyl 6-methyl 7-fluoro-3,4-dihydroquinoline-1,6(2H)-dicarboxylate (39.5 mg, 0.115 mmol) in MeOH (2.3 mL) and the reaction was evacuated and backfilled with H₂ (3×). The reaction stirred under a balloon of H₂ for 5 h at rt. The reaction was then heated at 45° C. for 1 h. Concentrated hydrochloric acid (47.9 μl, 0.575 mmol) was added and the reaction was heated at 45° C. overnight. Pd—C (20 mg) was added, and the reaction was evacuated and backfilled with H₂ (3×). The reaction stirred under a balloon of H₂ at 45° C. for 1 h. The reaction was filtered and concentrated under reduced pressure to afford methyl 7-fluoro-1,2,3,4-tetrahydroquinoline-6-carboxylate hydrochloride (20.6 mg, 0.084 mmol, 72.9% yield) as a brown solid: LC-MS (ES, m/z): 210 [M+H]⁺.

Step 5. Synthesis of methyl 7-fluoro-1-((4-fluorophenyl)sulfonyl)-1,2,3,4-tetrahydroquinoline-6-carboxylate

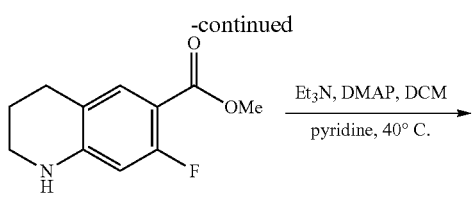

-continued

4-Fluorobenzenesulfonyl chloride (17.13 mg, 0.088 mmol) was added to a solution of methyl 7-fluoro-1,2,3,4-tetrahydroquinoline-6-carboxylate hydrochloride (20.6 mg, 0.084 mmol), Et₃N (46.7 μl, 0.335 mmol), and DMAP (1.024 mg, 8.38 μmol) in DCM (0.838 ml) and the reaction was stirred for 3 h at rt. pyridine (27.1 μl, 0.335 mmol) and DMAP (1.024 mg, 8.38 μmol) was added and the reaction was stirred for 2 h at rt. 4-Fluorobenzenesulfonyl chloride (17.13 mg, 0.088 mmol) was added and the reaction was stirred at 40° C. for 24 h. Added 85 mg (5 eq.) 4-fluorobenzenesulfonyl chloride (85 mg, 0.42 mmol) was added and the reaction was stirred at 40° C. overnight. The reaction was quenched with 1M HCl and diluted with CH₂Cl₂. The layers were separated, and aqueous layer was extracted with CH₂Cl₂ (2×). The combined organic layers were washed with sat. NaHCO₃ (2×) to try and remove excess sulfonyl chloride. The organics were filtered through a phase separator and concentrated under reduced pressure to give a dark brown oil that was used directly in the next reaction: LC-MS (ES, m/z): 368 [M+H]⁺.

Example 14 was prepared from methyl 7-fluoro-1-((4-fluorophenyl)sulfonyl)-1,2,3,4-tetrahydroquinoline-6-carboxylate according to the representative for ester hydrolysis.

Example 31: Synthesis of N-((4-(tert-butyl)phenyl)sulfonyl)-4-((2-(4-fluorophenyl)thiazole)-5-sulfonamido)benzamide Step 1. Synthesis of N-((4-(tert-butyl)phenyl)sulfonyl)-4-((2-(4-fluorophenyl)thiazole)-5-sulfonamido)benzamide

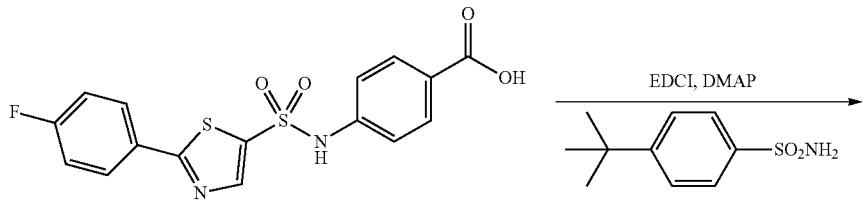

Representative Procedure for Acylsulfonamide Formation.

A mixture of 4-((2-(4-fluorophenyl)thiazole)-5-sulfonamido)benzoic acid (20 mg, 0.053 mmol), 4-(tert-butyl)benzenesulfonamide (22.55 mg, 0.106 mmol), DMAP (19.37 mg, 0.159 mmol), and EDCI (20.26 mg, 0.106 mmol) in DCM (1.762 ml) was stirred overnight. The reaction was quenched with brine and diluted with $CH_2Cl_2$. The layers were separated, and the aqueous layer was extracted with $CH_2Cl_2$ (2×). The combined organic layers were filtered through a phase separator and concentrated under reduced pressure. The resultant pale yellow gum was purified by reverse phase HPLC eluting with $H_2O$/ACN (containing 0.1% FA) 5% ACN to 95% ACN over 25 minutes to give N-((4-(tert-butyl)phenyl)sulfonyl)-4-((2-(4-fluorophenyl)thiazole)-4-sulfonamido)benzamide (17.4 mg, 0.030 mmol, 57.4% yield) as a white solid.

Example 32 was prepared from 4-((2-(4-fluorophenyl)thiazole)-5-sulfonamido)benzoic acid and N,N-dimethylsulfamide according to the representative procedure for acylsulfonamide formation.

Example 36: Synthesis of 2-(4-fluorophenyl)-N-(4-(hydroxymethyl)phenyl)thiazole-5-sulfonamide

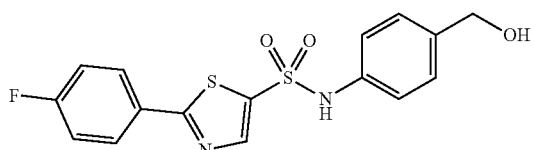

Step 1. Synthesis of 2-(4-fluorophenyl)-N-(4-(hydroxymethyl)phenyl)thiazole-5-sulfonamide

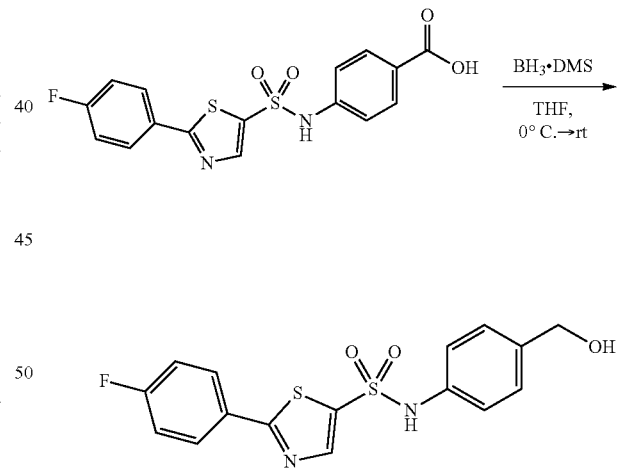

$BH_3 \cdot DMS$ (35.1 µl, 0.370 mmol) was added dropwise to a solution of 4-((2-(4-fluorophenyl)thiazole)-5-sulfonamido)benzoic acid (70 mg, 0.185 mmol) in THF (0.53 mL) at 0° C. The reaction was stirred overnight, warming gradually to room temperature. The reaction was cooled to 0° C. and quenched carefully with MeOH. The reaction was concentrated under reduced pressure. The resultant colorless gum was purified by column chromatography eluting with cyclohexane/Acetone (0% Acetone→50% Acetone) to give 2-(4-fluorophenyl)-N-(4-(hydroxymethyl)phenyl)thiazole-5-sulfonamide (10.4 mg, 0.029 mmol, 15.43% yield) as a white solid.

Example 38: Synthesis of 4-((2-(4-fluorophenyl)thiazole)-5-sulfonamido)benzyl ((4-(tert-butyl)phenyl)sulfonyl)carbamate

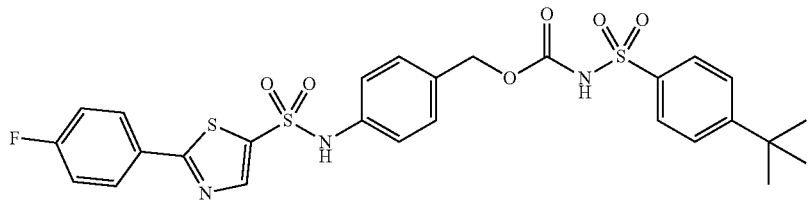

Step 1. Synthesis of 4-((2-(4-fluorophenyl)thiazole)-5-sulfonamido)benzyl ((4-(tert-butyl)phenyl)sulfonyl)carbamate

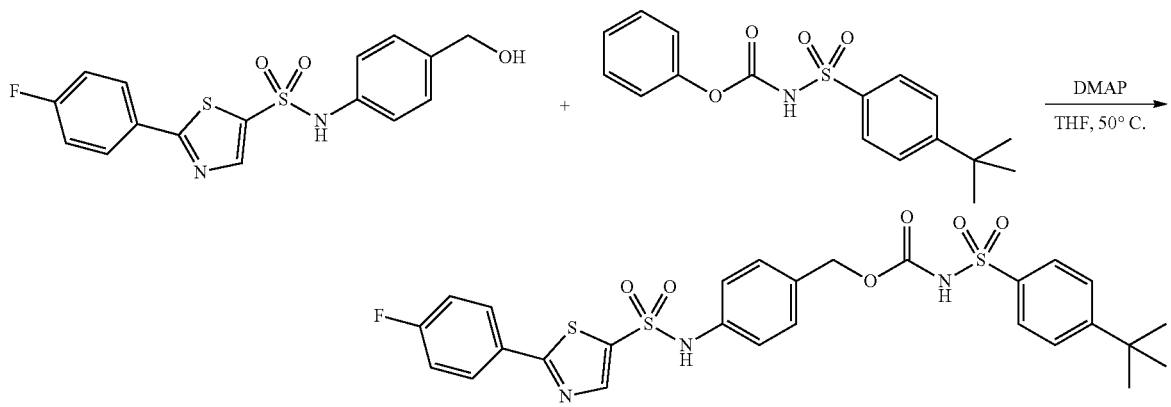

2-(4-Fluorophenyl)-N-(4-(hydroxymethyl)phenyl)thiazole-5-sulfonamide (9.2 mg, 0.025 mmol) and phenyl ((4-(tert-butyl)phenyl)sulfonyl)carbamate (10.10 mg, 0.030 mmol) (prepared according to US 2018/0148469) in THF (0.316 mL) were heated at 50° C. overnight. Phenyl ((4-(tert-butyl)phenyl)sulfonyl)carbamate (42 mg, 0.125 mmol) and DMAP (3.08 mg, 0.025 mmol) was added and the reaction was heated at 60° C. for 30 min. The reaction was purified directly by column chromatography eluting with cyclohexane/acetone (0% acetone→45% acetone) to give 4-((2-(4-fluorophenyl)thiazole)-5-sulfonamido)benzyl ((4-(tert-butyl)phenyl)sulfonyl)carbamate (12.3 mg, 0.020 mmol, 81% yield) as a colorless solid.

Example 40: Synthesis of 4-((2-(4-fluorophenyl)thiazole)-5-sulfonamido)-3-hydroxybenzoic acid

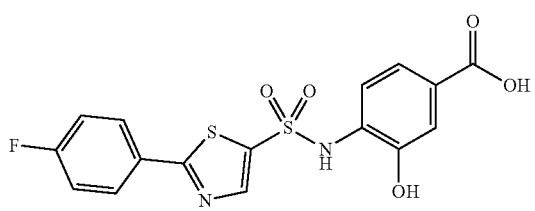

Step 1. Synthesis of 4-((2-(4-fluorophenyl)thiazole)-5-sulfonamido)-3-hydroxybenzoic acid

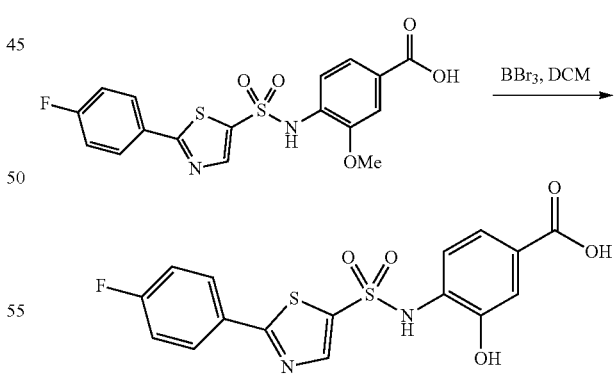

Representative Procedure for Methyl Cleavage.

BBr$_3$ (220 µL, 0.220 mmol) was added dropwise to a suspension of 4-((2-(4-fluorophenyl)thiazole)-5-sulfonamido)-3-methoxybenzoic acid (30 mg, 0.073 mmol) in CH$_2$Cl$_2$ (0.490 mL) and the reaction stirred for 2.5 h at rt. The reaction was quenched carefully with MeOH and concentrated under reduced pressure. The resultant dark brown gum was purified by column chromatography eluting with cyclohexane/acetone (0% acetone→70% acetone) to afford 4-((2-(4-fluorophenyl)thiazole)-5-sulfonamido)-3-hydroxybenzoic acid (11.2 mg, 0.028 mmol, 38.7% yield) as a white solid.

Examples 61 and 62 were prepared from the corresponding methoxy analog according to the representative procedure for methyl cleavage.

Example 41: Synthesis of 7-fluoro-1-((2-(4-fluorophenyl)thiazol-4-yl)sulfonyl)-1,2,3,4-tetrahydroquinoline-6-carboxylic acid

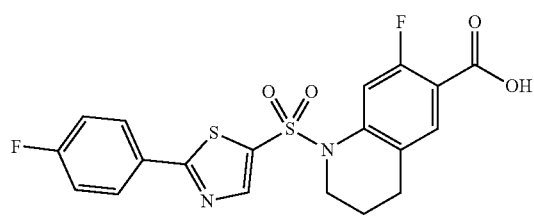 [SMILES: O=C(O)c1cc2c(cc1F)N(S(=O)(=O)c1cnc(-c3ccc(F)cc3)s1)CCC2]

Step 1. Synthesis of methyl 7-fluoro-1-((2-(4-fluorophenyl)thiazol-5-yl)sulfonyl)-1,2,3,4-tetrahydroquinoline-6-carboxylate

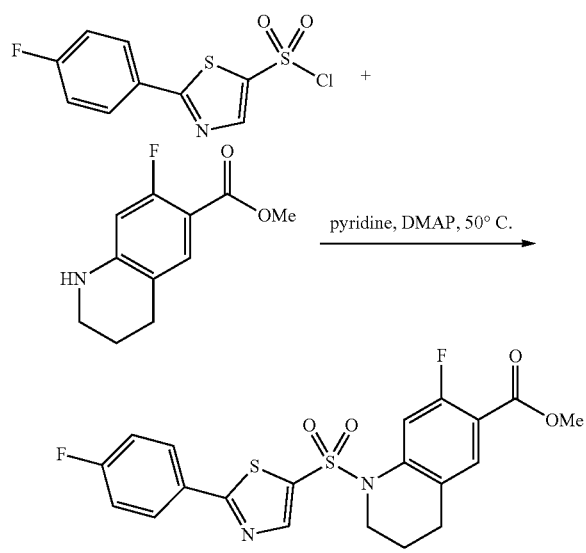

A solution of 2-(4-Fluorophenyl)thiazole-5-sulfonyl chloride (30 mg, 0.108 mmol) in pyridine (0.108 mL) was added slowly dropwise to a solution of methyl 7-fluoro-1,2,3,4-tetrahydroquinoline-6-carboxylate (45.2 mg, 0.216 mmol) and DMAP (1.32 mg, 10.80 μmol) in pyridine (0.108 mL) at 50° C. and the reaction was stirred at rt overnight. The reaction was acidified with 1M HCl and diluted with CH$_2$Cl$_2$. The layers were separated, and the aqueous layer was extracted with CH$_2$Cl$_2$ (2×). The combined organic layers were filtered through a phase separator, rinsing with CH$_2$Cl$_2$. The resultant filtrate was concentrated under reduced pressure to afford crude 3-ethoxy-4-((2-(4-fluorophenyl)thiazole)-5-sulfonamido)benzoate as a pink residue that was used directly in the next step: LC-MS (ES, m/z): 451 [M+H]$^+$.

Example 41 was prepared from methyl 7-fluoro-1-((2-(4-fluorophenyl)thiazol-5-yl)sulfonyl)-1,2,3,4-tetrahydroquinoline-6-carboxylate according to the representative procedure for ester hydrolysis.

Example 55: Synthesis of 4-((2-(4-fluorophenyl)-5-methylthiazole)-4-sulfonamido)benzoic acid

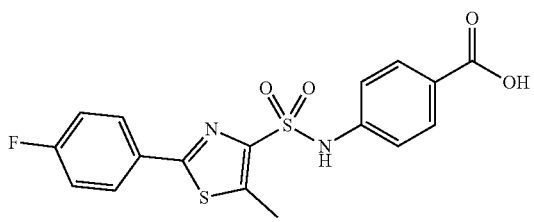 [SMILES: Cc1sc(-c2ccc(F)cc2)nc1S(=O)(=O)Nc1ccc(C(=O)O)cc1]

Step 1. Synthesis of methyl 4-((2-bromo-5-methylthiazole)-4-sulfonamido)benzoate

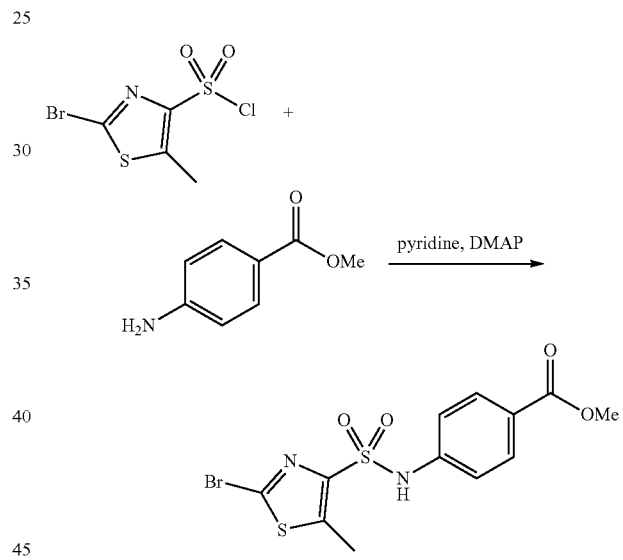

Methyl 4-((2-bromo-5-methylthiazole)-4-sulfonamido)benzoate was prepared according to the representative procedure for sulfonamide formation to afford a yellow solid (258 mg, 0.659 mmol, 91% yield): LC-MS (ES, m/z): 393 [M+H]$^+$; $^1$H NMR (500 MHz, DMSO-d$_6$) δ 11.20 (s, 1H), 7.90-7.86 (m, 2H), 7.26-7.21 (m, 2H), 3.80 (s, 3H), 2.65 (s, 3H).

Step 2. Synthesis of methyl 4-((2-(4-fluorophenyl)-5-methylthiazole)-4-sulfonamido)benzoate

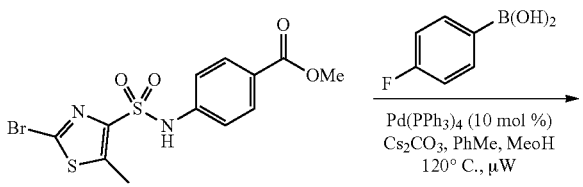

-continued

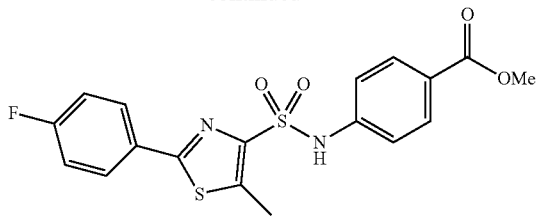

Representative Procedure for Suzuki Coupling.

Pd(Ph$_3$P)$_4$ (7.38 mg, 6.39 μmol) was added to a mixture of methyl 4-((2-bromo-5-methylthiazole)-4-sulfonamido)benzoate (25 mg, 0.064 mmol), (4-fluorophenyl)boronic acid (9.83 mg, 0.070 mmol), and Cs$_2$CO$_3$ (24.98 mg, 0.077 mmol) in PhMe (0.374 mL)/MeOH (0.100 mL). The reaction was heated at 120° C. for 30 minutes in the microwave. The reaction was filtered through Celite®, rinsing with DCM. The filtrate was concentrated under reduced pressure. The resultant yellow residue was purified by column chromatography eluting with cyclohexane/EtOAc (0% EtOAc→30% EtOAc) to afford methyl 4-((2-(4-fluorophenyl)-5-methylthiazole)-4-sulfonamido)benzoate as a colorless solid: LC-MS (ES, m/z): 407 [M+H]$^+$; $^1$H NMR (400 MHz, Chloroform-d) δ 7.97-7.91 (m, 2H), 7.82-7.75 (m, 2H), 7.25 (d, J=9.1 Hz, 2H), 7.17 (s, 1H), 7.15-7.08 (m, 2H), 3.87 (s, 3H), 2.68 (s, 3H).

Step 3. Synthesis of 4-((2-(4-fluorophenyl)-5-methylthiazole)-4-sulfonamido)benzoic acid

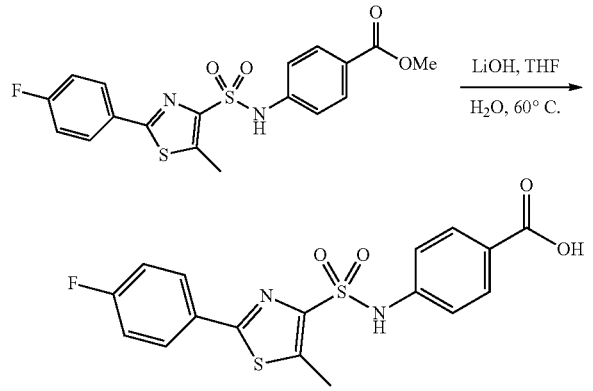

Methyl 4-((2-(4-fluorophenyl)-5-methylthiazole)-4-sulfonamido)benzoate (15.3 mg, 0.038 mmol) was dissolved in THF (0.113 mL)/H$_2$O (0.038 mL). LiOH—H$_2$O (15.80 mg, 0.376 mmol) was added and the reaction was heated at 50° C. for 4 h. Added LiOH—H$_2$O (15.80 mg, 0.376 mmol) and heated the reaction at 60° C. overnight. The reaction was cooled to rt and acidified 1M HCl and diluted with brine and EtOAc. The layers were separated and the aqueous layer extracted with EtOAc (2×). The combined organic layers were dried (Na$_2$SO$_4$), filtered, and concentrated under reduced pressure to afford 4-((2-(4-fluorophenyl)-5-methylthiazole)-4-sulfonamido)benzoic acid (14.7 mg, 0.037 mmol, 100% yield) as a colorless solid.

Example 56: Synthesis of 4-((2-(4-methoxyphenyl)thiazole)-4-sulfonamido)benzoic acid

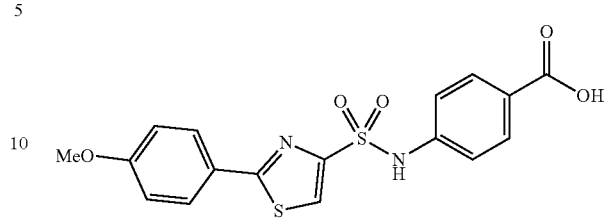

Step 1. Synthesis of methyl 4-((2-chlorothiazole)-4-sulfonamido)benzoate

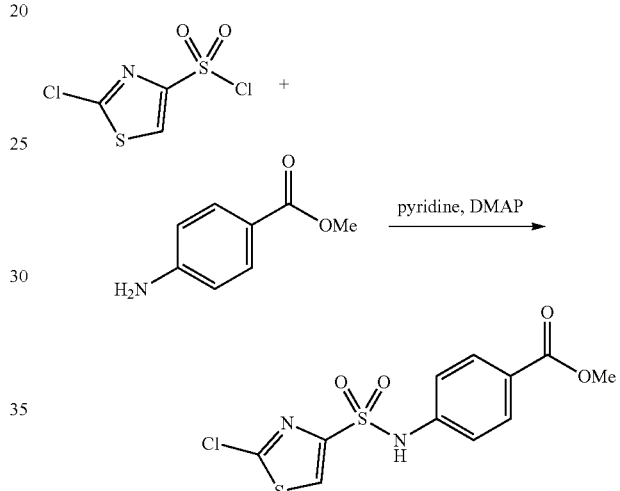

2-Chlorothiazole-4-sulfonyl chloride (200 mg, 0.917 mmol) was added to a solution of methyl 4-aminobenzoate (139 mg, 0.917 mmol) and DMAP (11.20 mg, 0.092 mmol) in pyridine (0.917 mL) and the reaction was stirred at rt overnight. The reaction was acidified with 1M HCl and diluted with CH$_2$Cl$_2$. The layers were separated, and aqueous layer was extracted with CH$_2$Cl$_2$ (2×). The combined organic layers were filtered through a phase separator. The remaining aqueous layer was extracted with EtOAc (3×), dried (MgSO$_4$), filtered, and combined with the DCM layer and concentrated under reduced pressure. The resultant brown crystalline solid was purified by column chromatography eluting with cyclohexane/acetone (0% acetone→25% acetone) to give methyl 4-((2-chlorothiazole)-4-sulfonamido)benzoate (223 mg, 0.670 mmol, 73.1% yield) as a yellow solid: LC-MS (ES, m/z): 333 [M+H]$^+$; $^1$H NMR (500 MHz, DMSO-d$_6$) δ 11.26 (s, 1H), 8.51 (s, 1H), 7.95-7.79 (m, 2H), 7.37-7.17 (m, 2H), 3.80 (s, 3H).

Example 56 was prepared from methyl 4-((2-chlorothiazole)-4-sulfonamido)benzoate according to the representative procedure for Suzuki coupling followed by the representative procedure for ester hydrolysis, with the following modification: during the ester hydrolysis the temperature was 60° C.

Example 63 was prepared from 4-((2-(4-methoxyphenyl)thiazole)-4-sulfonamido)benzoic acid according to the representative procedure for methyl cleavage.

Example 57: Synthesis of 4-((2-morpholinothiazole)-4-sulfonamido)benzoic acid

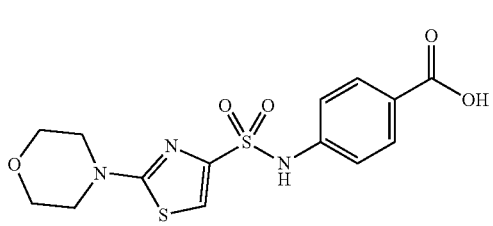 [SMILES: O=C(O)c1ccc(NS(=O)(=O)c2csc(N3CCOCC3)n2)cc1]

Step 1. Synthesis of methyl 4-((2-morpholinothiazole)-4-sulfonamido)benzoate

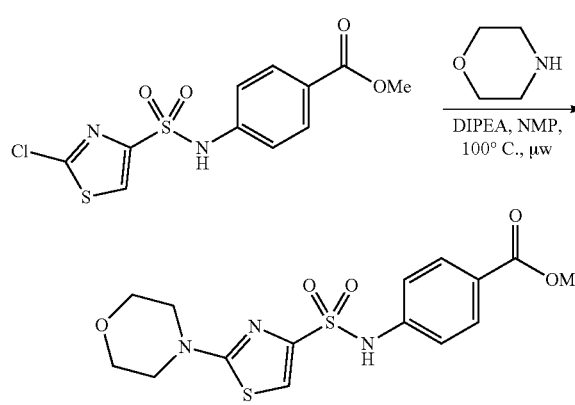

Representative Procedure for Aminothiazole Formation.

Morpholine (11.78 μL, 11.8 mg, 0.135 mmol) was added to a mixture of methyl 4-((2-chlorothiazole)-4-sulfonamido) benzoate (30 mg, 0.090 mmol) and Hunig's base (47.2 μL, 35.0 mg, 0.270 mmol) in NMP (0.902 ml) and the reaction was heated at 100° C. in the microwave for 60 minutes. The reaction was quenched with H$_2$O and diluted with EtOAc. The layers were separated, and the aqueous layer was extracted with EtOAc (1×). The combined organic layers were washed with water (2×), brine (1×), dried (MgSO$_4$), filtered, and concentrated under reduced pressure. The resultant orange oil was purified by column chromatography eluting with cyclohexane/EtOAc (0% EtOAc→50% EtOAc) to give methyl 4-((2-morpholinothiazole)-4-sulfonamido) benzoate (19.3 mg, 0.050 mmol, 55.8% yield) as a pale yellow amorphous solid: LC-MS (ES, m/z): 384 [M+H]$^+$.

Example 57 was prepared from methyl 4-((2-morpholinothiazole)-4-sulfonamido)benzoate according to the representative procedure for ester hydrolysis, with the following modification: during the ester hydrolysis the temperature was 60° C.

Example 58 was prepared from methyl 4-((2-chlorothiazole)-4-sulfonamido)benzoate according to the representative procedure for aminothiazole formation, followed by the representative procedure for ester hydrolysis, with the following modification: during the ester hydrolysis the temperature was 60° C.

Example 60: Synthesis of 4-((2-(4-fluorophenyl)thiazole)-5-sulfonamido)benzoic acid

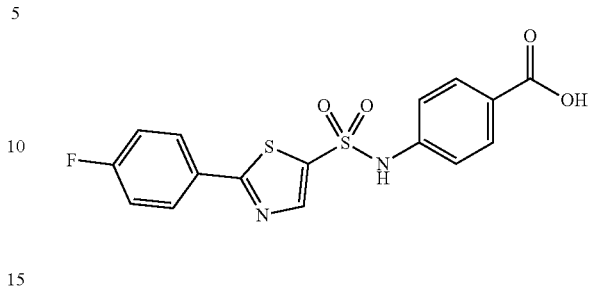

Step 1. Synthesis of methyl 4-((2-chlorothiazole)-5-sulfonamido)benzoate

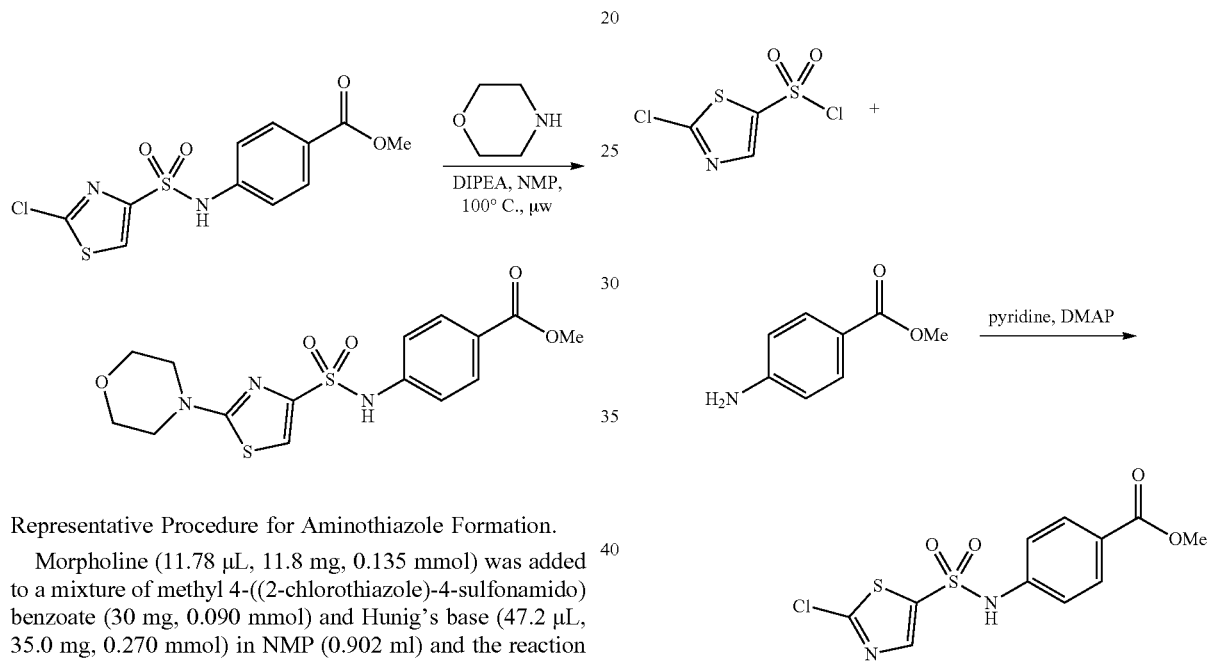

2-Chlorothiazole-5-sulfonyl chloride (200 mg, 0.917 mmol) was added to a solution of methyl 4-aminobenzoate (139 mg, 0.917 mmol) and DMAP (11.20 mg, 0.092 mmol) in pyridine (0.917 ml) and the reaction was stirred at rt overnight. The reaction was acidified with 1M HCl and diluted with CH$_2$Cl$_2$. The layers were separated, and aqueous layer was extracted with CH$_2$Cl$_2$ (2×) and then extracted with EtOAc (3×), dried (MgSO$_4$), filtered, and concentrated under reduced pressure The resultant pink gum was purified by column chromatography eluting with cyclohexane/acetone (0% acetone→25% acetone) to give methyl 4-((2-chlorothiazole)-5-sulfonamido)benzoate (43 mg, 0.129 mmol, 14.09% yield) as a light pink solid: LC-MS (ES, m/z): 331 [M–H]$^-$; $^1$H NMR (400 MHz, DMSO-d$_6$) δ 11.35 (s, 1H), 8.24 (s, 1H), 7.95-7.88 (m, 2H), 7.33-7.27 (m, 2H), 3.81 (s, 3H).

Example 60 was prepared from methyl 4-((2-chlorothiazole)-5-sulfonamido)benzoate according to the representative procedure for Suzuki coupling followed by the representative procedure for ester hydrolysis.

Example 69: Synthesis of 4-((2-(4-fluorophenyl)thiazole)-5-sulfonamido)-N-hydroxy-3-methoxybenzamide

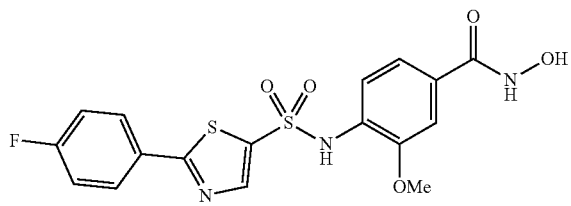

Step 1. Synthesis of 4-((2-(4-fluorophenyl)thiazole)-5-sulfonamido)-N-hydroxy-3-methoxybenzamide

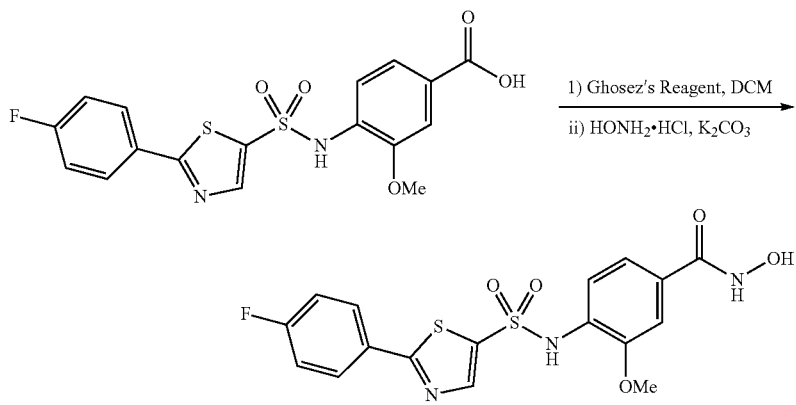

Representative Procedure for the Formation of Hydroxamic Acid Derivatives.

Ghosez's Reagent (7.13 µL, 5.6 mg, 0.054 mmol) was added to a suspension of 4-((2-(4-fluorophenyl)thiazole)-5-sulfonamido)-3-methoxybenzoic acid (11 mg, 0.027 mmol) CH₂Cl₂ (0.200 mL), and the mixture was stirred at rt for 30 min.

In a separate vial, hydroxylamine hydrochloride (5.61 mg, 0.081 mmol) and potassium carbonate (18.61 mg, 0.135 mmol) were dissolved in Ethyl acetate (0.4 mL) and Water (0.4 mL).

The above formed acyl chloride was added dropwise to the EtOAc layer, and the resulting mixture was stirred for 1 h at rt. The reaction was quenched with water and extracted with EtOAc (3×). The combined organic layers were dried (MgSO₄), filtered, and concentrated under reduced pressure. The resultant residue was purified by column chromatography eluting with CH₂Cl₂/MeOH (0% MeOH→20% MeOH) to afford 4-((2-(4-fluorophenyl)thiazole)-5-sulfonamido)-N-hydroxy-3-methoxybenzamide (6.6 mg, 0.016 mmol, 57.9% yield).

Example 69 was prepared from 4-((2-(4-fluorophenyl)thiazole)-5-sulfonamido)-3-methoxybenzoic acid and O-methylhydroxylamine hydrochloride according to the representative procedure for the formation of hydroxyamic acid derivatives.

Example 70 was prepared from 4-((2-(4-fluorophenyl)thiazole)-5-sulfonamido)-3-methoxybenzoic acid and N-methylhydroxylamine hydrochloride according to the representative procedure for the formation of hydroxyamic acid derivatives.

Example 166: 3-methoxy-4-((2-morpholinothiazole)-5-sulfonamido)benzoic acid

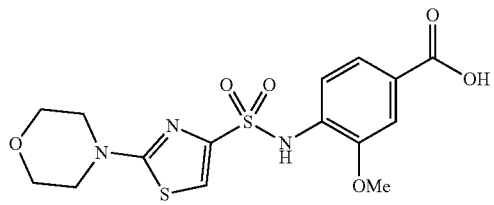 [SMILES: COc1cc(C(=O)O)ccc1NS(=O)(=O)c1csc(N2CCOCC2)n1]

Representative Procedure for Aminothiazole Formation.

Step 1. Synthesis of methyl 3-methoxy-4-((2-morpholinothiazole)-5-sulfonamido)benzoate

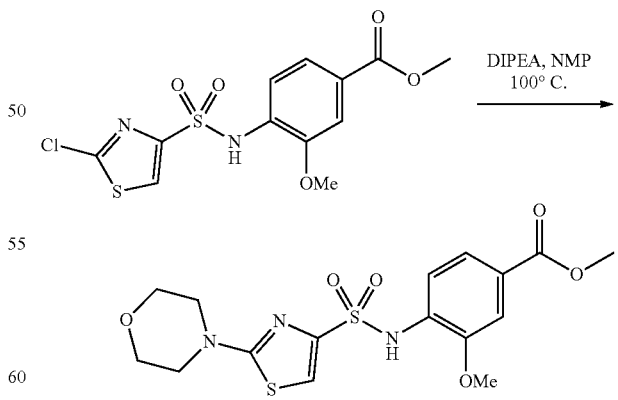

Morpholine (11.78 µL, 11.8 mg, 0.135 mmol) was added to a mixture of methyl 4-((2-chlorothiazole)-4-sulfonamido)-3-methoxybenzoate methyl (30 mg, 0.090 mmol) and Hunig's base (47.2 µL, 35.0 mg, 0.270 mmol) in NMP (0.902 ml) and the reaction was heated at 100° C. in the microwave for 60 minutes. The reaction was quenched with H₂O and diluted with EtOAc. The organic layer was separated, and the aqueous layer was extracted with EtOAc (1×). The combined organic layers were washed with water (2×), brine (1×), dried (MgSO₄), filtered, and concentrated under reduced pressure. The resultant orange oil was purified by column chromatography eluting with cyclohexane/EtOAc (0% EtOAc→50% EtOAc) to give methyl 3-methoxy-4-((2-morpholinothiazole)-5-sulfonamido)benzoate (19.3 mg, 0.050 mmol, 55.8% yield) as a pale yellow amorphous solid. ESI-MS m/z: 384[M+H]⁺.

Step 2. Synthesis of 3-methoxy-4-((2-morpholinothiazole)-5-sulfonamido)benzoic acid 3-methoxy-4-((2-morpholinothiazole)-4-sulfonamido) benzoic acid is synthesized in a similar way as in step 2 of synthesis of Example 254.

Example 176: 3-methoxy-4-((2-(p-tolylethynyl)thiazole)-4-sulfonamido)benzoic acid

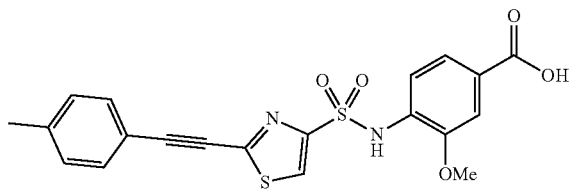 [SMILES: COc1cc(C(=O)O)ccc1NS(=O)(=O)c1csc(C#Cc2ccc(C)cc2)n1]

Step 1. methyl 4-((2-bromothiazole)-4-sulfonamido)-3-methoxybenzoate

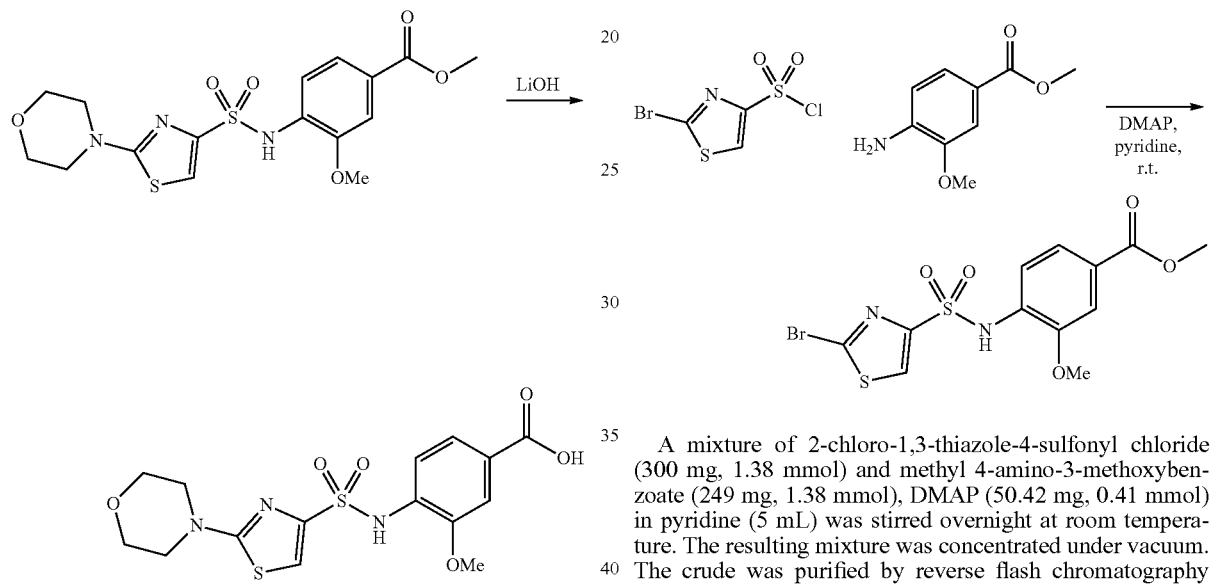

A mixture of 2-chloro-1,3-thiazole-4-sulfonyl chloride (300 mg, 1.38 mmol) and methyl 4-amino-3-methoxybenzoate (249 mg, 1.38 mmol), DMAP (50.42 mg, 0.41 mmol) in pyridine (5 mL) was stirred overnight at room temperature. The resulting mixture was concentrated under vacuum. The crude was purified by reverse flash chromatography with the following conditions: column, C18 silica gel; mobile phase, MeCN in water, 0% to 100% gradient in 20 min; detector, UV 254 nm. to afford methyl 4-(2-chloro-1,3-thiazole-4-sulfonamido)-3-methoxybenzoate (280 mg, 60%) as a red solid. LC-MS (ES, m/z): 408[M+H]⁺.
Representative Procedure for Sonogashira Coupling.

Step 2. methyl 3-methoxy-4-((2-(p-tolylethynyl) thiazole)-4-sulfonamido)benzoate

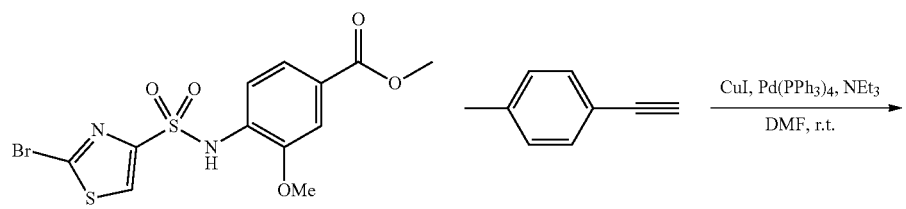

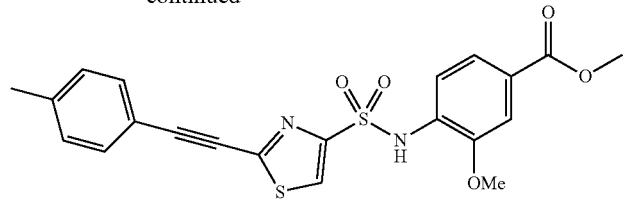

A mixture of methyl 4-(2-bromo-1,3-thiazole-4-sulfonamido)-3-methoxybenzoate (80 mg, 0.2 mmol), Et₃N (60 mg, 0.6 mmol), 1-ethynyl-4-methylbenzene (46 mg, 0.4 mmol), Pd(PPh₃)₄ (23 mg, 0.02 mmol), CuI (7.6 mg, 0.04 mmol) in DMF (3 mL) was stirred for overnight at room temperature under nitrogen atmosphere. The crude was purified by reverse flash chromatography with the following conditions: column, C18 silica gel; mobile phase, MeCN in water, 0% to 100% gradient in 20 min; detector, UV 254 nm. to afford methyl 3-methoxy-4-((2-(p-tolylethynyl)thiazole)-4-sulfonamido)benzoate as a yellow solid. LC-MS (ES, m/z): 443 [M+H]⁺.

Representative Procedure for Ester Hydrolysis.

Step 3. Synthesis of 3-methoxy-4-((2-(p-tolylethynyl)thiazole)-4-sulfonamido)benzoic acid (Example 176)

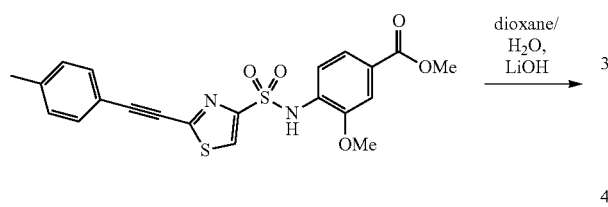

A mixture of methyl 3-methoxy-4-((2-(p-tolylethynyl)thiazole)-4-sulfonamido)benzoate (55 mg, 0.12 mmol), LiOH (29 mg, 1.2 mmol) in 1,4-dioxane (3 mL) and H₂O (3 mL) was stirred for 2 h at room temperature. The residue was purified by prep-HPLC to give 3-methoxy-4-((2-(p-tolylethynyl)thiazole)-4-sulfonamido)benzoic acid (Example 254) as a yellow solid. LC-MS (ES, m/z): 429.20 [M+H]⁺; ¹H NMR (400 MHz, DMSO-d₆) δ 7.91 (s, 1H), 7.57-7.50 (m, 2H), 7.31-7.25 (m, 3H), 7.16 (dd, J=8.2, 1.9 Hz, 1H), 7.01 (d, J=8.2 Hz, 1H), 3.65 (s, 3H), 2.35 (s, 3H).

Example 247: 3-methoxy-4-((2-((2-oxo-6-(trifluoromethyl)-1,2-dihydropyridin-4-yl)ethynyl)thiazole)-4-sulfonamido)benzoic acid

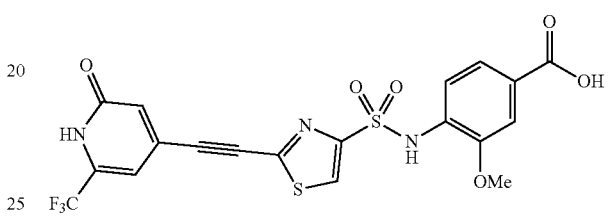

Step 1. Synthesis of 4-iodo-6-(trifluoromethyl)pyridin-2(1H)-one

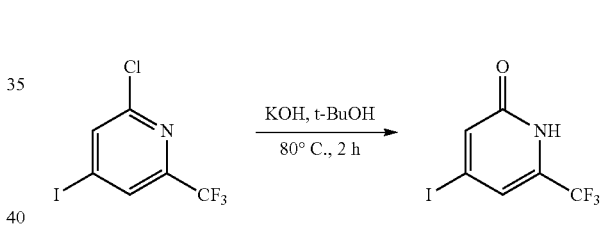

To a stirred mixture of 2-chloro-4-iodo-6-(trifluoromethyl)pyridine (2 g, 6.5 mmol) in t-BuOH (20 mL) was added KOH (3.65 g, 65 mmol) in portions at room temperature and stirred for 2 h at 80° C. under nitrogen atmosphere. The mixture was neutralized to pH 7 with HCl. The resulting mixture was extracted with EtOAc (2×50 ml). The combined organic layers were concentrated, and the residue was purified by silica gel column chromatography, (DCM/MeOH=5/1) to afford 4-iodo-6-(trifluoromethyl)-1H-pyridin-2-one (1.9 g, 91%) as a white solid.

Step 2. Synthesis of 6-(trifluoromethyl)-4-((triisopropylsilyl)ethynyl)pyridin-2(1H)-one

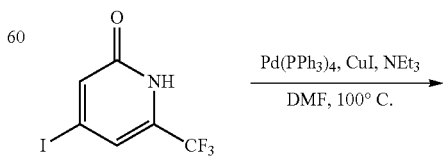

-continued

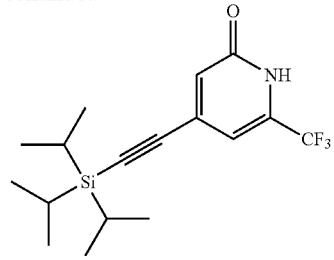

To a stirred solution of 4-iodo-6-(trifluoromethyl)-1H-pyridin-2-one (1.0 g, 3.46 mmol) and ethynyltriisopropylsilane (1.6 g, 8.7 mmol) in DMF (10 mL) was added Pd(PPh$_3$)$_4$ (400 mg, 0.35 mmol), TEA (3.5 g, 34.6 mmol) and CuI (131.8 mg, 0.69 mmol) in portions at room temperature under nitrogen atmosphere. After stirred for 2 h at room temperature, the resulting mixture was extracted with EtOAc (2×50 ml). The combined organic layers were washed with saturated salt water (50 ml). The organic phase was concentrated and the crude product was purified by reverse phase flash to afford 6-(trifluoromethyl)-4-[2-(triisopropylsilyl)ethynyl]-1H-pyridin-2-one (800 mg, 61%) as a yellow oil.

Step 3. Synthesis of 4-ethynyl-6-(trifluoromethyl)pyridin-2(1H)-one

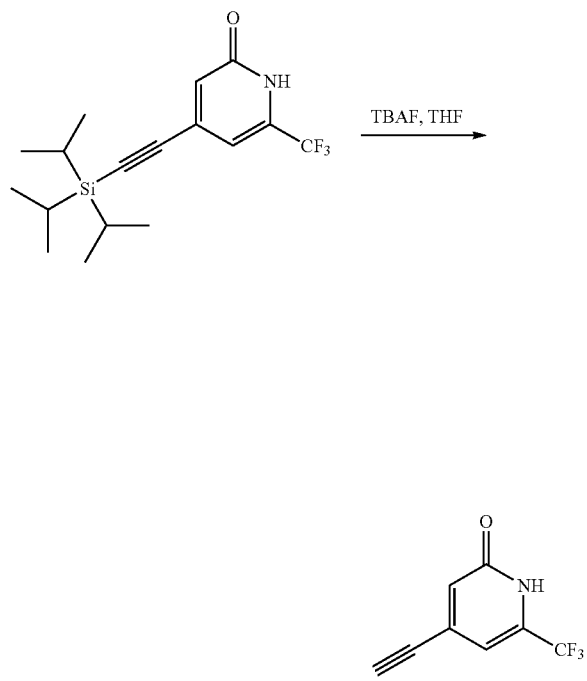

A mixture of 6-(trifluoromethyl)-4-[2-(triisopropylsilyl) ethynyl]-1H-pyridin-2-one (800 mg, 2.33 mmol) and TBAF in THF (1.0 mol/L, 10 mL) was stirred for 2 h at RT. The mixture was concentrated, and the crude was purified by reverse flash chromatography to give 4-ethynyl-6-(trifluoromethyl)-1H-pyridin-2-one (312 mg, 71.5%) as a yellow solid.

Step 4. Synthesis of methyl 3-methoxy-4-((2-((2-oxo-6-(trifluoromethyl)-1,2-dihydropyridin-4-yl)ethynyl)thiazole)-4-sulfonamido)benzoate

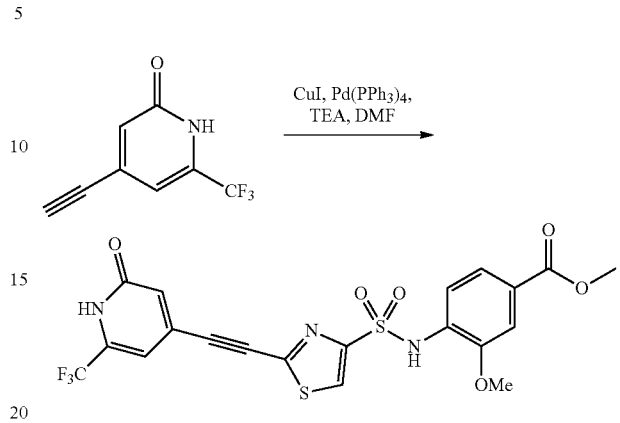

To a stirred mixture of methyl 4-(2-bromo-1,3-thiazole-4-sulfonamido)-3-methoxybenzoate (50 mg, 0.12 mmol) and 4-ethynyl-6-(trifluoromethyl)-1H-pyridin-2-one (34.5 mg, 0.18 mmol) in DMF (1 mL) was added TEA (124 mg, 1.2 mmol), Pd(PPh$_3$)$_4$ (28 mg, 0.025 mmol) and CuI (4.7 mg, 0.025 mmol) in portions at room temperature. The resulting mixture was stirred for 2 h at room temperature under nitrogen atmosphere. The residue was purified by reverse phase flash to afford methyl 3-methoxy-4-(2-{2-[2-oxo-6-(trifluoromethyl)-1H-pyridin-4-yl]ethynyl}-1,3-thiazole-4-sulfonamido)benzoate (30 mg, 42.8%) as a yellow solid.

Step 5. Synthesis of 3-methoxy-4-((2-((2-oxo-6-(trifluoromethyl)-1,2-dihydropyridin-4-yl)ethynyl)thiazole)-4-sulfonamido)benzoic acid

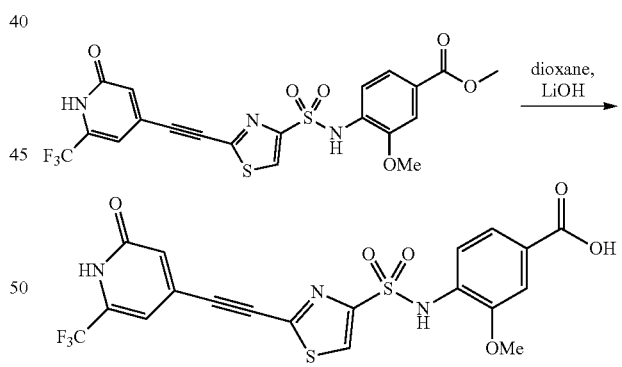

To a stirred mixture of methyl 3-methoxy-4-(2-{2-[2-oxo-6-(trifluoromethyl)-1H-pyridin-4-yl]ethynyl}-1,3-thiazole-4-sulfonamido)benzoate (30 mg, 0.058 mmol) in 1,4-dioxane (2 mL) and H$_2$O (5 mL) was added LiOH (70 mg, 2.9 mmol) in portions at room temperature. The resulting mixture was stirred overnight at room temperature. The mixture was neutralized to pH 7 with HCl and concentrated. The crude was purified by reverse flash chromatography to afford Synthesis of 3-methoxy-4-((2-((2-oxo-6-(trifluoromethyl)-1,2-dihydropyridin-4-yl)ethynyl)thiazole)-4-sulfonamido)benzoic acid (21.9 mg, 74.52%) as a yellow solid. ESI-MS m/z: 500.20, [M+H]$^+$; $^1$H NMR (400 MHz, DMSO-d$_6$) δ 12.53 (s, 1H), 10.21 (s, 1H), 8.51 (s, 1H), 7.63 (s, 1H), 7.51

(dd, J=8.2, 1.8 Hz, 1H), 7.45 (d, J=1.8 Hz, 1H), 7.39 (d, J=8.2 Hz, 1H), 7.24 (s, 1H), 3.71 (s, 3H).

Example 249: 4-((5-([1,1'-biphenyl]-3-yl)thiophene)-2-sulfonamido)-3-methoxybenzoic acid

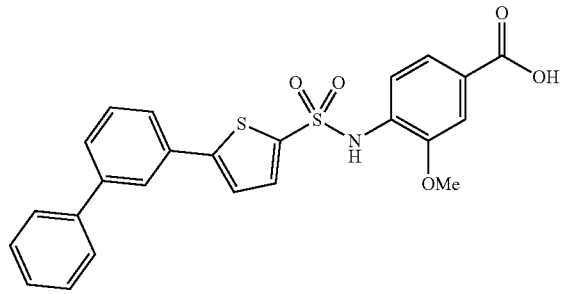 [SMILES: COc1cc(C(=O)O)ccc1NS(=O)(=O)c1ccc(-c2cccc(-c3ccccc3)c2)s1]

Step 1. Synthesis of methyl 4-((5-bromothiophene)-2-sulfonamido)-3-methoxybenzoate

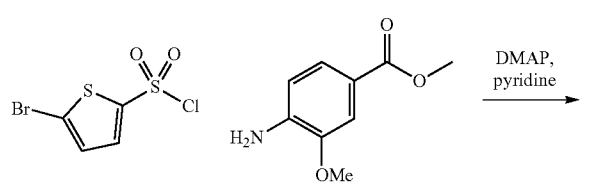

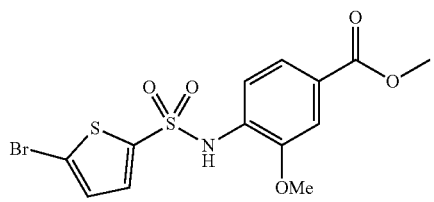

A solution of 5-bromothiophene-2-sulfonyl chloride (3.0 g, 11.4 mmol), methyl 4-amino-3-methoxybenzoate (3.12 g, 17.2 mmol) and DMAP (0.70 g, 5.7 mmol) in Pyridine (30 mL) was stirred for overnight at room temperature. The resulting mixture was diluted with EtOAc, washed with water, brine, dried, filtered and concentrated. The residue was purified by reverse phase C18 column chromatography (MeCN/H$_2$O) to give the methyl 4-((5-bromothiophene)-2-sulfonamido)-3-methoxybenzoate as a red solid (3.7 g, 71%). ESI-MS m/z: 405.90 [M+H]$^+$.

Step 2. Synthesis of methyl 4-((5-([1,1'-biphenyl]-3-yl)thiophene)-2-sulfonamido)-3-methoxybenzoate

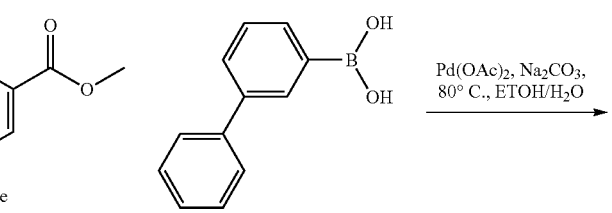

A solution of methyl 4-(5-bromothiophene-2-sulfonamido)-3-methoxybenzoate (200 mg, 0.49 mmol), [1,1'-biphenyl]-3-ylboronic acid (146 mg, 0.74 mmol), Pd(OAc)$_2$ (22 mg, 0.10 mmol) and Na$_2$CO$_3$ (104 mg, 0.98 mmol) in EtOH (1 mL) and H$_2$O (0.5 mL) was stirred overnight at 80° C. under nitrogen atmosphere. The mixture was extracted, evaporated, purified by reverse phase C18 column chromatography (MeCN/H$_2$O) to give the desired compound as a yellow solid (150 mg, 63%).

Step 3. Synthesis of 4-((5-([1,1'-biphenyl]-3-yl)thiophene)-2-sulfonamido)-3-methoxybenzoic acid (Example 249)

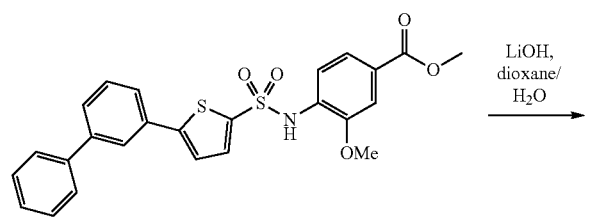

A solution of methyl 4-(5-{[1,1'-biphenyl]-3-yl}thiophene-2-sulfonamido)-3-methoxybenzoate (50 mg, 0.10 mmol), LiOH (49 mg, 2.08 mmol) in dioxane (2 mL) and H$_2$O (2 mL) was stirred overnight at room temperature. The mixture was acidified to pH 6 with 1M aq. HCl, and to the mixture was added EtOAc. The organic layer was separated, dried, filtered and concentrated and the residue was purified by reverse phase C18 column chromatography (MeCN/H$_2$O) to give 4-((5-([1,1'-biphenyl]-3-yl)thiophene)-2-sulfonamido)-3-methoxybenzoic acid as a white solid (24.8 mg, 51%). ESI-MS m/z: 464.05 [M−H]$^−$; $^1$H NMR (400 MHz, DMSO-d$_6$) δ 12.97 (s, 1H), 10.14 (s, 1H), 7.93 (t, J=1.8 Hz, 1H), 7.78-7.71 (m, 2H), 7.74-7.64 (m, 3H), 7.60-7.37 (m, 8H), 3.71 (s, 3H).

Example 250: 3-methoxy-4-((5-(4'-methyl-[1,1'-biphenyl]-3-yl)thiophene)-2-sulfonamido)benzoic acid

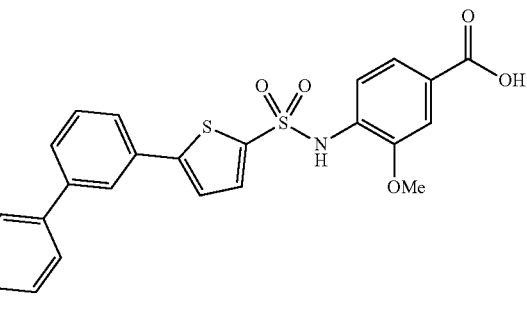

Step 1. Synthesis of 2-(3-bromophenyl)-6-methyl-1,3,6,2-dioxazaborocane-4,8-dione

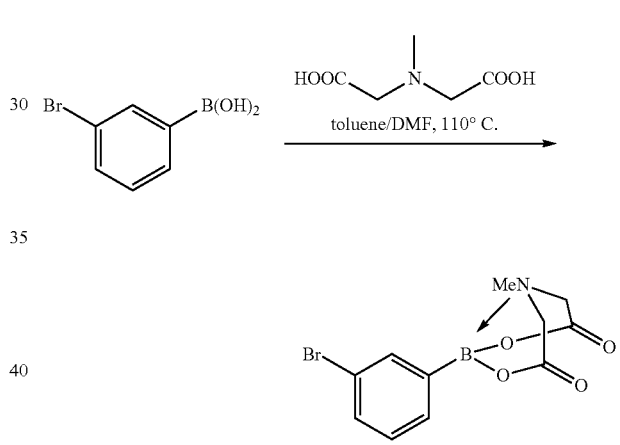

A solution of 3-bromophenylboronic acid (10 g, 49.8 mmol), toluene (200 mL) [(carboxymethyl)(methyl)amino]acetic acid (7.3 g, 49.8 mmol, 1 eq.) and DMSO (20 mL) was stirred for overnight at 110° C. The mixture was evaporated and purified by reverse phase C18 column chromatography (MeCN/H$_2$O) to give 2-(3-bromophenyl)-6-methyl-1,3,6,2-dioxazaborocane-4,8-dione as a white solid (13 g, 83%).

Step 2. Synthesis of 6-methyl-2-(4'-methyl-[1,1'-biphenyl]-3-yl)-1,3,6,2-dioxazaborocane-4,8-dione

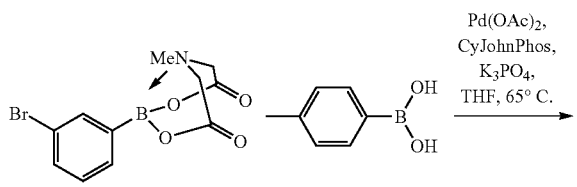

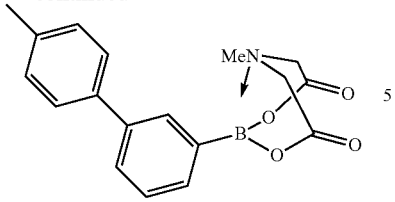

A solution of 2-(3-bromophenyl)-6-methyl-1,3,6,2-dioxazaborocane-4,8-dione (500 mg, 1.60 mmol), p-tolueneboronic acid (326 mg, 2.40 mmol), THF (15 mL), K₃PO₄ (1020 mg, 4.80 mmol), CyJohnPhos (22 mg, 0.06 mmol) and Pd(OAc)₂ (7 mg, 0.03 mmol) was stirred for overnight at 65° C. under nitrogen atmosphere. The resulting mixture was diluted with EtOAc/water and the organic layer was separated, and concentrated. The residue was purified by reverse phase C18 column chromatography (MeCN/H₂O) to give 6-methyl-2-(4'-methyl-[1,1'-biphenyl]-3-yl)-1,3,6,2-dioxazaborocane-4,8-dione as a white solid (260 mg, 50%).

Step 3. Synthesis of (4'-methyl-[1,1'-biphenyl]-3-yl) boronic acid

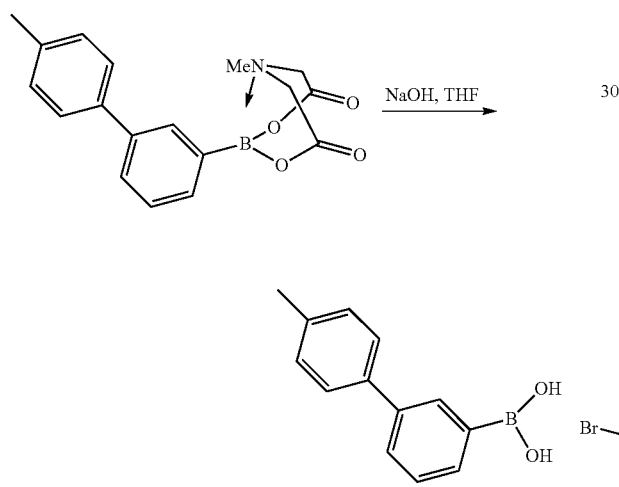

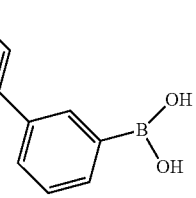

A solution of 6-methyl-2-{4'-methyl-[1,1'-biphenyl]-3-yl}-1,3,6,2-dioxazaborocane-4,8-dione (100 mg, 0.30 mmol), THF (2 mL), 1 M aq. NaOH (0.9 mL, 0.9 mmol) was stirred for 1 h at room temperature. The mixture was diluted with EtOAc/water and the organic layer was separated, and concentrated. The residue was purified by reverse phase C18 column chromatography (MeCN/H₂O) to give (4'-methyl-[1,1'-biphenyl]-3-yl)boronic acid as a yellow solid (50 mg, 76%).

Step 4. Synthesis of methyl 3-methoxy-4-((5-(4'-methyl-[1,1'-biphenyl]-3-yl)thiophene)-2-sulfonamido)benzoate

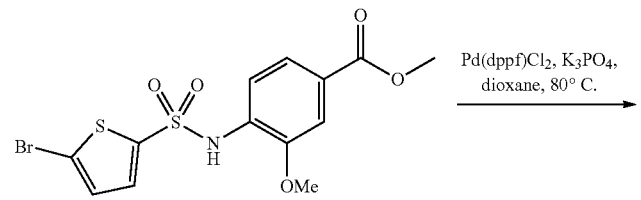

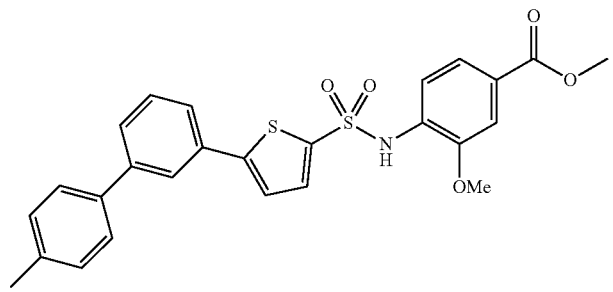

A solution of 4'-methyl-[1,1'-biphenyl]-3-ylboronic acid (50 mg, 0.23 mmol) and the compound from C2-237 step 1 (143 mg, 0.35 mmol), dioxane (2 mL), K$_3$PO$_4$ (150 mg, 0.70 mmol) and Pd(dppf)Cl$_2$·CH$_2$Cl$_2$ (19 mg, 0.02 mmol) was stirred for 4 h at 80° C. under nitrogen atmosphere. The mixture was diluted with EtOAc/water and the organic layer was separated, and concentrated. The residue was purified by reverse phase C18 column chromatography (MeCN/H$_2$O) to give methyl 3-methoxy-4-((5-(4'-methyl-[1,1'-biphenyl]-3-yl)thiophene)-2-sulfonamido)benzoate as a yellow solid (80 mg, 68%).

Step 5. Synthesis of 3-methoxy-4-((5-(4'-methyl-[1,1'-biphenyl]-3-yl)thiophene)-2-sulfonamido)benzoic acid

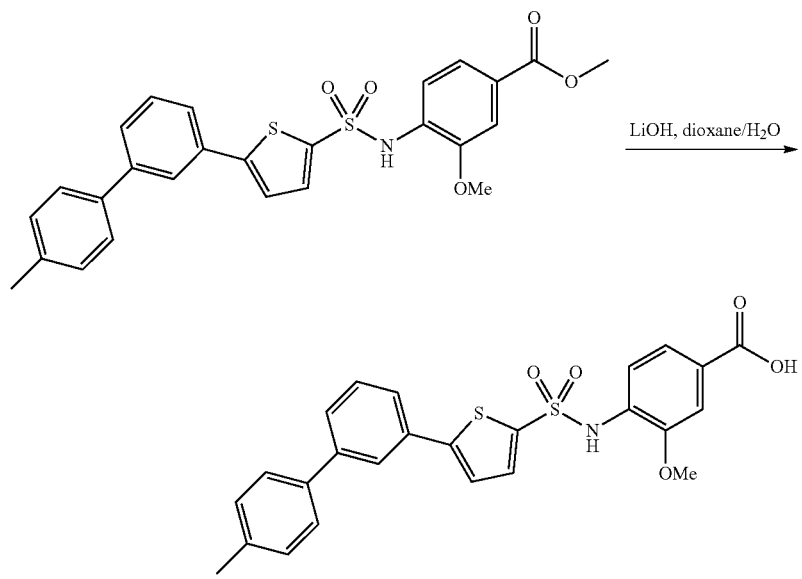

A solution of methyl 3-methoxy-4-(5-{4'-methyl-[1,1'-biphenyl]-3-yl}thiophene-2-sulfonamido)benzoate (50 mg, 0.10 mmol), dioxane (4 mL), LiOH (48 mg, 2.02 mmol) and H$_2$O (2 mL) was stirred for overnight at room temperature. The mixture was acidified to pH 3 with 1M aq. HCl, and then extracted with EtOAc. The organic layer was separated, concentrated, and the residue was purified by reverse phase C18 column chromatography (MeCN/H$_2$O) to give 3-methoxy-4-((5-(4'-methyl-[1,1'-biphenyl]-3-yl)thiophene)-2-sulfonamido)benzoic acid as a white solid (30.2 mg, 60%). ESI-MS m/z: 478.10, [M−H]$^-$; H NMR (400 MHz, DMSO-d6) δ 12.96 (s, 1H), 10.13 (s, 1H), 7.90 (t, J=1.9 Hz, 1H), 7.71-7.60 (m, 5H), 7.60-7.48 (m, 3H), 7.50-7.43 (m, 2H), 7.30 (d, J=8.0 Hz, 2H), 3.71 (s, 3H), 2.36 (s, 3H).

Example 281: 4-((2-(4-cyclohexylphenyl)thiazole)-4-sulfonamido)-3-methoxybenzoic acid Step 1. Synthesis of methyl 4-((2-(4-cyclohexylphenyl)thiazole)-4-sulfonamido)-3-methoxybenzoate

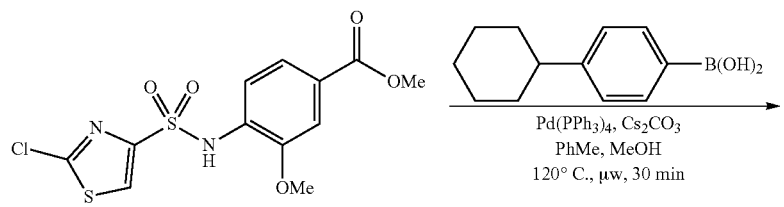

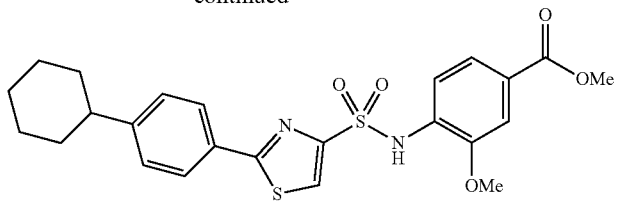

To a mixture of methyl 4-((2-chlorothiazole)-4-sulfonamido)-3-methoxybenzoate (50.0 mg, 0.138 mmol), (4-cyclohexylphenyl)boronic acid (28.1 mg, 0.138 mmol), and cesium carbonate (53.9 mg, 0.165 mmol) in PhCH$_3$ (0.806 mL)/MeOH (0.215 mL) was added Pd(PPh$_3$)$_4$ (15.93 mg, 0.014 mmol) and the resulting mixture was heated at 120° C. for 30 minutes under the microwave condition. The reaction mixture was filtered through celite, rinsing with DCM. The crude was purified by flash column chromatography eluting with 0-30% EtOAc/cyclohexane to give methyl 4-((2-(4-cyclohexylphenyl)thiazole)-4-sulfonamido)-3-methoxybenzoate (42.2 mg, 62.9% yield) as white solid.

Step 2. Synthesis of 4-((2-(4-cyclohexylphenyl)thiazole)-4-sulfonamido)-3-methoxybenzoic acid

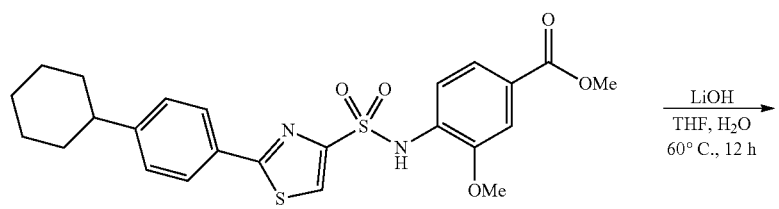

To a solution of methyl 4-((2-(4-cyclohexylphenyl)thiazole)-4-sulfonamido)-3-methoxybenzoate (40.3 mg, 0.083 mmol) in THF (1.656 mL) was added lithium hydroxide (1N, aq.) (0.414 mL, 0.414 mmol) and the resulting mixture was heated at 60° C. for 12 h. Then reaction mixture was allowed to cool to room temperature and quenched with 1N HCl and extracted with EtOAc (×2). The organic layers was combined, washed with brine and dried over Na$_2$SO$_4$, filtered, and concentrated to give 4-((2-(4-cyclohexylphenyl)thiazole)-4-sulfonamido)-3-methoxybenzoic acid (34.7 mg, 89% yield). LC-MS (ES, m/z): 473.1 [M+H]$^+$; $^1$H NMR (400 MHz, DMSO-d6) δ 12.93 (br, 1H), 10.03 (br, 1H), 8.34 (s, 1H), 7.86-7.80 (m, 2H), 7.53-7.50 (m, 2H), 7.44-7.36 (m, 3H), 3.67 (s, 3H), 2.64-2.52 (m, 1H), 1.87-1.75 (m, 4H), 1.49-1.14 (m, 6H).

Example 305: 4-((2-(4-(tert-butoxycarbonyl)piperazin-1-yl)thiazole)-4-sulfonamido)-3-methoxybenzoic acid

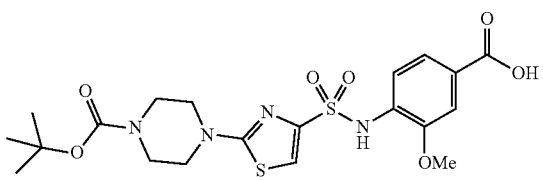 [SMILES: COc1cc(C(=O)O)ccc1NS(=O)(=O)c1csc(N2CCN(C(=O)OC(C)(C)C)CC2)n1]

Representative Procedure for Aminothiazole Formation

Step 1. Synthesis of tert-butyl 4-(4-(N-(2-methoxy-4-(methoxycarbonyl)phenyl)sulfamoyl)thiazol-2-yl)piperazine-1-carboxylate

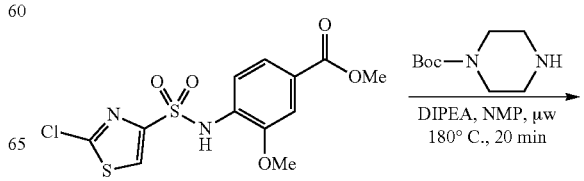

-continued

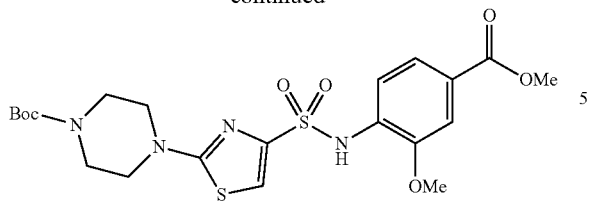

To a mixture of methyl 4-((2-chlorothiazole)-4-sulfonamido)-3-methoxybenzoate (60 mg, 0.165 mmol, 1.0 equiv.) and DIPEA (86.0 µL, 0.496 mmol, 3.0 equiv.) in NMP (1 mL) was added tert-butyl piperazine-1-carboxylate (92.0 mg, 0.496 mmol, 3.0 equiv.) and the resulting mixture was heated at 180° C. for 20 min under microwave condition. The reaction mixture was directly loaded into column for purification via reversed phase flash column chromatography eluting with water/acetonitrile (10% acetonitrile/water→90% acetonitrile/water) to yield tert-butyl 4-(4-(N-(2-methoxy-4-(methoxycarbonyl)phenyl)sulfamoyl)thiazol-2-yl)piperazine-1-carboxylate (57 mg, 67.2% yield) as white solid.

Step 2. Synthesis of 4-((2-(4-(tert-butoxycarbonyl)piperazin-1-yl)thiazole)-4-sulfonamido)-3-methoxybenzoic acid

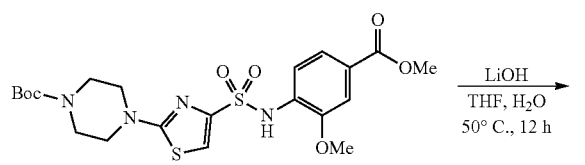

To a solution of tert-butyl 4-(4-(N-(2-methoxy-4-(methoxycarbonyl)phenyl)sulfamoyl)thiazol-2-yl)piperazine-1-carboxylate (57.0 mg, 0.111 mmol) in THF (0.363 mL) was added lithium hydroxide (1M in water) (0.555 mL, 0.555 mmol) and the resulting mixture was heated at 50° C. for 12 h. The reaction mixture was allowed to cool to room temperature and quenched with 1N HCl and extracted with EtOAc (×2). Combined organic layers was washed with brine and dried over Na₂SO₄. The residue was purified through reversed phase flash column chromatography eluting with water/acetonitrile (10% acetonitrile/water→90% acetonitrile/water) to yield 4-((2-(4-(tert-butoxycarbonyl)piperazin-1-yl)thiazole)-4-sulfonamido)-3-methoxybenzoic acid (47.0 mg, 85% yield) as white solid. LC-MS (ES, m/z): 499.3 [M+H]⁺; ¹H NMR (500 MHz, DMSO-d6) δ 9.64 (br, 1H), 7.55-7.38 (m, 4H), 3.76 (s, 4H), 3.47-3.27 (m, 8H), 1.41 (s, 9H).

Example 307: 4-((2-(4-(((cyclohexylmethoxy)carbonyl)piperazin-1-yl)thiazole)-4-sulfonamido)-3-methoxybenzoic acid

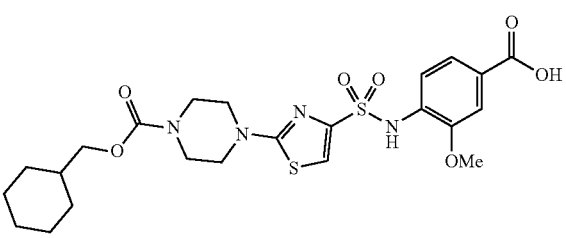 [SMILES: COc1cc(C(=O)O)ccc1NS(=O)(=O)c1csc(N2CCN(C(=O)OCC3CCCCC3)CC2)n1]

Step 1. Synthesis of 3-methoxy-4-((2-(piperazin-1-yl)thiazole)-4-sulfonamido)benzoic acid

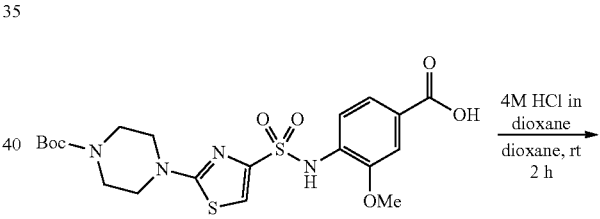

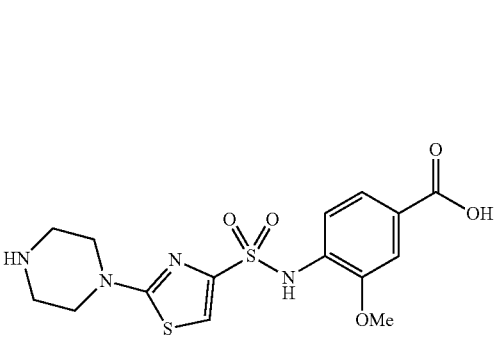

To a solution of 4-((2-(4-(tert-butoxycarbonyl)piperazin-1-yl)thiazole)-4-sulfonamido)-3-methoxybenzoic acid (20.0 mg, 0.040 mmol) in 1,4-dioxane (0.401 mL) was added 4M HCl in dioxane (0.5 mL, 2.006 mmol) and the resulting mixture was stirred at room temperature. After 2 h, the reaction mixture was concentrated to give 3-methoxy-4-((2-(piperazin-1-yl)thiazole)-4-sulfonamido)benzoic acid (15.0 mg, 94% yield). ESI-MS m/z: 399.5, [M+H]⁺.

Step 2. Synthesis of 4-((2-(4-((cyclohexylmethoxy)carbonyl)piperazin-1-yl)thiazole)-4-sulfonamido)-3-methoxybenzoic (cyclohexylmethyl carbonic) anhydride

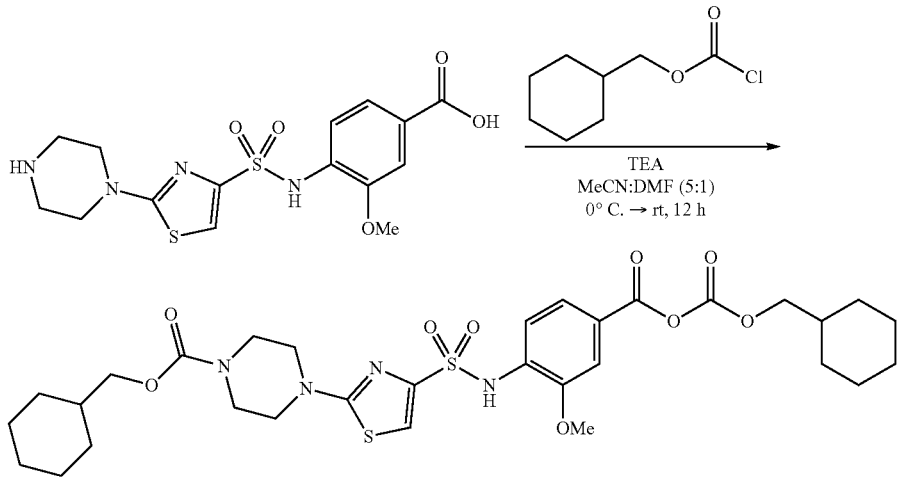

To a solution of 3-methoxy-4-((2-(piperazin-1-yl)thiazole)-4-sulfonamido)benzoic acid (15.0 mg, 0.038 mmol) in acetonitrile (0.314 ml)/DMF (0.063 ml) was added triethylamine (12.07 µl, 0.087 mmol) at room temperature. Then the reaction mixture was cooled down to 0° C. and cyclohexylmethyl carbonochloridate (13.30 mg, 0.075 mmol) was added. After addition, ice bath was removed and stirring was continued at room temperature. After 12 h, the reaction mixture was concentrated, and crude was purified through reversed phase flash column chromatography eluting with water/acetonitrile (10% acetonitrile→90% acetonitrile) to yield 4-((2-(4-((cyclohexylmethoxy)carbonyl)piperazin-1-yl)thiazole)-4-sulfonamido)-3-methoxybenzoic (cyclohexylmethyl carbonic) anhydride (17.3 mg, 67.7% yield). ESI-MS m/z: 679.6, [M+H]$^+$; $^1$H NMR (500 MHz, Chloroform-d) δ 7.69-7.63 (m, 2H), 7.57 (s, 1H), 7.48 (d, J=1.4 Hz, 1H), 7.40 (s, 1H), 4.14 (d, J=6.3 Hz, 2H), 3.94-3.90 (m, 5H), 3.61-3.53 (m, 4H), 3.47-3.40 (m, 4H), 1.84-0.80 (m, 22H).

Step 3. Synthesis of 4-((2-(4-((cyclohexylmethoxy)carbonyl)piperazin-1-yl)thiazole)-4-sulfonamido)-3-methoxybenzoic acid

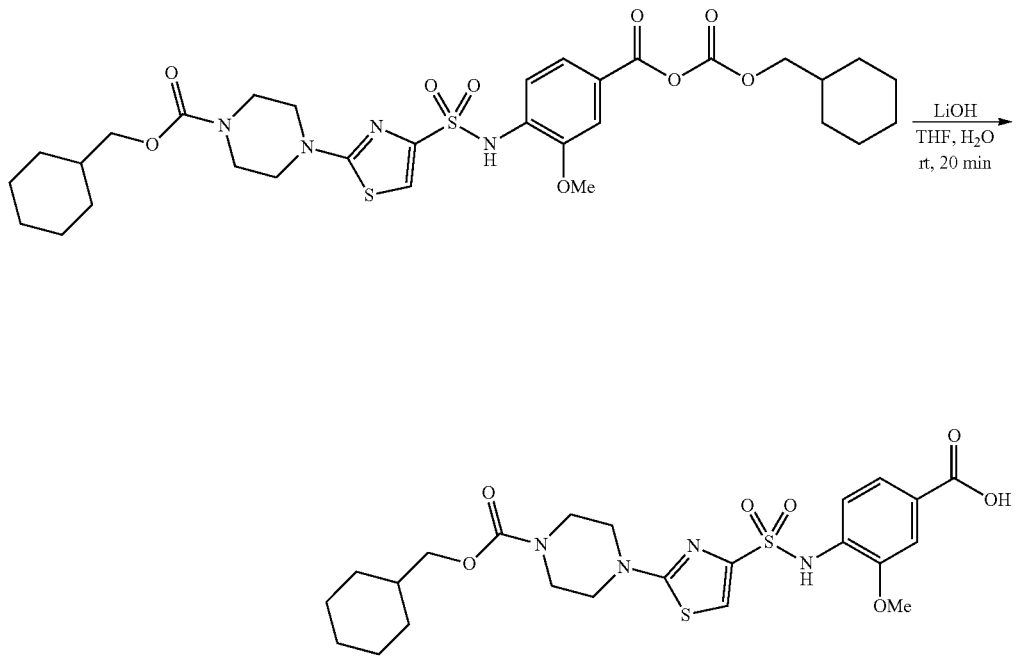

To a solution of 4-((2-(4-((cyclohexylmethoxy)carbonyl)piperazin-1-yl)thiazole)-4-sulfonamido)-3-methoxybenzoic (cyclohexylmethyl carbonic) anhydride (17.3 mg, 0.025 mmol) in THF (0.510 mL) was added lithium hydroxide (1 M in water) (0.127 ml, 0.127 mmol) and the resulting mixture was stirred at room temperature for 20 min. Then, the reaction mixture was quenched with 1N HCl and extracted with EtOAc (×2). Combined organic layers was washed with brine and dried over $Na_2SO_4$ and concentrated under vacuum. The crude was purified through reversed phase flash column chromatography eluting with water/acetonitrile (10% acetonitrile→90% acetonitrile) to yield 4-((2-(4-((cyclohexylmethoxy)carbonyl)piperazin-1-yl)thiazole)-4-sulfonamido)-3-methoxybenzoic acid (7.2 mg, 52.4% yield). ESI-MS m/z: 539.4, [M+H]$^+$; $^1$H NMR (500 MHz, DMSO-d$_6$) δ 12.87 (br, 1H), 9.67 (br, 1H), 7.55-7.41 (m, 4H), 3.84 (d, J=6.5 Hz, 2H), 3.77 (s, 3H), 3.56-3.37 (m, 8H), 1.73-1.54 (m, 6H), 1.27-1.08 (m, 3H), 1.01-0.89 (m, 2H).

Example 320: 3-methoxy-4-((3-phenoxypiperidine)-1-sulfonamido)benzoic acid

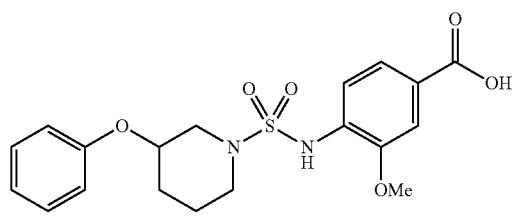 [SMILES: COc1cc(C(=O)O)ccc1NS(=O)(=O)N1CCCC(Oc2ccccc2)C1]

Step 1. Synthesis of (2-methoxy-4-(methoxycarbonyl)phenyl)sulfamic acid

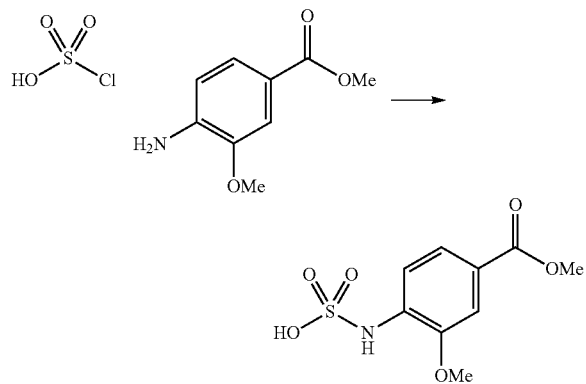

To a suspension of methyl 4-amino-3-methoxybenzoate (1 g, 5.52 mmol) in DCM (7 ml) at 0° C. was added sulfurochloridic acid (0.440 ml, 6.62 mmol) in DCM (2 ml) and the mixture first turned clear then cloudy. Stirred for 30 min, and the precipitates was collected by filtration, rinsed with DCM. To the solid was added water and stirred for 15 min. The mixture was filtered to give (2-methoxy-4-(methoxycarbonyl)phenyl)sulfamic acid (1.94 g) as a grey solid. $^1$H NMR (400 MHz, DMSO-d6) δ 7.41 (dd, J=8.2, 1.8 Hz, 1H), 7.33 (d, J=1.8 Hz, 1H), 6.72 (d, J=8.2 Hz, 1H), 3.83 (s, 3H), 3.77 (s, 3H).

Step 2. Synthesis of methyl 4-((chlorosulfonyl)amino)-3-methoxybenzoate

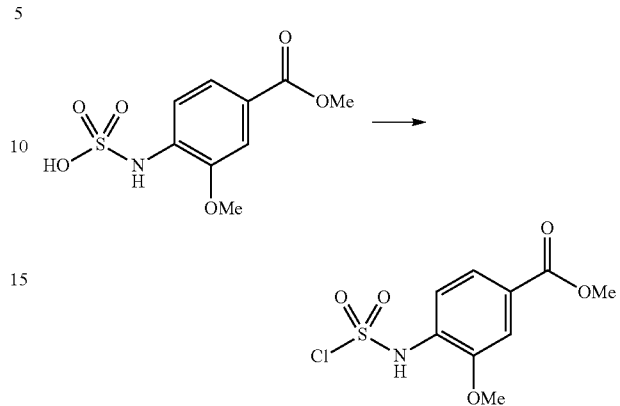

To a suspension of (2-methoxy-4-(methoxycarbonyl)phenyl)sulfamic acid (1.94 g, 7.43 mmol) in Toluene (30 ml) was added PCl$_5$ (1.624 g, 7.80 mmol), and heated up at 80° C. for 20 h. The mixture was filtered, and the filtrate was concentrated as a yellow oil. The residue was diluted with EtOAc/water and the organic layer was separated, washed with NaHCO$_3$ solution, brine, dried, filtered and concentrated to give methyl 4-((chlorosulfonyl)amino)-3-methoxybenzoate (187 mg) as yellow solid.

Step 3. Synthesis of methyl 3-methoxy-4-((3-phenoxypiperidine)-1-sulfonamido)benzoate

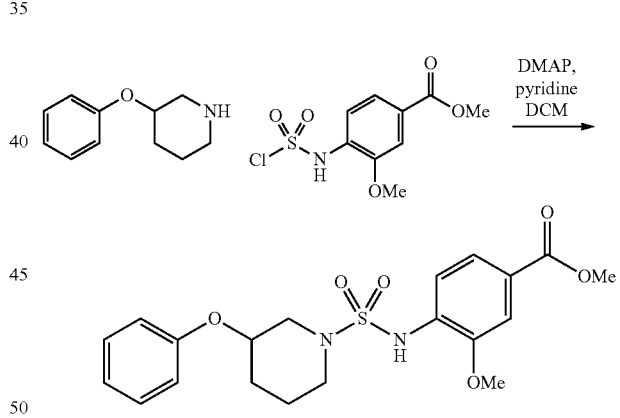

To a mixture of 3-phenoxypiperidine (33 mg, 0.186 mmol), methyl 4-((chlorosulfonyl)amino)-3-methoxybenzoate (67.7 mg, 0.242 mmol) in DCM (1.5 ml) was added DMAP (2.275 mg, 0.019 mmol), pyridine (60.2 μl, 0.745 mmol). The resulting mixture was stirred at RT for 18 h, and the mixture was concentrated, diluted with EtOAc, washed with HCl (1M), water, brine, dried, filtered and concentrated. The residue was purified by flash column chromatography on silica gel eluting with 0-30% EtOAc/cyclohexane to give methyl 3-methoxy-4-((3-phenoxypiperidine)-1-sulfonamido)benzoate (13 mg, 0.031 mmol, 16.6% yield). LC-MS (ES, m/z): 420.9 [M+H]$^+$; $^1$H NMR (400 MHz, Chloroform-d) δ 7.98 (d, J=1.8 Hz, 1H), 7.57-7.49 (m, 1H), 7.28 (d, J=3.7 Hz, 2H), 6.99 (tt, J=7.2, 1.1 Hz, 1H), 6.93-6.85 (m, 2H), 4.36 (tt, J=8.2, 3.9 Hz, 1H), 3.97 (s, 3H), 3.90 (s, 3H), 3.82 (dd, J=11.9, 3.9 Hz, 1H), 3.55

(dt, J=9.8, 4.4 Hz, 1H), 2.84 (td, J=11.5, 11.0, 8.6 Hz, 2H), 2.15-2.01 (m, 1H), 1.97-1.85 (m, 1H), 1.77-1.51 (m, 2H).

Step 4. Synthesis of 3-methoxy-4-((3-phenoxypiperidine)-1-sulfonamido)benzoic acid 3-methoxy-4-((3-phenoxypiperidine)-1-sulfonamido)benzoic acid was synthesized in a similar way as in step 2 of synthesis of Example 281. LC-MS (ES, m/z): 405.1 [M−H]⁻; ¹H NMR (400 MHz, Chloroform-d) δ 7.98 (d, J=1.7 Hz, 1H), 7.45 (d, J=1.8 Hz, 1H), 7.27-7.12 (m, 2H), 6.94-6.85 (m, 2H), 6.85-6.77 (m, 2H), 4.28 (tt, J=8.1, 3.8 Hz, 1H), 3.88 (s, 3H), 3.72 (dd, J=11.9, 3.8 Hz, 1H), 3.44 (dd, J=11.3, 5.4 Hz, 1H), 2.86-2.70 (m, 2H), 1.97 (d, J=3.5 Hz, 1H), 1.89-1.74 (m, 1H), 1.69-1.45 (m, 2H).

Example 326: 4-((4'-cyclohexyl-2-fluoro-[1,1'-biphenyl])-4-sulfonamido)-3-methoxybenzoic acid

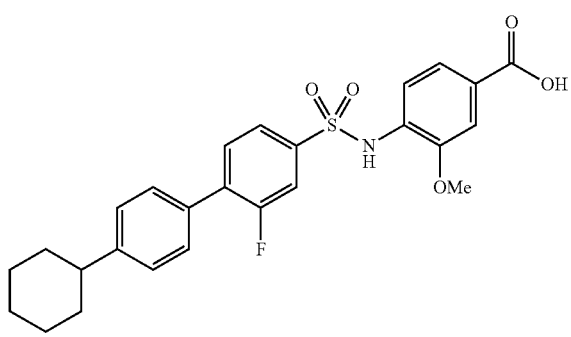 [SMILES: COc1cc(C(=O)O)ccc1NS(=O)(=O)c1ccc(-c2ccc(C3CCCCC3)cc2)c(F)c1]

Step 1. Synthesis of methyl 4-((4-bromo-3-fluorophenyl)sulfonamido)-3-methoxybenzoate

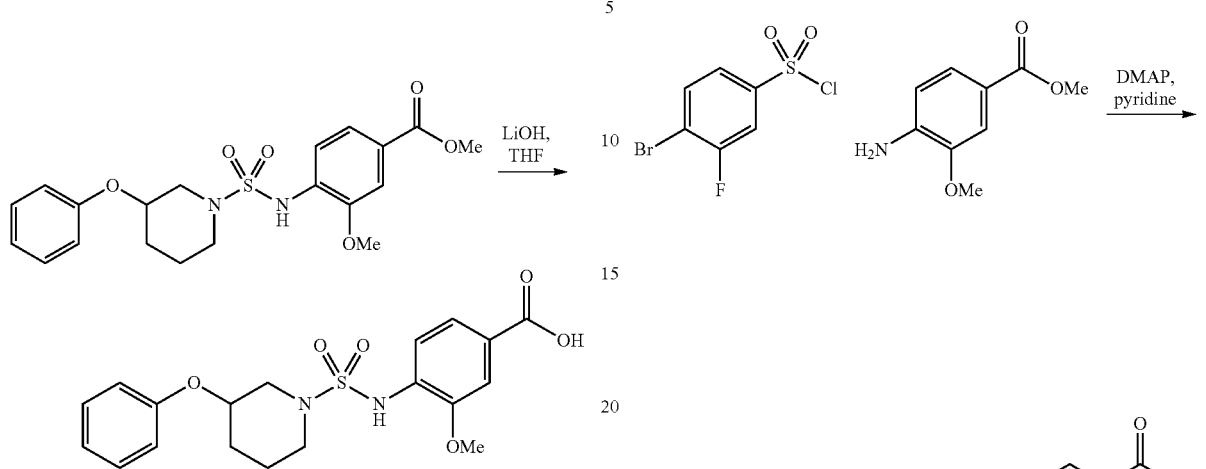

To a mixture of methyl 4-amino-3-methoxybenzoate (459 mg, 2.53 mmol), 4-bromo-3-fluorobenzenesulfonyl chloride (630 mg, 2.303 mmol) in DCM (6 ml) was added pyridine (745 µl, 9.21 mmol) and DMAP (28.1 mg, 0.230 mmol). The resulting mixture was stirred at RT for 18 h, then concentrated. The residue was dissolved in EtOAc, washed with HCl (1M), water, brine, dried, filtered, and concentrated. The residue was purified via column chromatography on silica gel eluting with 0-50% EtOAc/cyclohexane to give methyl 4-((4-bromo-3-fluorophenyl)sulfonamido)-3-methoxybenzoate (879 mg, 2.102 mmol, 91% yield) as white solid. LC-MS (ES, m/z): 418.1 [M−H]⁻; ¹H NMR (500 MHz, Chloroform-d) δ 7.60 (ddd, J=8.4, 4.1, 2.4 Hz, 2H), 7.55-7.51 (m, 2H), 7.46-7.41 (m, 2H), 7.26 (s, 1H), 3.86 (s, 3H), 3.79 (s, 3H).

Representative Procedure for Suzuki Coupling

Step 2. Synthesis of methyl 4-((4'-cyclohexyl-2-fluoro-[1,1'-biphenyl])-4-sulfonamido)-3-methoxybenzoate

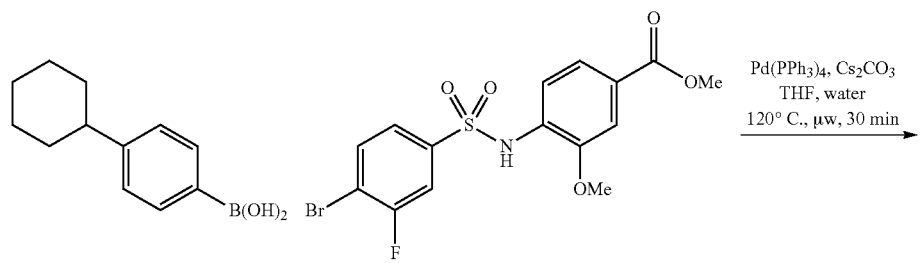

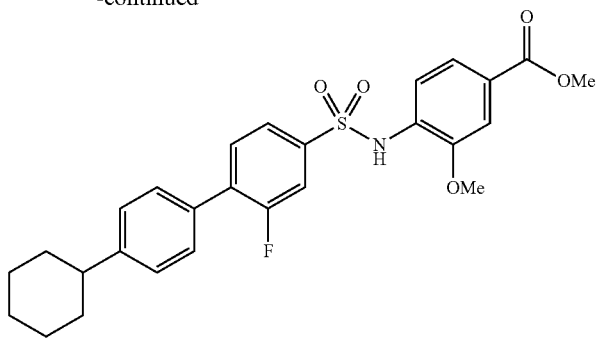

To a mixture of (4-cyclohexylphenyl)boronic acid (16.5 mg, 0.081 mmol), methyl 4-((4-bromo-3-fluorophenyl)sulfonamido)-3-methoxybenzoate (37.2 mg, 0.089 mmol), Pd(Ph3p)4 (9.34 mg, 8.09 μmol) and cesium carbonate (31.6 mg, 0.097 mmol) was added THF (0.6 ml) and Water (0.15 ml). The resulting mixture was at 120° C. for 30 minutes in the microwave reactor. The mixture was diluted with EtAOc/HCl (1M) and the organic layer was separated, washed with water, brine, dried, filtered and concentrated and the residue was purified via column chromatography on silica gel eluting with 0-50% EtOAc/cyclohexane to give methyl 4-((4'-cyclohexyl-2-fluoro-[1,1'-biphenyl])-4-sulfonamido)-3-methoxybenzoate (31 mg, 0.062 mmol, 77% yield). LC-MS (ES, m/z): 496.2 [M−H]⁻.

Step 3. Synthesis of 4-((4'-cyclohexyl-2-fluoro-[1,1'-biphenyl])-4-sulfonamido)-3-methoxybenzoic acid

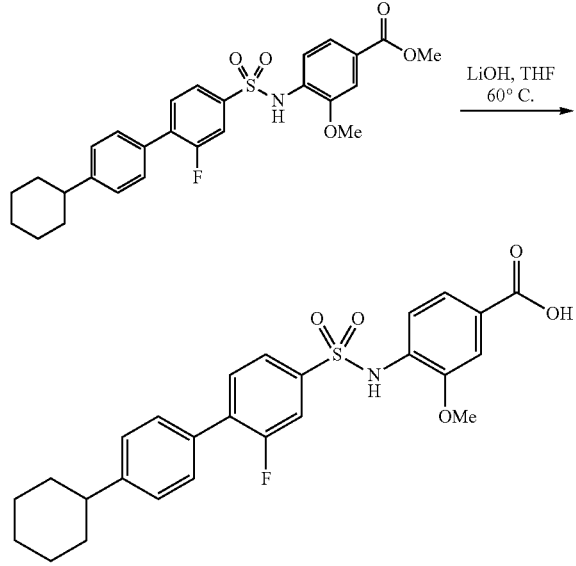

To methyl 4-((4'-cyclohexyl-2-fluoro-[1,1'-biphenyl])-4-sulfonamido)-3-methoxybenzoate (31 mg, 0.062 mmol) in Tetrahydrofuran (1 ml) was added LiOH (1M) (498 μl, 0.498 mmol) and the resulting mixture was stirred at 60° C. for 24 h. The reaction was quenched with HCl (1M) and diluted with EtOAc. The organic layers were separated, washed with water, brine, dried, filtered, and concentrated. The residue was purified via column chromatography on silica gel eluting with 0-60% acetone/cyclohexane to give 4-((4'-cyclohexyl-2-fluoro-[1,1'-biphenyl])-4-sulfonamido)-3-methoxybenzoic acid (24 mg, 0.050 mmol, 80% yield) as white solid. LC-MS (ES, m/z): 582.2 [M−H]⁻; ¹H NMR (400 MHz, Methanol-d4) δ 7.75 (s, 0.5H), 7.63-7.58 (m, 3H), 7.57 (s, 0.5H), 7.56-7.50 (m, 1H), 7.48 (d, J=1.7 Hz, 1H), 7.45-7.41 (m, 2H), 7.30-7.24 (m, 2H), 3.73 (s, 3H), 2.59-2.46 (m, 1H), 1.86 (s, 5H), 1.74 (t, J=12.0 Hz, 1H), 1.51-1.17 (m, 5H).

Example 328: 4-((N-(2-(4-fluorophenyl)benzo[d]thiazol-6-yl)sulfamoyl)amino)-3-methoxybenzoic acid

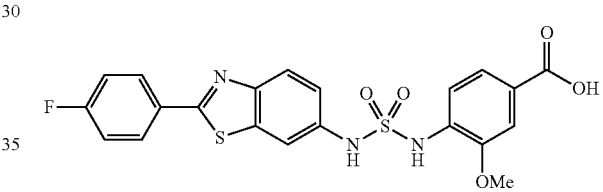

Step 1. Synthesis of methyl 4-((N-(2-chlorobenzo[d]thiazol-6-yl)sulfamoyl)amino)-3-methoxybenzoate

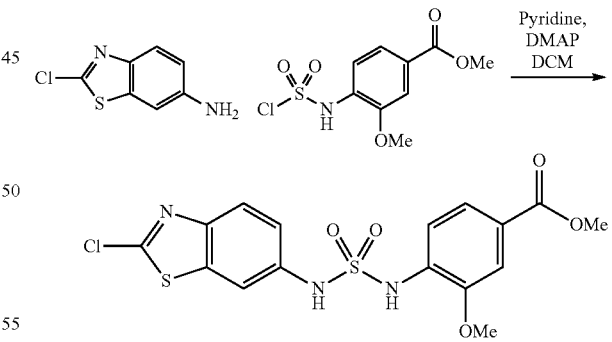

To a mixture of 2-chlorobenzo[d]thiazol-6-amine (70 mg, 0.379 mmol), methyl 4-((chlorosulfonyl)amino)-3-methoxybenzoate (138 mg, 0.493 mmol) in DCM (3 ml) was added pyridine (123 μl, 1.516 mmol) and DMAP (2.316 mg, 0.019 mmol). The resulting mixture was stirred at RT for 18 h. The mixture was concentrated, and the residue was purified flash column chromatography on silica gel eluting with 0-60% EtOAc/cyclohexane to give methyl 4-((N-(2-chlorobenzo[d]thiazol-6-yl)sulfamoyl)amino)-3-methoxybenzoate (38 mg, 0.089 mmol, 23.43% yield).

Step 2. Synthesis of 4-((N-(2-(4-fluorophenyl)benzo[d]thiazol-6-yl)sulfamoyl)amino)-3-methoxybenzoic acid

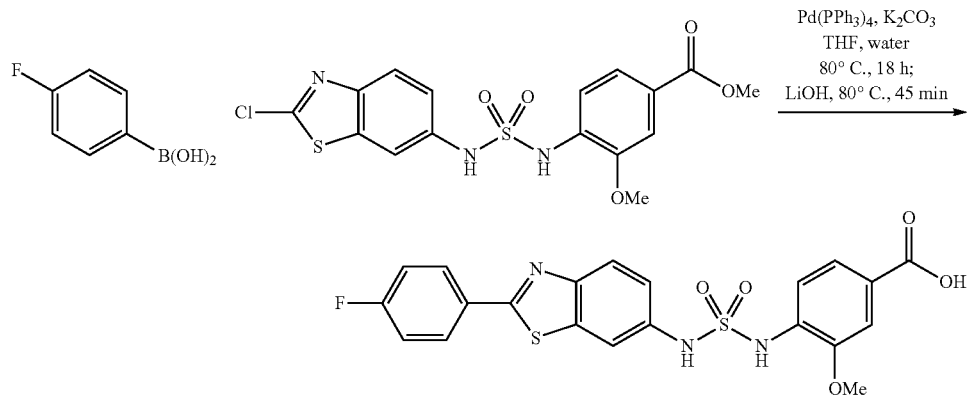

To methyl 4-((N-(2-chlorobenzo[d]thiazol-6-yl)sulfamoyl)amino)-3-methoxybenzoate (38 mg, 0.089 mmol), (4-fluorophenyl)boronic acid (18.64 mg, 0.133 mmol), potassium carbonate (49.1 mg, 0.355 mmol) in tetrahydrofuran (1 ml) and water (1.000 ml) was added Pd(Ph3p)4 (10.26 mg, 8.88 μmol) and the resulting mixture was stirred at 80° C. for 18 h. To the mixture was added LiOH (355 μl, 0.355 mmol) and stirred at 80° C. for 45 min until crude MS showed all the ester was converted to the acid. The mixture was cooled down to RT, acidified with 1N HCl, a lot of precipitates formed. To the mixture was added MTBE/water and the solid was collected to give 4-((N-(2-(4-fluorophenyl)benzo[d]thiazol-6-yl)sulfamoyl)amino)-3-methoxybenzoic acid (22 mg, 0.046 mmol, 52.3% yield). LC-MS (ES, m/z): 474.06 [M+H]+.

Example 331: 4-(((3aR,6aS)-5-(tert-butoxycarbonyl)octahydropyrrolo[3,4-c]pyrrole)-2-sulfonamido)-3-methoxybenzoic acid

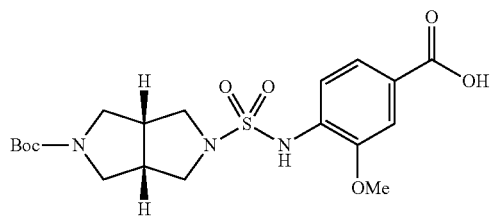 [SMILES: COc1cc(C(=O)O)ccc1NS(=O)(=O)N1C[C@H]2CN(C(=O)OC(C)(C)C)C[C@H]2C1]

Step 1. Synthesis of methyl 4-((fluorosulfonyl)amino)-3-methoxybenzoate

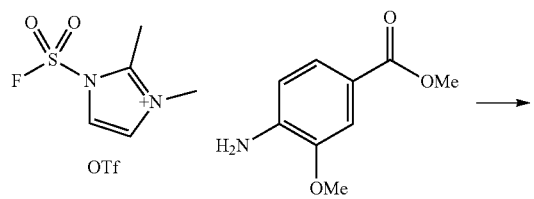

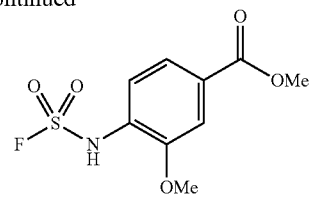

To methyl 4-amino-3-methoxybenzoate (300 mg, 1.656 mmol) in DCM (2 ml) at 0° C. was added ((trifluoromethyl)sulfonyl)-1-oxidane, 1-(fluorosulfonyl)-2,3-dimethyl-1H-imidazol-3-ium salt (571 mg, 1.738 mmol) and the resulting mixture was stirred for 20 min, then warmed up to RT and stirred for 2 h. the mixture was diluted with dichloromethane (100 ml), washed with 0.1 M hydrochloric acid and brine to give methyl 4-((fluorosulfonyl)amino)-3-methoxybenzoate (361 mg, 1.371 mmol, 83% yield) as reddish solid. LC-MS (ES, m/z): 262.01[M−H]−; This material was directly used to next step without further purification. 1H NMR (500 MHz, Chloroform-d) δ 7.69 (dd, J=8.4, 1.7 Hz, 1H), 7.58 (d, J=1.8 Hz, 1H), 7.55-7.49 (d, J=4.0 Hz, 1H), 3.95 (s, 3H), 3.90 (s, 3H).

Step 2. Synthesis of tert-butyl (3aR,6aS)-5-(N-(2-methoxy-4-(methoxycarbonyl)phenyl)sulfamoyl)hexahydropyrrolo[3,4-c]pyrrole-2(1H)-carboxylate

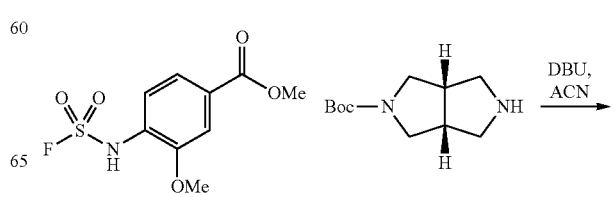

-continued

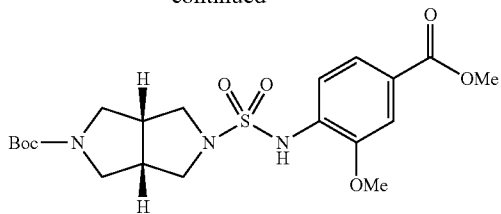

To methyl 4-((fluorosulfonyl)amino)-3-methoxybenzoate (55 mg, 0.209 mmol) and tert-butyl (3aR,6aS)-hexahydropyrrolo[3,4-c]pyrrole-2(1H)-carboxylate (26.6 mg, 0.125 mmol) in acetonitrile (1 ml) was added DBU (63.0 μl, 0.418 mmol) and the resulting mixture was stirred at 50° C. for 18 h. The mixture was concentrated, and the residue was purified via column chromatography on silica gel eluting with 0-50% EtOAc/cyclohexane to give tert-butyl (3aR,6aS)-5-(N-(2-methoxy-4-(methoxycarbonyl)phenyl)sulfamoyl)hexahydropyrrolo[3,4-c]pyrrole-2(1H)-carboxylate (32 mg, 0.070 mmol, 56% yield) as white solid. LC-MS (ES, m/z): 454.1 [M−H]−; $^1$H NMR (400 MHz, Chloroform-d) δ 7.59 (dd, J=8.4, 1.7 Hz, 1H), 7.48 (d, J=1.8 Hz, 1H), 7.44 (d, J=8.4 Hz, 1H), 7.11 (s, 1H), 3.87 (s, 3H), 3.83 (s, 3H), 3.55-3.37 (m, 3H), 3.21-2.90 (m, 5H), 2.88-2.60 (m, 2H), 1.35 (s, 9H).

Step 3. Synthesis of 4-(((3aR,6aS)-5-(tert-butoxycarbonyl)octahydropyrrolo[3,4-c]pyrrole)-2-sulfonamido)-3-methoxybenzoic acid (example 331)

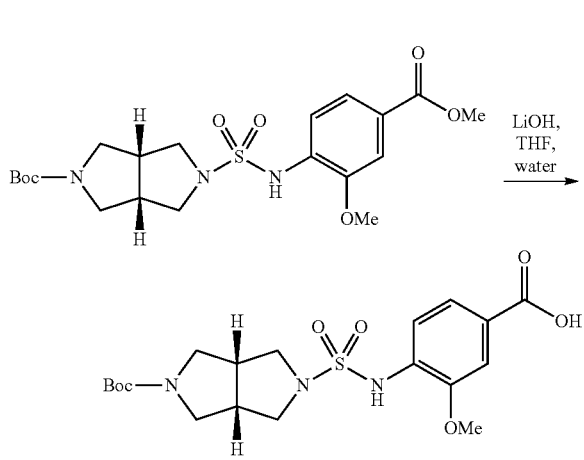

To a solution of tert-butyl (3aR,6aS)-5-(N-(2-methoxy-4-(methoxycarbonyl)phenyl)-sulfamoyl)hexahydropyrrolo[3,4-c]pyrrole-2(1H)-carboxylate (32 mg, 0.070 mmol) in Tetrahydrofuran (1 ml) was added LiOH (1 M) (562 μl, 0.562 mmol) and the resulting mixture was stirred at 60° C. for 18 h. The mixture was diluted with EtOAc and HCl (1M). The organic layer was separated, washed with water, brine, dried, filtered and concentrated, and the residue was purified via column chromatography on silica gel eluting with 0-50% EtOAc/cyclohexane to give 4-(((3aR,6aS)-5-(tert-butoxycarbonyl)octahydropyrrolo[3,4-c]pyrrole)-2-sulfonamido)-3-methoxybenzoic acid (32 mg). LC-MS (ES, m/z): 440.2 [M−H]−; $^1$H NMR (500 MHz, Chloroform-d) δ 7.73 (dd, J=8.4, 1.8 Hz, 1H), 7.58 (d, J=1.8 Hz, 1H), 7.53 (d, J=8.4 Hz, 1H), 7.27 (s, 1H), 3.95 (s, 3H), 3.55 (ddd, J=17.5, 10.4, 6.7 Hz, 4H), 3.26-3.04 (m, 4H), 2.86 (ddt, J=10.2, 7.9, 3.8 Hz, 2H), 1.42 (s, 9H).

Example 335: 4-((4-(cyclopentylethynyl)-3-fluorophenyl)sulfonamido)-3-methoxybenzoic acid

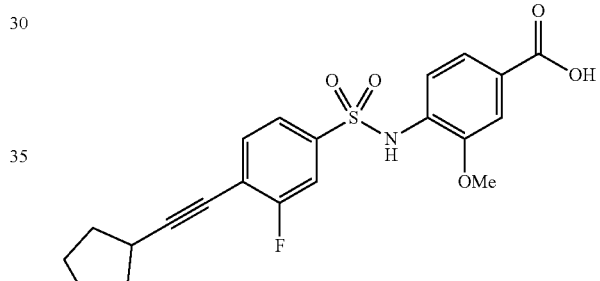

Representative One-Pot Procedure for Sonogashira Coupling and Ester Hydrolysis.

Step 1. Synthesis of 4-((4-(cyclopentylethynyl)-3-fluorophenyl)sulfonamido)-3-methoxybenzoic acid

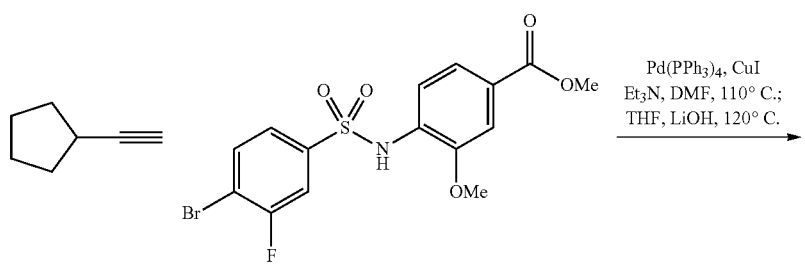

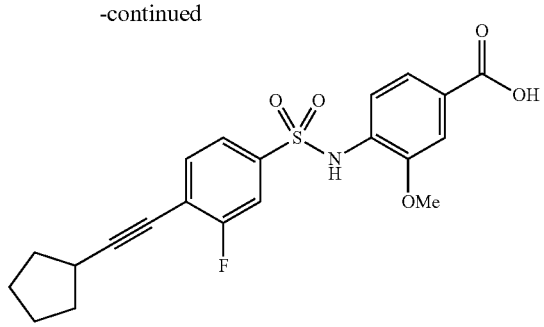

To a mixture of methyl 4-((4-bromo-3-fluorophenyl)sulfonamido)-3-methoxybenzoate (60 mg, 0.143 mmol), copper(I) iodide (5.46 mg, 0.029 mmol) and Pd(Ph₃P)₄ (16.58 mg, 0.014 mmol) in DMF (1 ml) was added ethynylcyclopentane (20.26 mg, 0.215 mmol) and TEA (400 μl, 2.87 mmol). The resulting mixture was stirred in microwave reactor at 110° C. for 2 h until the starting material was consumed. The mixture was diluted with EtAOc/HCl (1M) and the organic layer was separated, washed with water, brine, dried, filtered and concentrated.

The residue was dissolved in THF (2 mL) and LiOH (1M) (1148 μl, 1.148 mmol) was added. The resulting mixture was stirred at 120° C. for 30 min in microwave reactor and then diluted with EtOAc/HCl (1M), the organic layer was separated, washed with water, brine, dried, filtered and concentrated and the residue was purified via column chromatography on silica gel eluting with 0-50% EtOAc/cyclohexane to give 4-((4-(cyclopentylethynyl)-3-fluorophenyl)sulfonamido)-3-methoxybenzoic acid (35 mg, 0.084 mmol, 58.4% yield). LC-MS (ES, m/z): 416.1 [M−H]⁻; ¹H NMR (500 MHz, Chloroform-d) δ 7.65 (dd, J=8.5, 1.7 Hz, 1H), 7.56-7.51 (m, 1H), 7.50-7.44 (m, 2H), 7.38 (dd, J=8.3, 6.6 Hz, 1H), 7.30 (s, 1H), 3.80 (s, 3H), 2.82 (p, J=7.5 Hz, 1H), 2.00-1.90 (m, 2H), 1.81-1.61 (m, 2H), 1.62-1.48 (m, 2H).

Example 343: 4-((3-fluoro-2',3',4',5'-tetrahydro-[1,1':4',1''-terphenyl])-4-sulfonamido)-3-methoxybenzoic acid

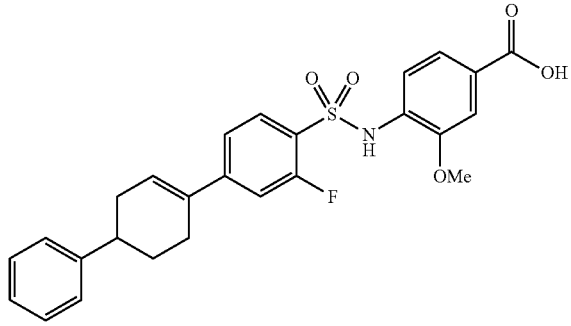 [SMILES: COc1cc(C(=O)O)ccc1NS(=O)(=O)c1ccc(C2=CCC(c3ccccc3)CC2)cc1F]

Representative One-Pot Procedure for Suzuki Coupling of Vinyl Borinic Ester Followed by Ester Hydrolysis.

To a mixture of 4,4,5,5-tetramethyl-2-(1,2,3,6-tetrahydro-[1,1'-biphenyl]-4-yl)-1,3,2-dioxaborolane (32.1 mg, 0.113 mmol), methyl 4-((4-bromo-2-fluorophenyl)sulfonamido)-3-methoxybenzoate (43 mg, 0.103 mmol), cesium carbonate (40.2 mg, 0.123 mmol) in Tetrahydrofuran (1 ml) and Water (0.500 ml) was added Pd(Ph3p)4 (11.88 mg, 10.28 μmol) and the resulting mixture was stirred at 120° C. for 45 min in microwave reactor. To the mixture was added LiOH (1M) (823 μl, 0.823 mmol) and the resulting mixture was stirred at 120° C. for another 30 min in microwave reactor. The mixture was diluted with EtOAc/1N HCl, the organic layer was separated, washed with water, brine, dried, filtered and concentrated. The residue was purified via column chromatography on silica gel eluting with 0-50% acetone/cyclohexane to give 4-((3-fluoro-2',3',4',5'-tetrahydro-[1,1':4',1''-terphenyl])-4-sulfonamido)-3-methoxybenzoic acid (27 mg, 0.056 mmol, 54.5% yield). LC-MS (ES, m/z): 480.1 [M−H]⁻. H NMR (400 MHz, Chloroform-d) δ 7.78 (t, J=8.0 Hz, 1H), 7.62 (s, 1H), 7.56 (dd, J=8.4, 1.7 Hz, 1H), 7.24 (dd, J=8.2, 6.9 Hz, 2H), 7.20-7.12 (m, 4H), 7.08 (dd, J=12.1, 1.7 Hz, 1H), 6.28 (dt, J=4.6, 2.4 Hz, 1H), 3.83 (s, 3H), 2.77 (tt, J=11.1, 2.8 Hz, 1H), 2.55-2.34 (m, 3H), 2.34-2.17 (m, 1H), 2.08-1.99 (m, 1H), 1.90-1.67 (m, 1H).

Example 353: 4-((2-(4-(4-(tert-butyl)cyclohexyl)phenyl)thiazole)-4-sulfonamido)-3-methoxybenzoic acid

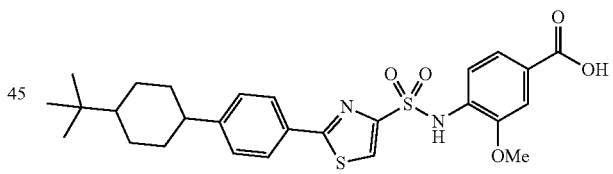

Step 1. Synthesis of 4,5,6,7-tetrachloro-1,3-dioxoisoindolin-2-yl 4-(tert-butyl)cyclohexane-1-carboxylate

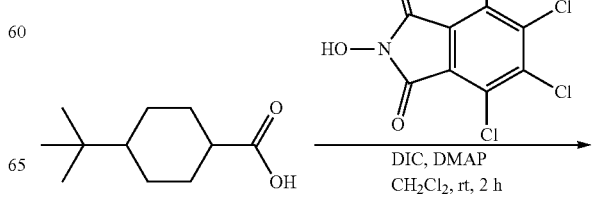

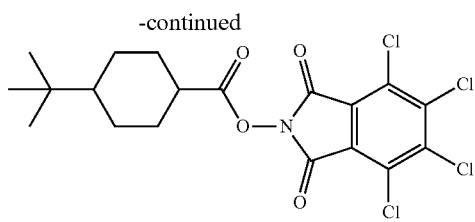

To a solution of 4-(tert-butyl)cyclohexane-1-carboxylic acid (700 mg, 3.8 mmol, 1.0 equiv), 4,5,6,7-tetrachloro-2-hydroxyisoindoline-1,3-dione (1.14 g, 3.8 mmol, 1.0 equiv), 4-dimethylaminopyridine (46.4 mg, 0.38 mmol, 0.1 equiv) in DCM (19 mL) was added diisopropylcarbodiimide (0.65 mL, 4.2 mmol, 1.1 eq.) dropwise via syringe and the resulting mixture was stirred for 2 h at room temperature. Then, the crude mixture was filtered through silica and rinsed with additional DCM. Purification was done by flash column chromatography eluting with cyclohexane/EtOAc (0% EtOAc→10% EtOAc) to isolate 4,5,6,7-tetrachloro-1,3-dioxoisoindolin-2-yl 4-(tert-butyl)cyclohexane-1-carboxylate (1.33 g, 75% yield) as white solid. $^1$H NMR (400 MHz, Chloroform-d) δ 3.13-3.03 (m, 1H, one diastereomer), 2.61 (tt, J=12.3, 3.6 Hz, 1H, other diastereomer), 2.40-2.17 (m, 2H), 1.98-1.82 (m, 1H), 1.81-1.50 (m, 3H), 1.32 (qd, J=13.3, 3.4 Hz, 1H), 1.17-0.96 (m, 2H), 0.87 (s, 9H, one diastereomer), 0.86 (S, 9H, other diastereomer).

Step 2. Synthesis of 1-bromo-4-(4-(tert-butyl)cyclohexyl)benzene

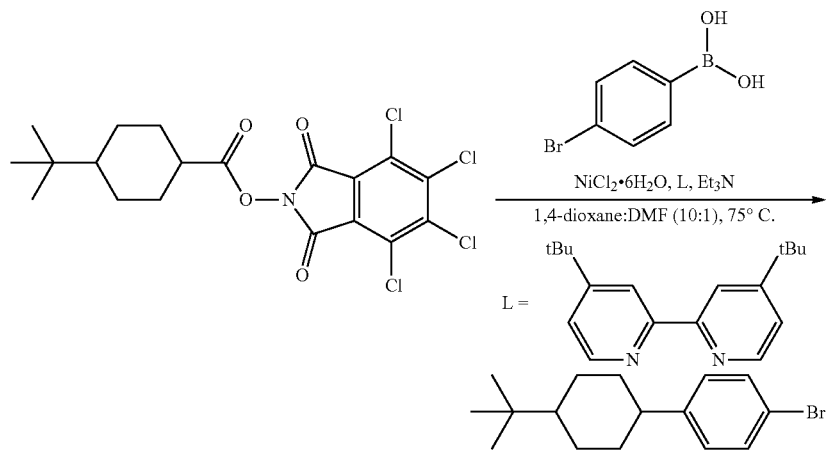

4,5,6,7-tetrachloro-1,3-dioxoisoindolin-2-yl 4-(tert-butyl)cyclohexane-1-carboxylate (1.33 g, 2.85 mmol) and (4-bromophenyl)boronic acid (1.715 g, 8.54 mmol) was taken in a 250 mL round bottom flask and flask was then evacuated and backfilled with nitrogen via Schlenk line (repeated three times). Dioxane (114 mL) was added, and the resulting mixture was stirred at room temperature. After 1 min, triethylamine (3.97 mL, 28.5 mmol) was added drop wise and stirred for 2 min until the solution become clear. Then, a solution of NiCl$_2$·6H$_2$O/4,4'-di-tert-butyl-2,2'-bipyridine (0.05M in DMF, 11.4 mL, 20 mol %) was added and the flask was heated at 75° C. in an oil bath for 12 h. [0.05 M of NiCl$_2$·6H$_2$O/ligand in DMF: NiCl$_2$·6H$_2$O (142.6 mg, 0.3 mmol) and 4,4'-di-tert-butyl-2,2'-bipyridine (161 mg, 0.3 mmol) were taken in a round bottom flask and flask was then evacuated and backfilled with nitrogen via Schlenk line (repeated three times). DMF (12.0 mL) was added, and the resulting mixture was stirred at room temperature for 3 h to give a homogeneous green solution.

Then, reaction mixture was cooled down to room temperature and diluted with ethyl acetate and washed with 0.1 N HCl (aq), water and brine successively. The organic layer was dried over Na$_2$SO$_4$ and concentrated under vacuum. The crude product was purified by flash column chromatography eluting with cyclohexane to isolate 1-bromo-4-(4-(tert-butyl)cyclohexyl)benzene (260 mg, 30.9% yield). $^1$H NMR (400 MHz, Chloroform-d) δ 7.46-7.35 (m, 2H), 7.25-7.19 (m, 2H, one diastereomer), 7.12-7.05 (m, 2H, other diastereomer), 3.03-2.94 (m, 1H, one diastereomer), 2.41 (tt, J=12.3, 3.4 Hz, 1H, other diastereomer), 2.28-1.55 (m, 4H), 1.44-1.32 (m, 2H), 1.32-1.00 (m, 3H), 0.89 (s, 9H, one diastereomer), 0.80 (s, 9H, other diastereomer).

Step 3. Synthesis of 2-(4-(4-(tert-butyl)cyclohexyl)phenyl)-4,4,5,5-tetramethyl-1,3,2-dioxaborolane

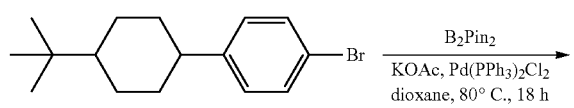

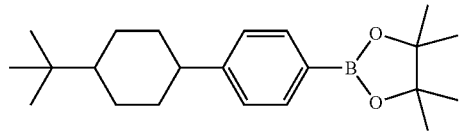

To a solution of 1-bromo-4-(4-(tert-butyl)cyclohexyl)benzene (260 mg, 0.881 mmol), 4,4,4',4',5,5,5',5'-octamethyl-2,2'-bi(1,3,2-dioxaborolane) (224 mg, 0.881 mmol) in dioxane (8.81 mL) was dichlorobis(triphenylphosphine)palladium (309 mg, 0.440 mmol) and potassium acetate (346 mg, 3.52 mmol) and resulting mixture was stirred at 80° C. for 18 hours. Then, crude was filtered through celite and rinsed with DCM. The solvent was removed under reduced pressure, and purified by column chromatography eluting with EtOAc/cyclohexane (0% EtOAc→20% EtOAc) to afford 2-(4-(4-(tert-butyl)cyclohexyl)phenyl)-4,4,5,5-tetramethyl-1,3,2-dioxaborolane (85 mg, 28.2% yield).

Step 4. Synthesis of methyl 4-((2-(4-(4-(tert-butyl)cyclohexyl)phenyl)thiazole)-4-sulfonamido)-3-methoxybenzoate

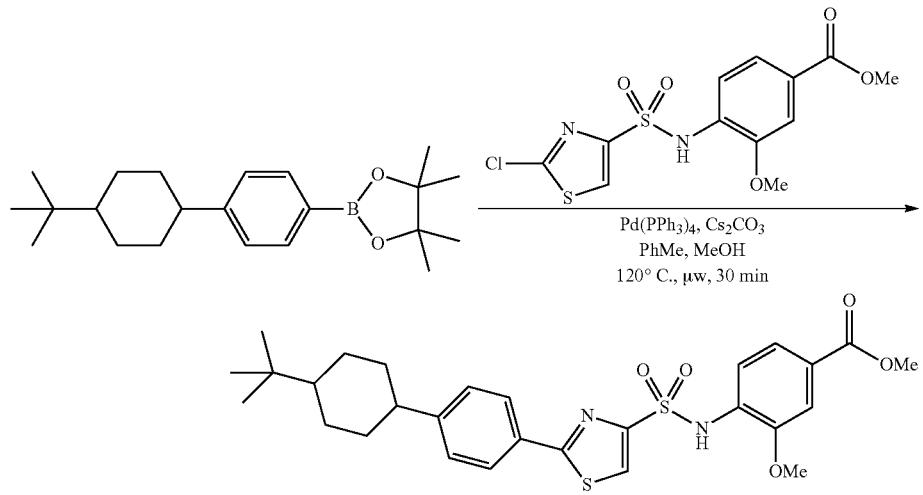

To a mixture of methyl 4-((2-chlorothiazole)-4-sulfonamido)-3-methoxybenzoate (30.0 mg, 0.083 mmol), 2-(4-(4-(tert-butyl)cyclohexyl)phenyl)-4,4,5,5-tetramethyl-1,3,2-dioxaborolane (36.8 mg, 0.107 mmol), and cesium carbonate (32.3 mg, 0.099 mmol) in PhCH₃ (0.484 mL)/MeOH (0.129 mL) was added Pd(PPh₃)₄ (9.56 mg, 0.0083 mmol) and the resulting mixture was heated at 120° C. for 30 min under microwave condition. The reaction mixture was filtered through celite, rinsing with DCM. The crude was purified by flash column chromatography eluting with cyclohexane/EtOAc (0% EtOAc→30% EtOAc) to isolate methyl 4-((2-(4-(4-(tert-butyl)cyclohexyl)phenyl)thiazole)-4-sulfonamido)-3-methoxybenzoate (13.3 mg, 29.6% yield) as white solid. ESI-MS m/z: 543.4, [M+H]⁺; ¹H NMR (400 MHz, Chloroform-d) δ 8.00 (s, 1H, one diastereomer), 7.98 (s, 1H, other diastereomer), 7.85-7.75 (m, 2H), 7.72-7.59 (m, 3H), 7.49-7.38 (m, 2H), 7.29-7.23 (m, 1H), 3.91-3.82 (m, 6H), 3.12-3.02 (m, 1H, one diastereomer), 2.56-2.42 (m, 1H, other diastereomer), 2.33-2.19 (m, 1H), 2.01-1.39 (m, 5H), 1.35-1.02 (m, 3H), 0.89 (s, 9H, one diastereomer), 0.79 (s, 9H, other diastereomer).

Step 5. Synthesis of 4-((2-(4-(4-(tert-butyl)cyclohexyl)phenyl)thiazole)-4-sulfonamido)-3-methoxybenzoic acid

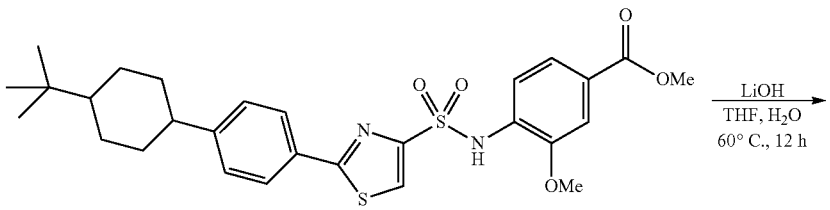

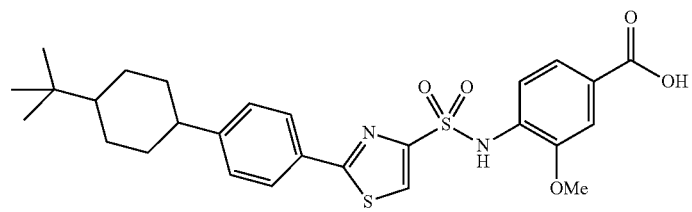

To a solution of methyl 4-((2-(4-(4-(tert-butyl)cyclohexyl)phenyl)thiazole)-4-sulfonamido)-3-methoxybenzoate (13.2 mg, 0.024 mmol) in THF (0.486 mL) was added lithium hydroxide (1M in water) (0.12 mL, 0.122 mmol) and the resulting mixture was heated at 60° C. for 12 h. Then reaction mixture was allowed to cool to room temperature and quenched with 1N HCl and extracted with EtOAc (×2). Combined organic layers was washed with brine and dried over Na$_2$SO$_4$, filtered, and concentrated. The crude was purified through reversed phase flash column chromatography eluting with water/acetonitrile (10% acetonitrile→90% acetonitrile) to provide 4-((2-(4-(4-(tert-butyl)cyclohexyl)phenyl)thiazole)-4-sulfonamido)-3-methoxybenzoic acid (7.6 mg, 59.1% yield). ESI-MS m/z: 529.5, [M+H]$^+$; $^1$H NMR (400 MHz, Chloroform-d) δ 8.02 (s, 1H, one diastereomer), 8.01 (s, 1H, other diastereomer), 7.84-7.76 (m, 2H), 7.75-7.39 (m, 4H), 7.30-7.22 (m, 1H), 3.87 (s, 3H, one diastereomer), 3.86 (s, 3H, other diastereomer), 3.10-3.02 (m, 1H, one diastereomer), 2.56-2.42 (m, 1H, other diastereomer), 2.32-1.38 (m, 6H), 1.33-1.02 (m, 3H), 0.88 (s, 9H, one diastereomer), 0.78 (s, 9H, other diastereomer).

Example 359: 3-methoxy-4-((2-(1,2,3,6-tetrahydro-[1,1'-biphenyl]-4-yl)-5,6-dihydro-4H-pyrrolo[3,4-d]thiazole)-5-sulfonamido)benzoic acid

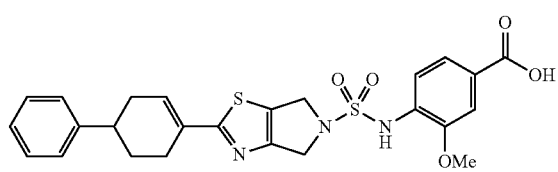 [SMILES: COc1cc(C(=O)O)ccc1NS(=O)(=O)N1Cc2nc(C3=CCC(c4ccccc4)CC3)sc2C1]

Step 1. Synthesis of methyl 4-((2-bromo-5,6-dihydro-4H-pyrrolo[3,4-d]thiazole)-5-sulfonamido)-3-methoxybenzoate

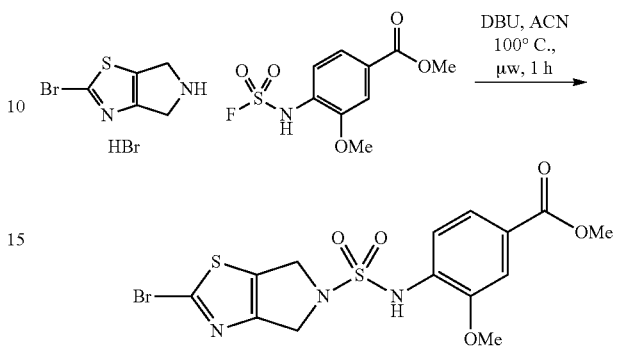

To methyl 4-((fluorosulfonyl)amino)-3-methoxybenzoate (288 mg, 1.093 mmol), 2-bromo-5,6-dihydro-4H-pyrrolo[3,4-d]thiazole hydrobromide (250 mg, 0.874 mmol) in acetonitrile (3 ml) was added DBU (395 μl, 2.62 mmol) and the resulting mixture was stirred at 100° C. for 1.5 h in microwave reactor. The mixture was concentrated, and the residue was purified via column chromatography on silica gel eluting with 0-50% EtOAc/cyclohexane to give methyl 4-((2-bromo-5,6-dihydro-4H-pyrrolo[3,4-d]thiazole)-5-sulfonamido)-3-methoxybenzoate (241 mg, 0.538 mmol, 61.5% yield). ESI-MS m/z: 446.0, 448.0 [M−H]$^-$; $^1$H NMR (400 MHz, Chloroform-d) δ 7.62 (dd, J=8.4, 1.7 Hz, 1H), 7.54-7.44 (m, 2H), 7.21 (s, 1H), 4.61 (dd, J=4.5, 2.5 Hz, 2H), 4.54 (dd, J=4.4, 2.6 Hz, 2H), 3.87 (s, 3H), 3.86 (s, 3H).

Step 2. Synthesis of methyl 3-methoxy-4-((2-(1,2,3,6-tetrahydro-[1,1'-biphenyl]-4-yl)-5,6-dihydro-4H-pyrrolo[3,4-d]thiazole)-5-sulfonamido)benzoate

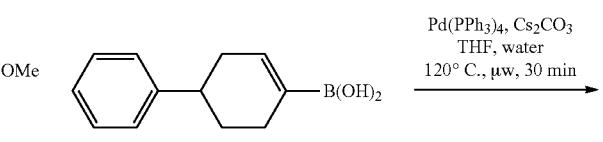

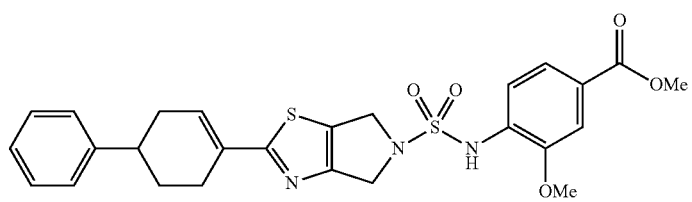

To a mixture of (1,2,3,6-tetrahydro-[1,1'-biphenyl]-4-yl) boronic acid (14.87 mg, 0.074 mmol), methyl 4-((2-bromo-5,6-dihydro-4H-pyrrolo[3,4-d]thiazole)-5-sulfonamido)-3-methoxybenzoate (30 mg, 0.067 mmol), cesium carbonate (26.2 mg, 0.080 mmol) in Tetrahydrofuran (1 ml) and Water (0.500 ml) was added Pd(PPh$_3$)$_4$ (7.73 mg, 6.69 μmol) and the resulting mixture was stirred at 120° C. for 30 min in microwave reactor. The mixture was diluted with EtOAc, washed with 1N HCl, water, brine, dried, filtered and concentrated. The residue was purified via column chromatography on silica gel eluting with 0-50% Acetone/cyclohexane to give methyl 3-methoxy-4-((2-(1,2,3,6-tetrahydro-[1,1'-biphenyl]-4-yl)-5,6-dihydro-4H-pyrrolo[3,4-d]thiazole)-5-sulfonamido)benzoate (22 mg, 0.042 mmol, 62.5% yield) as white solid. ESI-MS m/z: 524.1, [M–H]$^-$; $^1$H NMR (400 MHz, Chloroform-d) δ 7.58 (dd, J=8.4, 1.7 Hz, 1H), 7.50 (d, J=8.4 Hz, 1H), 7.44 (d, J=1.7 Hz, 1H), 7.32-7.08 (m, 5H), 6.65 (p, J=2.3 Hz, 1H), 4.61 (dd, J=4.4, 2.6 Hz, 2H), 4.50 (t, J=3.5 Hz, 2H), 3.83 (s, 3H), 3.82 (s, 3H), 2.81 (tt, J=11.0, 2.8 Hz, 1H), 2.72-2.59 (m, 1H), 2.58-2.42 (m, 2H), 2.36-2.24 (m, 1H), 2.04 (ddq, J=12.9, 5.3, 2.8 Hz, 1H), 1.90-1.68 (m, 1H).

Step 3. Synthesis of 3-methoxy-4-((2-(1,2,3,6-tetrahydro-[1,1'-biphenyl]-4-yl)-5,6-dihydro-4H-pyrrolo[3,4-d]thiazole)-5-sulfonamido)benzoic acid

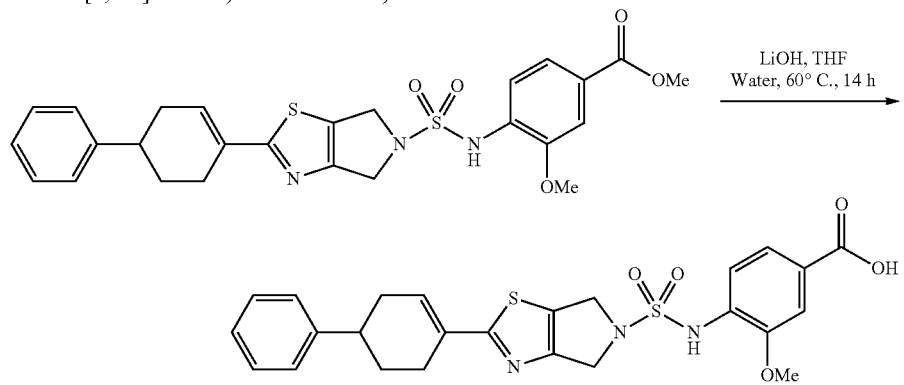

To methyl 3-methoxy-4-((2-(1,2,3,6-tetrahydro-[1,1'-biphenyl]-4-yl)-5,6-dihydro-4H-pyrrolo[3,4-d]thiazole)-5-sulfonamido)benzoate (9 mg, 0.017 mmol) in Tetrahydrofuran (0.6 ml) was added LiOH (1M, 137 μl, 0.137 mmol) and the resulting mixture was stirred at 60° C. for 14 h. The mixture was diluted with EtOAc/1N HCl and the organic layer was separated, washed with brine, dried, filtered and concentrated to give 3-methoxy-4-((2-(1,2,3,6-tetrahydro-[1,1'-biphenyl]-4-yl)-5,6-dihydro-4H-pyrrolo[3,4-d]thiaz-ole)-5-sulfonamido)benzoic acid (7.1 mg, 0.014 mmol, 81% yield) as white solid. ESI-MS m/z: 510.1, [M–H]$^-$.

Example 376: 3-methoxy-4-((2-(4-phenylcyclohexyl)-5,6-dihydro-4H-pyrrolo[3,4-d]thiazole)-5-sulfonamido)benzoic acid

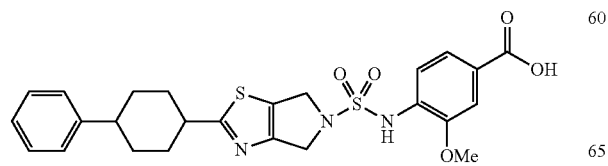

Synthesis of 3-methoxy-4-((2-(4-phenylcyclohexyl)-5,6-dihydro-4H-pyrrolo[3,4-d]thiazole)-5-sulfonamido)benzoic acid

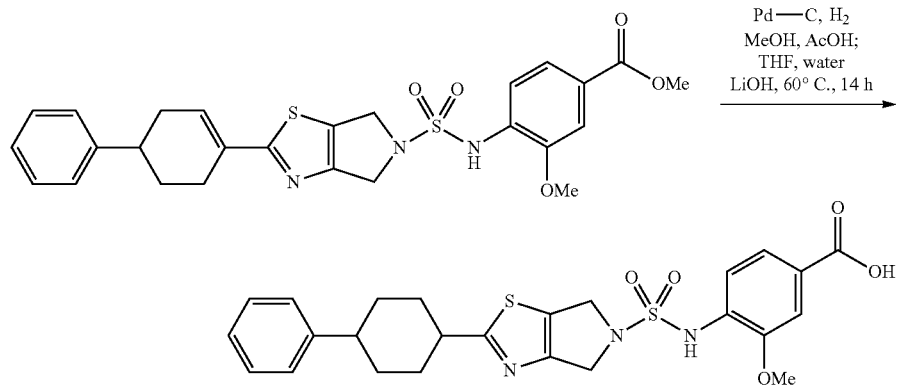

To methyl 3-methoxy-4-((2-(1,2,3,6-tetrahydro-[1,1'-biphenyl]-4-yl)-5,6-dihydro-4H-pyrrolo[3,4-d]thiazole)-5-sulfonamido)benzoate (12 mg, 0.023 mmol) and Pd—C (10%, 2.430 mg, 2.283 μmol) was added MeOH (0.8 ml) and the resulting mixture was stirred under $H_2$ balloon for 4 h. To the mixture was added Pd—C (10%, 24 mg), AcOH (0.1 ml) and the mixture was stirred under 60 PSI $H_2$ for 8 h. The mixture was filtered and concentrated. To this residue was added tetrahydrofuran (0.80 ml) and LiOH (228 μl, 0.228 mmol) and the resulting mixture was stirred at 60° C. for 14 h. The mixture was diluted with EtOAc, washed with 1N HCl, water, brine, dried, filtered and concentrated to give 3-methoxy-4-((2-(4-phenylcyclohexyl)-5,6-dihydro-4H-pyrrolo[3,4-d]thiazole)-5-sulfonamido)benzoic acid (6.5 mg, 0.013 mmol, 55.4% yield). ESI-MS m/z: 512.1, [M–H]⁻.

Example 377: 3-methoxy-4-((5-((1S,1's,4'S)-4'-propyl-[1,1'-bi(cyclohexan)]-3-en-4-yl)isoindoline)-2-sulfonamido)benzoic acid

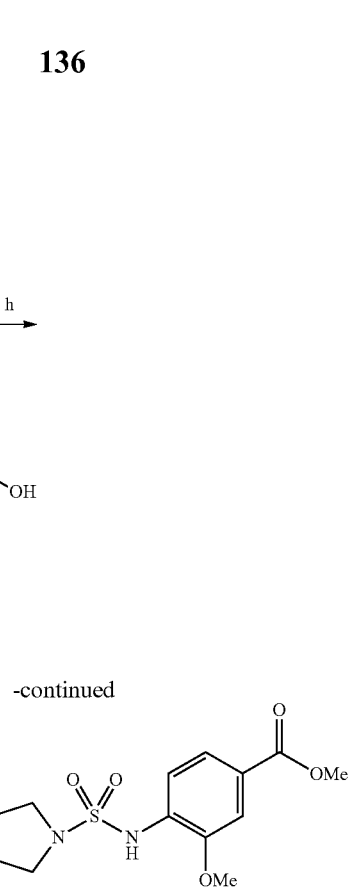

Step 1. Synthesis of methyl 4-((5-bromoisoindoline)-2-sulfonamido)-3-methoxybenzoate

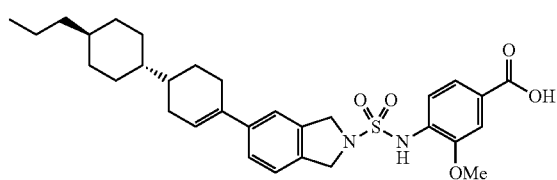 [SMILES: CCC[C@H]1CC[C@H](C2CC=C(c3ccc4c(c3)CN(S(=O)(=O)Nc3ccc(C(=O)O)cc3OC)C4)CC2)CC1]

To a mixture of 5-bromoisoindoline (350 mg, 1.767 mmol) and methyl 4-((fluorosulfonyl)amino)-3-methoxybenzoate (558 mg, 2.121 mmol) in acetonitrile (8 ml) was added DBU (1065 μl, 7.07 mmol) and the resulting mixture was stirred at 100° C. for 1 h in microwave reactor. The mixture was diluted with EtOAc, washed with 1N HCl, water, brine, dried, filtered and concentrated. The residue was purified via column chromatography on silica gel eluting with 0-35% EtOAc/cyclohexane to give methyl 4-((5-bromoisoindoline)-2-sulfonamido)-3-methoxybenzoate (401 mg, 0.909 mmol, 51.4% yield) as grey solid.

Step 2. Synthesis of 3-methoxy-4-((5-((1S,1's,4'S)-4'-propyl-[1,1'-bi(cyclohexan)]-3-en-4-yl)isoindoline)-2-sulfonamido)benzoic acid

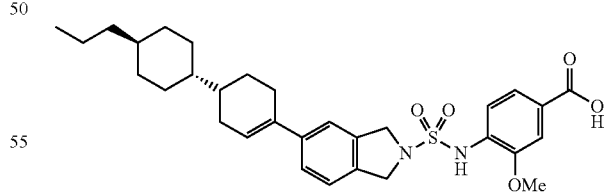

To a mixture of methyl 4-((5-bromoisoindoline)-2-sulfonamido)-3-methoxybenzoate (31.5 mg, 0.071 mmol), ((1S,1's,4'S)-4'-propyl-[1,1'-bi(cyclohexan)]-3-en-4-yl)boronic acid (18.75 mg, 0.075 mmol), cesium carbonate (27.9 mg, 0.086 mmol) in toluene (1 ml) and MeOH (0.25 ml) was added Pd(Ph₃p)₄ (8.25 mg, 7.14 μmol) and the resulting mixture was stirred at 100° C. for 45 min in microwave reactor. To the mixture was added LiOH (1N, (571 μl, 0.571 mmol) and the resulting mixture was stirred at 120° C. for 30 min in microwave reactor. The mixture was diluted with EtOAc, washed with 1N HCl, water, brine, dried, filtered and concentrated. The residue was purified via column chromatography on silica gel eluting with 0-50% EtOAc/cyclohexane to give 3-methoxy-4-((5-((1S,1's,4'S)-4'-propyl-[1,1'-bi(cyclohexan)]-3-en-4-yl)isoindoline)-2-sulfonamido)benzoic acid (9 mg, 0.016 mmol, 22.81% yield). ESI-MS m/z: 551.3, [M−H]−; ¹H NMR (400 MHz, Chloroform-d) δ 7.68 (dd, J=8.3, 1.8 Hz, 1H), 7.57 (d, J=8.4 Hz, 1H), 7.49 (d, J=2.0 Hz, 1H), 7.28-7.22 (m, 1H), 7.14 (d, J=1.6 Hz, 1H), 7.08 (d, J=8.0 Hz, 1H), 6.03 (d, J=4.3 Hz, 1H), 4.66 (s, 4H), 3.87 (s, 3H), 2.44-2.13 (m, 3H), 1.96-1.68 (m, 6H), 1.38-1.22 (m, 3H), 1.19-1.05 (m, 5H), 1.02-0.75 (m, 7H).

Example 378: 4-((4-(2-(4-cyclohexylphenyl)thiazol-5-yl)phenyl)sulfonamido)-3-methoxybenzoic acid

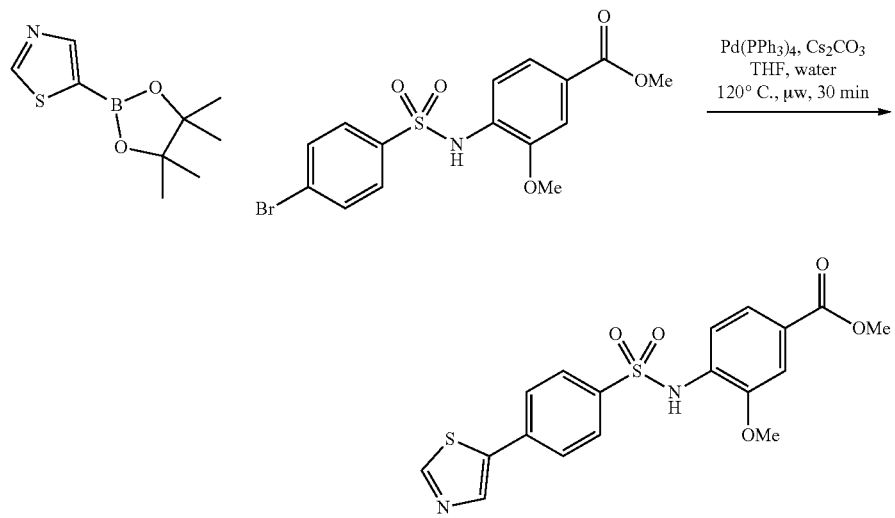

Step 1. Synthesis of methyl 3-methoxy-4-((4-(thiazol-5-yl)phenyl)sulfonamido)benzoate layer was separated, washed with water, brine, dried, filtered and concentrated. The residue was purified by via column chromatography on silica gel eluting with 0-40% EtOAc/cyclohexane to give methyl 3-methoxy-4-((4-(thiazol-5-yl)phenyl)sulfonamido)benzoate (147 mg, 0.363 mmol, 36.5% yield). ESI-MS m/z: 403.1, [M−H]−; ¹H NMR (400 MHz, Chloroform-d) δ 8.81 (s, 1H), 8.12 (s, 1H), 7.86-7.79 (m, 2H), 7.65-7.51 (m, 4H), 7.42 (d, J=1.7 Hz, 1H), 7.36 (s, 1H), 3.85 (s, 3H), 3.78 (s, 3H).

Step 2. Synthesis of methyl 4-((4-(2-bromothiazol-5-yl)phenyl)sulfonamido)-3-methoxybenzoate

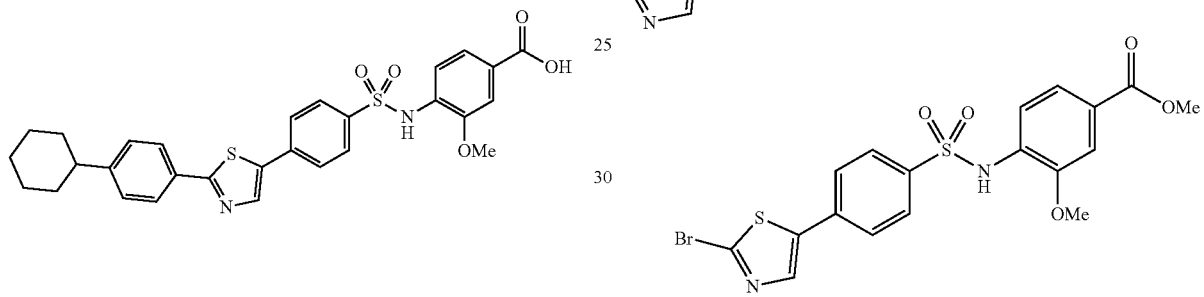

To a mixture of 5-(4,4,5,5-tetramethyl-1,3,2-dioxaborolan-2-yl)thiazole (210 mg, 0.995 mmol), methyl 4-((4-bromophenyl)sulfonamido)-3-methoxybenzoate (402 mg, 1.005 mmol), cesium carbonate (389 mg, 1.194 mmol) in tetrahydrofuran (5 ml) and water (2.5 ml) was added Pd(Ph₃P)₄ (115 mg, 0.099 mmol) and the resulting mixture was stirred at 120° C. for 75 min in microwave reactor. The mixture was diluted with EtOAc/1N HCl and the organic To methyl 3-methoxy-4-((4-(thiazol-5-yl)phenyl)sulfonamido)benzoate (20 mg, 0.049 mmol) in DCM (1 ml) was added NBS (8.80 mg, 0.049 mmol) and the resulting mixture was stirred at RT for 14 h. The mixture was diluted with EtOAc, washed with water, brine, dried, filtered and concentrated to give methyl 4-((4-(2-bromothiazol-5-yl)phenyl)sulfonamido)-3-methoxybenzoate (26 mg).

Step 3. Synthesis of methyl 4-((4-(2-(4-cyclohexylphenyl)thiazol-5-yl)phenyl)sulfonamido)-3-methoxybenzoate

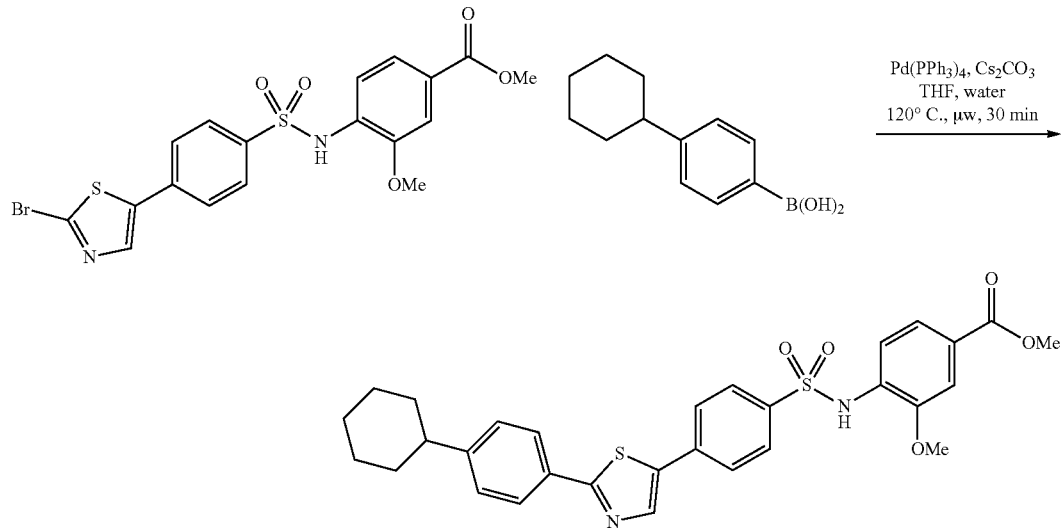

To a mixture of (4-cyclohexylphenyl)boronic acid (11.0 mg, 0.054 mmol), methyl 4-((4-(2-bromothiazol-5-yl)phenyl)sulfonamido)-3-methoxybenzoate (0.024 g, 0.049 mmol), cesium carbonate (0.019 g, 0.059 mmol) in tetrahydrofuran (1 ml) and water (0.500 ml) was added Pd(Ph₃p)₄ (5.66 mg, 4.90 μmol) and the resulting mixture was stirred at 100° C. for 45 min in microwave reactor. Another portion of (4-cyclohexylphenyl)boronic acid (11.00 mg, 0.054 mmol) and Pd(Ph₃p)₄ (5.66 mg, 4.90 μmol) was added and stirred at 120° C. for 30 min in microwave reactor. The mixture was diluted with EtOAc/1N HCl, the organic layer was separated, washed with water, brine, dried, filtered and concentrated. The residue was purified by flash column chromatography on silica gel eluting with 0-60% EtOAc/cyclohexane to give methyl 4-((4-(2-(4-cyclohexylphenyl)thiazol-5-yl)phenyl)sulfonamido)-3-methoxybenzoate (3.9 mg, 6.93 μmol, 14.14% yield). ESI-MS m/z: 561.2, [M−H]⁻; ¹H NMR (500 MHz, Methanol-d4) δ 8.88 (s, 1H), 8.09 (s, 1H), 7.53 (d, J=1.8 Hz, 1H), 7.51-7.41 (m, 4H), 7.36 (d, J=1.8 Hz, 1H), 7.21-7.15 (m, 2H), 7.08-6.97 (m, 2H), 3.79 (s, 3H), 3.53 (s, 3H), 3.26 (p, J=1.6 Hz, 2H), 2.35 (d, J=10.7 Hz, 1H), 1.72 (dt, J=9.4, 6.3 Hz, 2H), 1.63 (d, J=13.2 Hz, 1H), 1.29-1.19 (m, 5H).

Step 4. Synthesis of 4-((4-(2-(4-cyclohexylphenyl)thiazol-5-yl)phenyl)sulfonamido)-3-methoxybenzoic acid

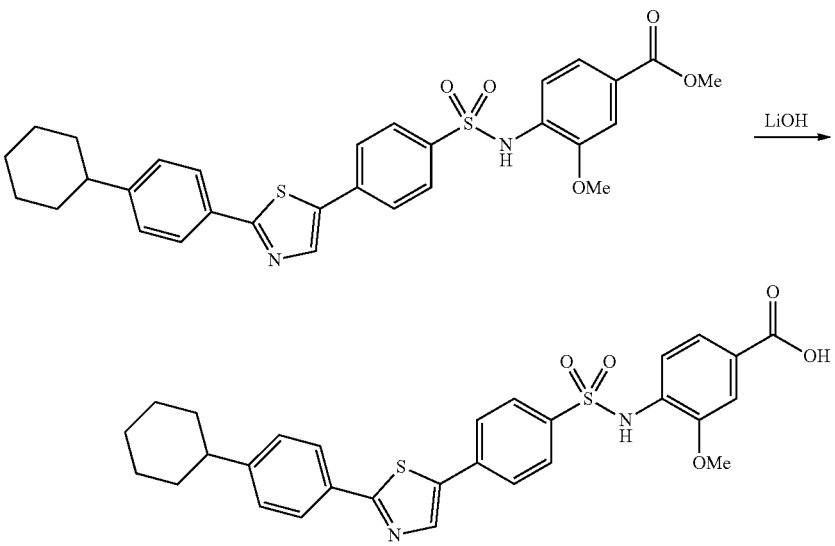

To methyl 4-((4-(2-(4-cyclohexylphenyl)thiazol-5-yl)phenyl)sulfonamido)-3-methoxybenzoate (3.9 mg, 6.93 µmol) in tetrahydrofuran (0.8 ml) was added LiOH (1 M) (69.3 µl, 0.069 mmol) and the resulting mixture was stirred at 110° C. for 45 min in microwave reactor. The mixture was diluted with EtOAc/1N HCl and the organic layer was separated, washed with water, brine, dried, filtered and concentrated. The residue was purified by flash column chromatography on silica gel eluting with 0-50% acetone/cyclohexane to give 4-((4-(2-(4-cyclohexylphenyl)thiazol-5-yl)phenyl)sulfonamido)-3-methoxybenzoic acid (1.4 mg, 2.55 µmol, 36.8% yield). ESI-MS m/z: 547.1, [M−H]⁻; $^1$H NMR (500 MHz, Chloroform-d) δ 8.91 (s, 1H), 8.19 (s, 1H), 7.69 (d, J=1.8 Hz, 1H), 7.64-7.56 (m, 2H), 7.55-7.51 (m, 2H), 7.49 (d, J=1.8 Hz, 1H), 7.33-7.27 (m, 2H), 7.15 (d, J=8.2 Hz, 2H), 6.51 (s, 1H), 3.64 (s, 3H), 2.50-2.37 (m, H), 1.92-1.77 (m, 2H), 1.72 (d, J=13.1 Hz, 1H), 1.46-1.28 (m, 5H).

Example 387: 6-((2-(4-fluorophenyl)thiazole)-5-sulfonamido)-2-naphthoic acid

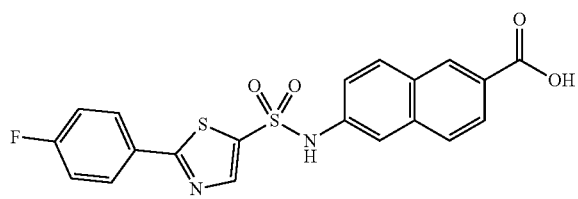 [SMILES: O=C(O)c1ccc2cc(NS(=O)(=O)c3cnc(-c4ccc(F)cc4)s3)ccc2c1]

Step 1. Synthesis of methyl 6-((2-(4-fluorophenyl)thiazole)-5-sulfonamido)-2-naphthoate

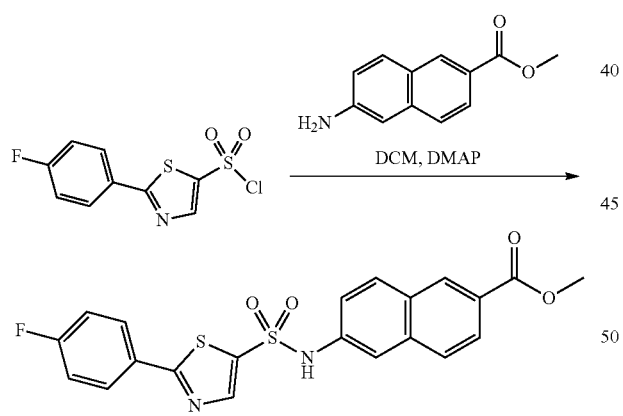

To a stirred mixture of 2-(4-fluorophenyl)-1,3-thiazole-5-sulfonyl chloride (50 mg, 0.18 mmol), and methyl 6-aminonaphthalene-2-carboxylate (54.3 mg, 0.27 mmol) in DCM (3.0 mL) were added DMAP (22.0 mg, 0.18 mmol) at room temperature under. The resulting mixture was stirred for overnight at room temperature. The resulting mixture was concentrated under reduced pressure. The residue was purified by reverse flash chromatography with the following conditions (column, C18 silica gel; mobile phase, ACN in FA water, 0% to 100% gradient in 20 min; detector, UV 254 nm) to afford methyl 6-((2-(4-fluorophenyl)thiazole)-5-sulfonamido)-2-naphthoate (45 mg, 56.5%) as a yellow solid.

Step 2. Synthesis of 6-((2-(4-fluorophenyl)thiazole)-5-sulfonamido)-2-naphthoic acid

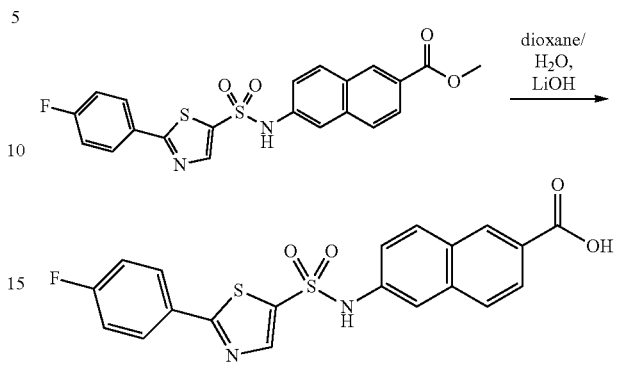

To a stirred mixture of methyl 6-[2-(4-fluorophenyl)-1,3-thiazole-5-sulfonamido]naphthalene-2-carboxylate (45 mg, 0.102 mmol) and LiOH (122 mg, 5 mmol) in dioxane (10 mL) and H₂O (5 mL) for 4 h at room temperature. The mixture was acidified to pH 7 with HCl (1 M). The resulting mixture was extracted with EA (2×100 mL). The combined organic layers were concentrated under reduced pressure. The residue was purified by Prep-HPLC with the following conditions (Column: XBridge Shield RP18 OBD Column, 30*150 mm, 5 m; Mobile Phase A: Water (0.1% FA), Mobile Phase B: ACN; Flow rate: 60 mL/min; Gradient: 52% B to 64% B in 7 min, 64% B; Wave Length: 254; 220 nm; RT1 (min): 5.95) to afford 6-[2-(4-fluorophenyl)-1,3-thiazole-5-sulfonamido]naphthalene-2-carboxylic acid (31.4 mg, 72%) as a white solid. ESI-MS m/z: 429.05, [M+H]⁺; $^1$H NMR (400 MHz, DMSO-d₆) δ 13.01 (s, 1H), 11.23 (s, 1H), 8.52 (s, 1H), 8.42 (s, 1H), 8.07 (d, J=8.8 Hz, 1H), 8.02-7.90 (m, 4H), 7.78 (d, J=2.2 Hz, 1H), 7.44 (dd, J=8.8, 2.2 Hz, 1H), 7.33 (t, J=8.6 Hz, 2H).

Example 388: 2-((2-(4-fluorophenyl)thiazole)-5-sulfonamido)benzo[d]thiazole-5-carboxylic acid

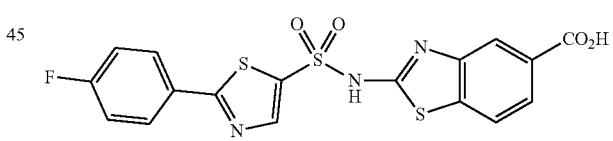

Step 1. Synthesis of methyl 2-aminobenzo[d]thiazole-5-carboxylate

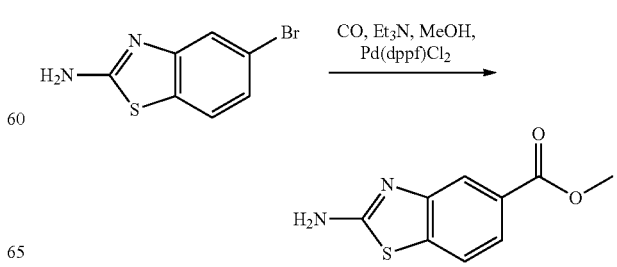

To a stirred mixture of 5-bromo-1,3-benzothiazol-2-amine (2.0 g, 8.7 mmol) and TEA (2.7 g, 26 mmol) in MeOH (20 mL) was added Pd(dppf)Cl$_2$ (639 mg, 0.87 mmol) in portions for 24 h at 100° C. under CO (10 atm) atmosphere. The resulting mixture was filtered and concentrated under reduced pressure. The residue was purified by reverse flash chromatography (CH$_3$CN/H$_2$O, UV 254 nm) to afford methyl 2-aminobenzo[d]thiazole-5-carboxylate (1.2 g, 66%) as a yellow solid.

Step 2. Synthesis of methyl 2-((2-(4-fluorophenyl)thiazole)-5-sulfonamido)benzo[d]thiazole-5-carboxylate

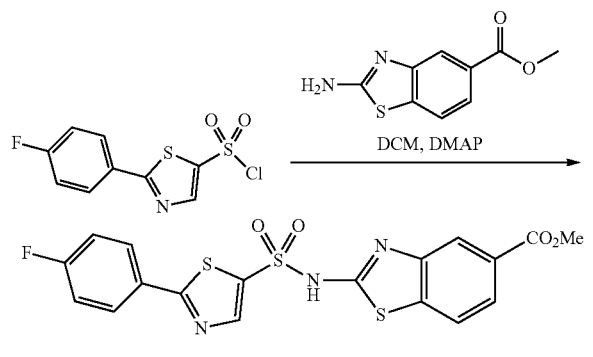

To a stirred mixture of 2-(4-fluorophenyl)-1,3-thiazole-5-sulfonyl chloride (50 mg, 0.18 mmol) and methyl 2-amino-1,3-benzothiazole-5-carboxylate (56.2 mg, 0.27 mmol) in DCM (3.0 mL) were added DMAP (22 mg, 0.18 mmol) in portions at room temperature. The resulting mixture was stirred for overnight at room temperature. The resulting mixture was concentrated under reduced pressure. The residue was purified by reverse flash chromatography (CH$_3$CN/H$_2$O, UV 254 nm) to afford of methyl 2-((2-(4-fluorophenyl)thiazole)-5-sulfonamido)benzo[d]thiazole-5-carboxylate (45 mg, 56%) as a yellow solid.

Step 3: Synthesis of 2-((2-(4-fluorophenyl)thiazole)-5-sulfonamido)benzo[d]thiazole-5-carboxylic acid

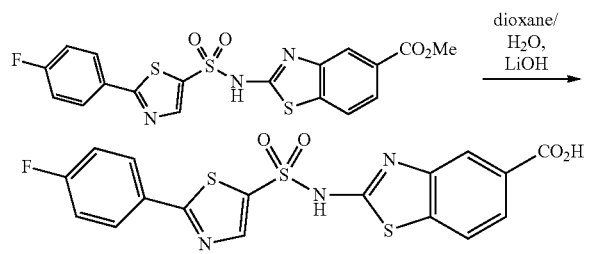

To a stirred mixture of methyl 2-[2-(4-fluorophenyl)-1,3-thiazole-5-sulfonamido]-1,3-benzothiazole-5-carboxylate (45 mg, 0.1 mmol) and LiOH (122 mg, 5 mmol) in dioxane (10 mL) and H$_2$O (5 mL) for 4 h at room temperature. The mixture was acidified to pH 7 with HCl (1 M). The resulting mixture was extracted with EtOAc (2×100 mL). The combined organic layers were concentrated under reduced pressure. The residue was purified by Prep-HPLC with the following conditions (Column: XSelect CSH Prep C18 OBD Column, 19*250 mm, 5 µm; Mobile Phase A: Water (0.1% FA), Mobile Phase B: ACN; Flow rate: 30 mL/min; Gradient: 48% B to 60% B in 7 min, 60% B; Wave Length: 254; 220 nm; RT1 (min): 6.93; to afford 2-[2-(4-fluorophenyl)-1,3-thiazole-5-sulfonamido]-1,3-benzothiazole-5-carboxylic acid (9.9 mg, 21%) as a white solid. ESI-MS m/z: 436.00 [M+H]$^+$; $^1$H NMR (400 MHz, DMSO-d$_6$) δ 8.35 (s, 1H), 8.09-7.95 (m, 3H), 7.89-7.77 (m, 2H), 7.37 (t, J=8.7 Hz, 2H).

Example 389: 4'-((2-(4-fluorophenyl)thiazole)-5-sulfonamido)-3'-methoxy-[1,1'-biphenyl]-4-carboxylic acid

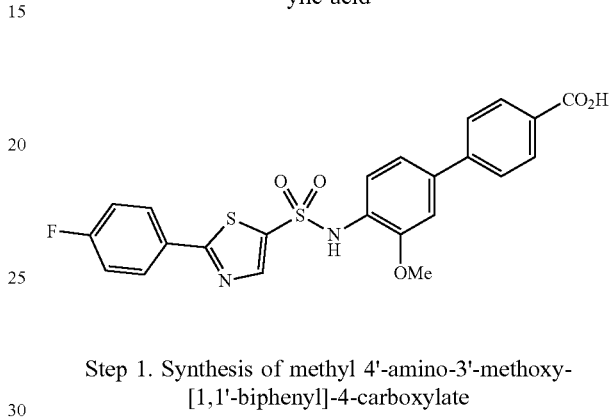

Step 1. Synthesis of methyl 4'-amino-3'-methoxy-[1,1'-biphenyl]-4-carboxylate

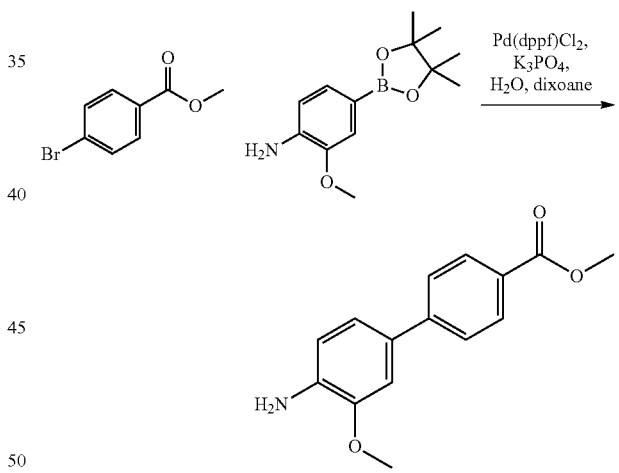

To a stirred mixture of methyl 4-bromobenzoate (800 mg, 3.7 mmol) and 2-methoxy-4-(4,4,5,5-tetramethyl-1,3,2-dioxaborolan-2-yl)aniline (1.4 g, 5.6 mmol) in dioxane (10 mL) and H$_2$O (5 mL) were added Pd(dppf)Cl$_2$CH$_2$Cl$_2$ (606 mg, 0.74 mmol) and K$_3$PO$_4$ (1.6 g, 7.4 mmol) at room temperature under nitrogen atmosphere. The resulting mixture was stirred overnight at 80° C. under nitrogen atmosphere. The resulting mixture was diluted with sat. NaCl and then extracted with EtOAc (2×100 mL). The combined organic layers were dried over anhydrous Na$_2$SO$_4$. After filtration, the filtrate was concentrated under reduced pressure. The residue was purified by reverse flash chromatography (CH$_3$CN/H$_2$O, UV 254 nm) to afford methyl 4'-amino-3'-methoxy-[1,1'-biphenyl]-4-carboxylate (750 mg, 78%) as a black solid.

Step 2. Synthesis of methyl 4'-((2-(4-fluorophenyl)thiazole)-5-sulfonamido)-3'-methoxy-[1,1'-biphenyl]-4-carboxylate

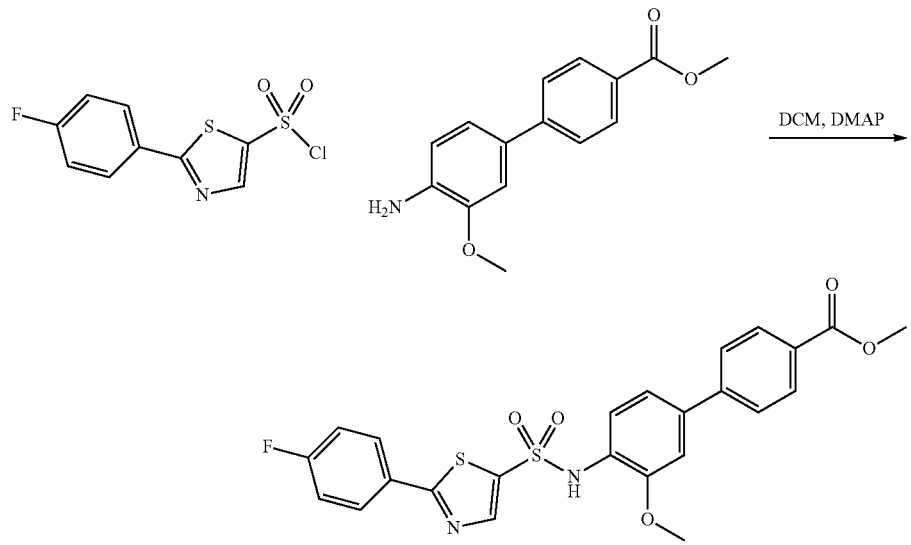

To a stirred mixture of 2-(4-fluorophenyl)-1,3-thiazole-5-sulfonyl chloride (50 mg, 0.18 mmol) and methyl 4'-amino-3'-methoxy-[1,1'-biphenyl]-4-carboxylate (69 mg, 0.27 mmol) in DCM (3.0 mL) were added DMAP (22 mg, 0.18 mmol). The resulting mixture was stirred for overnight at room temperature. The resulting mixture was concentrated under reduced pressure and the residue was purified by reverse flash chromatography ($CH_3CN/H_2O$, UV 254 nm) to afford methyl 4'-((2-(4-fluorophenyl)thiazole)-5-sulfonamido)-3'-methoxy-[1,1'-biphenyl]-4-carboxylate (45 mg, 50%) as a yellow solid.

Step 3. Synthesis of 4'-((2-(4-fluorophenyl)thiazole)-5-sulfonamido)-3'-methoxy-[1,1'-biphenyl]-4-carboxylic acid

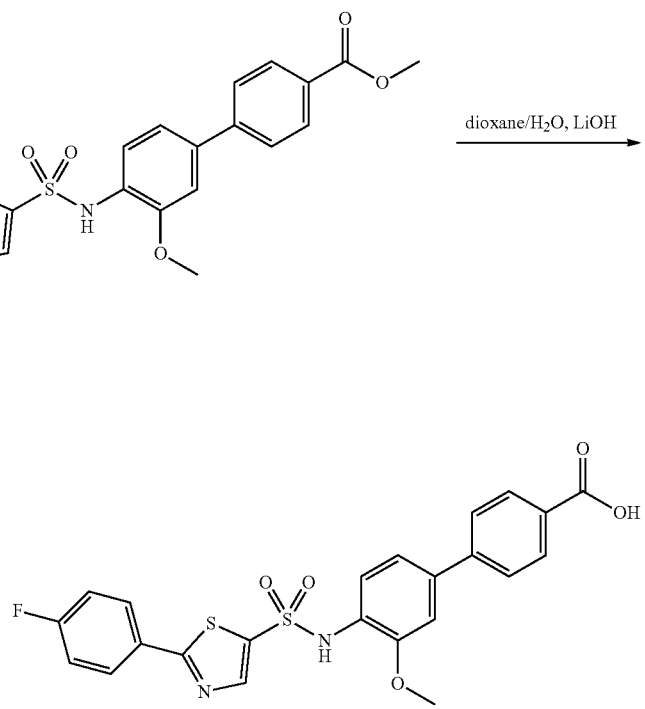

To a stirred mixture of compound 4 (45 mg, 0.09 mmol) and LiOH (122 mg, 5.1 mmol) in dioxane (10 mL) and H₂O (5 mL) for 4 h at room temperature under nitrogen atmosphere. The mixture was acidified to pH 7 with HCl (1 M). The resulting mixture was extracted with EA (2×100 mL). The combined organic layers were concentrated under reduced pressure. The residue was purified by Prep-HPLC with the following conditions (Column: XBridge Shield RP18 OBD Column, 30*150 mm, 5 m; Mobile Phase A: Water (0.1% FA), Mobile Phase B: ACN; Flow rate: 60 mL/min; Gradient: 53% B to 64% B in 7 min, 64% B; Wave Length: 254; 220 nm; RT1 (min): 6.15) to afford 4'-[2-(4-fluorophenyl)-1,3-thiazole-5-sulfonamido]-3'-methoxy-[1,1'-biphenyl]-4-carboxylic acid (31.0 mg, 66%) as a white solid. ESI-MS m/z: 485.15, [M+H]⁺; ¹H NMR (400 MHz, DMSO-d₆) δ 12.98 (s, 1H), 10.25 (s, 1H), 8.16 (s, 1H), 8.09-7.94 (m, 4H), 7.83 (d, J=8.2 Hz, 2H), 7.44-7.29 (m, 4H), 3.68 (s, 3H).

Example 393: 4-((2-((4-fluoro-3-(trifluoromethoxy)phenyl)ethynyl)thiazole)-4-sulfonamido)-3-methoxybenzoic acid

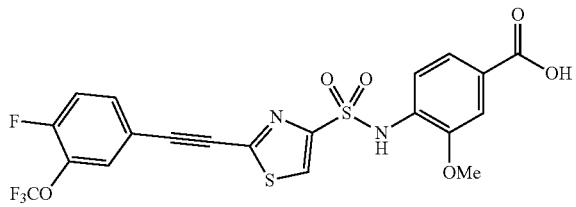 [SMILES: COc1cc(C(=O)O)ccc1NS(=O)(=O)c1csc(C#Cc2ccc(F)c(OC(F)(F)F)c2)n1]

Step 1. Synthesis of methyl 4-((2-((4-fluoro-3-(trifluoromethoxy)phenyl)ethynyl)thiazole)-4-sulfonamido)-3-methoxybenzoate

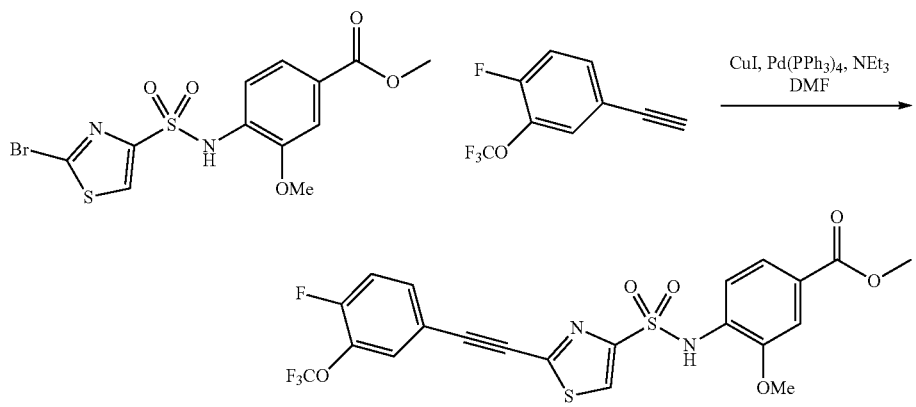

To a stirred mixture of methyl 4-(2-bromo-1,3-thiazole-4-sulfonamido)-3-methoxybenzoate (50 mg, 0.12 mmol), TEA (124 mg, 1.2 mmol) and 4-ethynyl-1-fluoro-2-(trifluoromethoxy)benzene (37.6 mg, 0.18 mmol) in DMF (2 mL) were added Pd(PPh₃)₄ (28 mg, 0.025 mmol) and CuI (4.7 mg, 0.025 mmol) under nitrogen atmosphere. The resulting mixture was stirred for 1 h at room temperature under nitrogen atmosphere. The mixture was purified by reverse flash chromatography (CH₃CN/H₂O, UV 254 nm) to afford methyl 4-((2-((4-fluoro-3-(trifluoromethoxy)phenyl)ethynyl)thiazole)-4-sulfonamido)-3-methoxybenzoate (30 mg, 46%) as a yellow oil.

Step 2. Synthesis of 4-((2-((4-fluoro-3-(trifluoromethoxy)phenyl)ethynyl)thiazole)-4-sulfonamido)-3-methoxybenzoic acid

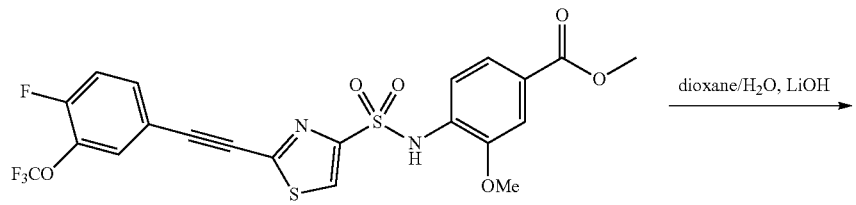

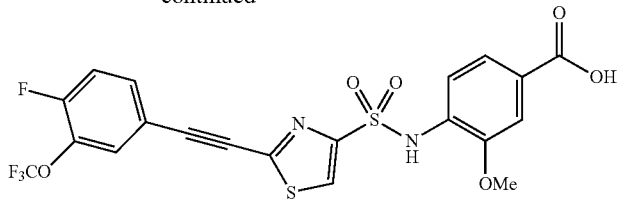

A mixture of methyl 4-(2-{2-[4-fluoro-3-(trifluoromethoxy)phenyl]ethynyl}-1,3-thiazole-4-sulfonamido)-3-methoxybenzoate (30 mg, 0.057 mmol) and LiOH (56.8 mg, 2.4 mmol) in dioxane (10 mL) and H₂O (5 mL) was stirred at room temperature for 4 h. The mixture was acidified to pH 7 with HCl (1 M). The resulting mixture was extracted with EtOAc (2×100 mL). The combined organic layers were concentrated under reduced pressure. The residue was purified by Prep-HPLC with the following conditions (Column: Xselect CSH C18 OBD Column 30*150 mm 5 μm, n; Mobile Phase A: Water (0.1% FA), Mobile Phase B: ACN; Flow rate: 60 mL/min; Gradient: 55% B to 66% B in 7 min, 66% B; Wave Length: 254; 220 nm; RT1 (min): 6.20) to afford 4-(2-{2-[4-fluoro-3-(trifluoromethoxy)phenyl]ethynyl}-1,3-thiazole-4-sulfonamido)-3-methoxybenzoic acid (15.8 mg, 54%) as a white solid. ESI-MS m/z: 515.05, [M−H]⁻; ¹H NMR (400 MHz, DMSO-d₆) δ 12.90 (s, 1H), 10.19 (s, 1H), 8.47 (s, 1H), 8.05 (dd, J=7.6, 1.9 Hz, 1H), 7.84 (ddd, J=8.6, 4.5, 2.1 Hz, 1H), 7.67 (dd, J=10.3, 8.7 Hz, 1H), 7.51 (dd, J=8.2, 1.8 Hz, 1H), 7.45 (d, J=1.8 Hz, 1H), 7.39 (d, J=8.2 Hz, 1H), 3.72 (s, 3H).

Example 399: 4-((2-((2-isopropyl-4-methoxyphenyl)ethynyl)thiazole)-4-sulfonamido)-3-methoxybenzoic acid

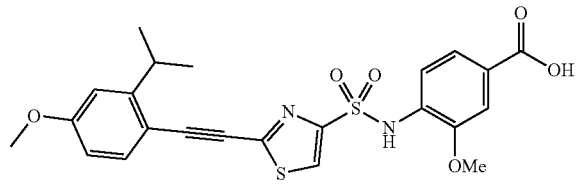 [SMILES: COc1ccc(C#Cc2nc(S(=O)(=O)Nc3ccc(C(=O)O)cc3OC)cs2)c(C(C)C)c1]

Step 1. Synthesis of methyl 2-bromo-4-methoxybenzoate

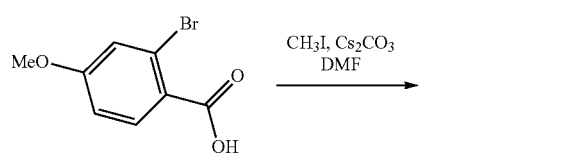

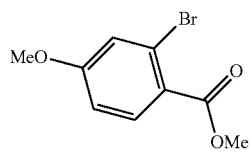

A solution of 2-bromo-4-methoxybenzoic acid (5.0 g, 21.6 mmol), Cs₂CO₃ (14.1 g, 43.3 mmol), CH₃I (3.1 g, 21.6 mmol) in DMF (12 mL) was stirred for 3 h at room temperature. The resulting solution was purified by reverse flash chromatography (column, C18 silica gel; mobile phase, ACN in water, 0% to 100% gradient in 20 min; detector, UV 254 nm) to afford methyl 2-bromo-4-methoxybenzoate (3 g, 56%) as a yellow solid.

Step 2. Synthesis of methyl 4-methoxy-2-(prop-1-en-2-yl)benzoate

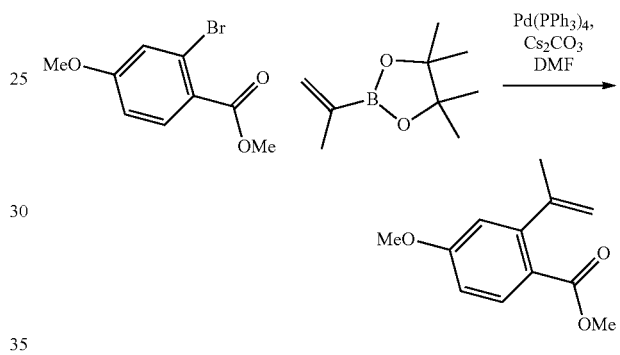

A mixture of methyl 2-bromo-4-methoxybenzoate (3 g, 12.2 mmol), 4,4,5,5-tetramethyl-2-(prop-1-en-2-yl)-1,3,2-dioxaborolane (6.3 g, 36.7 mmol), Na₂CO₃ (3 g, 30.6 mmol) and Pd(PPh₃)₂Cl₂ (0.6 g, 1.2 mmol) in DMF (10 mL) was stirred for 3 h at 100° C. under nitrogen atmosphere. The resulting mixture was concentrated under reduced pressure, then purified by reverse flash chromatography (column, C18 silica gel; mobile phase, ACN in water, 0% to 100% gradient in 20 min; detector, UV 254 nm) to afford methyl 4-methoxy-2-(prop-1-en-2-yl) benzoate hydrate (1.72 g, 67%) as a yellow oil.

Step 3. Synthesis of methyl 2-isopropyl-4-methoxybenzoate

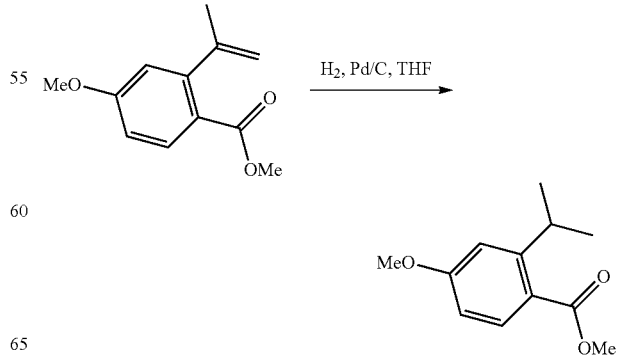

To a stirred mixture of methyl 4-methoxy-2-(prop-1-en-2-yl)benzoate (1.7 g, 8.2 mmol) in THF (10 mL) was added Pd/C (1.75 g) at room temperature under $H_2$ (3 atm) atmosphere. The mixture was stirred for 3 h at room temperature. The solution was filtered and concentrated under reduced pressure to afford methyl 2-isopropyl-4-methoxybenzoate (1.5 g, 87%) as a light yellow oil.

Step 4. Synthesis of (2-isopropyl-4-methoxyphenyl)methanol

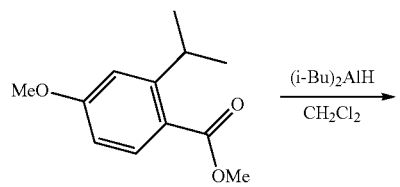

To a stirred solution of methyl 2-isopropyl-4-methoxybenzoate (1.5 g, 7.2 mmol) in $CH_2Cl_2$ was added diisobutylaluminum hydride (1M in n-hexane, 72 mmol) dropwise at 0° C. The resulting solution was stirred for 2 h at room temperature under nitrogen atmosphere. The reaction was quenched by the addition of water (150 mL) at room temperature. The resulting mixture was concentrated under reduced pressure to afford (2-isopropyl-4-methoxyphenyl)methanol (1.2 g) as a light yellow oil.

Step 5. Synthesis of 2-isopropyl-4-methoxybenzaldehyde

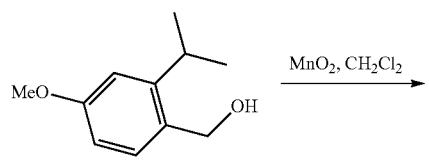

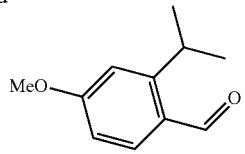

To a stirred mixture of (2-isopropyl-4-methoxyphenyl)methanol (1.2 g, 2.8 mmol) and $MnO_2$ (2.4 g, 27.7 mmol) in $CH_2Cl_2$ at room temperature for 4 h. The residue was filtered, concentrated and purified by reverse flash chromatography (column, C18 silica gel; mobile phase, ACN in water, 0% to 100% gradient in 30 min; detector, UV 254 nm) to afford 2-isopropyl-4-methoxybenzaldehyde (960 mg, 80.90%) as a yellow oil.

Step 6. Synthesis of 1-ethynyl-2-isopropyl-4-methoxybenzene

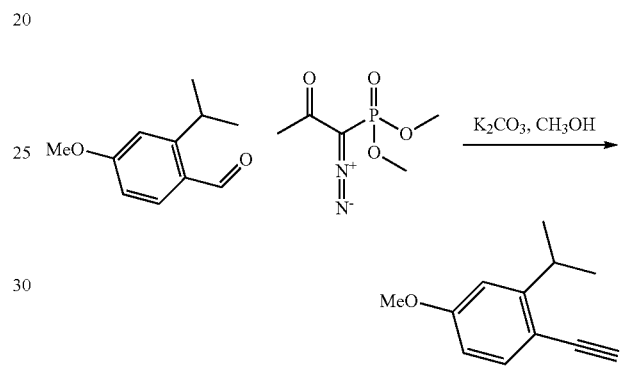

To a stirred mixture of 2-isopropyl-4-methoxybenzaldehyde (400 mg, 2.244 mmol) and $K_2CO_3$ (620 mg, 4.5 mmol) in $CH_3OH$ (10 mL) were added dimethyl (1-diazo-2-oxopropyl)phosphonate (647 mg, 3.4 mmol) dropwise at room temperature under nitrogen atmosphere. The mixture was stirred overnight at room temperature. The residue was filtered, concentrated and purified by reverse flash chromatography to give 1-ethynyl-2-isopropyl-4-methoxybenzene (210 mg, 53.70%) as a yellow oil.

Step 7. Synthesis of methyl 4-((2-((2-isopropyl-4-methoxyphenyl)ethynyl)thiazole)-4-sulfonamido)-3-methoxybenzoate

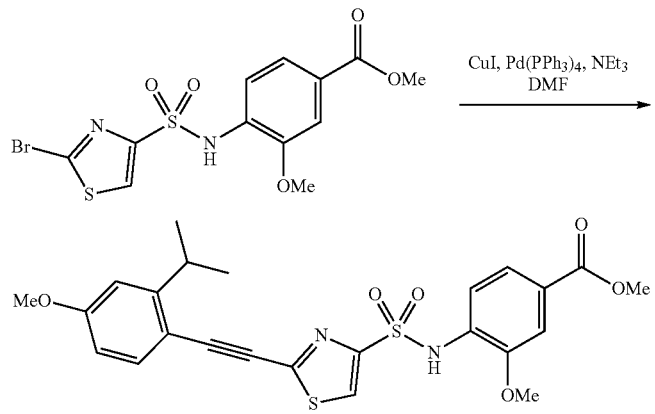

To a stirred mixture of methyl 4-(2-bromo-1,3-thiazole-4-sulfonamido)-3-methoxybenzoate (30 mg, 0.074 mmol), TEA (74 mg, 0.74 mmol) and 1-ethynyl-2-isopropyl-4-methoxybenzene (19.25 mg, 0.111 mmol) in DMF (2 mL) were added Pd(PPh$_3$)$_4$ (17 mg, 0.015 mmol) and CuI (2.81 mg, 0.015 mmol, 0.2 equiv) at room temperature under nitrogen atmosphere. The resulting mixture was stirred for 1 h at room temperature under nitrogen atmosphere. The residue was purified by reverse flash chromatography (column, C18 silica gel; mobile phase, ACN in FA water, 0% to 100% gradient in 30 min; detector, UV 254 nm) to afford methyl 4-{2-[2-(2-isopropyl-4-methoxyphenyl)ethynyl]-1,3-thiazole-4-sulfonamido}-3-methoxybenzoate (20 mg, 54.24%) as a yellow oil.

Step 8. Synthesis of 4-((2-((2-isopropyl-4-methoxyphenyl)ethynyl)thiazole)-4-sulfonamido)-3-methoxybenzoic acid

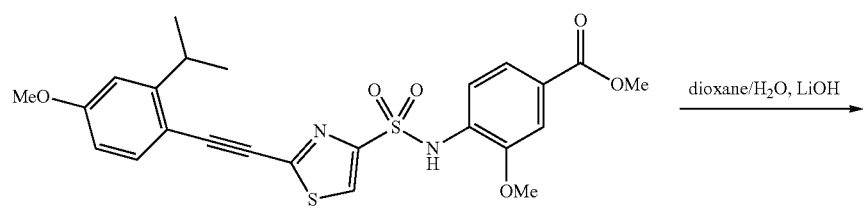

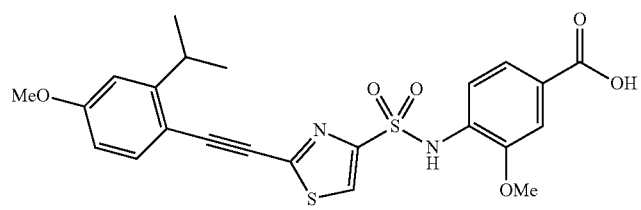

A mixture of methyl 4-{2-[2-(2-isopropyl-4-methoxyphenyl)ethynyl]-1,3-thiazole-4-sulfonamido}-3-methoxybenzoate (20 mg, 0.04 mmol) and LiOH (56.8 mg, 2.4 mmol) in dioxane (10 mL) and H$_2$O (5 mL) was stirred at room temperature for 4 h under nitrogen atmosphere. The mixture was acidified to pH 7 with HCl (1 M). The resulting mixture was extracted with EtOAc (2×100 mL). The combined organic layers were concentrated under reduced pressure. The residue was purified by Prep-HPLC (Column: Xselect CSH C18 OBD Column 30*150 mm 5 m, n; Mobile Phase A: Water (0.1% FA), Mobile Phase B: ACN; Flow rate: 60 mL/min; Gradient: 56% B to 67% B in 7 min, 67% B; Wave Length: 254; 220 nm) to afford 4-((2-((2-isopropyl-4-methoxyphenyl)ethynyl)thiazole)-4-sulfonamido)-3-methoxybenzoic acid (6.9 mg, 34.96%) as a white solid. ESI-MS m/z: 487.05, [M+H]$^+$; $^1$H NMR (400 MHz, DMSO-d$_6$) δ 10.18 (s, 1H), 8.39 (s, 1H), 7.58 (d, J=8.5 Hz, 1H), 7.51 (d, J=8.5 Hz, 1H), 7.47-7.37 (m, 2H), 6.95 (d, J=2.5 Hz, 1H), 6.89 (dd, J=8.5, 2.6 Hz, 1H), 3.83 (s, 3H), 3.71 (s, 3H), 1.26 (d, J=6.9 Hz, 6H).

Example 392: diethyl (3-methoxy-4-((2-((3-(trifluoromethoxy)phenyl)ethynyl)thiazole)-4-sulfonamido)phenyl)phosphonate

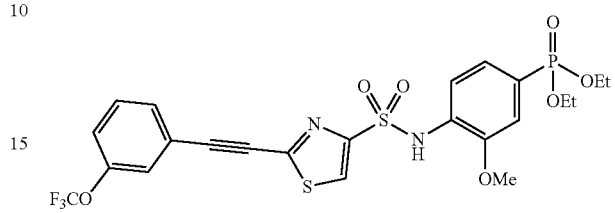

Step 1. Synthesis of tert-butyl (4-(diethoxyphosphoryl)-2-methoxyphenyl)carbamate

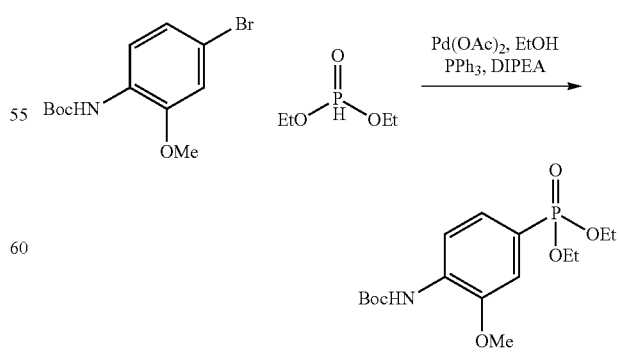

A solution of tert-butyl N-(4-bromo-2-methoxyphenyl) carbamate (2 g, 6.6 mmol), diethyl phosphonate (1.37 g, 9.9 mmol), DIPEA (1.03 g, 7.9 mmol), Pd(OAc)$_2$ (0.03 g, 0.1 mmol) and PPh$_3$ (0.1 g, 0.38 mmol) in EtOH (50 mL) was stirred for overnight at 80° C. under nitrogen atmosphere. The resulting mixture was concentrated and the residue was purified by reverse flash chromatography (MeCN/H$_2$O) to give tert-butyl (4-(diethoxyphosphoryl)-2-methoxyphenyl) carbamate as a colorless oil (2 g, 84%).

Step 2. Synthesis of diethyl (4-amino-3-methoxyphenyl)phosphonate

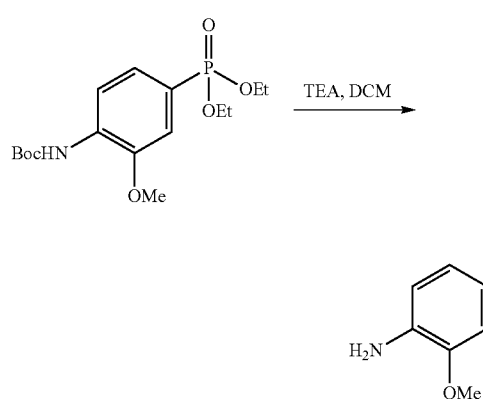

A solution of tert-butyl N-[4-(diethoxyphosphoryl)-2-methoxyphenyl]carbamate (1 g, 2.8 mmol) and TFA (5 mL) in DCM (10 mL) was stirred for 2 h at room temperature. The mixture was concentrated, then diluted with EtOAc/NaHCO$_3$ solution. The organic layer was separated, dried, filtered and concentrated. The residue was purified by reverse phase C18 column chromatography (MeCN/H$_2$O) to give diethyl (4-amino-3-methoxyphenyl)phosphonate as colorless oil (800 mg, 83%).

Step 3. Synthesis of diethyl (4-((2-bromothiazole)-4-sulfonamido)-3-methoxyphenyl)phosphonate

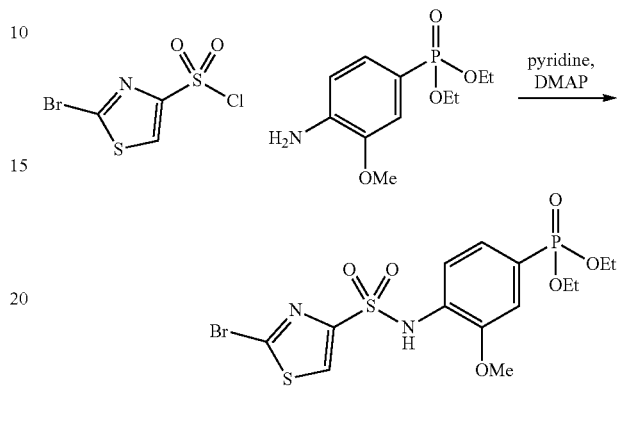

A solution of diethyl 4-amino-3-methoxyphenylphosphonate (200 mg, 0.77 mmol), 2-bromo-1,3-thiazole-4-sulfonyl chloride (202 mg, 0.77 mmol) and DMAP (10 mg, 0.07 mmol) in pyridine (4 mL) was stirred for overnight at room temperature. The mixture was concentrated and the residue was purified by reverse phase C18 column chromatography (MeCN/H$_2$O) to give diethyl (4-((2-bromothiazole)-4-sulfonamido)-3-methoxyphenyl)phosphonate as a yellow solid (220 mg, 59%).

Step 4. Synthesis of diethyl (3-methoxy-4-((2-((3-(trifluoromethoxy)phenyl)ethynyl)thiazole)-4-sulfonamido)phenyl)phosphonate

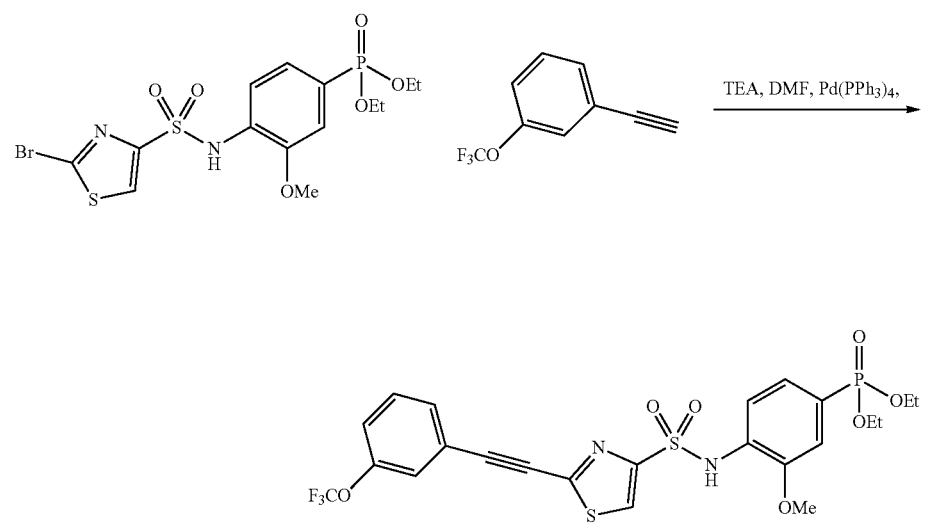

A solution of diethyl (4-((2-bromothiazole)-4-sulfonamido)-3-methoxyphenyl)phosphonate (70 mg, 0.14 mmol), 1-ethynyl-3-(trifluoromethoxy)benzene (40 mg, 0.21 mmol) in DMF (2 mL), TEA (43 mg, 0.43 mmol), CuI (6 mg, 0.03 mmol) and Pd(PPh$_3$)$_4$ (17 mg, 0.01 mmol). The resulting mixture was stirred for overnight at 40° C. under nitrogen atmosphere. The residue was diluted with EtOAc, washed with water, brine, dried, filtered and concentrated. The residue was purified by reverse flash chromatography (MeCN/H$_2$O) to give diethyl (3-methoxy-4-((2-((3-(trifluoromethoxy)phenyl)ethynyl)thiazole)-4-sulfonamido)phenyl)phosphonate as a yellow solid (13.5 mg, 16%).

Example 400: ethyl hydrogen (3-methoxy-4-((2-((3-(trifluoromethoxy)phenyl)ethynyl)thiazole)-4-sulfonamido)phenyl)phosphonate

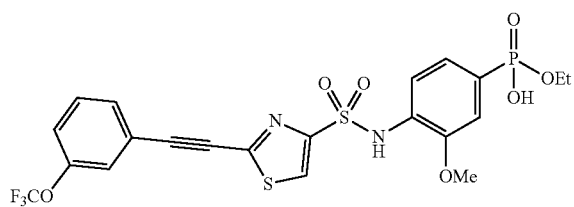 [SMILES: CCOP(=O)(O)c1ccc(NS(=O)(=O)c2csc(C#Cc3cccc(OC(F)(F)F)c3)n2)c(OC)c1]

A stirred solution of methoxy-4-(2-{2-[3-(trifluoromethoxy)phenyl]ethynyl}-1,3-thiazole-4-sulfonamido)phenylphosphonate (20 mg, 0.03 mmol) and LiOH (162 mg, 6.8 mmol), H$_2$O (3 mL) in dioxane (3 mL) was stirred for 6 h at 80° C. The residue diluted with EtOAc/1N HCl, the organic layer was separated, washed with water, brine, dried, filtered and concentrated. The residue was purified by reverse flash chromatography (MeCN/H$_2$O) to give ethyl hydrogen (3-methoxy-4-((2-((3-(trifluoromethoxy)phenyl)ethynyl)thiazole)-4-sulfonamido)phenyl)phosphonate as a white solid (4.5 mg, 23.62%). ESI-MS m/z: 561.10, [M+H]$^+$. $^1$H NMR (400 MHz, DMSO-d$_6$) δ 8.34 (d, J=2.5 Hz, 1H), 7.76 (d, J=9.0 Hz, 2H), 7.64 (t, J=7.9 Hz, 1H), 7.61-7.54 (m, 1H), 7.11 (d, J=12.7 Hz, 1H), 3.58 (s, 5H), 1.00 (t, J=7.1 Hz, 3H).

Example 401: 2-(3-methoxy-4-((2-((3-(trifluoromethoxy)phenyl)ethynyl)thiazole)-4-sulfonamido)phenyl)acetic acid

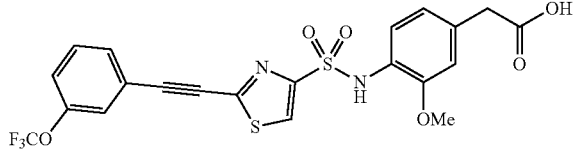 [SMILES: COc1cc(CC(=O)O)ccc1NS(=O)(=O)c1csc(C#Cc2cccc(OC(F)(F)F)c2)n1]

Step 1. Synthesis of methyl 2-(3-methoxy-4-nitrophenyl)acetate

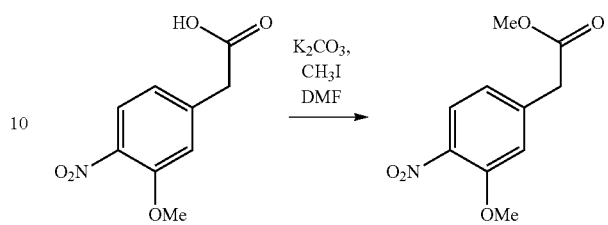

A solution of (3-methoxy-4-nitrophenyl)acetic acid (200 mg, 0.95 mmol), K$_2$CO$_3$ (65 mg, 0.47 mmol) and CH$_3$I (134 mg, 0.237 mmol) in DMF (5 mL) was stirred for 2 h at room temperature. The resulting mixture was filtered and purified by reverse flash chromatography (MeCN/H$_2$O) to give methyl 2-(3-methoxy-4-nitrophenyl)acetate as a brown oil (150 mg, 70%).

Step 2. Synthesis of methyl 2-(4-amino-3-methoxyphenyl)acetate

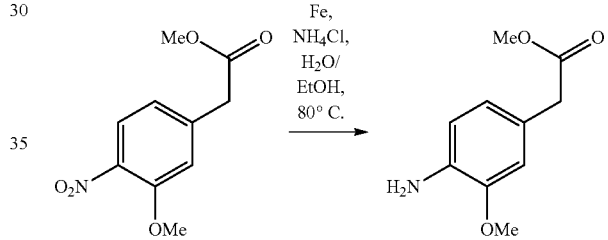

A solution of methyl 2-(3-methoxy-4-nitrophenyl)acetate (200 mg, 0.88 mmol), Fe (25 mg, 0.44 mmol) and NH$_4$Cl (475 mg, 8.88 mmol) in H$_2$O (2 mL) and EtOH (4 mL) was stirred for 2 h at 80° C. The mixture was extracted with EtOAc, and the organic layer was separated, dried, filtered and concentrated. The residue was purified by reverse phase C18 column chromatography (MeCN/H$_2$O) to give the methyl 2-(4-amino-3-methoxyphenyl)acetate as a brown oil (150 mg, 86%).

Step 3. Synthesis of methyl 2-(4-((2-bromothiazole)-4-sulfonamido)-3-methoxyphenyl)acetate

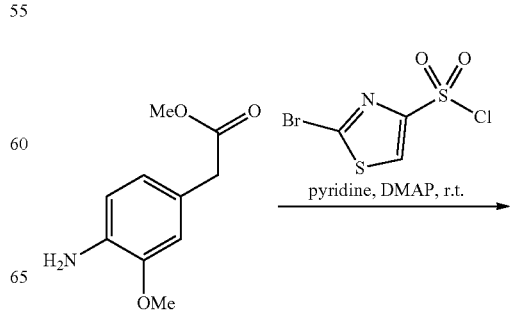

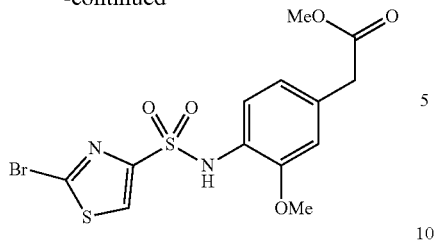

A solution of methyl 2-(4-amino-3-methoxyphenyl)acetate (110 mg, 0.56 mmol), 2-bromo-1,3-thiazole-4-sulfonyl chloride (100 mg, 0.38 mmol) and DMAP (4 mg, 0.04 mmol) in pyridine (5 mL) was stirred for 2 h at room temperature. The mixture was extracted with EtOAc, and the organic layer was separated, dried, filtered and concentrated. The residue was purified by reverse phase C18 column chromatography (MeCN/H$_2$O) to give the methyl 2-(4-((2-bromothiazole)-4-sulfonamido)-3-methoxyphenyl)acetate as a yellow oil (56 mg, 59%).

Step 4. Synthesis of methyl 2-(3-methoxy-4-((2-((3-(trifluoromethoxy)phenyl)ethynyl)thiazole)-4-sulfonamido)phenyl)acetate

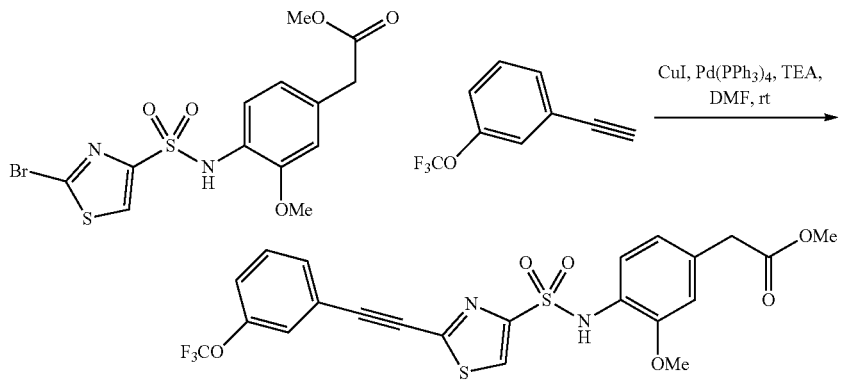

A solution of methyl 2-[4-(2-bromo-1,3-thiazole-4-sulfonamido)-3-methoxycyclohexyl]acetate (40 mg, 0.09 mmol), 1-ethynyl-2-(trifluoromethoxy)benzene (26 mg, 0.14 mmol), CuI (4 mg, 0.02 mmol) and TEA (28 mg, 0.28 mmol) and Pd(PPh$_3$)$_4$ (3 mg, 0.002 mmol) in DMF (2 mL) was stirred for overnight at room temperature under nitrogen atmosphere. The mixture was extracted with EtOAc, and the organic layer was separated, dried, filtered and concentrated. The residue was purified by reverse flash chromatography (MeCN/H$_2$O) to give methyl 2-(3-methoxy-4-((2-((3-(trifluoromethoxy)phenyl)ethynyl)thiazole)-4-sulfonamido) phenyl)acetate as a yellow oil (36 mg, 72%).

Step 5. Synthesis of 2-(3-methoxy-4-((2-((3-(trifluoromethoxy)phenyl)ethynyl)thiazole)-4-sulfonamido)phenyl)acetic acid

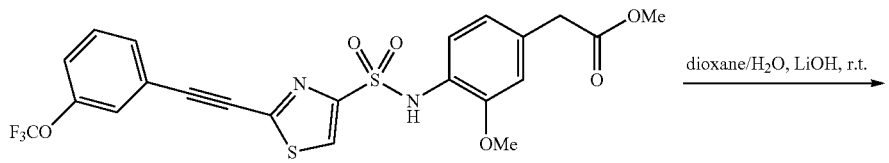

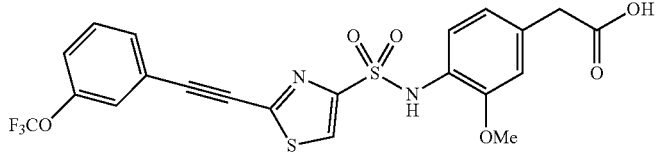

A stirred solution of methyl 2-[3-methoxy-4-(2-{2-[3-(trifluoromethoxy)phenyl]ethynyl}-1,3-thiazole-4-sulfonamido)cyclohexyl]acetate (50 mg, 0.09 mmol) and LiOH (23 mg, 0.9 mmol) and H$_2$O (3 mL) in dioxane (3 mL) was stirred for 2 h at room temperature. The mixture was extracted with EtOAc, and the organic layer was separated, dried, filtered and concentrated. The residue was purified by reverse flash chromatography (MeCN/H$_2$O) to give 2-(3-methoxy-4-((2-((3-(trifluoromethoxy)phenyl)ethynyl)thiazole)-4-sulfonamido)phenyl)acetic acid as a white solid (20.8 mg, 42%). ESI-MS m/z: 512.95, [M+H]$^+$; $^1$H NMR (400 MHz, DMSO-d$_6$) δ 8.00 (s, 1H), 7.57-7.42 (m, 4H), 7.38-7.29 (m, 2H), 6.88-6.81 (m, 1H), 6.76 (d, J=1.8 Hz, 1H), 3.80 (s, 3H), 3.60 (s, 2H), 1.27 (s, 1H).

The following examples were prepared using procedures similar to those described above:

| Example # | Structure | LC-MS [M + H]$^+$ unless otherwise noted | $^1$H-NMR |
|---|---|---|---|
| 1 | 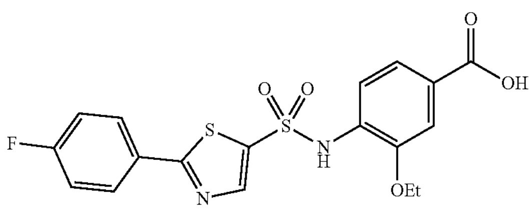 [SMILES: CCOc1cc(C(=O)O)ccc1NS(=O)(=O)c1cnc(-c2ccc(F)cc2)s1] | 423 | $^1$H NMR (400 MHz, DMSO-d$_6$) δ 12.98 (s, 1H), 10.33 (s, 1H), 8.18 (s, 1H), 8.05-8.00 (m, 2H), 7.54 (dd, J = 8.2, 1.7 Hz, 1H), 7.44 (d, J = 8.2 Hz, 1H), 7.41 (d, J = 1.8 Hz, 1H), 7.38 (dd, J = 9.9, 7.8 Hz, 2H), 3.91 (q, J = 6.9 Hz, 2H), 1.15 (t, J = 6.9 Hz, 3H). |
| 3 | 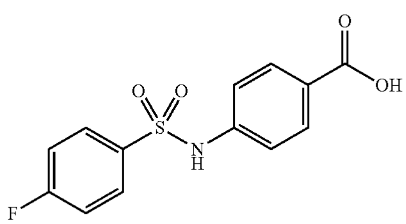 [SMILES: O=C(O)c1ccc(NS(=O)(=O)c2ccc(F)cc2)cc1] | 296 | $^1$H NMR (400 MHz, DMSO-d$_6$) δ 12.75 (br s, 1H), 10.82 (br s, 1H), 7.94-7.84 (m, 2H), 7.84-7.78 (m, 2H), 7.47-7.36 (m, 2H), 7.23-7.16 (m, 2H). |
| 4 | 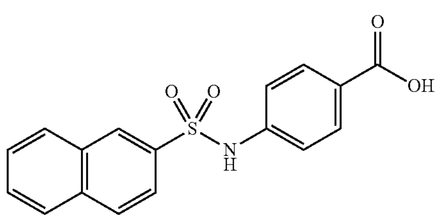 [SMILES: O=C(O)c1ccc(NS(=O)(=O)c2ccc3ccccc3c2)cc1] | 328 | $^1$H NMR (400 MHz, DMSO-d$_6$) δ 12.67 (br s, 1H), 10.91 (br s, 1H), 8.54 (d, J = 1.9 Hz, 1H), 8.16 (d, J = 7.7 Hz, 1H), 8.10 (d, J = 8.8 Hz, 1H), 8.00 (d, J = 8.0 Hz, 1H), 7.83-7.73 (m, 3H), 7.68 (dddd, J = 16.7, 8.2, 6.9, 1.4 Hz, 2H), 7.26-7.20 (m, 2H). |
| 5 | 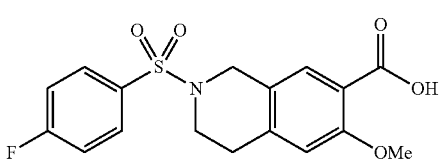 [SMILES: COc1cc2c(cc1C(=O)O)CN(S(=O)(=O)c1ccc(F)cc1)CC2] | 366 | $^1$H NMR (400 MHz, DMSO-d$_6$) δ 12.40 (br s, 1H), 7.97-7.84 (m, 2H), 7.54-7.42 (m, 3H), 6.87 (s, 1H), 4.16 (s, 2H), 3.75 (s, 3H), 3.34-3.28 (m, 2 H), 2.87 (t, J = 6.0 Hz, 2H). |
| 6 | 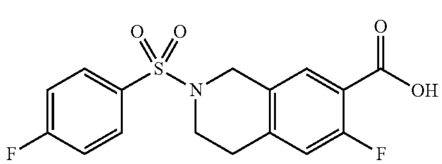 [SMILES: O=C(O)c1cc2c(cc1F)CCN(S(=O)(=O)c1ccc(F)cc1)C2] | 354 | $^1$H NMR (400 MHz, DMSO-d$_6$) δ 13.14 (br s, 1H), 7.94-7.86 (m, 2H), 7.69 (d, J = 7.4 Hz, 1H), 7.52-7.41 (m, 2H), 7.09 (d, J = 11.5 Hz, 1H), 4.25 (s, 2H), 3.34-3.29 (m, 2 H), 2.88 (t, J = 6.0 Hz, 2H). |

| Example # | Structure | LC-MS [M + H]+ unless otherwise noted | 1H-NMR |
|---|---|---|---|
| 7 | 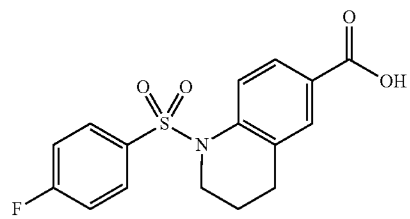 [SMILES: O=C(O)c1ccc2c(c1)CCCN2S(=O)(=O)c1ccc(F)cc1] | 336 | 1H NMR (400 MHz, DMSO-d6) δ 12.84 (br s, 1H), 7.79-7.74 (m, 2H), 7.72 (d, J = 1.2 Hz, 2H), 7.68-7.64 (m, 1H), 7.46-7.37 (m, 2H), 3.91-3.77 (m, 2H), 2.58 (t, J = 6.6 Hz, 2H), 1.65 (p, J = 6.3 Hz, 2H). |
| 8 | 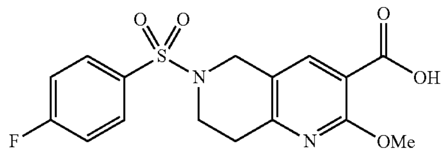 [SMILES: COc1nc2c(cc1C(=O)O)CN(S(=O)(=O)c1ccc(F)cc1)CC2] | 367 | 1H NMR (400 MHz, DMSO-d6) δ 12.84 (br s, 1H), 7.95 (s, 1H), 7.94-7.87 (m, 2H), 7.52-7.43 (m, 2H), 4.21 (s, 2H), 3.84 (s, 3H), 3.41 (t, J = 6.0 Hz, 2H), 2.86 (t, J = 6.0 Hz, 2H). |
| 9 | 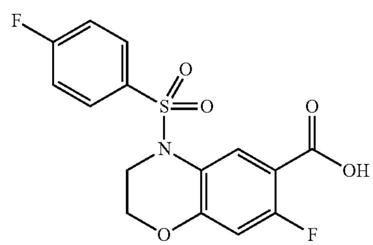 [SMILES: O=C(O)c1cc2c(cc1F)OCCN2S(=O)(=O)c1ccc(F)cc1] | 356 | 1H NMR (500 MHz, DMSO-d6) δ 13.11 (br s, 1H), 8.26 (d, J = 7.7 Hz, 1H), 7.72 (ddd, J = 10.2, 5.2, 2.6 Hz, 2H), 7.50-7.42 (m, 2H), 6.86 (d, J = 11.6 Hz, 1H), 3.94-3.90 (t, J = 4.6 Hz,, 2H), 3.76 (t, J = 4.6 Hz, 2H). |
| 10 | 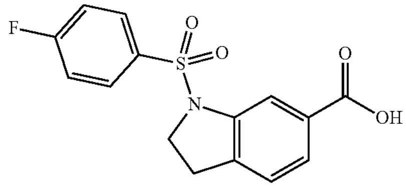 [SMILES: O=C(O)c1ccc2c(c1)N(S(=O)(=O)c1ccc(F)cc1)CC2] | 322 | 1H NMR (500 MHz, DMSO-d6) δ 13.04 (br s, 1H), 8.00 (d, J = 1.5 Hz, 1H), 7.89-7.81 (m, 2H), 7.61 (dd, J = 7.8, 1.5 Hz, 1H), 7.48-7.41 (m, 2H), 7.29 (d, J = 7.8 Hz, 1H), 3.97 (t, J = 8.5 Hz, 2H), 2.98 (t, J = 8.4 Hz, 2H). |
| 11 | 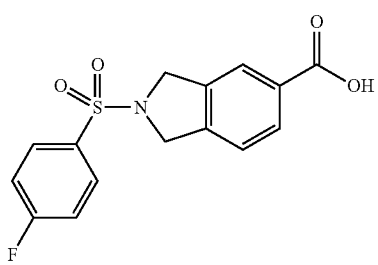 [SMILES: O=C(O)c1ccc2c(c1)CN(S(=O)(=O)c1ccc(F)cc1)C2] | 322 | 1H NMR (400 MHz, DMSO-d6) δ 7.98-7.90 (m, 2H), 7.83-7.78 (m, 2H), 7.49-7.40 (m, 2H), 7.31 (d, J = 8.3 Hz, 1H), 4.62 (s, 4H). |
| 12 | 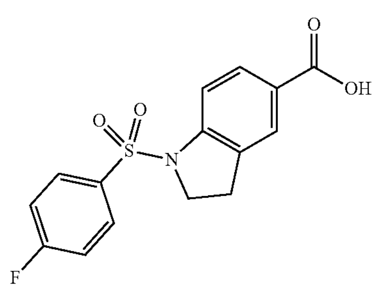 [SMILES: O=C(O)c1ccc2c(c1)CCN2S(=O)(=O)c1ccc(F)cc1] | 322 | 1H NMR (500 MHz, DMSO-d6) δ 12.74 (br s, 1H), 7.99-7.92 (m, 2H), 7.81 (dd, J = 8.4, 1.8 Hz, 1H), 7.71 (d, J = 1.7 Hz, 1H), 7.54 (d, J = 8.5 Hz, 1H), 7.50-7.39 (m, 2H), 3.98 (t, J = 8.5 Hz, 2H), 3.02 (t, J = 8.5 Hz, 2H). |

-continued

| Example # | Structure | LC-MS [M + H]+ unless otherwise noted | 1H-NMR |
|---|---|---|---|
| 13 | 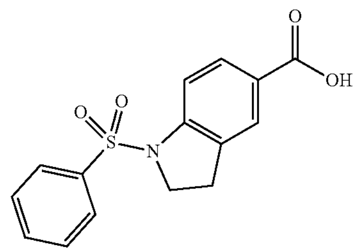 [SMILES: O=C(O)c1ccc2c(c1)CCN2S(=O)(=O)c1ccccc1] | 304 | 1H NMR (400 MHz, DMSO-d6) δ 12.72 (s, 1H), 7.90-7.85 (m, 2H), 7.80 (dd, J = 8.4, 1.8 Hz, 1H), 7.74-7.67 (m, 2H), 7.60 (dd, J = 8.4, 7.1 Hz, 2H), 7.54 (d, J = 8.4 Hz, 1H), 3.98 (t, J = 8.6 Hz, 2H), 3.01 (t, J = 8.5 Hz, 2H). |
| 14 | 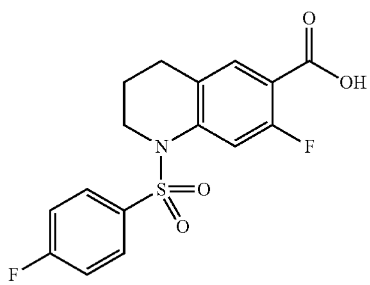 [SMILES: O=C(O)c1cc2c(cc1F)N(S(=O)(=O)c1ccc(F)cc1)CCC2] | 354 | 1H NMR (400 MHz, Chloroform-d) δ 7.77-7.67 (comp, 4H), 7.21-7.11 (m, 2H), 3.91-3.82 (m, 2H), 2.61 (t, J = 6.5 Hz, 2H), 1.80-1.69 (m, 2H). |
| 15 | 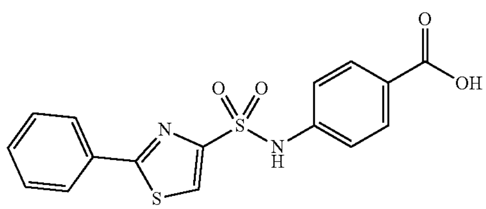 [SMILES: O=C(O)c1ccc(NS(=O)(=O)c2csc(-c3ccccc3)n2)cc1] | 361 | 1H NMR (500 MHz, DMSO-d6) δ 12.81 (br s, 1H), 11.25 (s, 1H), 8.39 (s, 1H), 7.99-7.94 (m, 2H), 7.91-7.86 (m, 2H), 7.64-7.46 (comp, 3H), 7.33-7.27 (m, 2H). |
| 16 | 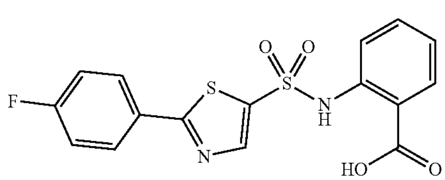 [SMILES: O=C(O)c1ccccc1NS(=O)(=O)c1cnc(-c2ccc(F)cc2)s1] | 379 | 1H NMR (500 MHz, DMSO-d6) δ 8.37 (s, 1H), 8.05-7.99 (m, 2H), 7.97-7.90 (m, 1H), 7.63-7.56 (m, 2H), 7.43-7.32 (m, 2H), 7.19-7.14 (m, 1H). |
| 17 | 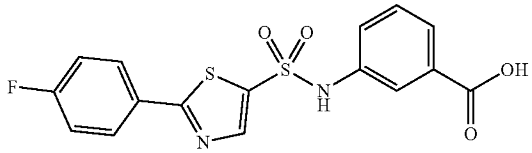 [SMILES: O=C(O)c1cccc(NS(=O)(=O)c2cnc(-c3ccc(F)cc3)s2)c1] | 379 | 1H NMR (500 MHz, DMSO-d6) δ 13.08 (br s, 1H), 10.99 (s, 1H), 8.26 (s, 1H), 8.05-7.99 (m, 2H), 7.77-7.76 (m, 1H), 7.69 (ddd, J = 6.3, 2.8, 1.6 Hz, 1H), 7.47-7.43 (comp, 2H), 7.40-7.33 (m, 2H). |
| 18 | 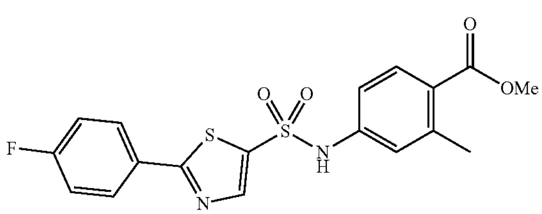 [SMILES: COC(=O)c1ccc(NS(=O)(=O)c2cnc(-c3ccc(F)cc3)s2)cc1C] | 407 | 1H NMR (500 MHz, DMSO-d6) δ 11.20 (s, 1H), 8.40 (s, 1H), 8.07-8.00 (m, 2H), 7.80 (d, J = 8.5 Hz, 1H), 7.42-7.33 (m, 2H), 7.15 (dd, J = 8.6, 2.3 Hz, 1H), 7.09 (d, J = 2.3 Hz, 1H), 3.76 (s, 3H), 2.46 (s, 3H). |
| 19 | 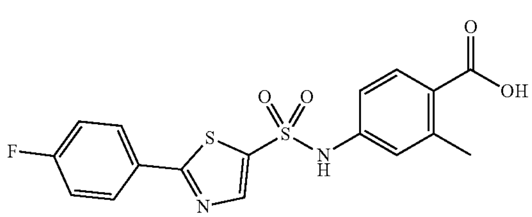 [SMILES: Cc1cc(NS(=O)(=O)c2cnc(-c3ccc(F)cc3)s2)ccc1C(=O)O] | 393 | 1H NMR (500 MHz, DMSO-d6) δ 12.66 (br s, 1H), 11.14 (s, 1H), 8.38 (s, 1H), 8.10-8.00 (m, 2H), 7.79 (d, J = 8.5 Hz, 1H), 7.41-7.34 (m, 2H), 7.12 (dd, J = 8.6, 2.2 Hz, 1H), 7.06 (d, J = 2.3 Hz, 1H), 2.46 (s, 3H). |

-continued

| Example # | Structure | LC-MS [M + H]+ unless otherwise noted | 1H-NMR |
|---|---|---|---|
| 20 | 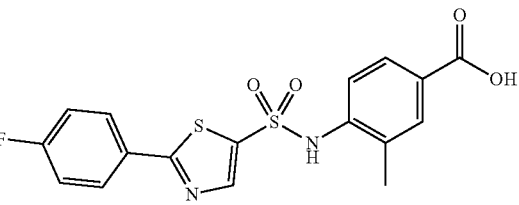 | 393 | 1H NMR (500 MHz, DMSO-d6) δ 12.80 (br s, 1H), 10.43 (s, 1H), 8.17 (s, 1H), 8.09-8.01 (m, 2H), 7.76 (d, J = 2.0 Hz, 1H), 7.75-7.70 (m, 1H), 7.41-7.35 (m, 2H), 7.27 (d, J = 8.3 Hz, 1H), 2.18 (s, 3H). |
| 21 | 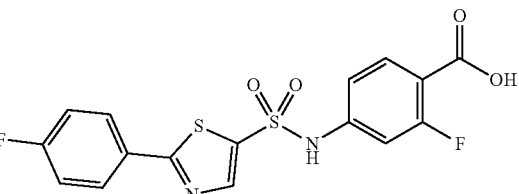 | 397 | 1H NMR (500 MHz, DMSO-d6) δ 13.06 (br s, 1H), 11.52 (s, 1H), 8.46 (s, 1H), 8.09-7.99 (m, 2H), 7.82 (t, J = 8.5 Hz, 1H), 7.43-7.33 (m, 2H), 7.09 (dd, J = 8.6, 2.1 Hz, 1H), 7.04 (dd, J = 12.5, 2.1 Hz, 1H). |
| 22 | 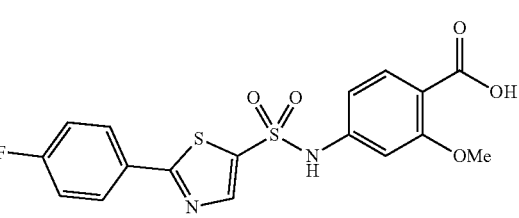 | 409 | 1H NMR (500 MHz, DMSO-d6) δ 12.42 (br s, 1H), 11.17 (s, 1H), 8.40 (s, 1H), 8.08-8.01 (m, 2H), 7.63 (d, J = 8.4 Hz, 1H), 7.41-7.33 (m, 2H), 6.91 (d, J = 2.0 Hz, 1H), 6.82 (dd, J = 8.4, 2.0 Hz, 1H), 3.76 (s, 3H). |
| 23 | 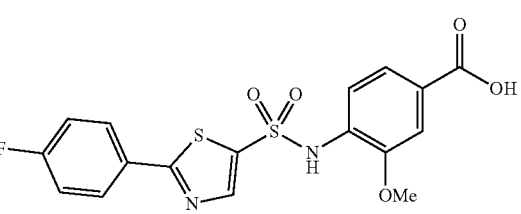 | 409 | 1H NMR (500 MHz, DMSO-d6) δ 12.96 (br s, 1H), 10.42 (s, 1H), 8.20 (s, 1H), 8.07-8.01 (m, 2H), 7.54 (dd, J = 8.2, 1.8 Hz, 1H), 7.47-7.41 (m, 2H), 7.41-7.34 (m, 2H), 3.67 (s, 3H). |
| 24 | 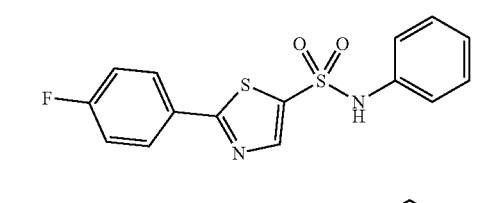 | 335 | 1H NMR (500 MHz, DMSO-d6) δ 10.73 (s, 1H), 8.24 (s, 1H), 8.06-7.98 (m, 2H), 7.40-7.34 (m, 2H), 7.34-7.28 (m, 2H), 7.21-7.16 (m, 2H), 7.16-7.10 (m, 1H). |
| 25 | 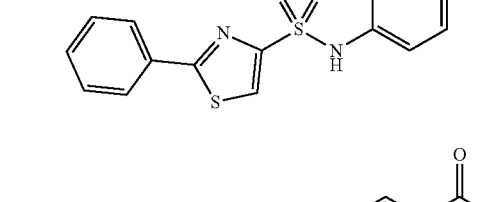 | 317 | 1H NMR (500 MHz, DMSO-d6) δ 10.72 (s, 1H), 8.24 (s, 1H), 7.98-7.92 (m, 2H), 7.61-7.47 (comp, 3H), 7.35-7.28 (m, 2H), 7.23-7.17 (m, 2H), 7.17-7.09 (m, 1H). |
| 26 | 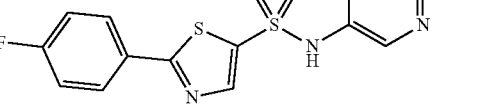 | 380 | 1H NMR (400 MHz, DMSO-d6) δ 13.00 (br s, 1H), 11.57 (s, 1H), 8.44 (d, J = 2.6 Hz, 1H), 8.40 (s, 1H), 8.07-8.01 (m, 2H), 7.99 (d, J = 8.6 Hz, 1H), 7.73 (dd, J = 8.6, 2.6 Hz, 1H), 7.42-7.32 (m, 2H). |

-continued

| Example # | Structure | LC-MS [M + H]+ unless otherwise noted | 1H-NMR |
|---|---|---|---|
| 27 | 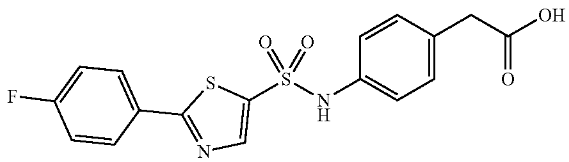 [SMILES: O=C(O)Cc1ccc(NS(=O)(=O)c2cnc(-c3ccc(F)cc3)s2)cc1] | 393 | 1H NMR (400 MHz, DMSO-d6) δ 12.29 (br s, 1H), 10.70 (s, 1H), 8.23 (s, 1H), 8.06-7.98 (m, 2H), 7.42-7.31 (m, 2H), 7.22-7.16 (m, 2H), 7.15-7.08 (m, 2H), 3.49 (s, 2H). |
| 28 | 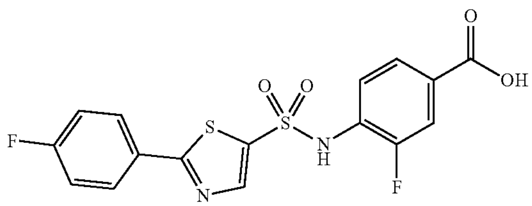 [SMILES: O=C(O)c1ccc(NS(=O)(=O)c2cnc(-c3ccc(F)cc3)s2)c(F)c1] | 397 | 1H NMR (500 MHz, DMSO-d6) δ 13.21 (s, 1H), 11.15 (s, 1H), 8.29 (s, 1H), 8.09-8.03 (m, 2H), 7.76 (dd, J = 8.5, 1.9 Hz, 1H), 7.68 (dd, J = 10.8, 1.9 Hz, 1H), 7.53 (t, J = 8.1 Hz, 1H), 7.42-7.35 (m, 2H). |
| 29 | 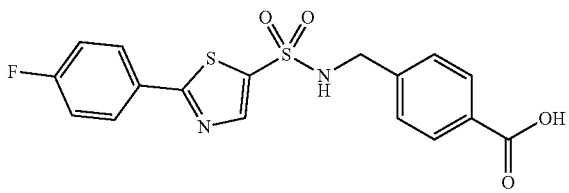 [SMILES: O=C(O)c1ccc(CNS(=O)(=O)c2cnc(-c3ccc(F)cc3)s2)cc1] | 393 | 1H NMR (500 MHz, DMSO-d6) δ 12.88 (br s, 1H), 8.83 (s, 1H), 8.25 (s, 1H), 8.06-8.00 (m, 2H), 7.88-7.83 (m, 2H), 7.43-7.35 (m, 4H), 4.37-4.11 (m, 2H). |
| 30 | 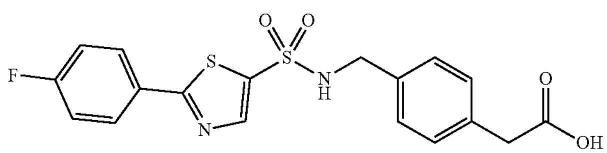 [SMILES: O=C(O)Cc1ccc(CNS(=O)(=O)c2cnc(-c3ccc(F)cc3)s2)cc1] | 407 | 1H NMR (500 MHz, DMSO-d6) δ 12.29 (br s, 1H), 8.69 (s, 1H), 8.27 (s, 1H), 8.09-8.02 (m, 2H), 7.46-7.35 (m, 2H), 7.22 (d, J = 8.2 Hz, 2H), 7.18 (d, J = 8.2 Hz, 2H), 4.13 (s, 2H), 3.49 (s, 2H). |
| 31 | 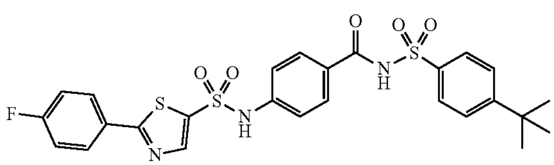 [SMILES: CC(C)(C)c1ccc(S(=O)(=O)NC(=O)c2ccc(NS(=O)(=O)c3cnc(-c4ccc(F)cc4)s3)cc2)cc1] | 574 | 1H NMR (400 MHz, DMSO-d6) δ 12.35 (s, 1H), 11.32 (s, 1H), 8.39 (s, 1H), 8.06-7.98 (m, 2H), 7.92-7.85 (m, 2H), 7.85-7.79 (m, 2H), 7.69-7.58 (m, 2H), 7.40-7.32 (m, 2H), 7.30-7.23 (m, 2H), 1.29 (s, 9H). |
| 32 | 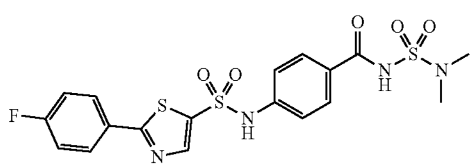 [SMILES: CN(C)S(=O)(=O)NC(=O)c1ccc(NS(=O)(=O)c2cnc(-c3ccc(F)cc3)s2)cc1] | 485 | 1H NMR (400 MHz, DMSO-d6) δ 11.49 (br s, 2H), 8.39 (s, 1H), 8.07-7.97 (m, 2H), 7.94-7.83 (m, 2H), 7.43-7.32 (m, 2H), 7.32-7.20 (m, 2H), 2.84 (s, 6H). |
| 33 | 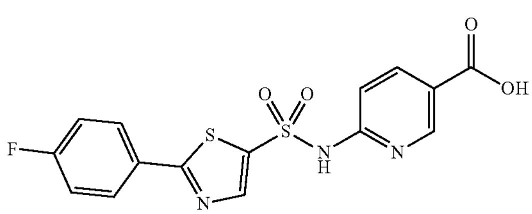 | 380 | 1H NMR (400 MHz, DMSO-d6) δ 13.31 (br s, 2H), 8.46 (s, 1H), 8.35 (s, 1H), 8.20 (dd, J = 9.2, 2.3 Hz, 1H), 8.08-7.99 (m, 2H), 7.40-7.32 (comp, 3H). |
| 34 | 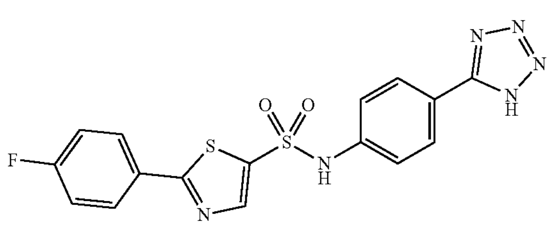 [SMILES: O=S(=O)(Nc1ccc(-c2nnn[nH]2)cc1)c1cnc(-c2ccc(F)cc2)s1] | 403 | 1H NMR (500 MHz, DMSO-d6) δ 11.19 (s, 1H), 8.39 (s, 1H), 8.06-8.00 (m, 2H), 8.00-7.95 (m, 2H), 7.42-7.39 (m, 2H), 7.39-7.34 (m, 2H). |

-continued

| Example # | Structure | LC-MS [M + H]+ unless otherwise noted | 1H-NMR |
|---|---|---|---|
| 35 | 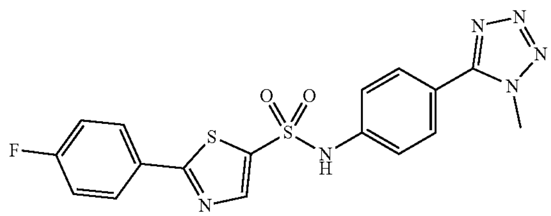 [SMILES: Cn1nnnc1-c1ccc(NS(=O)(=O)c2cnc(-c3ccc(F)cc3)s2)cc1] | 417 | 1H NMR (400 MHz, DMSO-d6) δ 11.29 (s, 1H), 8.41 (s, 1H), 8.08-8.00 (m, 2H), 7.87-7.81 (m, 2H), 7.44-7.40 (m, 2H), 7.40-7.34 (m, 2H), 4.13 (s, 3H). |
| 36 | 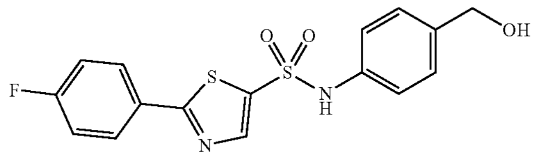 [SMILES: O=S(=O)(Nc1ccc(CO)cc1)c1cnc(-c2ccc(F)cc2)s1] | 365 | 1H NMR (400 MHz, Chloroform-d) δ 8.08 (s, 1H), 7.93-7.83 (m, 2H), 7.32 (d, J = 8.1 Hz, 2H), 7.22-7.10 (m, 5H), 6.92 (s, 1H), 4.66 (s, 2H). |
| 37 | 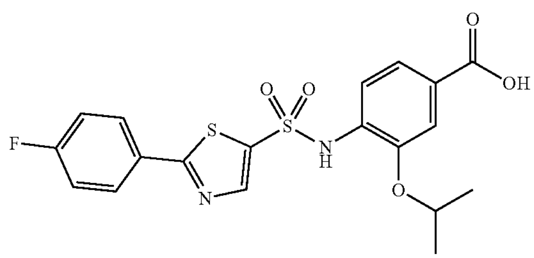 [SMILES: CC(C)Oc1cc(C(=O)O)ccc1NS(=O)(=O)c1cnc(-c2ccc(F)cc2)s1] | 437 | 1H NMR (400 MHz, DMSO-d6) δ 12.96 (s, 1H), 10.21 (s, 1H), 8.16 (s, 1H), 8.05-7.99 (m, 2H), 7.52 (dd, J = 8.2, 1.7 Hz, 1H), 7.46 (d, J = 8.2 Hz, 1H), 7.43-7.34 (m, 3H), 4.54 (hept, J = 6.4 Hz, 1H), 1.07 (d, J = 6.0 Hz, 6H). |
| 38 | 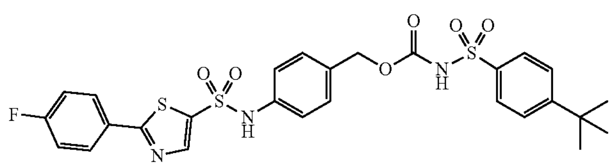 [SMILES: CC(C)(C)c1ccc(S(=O)(=O)NC(=O)OCc2ccc(NS(=O)(=O)c3cnc(-c4ccc(F)cc4)s3)cc2)cc1] | 604 | 1H NMR (400 MHz, Chloroform-d) δ 8.10 (s, 1H), 7.94-7.90 (m, 2H), 7.90-7.85 (m, 2H), 7.72 (s, 1H), 7.54-7.50 (m, 2H), 7.20 (d, J = 8.6 Hz, 2H), 7.17-7.10 (m, 4H), 7.08 (s, 1H), 5.03 (s, 2H), 1.34 (s, 9H). |
| 39 | 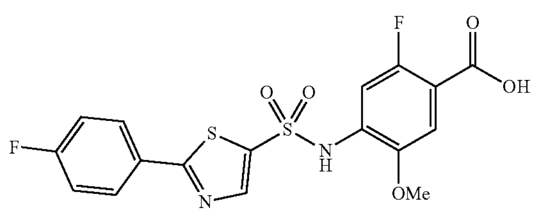 | 427 | 1H NMR (400 MHz, Chloroform-d) δ 8.26 (s, 1H), 7.95-7.87 (m, 2H), 7.59 (s, 1H), 7.48 (d, J = 11.5 Hz, 1H), 7.41 (d, J = 6.1 Hz, 1H), 7.15 (t, J = 8.6 Hz, 2H), 3.87 (s, 3H). |
| 40 | 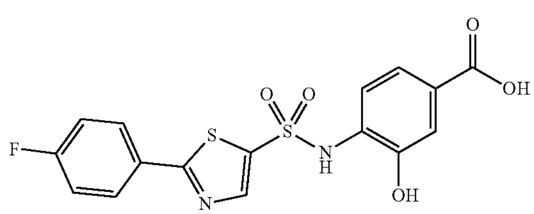 | 395 | 1H NMR (400 MHz, DMSO-d6) δ 12.81 (s, 1H), 10.18 (s, 2H), 8.20 (s, 1H), 8.08-8.00 (m, 2H), 7.42-7.34 (comp, 5H). |
| 41 | 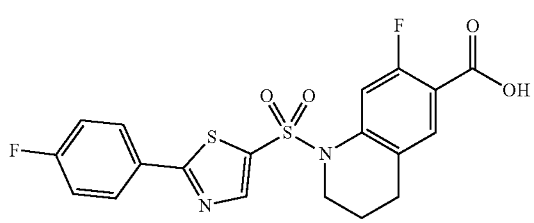 [SMILES: O=C(O)c1cc2c(cc1F)N(S(=O)(=O)c1cnc(-c3ccc(F)cc3)s1)CCC2] | 437 | 1H NMR (400 MHz, DMSO-d6) δ 13.14 (br s, 1H), 8.52 (s, 1H), 8.10-8.01 (m, 2H), 7.66 (d, J = 8.3 Hz, 1H), 7.55 (d, J = 13.2 Hz, 1H), 7.42-7.32 (m, 2H), 3.92-3.84 (m, 2H), 2.64 (t, J = 6.5 Hz, 2H), 1.84-1.69 (m, 2H). |

-continued

| Example # | Structure | LC-MS [M + H]+ unless otherwise noted | 1H-NMR |
|---|---|---|---|
| 42 | 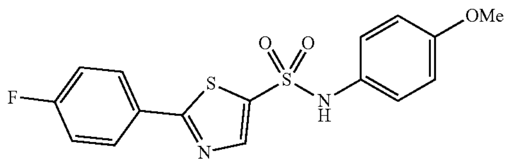 [SMILES: COc1ccc(NS(=O)(=O)c2cnc(-c3ccc(F)cc3)s2)cc1] | 365 | 1H NMR (400 MHz, DMSO-d6) δ 10.38 (s, 1H), 8.12 (s, 1H), 8.07-7.98 (m, 2H), 7.43-7.33 (m, 2H), 7.14-7.03 (m, 2H), 6.92-6.83 (m, 2H), 3.70 (s, 3H). |
| 43 | 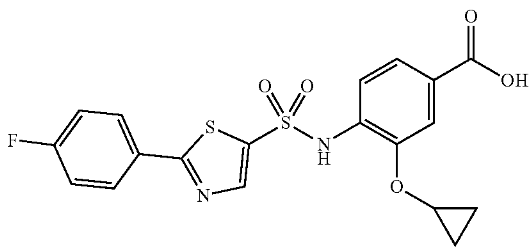 [SMILES: O=C(O)c1ccc(NS(=O)(=O)c2cnc(-c3ccc(F)cc3)s2)c(OC2CC2)c1] | 435 | 1H NMR (500 MHz, DMSO-d6) δ 12.94 (br s, 1H), 10.33 (s, 1H), 8.10 (s, 1H), 8.07-8.02 (m, 2H), 7.72 (d, J = 1.8 Hz, 1H), 7.59 (dd, J = 3.0, 1.8 Hz, 1H), 7.44 (d, J = 8.2 Hz, 1H), 7.41-7.36 (m, 2H), 3.83-3.76 (m, 1H), 0.67-0.61 (m, 2H), 0.38-0.32 (m, 2H). |
| 44 | 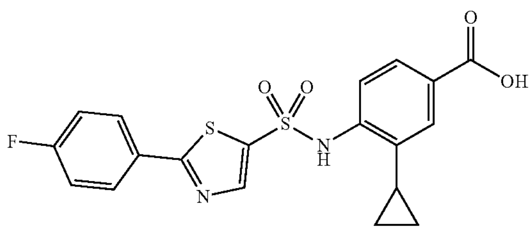 [SMILES: O=C(O)c1ccc(NS(=O)(=O)c2cnc(-c3ccc(F)cc3)s2)c(C2CC2)c1] | 419 | 1H NMR (500 MHz, DMSO-d6) δ 12.93 (br s, 1H), 10.55 (s, 1H), 8.17 (s, 1H), 8.05 (ddd, J = 8.8, 4.9, 2.4 Hz, 2H), 7.71 (dd, J = 8.3, 2.0 Hz, 1H), 7.41-7.36 (m, 2H), 7.35 (d, J = 2.0 Hz, 1H), 7.32 (d, J = 8.3 Hz, 1H), 2.12-2.05 (m, 1H), 0.84-0.77 (m, 2H), 0.50-0.43 (m, 2H). |
| 45 | 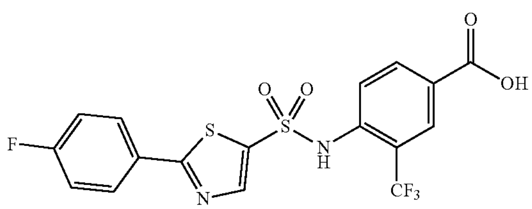 | 447 | 1H NMR (500 MHz, Chloroform-d) δ 8.28 (d, J = 11.5 Hz, 2H), 8.23 (s, 1H), 8.01 (d, J = 8.4 Hz, 1H), 7.90 (dd, J = 8.8, 5.2 Hz, 3H), 7.18-7.12 (m, 3H). |
| 46 | 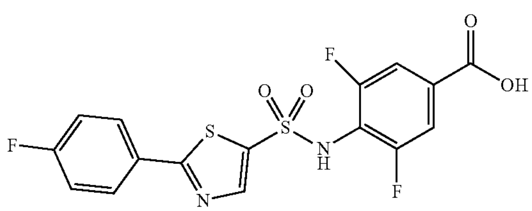 [SMILES: O=C(O)c1cc(F)c(NS(=O)(=O)c2cnc(-c3ccc(F)cc3)s2)c(F)c1] | 415 | 1H NMR (500 MHz, Methanol-d4) δ 7.29 (s, 1H), 7.27-7.20 (m, 2H), 6.80 (d, J = 8.4 Hz, 2H), 6.49-6.41 (m, 2H). |
| 47 | 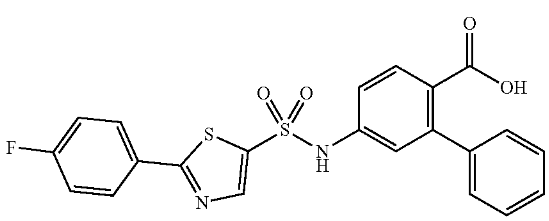 [SMILES: O=C(O)c1ccc(NS(=O)(=O)c2cnc(-c3ccc(F)cc3)s2)cc1-c1ccccc1] | 455 | 1H NMR (500 MHz, DMSO-d6) δ 12.63 (s, 1H), 11.22 (s, 1H), 8.38 (s, 1H), 8.07-8.02 (m, 2H), 7.74 (d, J = 8.5 Hz, 1H), 7.42-7.32 (comp, 5H), 7.29 (dd, J = 8.5, 2.3 Hz, 1H), 7.25-7.20 (m, 2H), 7.11 (d, J = 2.2 Hz, 1H). |
| 48 | 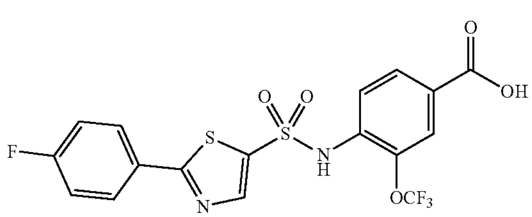 | 463 | 1H NMR (500 MHz, DMSO-d6) δ 13.35 (br s, 1H), 11.30 (brs, 1H), 8.35 (s, 1H), 8.08-8.00 (m, 2H), 7.92 (dd, J = 8.6, 1.9 Hz, 1H), 7.77 (t, J = 1.9 Hz, 1H), 7.66 (d, J = 8.5 Hz, 1H), 7.38 (t, J = 8.8 Hz, 2H). |

-continued

| Example # | Structure | LC-MS [M + H]+ unless otherwise noted | ¹H-NMR |
|---|---|---|---|
| 49 | 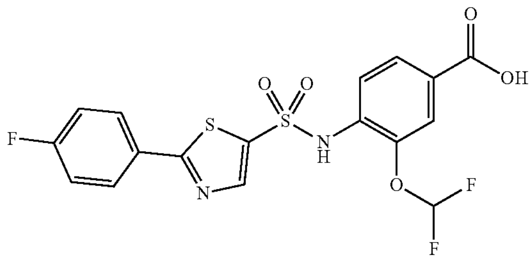 [SMILES: O=C(O)c1ccc(NS(=O)(=O)c2cnc(-c3ccc(F)cc3)s2)c(OC(F)F)c1] | 445 | ¹H NMR (500 MHz, DMSO-d₆) δ 13.21 (s, 1H), 10.90 (s, 1H), 8.28 (s, 1H), 8.06-7.99 (m, 2H), 7.79 (d, J = 8.5 Hz, 1H), 7.66 (s, 1H), 7.58 (d, J = 8.5 Hz, 1H), 7.42-7.35 (m, 2H), 7.18 (t, J = 73.1 Hz, 1H). |
| 50 | 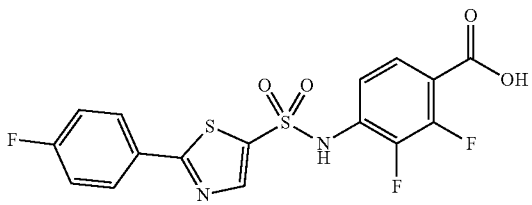 | 415 | ¹H NMR (500 MHz, DMSO-d₆) δ 13.46 (br s, 1H), 11.42 (brs, 1H), 8.35 (s, 1H), 8.10-8.03 (m, 2H), 7.66 (t, J = 7.7 Hz, 1H), 7.39 (t, J = 8.8 Hz, 2H), 7.31 (t, J = 7.9 Hz, 1H). |
| 51 | 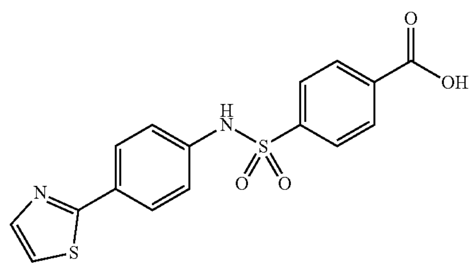 [SMILES: O=C(O)c1ccc(S(=O)(=O)Nc2ccc(-c3nccs3)cc2)cc1] | 361 | ¹H NMR (400 MHz, Methanol-d₄) δ 8.15-8.09 (m, 2H), 7.95-7.89 (m, 2H), 7.85-7.78 (m, 3H), 7.56 (d, J = 3.3 Hz, 1H), 7.27-7.21 (m, 2H). |
| 52 | 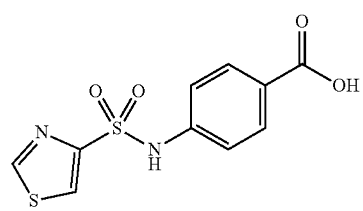 [SMILES: O=C(O)c1ccc(NS(=O)(=O)c2cscn2)cc1] | 285 | ¹H NMR (500 MHz, DMSO-d₆) δ 12.73 (s, 1H), 11.08 (s, 1H), 9.22 (d, J = 2.0 Hz, 1H), 8.61 (d, J = 2.0 Hz, 1H), 7.85-7.77 (m, 2H), 7.28-7.18 (m, 2H). |
| 53 | 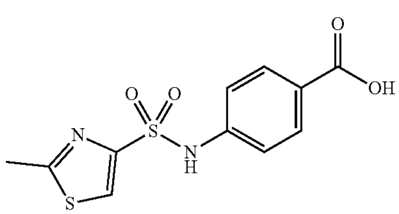 [SMILES: Cc1nc(S(=O)(=O)Nc2ccc(C(=O)O)cc2)cs1] | 299 | ¹H NMR (500 MHz, DMSO-d₆) δ 12.72 (s, 1H), 11.04 (s, 1H), 8.41 (s, 1H), 7.84-7.79 (m, 2H), 7.27-7.20 (m, 2H), 2.65 (s, 3H). |
| 54 | 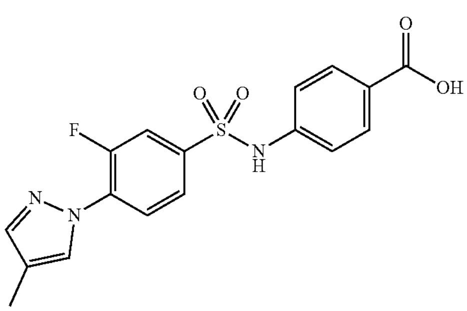 [SMILES: Cc1cnn(-c2ccc(S(=O)(=O)Nc3ccc(C(=O)O)cc3)cc2F)c1] | 376 | ¹H NMR (500 MHz, DMSO-d₆) δ 12.73 (s, 1H), 10.94 (s, 1H), 8.07 (d, J = 3.1 Hz, 1H), 8.03 (t, J = 8.1 Hz, 1H), 7.89-7.80 (m, 3H), 7.75 (dd, J = 8.7, 2.0 Hz, 1H), 7.68 (s, 1H), 7.25-7.21 (m, 2H), 2.09 (s, 3H). |

| Example # | Structure | LC-MS [M + H]+ unless otherwise noted | 1H-NMR |
|---|---|---|---|
| 55 | 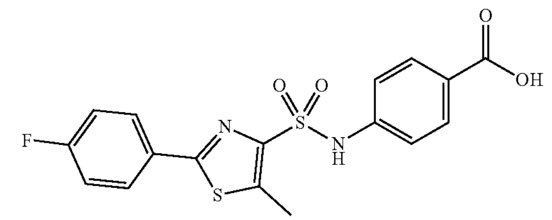 [SMILES: Cc1sc(-c2ccc(F)cc2)nc1S(=O)(=O)Nc1ccc(C(=O)O)cc1] | 393 | 1H NMR (400 MHz, DMSO-d6) δ 12.72 (s, 1H), 11.09 (s, 1H), 7.89-7.80 (comp, 4H), 7.39-7.32 (m, 2H), 7.31-7.24 (m, 2H), 2.72 (s, 3H). |
| 56 | 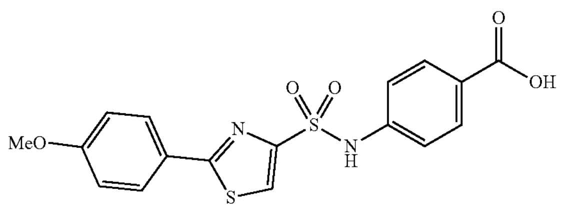 [SMILES: COc1ccc(-c2nc(S(=O)(=O)Nc3ccc(C(=O)O)cc3)cs2)cc1] | 391 | 1H NMR (400 MHz, DMSO-d6) δ 12.73 (s, 1H), 11.13 (s, 1H), 8.52 (d, J = 0.8 Hz, 1H), 7.89-7.79 (comp, 4H), 7.35-7.27 (m, 2H), 7.09-7.04 (m, 2H), 3.82 (s, 3H). |
| 57 | 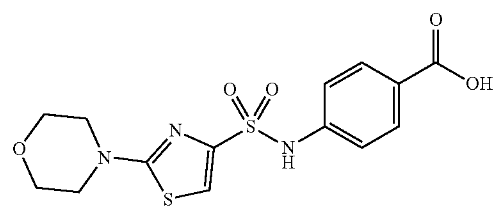 [SMILES: O=C(O)c1ccc(NS(=O)(=O)c2csc(N3CCOCC3)n2)cc1] | 370 | 1H NMR (400 MHz, DMSO-d6) δ 12.71 (s, 1H), 10.90 (s, 1H), 7.85-7.79 (m, 2H), 7.72 (s, 1H), 7.30-7.22 (m, 2H), 3.67 (dd, J = 5.9, 3.9 Hz, 4H), 3.35 (dd, J = 5.8, 4.1 Hz, 4H). |
| 58 | 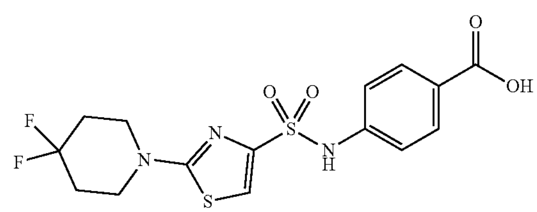 [SMILES: O=C(O)c1ccc(NS(=O)(=O)c2csc(N3CCC(F)(F)CC3)n2)cc1] | 404 | 1H NMR (400 MHz, DMSO-d6) δ 12.71 (s, 1H), 10.89 (s, 1H), 7.85-7.79 (m, 2H), 7.73 (s, 1H), 7.30-7.22 (m, 2H), 3.54 (t, J = 5.9 Hz, 4H), 2.05 (tt, J = 13.6, 6.0 Hz, 4H). |
| 59 | 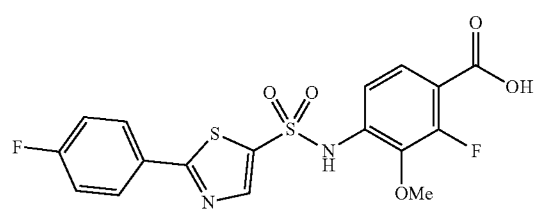 [SMILES: COc1c(NS(=O)(=O)c2cnc(-c3ccc(F)cc3)s2)ccc(C(=O)O)c1F] | 427 | 1H NMR (400 MHz, DMSO-d6) δ 13.18 (s, 1H), 10.88 (s, 1H), 8.36 (s, 1H), 8.10-8.00 (m, 2H), 7.57 (dd, J = 8.8, 7.7 Hz, 1H), 7.41-7.35 (m, 2H), 7.33 (dd, J = 8.8, 1.5 Hz, 1H), 3.74-3.68 (m, 3H). |
| 60 | 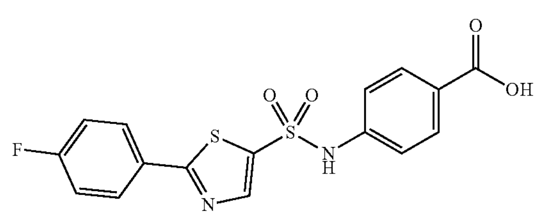 | 379 | 1H NMR (400 MHz, DMSO-d6) δ 12.81 (s, 1H), 11.26 (s, 1H), 8.38 (s, 1H), 8.06-8.00 (m, 2H), 7.91-7.85 (m, 2H), 7.40-7.33 (m, 2H), 7.33-7.27 (m, 2H). |
| 61 | 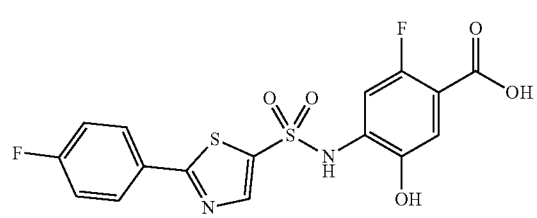 [SMILES: O=C(O)c1cc(O)c(NS(=O)(=O)c2cnc(-c3ccc(F)cc3)s2)cc1F] | 413 | 1H NMR (400 MHz, Methanol-d4) δ 8.15 (s, 1H), 8.02-7.96 (m, 2H), 7.28-7.20 (m, 3H), 7.16 (d, J = 6.6 Hz, 1H). |

-continued

| Example # | Structure | LC-MS [M + H]+ unless otherwise noted | ¹H-NMR |
|---|---|---|---|
| 62 | 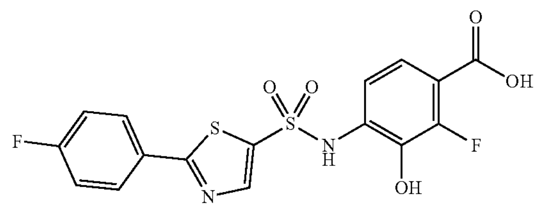 [SMILES: O=C(O)c1ccc(NS(=O)(=O)c2cnc(-c3ccc(F)cc3)s2)c(O)c1F] | 413 | ¹H NMR (400 MHz, Methanol-d₄) δ 8.14 (s, 1H), 8.04-7.95 (m, 2H), 7.42-7.32 (m, 2H), 7.23 (t, J = 8.7 Hz, 2H). |
| 63 | 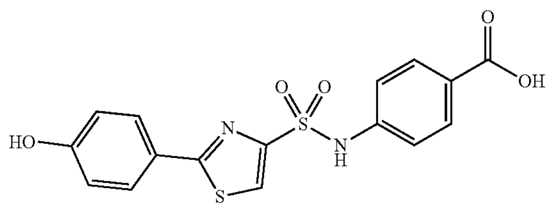 [SMILES: O=C(O)c1ccc(NS(=O)(=O)c2csc(-c3ccc(O)cc3)n2)cc1] | 377 | ¹H NMR (400 MHz, Methanol-d₄) δ 8.15 (s, 1H), 7.92-7.86 (m, 2H), 7.80-7.74 (m, 2H), 7.34-7.28 (m, 2H), 6.88-6.81 (m, 2H). |
| 64 | 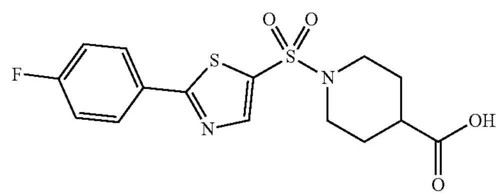 [SMILES: O=C(O)C1CCN(S(=O)(=O)c2cnc(-c3ccc(F)cc3)s2)CC1] | 371 | ¹H NMR (400 MHz, DMSO-d₆) δ 8.36 (s, 1H), 8.14-8.08 (m, 2H), 7.46-7.36 (m, 2H), 3.54 (dd, J = 10.6, 5.3 Hz, 2H), 2.65 (td, J = 11.4, 2.9 Hz, 2H), 2.31 (d, J = 12.5 Hz, 1H), 1.92 (dd, J = 13.7, 3.7 Hz, 2H), 1.60 (dtd, J = 14.8, 11.1, 4.0 Hz, 2H). |
| 65 | 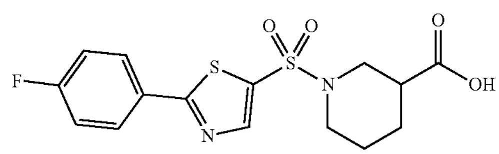 [SMILES: O=C(O)C1CCCN(S(=O)(=O)c2cnc(-c3ccc(F)cc3)s2)C1] | 371 | ¹H NMR (400 MHz, DMSO-d₆) δ 12.57 (s, 1H), 8.38 (s, 1H), 8.14-8.09 (m, 2H), 7.45-7.38 (m, 2H), 3.58 (dd, J = 11.6, 4.0 Hz, 1H), 3.42-3.30 (m, 1H), 2.80 (dd, J = 11.5, 9.5 Hz, 1H), 2.68 (td, J = 10.8, 3.1 Hz, 1H), 2.64-2.54 (m, 1H), 1.87-1.79 (m, 1H), 1.79-1.71 (m, 1H), 1.56 (dt, J = 13.7, 10.2 Hz, 1H), 1.51-1.36 (m, 1H). |
| 66 | 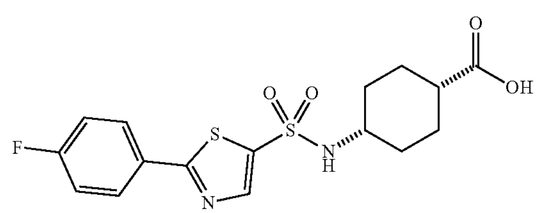 | 385 | ¹H NMR (400 MHz, DMSO-d₆) δ 12.10 (s, 1H), 8.27 (s, 1H), 8.23-8.16 (m, 1H), 8.11-8.05 (m, 2H), 7.40 (t, J = 8.8 Hz, 2H), 3.31-3.21 (m, 1H), 2.33 (d, J = 5.7 Hz, 1H), 1.81 (d, J = 10.9 Hz, 2H), 1.59-1.41 (m, 6H). |
| 67 | 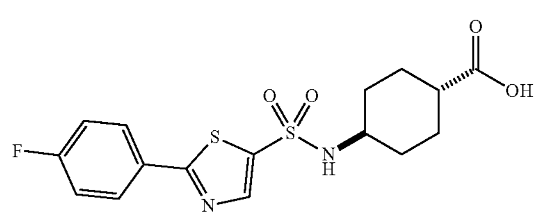 | 385 | ¹H NMR (400 MHz, DMSO-d₆) δ 8.29 (s, 1H), 8.25 (s, 1H), 8.12-8.04 (m, 2H), 7.44-7.36 (m, 2H), 3.10 (d, J = 10.6 Hz, 1H), 2.11-2.00 (m, 1H), 1.84 (d, J = 12.2 Hz, 2H), 1.80-1.72 (m, 2H), 1.41-1.15 (m, 4H). |
| 68 | 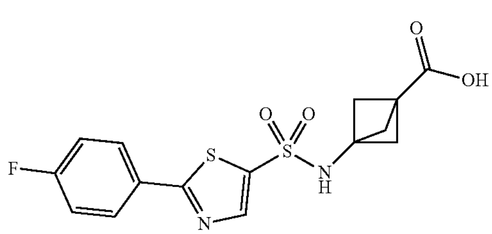 [SMILES: O=C(O)C12CC(NS(=O)(=O)c3cnc(-c4ccc(F)cc4)s3)(C1)C2] | 369 | ¹H NMR (400 MHz, DMSO-d₆) δ 12.50 (s, 1H), 9.27 (s, 1H), 8.33 (s, 1H), 8.16-8.05 (m, 2H), 7.45-7.33 (m, 2H), 2.07 (s, 6H). |

-continued

| Example # | Structure | LC-MS [M + H]+ unless otherwise noted | 1H-NMR |
|---|---|---|---|
| 69 | 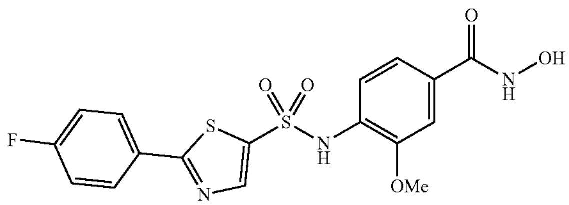 [SMILES: COc1cc(C(=O)NO)ccc1NS(=O)(=O)c1cnc(-c2ccc(F)cc2)s1] | 424 | 1H NMR (400 MHz, DMSO-d6) δ 11.20 (s, 1H), 10.32 (s, 1H), 9.05 (s, 1H), 8.17 (s, 1H), 8.08-8.01 (m, 2H), 7.43-7.27 (comp, 5H), 3.63 (s, 3H). |
| 70 | 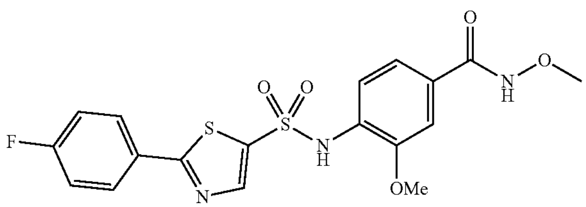 [SMILES: CONC(=O)c1ccc(NS(=O)(=O)c2cnc(-c3ccc(F)cc3)s2)c(OC)c1] | 438 | 1H NMR (400 MHz, DMSO-d6) δ 11.71 (s, 1H), 10.34 (s, 1H), 8.16 (d, J = 0.9 Hz, 1H), 8.07-8.01 (m, 2H), 7.43-7.29 (m, 5H), 3.69 (d, J = 0.6 Hz, 3H), 3.64 (s, 3H). |
| 71 | 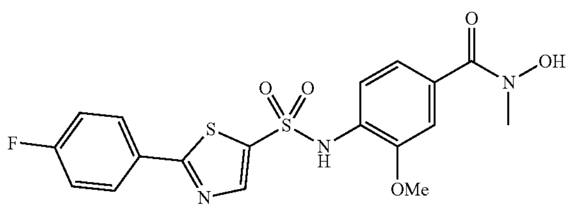 | 438 | 1H NMR (400 MHz, DMSO-d6) δ 10.28 (s, 1H), 10.02 (s, 1H), 8.15 (d, J = 0.7 Hz, 1H), 8.07-8.02 (m, 2H), 7.43-7.35 (m, 2H), 7.34-7.31 (m, 1H), 7.20 (d, J = 8.4 Hz, 2H), 3.60 (d, J = 0.7 Hz, 3H), 3.22 (s, 3H). |
| 72 | 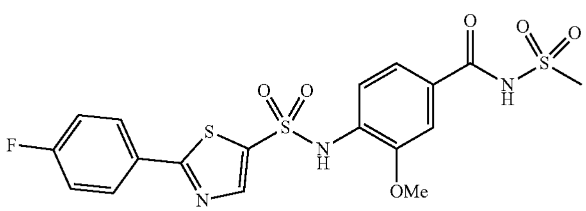 [SMILES: COc1cc(C(=O)NS(C)(=O)=O)ccc1NS(=O)(=O)c1cnc(-c2ccc(F)cc2)s1] | 486 | |
| 73 | 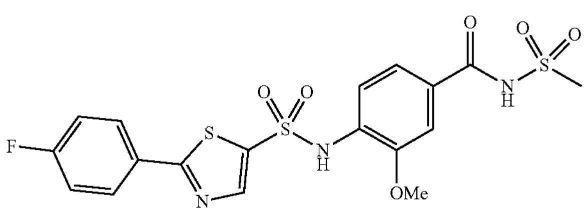 [SMILES: COc1cc(C(=O)NS(C)(=O)=O)ccc1NS(=O)(=O)c1cnc(-c2ccc(F)cc2)s1] | 512 | |
| 74 | 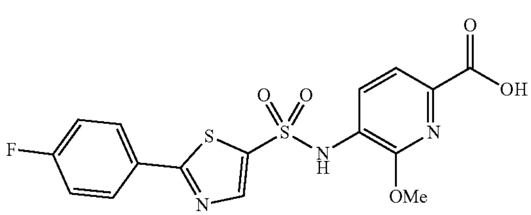 | 410.0 | 1H NMR (400 MHz, Methanol-d4) δ 8.20 (s, 1H), 8.06-7.96 (m, 3H), 7.80 (d, J = 8.0 Hz, 1H), 7.31-7.20 (m, 2H), 3.94 (s, 3H) |
| 75 | 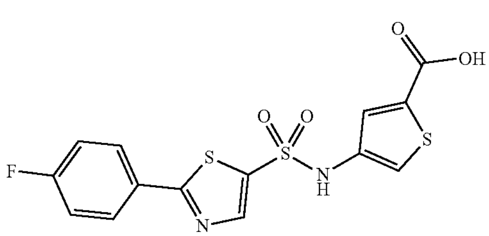 [SMILES: O=C(O)c1cc(NS(=O)(=O)c2cnc(-c3ccc(F)cc3)s2)cs1] | 384.8 | 1H NMR (400 MHz, Methanol-d4) δ 8.15 (s, 1H), 8.06-7.97 (m, 2H), 7.56 (d, J = 1.7 Hz, 1H), 7.33 (d, J = 1.7 Hz, 1H), 7.30-7.20 (m, 2H) |

-continued

| Example # | Structure | LC-MS [M + H]+ unless otherwise noted | 1H-NMR |
|---|---|---|---|
| 76 | 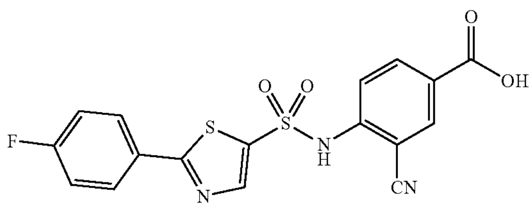 | 403.9 | 1H NMR (400 MHz, Methanol-d4) δ 8.32-8.22 (m, 2H), 8.18 (s, 1H), 8.09-8.00 (m, 2H), 7.69 (d, J = 8.6 Hz, 1H), 7.32-7.21 (m, 2H). |
| 77 | 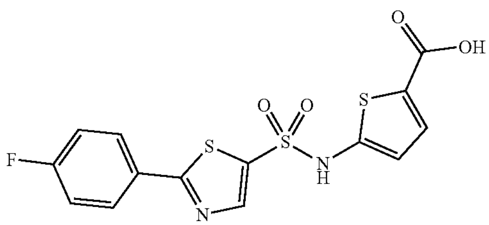 [SMILES: O=C(O)c1ccc(NS(=O)(=O)c2cnc(-c3ccc(F)cc3)s2)s1] | 384.8 | 1H NMR (400 MHz, Methanol-d4) δ 8.19 (s, 1H), 8.09-7.99 (m, 2H), 7.56 (d, J = 4.0 Hz, 1H), 7.26 (m, 2H), 6.75 (d, J = 4.1 Hz, 1H). |
| 78 | 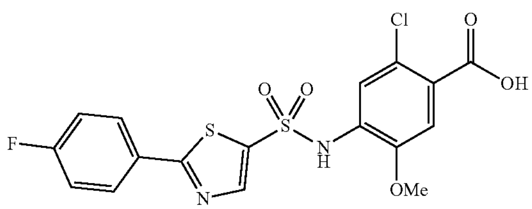 | 442.9 | 1H NMR (400 MHz, Methanol-d4) δ 8.15 (s, 1H), 8.06-7.98 (m, 2H), 7.64 (s, 1H), 7.41 (s, 1H), 7.26 (m, 2H), 3.75 (s, 3H), 0.12 (s, 1H). |
| 79 | 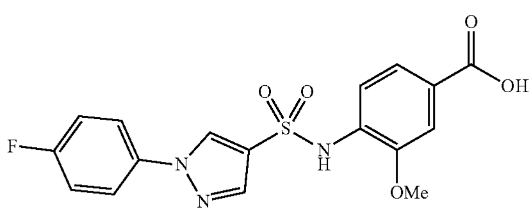 [SMILES: COc1cc(C(=O)O)ccc1NS(=O)(=O)c1cnn(-c2ccc(F)cc2)c1] | 389.9 [M − H]− | 1H NMR (400 MHz, DMSO-d6) δ 12.88 (s, 1H), 9.75 (s, 1H), 9.07 (s, 1H), 8.03 (s, 1H), 7.97-7.76 (m, 2H), 7.61-7.26 (m, 5H), 3.75 (s, 3H). |
| 80 | 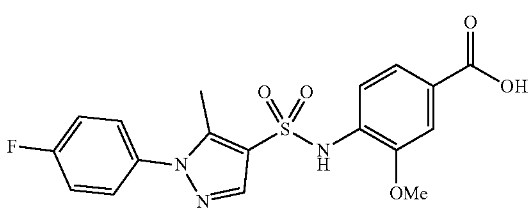 [SMILES: COc1cc(C(=O)O)ccc1NS(=O)(=O)c1cnn(-c2ccc(F)cc2)c1C] | 406.1 | 1H NMR (400 MHz, DMSO-d6) δ 12.87 (s, 1H), 9.80 (s, 1H), 8.89 (s, 1H), 8.04-7.76 (m, 2H), 7.51 (dd, J = 8.3, 1.8 Hz, 1H), 7.47-7.41 (m, 1H), 7.42 (d, J = 1.7 Hz, 1H), 7.37-7.30 (m, 2H), 3.71 (s, 3H), 2.34 (s, 3H). |
| 81 | 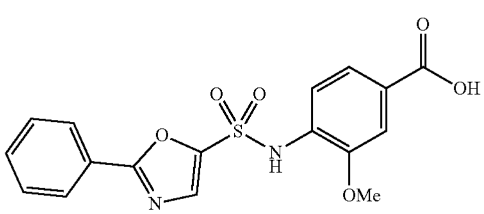 [SMILES: COc1cc(C(=O)O)ccc1NS(=O)(=O)c1cnc(-c2ccccc2)o1] | 375.0 | 1H NMR (400 MHz, DMSO-d6) δ 13.05 (s, 1H), 10.60 (s, 1H), 8.02-7.89 (m, 2H), 7.85 (s, 1H), 7.80-7.52 (m, 4H), 7.52-7.07 (m, 2H), 3.58 (s, 3H). |
| 82 | 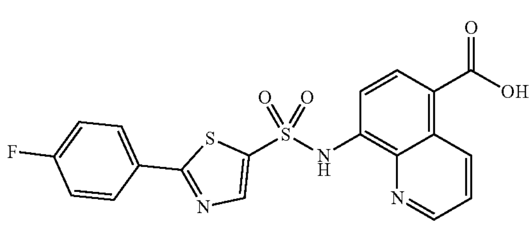 [SMILES: O=C(O)c1ccc(NS(=O)(=O)c2cnc(-c3ccc(F)cc3)s2)c2ncccc12] | 430.2 | 1H NMR (400 MHz, DMSO-d6) δ 9.43 (d, J = 8.7 Hz, 1H), 8.95 (d, J = 4.0 Hz, 1H), 8.49 (s, 1H), 8.32 (d, J = 8.3 Hz, 1H), 7.98 (dd, J = 8.8, 5.3 Hz, 2H), 7.88 (d, J = 8.2 Hz, 1H), 7.76 (dd, J = 8.8, 4.2 Hz, 1H), 7.34 (t, J = 8.8 Hz, 2H). |

| Example # | Structure | LC-MS [M + H]+ unless otherwise noted | ¹H-NMR |
|---|---|---|---|
| 83 | 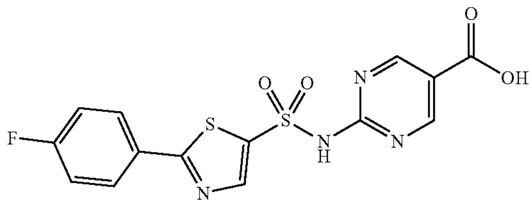 [SMILES: O=C(O)c1cnc(NS(=O)(=O)c2cnc(-c3ccc(F)cc3)s2)nc1] | 380.9 | ¹H NMR (400 MHz, DMSO-d₆) δ 13.01 (s, 1H), 8.92 (s, 2H), 8.37 (s, 1H), 8.06 (dd, J = 8.7, 5.4 Hz, 2H), 7.37 (m Hz, 2H). |
| 84 | 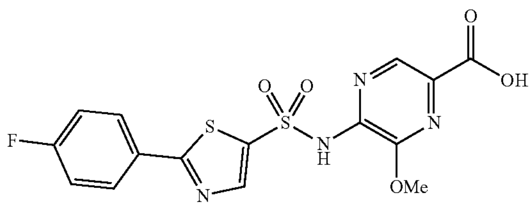 | 411.0 | ¹H NMR (400 MHz, DMSO-d₆) δ 8.43 (s, 1H), 8.38 (s, 1H), 8.11-7.99 (m, 3H), 7.49-7.33 (m, 3H), 3.94 (s, 3H). |
| 85 | 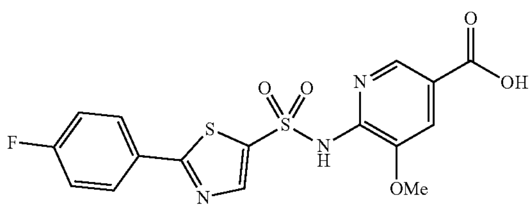 | 409.9 | ¹H NMR (400 MHz, DMSO-d₆) δ 13.20 (s, 1H), 8.46 (s, 1H), 8.08 (dd, J = 8.6, 5.3 Hz, 2H), 7.64 (s, 1H), 7.39 (t, J = 8.8 Hz, 2H), 3.88 (s, 3H). |
| 86 | 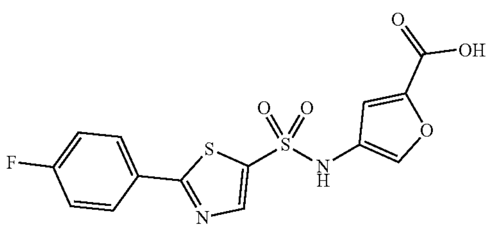 [SMILES: O=C(O)c1cc(NS(=O)(=O)c2cnc(-c3ccc(F)cc3)s2)co1] | 368.9 | ¹H NMR (400 MHz, DMSO-d₆) δ 8.32 (s, 1H), 8.11-8.02 (m, 2H), 7.81 (d, J = 1.0 Hz, 1H), 7.44-7.30 (m, 2H), 6.97 (d, J = 1.0 Hz, 1H). |
| 87 | 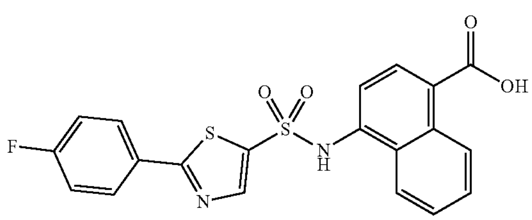 [SMILES: O=C(O)c1ccc(NS(=O)(=O)c2cnc(-c3ccc(F)cc3)s2)c2ccccc12] | 429.0 | ¹H NMR (400 MHz, DMSO-d₆) δ 13.14 (s, 1H), 11.10 (s, 1H), 8.90-8.84 (m, 1H), 8.20 (d, J = 10.0 Hz, 2H), 8.11 (d, J = 8.0 Hz, 1H), 8.06-7.97 (m, 2H), 7.63 (dd, J = 8.5, 6.8 Hz, 1H), 7.56 (dd, J = 8.3, 6.8 Hz, 1H), 7.45 (d, J = 7.9 Hz, 1H), 7.42-7.32 (m, 2H). |
| 88 | 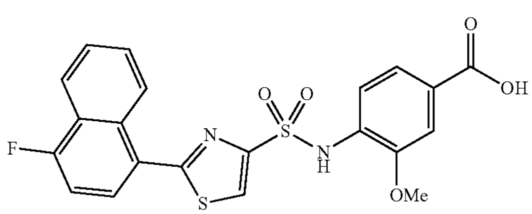 [SMILES: COc1cc(C(=O)O)ccc1NS(=O)(=O)c1csc(-c2ccc(F)c3ccccc23)n1] | 459.2 | ¹H NMR (400 MHz, DMSO-d₆) δ 12.95 (s, 1H), 10.16 (s, 1H), 8.72-8.66 (d, J = 8.2 Hz, 1H), 8.53 (s, 1H), 8.19 (d, J = 8.3 Hz, 1H), 8.01 (dd, J = 8.1, 5.3 Hz, 1H), 7.81-7.72 (m, 1H), 7.67 (ddd, J = 8.4, 6.9, 1.4 Hz, 1H), 7.62-7.44 (m, 4H), 3.69 (s, 3H). |
| 89 | 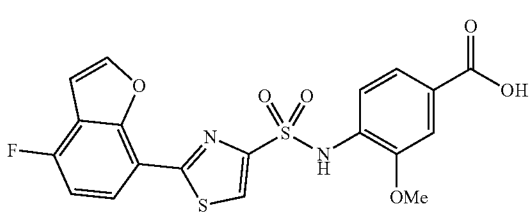 [SMILES: COc1cc(C(=O)O)ccc1NS(=O)(=O)c1csc(-c2ccc(F)c3ccoc23)n1] | 449.1 | ¹H NMR (400 MHz, Chloroform-d) δ 8.20 (s, 1H), 8.16 (dd, J = 8.6, 5.2 Hz, 1H), 7.84-7.66 (m, 4H), 7.51 (s, 1H), 7.08 (t, J = 8.7 Hz, 1H), 7.00 (d, J = 2.2 Hz, 1H), 3.88 (s, 3H). |

-continued

| Example # | Structure | LC-MS [M + H]+ unless otherwise noted | 1H-NMR |
|---|---|---|---|
| 90 | 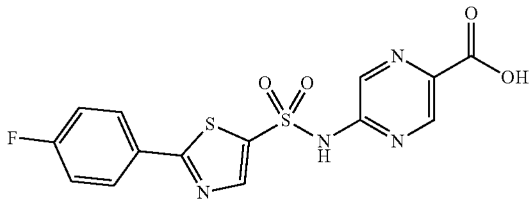 [SMILES: O=C(O)c1cnc(NS(=O)(=O)c2cnc(-c3ccc(F)cc3)s2)cn1] | 380.9 | 1H NMR (400 MHz, DMSO-d6) δ 8.87 (d, J = 1.4 Hz, 1H), 8.56 (s, 1H), 8.40 (d, J = 1.4 Hz, 1H), 8.13-8.03 (m, 2H), 7.44-7.34 (m, 2H). |
| 91 | 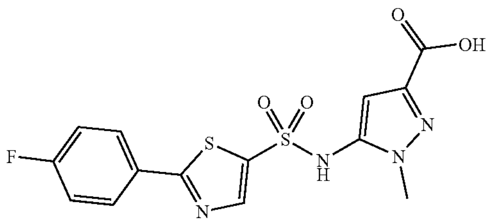 [SMILES: Cn1nc(C(=O)O)cc1NS(=O)(=O)c1cnc(-c2ccc(F)cc2)s1] | 383.0 | 1H NMR (400 MHz, DMSO-d6) δ 12.77 (s, 1H), 11.25 (s, 1H), 8.28 (s, 1H), 8.15-8.05 (m, 2H), 7.46-7.36 (m, 2H), 6.32 (s, 1H), 3.73 (s, 3H). |
| 92 | 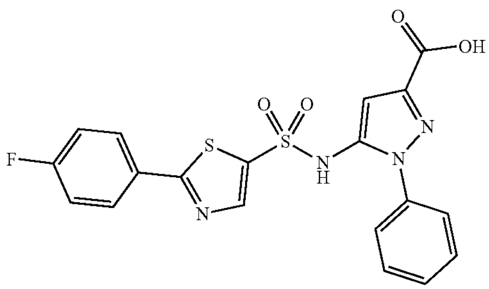 [SMILES: O=C(O)c1cc(NS(=O)(=O)c2cnc(-c3ccc(F)cc3)s2)n(-c2ccccc2)n1] | 445.0 | 1H NMR (400 MHz, DMSO-d6) δ 13.10 (s, 1H), 8.13 (s, 1H), 8.09-7.98 (m, 2H), 7.54-7.33 (m, 8H), 6.65 (s, 1H). |
| 93 | 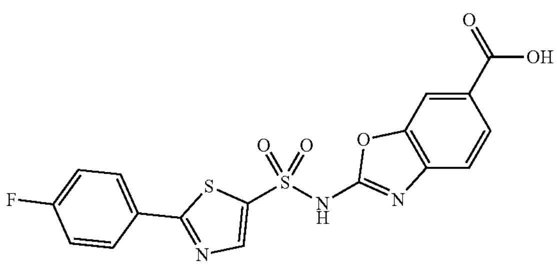 [SMILES: O=C(O)c1ccc2nc(NS(=O)(=O)c3cnc(-c4ccc(F)cc4)s3)oc2c1] | 420.0 | 1H NMR (400 MHz, DMSO-d6) δ 8.44 (s, 1H), 8.10-7.99 (m, 3H), 7.92 (d, J = 7.7 Hz, 1H), 7.40 (m, 3H). |
| 94 | 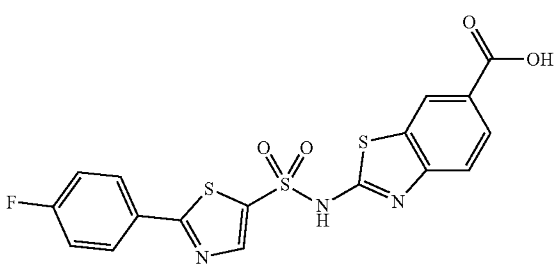 | 435.9 | 1H NMR (400 MHz, DMSO-d6) δ 13.80 (s, 1H), 13.08 (s, 1H), 8.50 (d, J = 1.7 Hz, 1H), 8.37 (s, 1H), 8.09-8.01 (m, 2H), 8.00 (dd, J = 8.4, 1.7 Hz, 1H), 7.44 (d, J = 8.4 Hz, 1H), 7.38 (t, J = 8.8 Hz, 2H). |
| 95 | 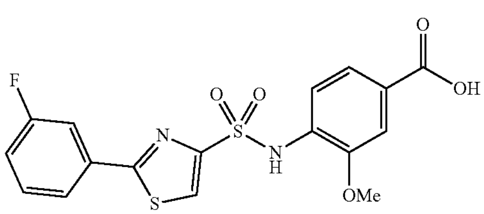 [SMILES: COc1cc(C(=O)O)ccc1NS(=O)(=O)c1csc(-c2cccc(F)c2)n1] | 409.0 | 1H NMR (400 MHz, DMSO-d6) δ 12.93 (s, 1H), 10.09 (s, 1H), 8.44 (s, 1H), 7.79 (dt, J = 7.8, 1.2 Hz, 1H), 7.74-7.67 (m, 1H), 7.60 (td, J = 8.1, 5.9 Hz, 1H), 7.56-7.48 (m, 2H), 7.47-7.37 (m, 2H), 3.66 (s, 3H). |

-continued

| Example # | Structure | LC-MS [M + H]+ unless otherwise noted | 1H-NMR |
|---|---|---|---|
| 96 | (2-fluorophenyl-thiazole sulfonamide-methoxybenzoic acid) | 406.9 [M − H]− | 1H NMR (400 MHz, DMSO-d6) δ 12.93 (s, 1H), 10.10 (s, 1H), 8.49 (s, 1H), 8.10 (td, J = 7.8, 1.8 Hz, 1H), 7.63 (dddd, J = 8.7, 7.2, 5.4, 1.8 Hz, 1H), 7.56-7.34 (m, 4H), 3.66 (s, 3H). |
| 97 | (4-methylphenyl-thiazole sulfonamide-methoxybenzoic acid) | 405.0 | 1H NMR (400 MHz, DMSO-d6) δ 12.92 (s, 1H), 10.03 (s, 1H), 8.34 (s, 1H), 7.89-7.76 (m, 2H), 7.57-7.48 (m, 2H), 7.42 (d, J = 1.6 Hz, 1H), 7.35 (d, J = 8.0 Hz, 2H), 3.66 (s, 3H). |
| 98 | (4-trifluoromethylphenyl-thiazole sulfonamide-methoxybenzoic acid) | 459.1 | |
| 99 | (4-methoxyphenyl-thiazole sulfonamide-methoxybenzoic acid) | 421.1 | |
| 100 | (pyridin-4-yl-thiazole sulfonamide-methoxybenzoic acid) | 392.0 | |
| 101 | (1-methylpyrazol-3-yl-thiazole sulfonamide-methoxybenzoic acid) | 392.9 [M − H]− | |
| 102 | (phenyl-thiazole sulfonamide-methoxybenzoic acid) | 391.0 | |

-continued

| Example # | Structure | LC-MS [M + H]+ unless otherwise noted | 1H-NMR |
|---|---|---|---|
| 103 | 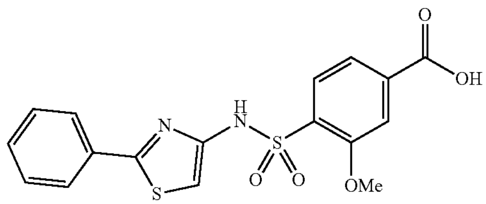 [SMILES: COc1cc(C(=O)O)ccc1S(=O)(=O)Nc1csc(-c2ccccc2)n1] | 391.0 | |
| 104 | 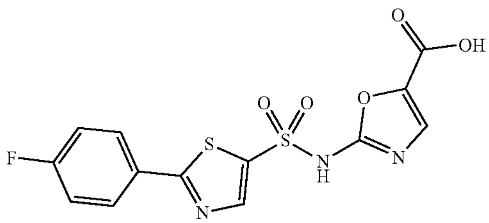 [SMILES: O=C(O)c1cnc(NS(=O)(=O)c2cnc(-c3ccc(F)cc3)s2)o1] | 369.8 | 1H NMR (400 MHz, Methanol-$d_4$) δ 8.33 (s, 1H), 8.05 (dd, J = 10.7, 5.5 Hz, 2H), 7.82 (s, 1H), 7.32-7.21 (m, 2H). |
| 105 | 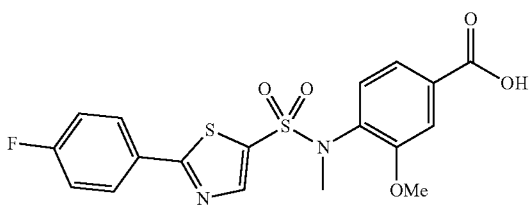 [SMILES: COc1cc(C(=O)O)ccc1N(C)S(=O)(=O)c1cnc(-c2ccc(F)cc2)s1] | 423.0 | |
| 106 | 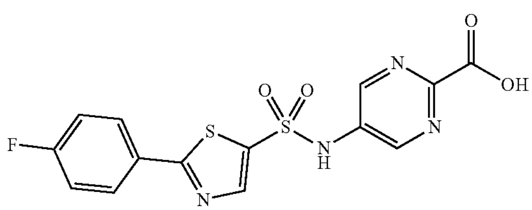 [SMILES: O=C(O)c1ncc(NS(=O)(=O)c2cnc(-c3ccc(F)cc3)s2)cn1] | 380.9 | 1H NMR (400 MHz, DMSO-$d_6$) δ 8.71 (s, 2H), 8.48 (s, 1H), 8.07 (m, 2H), 7.38 (m, 2H). |
| 107 | 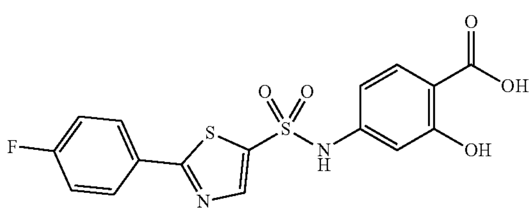 | 395.0 | |
| 108 | 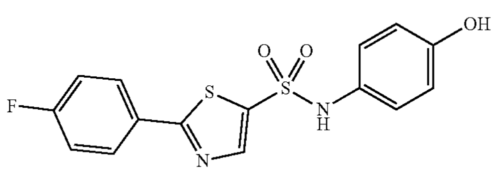 [SMILES: O=S(=O)(Nc1ccc(O)cc1)c1cnc(-c2ccc(F)cc2)s1] | 351.0 | |
| 109 | 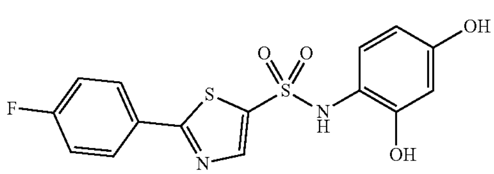 [SMILES: O=S(=O)(Nc1ccc(O)cc1O)c1cnc(-c2ccc(F)cc2)s1] | 367.0 | |

-continued

| Example # | Structure | LC-MS [M + H]+ unless otherwise noted | 1H-NMR |
|---|---|---|---|
| 110 | 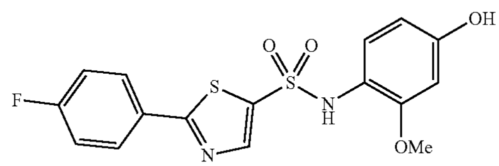 | 381.0 | |
| 111 | 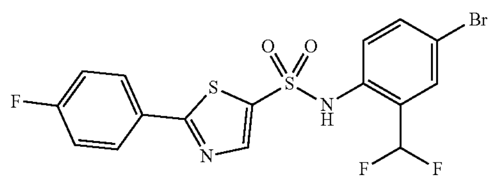 [SMILES: O=S(=O)(Nc1ccc(Br)cc1C(F)F)c1cnc(-c2ccc(F)cc2)s1] | 465.0 | |
| 112 | 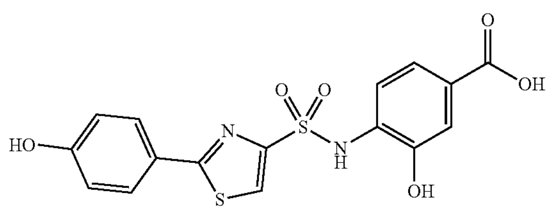 [SMILES: O=C(O)c1ccc(NS(=O)(=O)c2csc(-c3ccc(O)cc3)n2)c(O)c1] | 393.1 | |
| 113 | 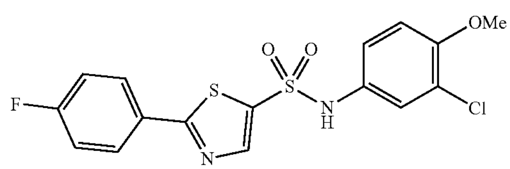 [SMILES: COc1ccc(NS(=O)(=O)c2cnc(-c3ccc(F)cc3)s2)cc1Cl] | 399.0 | |
| 114 | 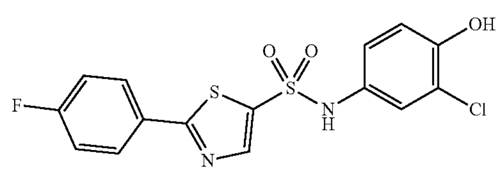 [SMILES: O=S(=O)(Nc1ccc(O)c(Cl)c1)c1cnc(-c2ccc(F)cc2)s1] | 385.0 | |
| 115 | 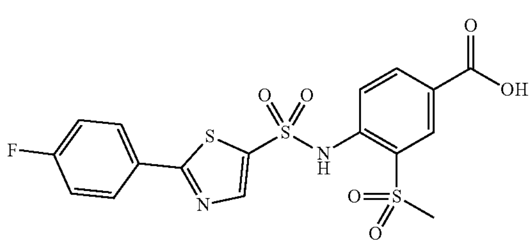 [SMILES: CS(=O)(=O)c1cc(C(=O)O)ccc1NS(=O)(=O)c1cnc(-c2ccc(F)cc2)s1] | 456.8 | 1H NMR (400 MHz, Methanol-d4) δ 8.53 (d, J = 2.0 Hz, 1H), 8.43 (s, 1H), 8.29 (d, J = 8.2 Hz, 2H), 8.09-8.01 (m, 2H), 7.97-7.87 (m, 2H), 7.26 (t, J = 8.7 Hz, 2H), 7.04 (d, J = 8.7 Hz, 1H), 3.88 (s, 1H), 3.22 (d, J = 7.6 Hz, 3H). |
| 116 | 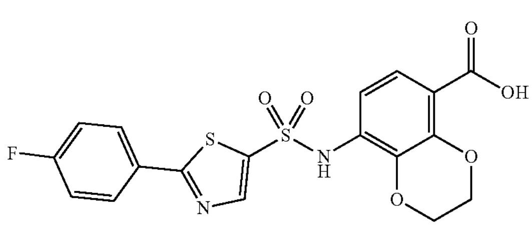 [SMILES: O=C(O)c1ccc(NS(=O)(=O)c2cnc(-c3ccc(F)cc3)s2)c2c1OCCO2] | 435.0 [M − H]− | 1H NMR (400 MHz, DMSO-d6) δ 12.69 (s, 1H), 10.41 (s, 1H), 8.23 (s, 1H), 8.11-8.02 (m, 2H), 7.44-7.34 (m, 2H), 7.27 (d, J = 8.6 Hz, 1H), 6.95 (d, J = 8.6 Hz, 1H), 4.24-4.17 (m, 2H), 4.12-4.05 (m, 2H). |

-continued

| Example # | Structure | LC-MS [M + H]+ unless otherwise noted | ¹H-NMR |
|---|---|---|---|
| 117 | 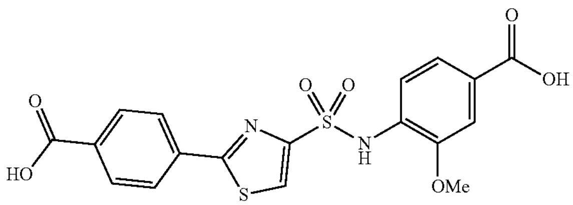 [SMILES: COc1cc(C(=O)O)ccc1NS(=O)(=O)c1csc(-c2ccc(C(=O)O)cc2)n1] | 433.0 [M − H]− | |
| 118 | 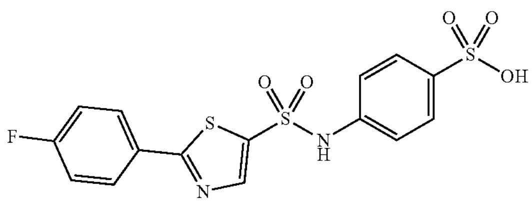 [SMILES: O=S(=O)(O)c1ccc(NS(=O)(=O)c2cnc(-c3ccc(F)cc3)s2)cc1] | 415.0 | |
| 119 | 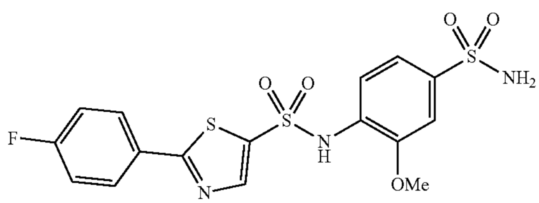 [SMILES: COc1cc(S(N)(=O)=O)ccc1NS(=O)(=O)c1cnc(-c2ccc(F)cc2)s1] | 444.2 | |
| 120 | 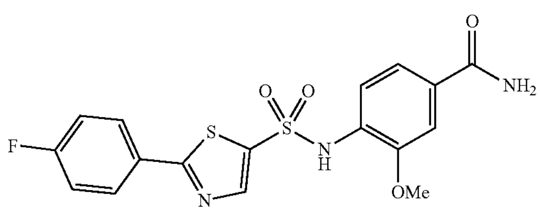 [SMILES: COc1cc(C(N)=O)ccc1NS(=O)(=O)c1cnc(-c2ccc(F)cc2)s1] | 408.1 | |
| 121 | 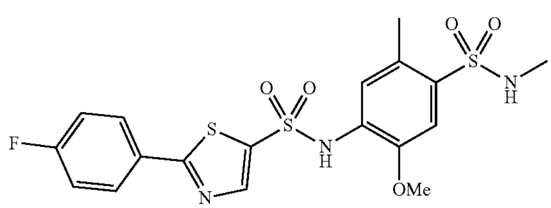 [SMILES: CNS(=O)(=O)c1cc(OC)c(NS(=O)(=O)c2cnc(-c3ccc(F)cc3)s2)cc1C] | 472.2 | |
| 122 | 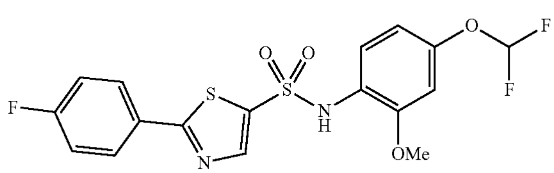 [SMILES: COc1cc(OC(F)F)ccc1NS(=O)(=O)c1cnc(-c2ccc(F)cc2)s1] | 431.1 | |
| 123 | 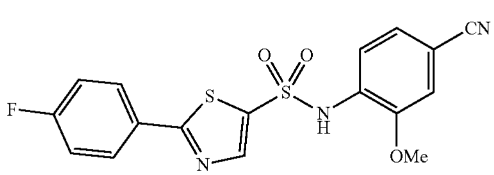 [SMILES: COc1cc(C#N)ccc1NS(=O)(=O)c1cnc(-c2ccc(F)cc2)s1] | 390.1 | |

| Example # | Structure | LC-MS [M + H]+ unless otherwise noted | ¹H-NMR |
|---|---|---|---|
| 124 | 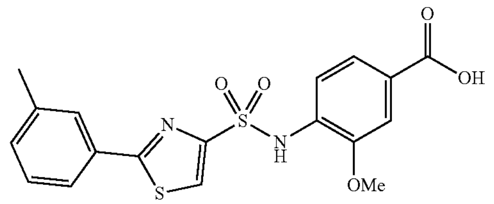 [SMILES: COc1cc(C(=O)O)ccc1NS(=O)(=O)c1csc(-c2cccc(C)c2)n1] | 405.0 | ¹H NMR (400 MHz, DMSO-d$_6$) δ 8.36 (s, 1H), 7.71 (d, J = 5.4 Hz, 2H), 7.60-7.47 (m, 3H), 7.46-7.39 (m, 2H), 7.36 (d, J = 7.6 Hz, 1H), 3.65 (s, 3H), 2.38 (s, 3H), 2.29 (s, 1H). |
| 125 | 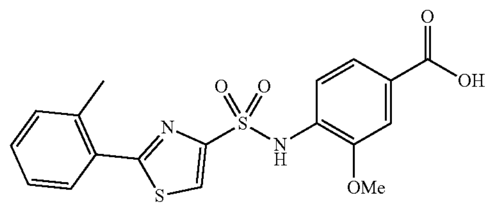 [SMILES: COc1cc(C(=O)O)ccc1NS(=O)(=O)c1csc(-c2ccccc2C)n1] | 405.0 | ¹H NMR (400 MHz, DMSO-d$_6$) δ 10.09 (s, 1H), 8.48 (s, 1H), 7.72 (d, J = 7.5 Hz, 1H), 7.61 (s, 1H), 7.54 (q, J = 8.3 Hz, 2H), 7.43 (d, J = 7.7 Hz, 2H), 7.36 (dd, J = 16.4, 8.4 Hz, 2H), 3.70 (d, J = 3.9 Hz, 3H), 2.41 (d, J = 3.4 Hz, 3H). |
| 126 | 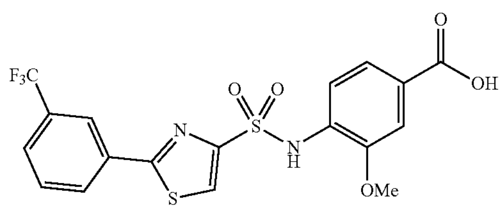 [SMILES: COc1cc(C(=O)O)ccc1NS(=O)(=O)c1csc(-c2cccc(C(F)(F)F)c2)n1] | 459.0 | ¹H NMR (400 MHz, DMSO-d$_6$) δ 10.15 (s, 1H), 8.47 (s, 1H), 8.22 (d, J = 7.8 Hz, 1H), 8.15 (d, J = 2.3 Hz, 1H), 7.93 (d, J = 7.8 Hz, 1H), 7.79 (t, J = 7.8 Hz, 1H), 7.58-7.47 (m, 2H), 7.43 (d, J = 1.6 Hz, 1H), 3.64 (s, 3H). |
| 127 | 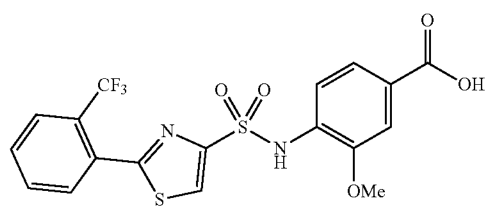 | 459.0 | ¹H NMR (400 MHz, DMSO-d$_6$) δ 8.55 (s, 1H), 7.95 (dd, J = 7.4, 1.7 Hz, 1H), 7.88-7.73 (m, 4H), 7.46 (m, 3H), 3.74 (s, 3H). |
| 128 | 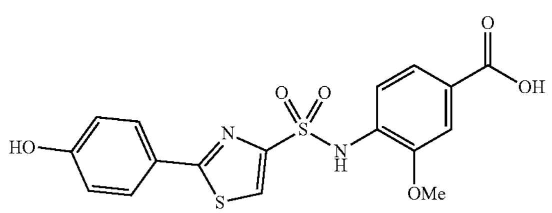 [SMILES: COc1cc(C(=O)O)ccc1NS(=O)(=O)c1csc(-c2ccc(O)cc2)n1] | 407.0 | ¹H NMR (400 MHz, DMSO-d$_6$) δ 8.23 (s, 1H), 7.79-7.71 (m, 2H), 7.56-7.46 (m, 2H), 7.42 (d, J = 1.7 Hz, 1H), 6.93-6.85 (m, 2H), 3.68 (s, 3H). |
| 129 | 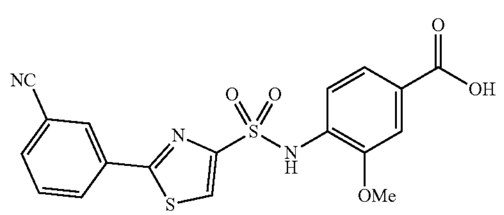 [SMILES: COc1cc(C(=O)O)ccc1NS(=O)(=O)c1csc(-c2cccc(C#N)c2)n1] | 413.8 [M − H]⁻ | ¹H NMR (400 MHz, DMSO-d$_6$) δ 8.35 (d, J = 1.6 Hz, 2H), 8.24 (m, 1H), 8.04-7.97 (m, 1H), 7.75 (m, 1H), 7.49-7.38 (m, 2H), 7.41-7.34 (m, 1H), 3.66 (s, 3H). |
| 130 | 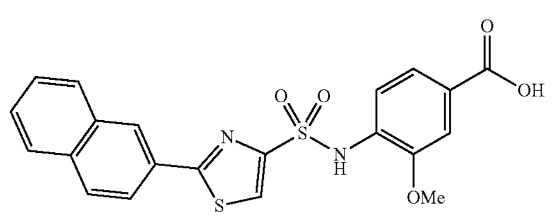 [SMILES: COc1cc(C(=O)O)ccc1NS(=O)(=O)c1csc(-c2ccc3ccccc3c2)n1] | 441.1 | ¹H NMR (400 MHz, DMSO-d$_6$) δ 10.11 (s, 1H), 8.52 (d, J = 1.8 Hz, 1H), 8.43 (s, 1H), 8.12-7.95 (m, 4H), 7.67-7.53 (m, 4H), 7.52 (s, 1H), 7.45 (d, J = 1.6 Hz, 1H), 3.66 (s, 3H). |

-continued

| Example # | Structure | LC-MS [M + H]+ unless otherwise noted | 1H-NMR |
|---|---|---|---|
| 131 | 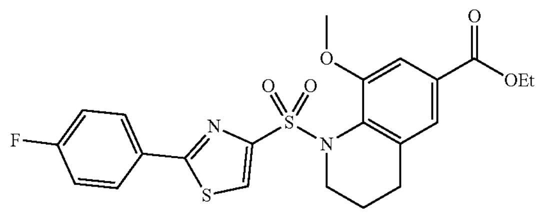 [SMILES: CCOC(=O)c1cc2c(c(OC)c1)N(S(=O)(=O)c1csc(-c3ccc(F)cc3)n1)CCC2] | 477.3 | |
| 132 | 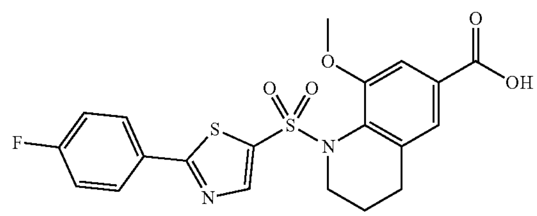 [SMILES: COc1cc(C(=O)O)cc2c1N(S(=O)(=O)c1cnc(-c3ccc(F)cc3)s1)CCC2] | 449.2 | |
| 133 | 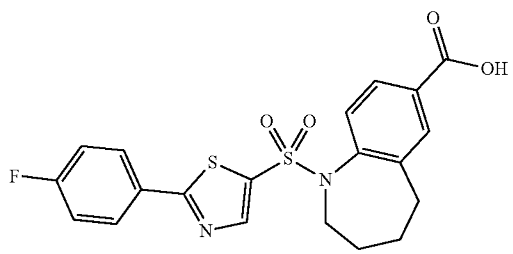 [SMILES: O=C(O)c1ccc2c(c1)CCCCN2S(=O)(=O)c1cnc(-c2ccc(F)cc2)s1] | 433.2 | |
| 134 | 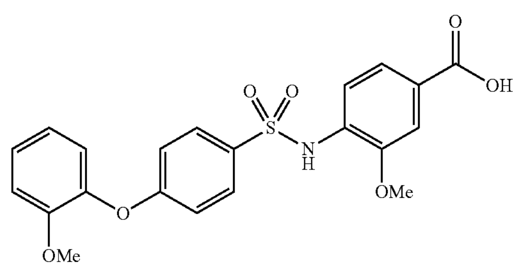 [SMILES: COc1cc(C(=O)O)ccc1NS(=O)(=O)c1ccc(Oc2ccccc2OC)cc1] | 430.2 | |
| 135 | 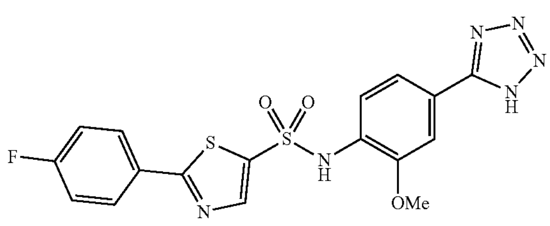 [SMILES: COc1cc(-c2nnn[nH]2)ccc1NS(=O)(=O)c1cnc(-c2ccc(F)cc2)s1] | 433.1 | |
| 136 | 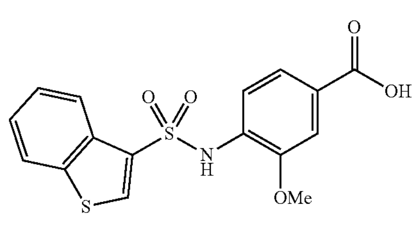 [SMILES: COc1cc(C(=O)O)ccc1NS(=O)(=O)c1csc2ccccc12] | 364.0 | |

-continued

| Example # | Structure | LC-MS [M + H]+ unless otherwise noted | 1H-NMR |
|---|---|---|---|
| 137 | 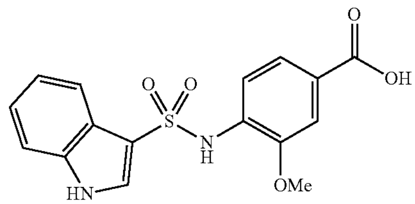 [SMILES: COc1cc(C(=O)O)ccc1NS(=O)(=O)c1c[nH]c2ccccc12] | 347.0 | |
| 138 | 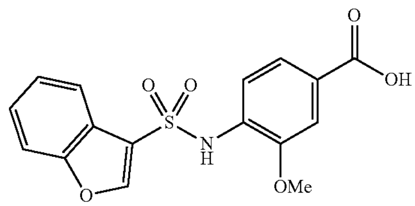 [SMILES: COc1cc(C(=O)O)ccc1NS(=O)(=O)c1coc2ccccc12] | 348.0 | |
| 139 | 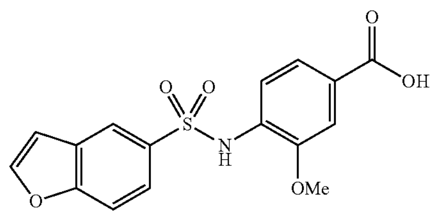 [SMILES: COc1cc(C(=O)O)ccc1NS(=O)(=O)c1ccc2occc2c1] | 348.0 | |
| 140 | 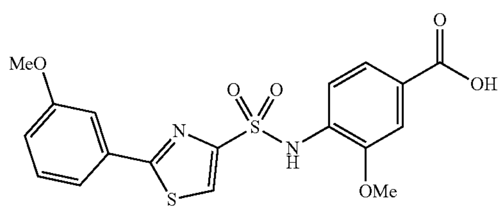 [SMILES: COc1cccc(-c2nc(S(=O)(=O)Nc3ccc(C(=O)O)cc3OC)cs2)c1] | 421.0 | ¹H NMR (400 MHz, DMSO-d₆) δ 7.97 (s, 1H), 7.46 (m, 1H), 7.46-7.37 (m, 2H), 7.33 (d, J = 8.4 Hz, 1H), 7.28 (d, J = 8.5 Hz, 1H), 7.21 (s, 1H), 7.07 (dd, J = 8.0, 2.6 Hz, 1H), 3.83 (s, 3H), 3.66 (s, 3H), 1.24 (s, 1H). |
| 141 | 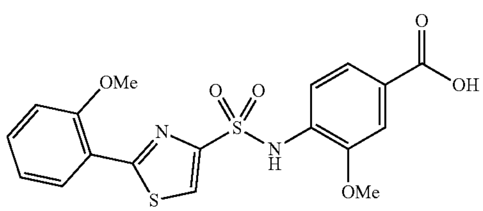 [SMILES: COc1cc(C(=O)O)ccc1NS(=O)(=O)c1csc(-c2ccccc2OC)n1] | 421.0 | ¹H NMR (400 MHz, DMSO-d₆) δ 8.19 (dd, J = 7.9, 1.8 Hz, 1H), 8.01 (s, 1H), 7.48 (dd, J = 8.8, 7.3 Hz, 1H), 7.36-7.26 (m, 2H), 7.25 (dd, J = 8.5, 1.0 Hz, 1H), 7.23 (s, 1H), 7.16-7.08 (m, 1H), 4.01 (s, 3H), 3.65 (s, 3H). |
| 142 | 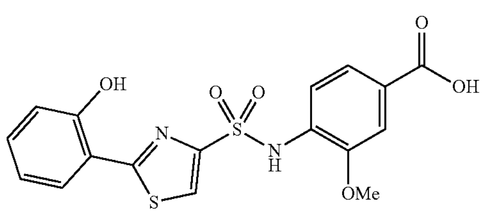 [SMILES: COc1cc(C(=O)O)ccc1NS(=O)(=O)c1csc(-c2ccccc2O)n1] | 407.0 | ¹H NMR (400 MHz, DMSO-d₆) δ 11.30 (s, 1H), 8.32 (s, 1H), 8.04 (dd, J = 7.9, 1.7 Hz, 1H), 7.52 (s, 2H), 7.41 (s, 1H), 7.36 (dd, J = 8.7, 7.3 Hz, 1H), 7.05 (d, J = 8.2 Hz, 1H), 7.01-6.93 (m, 1H), 3.67 (s, 3H). |
| 143 | 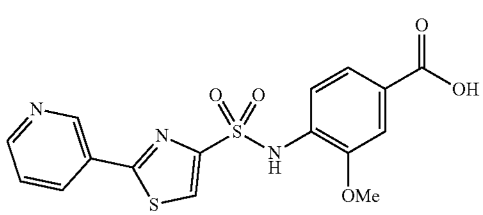 [SMILES: COc1cc(C(=O)O)ccc1NS(=O)(=O)c1csc(-c2cccnc2)n1] | 392.0 | ¹H NMR (400 MHz, DMSO-d₆) δ 12.92 (s, 1H), 10.13 (s, 1H), 9.11 (d, J = 2.2 Hz, 1H), 8.73 (dd, J = 4.8, 1.6 Hz, 1H), 8.45 (s, 1H), 8.30 (dd, J = 8.0, 2.4 Hz, 1H), 7.59 (dd, J = 8.0, 4.8 Hz, 1H), 7.56-7.47 (m, 2H), 7.42 (d, J = 1.7 Hz, 1H), 3.66 (s, 3H). |

-continued

| Example # | Structure | LC-MS [M + H]+ unless otherwise noted | 1H-NMR |
|---|---|---|---|
| 144 | 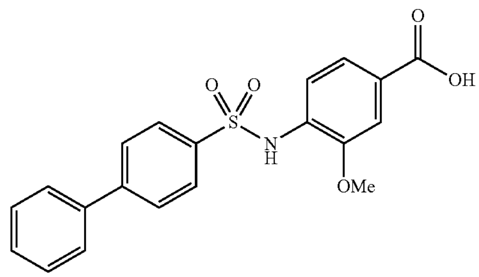 [SMILES: COc1cc(C(=O)O)ccc1NS(=O)(=O)c1ccc(-c2ccccc2)cc1] | 384.1 | |
| 145 | 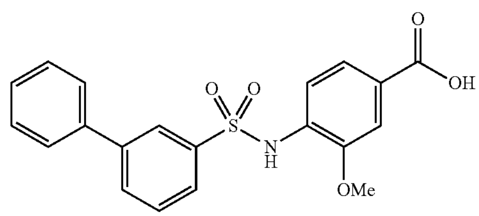 [SMILES: COc1cc(C(=O)O)ccc1NS(=O)(=O)c1cccc(-c2ccccc2)c1] | 384.1 | |
| 146 | 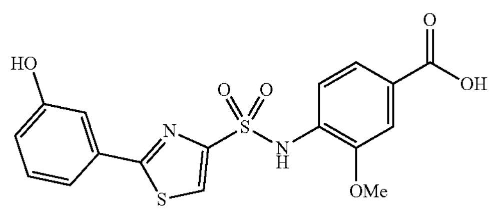 [SMILES: COc1cc(C(=O)O)ccc1NS(=O)(=O)c1csc(-c2cccc(O)c2)n1] | 407.0 | 1H NMR (400 MHz, DMSO-d6) δ 8.35 (s, 1H), 7.57-7.47 (m, 2H), 7.43 (d, J = 1.6 Hz, 1H), 7.37-7.28 (m, 3H), 6.99-6.89 (m, 1H), 3.68 (s, 3H). |
| 147 | 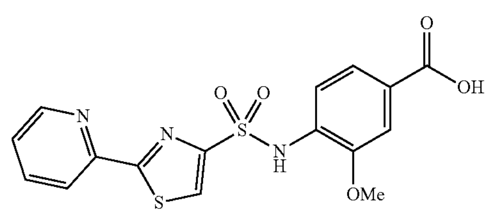 [SMILES: COc1cc(C(=O)O)ccc1NS(=O)(=O)c1csc(-c2ccccn2)n1] | 392.0 | 1H NMR (400 MHz, DMSO-d6) δ 8.35 (s, 1H), 7.57-7.47 (m, 2H), 7.43 (d, J = 1.6 Hz, 1H), 7.37-7.28 (m, 3H), 6.99-6.89 (m, 1H), 3.68 (s, 3H). |
| 148 | 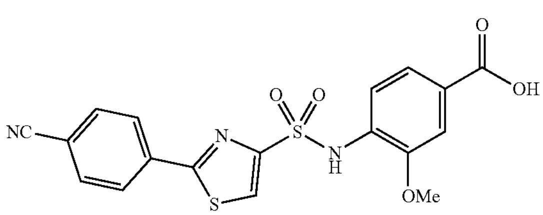 [SMILES: COc1cc(C(=O)O)ccc1NS(=O)(=O)c1csc(-c2ccc(C#N)cc2)n1] | 416.0 | 1H NMR (400 MHz, DMSO-d6) δ 10.15 (s, 1H), 8.49 (s, 1H), 8.12 (d, J = 8.4 Hz, 2H), 8.02 (d, J = 8.4 Hz, 2H), 7.57-7.46 (m, 2H), 7.42 (d, J = 1.7 Hz, 1H), 3.65 (s, 3H). |
| 149 | 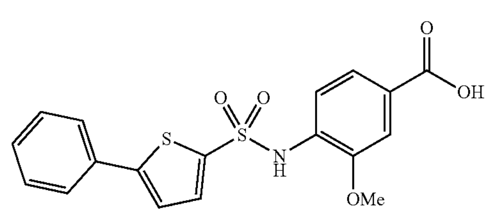 [SMILES: COc1cc(C(=O)O)ccc1NS(=O)(=O)c1ccc(-c2ccccc2)s1] | 388.0 [M − H]− | |

| Example # | Structure | LC-MS [M + H]+ unless otherwise noted | 1H-NMR |
|---|---|---|---|
| 150 | 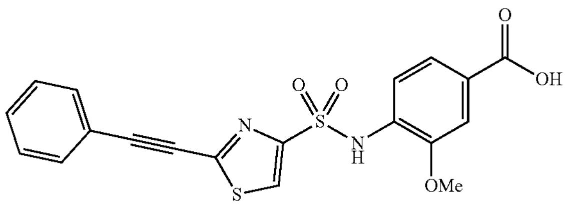 [SMILES: COc1cc(C(=O)O)ccc1NS(=O)(=O)c1csc(C#Cc2ccccc2)n1] | 413.0 [M − H]− | |
| 151 | 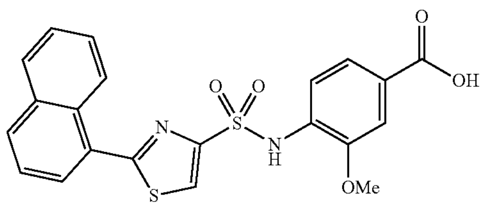 [SMILES: COc1cc(C(=O)O)ccc1NS(=O)(=O)c1csc(-c2cccc3ccccc23)n1] | 441.2 | |
| 152 | 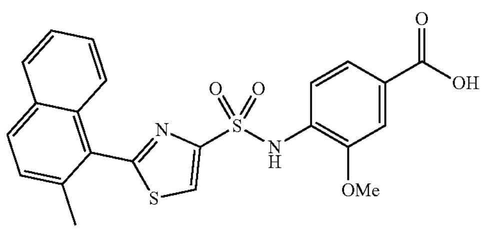 [SMILES: COc1cc(C(=O)O)ccc1NS(=O)(=O)c1csc(-c2c(C)ccc3ccccc23)n1] | 455.2 | |
| 153 | 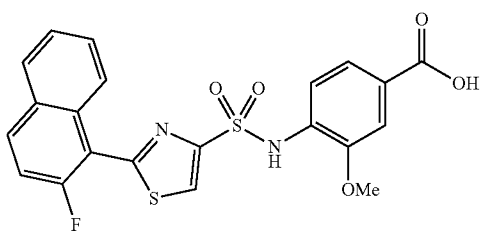 [SMILES: COc1cc(C(=O)O)ccc1NS(=O)(=O)c1csc(-c2c(F)ccc3ccccc23)n1] | 459.2 | |
| 154 | 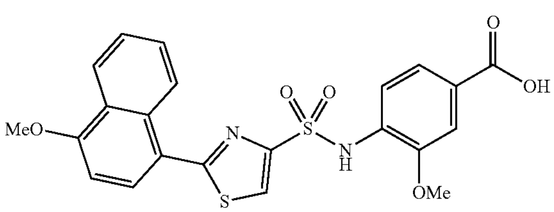 [SMILES: COc1cc(C(=O)O)ccc1NS(=O)(=O)c1csc(-c2ccc(OC)c3ccccc23)n1] | 471.2 | |
| 155 | 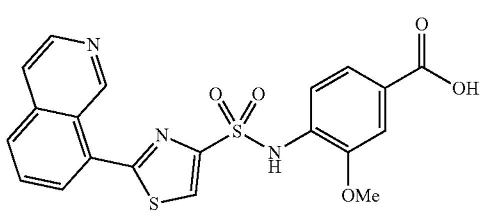 [SMILES: COc1cc(C(=O)O)ccc1NS(=O)(=O)c1csc(-c2cccc3ccncc23)n1] | 442.2 | |
| 156 | 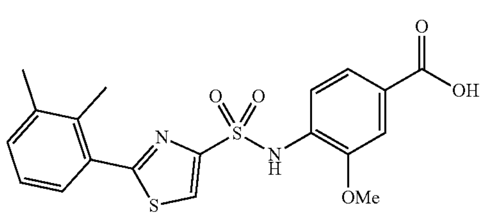 [SMILES: COc1cc(C(=O)O)ccc1NS(=O)(=O)c1csc(-c2cccc(C)c2C)n1] | 419.1 | |

| Example # | Structure | LC-MS [M + H]+ unless otherwise noted | 1H-NMR |
|---|---|---|---|
| 157 | 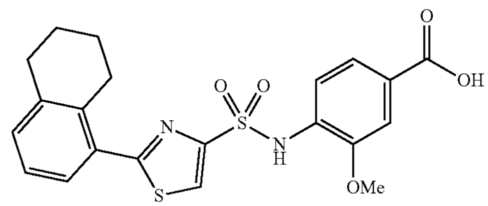 [SMILES: COc1cc(C(=O)O)ccc1NS(=O)(=O)c1csc(-c2cccc3c2CCCC3)n1] | 445.2 | |
| 158 | 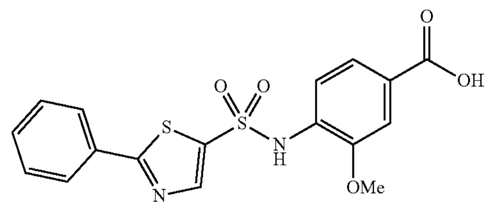 [SMILES: COc1cc(C(=O)O)ccc1NS(=O)(=O)c1cnc(-c2ccccc2)s1] | 391.2 | |
| 159 | 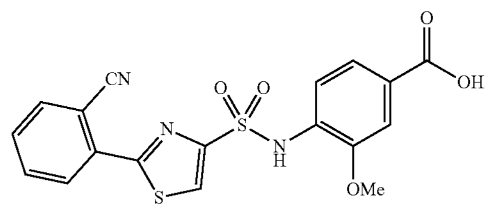 [SMILES: COc1cc(C(=O)O)ccc1NS(=O)(=O)c1csc(-c2ccccc2C#N)n1] | 414.0 | 1H NMR (400 MHz, DMSO-d6) δ 12.86 (s, 1H), 10.13 (s, 1H), 8.55 (s, 1H), 8.07 (dd, J = 7.8, 3.6 Hz, 2H), 7.89 (m, 1H), 7.76 (m, 1H), 7.60 (d, J = 8.3 Hz, 1H), 7.51 (dd, J = 8.3, 1.8 Hz, 1H), 7.43 (d, J = 1.9 Hz, 1H), 3.70 (s, 3H). |
| 160 | 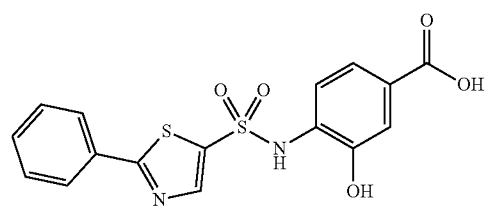 [SMILES: O=C(O)c1ccc(NS(=O)(=O)c2cnc(-c3ccccc3)s2)c(O)c1] | 377.0 | |
| 161 | 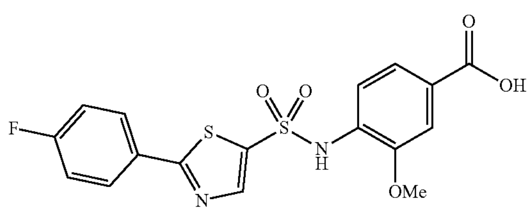 [SMILES: COc1cc(C(=O)O)ccc1NS(=O)(=O)c1cnc(-c2ccc(F)cc2)s1] | 407.0 [M − H]− | |
| 162 | 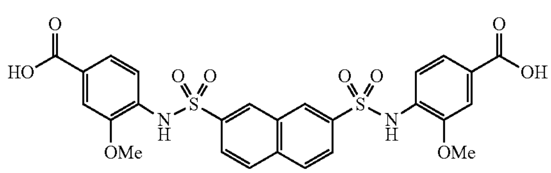 [SMILES: COc1cc(C(=O)O)ccc1NS(=O)(=O)c1ccc2ccc(S(=O)(=O)Nc3ccc(C(=O)O)cc3OC)cc2c1] | 587.2 | |
| 163 | 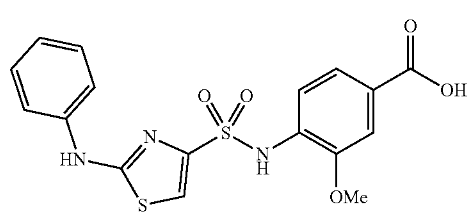 [SMILES: COc1cc(C(=O)O)ccc1NS(=O)(=O)c1csc(Nc2ccccc2)n1] | 406.1 | |

-continued

| Example # | Structure | LC-MS [M + H]+ unless otherwise noted | 1H-NMR |
|---|---|---|---|
| 164 | 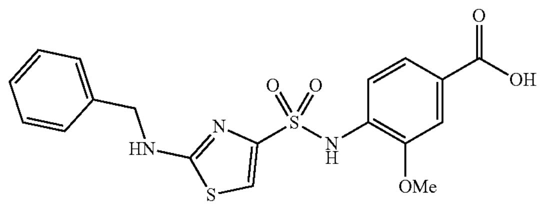 [SMILES: COc1cc(C(=O)O)ccc1NS(=O)(=O)c1csc(NCc2ccccc2)n1] | 418.0 [M − H]− | |
| 165 | 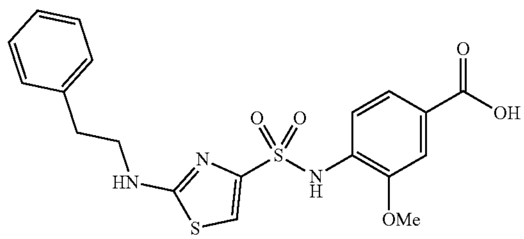 [SMILES: COc1cc(C(=O)O)ccc1NS(=O)(=O)c1csc(NCCc2ccccc2)n1] | 434.2 | |
| 166 | 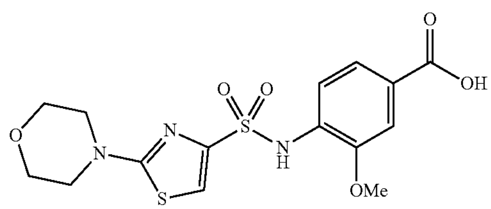 [SMILES: COc1cc(C(=O)O)ccc1NS(=O)(=O)c1csc(N2CCOCC2)n1] | 400.0 | |
| 167 | 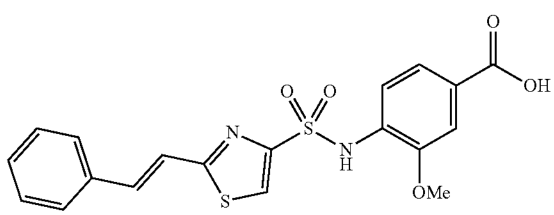 [SMILES: COc1cc(C(=O)O)ccc1NS(=O)(=O)c1csc(/C=C/c2ccccc2)n1] | 417.0 | |
| 168 | 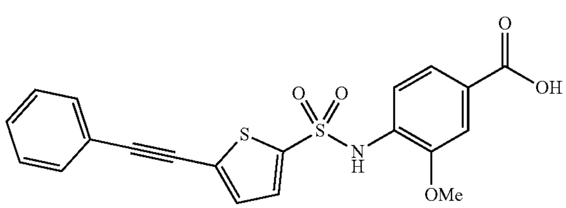 [SMILES: COc1cc(C(=O)O)ccc1NS(=O)(=O)c1ccc(C#Cc2ccccc2)s1] | 412.0 [M − H]− | |
| 169 | 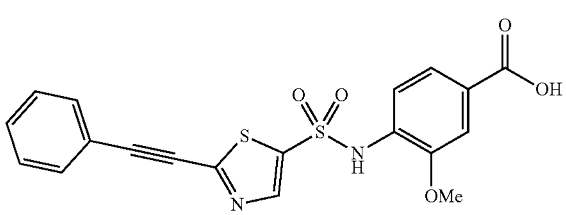 [SMILES: COc1cc(C(=O)O)ccc1NS(=O)(=O)c1cnc(C#Cc2ccccc2)s1] | 415.2 | |
| 170 | 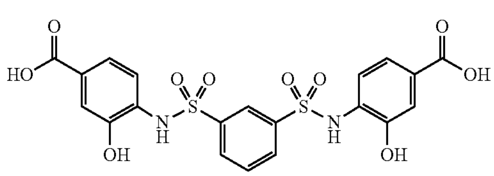 [SMILES: O=C(O)c1ccc(NS(=O)(=O)c2cccc(S(=O)(=O)Nc3ccc(C(=O)O)cc3O)c2)c(O)c1] | 509.1 | |

| Example # | Structure | LC-MS [M + H]+ unless otherwise noted | 1H-NMR |
|---|---|---|---|
| 171 | 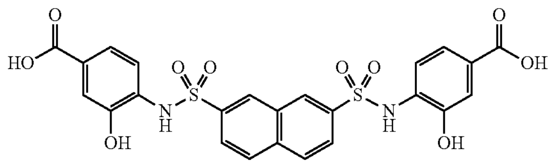 [SMILES: O=C(O)c1ccc(NS(=O)(=O)c2ccc3ccc(S(=O)(=O)Nc4ccc(C(=O)O)cc4O)cc3c2)c(O)c1] | 557.1 [M − H]− | |
| 172 | 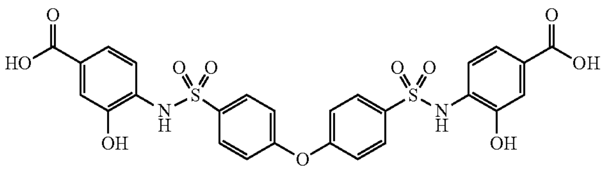 [SMILES: O=C(O)c1ccc(NS(=O)(=O)c2ccc(Oc3ccc(S(=O)(=O)Nc4ccc(C(=O)O)cc4O)cc3)cc2)c(O)c1] | 599.1 [M − H]− | |
| 173 | 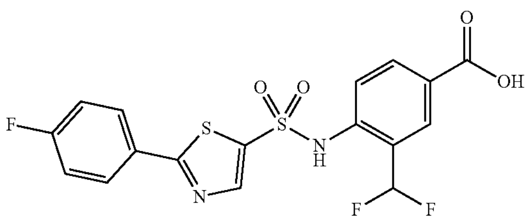 [SMILES: O=C(O)c1ccc(NS(=O)(=O)c2cnc(-c3ccc(F)cc3)s2)c(C(F)F)c1] | 429.1 | |
| 174 | 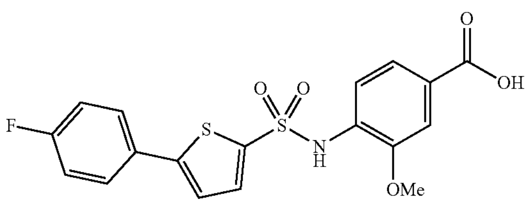 [SMILES: COc1cc(C(=O)O)ccc1NS(=O)(=O)c1ccc(-c2ccc(F)cc2)s1] | 406.0 [M − H]− | 1H NMR (400 MHz, DMSO-d6) δ 12.95 (s, 1H), 10.11 (s, 1H), 7.80-7.70 (m, 2H), 7.58-7.51 (m, 2H), 7.51-7.42 (m, 3H), 7.35-7.24 (m, 2H), 3.70 (s, 3H). |
| 175 | 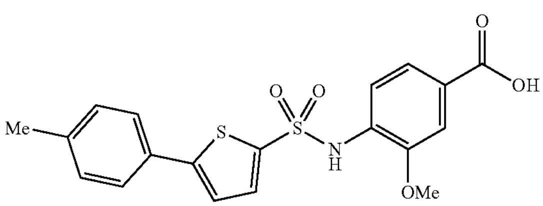 [SMILES: COc1cc(C(=O)O)ccc1NS(=O)(=O)c1ccc(-c2ccc(C)cc2)s1] | 402.0 [M − H]− | 1H NMR (400 MHz, DMSO-d6) δ 12.94 (s, 1H), 10.06 (s, 1H), 7.60-7.50 (m, 4H), 7.49-7.42 (m, 3H), 7.26 (d, J = 8.0 Hz, 2H), 3.70 (s, 3H), 2.33 (s, 3H). |
| 176 | 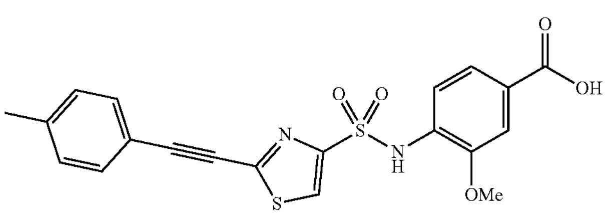 [SMILES: COc1cc(C(=O)O)ccc1NS(=O)(=O)c1csc(C#Cc2ccc(C)cc2)n1] | 429.2 | 1H NMR (400 MHz, DMSO-d6) δ 7.91 (s, 1H), 7.57-7.50 (m, 2H), 7.31-7.25 (m, 3H), 7.16 (dd, J = 8.2, 1.9 Hz, 1H), 7.01 (d, J = 8.2 Hz, 1H), 3.65 (s, 3H), 2.35 (s, 3H). |
| 177 | 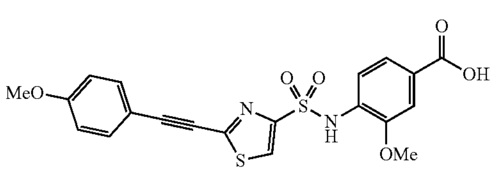 [SMILES: COc1ccc(C#Cc2nc(S(=O)(=O)Nc3ccc(C(=O)O)cc3OC)cs2)cc1] | 445.2 | 1H NMR (400 MHz, DMSO-d6) δ 12.94 (s, 1H), 10.14 (s, 1H), 8.41 (s, 1H), 7.68-7.58 (m, 2H), 7.52 (dd, J = 8.2, 1.8 Hz, 1H), 7.45 (d, J = 1.8 Hz, 1H), 7.39 (d, J = 8.2 Hz, 1H), 7.09-7.01 (m, 2H), 3.83 (s, 3H), 3.72 (s, 3H). |

-continued
| Example # | Structure | LC-MS [M + H]+ unless otherwise noted | 1H-NMR |
|---|---|---|---|
| 178 | 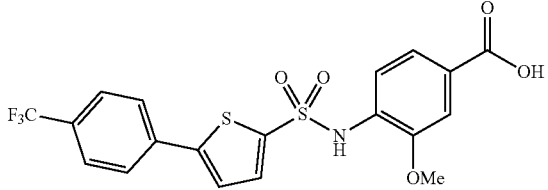 [SMILES: COc1cc(C(=O)O)ccc1NS(=O)(=O)c1ccc(-c2ccc(C(F)(F)F)cc2)s1] | 456.0 [M − H]− | 1H NMR (400 MHz, DMSO-d6) δ 12.97 (s, 1H), 10.18 (s, 1H), 7.92 (d, J = 8.1 Hz, 2H), 7.80 (d, J = 8.3 Hz, 2H), 7.68 (d, J = 4.0 Hz, 1H), 7.63-7.52 (m, 2H), 7.51-7.43 (m, 2H), 3.69 (s, 3H). |
| 179 | 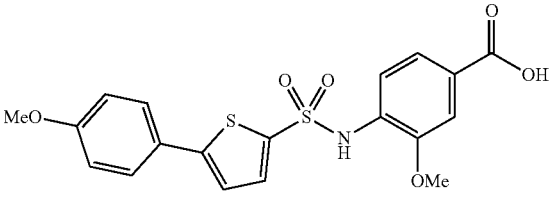 [SMILES: COc1ccc(-c2ccc(S(=O)(=O)Nc3ccc(C(=O)O)cc3OC)s2)cc1] | 418.0 [M − H]− | 1H NMR (400 MHz, DMSO-d6) δ 12.91 (s, 1H), 10.02 (s, 1H), 7.66-7.59 (m, 2H), 7.62-7.49 (m, 2H), 7.49-7.42 (m, 2H), 7.38 (d, J = 3.9 Hz, 1H), 7.05-6.96 (m, 2H), 3.80 (s, 3H), 3.71 (s, 3H). |
| 180 | 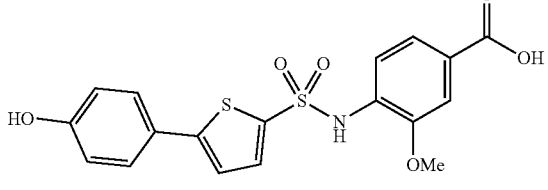 | 404.0 [M − H]− | 1H NMR (400 MHz, DMSO-d6) δ 12.92 (s, 1H), 9.99 (s, 1H), 9.88 (s, 1H), 7.54 (dd, J = 8.3, 1.8 Hz, 1H), 7.54-7.46 (m, 3H), 7.49-7.42 (m, 2H), 7.30 (d, J = 4.0 Hz, 1H), 6.86-6.78 (m, 2H), 3.71 (s, 3H). |
| 181 | 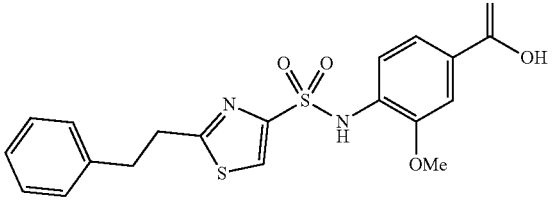 | 417.1 [M − H]− | |
| 182 | 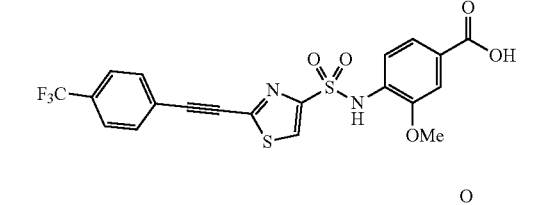 | 483.2 | 1H NMR (400 MHz, DMSO-d6) δ 7.91-7.80 (m, 4H), 7.30 (d, J = 1.9 Hz, 1H), 7.19 (dd, J = 8.2, 1.9 Hz, 1H), 7.03 (d, J = 8.2 Hz, 1H), 3.66 (s, 3H). |
| 183 | 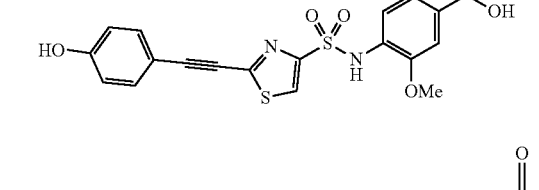 | 431.2 | 1H NMR (400 MHz, DMSO-d6) δ 10.26 (s, 1H), 10.20 (s, 1H), 9.88 (s, 1H), 8.38 (s, 1H), 7.55-7.47 (m, 2H), 7.41-7.31 (m, 3H), 6.90-6.81 (m, 2H), 3.80 (s, 3H). |
| 184 | 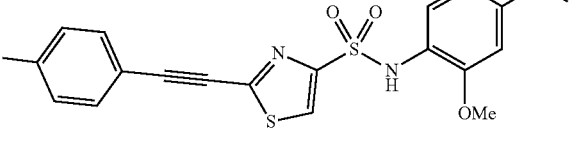 | 433.2 | 1H NMR (400 MHz, DMSO-d6) δ 8.32 (s, 1H), 7.82-7.72 (m, 2H), 7.43 (d, J = 7.8 Hz, 1H), 7.40-7.29 (m, 4H), 3.71 (s, 3H). |

-continued

| Example # | Structure | LC-MS [M + H]+ unless otherwise noted | 1H-NMR |
|---|---|---|---|
| 185 | 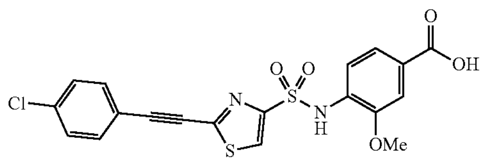 [SMILES: COc1cc(C(=O)O)ccc1NS(=O)(=O)c1csc(C#Cc2ccc(Cl)cc2)n1] | 449.2 | 1H NMR (400 MHz, DMSO-d6) δ 12.92 (s, 1H), 10.18 (s, 1H), 8.45 (s, 1H), 7.77-7.69 (m, 2H), 7.62-7.54 (m, 2H), 7.51 (dd, J = 8.2, 1.8 Hz, 1H), 7.44 (d, J = 1.8 Hz, 1H), 7.39 (d, J = 8.2 Hz, 1H), 3.72 (s, 3H). |
| 186 | 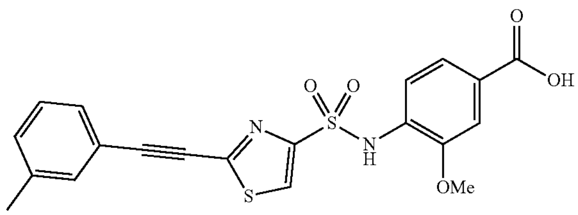 [SMILES: COc1cc(C(=O)O)ccc1NS(=O)(=O)c1csc(C#Cc2cccc(C)c2)n1] | 429.2 | 1H NMR (400 MHz, DMSO-d6) δ 12.94 (s, 1H), 10.17 (s, 1H), 8.44 (s, 1H), 7.55-7.35 (m, 7H), 3.72 (s, 3H), 2.35 (s, 3H). |
| 187 | 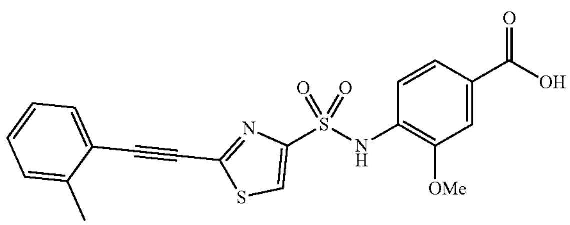 [SMILES: COc1cc(C(=O)O)ccc1NS(=O)(=O)c1csc(C#Cc2ccccc2C)n1] | 429.2 | 1H NMR (400 MHz, DMSO-d6) δ 12.96 (s, 1H), 10.19 (s, 1H), 8.44 (s, 1H), 7.67-7.61 (m, 1H), 7.52 (dd, J = 8.3, 1.8 Hz, 1H), 7.49-7.37 (m, 4H), 7.31 (t, J = 7.5 Hz, 1H), 3.72 (s, 3H), 2.48 (s, 3H). |
| 188 | 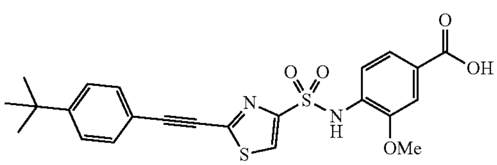 [SMILES: COc1cc(C(=O)O)ccc1NS(=O)(=O)c1csc(C#Cc2ccc(C(C)(C)C)cc2)n1] | 471.2 | 1H NMR (400 MHz, DMSO-d6) δ 12.96 (s, 1H), 10.16 (s, 1H), 8.43 (s, 1H), 7.67-7.59 (m, 2H), 7.56-7.48 (m, 3H), 7.45 (d, J = 1.8 Hz, 1H), 7.39 (d, J = 8.3 Hz, 1H), 3.72 (s, 3H), 1.30 (s, 9H). |
| 189 | 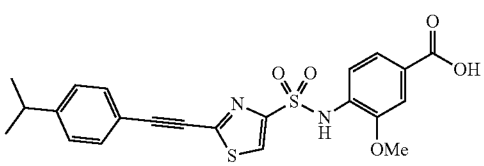 [SMILES: COc1cc(C(=O)O)ccc1NS(=O)(=O)c1csc(C#Cc2ccc(C(C)C)cc2)n1] | 457.3 | 1H NMR (400 MHz, DMSO-d6) δ 12.96 (s, 1H), 10.16 (s, 1H), 8.43 (s, 1H), 7.67-7.59 (m, 2H), 7.56-7.48 (m, 3H), 7.45 (d, J = 1.8 Hz, 1H), 7.39 (m, 2H), 3.72 (s, 3H), 1.30 (s, 6H). |
| 190 | 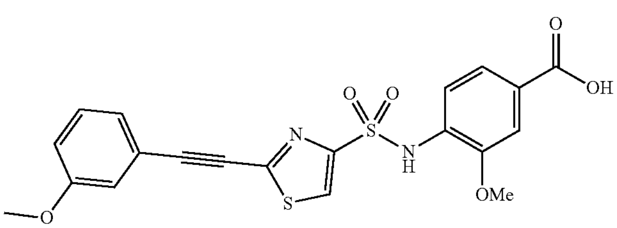 [SMILES: COc1cccc(C#Cc2nc(S(=O)(=O)Nc3ccc(C(=O)O)cc3OC)cs2)c1] | 445.2 | 1H NMR (400 MHz, DMSO-d6) δ 12.82 (s, 1H), 10.20 (s, 1H), 8.43 (s, 1H), 7.51 (dd, J = 8.3, 1.8 Hz, 1H), 7.47-7.35 (m, 3H), 7.27 (m, 2H), 7.16-7.08 (m, 1H), 3.81 (s, 3H), 3.72 (s, 3H). |
| 191 | 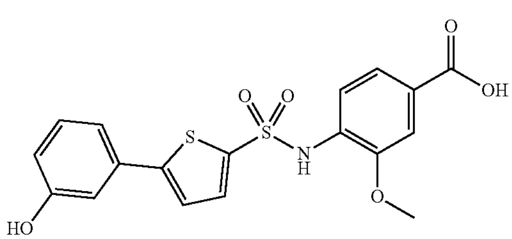 [SMILES: COc1cc(C(=O)O)ccc1NS(=O)(=O)c1ccc(-c2cccc(O)c2)s1] | 404.0 [M − H]− | 1H NMR (400 MHz, DMSO-d6) δ 12.97 (s, 1H), 10.10 (s, 1H), 9.74 (s, 1H), 7.58-7.49 (m, 2H), 7.49-7.40 (m, 3H), 7.25 (m, 1H), 7.10 (m, 1H), 7.02 (t, J = 2.1 Hz, 1H), 6.81 (dd, J = 8.2, 2.3 Hz, 1H), 3.70 (s, 3H). |

-continued

| Example # | Structure | LC-MS [M + H]+ unless otherwise noted | 1H-NMR |
|---|---|---|---|
| 192 | 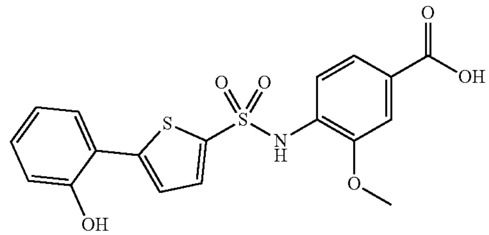 [SMILES: COc1cc(C(=O)O)ccc1NS(=O)(=O)c1ccc(-c2ccccc2O)s1] | 404.0 [M − H]− | 1H NMR (400 MHz, DMSO-d6) δ 12.92 (s, 1H), 10.77 (s, 1H), 9.94 (s, 1H), 7.76 (dd, J = 8.0, 1.6 Hz, 1H), 7.60 (d, J = 4.2 Hz, 1H), 7.57-7.49 (m, 2H), 7.49-7.41 (m, 2H), 7.21 (dd, J = 8.6, 7.2 Hz, 1H), 6.98 (dd, J = 8.2, 1.2 Hz, 1H), 6.89 (dd, J = 8.2, 7.3 Hz, 1H), 3.71 (s, 3H). |
| 193 | 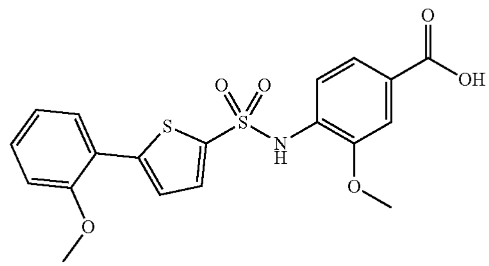 [SMILES: COc1cc(C(=O)O)ccc1NS(=O)(=O)c1ccc(-c2ccccc2OC)s1] | 418.0 [M − H]− | 1H NMR (400 MHz, DMSO-d6) δ 12.93 (s, 1H), 9.98 (s, 1H), 7.83 (dd, J = 7.9, 1.7 Hz, 1H), 7.62 (d, J = 4.1 Hz, 1H), 7.57-7.49 (m, 2H), 7.49-7.35 (m, 3H), 7.19 (dd, J = 8.3, 1.1 Hz, 1H), 7.06 (td, J = 7.6, 1.1 Hz, 1H), 3.93 (s, 3H), 3.70 (s, 3H). |
| 194 | 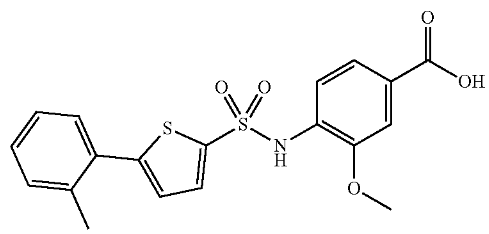 [SMILES: COc1cc(C(=O)O)ccc1NS(=O)(=O)c1ccc(-c2ccccc2C)s1] | 404.0 | 1H NMR (400 MHz, DMSO-d6) δ 12.98 (s, 1H), 10.09 (s, 1H), 7.59-7.50 (m, 2H), 7.49-7.43 (m, 2H), 7.36 (dd, J = 11.2, 5.9 Hz, 3H), 7.28 (dd, J = 8.0, 4.6 Hz, 1H), 7.21 (d, J = 3.8 Hz, 1H), 3.71 (s, 3H), 2.34 (s, 3H). |
| 195 | 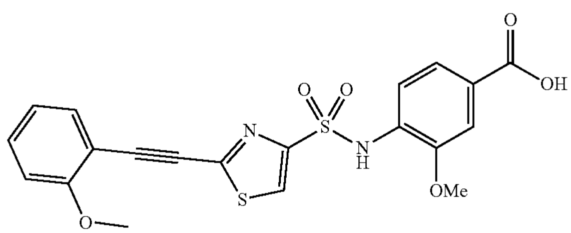 [SMILES: COc1ccccc1C#Cc1nc(S(=O)(=O)Nc2ccc(C(=O)O)cc2OC)cs1] | 445.2 | 1H NMR (400 MHz, DMSO-d6) δ 12.93 (s, 1H), 10.17 (s, 1H), 8.42 (s, 1H), 7.61 (dd, J = 7.6, 1.7 Hz, 1H), 7.57-7.48 (m, 2H), 7.45 (d, J = 1.8 Hz, 1H), 7.39 (d, J = 8.3 Hz, 1H), 7.17 (d, J = 8.4 Hz, 1H), 7.04 (td, J = 7.5, 1.0 Hz, 1H), 3.89 (s, 3H), 3.72 (s, 3H). |
| 196 | 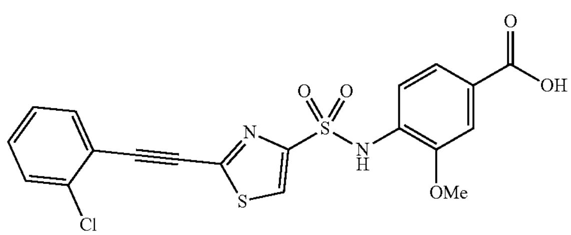 | 449.2 | 1H NMR (400 MHz, DMSO-d6) δ 8.38 (s, 1H), 7.82 (dd, J = 7.8, 1.7 Hz, 1H), 7.67 (dd, J = 8.2, 1.2 Hz, 1H), 7.57 (m, 1H), 7.47 (dd, J = 10.2, 5.8 Hz, 2H), 7.39 (s, 1H), 7.34 (d, J = 8.2 Hz, 1H), 3.70 (s, 3H). |
| 197 | 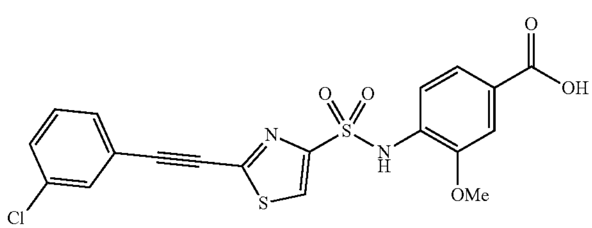 [SMILES: COc1cc(C(=O)O)ccc1NS(=O)(=O)c1csc(C#Cc2cccc(Cl)c2)n1] | 449.2 | 1H NMR (400 MHz, DMSO-d6) δ 8.43 (s, 1H), 7.82 (m, 1H), 7.71-7.59 (m, 2H), 7.57-7.46 (m, 2H), 7.43 (d, J = 1.8 Hz, 1H), 7.38 (d, J = 8.3 Hz, 1H), 3.33 (s, 3H). |

-continued

| Example # | Structure | LC-MS [M + H]+ unless otherwise noted | 1H-NMR |
|---|---|---|---|
| 198 | 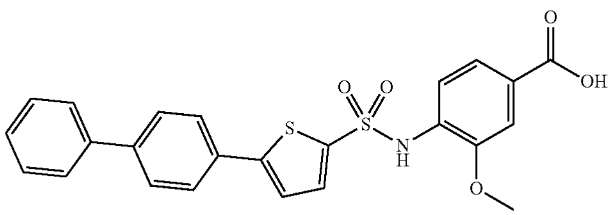 [SMILES: COc1cc(C(=O)O)ccc1NS(=O)(=O)c1ccc(-c2ccc(-c3ccccc3)cc2)s1] | 464.0 [M − H]− | 1H NMR (400 MHz, DMSO-d6) δ 12.96 (s, 1H), 10.13 (s, 1H), 7.82-7.73 (m, 4H), 7.76-7.68 (m, 2H), 7.61-7.51 (m, 3H), 7.53-7.44 (m, 4H), 7.44-7.36 (m, 1H), 3.71 (s, 3H). |
| 199 | 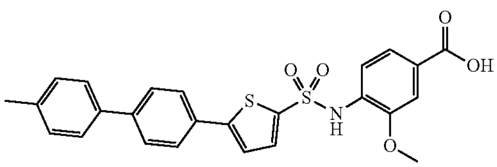 [SMILES: COc1cc(C(=O)O)ccc1NS(=O)(=O)c1ccc(-c2ccc(-c3ccc(C)cc3)cc2)s1] | 478.1 [M − H]− | 1H NMR (400 MHz, DMSO-d6) δ 7.70 (s, 4H), 7.64-7.57 (m, 2H), 7.42 (d, J = 3.8 Hz, 1H), 7.39-7.32 (m, 2H), 7.32-7.24 (m, 4H), 3.70 (s, 3H), 2.35 (s, 3H). |
| 200 | 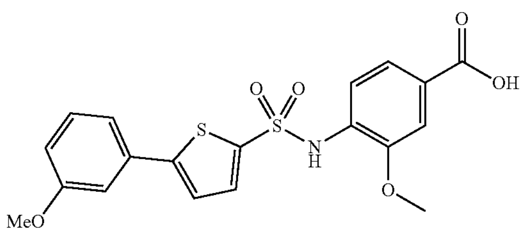 [SMILES: COc1cccc(-c2ccc(S(=O)(=O)Nc3ccc(C(=O)O)cc3OC)s2)c1] | 418.0 [M − H]− | 1H NMR (400 MHz, DMSO-d6) δ 12.93 (s, 1H), 10.10 (s, 1H), 7.58-7.51 (m, 3H), 7.49-7.42 (m, 2H), 7.37 (t, J = 7.9 Hz, 1H), 7.27-7.19 (m, 2H), 6.99 (dd, J = 8.3, 2.5 Hz, 1H), 3.81 (s, 3H), 3.70 (s, 3H). |
| 201 | 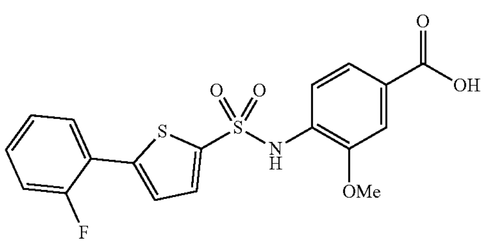 [SMILES: COc1cc(C(=O)O)ccc1NS(=O)(=O)c1ccc(-c2ccccc2F)s1] | 406.0 [M − H]− | 1H NMR (400 MHz, DMSO-d6) δ 12.96 (s, 1H), 10.16 (s, 1H), 7.85 (m, 1H), 7.63-7.52 (m, 3H), 7.52-7.43 (m, 3H), 7.39 (dd, J = 11.6, 8.4 Hz, 1H), 7.32 (m, 1H), 3.69 (s, 3H). |
| 202 | 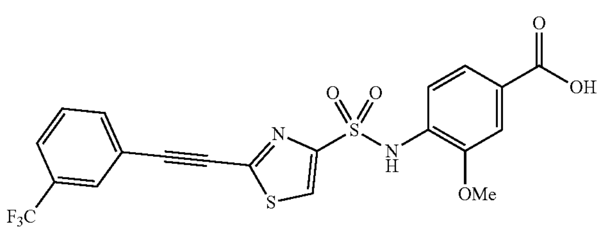 [SMILES: COc1cc(C(=O)O)ccc1NS(=O)(=O)c1csc(C#Cc2cccc(C(F)(F)F)c2)n1] | 483.2 | 1H NMR (400 MHz, DMSO-d6) δ 8.38 (s, 1H), 8.11 (s, 1H), 8.01 (d, J = 7.8 Hz, 1H), 7.90 (d, J = 7.9 Hz, 1H), 7.74 (m, 1H), 7.45 (d, J = 8.4 Hz, 1H), 7.39 (s, 1H), 7.34 (d, J = 8.2 Hz, 1H), 3.71 (s, 3H). |
| 203 | 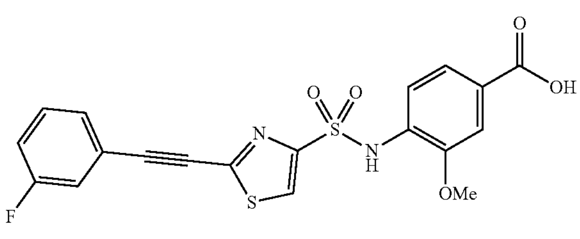 [SMILES: COc1cc(C(=O)O)ccc1NS(=O)(=O)c1csc(C#Cc2cccc(F)c2)n1] | 433.2 | 1H NMR (400 MHz, DMSO-d6) δ 8.10 (d, J = 1.6 Hz, 1H), 7.57 (dd, J = 9.8, 2.8 Hz, 1H), 7.52 (dd, J = 6.3, 4.3 Hz, 2H), 7.38 (m, 1H), 7.28-7.20 (m, 2H), 7.17 (d, J = 8.3 Hz, 1H), 3.69 (s, 3H). |

-continued

| Example # | Structure | LC-MS [M + H]+ unless otherwise noted | 1H-NMR |
|---|---|---|---|
| 204 | 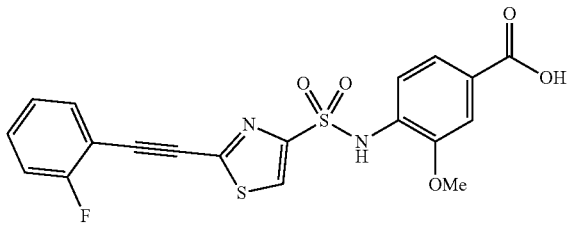 [SMILES: COc1cc(C(=O)O)ccc1NS(=O)(=O)c1csc(C#Cc2ccccc2F)n1] | 433.2 | 1H NMR (400 MHz, DMSO-d6) δ 8.28 (s, 1H), 7.76 (m, 1H), 7.65-7.55 (m, 1H), 7.46-7.30 (m, 4H), 7.28 (d, J = 8.3 Hz, 1H), 3.70 (s, 3H). |
| 205 | 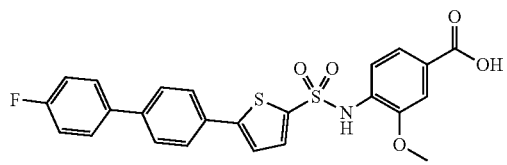 [SMILES: COc1cc(C(=O)O)ccc1NS(=O)(=O)c1ccc(-c2ccc(-c3ccc(F)cc3)cc2)s1] | 482.1 [M − H]− | 1H NMR (400 MHz, DMSO-d6) δ 12.76 (broad, 1H), 9.89 (broad, 1H), 7.81-7.70 (m, 6H), 7.59-7.50 (m, 3H), 7.48-7.41 (m, 2H), 7.37-7.26 (m, 2H), 3.71 (s, 3H). |
| 206 | 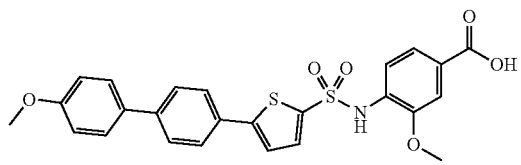 [SMILES: COc1ccc(-c2ccc(-c3ccc(S(=O)(=O)Nc4ccc(C(=O)O)cc4OC)s3)cc2)cc1] | 494.0 [M − H]− | 1H NMR (400 MHz, DMSO-d6) δ 7.76-7.62 (m, 6H), 7.53-7.45 (m, 3H), 7.40 (t, J = 4.2 Hz, 2H), 7.04 (d, J = 8.3 Hz, 2H), 3.81 (s, 3H), 3.70 (s, 3H) |
| 207 | 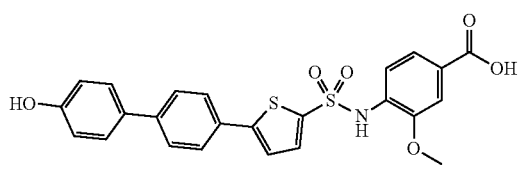 [SMILES: COc1cc(C(=O)O)ccc1NS(=O)(=O)c1ccc(-c2ccc(-c3ccc(O)cc3)cc2)s1] | 480.0 [M − H]− | 1H NMR (400 MHz, DMSO-d6) δ 7.66 (q, J = 8.6 Hz, 4H), 7.54 (d, J = 8.8 Hz 2H), 7.46-7.36 (m, 3H), 7.32 (m, 2H), 6.86 (d, J = 8.8 Hz, 2H), 3.70 (s, 3H). |
| 208 | 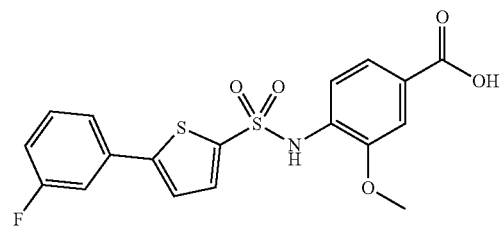 [SMILES: COc1cc(C(=O)O)ccc1NS(=O)(=O)c1ccc(-c2cccc(F)c2)s1] | 406.0 [M − H]− | 1H NMR (400 MHz, DMSO-d6) δ 12.97 (s, 1H), 10.16 (s, 1H), 7.65-7.43 (m, 8H), 7.25 (t, J = 7.7 Hz, 1H), 3.70 (s, 3H) |
| 209 | 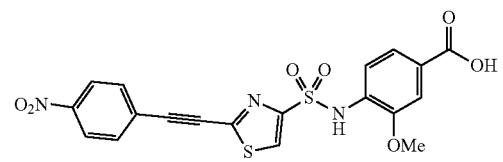 [SMILES: COc1cc(C(=O)O)ccc1NS(=O)(=O)c1csc(C#Cc2ccc([N+](=O)[O-])cc2)n1] | 460.2 | 1H NMR (400 MHz, DMSO-d6) δ 8.32 (s, 1H), 8.31 (d, J = 8.2 Hz, 2H), 7.97 (d, J = 8.2 Hz, 2H), 7.45-7.27 (m, 3H), 3.70 (s, 3H) |
| 210 | 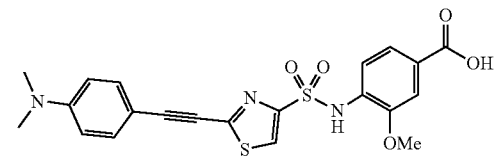 | 458.2 | 1H NMR (400 MHz, DMSO-d6) δ 8.24 (s, 1H), 7.46 (d, J = 8.9 Hz, 2H), 7.38 (s, 1H), 7.34 (d, J = 8.3 Hz, 1H), 6.74 (d, J = 9.0 Hz, 2H), 3.71 (s, 3H), 2.99 (s, 7H). |

-continued

| Example # | Structure | LC-MS [M + H]+ unless otherwise noted | 1H-NMR |
|---|---|---|---|
| 211 | 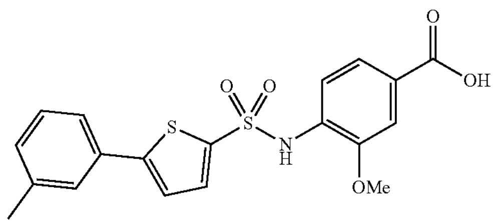 [SMILES: COc1cc(C(=O)O)ccc1NS(=O)(=O)c1ccc(-c2cccc(C)c2)s1] | 402.0 [M − H]− | 1H NMR (400 MHz, DMSO-d6) δ 7.52-7.43 (m, 5H), 7.43-7.37 (m, 2H), 7.36-7.29 (t, J = 8.0 Hz, 1H), 7.20 (d, J = 8.0 Hz, 1H), 3.69 (s, 3H), 2.34 (s, 3H). |
| 212 | 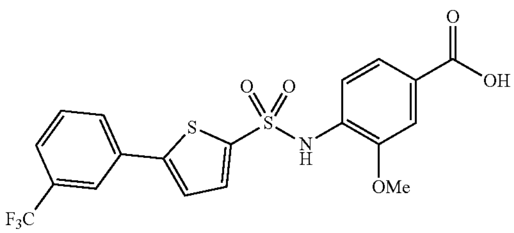 [SMILES: COc1cc(C(=O)O)ccc1NS(=O)(=O)c1ccc(-c2cccc(C(F)(F)F)c2)s1] | 456.0 [M − H]− | 1H NMR (400 MHz, DMSO-d6) δ 8.04-7.93 (m, 2H), 7.78-7.72 (m, 1H), 7.72-7.64 (m, 2H), 7.55-7.46 (m, 2H), 7.41 (dd, J = 5.1, 3.2 Hz, 2H), 3.70 (s, 3H). |
| 213 | 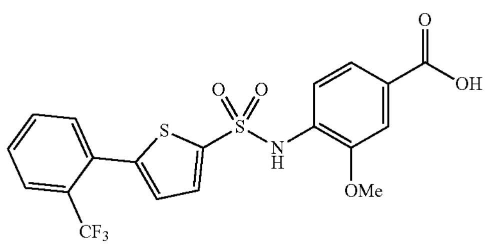 [SMILES: COc1cc(C(=O)O)ccc1NS(=O)(=O)c1ccc(-c2ccccc2C(F)(F)F)s1] | 456.0 [M − H]− | 1H NMR (400 MHz, DMSO-d6) δ 12.99 (s, 1H), 10.17 (s, 1H), 7.93-7.86 (m, 1H), 7.80-7.66 (m, 2H), 7.61-7.51 (m, 2H), 7.51 (d, J = 3.9 Hz, 1H), 7.49-7.40 (m, 2H), 7.15 (d, J = 3.9 Hz, 1H), 3.71 (s, 3H). |
| 214 | 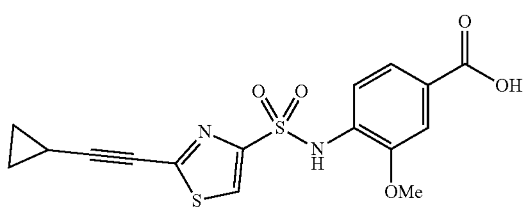 [SMILES: COc1cc(C(=O)O)ccc1NS(=O)(=O)c1csc(C#CC2CC2)n1] | 379.1 | 1H NMR (400 MHz, DMSO-d6) δ 8.07 (d, J = 2.3 Hz, 1H), 7.37-7.27 (m, 2H), 7.22 (d, J = 8.3 Hz, 1H), 3.69 (s, 3H), 1.66 (m, 1H), 0.98 (m, 2H), 0.90-0.82 (m, 2H). |
| 215 | 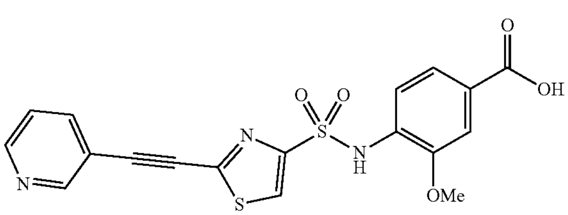 [SMILES: COc1cc(C(=O)O)ccc1NS(=O)(=O)c1csc(C#Cc2cccnc2)n1] | 416.2 | 1H NMR (400 MHz, DMSO-d6) δ 12.97 (s, 1H), 10.21 (s, 1H), 8.89 (d, J = 2.2 Hz, 1H), 8.70 (dd, J = 4.9, 1.7 Hz, 1H), 8.48 (s, 1H), 8.14 (dt, J = 7.9, 1.9 Hz, 1H), 7.58-7.48 (m, 2H), 7.45 (d, J = 1.8 Hz, 1H), 7.39 (d, J = 8.2 Hz, 1H), 3.72 (s, 3H). |
| 216 | 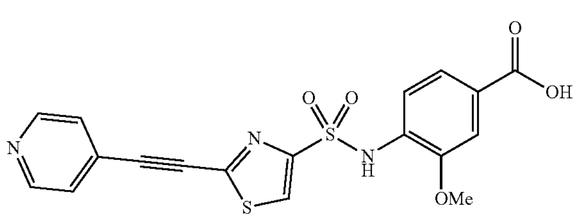 [SMILES: COc1cc(C(=O)O)ccc1NS(=O)(=O)c1csc(C#Cc2ccncc2)n1] | 416.0 | 1H NMR (400 MHz, DMSO-d6) δ 10.23 (s, 1H), 8.72 (d, J = 5.0 Hz, 2H), 8.49 (s, 1H), 7.68 (d, J = 5.1 Hz, 2H), 7.51 (d, J = 8.4 Hz, 1H), 7.44 (s, 1H), 7.38 (d, J = 8.3 Hz, 1H), 3.71 (s, 3H). |

-continued

| Example # | Structure | LC-MS [M + H]+ unless otherwise noted | 1H-NMR |
|---|---|---|---|
| 217 | 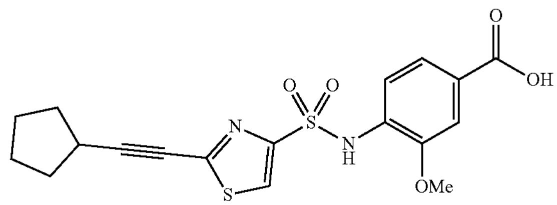 [SMILES: COc1cc(C(=O)O)ccc1NS(=O)(=O)c1csc(C#CC2CCCC2)n1] | 407.2 | 1H NMR (400 MHz, DMSO-d6) δ 8.19 (s, 1H), 7.40 (dd, J = 8.3, 1.8 Hz, 1H), 7.35 (d, J = 1.9 Hz, 1H), 7.28 (d, J = 8.3 Hz, 1H), 3.70 (s, 3H), 2.98 (m, 1H), 2.05-1.94 (m, 2H), 1.76-1.55 (m, 3H). |
| 218 | 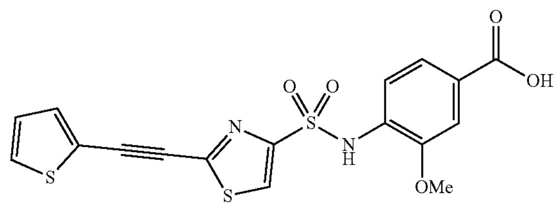 [SMILES: COc1cc(C(=O)O)ccc1NS(=O)(=O)c1csc(C#Cc2cccs2)n1] | 421.2 | 1H NMR (400 MHz, DMSO-d6) δ 8.22 (s, 1H), 7.85 (dd, J = 5.1, 1.2 Hz, 1H), 7.65 (dd, J = 3.7, 1.2 Hz, 1H), 7.38-7.32 (m, 1H), 7.30 (d, J = 1.9 Hz, 1H), 7.26 (d, J = 8.4 Hz, 1H), 7.21 (dd, J = 5.1, 3.7 Hz, 1H), 3.70 (s, 3H). |
| 219 | 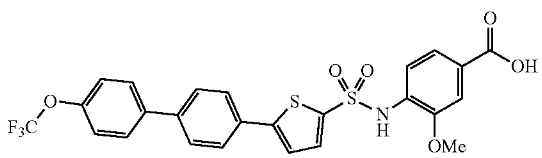 [SMILES: COc1cc(C(=O)O)ccc1NS(=O)(=O)c1ccc(-c2ccc(-c3ccc(OC(F)(F)F)cc3)cc2)s1] | 548.0 [M − H]− | 1H NMR (400 MHz, DMSO-d6) δ 12.98 (s, 1H), 10.14 (s, 1H), 7.89-7.82 (m, 1H), 7.86-7.75 (m, 5H), 7.60 (d, J = 4.0 Hz, 1H), 7.59-7.52 (m, 2H), 7.51-7.43 (m, 4H), 3.71 (s, 3H). |
| 220 | 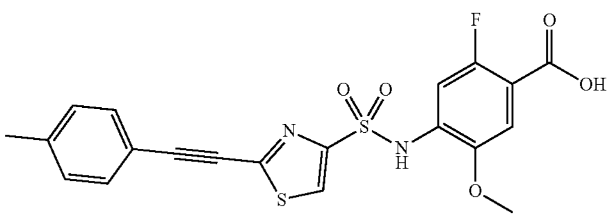 [SMILES: COc1cc(C(=O)O)c(F)cc1NS(=O)(=O)c1csc(C#Cc2ccc(C)cc2)n1] | 447.2 | 1H NMR (400 MHz, DMSO-d6) δ 13.21 (s, 1H), 10.48 (s, 1H), 8.56 (s, 1H), 7.61-7.55 (m, 2H), 7.32 (dd, J = 9.3, 7.3 Hz, 3H), 7.26 (d, J = 11.9 Hz, 1H), 3.73 (s, 3H), 2.37 (s, 3H). |
| 221 | 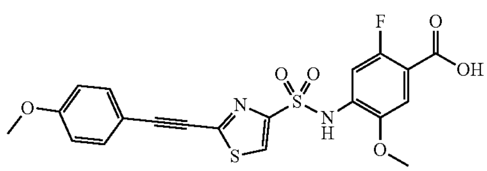 [SMILES: COc1ccc(C#Cc2nc(S(=O)(=O)Nc3cc(F)c(C(=O)O)cc3OC)cs2)cc1] | 463.2 | 1H NMR (400 MHz, DMSO-d6) δ 13.22 (s, 1H), 10.46 (s, 1H), 8.54 (s, 1H), 7.68-7.60 (m, 2H), 7.34 (d, J = 6.6 Hz, 1H), 7.26 (d, J = 11.9 Hz, 1H), 7.09-7.01 (m, 2H), 3.83 (s, 3H), 3.73 (s, 3H). |
| 222 | 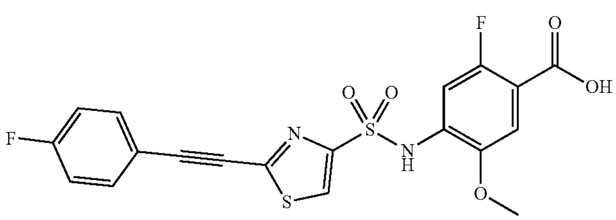 [SMILES: COc1cc(C(=O)O)c(F)cc1NS(=O)(=O)c1csc(C#Cc2ccc(F)cc2)n1] | 451.2 | 1H NMR (400 MHz, DMSO-d6) δ 13.23 (s, 1H), 10.49 (s, 1H), 8.58 (s, 1H), 7.83-7.73 (m, 2H), 7.41-7.30 (m, 3H), 7.26 (d, J = 11.8 Hz, 1H), 3.73 (s, 3H). |
| 223 | 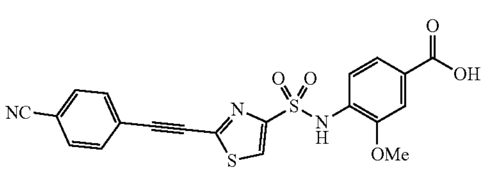 [SMILES: COc1cc(C(=O)O)ccc1NS(=O)(=O)c1csc(C#Cc2ccc(C#N)cc2)n1] | 440.2 | 1H NMR (400 MHz, DMSO-d6) δ 8.10 (s, 1H), 7.95 (d, J = 8.4 Hz, 2H), 7.86 (d, J = 8.4 Hz, 2H), 7.23 (dd, J = 11.2, 2.9 Hz, 2H), 7.15 (d, J = 8.3 Hz, 1H), 3.68 (s, 3H). |

| Example # | Structure | LC-MS [M + H]+ unless otherwise noted | 1H-NMR |
|---|---|---|---|
| 224 | H2NOC-C6H4-C≡C-thiazole-SO2NH-C6H3(OMe)-COOH | 458.0 | 1H NMR (400 MHz, Methanol-d4) δ 8.32 (s, 1H), 7.99-7.92 (m, 2H), 7.77-7.70 (m, 2H), 7.61 (d, J = 2.3 Hz, 2H), 7.56 (s, 1H), 3.84 (s, 3H). |
| 225 | 2-CF3-C6H4-C≡C-thiazole-SO2NH-C6H3(OMe)-COOH | 483.2 | 1H NMR (400 MHz, DMSO-d6) δ 8.42 (s, 1H), 7.98 (d, J = 7.6 Hz, 1H), 7.92 (d, J = 8.0 Hz, 1H), 7.78 (m, 2H), 7.48 (dd, J = 8.3, 1.8 Hz, 1H), 7.43-7.33 (m, 2H), 3.69 (s, 3H). |
| 226 | 4-F3CO-C6H4-C≡C-thiazole-SO2NH-C6H3(OMe)-COOH | 499.2 | 1H NMR (400 MHz, DMSO-d6) δ 8.40 (s, 1H), 7.89-7.81 (m, 2H), 7.54-7.44 (m, 3H), 7.41 (d, J = 1.8 Hz, 1H), 7.36 (d, J = 8.2 Hz, 1H), 3.71 (s, 3H). |
| 227 | 4-F3C-C6H4-C≡C-thiazole-SO2NH-C6H2(F)(OMe)-COOH | 501.2 | 1H NMR (400 MHz, DMSO-d6) δ 10.52 (s, 1H), 8.63 (s, 1H), 7.97-7.84 (m, 5H), 7.34 (d, J = 6.6 Hz, 1H), 7.27 (d, J = 11.9 Hz, 1H), 3.73 (s, 3H). |
| 228 | 4-Cl-C6H4-C≡C-thiazole-SO2NH-C6H2(F)(OMe)-COOH | 467.2 | 1H NMR (400 MHz, DMSO-d6) δ 10.51 (s, 1H), 8.58 (s, 1H), 7.73 (d, J = 8.4 Hz, 2H), 7.61-7.54 (m, 2H), 7.33 (d, J = 6.6 Hz, 1H), 7.25 (d, J = 11.9 Hz, 1H), 3.73 (s, 3H). |
| 229 | 4-HO-C6H4-C≡C-thiazole-SO2NH-C6H2(F)(OMe)-COOH | 449.0 | 1H NMR (400 MHz, DMSO-d6) δ 13.25 (s, 1H), 10.45 (s, 1H), 10.29 (s, 1H), 8.52 (s, 1H), 7.55-7.47 (m, 2H), 7.33 (d, J = 6.6 Hz, 1H), 7.26 (d, J = 11.8 Hz, 1H), 6.89-6.81 (m, 2H), 3.73 (s, 3H). |
| 230 | 4-F3C-C6H4-thiophene-SO2NH-C6H2(F)(OMe)-COOH | 474.0 [M − H]− | 1H NMR (400 MHz, DMSO-d6) δ 13.20 (s, 1H), 10.52 (s, 1H), 7.94 (d, J = 8.1 Hz, 2H), 7.80 (d, J = 8.1 Hz, 2H), 7.69 (m, 2H), 7.33 (d, J = 6.6 Hz, 1H), 7.25 (d, J = 11.9 Hz, 1H), 3.70 (s, 3H). |
| 231 | 4-F-C6H4-thiophene-SO2NH-C6H2(F)(OMe)-COOH | 424.0 [M − H]− | 1H NMR (400 MHz, DMSO-d6) δ 13.20 (s, 1H), 10.44 (s, 1H), 7.80-7.72 (m, 2H), 7.64 (d, J = 3.9 Hz, 1H), 7.51 (d, J = 4.0 Hz, 1H), 7.36-7.21 (m, 4H), 3.71 (s, 3H). |

-continued

| Example # | Structure | LC-MS [M + H]+ unless otherwise noted | 1H-NMR |
|---|---|---|---|
| 232 | 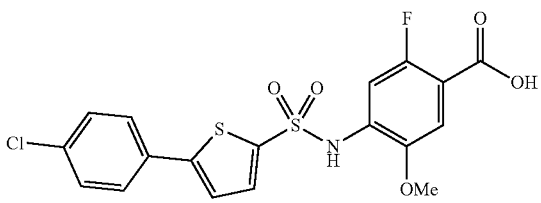 [SMILES: COc1cc(C(=O)O)c(F)cc1NS(=O)(=O)c1ccc(-c2ccc(Cl)cc2)s1] | 440.0 [M − H]− | 1H NMR (400 MHz, DMSO-d6) δ 13.21 (s, 1H), 10.46 (s, 1H), 7.77-7.70 (m, 2H), 7.65 (d, J = 4.0 Hz, 1H), 7.57 (d, J = 4.0 Hz, 1H), 7.55-7.47 (m, 2H), 7.33 (d, J = 6.6 Hz, 1H), 7.25 (d, J = 11.9 Hz, 1H), 3.71 (s, 3H). |
| 233 | 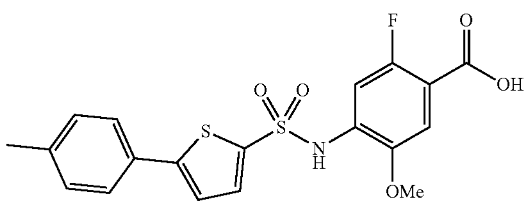 [SMILES: COc1cc(C(=O)O)c(F)cc1NS(=O)(=O)c1ccc(-c2ccc(C)cc2)s1] | 420.0 [M − H]− | 1H NMR (400 MHz, DMSO-d6) δ 13.19 (s, 1H), 10.40 (s, 1H), 7.65-7.56 (m, 3H), 7.48 (d, J = 4.0 Hz, 1H), 7.33 (d, J = 6.6 Hz, 1H), 7.30-7.21 (m, 3H), 3.71 (s, 3H), 2.33 (s, 3H). |
| 234 | 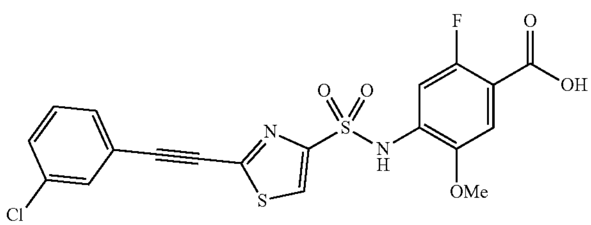 [SMILES: COc1cc(C(=O)O)c(F)cc1NS(=O)(=O)c1csc(C#Cc2cccc(Cl)c2)n1] | 465.0 [M − H]− | 1H NMR (400 MHz, DMSO-d6) δ 13.19 (s, 1H), 10.53 (s, 1H), 8.59 (s, 1H), 7.82 (m, 1H), 7.67 (m, 1H), 7.65-7.59 (m, 1H), 7.52 (m, 1H), 7.33 (d, J = 6.6 Hz, 1H), 7.25 (d, J = 12.0 Hz, 1H), 3.73 (s, 3H). |
| 235 | 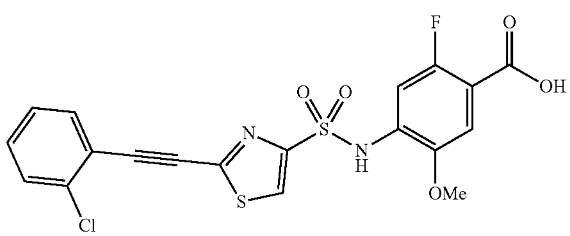 [SMILES: COc1cc(C(=O)O)c(F)cc1NS(=O)(=O)c1csc(C#Cc2ccccc2Cl)n1] | 467.2 | 1H NMR (400 MHz, DMSO-d6) δ 13.25 (s, 1H), 10.53 (s, 1H), 8.62 (s, 1H), 7.82 (dd, J = 7.7, 1.7 Hz, 1H), 7.67 (dd, J = 8.1, 1.2 Hz, 1H), 7.57 (m, 1H), 7.47 (m, 1H), 7.34 (d, J = 6.7 Hz, 1H), 7.28 (d, J = 11.8 Hz, 1H), 3.73 (s, 3H). |
| 236 | 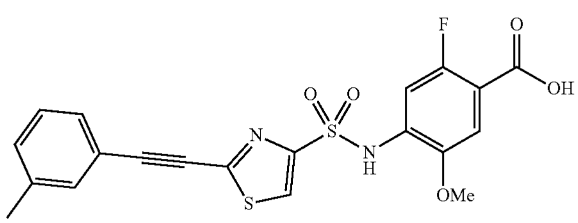 [SMILES: COc1cc(C(=O)O)c(F)cc1NS(=O)(=O)c1csc(C#Cc2cccc(C)c2)n1] | 447.2 | 1H NMR (400 MHz, DMSO-d6) δ 13.24 (s, 1H), 10.50 (s, 1H), 8.58 (s, 1H), 7.54-7.45 (m, 2H), 7.37 (m, 3H), 7.27 (d, J = 11.9 Hz, 1H), 3.73 (s, 3H), 2.34 (s, 3H) |
| 237 | 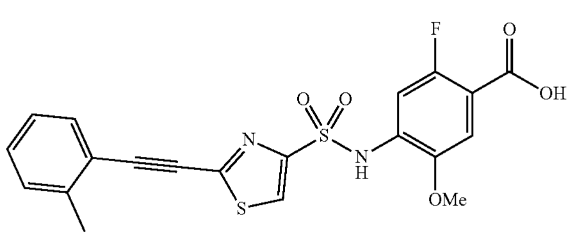 [SMILES: COc1cc(C(=O)O)c(F)cc1NS(=O)(=O)c1csc(C#Cc2ccccc2C)n1] | 447.2 | 1H NMR (400 MHz, DMSO-d6) δ 13.24 (s, 1H), 10.51 (s, 1H), 8.58 (s, 1H), 7.67-7.60 (m, 1H), 7.44 (m, 1H), 7.39 (d, J = 7.6 Hz, 1H), 7.36-7.24 (m, 3H), 3.73 (s, 3H), 2.47 (s, 3H). |

| Example # | Structure | LC-MS [M + H]+ unless otherwise noted | 1H-NMR |
|---|---|---|---|
| 238 | 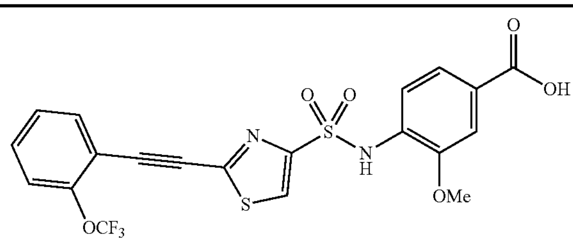 | 499.2 | 1H NMR (400 MHz, DMSO-d6) δ 12.96 (s, 1H), 10.21 (s, 1H), 8.47 (s, 1H), 7.90 (dd, J = 7.6, 1.7 Hz, 1H), 7.70 (m, 1H), 7.63-7.48 (m, 3H), 7.47-7.38 (m, 2H), 3.70 (s, 3H). |
| 239 | 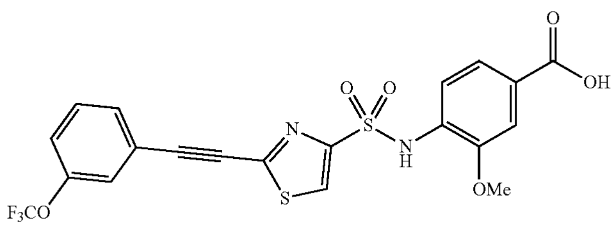 [SMILES: COc1cc(C(=O)O)ccc1NS(=O)(=O)c1csc(C#Cc2cccc(OC(F)(F)F)c2)n1] | 499.2 | 1H NMR (400 MHz, DMSO-d6) δ 12.97 (s, 1H), 10.20 (s, 1H), 8.47 (s, 1H), 7.80-7.72 (m, 2H), 7.65 (m, 1H), 7.61-7.55 (m, 1H), 7.52 (dd, J = 8.3, 1.8 Hz, 1H), 7.45 (d, J = 1.8 Hz, 1H), 7.40 (d, J = 8.3 Hz, 1H), 3.72 (s, 3H). |
| 240 | 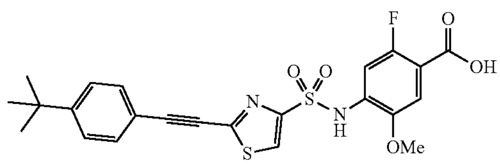 [SMILES: COc1cc(C(=O)O)c(F)cc1NS(=O)(=O)c1csc(C#Cc2ccc(C(C)(C)C)cc2)n1] | 489.3 | 1H NMR (400 MHz, DMSO-d6) δ 13.23 (s, 1H), 10.49 (s, 1H), 8.57 (s, 1H), 7.66-7.58 (m, 2H), 7.56-7.48 (m, 2H), 7.34 (d, J = 6.6 Hz, 1H), 7.26 (d, J = 11.9 Hz, 1H), 3.73 (s, 3H), 1.30 (s, 9H). |
| 241 | 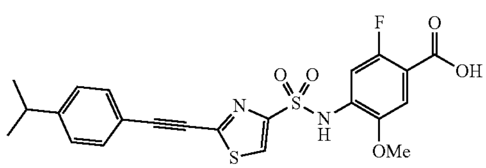 [SMILES: COc1cc(C(=O)O)c(F)cc1NS(=O)(=O)c1csc(C#Cc2ccc(C(C)C)cc2)n1] | 475.2 | 1H NMR (400 MHz, DMSO-d6) δ 13.24 (s, 1H), 10.49 (s, 1H), 8.57 (s, 1H), 7.64-7.58 (m, 2H), 7.40-7.31 (m, 3H), 7.27 (d, J = 11.8 Hz, 1H), 3.73 (s, 3H), 2.95 (m, 1H), 1.21 (d, J = 6.9 Hz, 6H). |
| 242 | 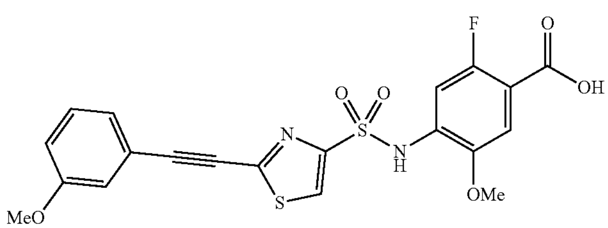 [SMILES: COc1cccc(C#Cc2nc(S(=O)(=O)Nc3cc(F)c(C(=O)O)cc3OC)cs2)c1] | 463.2 | 1H NMR (400 MHz, DMSO-d6) δ 10.55-10.47 (m, 1H), 8.58 (s, 1H), 7.41 (m, 1H), 7.34 (d, J = 6.6 Hz, 1H), 7.30-7.22 (m, 3H), 7.15-7.09 (m, 1H), 3.80 (s, 3H), 3.73 (s, 3H). |
| 243 | 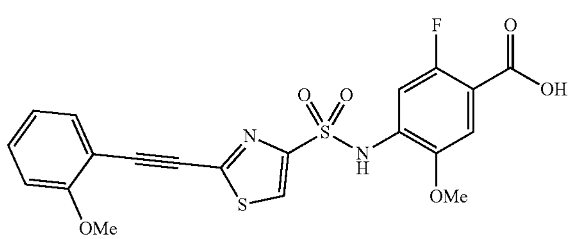 [SMILES: COc1ccccc1C#Cc1nc(S(=O)(=O)Nc2cc(F)c(C(=O)O)cc2OC)cs1] | 461.0 [M − H]− | 1H NMR (400 MHz, DMSO-d6) δ 10.49 (s, 1H), 8.55 (s, 1H), 7.60 (dd, J = 7.6, 1.8 Hz, 1H), 7.52 (dd, J = 8.9, 7.4 Hz, 1H), 7.33 (d, J = 6.6 Hz, 1H), 7.26 (d, J = 11.9 Hz, 1H), 7.16 (d, J = 8.4 Hz, 1H), 7.04 (m, 1H), 3.89 (s, 3H), 3.73 (s, 3H). |
| 244 | 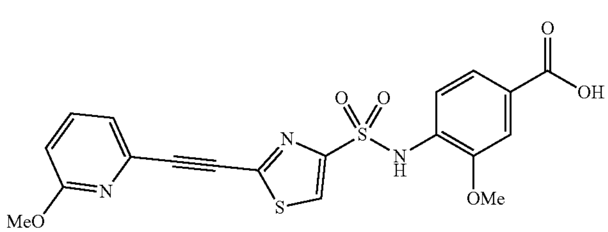 [SMILES: COc1cccc(C#Cc2nc(S(=O)(=O)Nc3ccc(C(=O)O)cc3OC)cs2)n1] | 446.0 | 1H NMR (400 MHz, DMSO-d6) δ 12.97 (s, 1H), 10.20 (s, 1H), 8.50 (s, 1H), 7.83 (dd, J = 8.5, 7.3 Hz, 1H), 7.67-7.49 (m, 2H), 7.48-7.42 (m, 2H), 7.40 (d, J = 8.3 Hz, 1H), 7.03-6.96 (m, 1H), 3.89 (s, 3H), 3.72 (s, 3H). |

| Example # | Structure | LC-MS [M + H]+ unless otherwise noted | 1H-NMR |
|---|---|---|---|
| 245 | 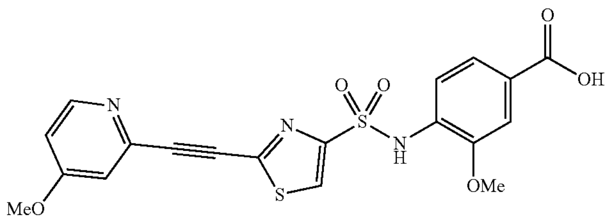 [SMILES: COc1ccnc(C#Cc2nc(S(=O)(=O)Nc3ccc(C(=O)O)cc3OC)cs2)c1] | 446.2 | 1H NMR (400 MHz, DMSO-d6) δ 12.94 (s, 1H), 10.20 (s, 1H), 8.48 (d, J = 6.4 Hz, 2H), 7.52 (dd, J = 8.2, 1.8 Hz, 1H), 7.45 (d, J = 2.5 Hz, 2H), 7.40 (d, J = 8.3 Hz, 1H), 7.12 (dd, J = 5.8, 2.6 Hz, 1H), 3.89 (s, 3H), 3.71 (s, 3H). |
| 246 | 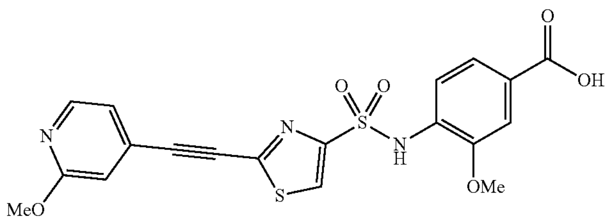 [SMILES: COc1cc(C#Cc2nc(S(=O)(=O)Nc3ccc(C(=O)O)cc3OC)cs2)ccn1] | 446.2 | 1H NMR (400 MHz, Chloroform-d) δ 8.22 (d, J = 5.4 Hz, 1H), 8.16 (s, 1H), 7.68 (d, J = 8.7 Hz, 2H), 7.54 (s, 1H), 7.01 (d, J = 5.7 Hz, 1H), 6.91 (s, 1H), 3.95 (d, J = 18.0 Hz, 6H). |
| 247 | 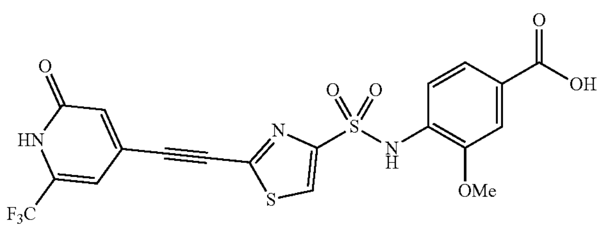 [SMILES: COc1cc(C(=O)O)ccc1NS(=O)(=O)c1csc(C#Cc2cc(C(F)(F)F)[nH]c(=O)c2)n1] | 500.2 | 1H NMR (400 MHz, DMSO-d6) δ 12.53 (s, 1H), 10.21 (s, 1H), 8.51 (s, 1H), 7.63 (s, 1H), 7.51 (dd, J = 8.2, 1.8 Hz, 1H), 7.45 (d, J = 1.8 Hz, 1H), 7.39 (d, J = 8.2 Hz, 1H), 7.24 (s, 1H), 3.71 (s, 3H), 2.08 (s, 1H). |
| 248 | 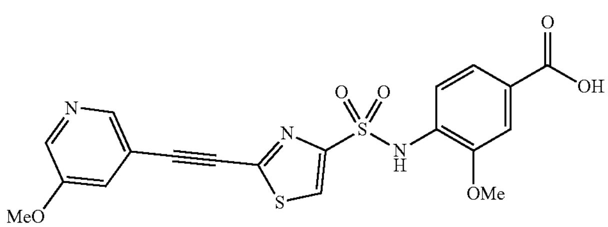 [SMILES: COc1cncc(C#Cc2nc(S(=O)(=O)Nc3ccc(C(=O)O)cc3OC)cs2)c1] | 446.2 | 1H NMR (400 MHz, DMSO-d6) δ 10.20 (s, 1H), 8.47 (d, J = 7.4 Hz, 2H), 8.42 (d, J = 2.9 Hz, 1H), 7.78-7.72 (m, 1H), 7.52 (dd, J = 8.2, 1.8 Hz, 1H), 7.45 (d, J = 1.8 Hz, 1H), 7.40 (d, J = 8.2 Hz, 1H), 3.89 (s, 3H), 3.72 (s, 3H). |
| 249 | 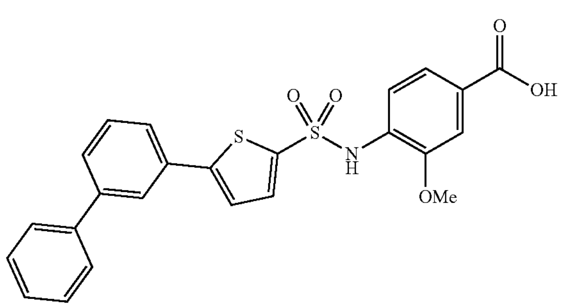 [SMILES: COc1cc(C(=O)O)ccc1NS(=O)(=O)c1ccc(-c2cccc(-c3ccccc3)c2)s1] | 464.0 [M − H]− | 1H NMR (400 MHz, DMSO-d6) δ 12.97 (s, 1H), 10.14 (s, 1H), 7.93 (t, J = 1.8 Hz, 1H), 7.78-7.71 (m, 2H), 7.74-7.64 (m, 3H), 7.60-7.37 (m, 8H), 3.71 (s, 3H). |

-continued

| Example # | Structure | LC-MS [M + H]+ unless otherwise noted | 1H-NMR |
|---|---|---|---|
| 250 | 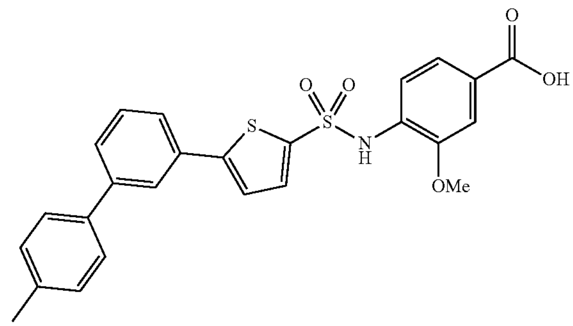 [SMILES: COc1cc(C(=O)O)ccc1NS(=O)(=O)c1ccc(-c2cccc(-c3ccc(C)cc3)c2)s1] | 478.1 [M − H]− | 1H NMR (400 MHz, DMSO-d6) δ 12.96 (s, 1H), 10.13 (s, 1H), 7.90 (t, J = 1.9 Hz, 1H), 7.71-7.60 (m, 5H), 7.60-7.48 (m, 3H), 7.50-7.43 (m, 2H), 7.30 (d, J = 8.0 Hz, 2H), 3.71 (s, 3H), 2.36 (s, 3H). |
| 251 | 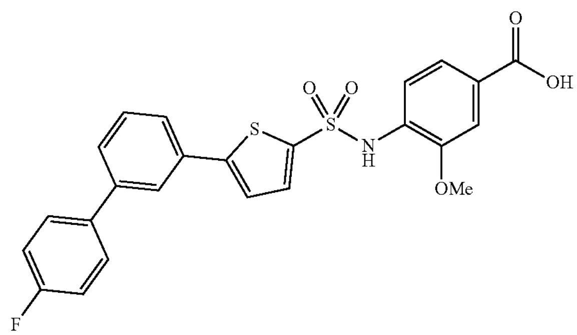 [SMILES: COc1cc(C(=O)O)ccc1NS(=O)(=O)c1ccc(-c2cccc(-c3ccc(F)cc3)c2)s1] | 482.1 [M − H]− | 1H NMR (400 MHz, DMSO-d6) δ 12.96 (s, 1H), 10.13 (s, 1H), 7.92 (t, J = 1.9 Hz, 1H), 7.85-7.75 (m, 2H), 7.71-7.62 (m, 3H), 7.58 (d, J = 4.0 Hz, 1H), 7.59-7.50 (m, 2H), 7.50-7.43 (m, 2H), 7.37-7.26 (m, 2H), 3.71 (s, 3H). |
| 252 | 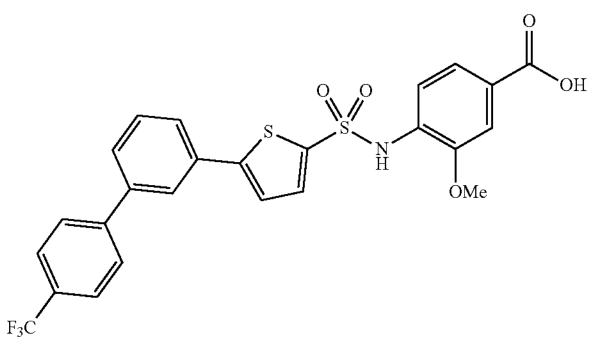 [SMILES: COc1cc(C(=O)O)ccc1NS(=O)(=O)c1ccc(-c2cccc(-c3ccc(C(F)(F)F)cc3)c2)s1] | 532.2 [M − H]− | 1H NMR (400 MHz, DMSO-d6) δ 12.95 (s, 1H), 10.15 (s, 1H), 8.04-7.96 (m, 3H), 7.84 (d, J = 8.2 Hz, 2H), 7.80-7.70 (m, 2H), 7.68 (d, J = 3.9 Hz, 1H), 7.66-7.55 (m, 2H), 7.58-7.51 (m, 1H), 7.50-7.43 (m, 2H), 3.71 (s, 3H). |
| 253 | 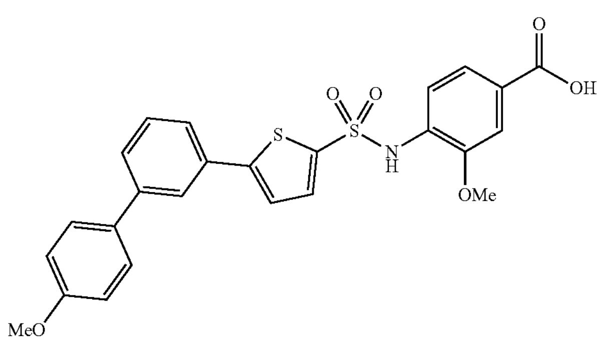 [SMILES: COc1ccc(-c2cccc(-c3ccc(S(=O)(=O)Nc4ccc(C(=O)O)cc4OC)s3)c2)cc1] | 494.2 [M − H]− | 1H NMR (400 MHz, DMSO-d6) δ 12.93 (s, 1H), 10.12 (s, 1H), 7.88 (t, J = 1.8 Hz, 1H), 7.74-7.66 (m, 2H), 7.69-7.42 (m, 8H), 7.09-7.01 (m, 2H), 3.81 (s, 3H), 3.71 (s, 3H). |

-continued

| Example # | Structure | LC-MS [M + H]+ unless otherwise noted | ¹H-NMR |
|---|---|---|---|
| 254 | 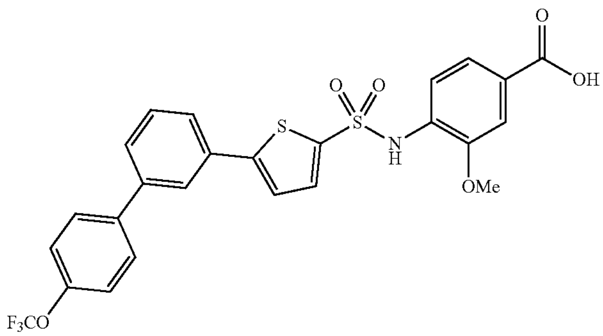 [SMILES: COc1cc(C(=O)O)ccc1NS(=O)(=O)c1ccc(-c2cccc(-c3ccc(OC(F)(F)F)cc3)c2)s1] | 548.2 [M − H]⁻ | ¹H NMR (400 MHz, DMSO-d₆) δ 7.96 (t, J = 1.9 Hz, 1H), 7.93-7.85 (m, 2H), 7.75-7.62 (m, 3H), 7.60-7.40 (m, 7H), 3.71 (s, 3H). |
| 255 | 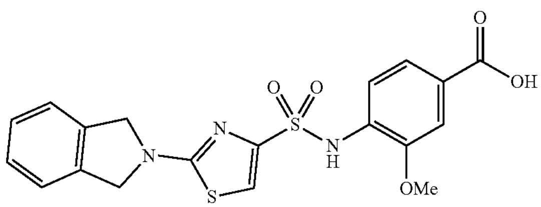 [SMILES: COc1cc(C(=O)O)ccc1NS(=O)(=O)c1csc(N2Cc3ccccc3C2)n1] | 432.1 | ¹H NMR (500 MHz, DMSO-d₆) δ 12.87 (br, 1H), 9.68 (br, 1H), 7.54-7.52 (m, 2H), 7.45 (d, J = 1.6 Hz, 1H), 7.42 (dd, J = 5.5, 3.2 Hz, 2H), 7.34 (dd, J = 5.7, 3.2 Hz, 2H), 4.74 (s, 4H), 3.79 (s, 3H). |
| 256 | 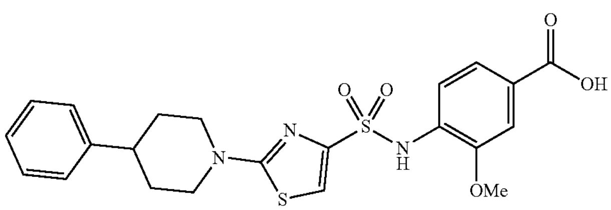 | 474.1 | ¹H NMR (500 MHz, DMSO-d₆) δ 7.47-7.37 (m, 4H), 7.34-7.28 (m, 2H), 7.26-7.22 (m, 2H), 7.22-7.17 (m, 1H), 3.98-3.91 (m, 2H), 3.75 (s, 3H), 3.13 (td, J = 12.8, 2.7 Hz, 2H), 2.84-2.70 (m, 1H), 1.89-1.82 (m, 2H), 1.66 (qd, J = 12.7, 4.3 Hz, 2H). |
| 257 | 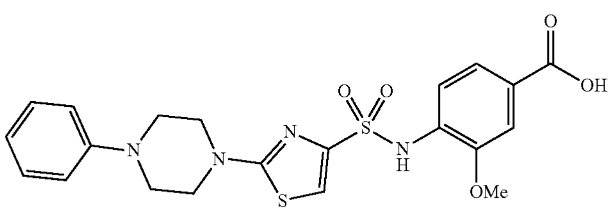 | 475.1 | ¹H NMR (400 MHz, DMSO-d₆) δ 7.53-7.45 (m, 3H), 7.42 (s, 1H), 7.28-7.20 (m, 2H), 6.99 (d, J = 8.2 Hz, 2H), 6.82 (t, J = 7.2 Hz, 1H), 3.76 (s, 3H), 3.58-3.50 (m, 4H), 3.29-3.20 (m, 4H). |
| 258 | 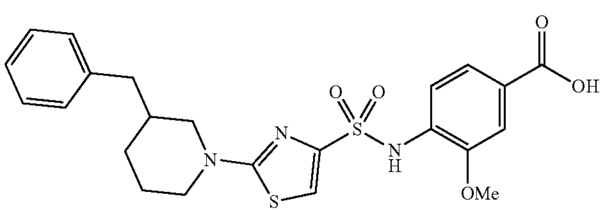 [SMILES: COc1cc(C(=O)O)ccc1NS(=O)(=O)c1csc(N2CCCC(Cc3ccccc3)C2)n1] | 488.2 | ¹H NMR (400 MHz, DMSO-d₆) δ 12.84 (br, 1H), 9.61 (br, 1H), 7.52-7.36 (m, 4H), 7.29 (t, J = 7.4 Hz, 2H), 7.23-7.15 (m, 3H), 3.76 (s, 3H), 3.75-3.61 (m, 2H), 3.07-2.95 (m, 1H), 2.84-2.75 (m, 1H), 2.62-2.54 (m, 2H), 1.88-7.75 (m, 1H), 1.74-1.24 (m, 2H), 1.51-1.37 (m, 1H), 1.25-1.12 (m, 1H). |
| 259 | 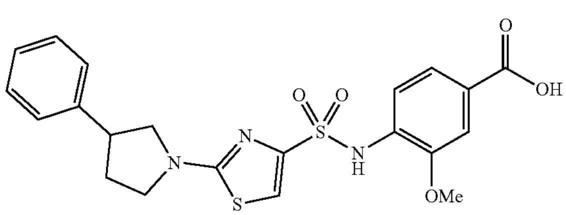 [SMILES: COc1cc(C(=O)O)ccc1NS(=O)(=O)c1csc(N2CCC(c3ccccc3)C2)n1] | 460.2 | |

| Example # | Structure | LC-MS [M + H]+ unless otherwise noted | 1H-NMR |
|---|---|---|---|
| 260 | 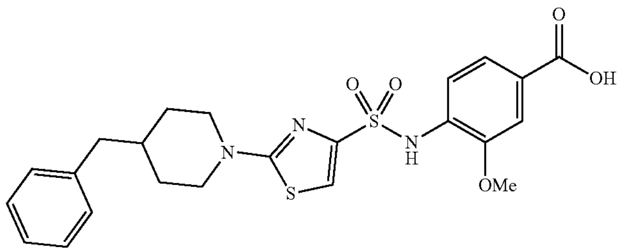 [SMILES: COc1cc(C(=O)O)ccc1NS(=O)(=O)c1csc(N2CCC(Cc3ccccc3)CC2)n1] | 488.2 | |
| 261 | 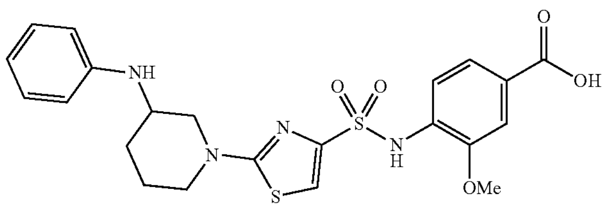 [SMILES: COc1cc(C(=O)O)ccc1NS(=O)(=O)c1csc(N2CCCC(Nc3ccccc3)C2)n1] | 489.3 | 1H NMR (400 MHz, DMSO-d6) δ 12.85 (br, 1H), 9.64 (br, 1H), 7.52-7.40 (m, 4H), 7.08 (t, J = 8.0 Hz, 2H), 6.64 (d, J = 8.0 Hz, 2H), 6.54 (t, J = 7.3 Hz, 1H), 5.58 (d, J = 8.2 Hz, 1H), 4.00-3.89 (m, 1H), 3.76 (s, 3H), 3.70-3.60 (m, 1H), 3.48-3.36 (m, 1H), 3.20-3.10 (m, 1H), 2.86 (dd, J = 12.7, 9.2 Hz, 1H), 2.03-1.92 (m, 1H), 1.87-1.75 (m, 1H), 1.67-1.57 (m, 1H), 1.53-1.40 (m, 1H). |
| 262 | 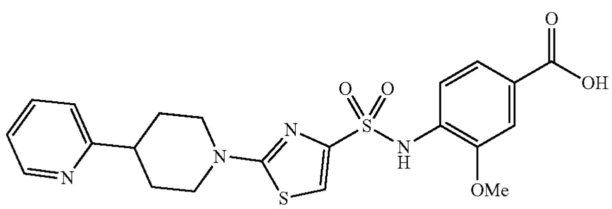 [SMILES: COc1cc(C(=O)O)ccc1NS(=O)(=O)c1csc(N2CCC(c3ccccn3)CC2)n1] | 475.2 | 1H NMR (500 MHz, DMSO-d6) δ 12.82 (br, 1H), 9.62 (br, 1H), 8.53-8.47 (m, 1H), 7.72 (td, J = 7.7, 1.9 Hz, 1H), 7.51-7.47 (m, 3H), 7.44 (s, 1H), 7.32-7.27 (m, 1H), 7.22 (ddd, J = 7.5, 4.8, 1.1 Hz, 1H), 3.96-3.89 (m, 2H), 3.77 (s, 3H), 3.16 (td, J = 12.7, 2.8 Hz, 2H), 2.95 (tt, J = 11.9, 3.6 Hz, 1H), 1.95-1.88 (m, 2H), 1.75 (qd, J = 12.7, 4.4 Hz, 2H). |
| 263 | 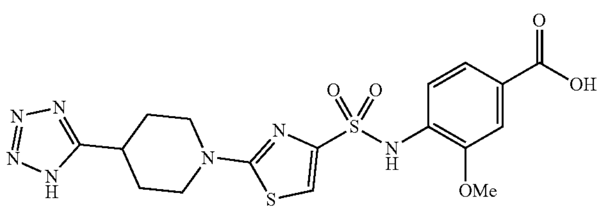 [SMILES: COc1cc(C(=O)O)ccc1NS(=O)(=O)c1csc(N2CCC(c3nnn[nH]3)CC2)n1] | 466.2 | 1H NMR (400 MHz, DMSO-d6) δ 9.63 (br, 1H), 7.56-7.47 (m, 3H), 7.44 (s, 1H), 3.92-3.82 (m, 1H), 3.78 (s, 3H), 3.31-3.19 (m, 4H), 2.12-2.03 (m, 2H), 1.84-1.69 (m, 2H). |
| 264 | 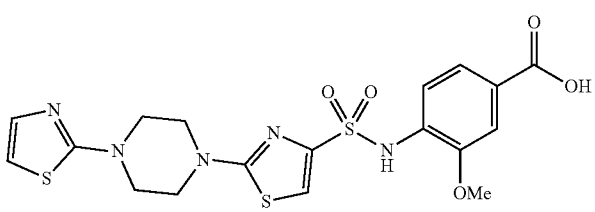 [SMILES: COc1cc(C(=O)O)ccc1NS(=O)(=O)c1csc(N2CCN(c3nccs3)CC2)n1] | 482.1 | 1H NMR (500 MHz, DMSO-d6) δ 12.82 (br, 1H), 9.69 (br, 1H), 7.55 (s, 1H), 7.52-7.45 (m, 2H), 7.43 (d, J = 1.7 Hz, 1H), 7.19 (d, J = 3.6 Hz, 1H), 6.90 (d, J = 3.6 Hz, 1H), 3.77 (s, 3H), 3.60-3.48 (m, 8H). |
| 265 | 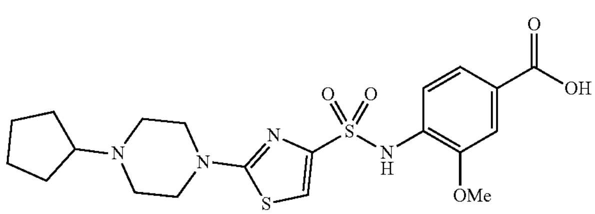 [SMILES: COc1cc(C(=O)O)ccc1NS(=O)(=O)c1csc(N2CCN(C3CCCC3)CC2)n1] | 467.2 | 1H NMR (400 MHz, DMSO-d6) δ 9.64 (br, 1H), 7.55-7.24 (m, 4H), 3.77 (s, 3H), 3.49-3.28 (m, 8H), 2.54-2.44 (m, 1H), 1.84-1.28 (m, 8H). |
| 266 | 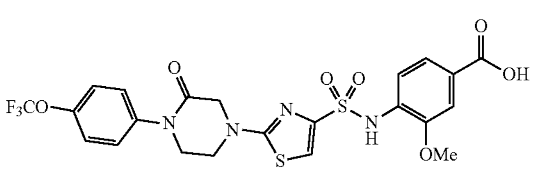 [SMILES: COc1cc(C(=O)O)ccc1NS(=O)(=O)c1csc(N2CCN(c3ccc(OC(F)(F)F)cc3)C(=O)C2)n1] | 573.0 | 1H NMR (500 MHz, DMSO-d6) δ 12.90 (br, 1H), 9.73 (br, 1H), 7.59 (s, 1H), 7.52-7.47 (m, 4H), 7.46-7.40 (m, 3H), 4.20 (s, 2H), 3.89 (dd, J = 6.7, 4.0 Hz, 2H), 3.81 (dd, J = 6.6, 4.1 Hz, 2H), 3.78 (s, 3H). |

| Example # | Structure | LC-MS [M + H]+ unless otherwise noted | 1H-NMR |
|---|---|---|---|
| 267 | 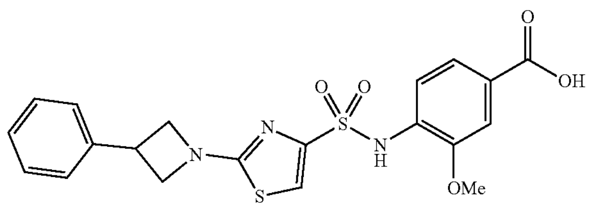 [SMILES: COc1cc(C(=O)O)ccc1NS(=O)(=O)c1csc(N2CC(c3ccccc3)C2)n1] | 446.2 | 1H NMR (400 MHz, DMSO-d6) δ 7.52 (s, 1H), 7.50-7.34 (m, 7H), 7.33-7.23 (m, 1H), 4.44 (t, J = 7.8 Hz, 2H), 4.12-3.98 (m, 3H), 3.76 (s, 3H). |
| 268 | 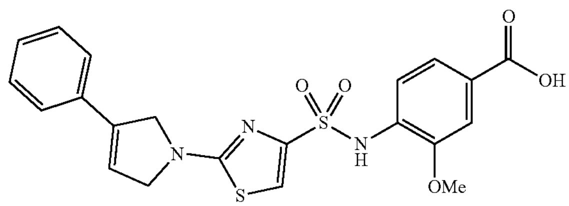 [SMILES: COc1cc(C(=O)O)ccc1NS(=O)(=O)c1csc(N2CC=C(c3ccccc3)C2)n1] | 458.1 | 1H NMR (400 MHz, DMSO-d6) δ 9.66 (br, 1H), 7.56-7.46 (m, 5H), 7.45-7.35 (m, 3H), 7.38-7.29 (m, 1H), 6.52 (t, J = 2.2 Hz, 1H), 4.59-4.51 (m, 2H), 4.42-4.31 (m, 2H), 3.77 (s, 3H). |
| 269 | 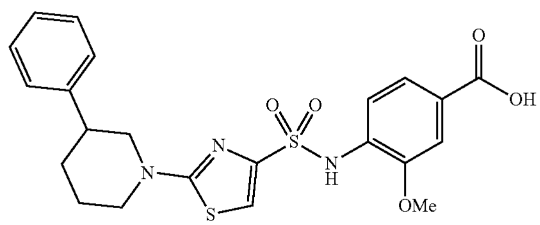 [SMILES: COc1cc(C(=O)O)ccc1NS(=O)(=O)c1csc(N2CCCC(c3ccccc3)C2)n1] | 474.2 | 1H NMR (400 MHz, DMSO-d6) δ 9.68 (br, 1H), 7.51-7.40 (m, 4H), 7.38-7.20 (m, 5H), 3.94-3.86 (m, 1H), 3.83-3.75 (m, 1H), 3.75 (s, 3H), 3.17-3.04 (m, 2H), 2.84-2.71 (m, 1H), 1.98-1.56 (m, 4H). |
| 270 | 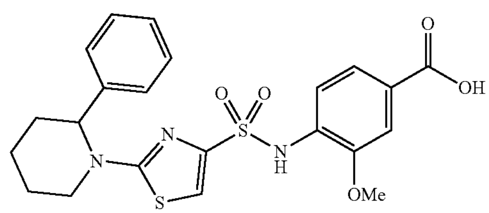 [SMILES: COc1cc(C(=O)O)ccc1NS(=O)(=O)c1csc(N2CCCCC2c2ccccc2)n1] | 474.2 | 1H NMR (400 MHz, DMSO-d6) δ 9.51 (br, 1H), 7.46-7.39 (m, 4H), 7.33 (t, J = 7.5 Hz, 2H), 7.24 (t, J = 1.3 Hz, 1H), 7.17 (d, J = 7.7 Hz, 2H), 3.86-3.78 (m, 1H), 3.73 (s, 3H), 3.28-3.20 (m, 2H), 2.31-2.21 (m, 1H), 1.99-1.88 (m, 1H), 1.73-1.49 (m, 3H), 1.39-1.27 (m, 1H). |
| 271 | 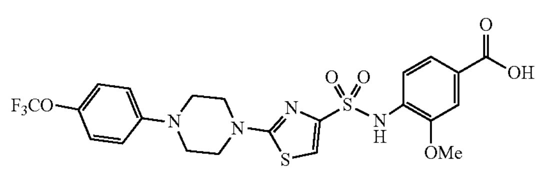 [SMILES: COc1cc(C(=O)O)ccc1NS(=O)(=O)c1csc(N2CCN(c3ccc(OC(F)(F)F)cc3)CC2)n1] | 559.1 | 1H NMR (500 MHz, DMSO-d6) δ 12.90 (br, 1H), 9.67 (br, 1H), 7.55 (s, 1H), 7.52-7.48 (m, 2H), 7.46-7.43 (m, 1H), 7.22 (d, J = 8.6 Hz, 2H), 7.09-7.03 (m, 2H), 3.78 (s, 3H), 3.57-3.51 (m, 4H), 3.31-3.26 (m, 4H). |
| 272 | 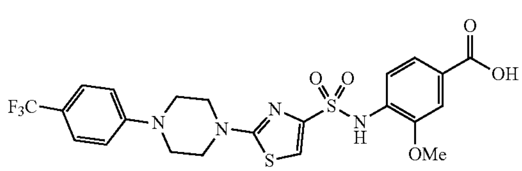 [SMILES: COc1cc(C(=O)O)ccc1NS(=O)(=O)c1csc(N2CCN(c3ccc(C(F)(F)F)cc3)CC2)n1] | 543.2 | 1H NMR (500 MHz, DMSO-d6) δ 12.89 (br, 1H), 9.68 (br, 1H), 7.57-7.48 (m, 5H), 7.44 (s, 1H), 7.11 (d, J = 8.6 Hz, 2H), 3.78 (s, 3H), 3.54 (dd, J = 6.7, 3.7 Hz, 4H), 3.43 (dd, J = 6.7, 3.8 Hz, 4H). |
| 273 | 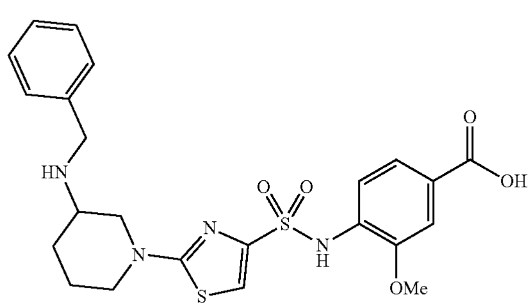 [SMILES: COc1cc(C(=O)O)ccc1NS(=O)(=O)c1csc(N2CCCC(NCc3ccccc3)C2)n1] | 503.2 | 1H NMR (500 MHz, DMSO-d6) δ 7.55-7.47 (m, 2H), 7.46-7.41 (m, 2H), 7.30 (dt, J = 14.9, 7.5 Hz, 4H), 7.21 (t, J = 7.1 Hz, 1H), 3.80 (dd, J = 12.6, 3.9 Hz, 1H), 3.77-3.70 (m, J = 8.9 Hz, 5H), 3.66-3.56 (m, 1H), 3.12-3.03 (m, 1H), 2.91 (dd, J = 12.7, 9.0 Hz, 1H), 2.60-2.51 (m, 1H), 1.95-1.88 (m, 1H), 1.79-1.69 (m, 1H), 1.48-1.28 (m, 2H), |

| Example # | Structure | LC-MS [M + H]+ unless otherwise noted | 1H-NMR |
|---|---|---|---|
| 274 | 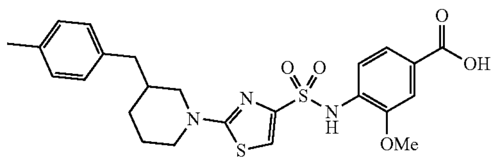 [SMILES: COc1cc(C(=O)O)ccc1NS(=O)(=O)c1csc(N2CCCC(Cc3ccc(C)cc3)C2)n1] | 502.2 | 1H NMR (400 MHz, DMSO-d$_6$) δ 7.51-7.40 (m, 4H), 7.13-7.03 (m, 4H), 3.76 (s, 3H), 3.73-3.59 (m, 2H), 3.00 (td, J = 12.0, 2.8 Hz, 1H), 2.78 (dd, J = 12.7, 10.4 Hz, 1H), 2.57-2.38 (m, 2H), 2.26 (s, 3H), 1.84-1.63 (m, 3H), 1.50-1.34 (m, 1H), 1.26-1.09 (m, 1H). |
| 275 | 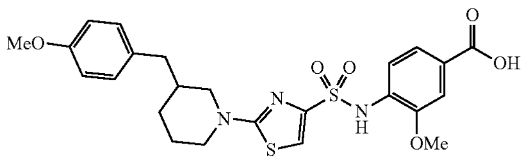 [SMILES: COc1ccc(CC2CCCN(c3nc(S(=O)(=O)Nc4ccc(C(=O)O)cc4OC)cs3)C2)cc1] | 518.2 | 1H NMR (400 MHz, DMSO-d$_6$) δ 12.83 (br, 1H), 9.62 (br, 1H), 7.50-7.41 (m, 4H), 7.13-7.05 (m, 2H), 6.89-6.81 (m, 2H), 3.76 (s, 3H), 3.72 (s, 3H), 3.70-3.59 (m, 2H), 3.06-2.95 (m, 1H), 2.77 (dd, J = 12.7, 10.3 Hz, 1H), 2.57-2.37 (m, 2H), 1.81-1.63 (m, 3H), 1.51-1.35 (m, 1H), 1.25-1.09 (m, 1H). |
| 276 | 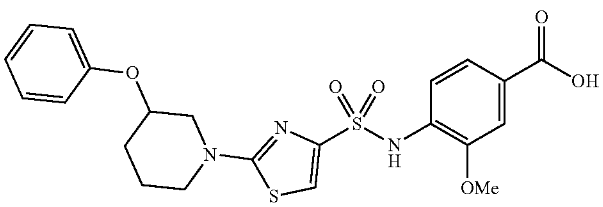 | 490.2 | 1H NMR (500 MHz, DMSO-d$_6$) δ 12.86 (br, 1H), 9.62 (br, 1H), 7.50-7.41 (m, 4H), 7.31-7.23 (m, 2H), 6.97-6.91 (m, 3H), 4.57-4.51 (m, 1H), 3.80 (dd, J = 13.1, 3.3 Hz, 1H), 3.75 (s, 3H), 3.52-3.37 (m, 3H), 2.02-1.93 (m, 1H), 1.88-1.71 (m, 2H), 1.66-1.56 (m, 1H). |
| 277 | 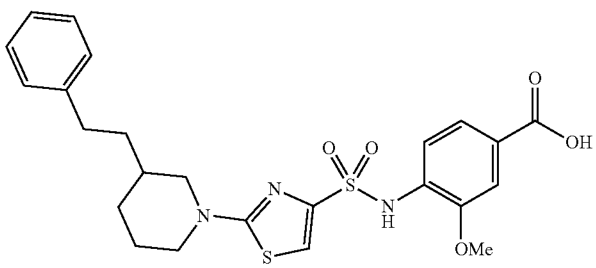 [SMILES: COc1cc(C(=O)O)ccc1NS(=O)(=O)c1csc(N2CCCC(CCc3ccccc3)C2)n1] | 502.3 | 1H NMR (500 MHz, DMSO-d$_6$) δ 12.87 (br, 1H), 9.61 (br, 1H), 7.54-7.42 (m, 4H), 7.29-7.24 (m, 2H), 7.22-7.14 (m, 3H), 3.81-3.75 (m, 1H), 3.75 (s, 3H), 3.72-3.64 (m, 1H), 3.07-2.98 (m, 1H), 2.78 (dd, J = 12.8, 9.6 Hz, 1H), 2.60 (t, J = 1.3 Hz, 2H), 1.88-1.81 (m, 1H), 1.74-1.65 (m, 1H), 1.59-1.37 (m, 4H), 1.26-1.13 (m, 1H). |
| 278 | 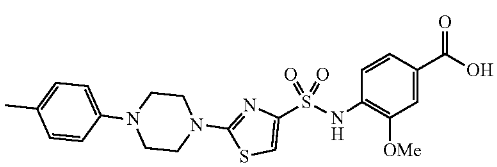 [SMILES: COc1cc(C(=O)O)ccc1NS(=O)(=O)c1csc(N2CCN(c3ccc(C)cc3)CC2)n1] | 489.2 | 1H NMR (500 MHz, DMSO-d$_6$) δ 12.88 (br, 1H), 9.67 (br, 1H), 7.54 (s, 1H), 7.51-7.48 (m, 2H), 7.45-7.43 (m, 1H), 7.09-7.03 (m, 2H), 6.92-6.85 (m, 2H), 3.77 (s, 3H), 3.55-3.49 (m, 4H), 3.20-3.15 (m, 4H), 2.21 (s, 3H). |
| 279 | 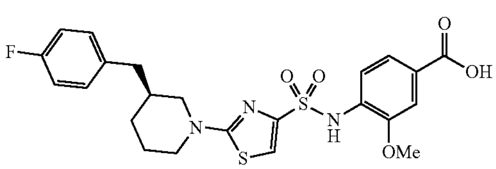 [SMILES: COc1cc(C(=O)O)ccc1NS(=O)(=O)c1csc(N2CCC[C@@H](Cc3ccc(F)cc3)C2)n1] | 506.2 | 1H NMR (500 MHz, DMSO-d$_6$) δ 12.87 (br, 1H), 9.60 (br, 1H), 7.51-7.42 (m, 4H), 7.26-7.18 (m, 2H), 7.15-7.06 (m, 2H), 3.77 (s, 3H), 3.74-3.67 (m, 1H), 3.66-3.59 (m, 1H), 3.01 (td, J = 12.6, 12.1, 2.9 Hz, 1H), 2.80 (dd, J = 12.8, 10.4 Hz, 1H), 2.61-2.54 (m, 1H), 2.50-2.43 (m, 1H), 1.84-1.62 (m, 3H), 1.48-1.37 (m, 1H), 1.25-1.11 (m, 1H). |
| 280 | 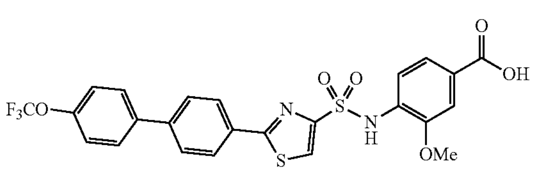 [SMILES: COc1cc(C(=O)O)ccc1NS(=O)(=O)c1csc(-c2ccc(-c3ccc(OC(F)(F)F)cc3)cc2)n1] | 551.1 | 1H NMR (400 MHz, DMSO-d$_6$) δ 12.93 (br, 1H), 10.08 (br, 1H), 8.40 (s, 1H), 8.07-7.99 (m, 2H), 7.93-7.84 (m, 4H), 7.58-7.47 (m, 2H), 7.43 (s, 1H), 3.68 (s, 3H). |

-continued

| Example # | Structure | LC-MS [M + H]+ unless otherwise noted | 1H-NMR |
|---|---|---|---|
| 281 | 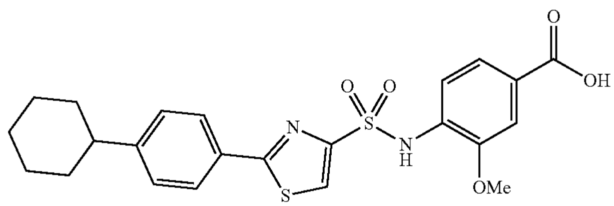 | 473.1 | 1H NMR (400 MHz, DMSO-d6) δ 12.93 (br, 1H), 10.03 (br, 1H), 8.34 (s, 1H), 7.86-7.80 (m, 2H), 7.53-7.50 (m, 2H), 7.44-7.36 (m, 3H), 3.67 (s, 3H), 2.64-2.52 (m, 1H), 1.87-1.75 (m, 4H), 1.49-1.14 (m, 6H). |
| 282 | 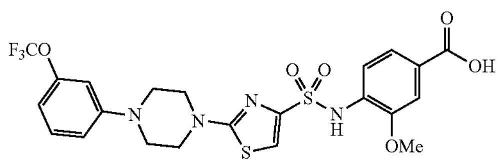 [SMILES: COc1cc(C(=O)O)ccc1NS(=O)(=O)c1csc(N2CCN(c3cccc(OC(F)(F)F)c3)CC2)n1] | 559.1 | 1H NMR (400 MHz, DMSO-d6) δ 12.87 (br, 1H), 9.69 (br, 1H), 7.55 (s, 1H), 7.52-7.48 (m, 2H), 7.44 (s, 1H), 7.34 (t, J = 8.2 Hz, 1H), 7.00 (dd, J = 8.4, 2.4 Hz, 1H), 6.92-6.89 (m, 1H), 6.75 (d, J = 8.2 Hz, 1H), 3.78 (s, 3H), 3.53 (dd, J = 6.7, 3.7 Hz, 4H), 3.41-3.30 (m, 4H). |
| 283 | 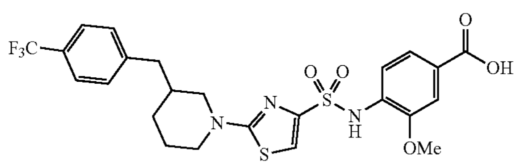 [SMILES: COc1cc(C(=O)O)ccc1NS(=O)(=O)c1csc(N2CCCC(Cc3ccc(C(F)(F)F)cc3)C2)n1] | 556.1 | 1H NMR (400 MHz, DMSO-d6) δ 12.87 (br, 1H), 9.59 (br, 1H), 7.65 (d, J = 8.0 Hz, 2H), 7.52-7.40 (m, 6H), 3.76 (s, 3H), 3.73-3.62 (m, 2H), 3.09-2.98 (m, 1H), 2.85 (dd, J = 12.8, 10.2 Hz, 1H), 2.76-2.64 (m, 1H), 2.63-2.53 (m, 1H), 1.92-1.79 (m, 1H), 1.75-1.62 (m, 2H), 1.51-1.37 (m, 1H), 1.27-1.12 (m, 1H). |
| 284 | 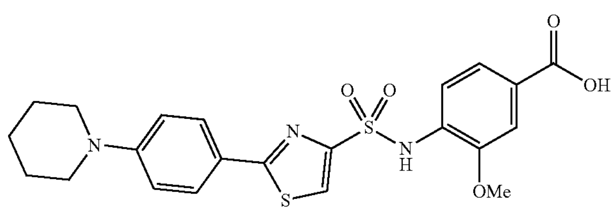 [SMILES: COc1cc(C(=O)O)ccc1NS(=O)(=O)c1csc(-c2ccc(N3CCCCC3)cc2)n1] | 474.2 | 1H NMR (400 MHz, Chloroform-d) δ 7.90 (s, 1H), 7.76-7.64 (m, 5H), 7.51-7.46 (m, 1H), 6.87 (d, J = 8.5 Hz, 2H), 3.86 (s, 3H), 3.30 (t, J = 5.3 Hz, 4H), 1.76-1.57 (m, 6H). |
| 285 | 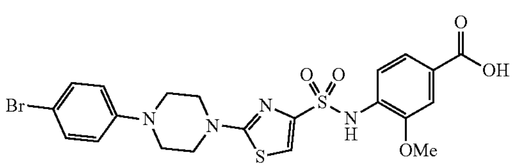 [SMILES: COc1cc(C(=O)O)ccc1NS(=O)(=O)c1csc(N2CCN(c3ccc(Br)cc3)CC2)n1] | 554.8 | 1H NMR (400 MHz, DMSO-d6) δ 12.77 (br, 1H), 9.63 (br, 1H), 7.54 (s, 1H), 7.50-7.48 (m, 2H), 7.44 (s, 1H), 7.41-7.34 (m, 2H), 6.99-6.91 (m, 2H), 3.77 (s, 3H), 3.52 (dd, J = 6.6, 3.7 Hz, 4H), 3.26 (dd, J = 6.6, 3.8 Hz, 4H). |
| 286 | 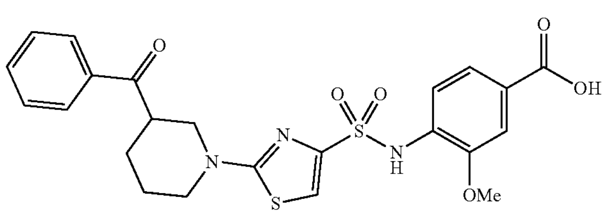 [SMILES: COc1cc(C(=O)O)ccc1NS(=O)(=O)c1csc(N2CCCC(C(=O)c3ccccc3)C2)n1] | 502.2 | 1H NMR (400 MHz, DMSO-d6) δ 12.74 (br, 1H), 9.66 (br, 1H), 8.05-7.98 (m, 2H), 7.70-7.62 (m, 1H), 7.58-7.36 (m, 6H), 4.08-3.99 (m, 1H), 3.75 (s, 3H), 3.79-3.63 (m, 2H), 3.27-3.08 (m, 2H), 2.04-1.94 (m, 1H), 1.82-1.53 (m, 3H). |
| 287 | 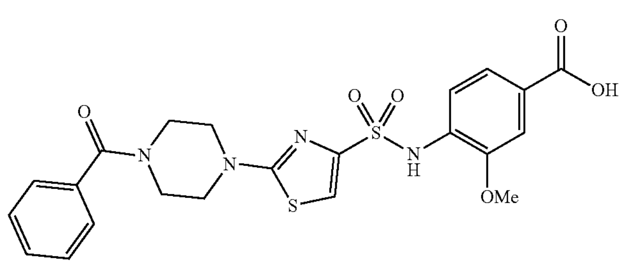 [SMILES: COc1cc(C(=O)O)ccc1NS(=O)(=O)c1csc(N2CCN(C(=O)c3ccccc3)CC2)n1] | 503.2 | 1H NMR (400 MHz, DMSO-d6) δ 12.87 (br, 1H), 9.67 (br, 1H), 7.54 (s, 1H), 7.51-7.40 (m, 8H), 3.77 (s, 3H), 3.77-3.36 (br, 8H). |

| Example # | Structure | LC-MS [M + H]+ unless otherwise noted | 1H-NMR |
|---|---|---|---|
| 288 | 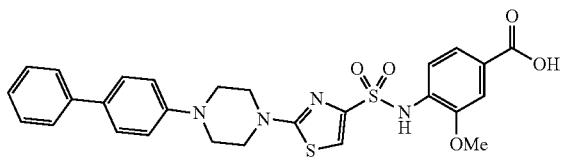 [SMILES: COc1cc(C(=O)O)ccc1NS(=O)(=O)c1csc(N2CCN(c3ccc(-c4ccccc4)cc3)CC2)n1] | 551.2 | 1H NMR (400 MHz, DMSO-d6) δ 12.83 (br, 1H), 9.64 (br, 1H), 7.64-7.47 (m, 7H), 7.46-7.37 (m, 3H), 7.32-7.23 (m, 1H), 7.12-7.04 (m, 2H), 3.78 (s, 3H), 3.56 (dd, J = 6.6, 3.7 Hz, 4H), 3.36-3.31 (m, 4H). |
| 289 | 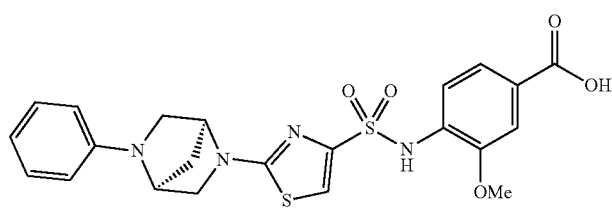 [SMILES: COc1cc(C(=O)O)ccc1NS(=O)(=O)c1csc(N2C[C@@H]3C[C@H]2CN3c2ccccc2)n1] | 487.1 | 1H NMR (400 MHz, DMSO-d6) δ 12.83 (br, 1H), 9.55 (br, 1H), 7.49-7.34 (m, 4H), 7.19-7.10 (m, 2H), 6.62 (t, J = 7.3 Hz, 1H), 6.61-6.54 (m, 2H), 4.63 (s, 1H), 4.55 (s, 1H), 3.62 (s, 3H), 3.61-3.52 (m, 2H), 3.21 (d, J = 9.3 Hz, 1H), 2.96 (d, J = 9.2 Hz, 1H), 2.12-2.03 (m, 2H). |
| 290 | 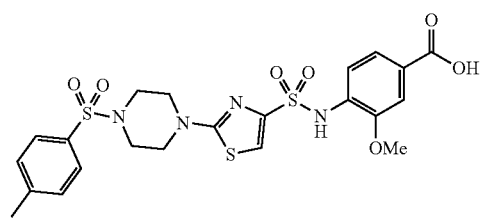 [SMILES: COc1cc(C(=O)O)ccc1NS(=O)(=O)c1csc(N2CCN(S(=O)(=O)c3ccc(C)cc3)CC2)n1] | 553.1 | 1H NMR (400 MHz, DMSO-d6) δ 12.87 (br, 1H), 9.66 (br, 1H), 9.64 (s, 1H), 7.66-7.60 (m, 2H), 7.49-7.38 (m, 6H), 3.69 (s, 3H), 3.53-3.45 (m, 4H), 3.01-2.94 (m, 4H), 2.40 (s, 3H). |
| 291 | 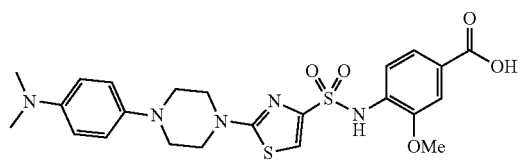 [SMILES: COc1cc(C(=O)O)ccc1NS(=O)(=O)c1csc(N2CCN(c3ccc(N(C)C)cc3)CC2)n1] | 518.2 | 1H NMR (400 MHz, DMSO-d6) δ 12.79 (br, 1H), 9.68 (br, 1H), 7.54-7.46 (m, 3H), 7.43 (s, 1H), 6.93-6.84 (m, 2H), 6.73-6.66 (m, 2H), 3.77 (s, 3H), 3.52 (dd, J = 6.5, 3.8 Hz, 4H), 3.09-3.01 (m, 4H), 2.79 (s, 6H). |
| 292 | 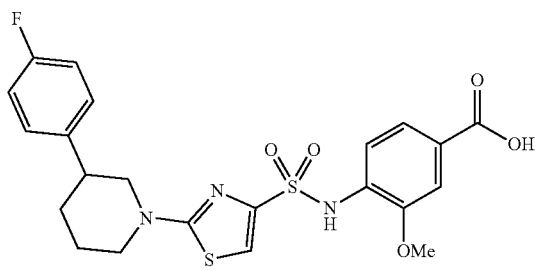 [SMILES: COc1cc(C(=O)O)ccc1NS(=O)(=O)c1csc(N2CCCC(c3ccc(F)cc3)C2)n1] | 492.1 | 1H NMR (400 MHz, DMSO-d6) δ 12.88 (br, 1H), 9.63 (br, 1H), 7.53-7.41 (m, 4H), 7.37-7.27 (m, 2H), 7.20-7.10 (m, 2H), 3.93-3.84 (m, 1H), 3.82-3.72 (m, 1H), 3.76 (s, 3H), 3.17-3.03 (m, 2H), 2.84-2.73 (m, 1H), 1.98-1.53 (m, 4H). |
| 293 | 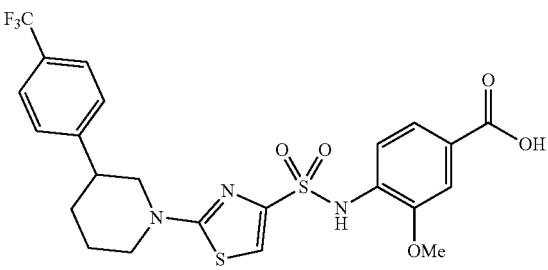 [SMILES: COc1cc(C(=O)O)ccc1NS(=O)(=O)c1csc(N2CCCC(c3ccc(C(F)(F)F)cc3)C2)n1] | 542.1 | 1H NMR (400 MHz, DMSO-d6) δ 12.88 (br, 1H), 9.63 (br, 1H), 7.70 (d, J = 8.1 Hz, 2H), 7.55-7.42 (m, 6H), 3.96-3.87 (m, 1H), 3.85-3.76 (m, 1H), 3.76 (s, 3H), 3.23-3.09 (m, 2H), 2.96-2.85 (m, 1H), 2.01-1.56 (m, 4H). |

| Example # | Structure | LC-MS [M + H]+ unless otherwise noted | ¹H-NMR |
|---|---|---|---|
| 294 | 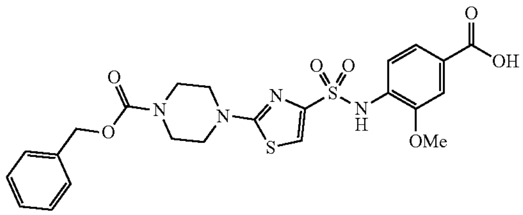 [SMILES: COc1cc(C(=O)O)ccc1NS(=O)(=O)c1csc(N2CCN(C(=O)OCc3ccccc3)CC2)n1] | 533.2 | ¹H NMR (400 MHz, DMSO-d₆) δ 12.77 (br, 1H), 9.69 (br, 1H), 7.53-7.29 (m, 9H), 5.11 (s, 2H), 3.76 (s, 3H), 3.59-3.48 (m, 4H), 3.46-3.38 (m, 4H). |
| 295 | 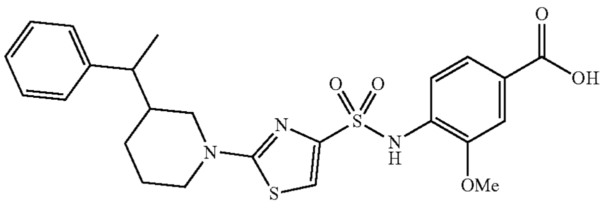 [SMILES: COc1cc(C(=O)O)ccc1NS(=O)(=O)c1csc(N2CCCC(C(C)c3ccccc3)C2)n1] | 502.2 | ¹H NMR (400 MHz, DMSO-d₆) δ 12.81 (br, 1H), 9.63 (br, 1H), 7.60-7.39 (m, 4H), 7.35-7.14 (m, 5H), 3.96-3.88 (m, 1H), 3.78 (s, 3H), 3.67-3.58 (m, 1H), 3.05-2.92 (m, 1H), 2.84 (dd, J = 12.9, 10.4 Hz, 1H), 2.59-2.50 (m, 1H), 1.72-1.56 (m, 2H), 1.46-1.30 (m, 2H), 1.19 (d, J = 7.0 Hz, 3H), 1.06-0.93 (m, 1H). |
| 296 | 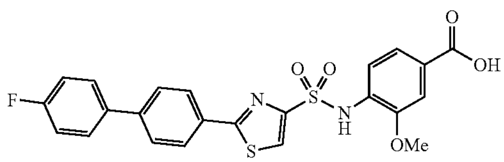 [SMILES: COc1cc(C(=O)O)ccc1NS(=O)(=O)c1csc(-c2ccc(-c3ccc(F)cc3)cc2)n1] | 485.2 | ¹H NMR (400 MHz, DMSO-d₆) δ 12.91 (br, 1H), 10.09 (br, 1H), 8.38 (s, 1H), 8.05-7.96 (m, 2H), 7.89-7.77 (m, 4H), 7.55-7.50 (m, 2H), 7.42 (s, 1H), 7.39-7.28 (m, 2H), 3.67 (s, 3H). |
| 297 | 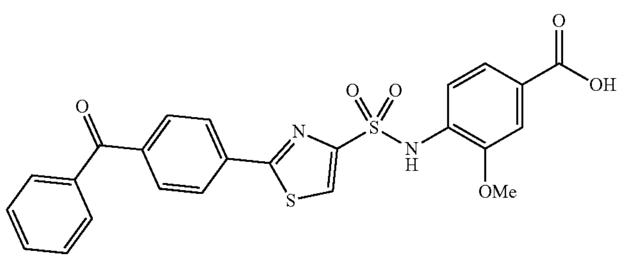 [SMILES: COc1cc(C(=O)O)ccc1NS(=O)(=O)c1csc(-c2ccc(C(=O)c3ccccc3)cc2)n1] | 495.3 | ¹H NMR (400 MHz, DMSO-d₆) δ 12.90 (br, 1H), 10.14 (br, 1H), 8.46 (s, 1H), 8.14-8.09 (m, 2H), 7.93-7.87 (m, 2H), 7.82-7.75 (m, 2H), 7.75-7.68 (m, 1H), 7.64-7.56 (m, 2H), 7.56-7.47 (m, 2H), 7.42 (d, J = 1.7 Hz, 1H), 3.66 (s, 3H). |
| 298 | 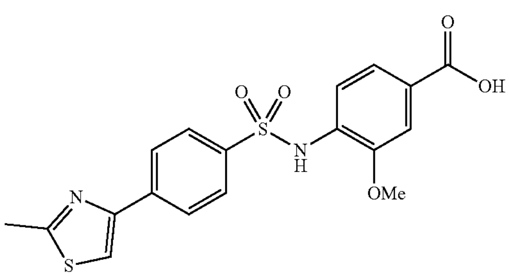 [SMILES: COc1cc(C(=O)O)ccc1NS(=O)(=O)c1ccc(-c2csc(C)n2)cc1] | 405.1 | ¹H NMR (400 MHz, DMSO-d₆) δ 12.87 (br, 1H), 9.88 (br, 1H), 8.13 (s, 1H), 8.11-8.05 (m, 2H), 7.86-7.80 (m, 2H), 7.48 (dd, J = 8.3, 1.8 Hz, 1H), 7.41-7.34 (m, 2H), 3.64 (s, 3H), 2.71 (s, 3H). |
| 299 | 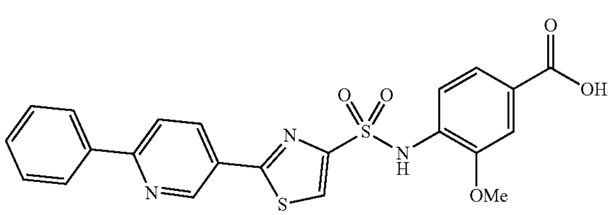 [SMILES: COc1cc(C(=O)O)ccc1NS(=O)(=O)c1csc(-c2ccc(-c3ccccc3)nc2)n1] | 468.2 | ¹H NMR (400 MHz, Methanol-d₄) δ 9.17 (d, J = 2.3 Hz, 1H), 8.36 (dd, J = 8.4, 2.4 Hz, 1H), 8.31 (s, 1H), 8.10-8.04 (m, 2H), 8.01 (d, J = 8.4 Hz, 1H), 7.63 (d, J = 9.8 Hz, 2H), 7.56-7.44 (m, 4H), 3.77 (s, 3H). |

| Example # | Structure | LC-MS [M + H]+ unless otherwise noted | 1H-NMR |
|---|---|---|---|
| 300 | 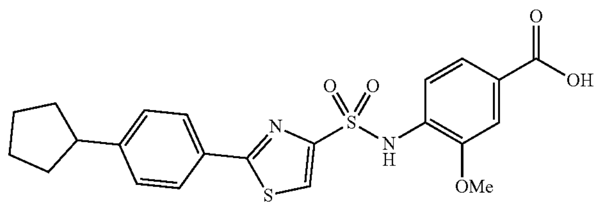 [SMILES: COc1cc(C(=O)O)ccc1NS(=O)(=O)c1csc(-c2ccc(C3CCCC3)cc2)n1] | 459.2 | 1H NMR (400 MHz, DMSO-d6) δ 12.89 (br, 1H), 10.07 (br, 1H), 8.32 (s, 1H), 7.86-7.79 (m, 2H), 7.55-7.47 (m, 2H), 7.47-7.36 (m, 3H), 3.67 (s, 3H), 3.10-2.97 (m, 1H), 2.11-1.97 (m, 2H), 1.86-1.46 (m, 6H). |
| 301 | 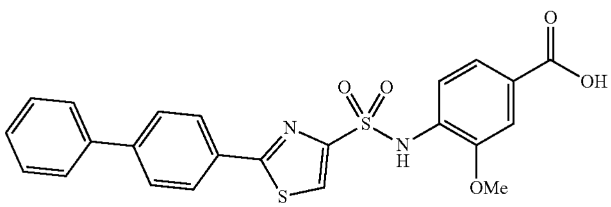 [SMILES: COc1cc(C(=O)O)ccc1NS(=O)(=O)c1csc(-c2ccc(-c3ccccc3)cc2)n1] | 465.0 [M − H]− | 1H NMR (400 MHz, DMSO-d6) δ 12.92 (br, 1H), 10.08 (br, 1H), 8.39 (s, 1H), 8.06-7.98 (m, 2H), 7.90-7.82 (m, 2H), 7.80-7.71 (m, 2H), 7.59-7.47 (m, 4H), 7.46-7.39 (m, 2H), 3.68 (s, 3H). |
| 302 | 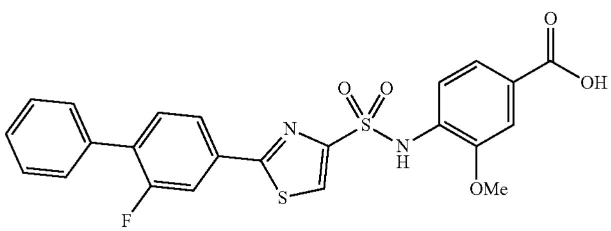 [SMILES: COc1cc(C(=O)O)ccc1NS(=O)(=O)c1csc(-c2ccc(-c3ccccc3)c(F)c2)n1] | 483.0 [M − H]− | 1H NMR (400 MHz, DMSO-d6) δ 12.92 (br, 1H), 10.10 (br, 1H), 8.44 (s, 1H), 7.90-7.79 (m, 2H), 7.72 (t, J = 8.0 Hz, 1H), 7.66-7.59 (m, 2H), 7.57-7.40 (m, 6H), 3.67 (s, 3H). |
| 303 | 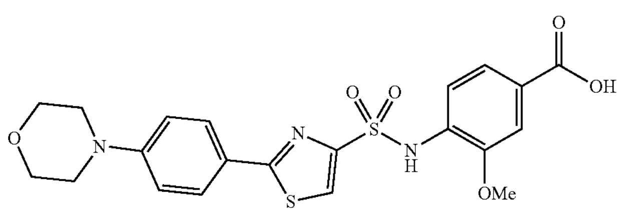 [SMILES: COc1cc(C(=O)O)ccc1NS(=O)(=O)c1csc(-c2ccc(N3CCOCC3)cc2)n1] | 474.1 [M − H]− | 1H NMR (400 MHz, DMSO-d6) δ 12.90 (br, 1H), 9.96 (br, 1H), 8.22 (s, 1H), 7.81-7.72 (m, 2H), 7.54-7.49 (m, 2H), 7.44-7.40 (m, 1H), 7.10-7.00 (m, 2H), 3.78-3.71 (m, 4H), 3.68 (s, 3H), 3.28-3.22 (m, 4H). |
| 304 | 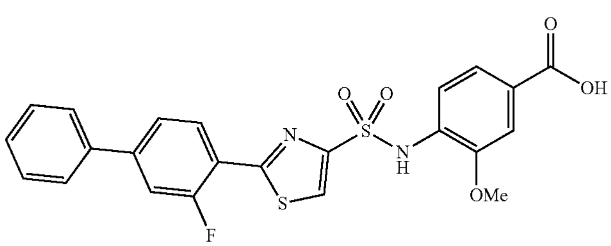 [SMILES: COc1cc(C(=O)O)ccc1NS(=O)(=O)c1csc(-c2ccc(-c3ccccc3)cc2F)n1] | 483.0 [M − H]− | 1H NMR (400 MHz, DMSO-d6) δ 12.93 (br, 1H), 10.12 (br, 1H), 8.48 (s, 1H), 8.17 (t, J = 8.1 Hz, 1H), 7.88-7.79 (m, 3H), 7.78 (dd, J = 8.3, 1.8 Hz, 1H), 7.57-7.40 (m, 6H), 3.67 (s, 3H). |
| 305 | 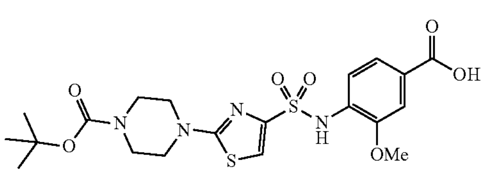 [SMILES: COc1cc(C(=O)O)ccc1NS(=O)(=O)c1csc(N2CCN(C(=O)OC(C)(C)C)CC2)n1] | 499.3 | 1H NMR (500 MHz, DMSO-d6) δ 9.64 (br, 1H), 7.55-7.38 (m, 4H), 3.76 (s, 4H), 3.47-3.27 (m, 8H), 1.41 (s, 9H). |

-continued

| Example # | Structure | LC-MS [M + H]+ unless otherwise noted | ¹H-NMR |
|---|---|---|---|
| 306 | 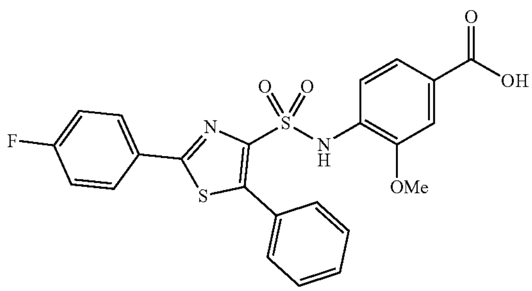 [SMILES: COc1cc(C(=O)O)ccc1NS(=O)(=O)c1nc(-c2ccc(F)cc2)sc1-c1ccccc1] | 485.3 | ¹H NMR (400 MHz, DMSO-d₆) δ 10.28 (br, 1H), 8.11-7.99 (m, 2H), 7.82-7.71 (m, 2H), 7.52-7.33 (m, 7H), 7.28 (d, J = 8.2 Hz, 1H), 3.57 (s, 3H). |
| 307 | 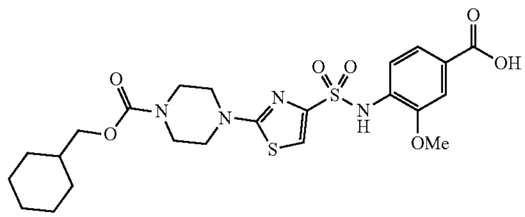 [SMILES: COc1cc(C(=O)O)ccc1NS(=O)(=O)c1csc(N2CCN(C(=O)OCC3CCCCC3)CC2)n1] | 539.4 | ¹H NMR (500 MHz, DMSO-d₆) δ 12.87 (br, 1H), 9.67 (br, 1H), 7.55-7.41 (m, 4H), 3.84 (d, J = 6.5 Hz, 2H), 3.77 (s, 3H), 3.56-3.37 (m, 8H), 1.73-1.54 (m, 6H), 1.27-1.08 (m, 3H), 1.01-0.89 (m, 2H). |
| 308 | 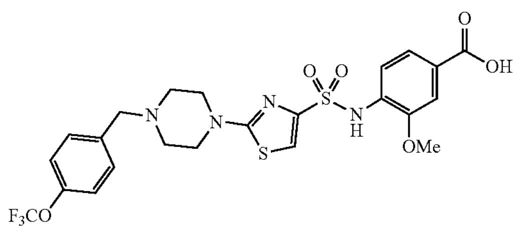 [SMILES: COc1cc(C(=O)O)ccc1NS(=O)(=O)c1csc(N2CCN(Cc3ccc(OC(F)(F)F)cc3)CC2)n1] | 573.3 | ¹H NMR (400 MHz, DMSO-d₆) δ 12.88 (br, 1H), 9.65 (s, 1H), 7.67-7.22 (m, 8H), 3.77 (s, 3H), 3.55 (s, 2H), 3.47-3.34 (m, 4H), 2.46 (br, 4H). |
| 309 | 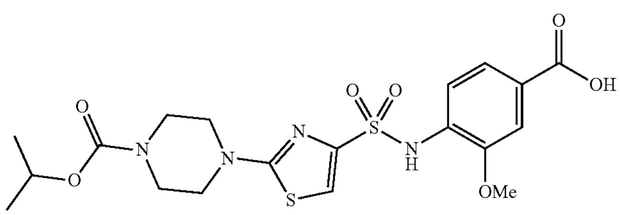 [SMILES: COc1cc(C(=O)O)ccc1NS(=O)(=O)c1csc(N2CCN(C(=O)OC(C)C)CC2)n1] | 485.4 | ¹H NMR (400 MHz, Methanol-d₄) δ 7.58-7.52 (m, 3H), 7.46 (s, 1H), 3.85 (s, 3H), 3.60-3.51 (m, 4H), 3.48-3.41 (m, 4H), 1.26 (d, J = 6.2 Hz, 6H). |
| 310 | 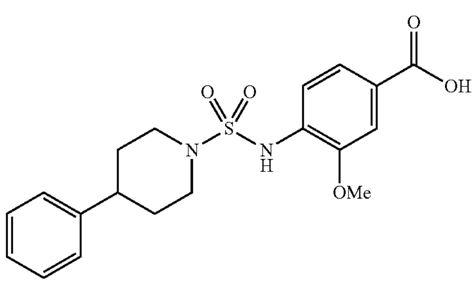 [SMILES: COc1cc(C(=O)O)ccc1NS(=O)(=O)N1CCC(c2ccccc2)CC1] | 391.1 | |
| 311 | 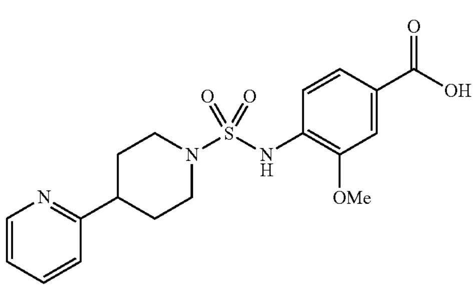 [SMILES: COc1cc(C(=O)O)ccc1NS(=O)(=O)N1CCC(c2ccccn2)CC1] | 392.1 | |

| Example # | Structure | LC-MS [M + H]+ unless otherwise noted | 1H-NMR |
|---|---|---|---|
| 312 | 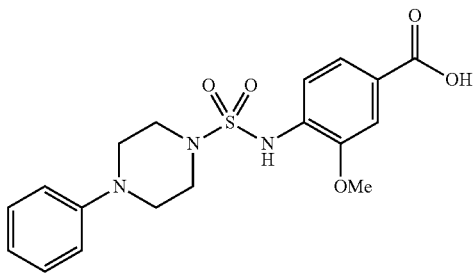 [SMILES: COc1cc(C(=O)O)ccc1NS(=O)(=O)N1CCN(c2ccccc2)CC1] | 392.1 | |
| 313 | 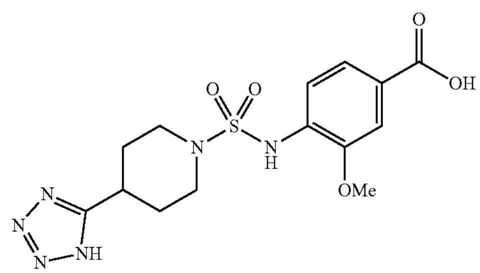 [SMILES: COc1cc(C(=O)O)ccc1NS(=O)(=O)N1CCC(c2nnn[nH]2)CC1] | 383.1 | 1H NMR (500 MHz, Methanol-d4) δ 7.88 (d, J = 1.7 Hz, 1H), 7.45 (d, J = 1.8 Hz, 1H), 7.23 (s, 1H), 3.88 (s, 3H), 3.76 (dt, J = 12.2, 3.7 Hz, 2H), 2.98 (tt, J = 11.5, 3.8 Hz, 1H), 2.65 (td, J = 11.9, 2.6 Hz, 2H), 2.18-2.03 (m, 2H), 1.85 (qd, J = 11.6, 3.9 Hz, 2H). |
| 314 | 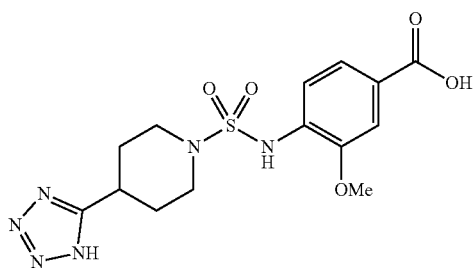 | 399.1 | |
| 315 | 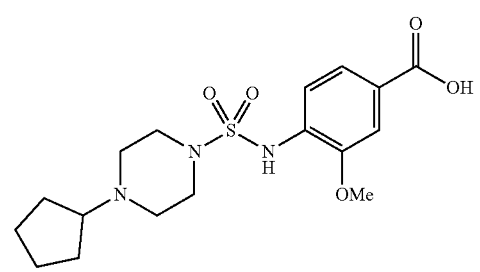 [SMILES: COc1cc(C(=O)O)ccc1NS(=O)(=O)N1CCN(C2CCCC2)CC1] | 384.2 | |
| 316 | 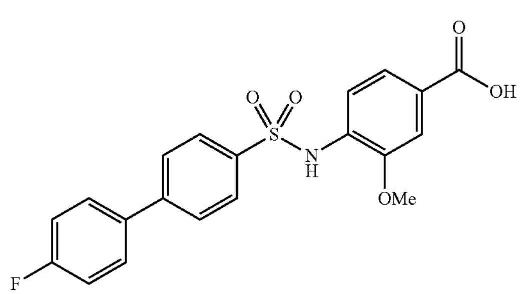 [SMILES: COc1cc(C(=O)O)ccc1NS(=O)(=O)c1ccc(-c2ccc(F)cc2)cc1] | 400.1 [M − H]− | 1H NMR (400 MHz, Methanol-d4) δ 7.82 (d, J = 9.7 Hz, 2H), 7.74-7.20 (m, 7H), 7.10 (s, 2H), 3.32 (s, 3H). |

-continued
| Example # | Structure | LC-MS [M + H]+ unless otherwise noted | 1H-NMR |
|---|---|---|---|
| 317 | 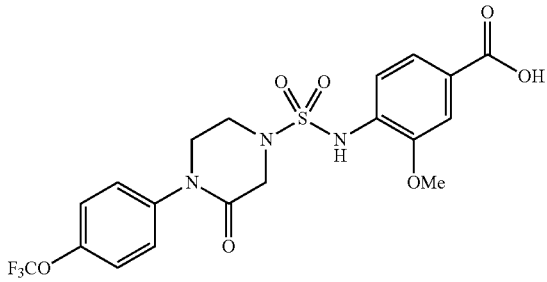 [SMILES: COc1cc(C(=O)O)ccc1NS(=O)(=O)N1CCN(c2ccc(OC(F)(F)F)cc2)C(=O)C1] | 490.1 | |
| 318 | 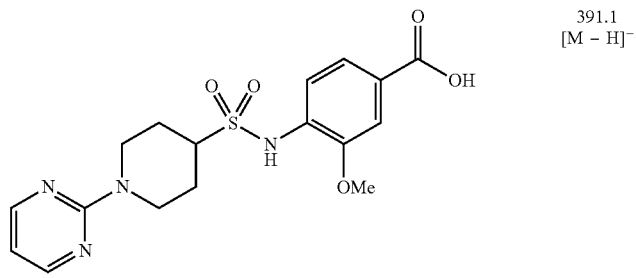 | 391.1 [M − H]− | |
| 319 | 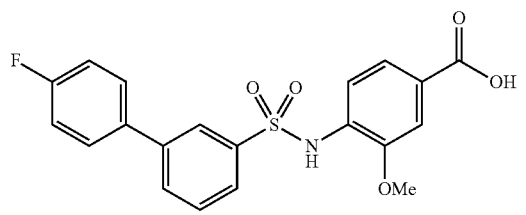 | 400.1 [M − H]− | |
| 320 | 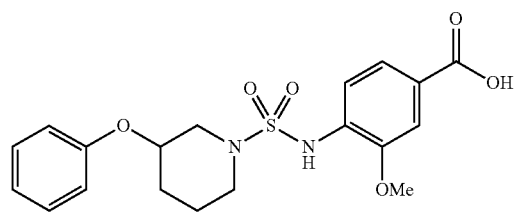 [SMILES: COc1cc(C(=O)O)ccc1NS(=O)(=O)N1CCCC(Oc2ccccc2)C1] | 405.1 [M − H]− | 1H NMR (400 MHz, Chloroform-d) δ 7.98 (d, J = 1.7 Hz, 1H), 7.45 (d, J = 1.8 Hz, 1H), 7.27-7.12 (m, 2H), 6.94-6.85 (m, 2H), 6.85-6.77 (m, 2H), 4.28 (tt, J = 8.1, 3.8 Hz, 1H), 3.88 (s, 3H), 3.72 (dd, J = 11.9, 3.8 Hz, 1H), 3.44 (dd, J = 11.3, 5.4 Hz, 1H), 2.86-2.70 (m, 2H), 1.97 (d, J = 3.5 Hz, 1H), 1.89-1.74 (m, 1H), 1.69-1.45 (m, 2H). |
| 321 | 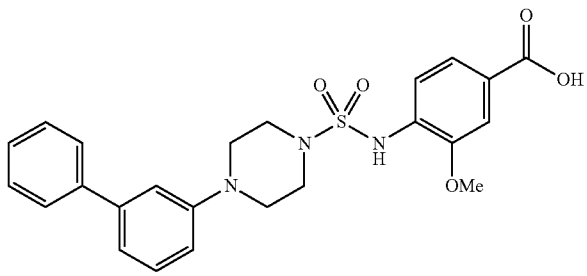 [SMILES: COc1cc(C(=O)O)ccc1NS(=O)(=O)N1CCN(c2cccc(-c3ccccc3)c2)CC1] | 468.2 | |

-continued

| Example # | Structure | LC-MS [M + H]+ unless otherwise noted | ¹H-NMR |
|---|---|---|---|
| 322 | 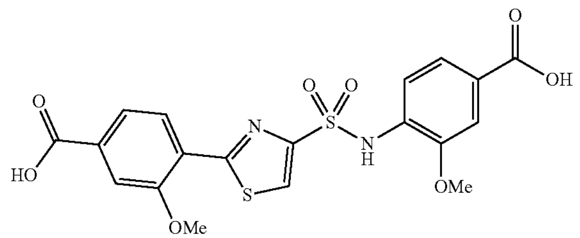 [SMILES: COc1cc(C(=O)O)ccc1NS(=O)(=O)c1csc(-c2ccc(C(=O)O)cc2OC)n1] | 463.0 [M − H]⁻ | |
| 323 | 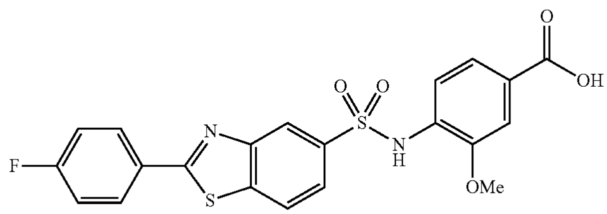 [SMILES: COc1cc(C(=O)O)ccc1NS(=O)(=O)c1ccc2sc(-c3ccc(F)cc3)nc2c1] | 457.0 [M − H]⁻ | |
| 324 | 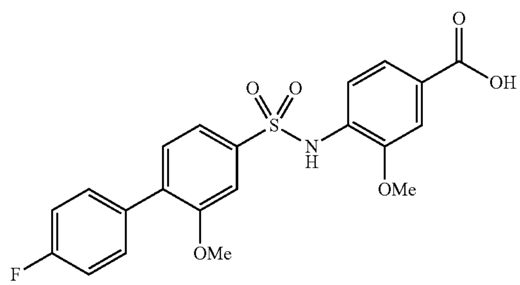 [SMILES: COc1cc(C(=O)O)ccc1NS(=O)(=O)c1ccc(-c2ccc(F)cc2)c(OC)c1] | 430.1 [M − H]⁻ | |
| 325 | 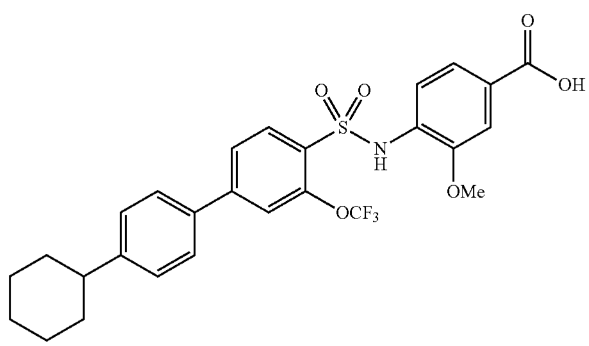 [SMILES: COc1cc(C(=O)O)ccc1NS(=O)(=O)c1ccc(-c2ccc(C3CCCCC3)cc2)cc1OC(F)(F)F] | 548.1 [M − H]⁻ | |
| 326 | 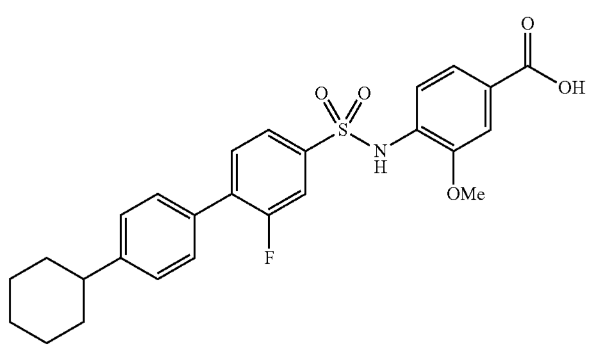 [SMILES: COc1cc(C(=O)O)ccc1NS(=O)(=O)c1ccc(-c2ccc(C3CCCCC3)cc2)c(F)c1] | 582.2 [M − H]⁻ | ¹H NMR (400 MHz, Methanol-d₄) δ 7.63-7.58 (m, 3H), 7.57-7.50 (m, 2H), 7.48 (d, J = 1.7 Hz, 1H), 7.45-7.41 (m, 2H), 7.30-7.24 (m, 2H), 3.73 (s, 3H), 2.59-2.46 (m, 1H), 1.86 (s, 5H), 1.74 (t, J = 12.0 Hz, 1H), 1.51-1.17 (m, 5H). |

| Example # | Structure | LC-MS [M + H]+ unless otherwise noted | 1H-NMR |
|---|---|---|---|
| 327 | 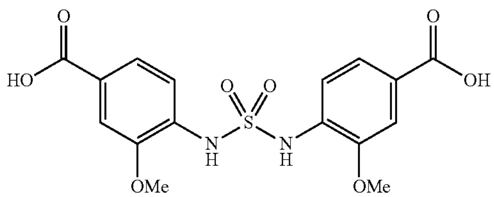 [SMILES: COc1cc(C(=O)O)ccc1NS(=O)(=O)Nc1ccc(C(=O)O)cc1OC] | 395.1 [M − H]− | |
| 328 | 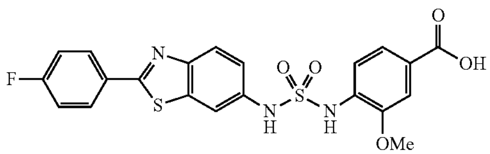 [SMILES: COc1cc(C(=O)O)ccc1NS(=O)(=O)Nc1ccc2nc(-c3ccc(F)cc3)sc2c1] | 474.1 | |
| 329 | 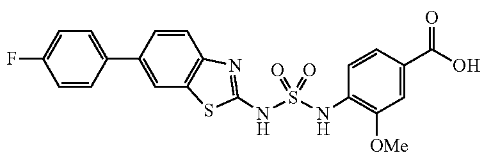 [SMILES: COc1cc(C(=O)O)ccc1NS(=O)(=O)Nc1nc2ccc(-c3ccc(F)cc3)cc2s1] | 472.0 [M − H]− | |
| 330 | 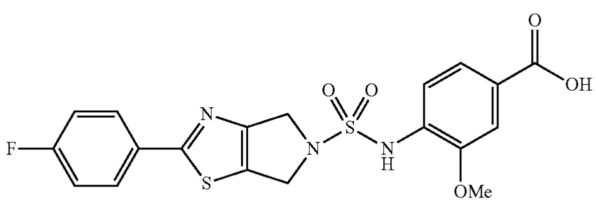 [SMILES: COc1cc(C(=O)O)ccc1NS(=O)(=O)N1Cc2nc(-c3ccc(F)cc3)sc2C1] | 440.2 [M − H]− | |
| 331 | 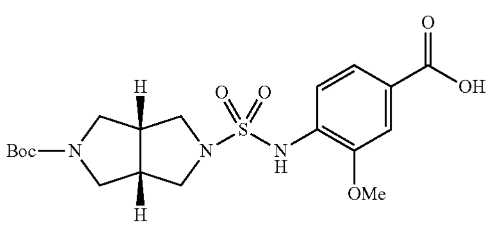 [SMILES: COc1cc(C(=O)O)ccc1NS(=O)(=O)N1C[C@H]2CN(C(=O)OC(C)(C)C)C[C@H]2C1] | 440.2 [M − H]− | 1H NMR (500 MHz, Chloroform-d) δ 7.73 (dd, J = 8.4. 1.8 Hz, 1H), 7.58 (d, J = 1.8 Hz, 1H), 7.53 (d, J = 8.4 Hz, 1H), 7.27 (s, 1H), 3.95 (s, 3H), 3.55 (ddd, J = 17.5, 10.4, 6.7 Hz, 4H), 3.26-3.04 (m, 4H), 2.86 (ddt, J = 10.2, 7.9, 3.8 Hz, 2H), 1.42 (s, 9H). |
| 332 | 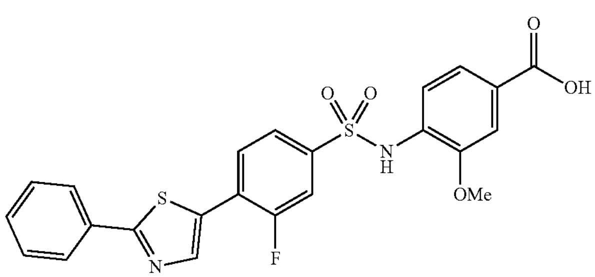 [SMILES: COc1cc(C(=O)O)ccc1NS(=O)(=O)c1ccc(-c2cnc(-c3ccccc3)s2)c(F)c1] | 483.0 [M − H]− | 1H NMR (500 MHz, Methanol-$d_4$) δ 8.33 (d, J = 1.0 Hz, 1H), 8.05-7.97 (m, 2H), 7.92 (dd, J = 8.2, 7.2 Hz, 1H), 7.70 (dd, J = 10.6, 1.8 Hz, 1H), 7.68-7.54 (m, 3H), 7.50 (ddd, J = 7.7, 3.8, 1.8 Hz, 4H), 3.71 (s, 3H). |
| 333 | 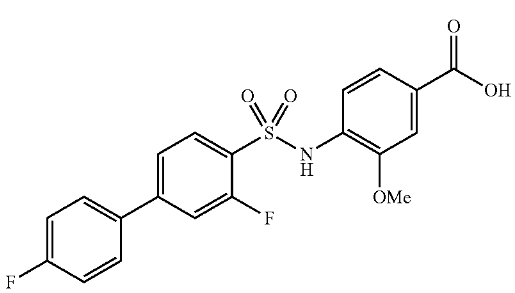 [SMILES: COc1cc(C(=O)O)ccc1NS(=O)(=O)c1ccc(-c2ccc(F)cc2)cc1F] | 418.1 [M − H]− | 1H NMR (400 MHz, Chloroform-d) δ 7.93 (t, J = 7.9 Hz, 1H), 7.74-7.55 (m, 2H), 7.55-7.38 (m, 3H), 7.36 (dd, J = 8.3, 1.7 Hz, 1H), 7.27 (dd, J = 11.3, 1.7 Hz, 1H), 7.11 (t, J = 8.6 Hz, 2H), 3.87 (d, J = 1.9 Hz, 3H). |

| Example # | Structure | LC-MS [M + H]+ unless otherwise noted | 1H-NMR |
|---|---|---|---|
| 334 | 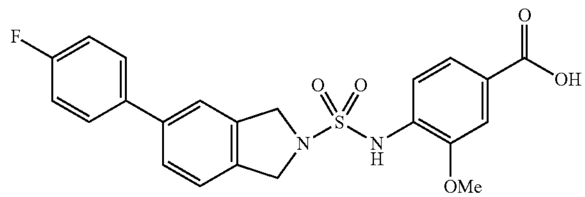 [SMILES: COc1cc(C(=O)O)ccc1NS(=O)(=O)N1Cc2ccc(-c3ccc(F)cc3)cc2C1] | 441.1 [M − H]− | 1H NMR (400 MHz, Chloroform-d) δ 7.65 (dd, J = 8.4, 1.7 Hz, 1H), 7.54 (d, J = 8.4 Hz, 1H), 7.45 (d, J = 1.7 Hz, 1H), 7.43-7.34 (m, 3H), 7.26 (d, J = 2.0 Hz, 2H), 7.04 (t, J = 8.7 Hz, 1H), 4.68 (q, J = 2.6 Hz, 4H), 3.84 (d, J = 2.4 Hz, 3H). |
| 335 | 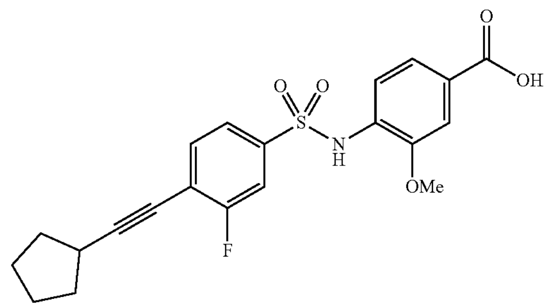 [SMILES: COc1cc(C(=O)O)ccc1NS(=O)(=O)c1ccc(C#CC2CCCC2)c(F)c1] | 416.1 [M − H]− | 1H NMR (500 MHz, Chloroform-d) δ 7.65 (dd, J = 8.5, 1.7 Hz, 1H), 7.56-7.51 (m, 1H), 7.50-7.44 (m, 2H), 7.38 (dd, J = 8.3, 6.6 Hz, 1H), 7.30 (s, 1H), 3.80 (s, 3H), 2.82 (p, J = 7.5 Hz, 1H), 2.00-1.90 (m, 2H), 1.81-1.61 (m, 2H), 1.62-1.48 (m, 2H). |
| 336 | 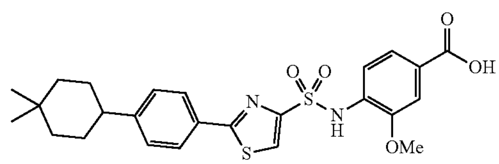 [SMILES: COc1cc(C(=O)O)ccc1NS(=O)(=O)c1csc(-c2ccc(C3CCC(C)(C)CC3)cc2)n1] | 501.3 | 1H NMR (400 MHz, DMSO-d6) δ 12.92 (br, 1H), 8.34 (br, 1H), 7.89-7.79 (m, 2H), 7.58-7.48 (m, 2H), 7.47-7.37 (m, 3H), 3.67 (s, 3H), 2.49-2.44 (m, 1H), 2.46 (d, J = 8.2 Hz, 1H), 1.68-1.56 (m, 4H), 1.51-1.42 (m, 2H), 1.40-1.26 (m, 2H), 0.98 (s, 3H), 0.94 (s, 3H). |
| 337 | 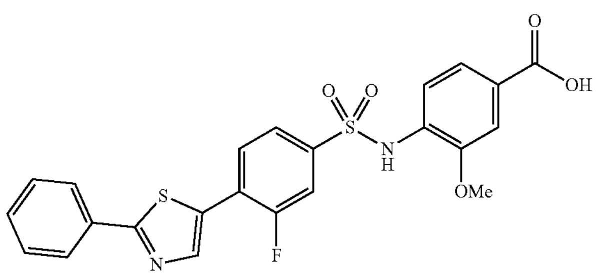 [SMILES: COc1cc(C(=O)O)ccc1NS(=O)(=O)c1ccc(-c2cnc(-c3ccccc3)s2)c(F)c1] | 483.1 [M − H]− | 1H NMR (500 MHz, Methanol-d4) δ 8.24 (d, J = 1.0 Hz, 1H), 7.96-7.88 (m, 2H), 7.83 (dd, J = 8.2, 7.2 Hz, 1H), 7.62 (dd, J = 10.6, 1.8 Hz, 1H), 7.55 (dd, J = 8.3, 1.8 Hz, 1H), 7.51 (dd, J = 8.3, 1.7 Hz, 1H), 7.47 (d, J = 8.3 Hz, 1H), 7.41 (ddd, J = 7.7, 3.8, 1.8 Hz, 4H), 3.62 (s, 3H). |
| 338 | 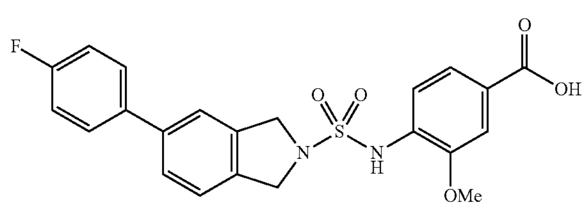 [SMILES: COc1cc(C(=O)O)ccc1NS(=O)(=O)N1Cc2ccc(-c3ccc(F)cc3)cc2C1] | 441.1 [M − H]− | 1H NMR (400 MHz, Chloroform-d) δ 7.70 (dd, J = 8.4, 1.7 Hz, 1H), 7.59 (d, J = 8.4 Hz, 1H), 7.50 (d, J = 1.7 Hz, 1H), 7.48-7.42 (m, 2H), 7.41 (dd, J = 7.9, 1.7 Hz, 1H), 7.31 (s, 2H), 7.22 (d, J = 8.1 Hz, 1H), 7.09 (t, J = 8.7 Hz, 1H), 4.79-4.68 (m, 4H), 3.88 (s, 3H). |
| 339 | 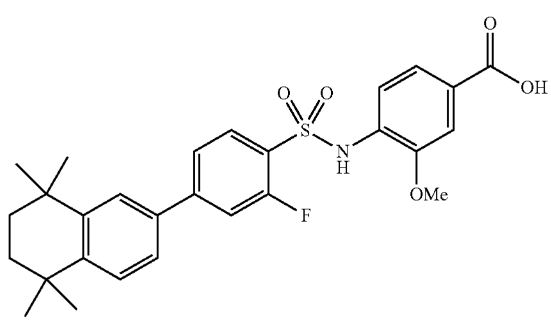 [SMILES: COc1cc(C(=O)O)ccc1NS(=O)(=O)c1ccc(-c2ccc3c(c2)C(C)(C)CCC3(C)C)cc1F] | 510.2 [M − H]− | 1H NMR (400 MHz, Chloroform-d) δ 7.93 (t, J = 7.9 Hz, 1H), 7.73 (s, 1H), 7.64 (dd, J = 8.4, 1.7 Hz, 1H), 7.54 (d, J = 8.4 Hz, 1H), 7.50 (d, J = 1.7 Hz, 1H), 7.43 (d, J = 2.1 Hz, 1H), 7.40 (dd, J = 8.2, 1.7 Hz, 1H), 7.37 (d, J = 8.2 Hz, 1H), 7.31 (dd, J = 11.5, 1.6 Hz, 1H), 7.27 (dd, J = 8.2, 2.1 Hz, 1H), 3.88 (s, 3H), 1.69 (s, 4H), 1.29 (s, 7H), 1.28 (s, 6H). |

-continued

| Example # | Structure | LC-MS [M + H]+ unless otherwise noted | 1H-NMR |
|---|---|---|---|
| 340 | 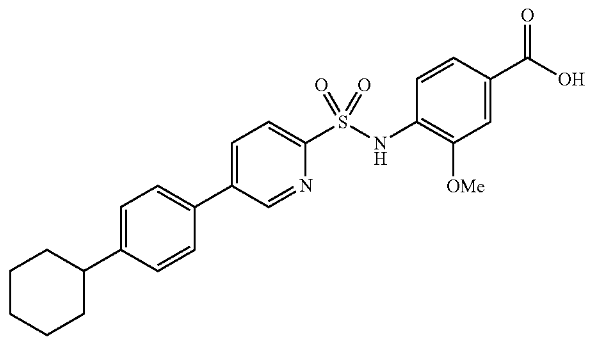 [SMILES: COc1cc(C(=O)O)ccc1NS(=O)(=O)c1ccc(-c2ccc(C3CCCCC3)cc2)cn1] | 465.2 [M − H]− | 1H NMR (400 MHz, Methanol-d4) δ 9.14 (dd, J = 2.3, 0.8 Hz, 1H), 8.44-8.22 (m, 2H), 7.96-7.87 (m, 2H), 7.85-7.80 (m, 2H), 7.80-7.75 (m, 1H), 7.70-7.54 (m, 2H), 4.11 (s, 3H), 3.64 (p, J = 1.7 Hz, 1H), 2.94-2.72 (m, 1H), 2.24-2.11 (m, 4H), 2.06 (d, J = 12.9 Hz, 1H), 1.82-1.64 (m, 4H). |
| 341 | 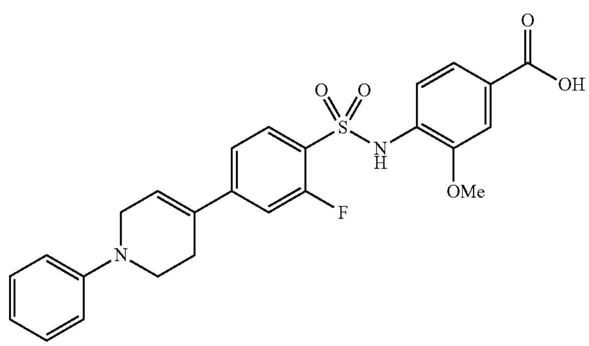 [SMILES: COc1cc(C(=O)O)ccc1NS(=O)(=O)c1ccc(C2=CCN(c3ccccc3)CC2)cc1F] | 481.2 [M − H]− | 1H NMR (500 MHz, Methanol-d4) δ 7.74 (t, J = 7.9 Hz, 1H), 7.54-7.47 (m, 1H), 7.41-7.40 (m, 1H), 7.25-7.17 (m, 3H), 7.13 (dd, J = 11.8, 1.7 Hz, 1H), 6.99-6.92 (m, 2H), 6.82 (t, J = 7.3 Hz, 1H), 6.28 (tt, J = 3.4, 1.4 Hz, 1H), 3.84 (q, J = 3.0 Hz, 2H), 3.78 (s, 3H), 3.43 (t, J = 5.6 Hz, 2H), 2.57 (d, J = 4.2 Hz, 2H). |
| 342 | 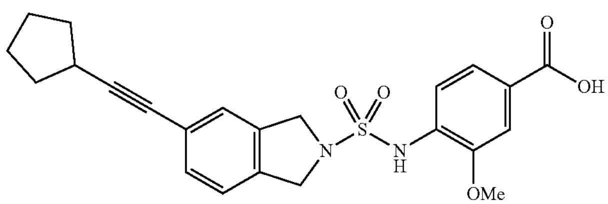 [SMILES: COc1cc(C(=O)O)ccc1NS(=O)(=O)N1Cc2ccc(C#CC3CCCC3)cc2C1] | 439.1 [M − H]− | |
| 343 | 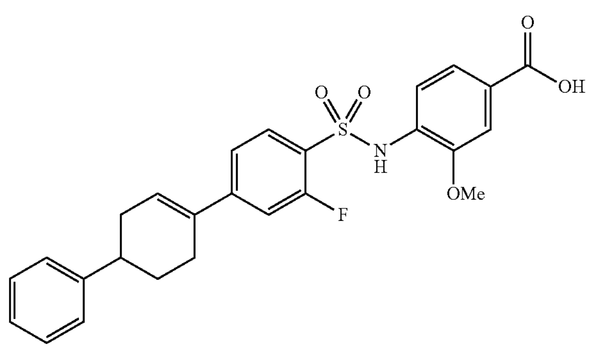 | 480.1 [M − H]− | 1H NMR (400 MHz, Chloroform-d) δ 7.78 (t, J = 8.0 Hz, 1H), 7.62 (s, 1H), 7.56 (dd, J = 8.4, 1.7 Hz, 1H), 7.24 (dd, J = 8.2, 6.9 Hz, 2H), 7.20-7.12 (m, 4H), 7.08 (dd, J = 12.1, 1.7 Hz, 1H), 6.28 (dt, J = 4.6, 2.4 Hz, 1H), 3.83 (s, 3H), 2.77 (tt, J = 11.1, 2.8 Hz, 1H), 2.55-2.34 (m, 3H), 2.34-2.17 (m, 1H), 2.08-1.99 (m, 1H), 1.90-1.67 (m, 1H). |
| 344 | 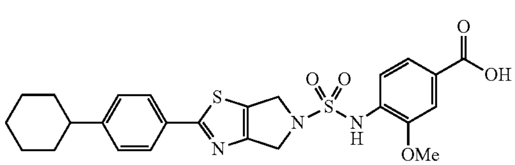 [SMILES: COc1cc(C(=O)O)ccc1NS(=O)(=O)N1Cc2nc(-c3ccc(C4CCCCC4)cc3)sc2C1] | 512.1 [M − H]− | |

| Example # | Structure | LC-MS [M + H]+ unless otherwise noted | 1H-NMR |
|---|---|---|---|
| 345 | 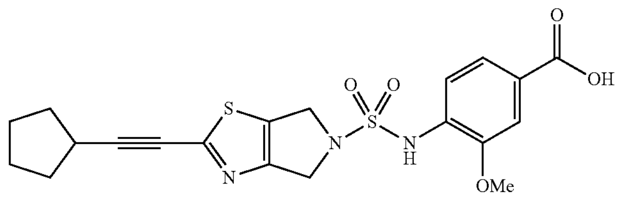 [SMILES: COc1cc(C(=O)O)ccc1NS(=O)(=O)N1Cc2nc(C#CC3CCCC3)sc2C1] | 446.1 [M − H]− | |
| 346 | 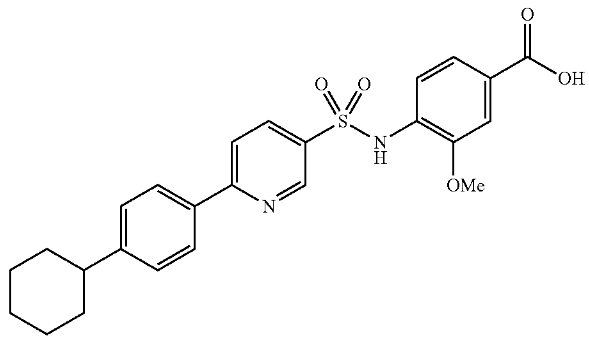 [SMILES: COc1cc(C(=O)O)ccc1NS(=O)(=O)c1ccc(-c2ccc(C3CCCCC3)cc2)nc1] | 465.2 [M − H]− | |
| 347 | 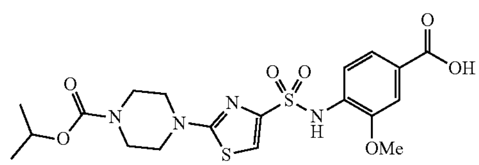 [SMILES: COc1cc(C(=O)O)ccc1NS(=O)(=O)c1csc(N2CCN(C(=O)OC(C)C)CC2)n1] | 485.4 | 1H NMR (400 MHz, Methanol-d4) δ 7.58-7.52 (m, 3H), 7.46 (s, 1H), 3.85 (s, 3H), 3.60-3.51 (m, 4H), 3.48-3.41 (m, 4H), 1.26 (d, J = 6.2 Hz, 6H). |
| 348 | 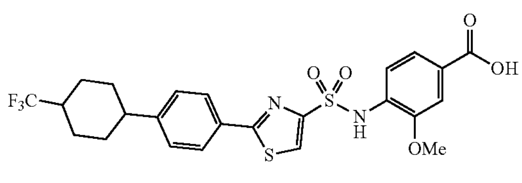 [SMILES: COc1cc(C(=O)O)ccc1NS(=O)(=O)c1csc(-c2ccc(C3CCC(C(F)(F)F)CC3)cc2)n1] | 541.4 | 1H NMR (400 MHz, DMSO-d6) δ 10.05 (s, 1H), 8.34 (s, 1H), 7.89-7.81 (m, 2H), 7.55-7.47 (m, 2H), 7.47-7.36 (m, 3H), 3.67 (s, 4H), 2.89-2.28 (m, 2H), 2.03-1.68 (m, 5H), 1.63-1.35 (m, 3H). |
| 349 | 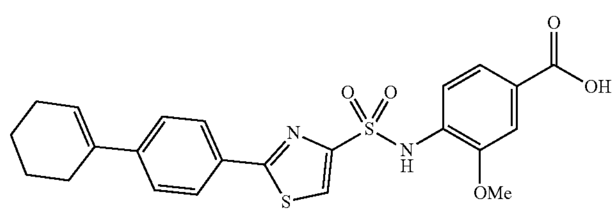 [SMILES: COc1cc(C(=O)O)ccc1NS(=O)(=O)c1csc(-c2ccc(C3=CCCCC3)cc2)n1] | 471.4 | 1H NMR (400 MHz, DMSO-d6) δ 10.10 (br, 1H), 8.34 (s, 1H), 7.93-7.81 (m, 2H), 7.65-7.48 (m, 4H), 7.46-7.38 (m, 1H), 6.36-6.30 (m, 1H), 3.66 (s, 3H), 2.44-2.34 (m, 2H), 2.26-2.16 (m, 2H), 1.79-1.68 (m, 2H), 1.66-1.56 (m, 2H). |
| 350 | 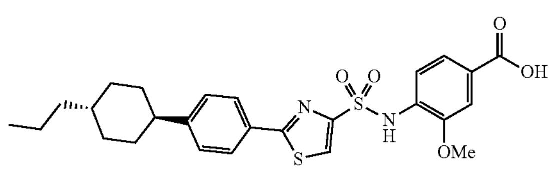 [SMILES: CCC[C@H]1CC[C@H](c2ccc(-c3nc(S(=O)(=O)Nc4ccc(C(=O)O)cc4OC)cs3)cc2)CC1] | 515.5 | 1H NMR (400 MHz, DMSO-d6) δ 10.03 (br, 1H), 8.33 (s, 1H), 7.87-7.77 (m, 2H), 7.55-7.48 (m, 2H), 7.45-7.36 (m, 3H), 3.67 (s, 3H), 2.60-2.50 (m, 1H), 1.89-1.76 (m, 4H), 1.55-1.14 (m, 7H), 1.12-0.96 (m, 2H), 0.88 (t, J = 7.2 Hz, 3H). |
| 351 | 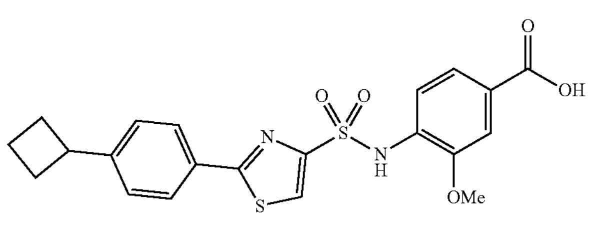 [SMILES: COc1cc(C(=O)O)ccc1NS(=O)(=O)c1csc(-c2ccc(C3CCC3)cc2)n1] | 445.3 | 1H NMR (400 MHz, DMSO-d6) δ 10.06 (br, 1H), 8.32 (s, 1H), 7.92-7.79 (m, 2H), 7.55-7.47 (m, 2H), 7.48-7.32 (m, 3H), 3.66 (s, 3H), 3.64-3.51 (m, 1H), 2.38-2.26 (m, 2H), 2.19-1.95 (m, 3H), 1.88-1.77 (m, 1H). |

-continued

| Example # | Structure | LC-MS [M + H]+ unless otherwise noted | 1H-NMR |
|---|---|---|---|
| 352 | 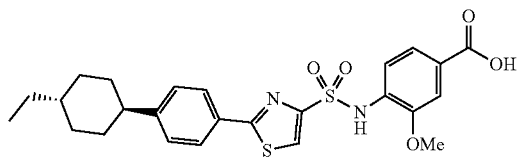 [SMILES: CC[C@H]1CC[C@H](c2ccc(-c3nc(S(=O)(=O)Nc4ccc(C(=O)O)cc4OC)cs3)cc2)CC1] | 501.5 | 1H NMR (400 MHz, DMSO-d6) δ 8.29 (s, 1H), 7.86-7.79 (m, 2H), 7.54-7.46 (m, 2H), 7.43-7.36 (m, 3H), 3.66 (s, 3H), 2.60-2.52 (m, 1H), 1.90-1.78 (m, 4H), 1.54-1.39 (m, 2H), 1.30-1.15 (m, 3H), 1.11-0.99 (m, 2H), 0.89 (t, J = 7.2 Hz, 3H). |
| 353 | 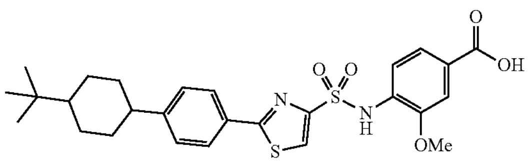 [SMILES: COc1cc(C(=O)O)ccc1NS(=O)(=O)c1csc(-c2ccc(C3CCC(C(C)(C)C)CC3)cc2)n1] | 529.5 | 1H NMR (400 MHz, Chloroform-d) δ 8.02 (s, 1H, one diastereomer), 8.01 (s, 1H, other diastereomer), 7.84-7.76 (m, 2H), 7.75-7.39 (m, 4H), 7.30-7.22 (m, 1H), 3.87 (s, 3H, one diastereomer), 3.86 (s, 3H, other diastereomer), 3.10-3.02 (m, 1H, one diastereomer), 2.56-2.42 (m, 1H, other diastereomer), 2.32-1.38 (m, 6H), 1.33-1.02 (m, 3H), 0.88 (s, 9H, one diastereomer), 0.78 (s, 9H, other diastereomer). |
| 354 | 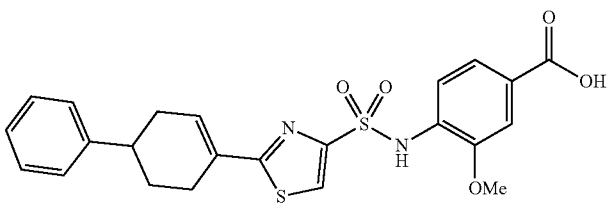 [SMILES: COc1cc(C(=O)O)ccc1NS(=O)(=O)c1csc(C2=CCC(c3ccccc3)CC2)n1] | 471.4 | 1H NMR (400 MHz, DMSO-d6) δ 9.92 (br, 1H), 8.22 (s, 1H), 7.55-7.38 (m, 3H), 7.38-7.18 (m, 5H), 6.83-6.76 (m, 1H), 3.71 (s, 3H), 2.92-2.80 (m, 1H), 2.70-2.51 (m, 3H), 2.42-2.28 (m, 1H), 2.04-1.94 (m, 1H), 1.90-1.76 (m, 1H). |
| 355 | 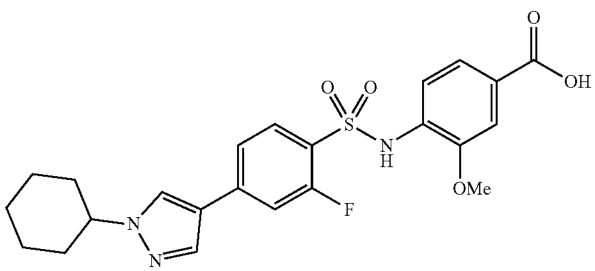 [SMILES: COc1cc(C(=O)O)ccc1NS(=O)(=O)c1ccc(-c2cnn(C3CCCCC3)c2)cc1F] | 472.1 [M − H]− | 1H NMR (400 MHz, Chloroform-d) δ 7.82 (t, J = 7.9 Hz, 1H), 7.74 (s, 1H), 7.68 (s, 1H), 7.66 (s, 1H), 7.59 (dt, J = 8.3, 2.1 Hz, 1H), 7.51-7.42 (m, 2H), 7.29-7.22 (m, 1H), 7.16 (dd, J = 11.4, 1.6 Hz, 1H), 4.22-4.03 (m, 1H), 3.86 (s, 3H), 2.19-2.17 (m, 2H), 1.93-1.82 (m, 2H), 1.77-1.60 (m, 3H), 1.45-1.32 (m, 2H), 1.26-1.19 (m, 1H). |
| 356 | 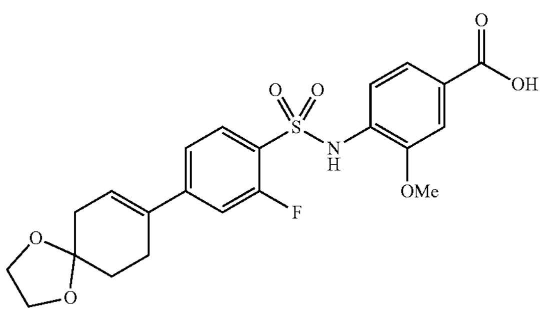 [SMILES: COc1cc(C(=O)O)ccc1NS(=O)(=O)c1ccc(C2=CCC3(CC2)OCCO3)cc1F] | 462.1 [M − H]− | 1H NMR (500 MHz, Chloroform-d) δ 7.79 (t, J = 8.0 Hz, 1H), 7.64 (s, 1H), 7.59 (dd, J = 8.4, 1.7 Hz, 1H), 7.46 (dd, J = 5.1, 3.3 Hz, 2H), 7.20 (dd, J = 8.3, 1.7 Hz, 1H), 7.11 (dd, J = 11.9, 1.7 Hz, 1H), 6.10 (tt, J = 4.1, 1.6 Hz, 1H), 3.98 (s, 4H), 3.86 (s, 3H), 2.55 (ddt, J = 6.8, 4.7, 2.1 Hz, 2H), 2.44 (dt, J = 4.6, 2.4 Hz, 2H), 1.86 (t, J = 6.5 Hz, 2H). |
| 357 | 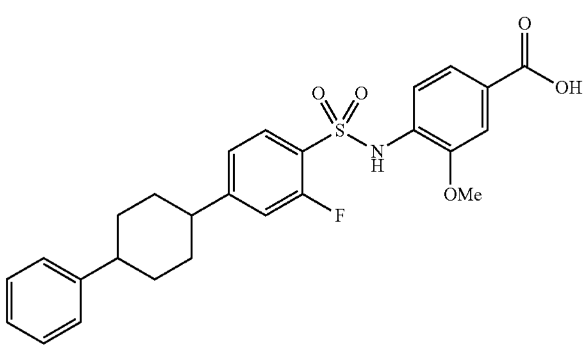 [SMILES: COc1cc(C(=O)O)ccc1NS(=O)(=O)c1ccc(C2CCC(c3ccccc3)CC2)cc1F] | 482.2 [M − H]− | 1H NMR (500 MHz, Chloroform-d) δ 7.82 (dt, J = 9.8, 7.8 Hz, 1H), 7.65 (s, 0.5H), 7.64 (s, 0.5H), 7.62 (dd, J = 4.7, 1.8 Hz, 0.5H), 7.60 (dd, J = 4.8, 1.8 Hz, 0.5 H), 7.51-7.44 (m, 2H), 7.31-7.25 (m, 2H), 7.22-7.14 (m, 3H), 7.13-7.18 (m, 1H), 7.03 (dd, J = 6.2, 1.6 Hz, 0.5H), 7.01 (dd, J = 5.9, 1.6 Hz, 0.5H), 3.88 (s, 1.5H), 3.87 (s, 1.5H), 2.87 (s, 1H), 2.65-2.39 (m, 1H), 2.06-1.70 (m, 5H), 1.65-1.39 (m, 2.5H), 1.27-1.21 (m, 0.5H). |

| Example # | Structure | LC-MS [M + H]+ unless otherwise noted | 1H-NMR |
|---|---|---|---|
| 358 | 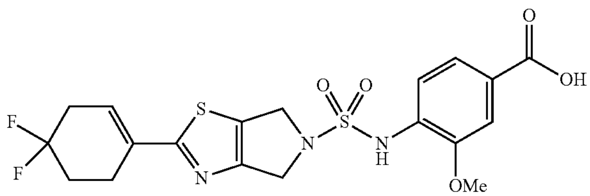 [SMILES: COc1cc(C(=O)O)ccc1NS(=O)(=O)N1Cc2nc(C3=CCC(F)(F)CC3)sc2C1] | 450.1 [M − HF − H]− | |
| 359 | 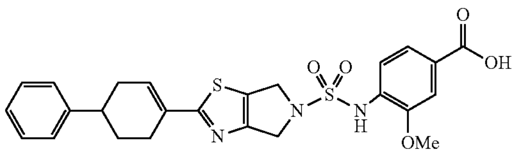 [SMILES: COc1cc(C(=O)O)ccc1NS(=O)(=O)N1Cc2nc(C3=CCC(c4ccccc4)CC3)sc2C1] | 510.1 [M − H]− | |
| 360 | 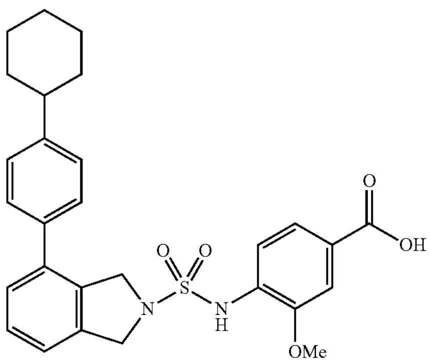 [SMILES: COc1cc(C(=O)O)ccc1NS(=O)(=O)N1Cc2cccc(-c3ccc(C4CCCCC4)cc3)c2C1] | 505.2 [M − H]− | |
| 361 | 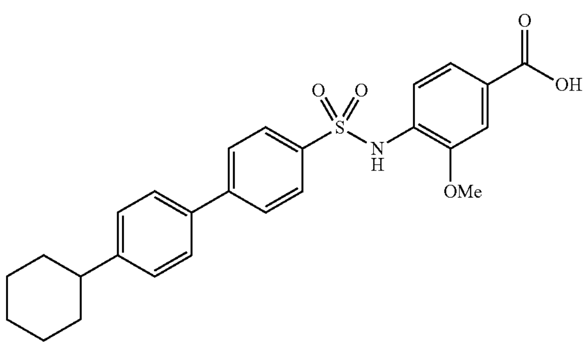 [SMILES: COc1cc(C(=O)O)ccc1NS(=O)(=O)c1ccc(-c2ccc(C3CCCCC3)cc2)cc1] | 464.2 [M − H]− | |
| 362 | 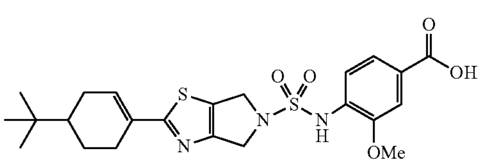 [SMILES: COc1cc(C(=O)O)ccc1NS(=O)(=O)N1Cc2nc(C3=CCC(C(C)(C)C)CC3)sc2C1] | 492.2 | |
| 363 | 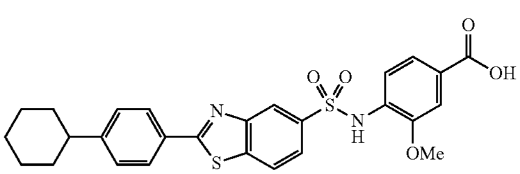 [SMILES: COc1cc(C(=O)O)ccc1NS(=O)(=O)c1ccc2sc(-c3ccc(C4CCCCC4)cc3)nc2c1] | 421.1 [M − H]− | |

-continued

| Example # | Structure | LC-MS [M + H]+ unless otherwise noted | 1H-NMR |
|---|---|---|---|
| 364 | 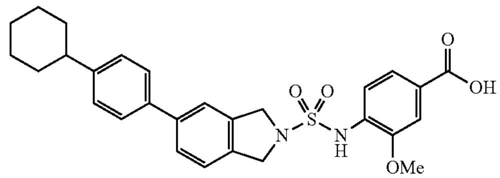 [SMILES: COc1cc(C(=O)O)ccc1NS(=O)(=O)N1Cc2ccc(-c3ccc(C4CCCCC4)cc3)cc2C1] | 505.2 [M − H]− | |
| 365 | 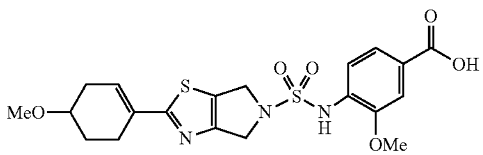 | 466.1 | |
| 366 | 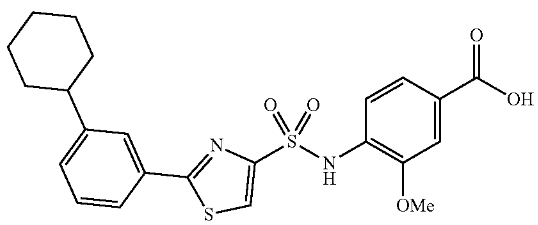 [SMILES: COc1cc(C(=O)O)ccc1NS(=O)(=O)c1csc(-c2cccc(C3CCCCC3)c2)n1] | 473.4 | 1H NMR (400 MHz, DMSO-d6) δ 10.02 (br, 1H), 8.35 (s, 1H), 7.73-7.67 (m, 2H), 7.55-7.50 (m, 2H), 7.47-7.37 (m, 3H), 3.65 (s, 3H), 2.62-2.52 (m, 1H), 1.88-1.66 (m, 5H), 1.48-1.17 (m, 5H). |
| 367 | 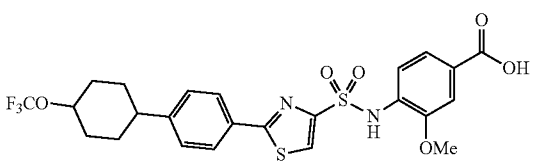 [SMILES: COc1cc(C(=O)O)ccc1NS(=O)(=O)c1csc(-c2ccc(C3CCC(OC(F)(F)F)CC3)cc2)n1] | 557.3 | 1H NMR (400 MHz, DMSO-d6) δ 10.02 (br, 1H), 8.31 (s, 1H), 7.88-7.81 (m, 2H), 7.53-7.45 (m, 2H), 7.44-7.37 (m, 3H), 4.77-4.72 (m, 1H, one diastereomer), 4.51-4.40 (m, 1H, other diastereomer), 3.66 (s, 3H), 2.78-2.59 (m, 1H), 2.18-1.92 (m, 2H), 1.89-1.57 (m, 6H). |
| 368 | 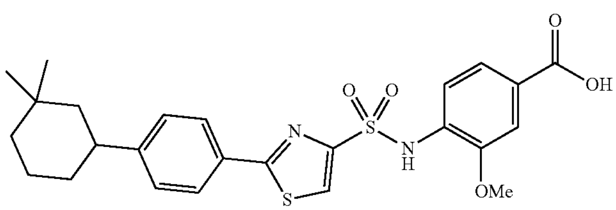 [SMILES: COc1cc(C(=O)O)ccc1NS(=O)(=O)c1csc(-c2ccc(C3CCCC(C)(C)C3)cc2)n1] | 501.4 | 1H NMR (400 MHz, DMSO-d6) δ 9.96 (br, 1H), 8.32 (s, 1H), 7.82 (d, J = 8.2 Hz, 2H), 7.54-7.46 (m, 2H), 7.44-7.33 (m, 3H), 3.66 (s, 3H), 2.77 (tt, J = 12.4, 3.5 Hz, 1H), 1.83-1.73 (m, 1H), 1.68-1.12 (m, 7H), 0.99 (s, 3H), 0.93 (s, 3H). |
| 369 | 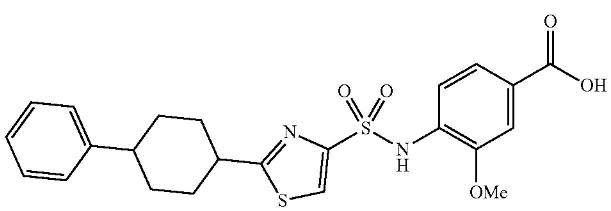 [SMILES: COc1cc(C(=O)O)ccc1NS(=O)(=O)c1csc(C2CCC(c3ccccc3)CC2)n1] | 473.4 | 1H NMR (400 MHz, Methanol-d4) δ 8.24 (s, 1H, diastereomer-1), 8.10 (s, 1H, diastereomer-2), 7.65-7.44 (m, 3H), 7.30-7.19 (m, 3H), 7.19-7.09 (m, 1H), 6.99-6.93 (m, 1H), 3.82 (s, 3H, diastereomer-2), 3.69 (s, 3H, diastereomer-1), 3.40-3.35 (m, 1H, diastereomer-1), 3.11-3.03 (m, 1H, diastereomer-2), 2.65-2.52 (m, 1H), 2.36-2.17 (m, 1H), 2.03-1.92 (m, 2H), 1.75-1.44 (m, 4H). |
| 370 | 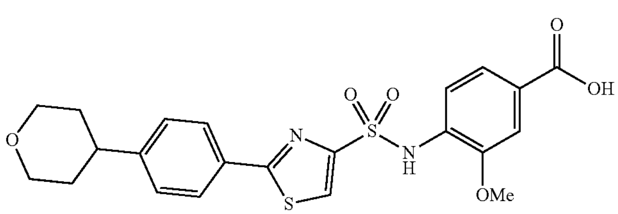 [SMILES: COc1cc(C(=O)O)ccc1NS(=O)(=O)c1csc(-c2ccc(C3CCOCC3)cc2)n1] | 475.4 | 1H NMR (400 MHz, DMSO-d6) δ 12.87 (br, 1H), 10.06 (br, 1H), 8.33 (s, 1H), 7.88-7.82 (m, 2H), 7.54-7.47 (m, 2H), 7.46-7.38 (m, 3H), 4.01-3.91 (m, 2H), 3.67 (s, 3H), 3.44 (td, J = 11.2, 3.4 Hz, 2H), 2.90-2.79 (m, 1H), 1.77-1.61 (m, 4H). |

-continued

| Example # | Structure | LC-MS [M + H]+ unless otherwise noted | 1H-NMR |
|---|---|---|---|
| 371 | 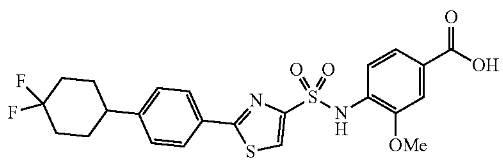 [SMILES: COc1cc(C(=O)O)ccc1NS(=O)(=O)c1csc(-c2ccc(C3CCC(F)(F)CC3)cc2)n1] | 509.3 | 1H NMR (400 MHz, DMSO-d6) δ 12.92 (br, 1H), 10.04 (br, 1H), 8.35 (s, 1H), 7.89-7.82 (m, 2H), 7.57-7.47 (m, 2H), 7.47-7.39 (m, 3H), 3.67 (s, 3H), 2.85-2.73 (m, 1H), 2.19-1.84 (m, 6H), 1.79-1.59 (m, 2H). |
| 372 | 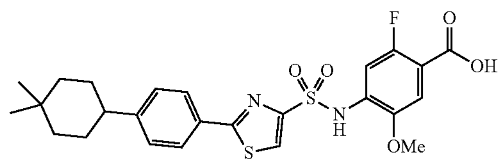 [SMILES: COc1cc(C(=O)O)c(F)cc1NS(=O)(=O)c1csc(-c2ccc(C3CCC(C)(C)CC3)cc2)n1] | 519.4 | 1H NMR (400 MHz, DMSO-d6) δ 13.18 (br, 1H), 10.37 (br, 1H), 8.46 (s, 1H), 7.88-7.75 (m, 2H), 7.48-7.36 (m, 3H), 7.30 (d, J = 6.6 Hz, 1H), 3.69 (s, 3H), 2.53-2.41 (m, 1H), 1.69-1.55 (m, 4H), 1.52-1.42 (m, 2H), 1.40-1.26 (m, 2H), 0.98 (s, 3H), 0.94 (s, 3H). |
| 373 | 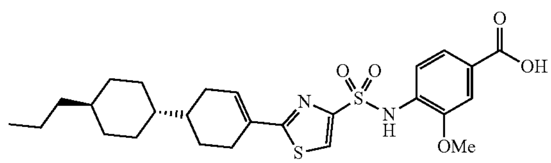 [SMILES: CCC[C@H]1CC[C@H](C2CC=C(c3nc(S(=O)(=O)Nc4ccc(C(=O)O)cc4OC)cs3)CC2)CC1] | 519.4 | 1H NMR (400 MHz, DMSO-d6) δ 12.91 (br, 1H), 9.91 (br, 1H), 8.20 (s, 1H), 7.54-7.39 (m, 3H), 6.72-6.66 (m, 1H), 3.70 (s, 3H), 2.64-2.50 (br, 1H), 2.37-2.21 (m, 2H), 2.05-1.65 (m, 6H), 1.44-0.77 (m, 15H). |
| 374 | 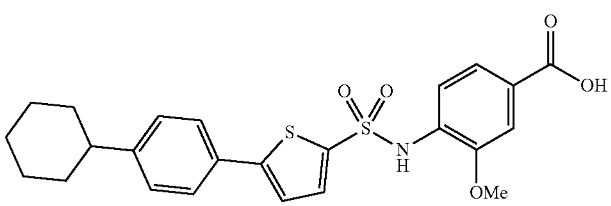 [SMILES: COc1cc(C(=O)O)ccc1NS(=O)(=O)c1ccc(-c2ccc(C3CCCCC3)cc2)s1] | 470.1 [M − H]− | 1H NMR (500 MHz, Methanol-d4) δ 7.65 (dd, J = 8.3, 1.7 Hz, 1H), 7.60 (d, J = 8.3 Hz, 1H), 7.49 (d, J = 1.7 Hz, 1H), 7.49-7.46 (m, 2H), 7.45-7.44 (m, 1H), 7.23 (d, J = 2.0 Hz, 1H), 7.22 (d, J = 1.9 Hz, 1H), 7.15 (d, J = 4.0 Hz, 1H), 3.78 (s, 3H), 2.61-2.42 (m, 1H), 1.91-1.78 (m, 4H), 1.75 (ddq, J = 13.0, 4.7, 2.6 Hz, 1H), 1.48-1.34 (m, 4H), 1.30-1.16 (m, 1H). |
| 375 | 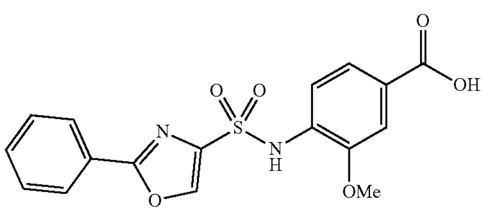 [SMILES: COc1cc(C(=O)O)ccc1NS(=O)(=O)c1coc(-c2ccccc2)n1] | | 1H NMR (400 MHz, DMSO-d6) δ 12.94 (b, 1H), 10.21 (b, 1H), 8.87 (s, 1H), 8.0 (t, J = 3.8 Hz, 1H), 7.62-7.45 (m, 4H), 3.70 (s, 3H). |
| 376 | 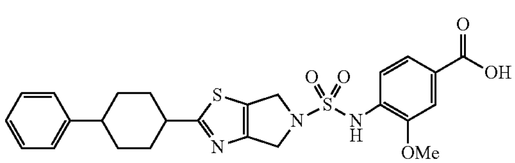 [SMILES: COc1cc(C(=O)O)ccc1NS(=O)(=O)N1Cc2nc(C3CCC(c4ccccc4)CC3)sc2C1] | 512.1 [M − H]− | |
| 377 | 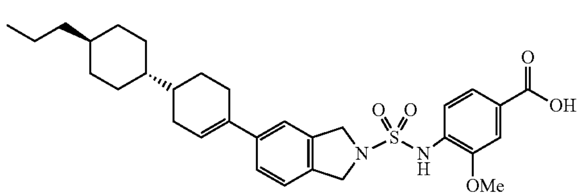 [SMILES: CCC[C@H]1CC[C@H](C2CC=C(c3ccc4c(c3)CN(S(=O)(=O)Nc3ccc(C(=O)O)cc3OC)C4)CC2)CC1] | 551.3 [M − H]− | 1H NMR (400 MHz, Chloroform-d) δ 7.68 (dd, J = 8.3, 1.8 Hz, 1H), 7.57 (d, J = 8.4 Hz, 1H), 7.49 (d, J = 2.0 Hz, 1H), 7.28-7.22 (m, 1H), 7.14 (d, J = 1.6 Hz, 1H), 7.08 (d, J = 8.0 Hz, 1H), 6.03 (d, J = 4.3 Hz, 1H), 4.66 (s, 4H), 3.87 (s, 3H), 2.44-2.13 (m, 3H), 1.96-1.68 (m, 6H), 1.38-1.22 (m, 3H), 1.19-1.05 (m, 5H), 1.02-0.75 (m, 7H). |
| 378 | 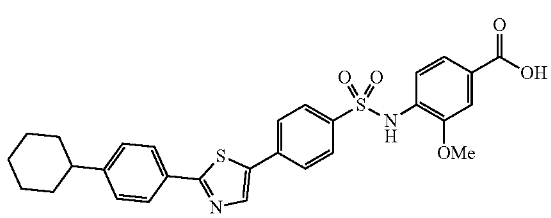 [SMILES: COc1cc(C(=O)O)ccc1NS(=O)(=O)c1ccc(-c2cnc(-c3ccc(C4CCCCC4)cc3)s2)cc1] | 547.1 [M − H]− | 1H NMR (500 MHz, Chloroform-d) δ 8.91 (s, 1H), 8.19 (s, 1H), 7.69 (d, J = 1.8 Hz, 1H), 7.64-7.56 (m, 2H), 7.55-7.51 (m, 2H), 7.49 (d, J = 1.8 Hz, 1H), 7.33-7.27 (m, 2H), 7.15 (d, J = 8.2 Hz, 2H), 6.51 (s, 1H), 3.64 (s, 3H), 2.50-2.37 (m, 1H), 1.92-1.77 (m, 2H), 1.72 (d, J = 13.1 Hz, 1H), 1.46-1.28 (m, 5H). |

-continued

| Example # | Structure | LC-MS [M + H]+ unless otherwise noted | 1H-NMR |
|---|---|---|---|
| 379 | 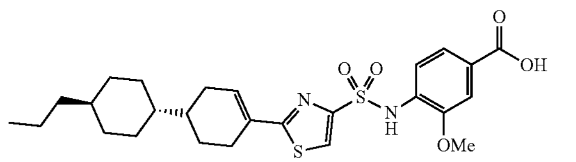 [SMILES: CCC[C@H]1CC[C@H](C2CC=C(c3nc(S(=O)(=O)Nc4ccc(C(=O)O)cc4OC)cs3)CC2)CC1] | 519.4 | 1H NMR (400 MHz, DMSO-d6) δ 12.91 (br, 1H), 9.91 (br, 1H), 8.20 (s, 1H), 7.54-7.39 (m, 3H), 6.72-6.66 (m, 1H), 3.70 (s, 3H), 2.64-2.50 (br, 1H), 2.37-2.21 (m, 2H), 2.05-1.65 (m, 6H), 1.44-0.77 (m, 15H). |
| 380 | 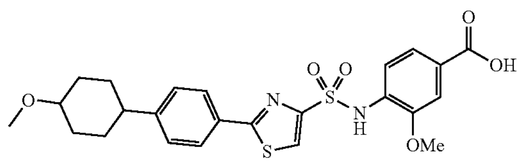 [SMILES: COc1cc(C(=O)O)ccc1NS(=O)(=O)c1csc(-c2ccc(C3CCC(OC)CC3)cc2)n1] | 503.4 | 1H NMR (500 MHz, Methanol-d4) δ 8.15 (s, 1H), 7.86-7.78 (m, 2H), 7.65-7.57 (m, 2H), 7.50 (d, J = 1.7 Hz, 1H), 7.37-7.30 (m, 2H), 3.74 (s, 3H), 3.58-3.54 (m, 1H), 3.36 (s, 3H), 2.70-2.58 (m, 1H), 2.12-2.04 (m, 2H), 1.86-1.73 (m, 2H), 1.66-1.55 (m, 4H). |
| 381 | 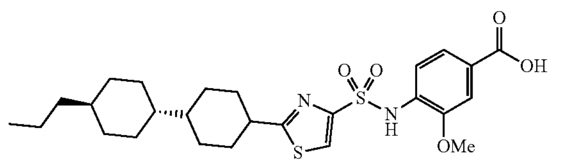 | 521.5 | 1H NMR (400 MHz, DMSO-d6) δ 9.80 (br, 1H), 8.28 (s, 1H), 7.51-7.36 (m, 3H), 3.74 (s, 3H), 3.30-3.22 (m, 1H), 2.06-1.93 (m, 2H), 1.82-1.02 (m, 16H), 1.00-0.67 (m, 8H). |
| 382 | 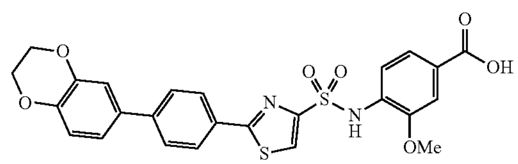 [SMILES: COc1cc(C(=O)O)ccc1NS(=O)(=O)c1csc(-c2ccc(-c3ccc4c(c3)OCCO4)cc2)n1] | 523.1 [M − H]− | |
| 383 | 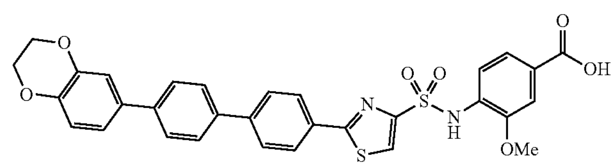 [SMILES: COc1cc(C(=O)O)ccc1NS(=O)(=O)c1csc(-c2ccc(-c3ccc(-c4ccc5c(c4)OCCO5)cc3)cc2)n1] | 599.1 [M − H]− | |
| 384 | 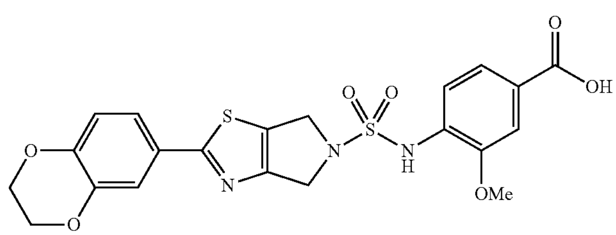 [SMILES: COc1cc(C(=O)O)ccc1NS(=O)(=O)N1Cc2nc(-c3ccc4c(c3)OCCO4)sc2C1] | 488.1 [M − H]− | |
| 385 | 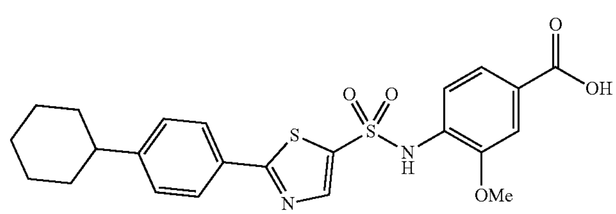 [SMILES: COc1cc(C(=O)O)ccc1NS(=O)(=O)c1cnc(-c2ccc(C3CCCCC3)cc2)s1] | 471.1 [M − H]− | |
| 386 | 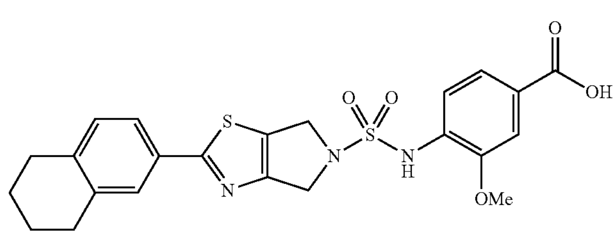 [SMILES: COc1cc(C(=O)O)ccc1NS(=O)(=O)N1Cc2nc(-c3ccc4c(c3)CCCC4)sc2C1] | 484.1 [M − H]− | |

| Example # | Structure | LC-MS [M + H]+ unless otherwise noted | 1H-NMR |
|---|---|---|---|
| 387 | 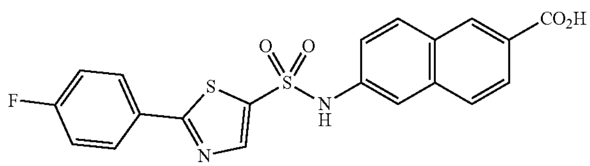 [SMILES: O=C(O)c1ccc2cc(NS(=O)(=O)c3cnc(-c4ccc(F)cc4)s3)ccc2c1] | 429.0 | 1H NMR (400 MHz, DMSO-d6) δ 13.01 (s, 1H), 11.23 (s, 1H), 8.52 (s, 1H), 8.42 (s, 1H), 8.07 (d, J = 8.8 Hz, 1H), 8.02-7.90 (m, 4H), 7.78 (d, J = 2.2 Hz, 1H), 7.48-7.40 (m, 1H), 7.33 (t, J = 8.6 Hz, 2H). |
| 388 | 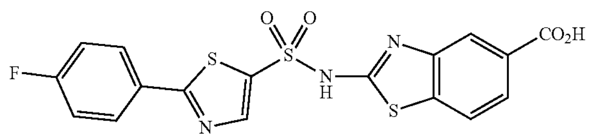 [SMILES: O=C(O)c1ccc2sc(NS(=O)(=O)c3cnc(-c4ccc(F)cc4)s3)nc2c1] | 436.0 | 1H NMR (400 MHz, DMSO-d6) δ 8.35 (s, 1H), 8.09-7.95 (m, 3H), 7.89-7.77 (m, 2H), 7.37 (t, J = 8.7 Hz, 2H). |
| 389 | 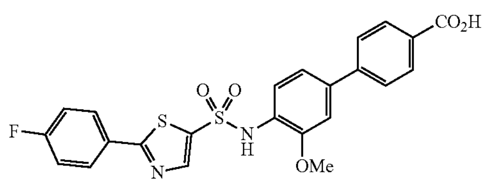 [SMILES: COc1cc(-c2ccc(C(=O)O)cc2)ccc1NS(=O)(=O)c1cnc(-c2ccc(F)cc2)s1] | 485.2 | 1H NMR (400 MHz, DMSO-d6) δ 12.98 (s, 1H), 10.25 (s, 1H), 8.16 (s, 1H), 8.09-7.94 (m, 4H), 7.83 (d, J = 8.2 Hz, 2H), 7.44-7.29 (m, 4H), 3.68 (s, 3H) |
| 390 | 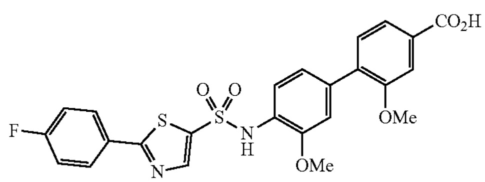 [SMILES: COc1cc(-c2ccc(C(=O)O)cc2OC)ccc1NS(=O)(=O)c1cnc(-c2ccc(F)cc2)s1] | 515.2 | 1H NMR (400 MHz, DMSO-d6) δ 10.21 (s, 1H), 8.18 (s, 1H), 8.10-8.01 (m, 2H), 7.64-7.56 (m, 2H), 7.49-7.29 (m, 4H), 7.20-7.10 (m, 2H), 3.83 (s, 3H), 3.60 (s, 3H). |
| 391 | 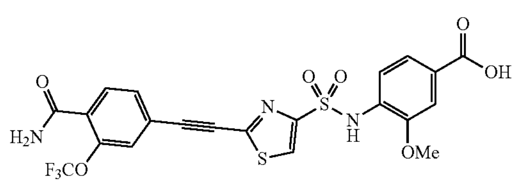 [SMILES: COc1cc(C(=O)O)ccc1NS(=O)(=O)c1csc(C#Cc2ccc(C(N)=O)c(OC(F)(F)F)c2)n1] | 540.0 [M − H]− | 1H NMR (400 MHz, DMSO-d6) δ 8.45 (s, 1H), 8.01 (s, 1H), 7.83-7.73 (m, 3H), 7.70-7.66 (m, 1H), 7.51-7.34 (m, 3H), 3.71 (s, 3H). |
| 392 | 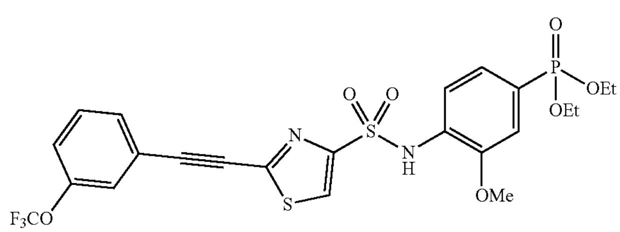 [SMILES: CCOP(=O)(OCC)c1ccc(NS(=O)(=O)c2csc(C#Cc3cccc(OC(F)(F)F)c3)n2)c(OC)c1] | 591.0 | 1H NMR (400 MHz, DMSO-d6) δ 10.24 (s, 1H), 8.47 (s, 1H), 7.71-7.79 (m, 2H), 7.65 (t, J = 7.9 Hz, 1H), 7.60-7.55 (m, 1H), 7.46-7.41 (m, 1H), 7.29-7.20 (m, 1H), 7.20-7.12 (m, 1H), 4.08-3.90 (m, 4H), 3.71 (s, 3H), 1.22 (t, J = 7.0 Hz, 6H). |
| 393 | 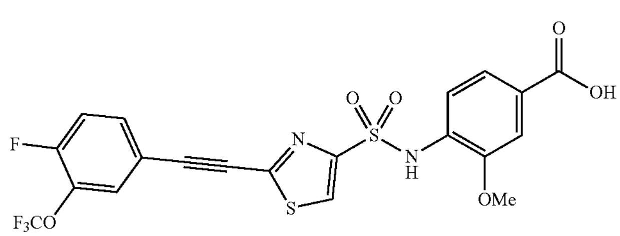 [SMILES: COc1cc(C(=O)O)ccc1NS(=O)(=O)c1csc(C#Cc2ccc(F)c(OC(F)(F)F)c2)n1] | 515.0 [M − H]− | 1H NMR (400 MHz, DMSO-d6) δ 12.90 (s, 1H), 10.19 (s, 1H), 8.47 (s, 1H), 8.10-8.00 (m, 1H), 7.90-7.80 (m, 1H), 7.70-7.61 (m, 1H), 7.51 (m, 1H), 7.45 (d, J = 1.8 Hz, 1H), 7.39 (d, J = 8.2 Hz, 1H), 3.72 (s, 3H). |
| 394 | 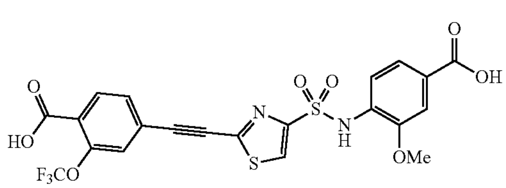 [SMILES: COc1cc(C(=O)O)ccc1NS(=O)(=O)c1csc(C#Cc2ccc(C(=O)O)c(OC(F)(F)F)c2)n1] | 543.2 | 1H NMR (400 MHz, DMSO-d6) δ 10.19 (s, 1H), 8.50 (s, 1H), 7.99 (d, J = 8.1 Hz, 1H), 7.89-7.80 (m, 2H), 7.60-7.50 (m, 1H), 7.45 (d, J = 1.8 Hz, 1H), 7.40 (d, J = 8.3 Hz, 1H), 3.71 (s, 3H), 1.24 (s, 1H). |

-continued

| Example # | Structure | LC-MS [M + H]+ unless otherwise noted | 1H-NMR |
|---|---|---|---|
| 395 | 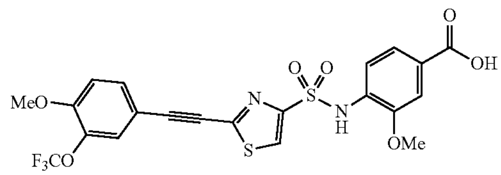 [SMILES: COc1cc(C(=O)O)ccc1NS(=O)(=O)c1csc(C#Cc2ccc(OC)c(OC(F)(F)F)c2)n1] | 529.2 | 1H NMR (400 MHz, DMSO-d6) δ 10.17 (s, 1H), 8.43 (s, 1H), 7.74 (d, J = 9.0 Hz, 2H), 7.55-7.48 (m, 1H), 7.45 (s, 1H), 7.40-7.35 (m, 8.4 Hz, 2H), 3.93 (s, 3H), 3.72 (s, 3H). |
| 396 | 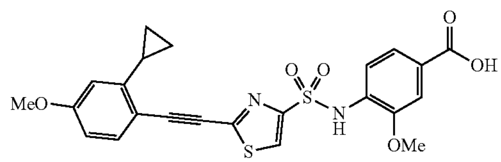 [SMILES: COc1ccc(C#Cc2nc(S(=O)(=O)Nc3ccc(C(=O)O)cc3OC)cs2)c(C2CC2)c1] | 483.2 | 1H NMR (400 MHz, DMSO-d6) δ 8.39 (s, 1H), 7.55 (d, J = 8.6 Hz, 1H), 7.50 (m, 1H), 7.46-7.36 (m, 2H), 6.89-6.80 (m, 1H), 6.47 (d, J = 2.5 Hz, 1H), 3.79 (s, 3H), 3.71 (s, 3H), 2.30-2.20 (m, 1H), 1.12-1.01 (m, 2H), 0.86-0.77 (m, 2H). |
| 397 | 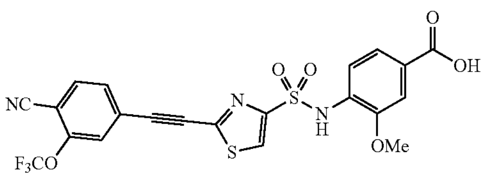 [SMILES: COc1cc(C(=O)O)ccc1NS(=O)(=O)c1csc(C#Cc2ccc(C#N)c(OC(F)(F)F)c2)n1] | 524.0 | 1H NMR (400 MHz, DMSO-d6) δ 8.44 (s, 1H), 8.18 (d, J = 8.1 Hz, 1H), 8.11 (s, 1H), 7.99-7.80 (m, 1H), 7.45 (s, 1H), 7.38 (d, J = 16.5 Hz, 2H), 3.70 (s, 3H). |
| 398 | 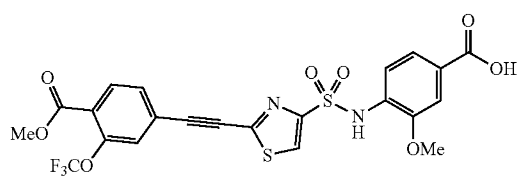 [SMILES: COC(=O)c1ccc(C#Cc2nc(S(=O)(=O)Nc3ccc(C(=O)O)cc3OC)cs2)cc1OC(F)(F)F] | 557.0 | 1H NMR (400 MHz, DMSO-d6) δ 10.20 (s, 1H), 8.50 (s, 1H), 8.03 (d, J = 8.1 Hz, 1H), 7.92 (s, 1H), 7.90-7.84 (m, 1H), 7.59-7.50 (m, 1H), 7.45 (d, J = 1.8 Hz, 1H), 7.40 (d, J = 8.3 Hz, 1H), 3.89 (s, 3H), 3.71 (s, 3H). |
| 399 | 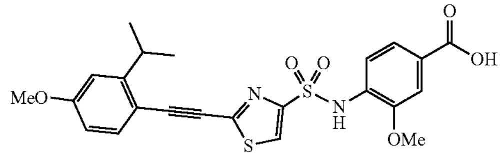 [SMILES: COc1ccc(C#Cc2nc(S(=O)(=O)Nc3ccc(C(=O)O)cc3OC)cs2)c(C(C)C)c1] | 487.0 | 1H NMR (400 MHz, DMSO-d6) δ 10.18 (s, 1H), 8.39 (s, 1H), 7.58 (d, J = 8.5 Hz, 1H), 7.51 (d, J = 8.5 Hz, 1H), 7.47-7.37 (m, 2H), 6.95 (d, J = 2.5 Hz, 1H), 6.93-6.85 (m, J = 8.5, 2.6 Hz, 1H), 3.83 (s, 3H), 3.71 (s, 3H), 1.26 (d, J = 6.9 Hz, 6H). |
| 400 | 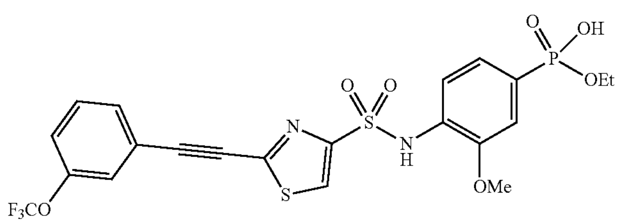 [SMILES: CCOP(=O)(O)c1ccc(NS(=O)(=O)c2csc(C#Cc3cccc(OC(F)(F)F)c3)n2)c(OC)c1] | 561.1 | 1H NMR (400 MHz, DMSO-d6) δ 8.34 (d, J = 2.5 Hz, 1H), 7.76 (d, J = 9.0 Hz, 2H), 7.64 (t, J = 7.9 Hz, 1H), 7.61-7.54 (m, 1H), 7.11 (d, J = 12.7 Hz, 1H), 3.58 (s, 5H), 1.00 (t, J = 7.1 Hz, 3H). |
| 401 | 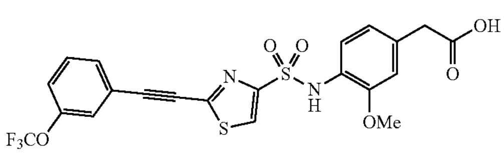 [SMILES: COc1cc(CC(=O)O)ccc1NS(=O)(=O)c1csc(C#Cc2cccc(OC(F)(F)F)c2)n1] | 513.0 | 1H NMR (400 MHz, Chloroform-d) δ 8.00 (s, 1H), 7.57-7.42 (m, 4H), 7.38-7.29 (m, 2H), 6.88-6.81 (m, 1H), 6.76 (d, J = 1.8 Hz, 1H), 3.80 (s, 3H), 3.60 (s, 2H), 1.27 (s, 1H). |
| 402 | 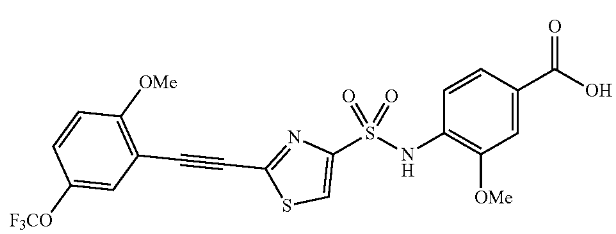 [SMILES: COc1ccc(OC(F)(F)F)cc1C#Cc1nc(S(=O)(=O)Nc2ccc(C(=O)O)cc2OC)cs1] | 529.0 | 1H NMR (400 MHz, DMSO-d6) δ 10.20 (s, 1H), 8.44 (s, 1H), 7.70 (d, J = 3.0 Hz, 1H), 7.58-7.47 (m, 2H), 7.44 (d, J = 1.8 Hz, 1H), 7.38 (d, J = 8.2 Hz, 1H), 7.26 (d, J = 9.3 Hz, 1H), 3.92 (s, 3H), 3.71 (s, 3H). |

| Example # | Structure | LC-MS [M + H]+ unless otherwise noted | 1H-NMR |
|---|---|---|---|
| 403 | 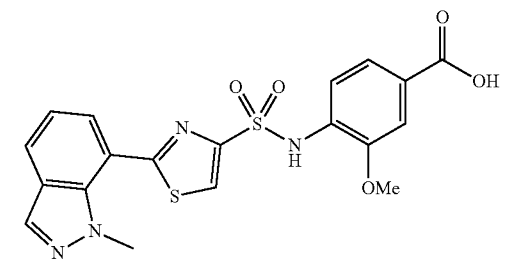 [SMILES: COc1cc(C(=O)O)ccc1NS(=O)(=O)c1csc(-c2cccc3cnn(C)c23)n1] | 445.2 | 1H NMR (400 MHz, DMSO-d6) δ 10.22 (s, 1H), 8.53 (s, 1H), 8.48 (s, 1H), 7.87 (d, J = 8.4 Hz, 1H), 7.75 (d, J = 7.2 Hz, 1H), 7.60-7.48 (m, 3H), 7.40 (d, J = 1.7 Hz, 1H), 4.12 (s, 3H), 3.64 (s, 3H). |
| 404 | 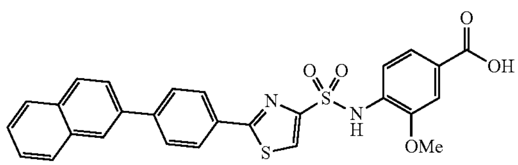 [SMILES: COc1cc(C(=O)O)ccc1NS(=O)(=O)c1csc(-c2ccc(-c3ccc4ccccc4c3)cc2)n1] | 517.2 | 1H NMR (400 MHz, DMSO-d6) δ 10.10 (s, 1H), 8.41 (s, 1H), 8.35 (d, J = 1.7 Hz, 1H), 8.10-8.00 (m, 6H), 8.00-7.90 (m, 2H), 7.62-7.53 (m, 4H), 7.45 (s, 1H), 3.69 (s, 3H). |

Example 484: (4-((2-(4-cyclohexylphenyl)thiazole)-4-sulfonamido)-3-methoxyphenyl)phosphonic acid

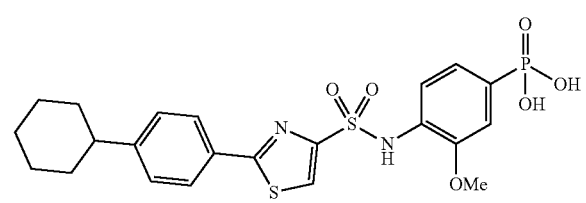 [SMILES: COc1cc(P(=O)(O)O)ccc1NS(=O)(=O)c1csc(-c2ccc(C3CCCCC3)cc2)n1]

A solution of diethyl 4-[2-(4-cyclohexylphenyl)-1,3-thiazole-4-sulfonamido]-3-methoxyphenylphosphonate (21 mg, 0.035 mmol) and bromotrimethylsilane (54 mg, 0.35 mmol) in acetonitrile (4 mL) was stirred for 48 h at room temperature. The resulting mixture was extracted, concentrated, purified by reverse flash chromatography to give (4-((2-(4-cyclohexylphenyl)thiazole)-4-sulfonamido)-3-methoxyphenyl)phosphonic acid as a white solid (7.3 mg, 40%). ESI-MS m/z: 509.10 [M+H]+. 1H NMR (400 MHz, DMSO-d6) δ 8.19 (s, 1H), 7.83 (d, J=7.9 Hz, 2H), 7.39 (d, J=8.0 Hz, 2H), 7.27-7.21 (m, 1H), 7.20-7.10 (m, 2H), 3.43 (s, 3H), 2.59-2.53 (m, 1H), 1.84-1.66 (m, 5H), 1.49-1.23 (m, 5H).

Example 403: 3-methoxy-4-((2-(1-methyl-1H-indazol-7-yl)thiazole)-4-sulfonamido)benzoic acid Step 1. Synthesis of methyl 3-methoxy-4-((2-(1-methyl-1H-indazol-7-yl)thiazole)-4-sulfonamido)benzoate

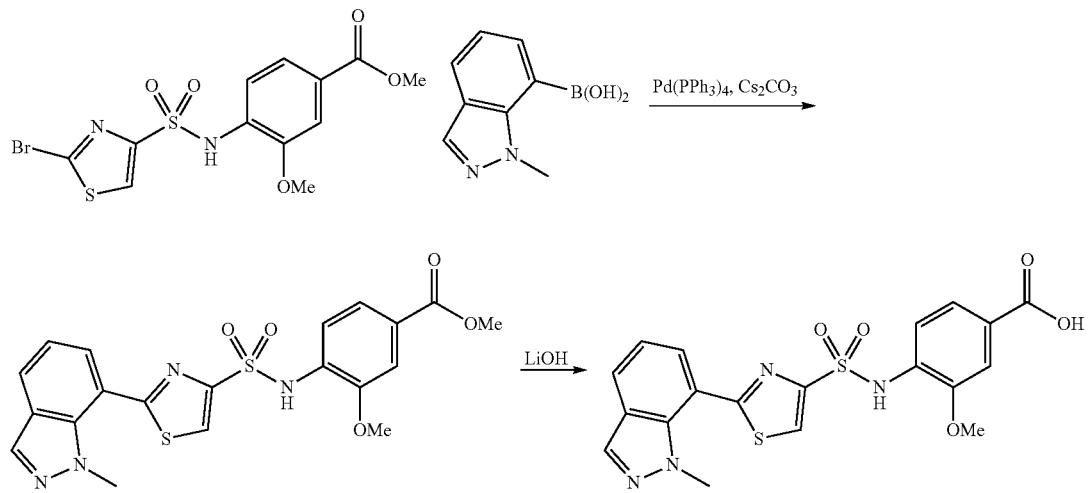

Example 403

A solution of methyl 4-((2-bromothiazole)-4-sulfonamido)-3-methoxybenzoate (30 mg, 0.07 mmol), Cs₂CO₃ (29 mg, 0.09 mmol), (1-methyl-1H-indazol-7-yl)boronic acid (26 mg, 0.15 mmol), Pd(PPh₃)₄ (9 mg, 0.007 mmol) in toluene (2 mL) and MeOH (0.5 mL) was stirred at microwave reactor for 1 h at 130° C. The mixture was diluted with EtOAc/water, and the organic layer was separated, washed with water, brine, dried, filtered and concentrated. The residue was purified by reverse phase C18 column chromatography to give methyl 3-methoxy-4-((2-(1-methyl-1H-indazol-7-yl)thiazole)-4-sulfonamido)benzoate (30 mg, 89%).

Step 2. Synthesis of 3-methoxy-4-((2-(1-methyl-1H-indazol-7-yl)thiazole)-4-sulfonamido)benzoic acid A mixture of 3-methoxy-4-((2-(1-methyl-1H-indazol-7-yl)thiazole)-4-sulfonamido)benzoate (30 mg, 0.06 mmol) and lithium hydroxide (78 mg, 3.2 mmol) in dioxane (10 mL) and H₂O (5 mL) was stirred for overnight at room temperature. The mixture was acidified to pH=5 with 1M HCl. The mixture was diluted with EtOAc/water, and the organic layer was separated, washed with water, brine, dried, filtered and concentrated. The residue was purified by reverse phase C18 column chromatography to give 3-methoxy-4-((2-(1-methyl-1H-indazol-7-yl)thiazole)-4-sulfonamido)benzoic acid as a white solid (11.1 mg, 38%).

ESI-MS m/z: 445.15 [M+H]*, ¹HNMR (400 MHz, DMSO-d₆) δ 10.22 (s, 1H), 8.53 (s, 1H), 8.48 (s, 1H), 7.87 (d, J=8.4 Hz, 1H), 7.75 (d, J=7.2 Hz, 1H), 7.60-7.48 (m, 3H), 7.40 (d, J=1.7 Hz, 1H), 4.12 (s, 3H), 3.64 (s, 3H).

Example 405, 462, 502 are prepared analogous to the synthesis of Example 403 where (1-methyl-1H-indazol-7-yl)boronic acid is replaced with corresponding aryl boronic acid.

Example 406: 3-methoxy-4-((2-(4-(3-methoxyprop-1-en-2-yl)phenyl)thiazole)-4-sulfonamido)benzoic acid

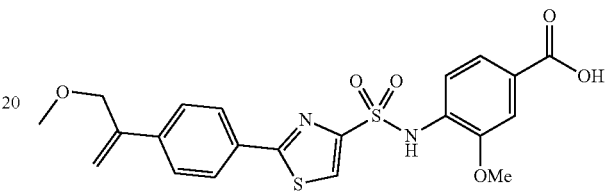

Step 1. Synthesis of methyl 4-((2-(4-chlorophenyl)thiazole)-4-sulfonamido)-3-methoxybenzoate

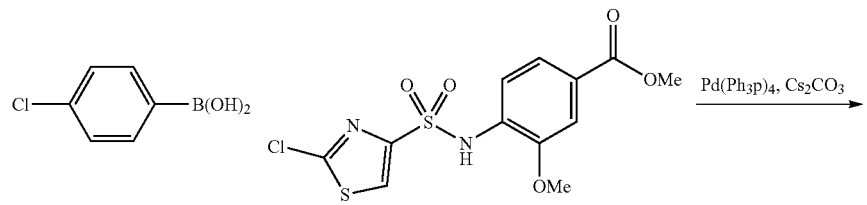

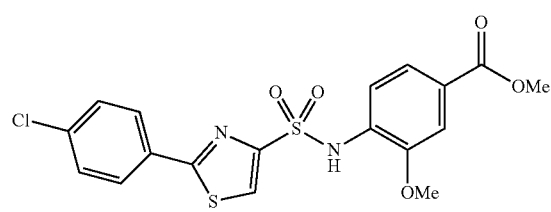

To (4-chlorophenyl)boronic acid (20.34 mg, 0.130 mmol), methyl 4-((2-chlorothiazole)-4-sulfonamido)-3-methoxybenzoate (36.3 mg, 0.100 mmol), cesium carbonate (42.4 mg, 0.130 mmol) in toluene (0.8 ml) and MeOH (0.200 ml) was added Pd(PPh₃)₄ (5.78 mg, 5.00 μmol) and the mixture was stirred at 100° C. in microwave reactor for 45 min. The mixture was diluted with EtOAc/1N HCl, the organic layer was separated, washed with water, brine, dried, filtered and concentrated. The residue was purified by flash column chromatography eluting with 0-50% EtOAc/cyclohexane to give methyl 4-((2-(4-chlorophenyl)thiazole)-4-sulfonamido)-3-methoxybenzoate (29.2 mg, 0.067 mmol, 66.5% yield). ¹H NMR (500 MHz, Chloroform-d) δ 8.01 (s, 1H), 7.85-7.75 (m, 2H), 7.66 (d, J=8.4 Hz, 1H), 7.61 (d, J=1.7 Hz, 1H), 7.59 (t, J=1.5 Hz, 1H), 7.44 (d, J=1.7 Hz, 1H), 7.42-7.37 (m, 2H), 3.85 (s, 4H), 3.82 (s, 3H).

Step 2. Synthesis of 3-methoxy-4-((2-(4-(3-methoxyprop-1-en-2-yl)phenyl)thiazole)-4-sulfonamido)benzoic acid

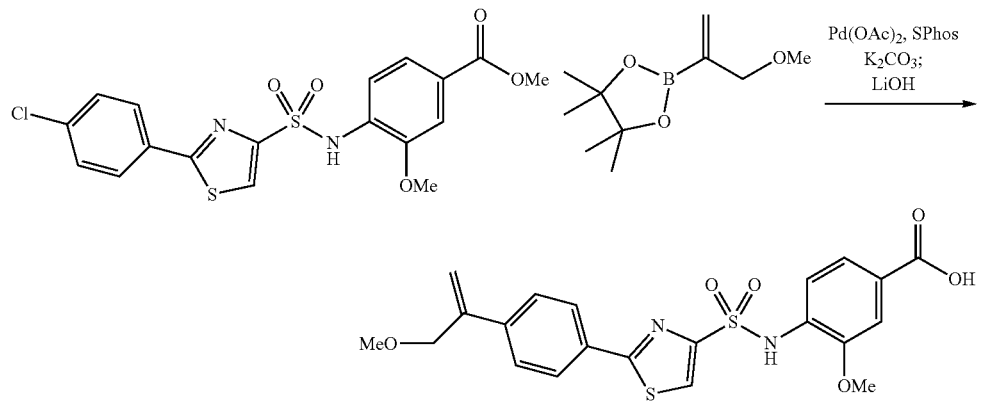

To methyl 4-((2-(4-chlorophenyl)thiazole)-4-sulfonamido)-3-methoxybenzoate (23 mg, 0.052 mmol), 2-(3-methoxyprop-1-en-2-yl)-4,4,5,5-tetramethyl-1,3,2-dioxaborolane (15.57 mg, 0.079 mmol), potassium carbonate (1M) (105 μl, 0.105 mmol) in Tetrahydrofuran (0.8 ml) was added Pd(OAc)₂ (1.177 mg, 5.24 μmol) and SPhos (4.30 mg, 10.48 μmol). The resulting mixture was stirred at 120° C. in microwave reactor for 30 min.

To the mixture was added LiOH (524 μl, 0.524 mmol) and the mixture was stirred at 100° C. in microwave reactor for 30 min. The mixture was diluted with EtOAc/1N HCl, and the organic layer was separated, washed with water, brine, dried, filtered and concentrated. The residue was purified by flash column chromatography eluting with 0 to 70% acetone/cyclohexane to give 3-methoxy-4-((2-(4-(3-methoxyprop-1-en-2-yl)phenyl)thiazole)-4-sulfonamido)benzoic acid (14 mg, 0.030 mmol, 58.0% yield). ESI-MS m/z: 459.1 [M−H]⁻, ¹H NMR (400 MHz, Chloroform-d) δ 8.02 (s, 1H), 7.83 (d, J=8.5 Hz, 1H), 7.76-7.62 (m, 4H), 7.56-7.49 (m, 2H), 7.47 (d, J=1.6 Hz, 1H), 5.61 (d, J=1.0 Hz, 1H), 5.39 (t, J=1.2 Hz, 1H), 4.31 (d, J=1.2 Hz, 2H), 3.84 (s, 4H), 3.35 (s, 3H).

Example 411: 4-((6-(4-fluorophenyl)pyridine)-2-sulfonamido)-3-methoxybenzoic acid

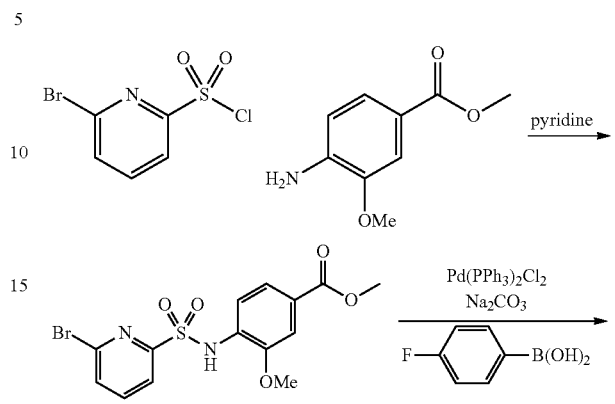

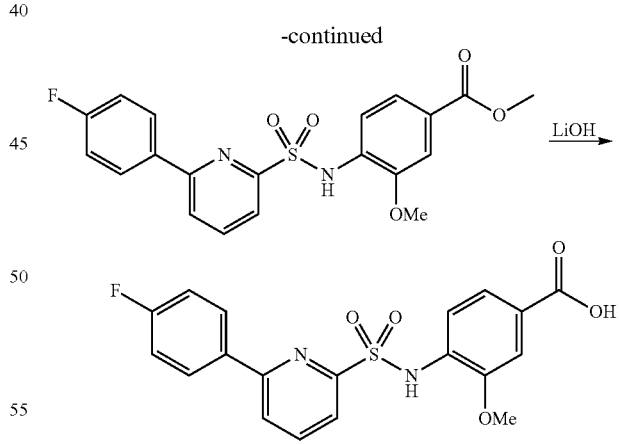

Step 1. Synthesis of methyl 4-((6-bromopyridine)-2-sulfonamido)-3-methoxybenzoate A solution of methyl 4-amino-3-methoxybenzoate (1.06 g, 5.85 mmol) and pyridine (0.62 g, 7.8 mmol) in DCM (30 mL) was stirred for 5 min at room temperature. 6-bromopyridine-2-sulfonyl chloride (1 g, 3.90 mmol) was added and the resulting mixture was stirred for 1 h at room temperature. The mixture was diluted with EtOAc/HCl (1M)

and the organic layer was separated, washed with water, brine, dried, filtered and concentrated. The residue was purified by reverse flash chromatography to give methyl 4-((6-bromopyridine)-2-sulfonamido)-3-methoxybenzoate as a white solid (800 mg, 51%). ESI-MS m/z: 402.85 [M+H]+.

Step 2. Synthesis of methyl 4-((6-(4-fluorophenyl)pyridine)-2-sulfonamido)-3-methoxybenzoate A solution of methyl 4-((6-bromopyridine)-2-sulfonamido)-3-methoxybenzoate (100 mg, 0.25 mmol), 4-fluorophenylboronic acid (52 mg, 0.38 mmol), Na₂CO₃ (40 mg, 0.38 mmol) and Pd(PPh₃)₂Cl₂ (18 mg, 0.03 mmol) in THF (10 mL) and H₂O (2 mL) was stirred for 2 h at 65° C. under nitrogen atmosphere. The mixture diluted with EtOAc/water and the organic layer was separated, washed with water, brine, dried, filtered and concentrated. The residue was purified by reverse flash chromatography to give methyl 4-((6-(4-fluorophenyl)pyridine)-2-sulfonamido)-3-methoxybenzoate as a white solid (50 mg, 48%). ESI-MS m/z: 416.95 [M+H]+.

Step 3. Synthesis of 4-((6-(4-fluorophenyl)pyridine)-2-sulfonamido)-3-methoxybenzoic acid A solution of 4-((6-(4-fluorophenyl)pyridine)-2-sulfonamido)-3-methoxybenzoate (40 mg, 0.10 mmol), LiOH (46 mg, 1.92 mmol) in dioxane (2 mL) and H₂O (1 mL) was stirred for overnight at room temperature. The mixture was acidified to pH=5 with 1M HCl, and the mixture was extracted with EtOAc. The organic layer was separated, washed with water, brine, dried, filtered and concentrated. The residue was purified by reverse flash chromatography to give 4-((6-(4-fluorophenyl)pyridine)-2-sulfonamido)-3-methoxybenzoic acid as a white solid (10.9 mg, 28%). ESI-MS m/z: 403.10 [M+H]+. ¹HNMR (400 MHz, DMSO-d₆) δ 9.98 (s, 1H), 8.22 (d, J=8.0 Hz, 1H), 8.13 (t, J=7.8 Hz, 1H), 8.10-8.00 (m, 2H), 7.86 (d, J=7.6 Hz, 1H), 7.60-7.49 (m, 2H), 7.39 (d, J=1.7 Hz, 1H), 7.32 (t, J=8.7 Hz, 2H), 3.61 (s, 3H).

Example 412 is prepared analogous to the synthesis of Example 411 where 4-fluorophenylboronic acid is replaced with corresponding aryl boronic acid.

Example 463: 3-methoxy-4-((6-((3-(trifluoromethoxy)phenyl)ethynyl)pyridine)-2-sulfonamido)benzoic acid

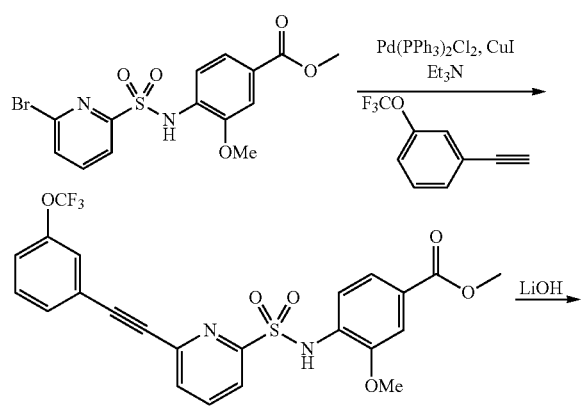

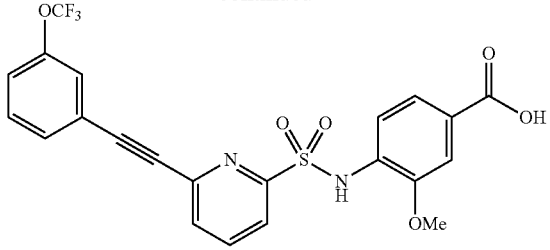

Step 1. Synthesis of methyl 3-methoxy-4-((6-((3-(trifluoromethoxy)phenyl)ethynyl)pyridine)-2-sulfonamido)benzoate A solution of methyl 4-((6-bromopyridine)-2-sulfonamido)-3-methoxybenzoate (200 mg, 0.50 mmol), Pd(PPh₃)₄ (114 mg, 0.10 mmol), CuI (38 mg, 0.20 mmol) and Et₃N (504 mg, 5.0 mmol) in DMF (5 mL) was stirred for 1 min at 0° C. 1-ethynyl-3-(trifluoromethoxy)benzene (112 mg, 0.58 mmol) was added dropwise at 0° C. The resulting mixture was stirred for 6 h at room temperature. The resulting mixture was diluted with EtOAc/water and the organic layer was separated, washed with water, brine, dried, filtered and concentrated. The residue was purified by reverse flash chromatography to give methyl 3-methoxy-4-((6-((3-(trifluoromethoxy)phenyl)ethynyl)pyridine)-2-sulfonamido)benzoate as a white solid (50 mg, 20%). ESI-MS m/z: 507.00 [M+H]+.

Step 2. Synthesis of 3-methoxy-4-((6-((3-(trifluoromethoxy)phenyl)ethynyl)pyridine)-2-sulfonamido)benzoic A solution of methyl 3-methoxy-4-((6-((3-(trifluoromethoxy)phenyl)ethynyl)pyridine)-2-sulfonamido)benzoate (50 mg, 0.10 mmol), LiOH (95 mg, 3.96 mmol) in H₂O (2 mL) and dioxane (4 mL) was stirred for overnight at room temperature. The mixture was acidified to pH=5 with 1M HCl, and the mixture was extracted with EtOAc. The organic layer was separated, washed with water, brine, dried, filtered and concentrated. The residue was purified by reverse flash chromatography to give 3-methoxy-4-((6-((3-(trifluoromethoxy)phenyl)-ethynyl)pyridine)-2-sulfonamido)benzoic as a white solid (10.9 mg, 22%). ESI-MS m/z: 493.10 [M+H]+. ¹HNMR (400 MHz, DMSO-d₆) δ 12.87 (s, 1H), 10.18 (s, 1H), 8.14 (t, J=7.8 Hz, 1H), 7.98-7.87 (m, 2H), 7.74-7.67 (m, 2H), 7.63 (t, J=7.9 Hz, 1H), 7.58-7.47 (m, 2H), 7.42 (d, J=1.8 Hz, 1H), 7.37 (d, J=8.2 Hz, 1H), 3.62 (s, 3H).

Example 426: 3-methoxy-4-((2-(4-(3-methoxycyclohexyl)phenyl)thiazole)-4-sulfonamido)benzoic acid

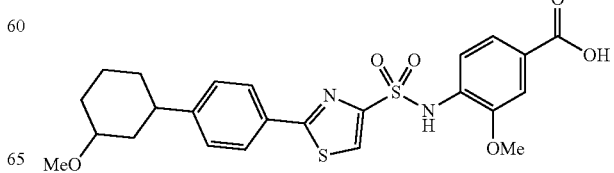

Synthesis of 2-(5'-methoxy-2',3',4',5'-tetrahydro-[1,1'-biphenyl]-4-yl)-4,4,5,5-tetramethyl-1,3,2-dioxaborolane

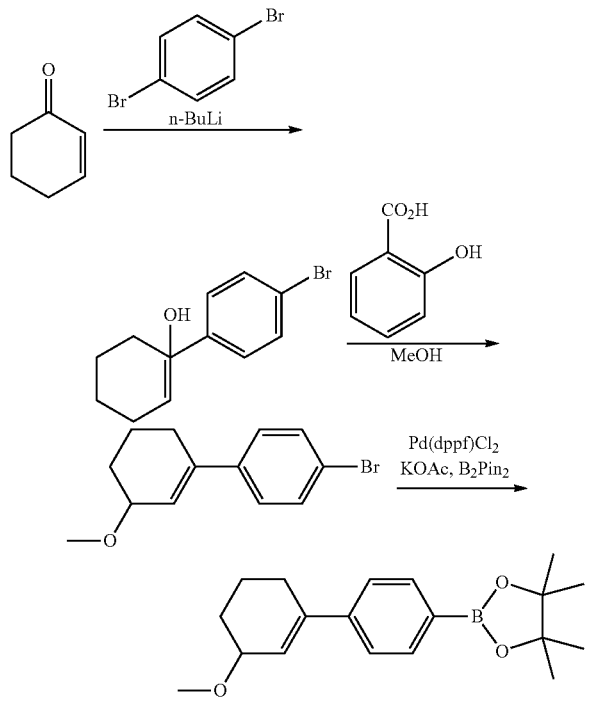

Step 1. Synthesis of 4'-bromo-3,4-dihydro-[1,1'-biphenyl]-1(2H)-ol

To a solution of dibromobenzene (3.07 g, 13.004 mmol) in THF (10 mL) at −78° C. under nitrogen atmosphere was added n-butyllithium (1.6 M in hexane, 8.06 ml, 12.90 mmol), after 20 min cyclohexenone (1 g, 7.924 mmol) was added and stirred for 30 min. The resulting mixture was quenched with NH₄Cl solution, and extracted with EtOAc. The organic layer was separated, dried and concentrated. The residue was purified by reverse phase C18 column chromatography to give 4'-bromo-3,4-dihydro-[1,1'-biphenyl]-1(2H)-ol as a yellow solid (1 g, 39%).

Step 2. Synthesis of 4'-bromo-5-methoxy-2,3,4,5-tetrahydro-1,1'-biphenyl

A solution of 4'-bromo-3,4-dihydro-[1,1'-biphenyl]-1(2H)-ol (1 g, 3.9 mmol), salicyclic acid (55 mg, 0.40 mmol) in ACN (10 mL) and CH₃OH (2 mL) was stirred for overnight at room temperature. The solution was evaporated and the residue was purified by reverse phase C18 column chromatography to give 4'-bromo-5-methoxy-2,3,4,5-tetrahydro-1,1'-biphenyl as a yellow solid (500 mg, 48%). ESI-MS m/z: 267.10 [M+H]⁺.

Step 3. Synthesis of 2-(5'-methoxy-2',3',4',5'-tetrahydro-[1,1'-biphenyl]-4-yl)-4,4,5,5-tetramethyl-1,3,2-dioxaborolane A solution of 4'-bromo-5-methoxy-2,3,4,5-tetrahydro-1,1'-biphenyl (200 mg, 0.75 mmol) and bis(pinacolato)diboron (380 mg, 1.5 mmol), K₃PO₄ (476 mg, 2.3 mmol), Pd(dppf)Cl₂CH₂Cl₂ (61 mg, 0.075 mmol) in dioxane (5 mL) was stirred for overnight at 80° C. under nitrogen atmosphere. The solution was evaporated and the residue was purified by reverse phase C18 column chromatography to give 2-(5'-methoxy-2',3',4',5'-tetrahydro-[1,1'-biphenyl]-4-yl)-4,4,5,5-tetramethyl-1,3,2-dioxaborolane as a yellow solid (100 mg, 42%). ESI-MS m/z: 314.20 [M+H]⁺.

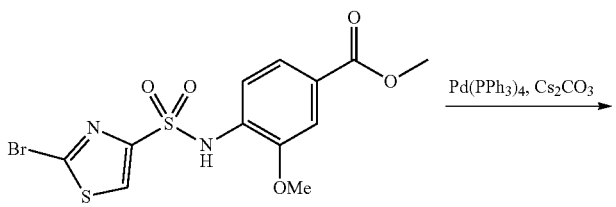

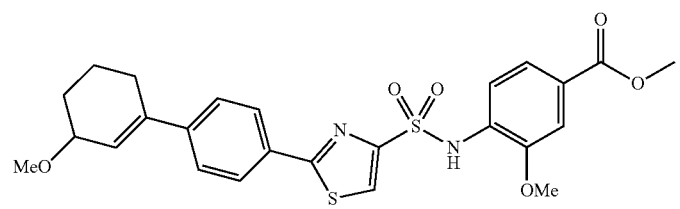

Step 4. Synthesis of methyl 3-methoxy-4-((2-(5'-methoxy-2',3',4',5'-tetrahydro-[1,1'-biphenyl]-4-yl)thiazole)-4-sulfonamido)benzoate A solution of methyl 4-(5-bromopyridine-3-sulfonamido)-3-methoxybenzoate (50 mg, 0.1 mmol), 2-(5'-methoxy-2',3',4',5'-tetrahydro-[1,1'-biphenyl]-4-yl)-4,4,5,5-tetramethyl-1,3,2-dioxaborolane (62.8 mg, 0.2 mmol), $Cs_2CO_3$ (20 mg, 0.2 mmol) and $Pd(PPh_3)_4$ (9 mg, 0.01 mmol) in toluene (4 mL) and $CH_3OH$ (1 mL) was stirred for 30 min at 130° C. in microwave reactor. The mixture was diluted with EtOAc/water and the organic layer was separated, washed with water, brine, dried, filtered and concentrated. The residue was purified by reverse phase C18 column chromatography to give methyl 3-methoxy-4-((2-(5'-methoxy-2',3',4',5'-tetrahydro-[1,1'-biphenyl]-4-yl)thiazole)-4-sulfonamido)benzoate as a yellow solid (35 mg, 58%).

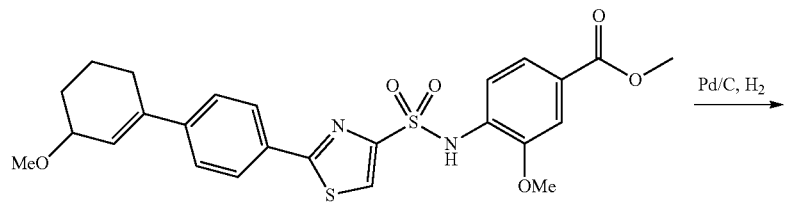

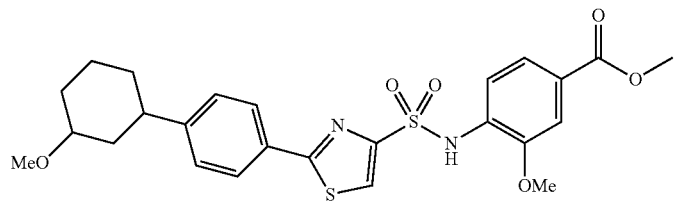

Step 5. Synthesis of methyl 3-methoxy-4-((2-(4-(3-methoxycyclohexyl)phenyl)thiazole)-4-sulfonamido)benzoate A solution of methyl 3-methoxy-4-((2-(5'-methoxy-2',3',4',5'-tetrahydro-[1,1'-biphenyl]-4-yl)thiazole)-4-sulfonamido)benzoate (20 mg, 0.039 mmol), Pd/C (83 mg, 0.78 mmol) in THF (4 mL) was stirred for 2 h at room temperature under hydrogen (balloon) atmosphere. The solution was filtered through celite and the filtrate was concentrated to give methyl 3-methoxy-4-((2-(4-(3-methoxycyclohexyl)phenyl)thiazole)-4-sulfonamido)benzoate. This material was used directly in the next step without further purification. ESI-MS m/z: 517.05 $[M+H]^+$.

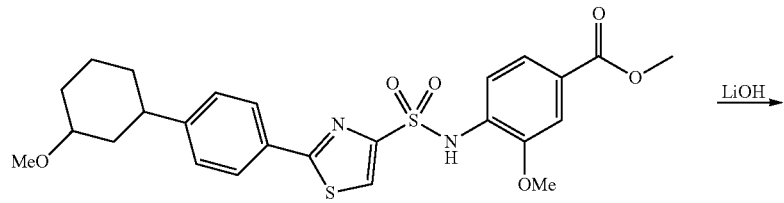

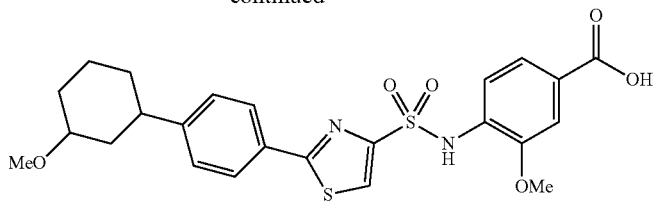

Step 6. Synthesis of 3-methoxy-4-((2-(4-(3-methoxycyclohexyl)phenyl)thiazole)-4-sulfonamido)benzoic acid A solution of methyl 3-methoxy-4-((2-(4-(3-methoxycyclohexyl)phenyl) thiazole)-4-sulfonamido)benzoate (20 mg, 0.039 mmol), LiOH (50 mg, 2 mmol) in dioxane (4 mL) and H$_2$O (1 mL) was stirred overnight at room temperature. The mixture was acidified to pH 6 with HCl (aq, 1M) and extracted with EtOAc. The organic layer was separated, washed with water, brine, dried, filtered and concentrated. The residue was purified by reverse phase C18 column chromatography to give 3-methoxy-4-((2-(4-(3-methoxycyclohexyl)phenyl) thiazole)-4-sulfonamido)benzoic acid as a white solid (2.2 mg, 11%). ESI-MS m/z: 503.10 [M+H]$^+$, $^1$HNMR (400 MHZ, DMSO-d6) δ 8.31 (s, 1H), 7.84 (d, J=8.0 Hz, 2H), 7.50 (s, 2H), 7.42 (d, J=7.8 Hz, 3H), 3.67 (s, 3H), 3.26 (s, 3H), 3.30-3.19 (m, 1H), 2.66-2.62 (m, 1H), 2.14 (d, J=11.9 Hz, 1H), 2.06 (d, J=12.2 Hz, 1H), 1.88-1.80 (m, 1H), 1.74 (d, J=11.0 Hz, 1H), 1.47-1.22 (m, 3H), 1.19-1.05 (m, 1H).

Example 430: 4-((5-(4-(1-hydroxy-4,4-dimethylcyclohexyl)phenyl)thiophene)-2-sulfonamido)-3-methoxybenzoic acid

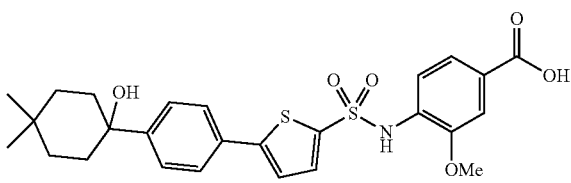 [SMILES: COc1cc(C(=O)O)ccc1NS(=O)(=O)c1ccc(-c2ccc(C3(O)CCC(C)(C)CC3)cc2)s1]

Synthesis of 4,4-dimethyl-1-(4-(4,4,5,5-tetramethyl-1,3,2-dioxaborolan-2-yl)phenyl)-cyclohexan-1-ol

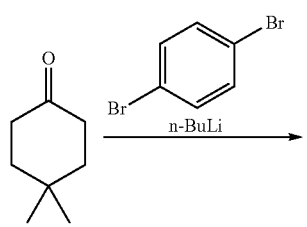

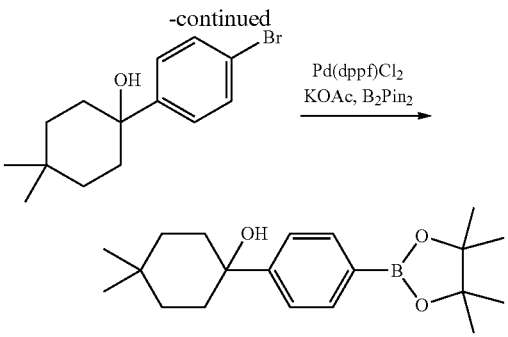

Step 1. Synthesis of 1-(4-bromophenyl)-4,4-dimethylcyclohexan-1-ol

To a solution of dibromobenzene (4.68 g, 19.8 mmol) in THF (20 mL) was added n-butyllithium (1.6 M in hexane, 12.4 ml, 19.8 mmol) and the resulting mixture was stirred for 30 min at −78° C. under nitrogen atmosphere. 4,4-dimethylcyclohexan-1-one (2 g, 15.8 mmol) in THF (5 mL) was added dropwise. The resulting mixture was stirred for 3 h at −78° C. and then quenched with NH$_4$Cl solution. The mixture was diluted with EtOAc/water and the organic layer was separated, washed with water, brine, dried, filtered and concentrated. The residue was purified by reverse phase C18 column chromatography to give 1-(4-bromophenyl)-4,4-dimethylcyclohexan-1-ol as a white solid (1.6 g, 36%).

Step 2. Synthesis of 4,4-dimethyl-1-(4-(4,4,5,5-tetramethyl-1,3,2-dioxaborolan-2-yl)phenyl)cyclohexan-1-ol A solution of 1-(4-bromophenyl)-4,4-dimethylcyclohexan-1-ol (1 g, 3.53 mmol), bis(pinacolato)diboron (1.79 g, 7.06 mmol), Pd(PPh$_3$)$_2$C$_{12}$ (0.25 g, 0.35 mmol) and KOAc (1.39 g, 14.12 mmol) in dioxane (30 mL) was stirred 12 h at 90° C. under nitrogen atmosphere. The mixture was diluted with EtOAc/water and the organic layer was separated, washed with water, brine, dried, filtered and concentrated. The residue was purified by reverse phase C18 column chromatography to give 4,4-dimethyl-1-(4-(4,4,5,5-tetramethyl-1,3,2-dioxaborolan-2-yl)phenyl)cyclohexan-1-ol as a yellow solid (285 mg, 24%). ESI-MS m/z: 313.25 [M−17]$^+$, $^1$HNMR (400 MHz, DMSO-d$_6$) δ 7.62 (d, J=7.9 Hz, 2H), 7.51 (d, J=7.9 Hz, 2H), 4.70 (s, 1H), 1.86-1.80 (m, 2H), 1.71-1.65 (m, 2H), 1.45 (d, J=13.1 Hz, 2H), 1.29 (s, 12H), 1.16 (d, J=13.2 Hz, 2H), 0.96 (d, J=10.6 Hz, 6H).

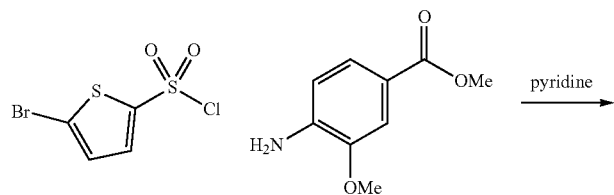

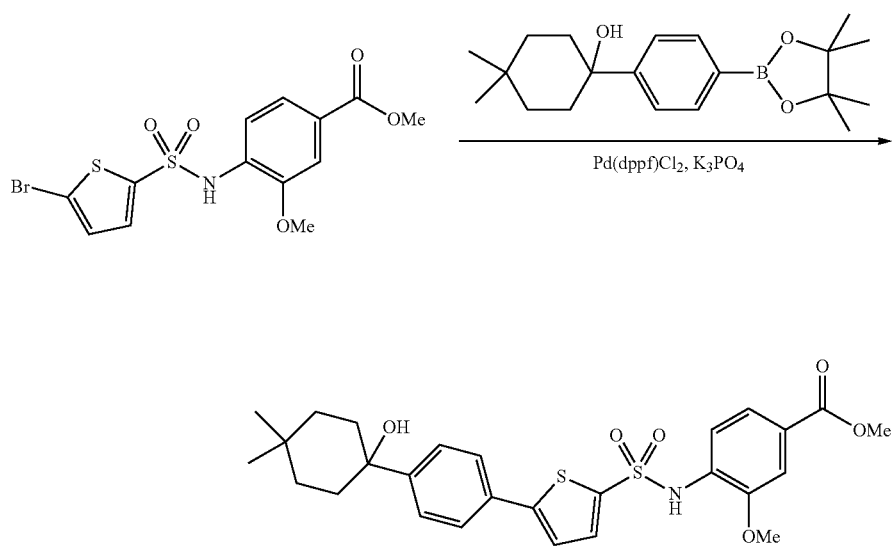

Step 3. Synthesis of methyl 4-((5-bromothiophene)-2-sulfonamido)-3-methoxybenzoate A solution of methyl 4-amino-3-methoxybenzoate (3.12 g, 17.2 mmol) and pyridine (0.70 g, 5.7 mmol) in DCM (30 mL) was stirred for 5 min at room temperature. 5-bromothiophene-2-sulfonyl chloride (3.0 g, 11.4 mmol) was added and the resulting mixture was stirred for overnight at room temperature. The mixture was diluted with EtOAc/water and the organic layer was separated, washed with water, brine, dried, filtered and concentrated. The residue was purified by reverse phase C18 column chromatography to give methyl 4-((5-bromothiophene)-2-sulfonamido)-3-methoxybenzoate as a red solid (3.7 g, 71%). ESI-MS m/z: 405.90 [M+H]$^+$.

Step 4. Synthesis of methyl 4-((5-(4-(1-hydroxy-4,4-dimethylcyclohexyl)phenyl)thiophene)-2-sulfonamido)-3-methoxybenzoate A solution of 4,4-dimethyl-1-(4-(4,4,5,5-tetramethyl-1,3,2-dioxaborolan-2-yl)phenyl)-cyclohexan-1-ol (122 mg, 0.38 mmol), methyl 4-((5-bromothiophene)-2-sulfonamido)-3-methoxybenzoate (100 mg, 0.25 mmol), Pd(PPh$_3$)$_2$Cl$_2$ (18 mg, 0.025 mmol) and K$_3$PO$_4$ (157 mg, 0.74 mmol) in dioxane (5 mL) was stirred overnight at 90° C. under nitrogen atmosphere. The mixture was diluted with EtOAc/water and the organic layer was separated, washed with water, brine, dried, filtered and concentrated. The residue was purified by reverse phase C18 column chromatography to give methyl 4-((5-(4-(1-hydroxy-4,4-dimethylcyclohexyl)phenyl)thiophene)-2-sulfonamido)-3-methoxybenzoate as a yellow solid (60 mg, 46%). ESI-MS m/z: 506.15 [M+H]$^+$.

Step 5. Synthesis of 4-((5-(4-(1-hydroxy-4,4-dimethylcyclohexyl)phenyl)thiophene)-2-sulfonamido)-3-methoxybenzoic acid 4-((5-(4-(1-hydroxy-4,4-dimethylcyclohexyl)phenyl)thiophene)-2-sulfonamido)-3-methoxybenzoic acid was prepared analogous to step 2 in the synthesis of Example 403.

Example 429: 4-((5-(4',4'-dimethyl-2',3',4',5'-tetrahydro-[1,1'-biphenyl]-4-yl)thiophene)-2-sulfonamido)-3-methoxybenzoic acid

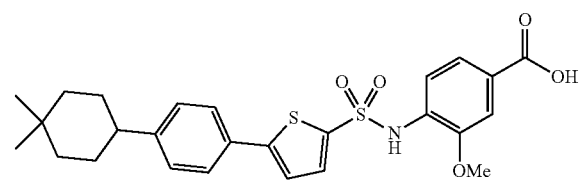 [SMILES: COc1cc(C(=O)O)ccc1NS(=O)(=O)c1ccc(-c2ccc(C3CCC(C)(C)CC3)cc2)s1]

Synthesis of methyl 4-((5-(4',4'-dimethyl-2',3',4',5'-tetrahydro-[1,1'-biphenyl]-4-yl)thiophene)-2-sulfonamido)-3-methoxybenzoate

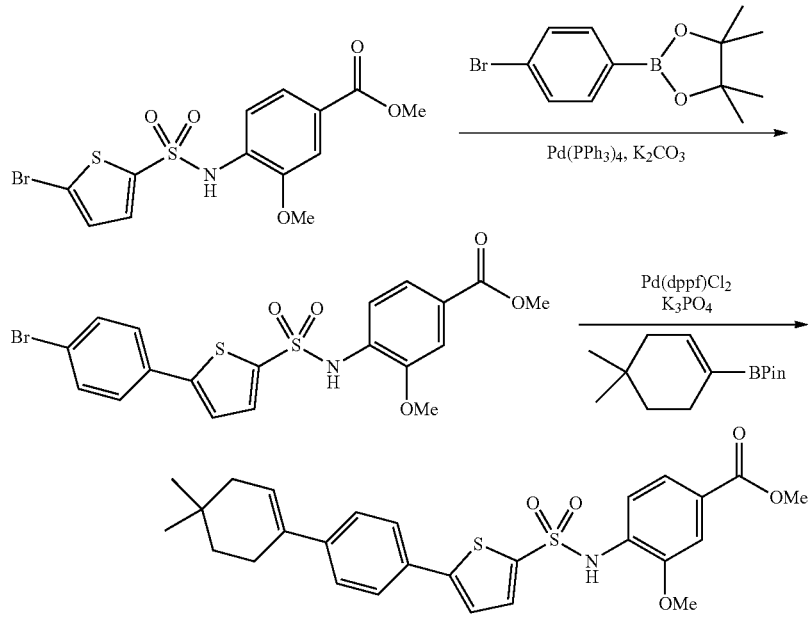

Step 1. Synthesis of methyl 4-((5-(4-bromophenyl)thiophene)-2-sulfonamido)-3-methoxybenzoate A solution of 2-(4-bromophenyl)-4,4,5,5-tetramethyl-1,3,2-dioxaborolane (209 mg, 0.74 mmol), methyl 4-((5-bromothiophene)-2-sulfonamido)-3-methoxybenzoate (200 mg, 0.49 mmol), K₂CO₃ (157 mg, 1.47 mmol) and Pd(PPh₃)₄ (11 mg, 0.05 mmol) in THF (4 mL) was stirred 3 h at 66° C. under nitrogen atmosphere. The mixture was diluted with EtOAc/water and the organic layer was separated, washed with water, brine, dried, filtered and concentrated. The residue was purified by reverse phase C18 column chromatography to give methyl 4-((5-(4-bromophenyl)thiophene)-2-sulfonamido)-3-methoxybenzoate as a yellow solid (150 mg, 63%). ESI-MS m/z: 483.85 [M+H]⁺.

Step 2. Synthesis of methyl 4-((5-(4',4'-dimethyl-2',3',4',5'-tetrahydro-[1,1'-biphenyl]-4-yl)thiophene)-2-sulfonamido)-3-methoxybenzoate A solution of methyl 4-((5-(4-bromophenyl)thiophene)-2-sulfonamido)-3-methoxybenzoate (100 mg, 0.20 mmol), 2-(4,4-dimethylcyclohex-1-en-1-yl)-4,4,5,5-tetramethyl-1,3,2-dioxaborolane (75 mg, 0.30 mmol), K₃PO₄ (125 mg, 0.60 mmol) and Pd(dppf)Cl₂CH₂Cl₂ (20 mg, 0.02 mmol) in dioxane (2 mL) was stirred for overnight at 80° C. under nitrogen atmosphere. The mixture was diluted with EtOAc/water and the organic layer was separated, washed with water, brine, dried, filtered and concentrated. The residue was purified by reverse phase C18 column chromatography to give methyl 4-((5-(4',4'-dimethyl-2',3',4',5'-tetrahydro-[1,1'-biphenyl]-4-yl)thiophene)-2-sulfonamido)-3-methoxybenzoate as a white solid (80 mg, 75%).

Step 3. Synthesis of 4-((5-(4',4'-dimethyl-2',3',4',5'-tetrahydro-[1,1'-biphenyl]-4-yl)thiophene)-2-sulfonamido)-3-methoxybenzoic acid 4-((5-(4',4'-dimethyl-2',3',4',5'-tetrahydro-[1,1'-biphenyl]-4-yl)thiophene)-2-sulfonamido)-3-methoxybenzoic acid was prepared analogous to step 2 in the synthesis of Example 403. ESI-MS m/z: 496.10 [M−H]⁻, ¹HNMR (400 MHz, DMSO-d₆) δ 7.63 (d, J=8.4 Hz, 2H), 7.47-7.57 (m, 5H), 7.41-7.47 (m, 2H), 6.22 (s, 1H), 3.70 (s, 3H), 2.39 (s, 2H), 2.00 (d, J=3.6 Hz, 2H), 1.49 (t, J=6.4 Hz, 2H), 0.94 (s, 6H).

Example 428: 4-((5-(4-(4,4-dimethylcyclohexyl)phenyl)thiophene)-2-sulfonamido)-3-methoxybenzoic acid

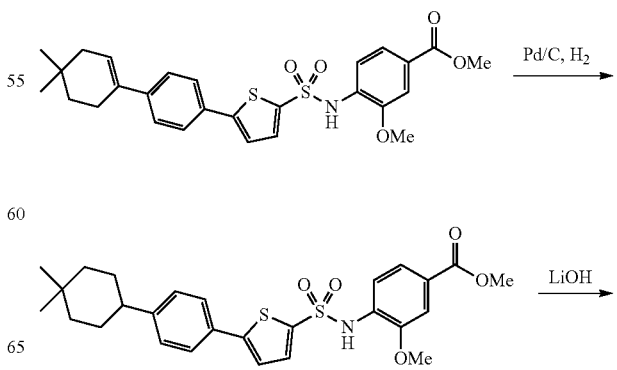

-continued

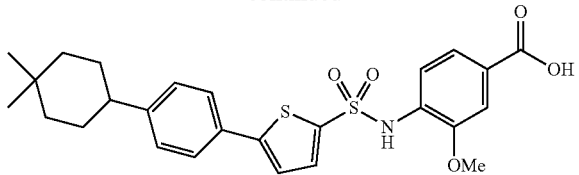

Step 1. Synthesis of methyl 4-((5-(4-(4,4-dimethylcyclohexyl)phenyl)thiophene)-2-sulfonamido)-3-methoxybenzoate A solution of methyl 4-((5-(4',4'-dimethyl-2',3',4',5'-tetrahydro-[1,1'-biphenyl]-4-yl)thiophene)-2-sulfonamido)-3-methoxybenzoate (60 mg, 0.12 mmol), Pd/C (20 mg, 0.2 mmol) in THF (4 mL) was stirred for 1 h at room temperature under hydrogen (balloon) atmosphere. The resulting mixture was filtered through celite and the filtrate was evaporated and the residue was purified by reverse phase C18 column chromatography (MeCN/H₂O) to methyl 4-((5-(4-(4,4-dimethylcyclohexyl)phenyl)thiophene)-2-sulfonamido)-3-methoxybenzoate as a white solid (50 mg, 85%).

Step 2. Synthesis of 4-((5-(4-(4,4-dimethylcyclohexyl)phenyl)thiophene)-2-sulfonamido)-3-methoxybenzoic acid 4-((5-(4-(4,4-dimethylcyclohexyl)phenyl)thiophene)-2-sulfonamido)-3-methoxybenzoic acid was prepared analogous to step 2 in the synthesis of Example 403. ESI-MS m/z: 498.10 [M−H]⁻, ¹HNMR (400 MHz, DMSO-$d_6$) δ 12.90 (s, 1H), 10.09 (s, 1H), 7.55-7.62 (m, 2H), 7.47-7.55 (m, 2H), 7.40-7.47 (m, 3H), 7.36-7.36 (m, 2H), 3.69 (s, 3H), 2.39-2.47 (m, 1H), 1.55-1.65 (m, 4H), 1.46 (d, J=12.7 Hz, 2H), 1.22-1.38 (m, 2H), 0.96 (d, J=12.3 Hz, 6H).

Example 433: 4-((5-(4-cyclohexylphenyl)pyridine)-3-sulfonamido)-3-methoxybenzoic acid

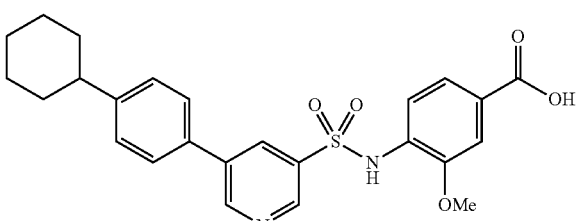

Synthesis of methyl 4-((5-(4-cyclohexylphenyl)pyridine)-3-sulfonamido)-3-methoxybenzoate

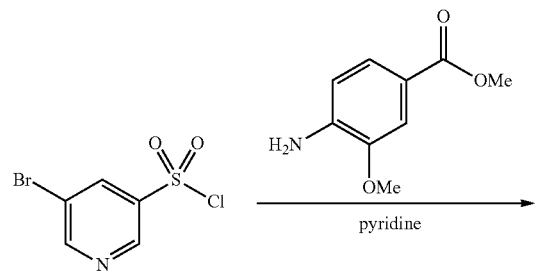

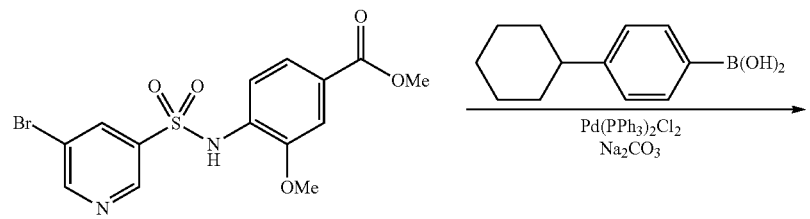

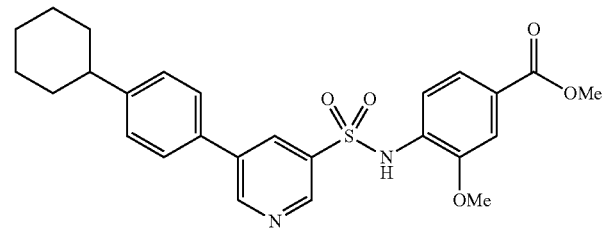

Step 1. Synthesis of methyl 4-((5-bromopyridine)-3-sulfonamido)-3-methoxybenzoate A solution of methyl 4-amino-3-methoxybenzoate (530 mg, 3 mmol), pyridine (308 mg, 3.9 mmol) and in DCM (6 mL) was stirred for 5 min at room temperature. 5-bromopyridine-3-sulfonyl chloride (500 mg, 2 mmol) and DCM (4 mL) was added dropwise. The mixture was stirred for overnight at room temperature. The mixture was diluted with EtOAc/water and the organic layer was separated, washed with water, brine, dried, filtered and concentrated. The residue was purified by reverse phase C18 column chromatography to give methyl 4-((5-bromopyridine)-3-sulfonamido)-3-methoxybenzoate as a yellow solid (380 mg, 49%). ESI-MS m/z: 405.90 [M+H]$^+$.

Step 2. Synthesis of methyl 4-((5-(4-cyclohexylphenyl)pyridine)-3-sulfonamido)-3-methoxybenzoate A solution of methyl 4-(5-bromopyridine-3-sulfonamido)-3-methoxybenzoate (50 mg, 0.1 mmol), 4-cyclohexylphenylboronic acid (38 mg, 0.2 mmol), THF (4 mL), H$_2$O (1 mL), Na$_2$CO$_3$ (20 mg, 0.2 mmol) and Pd(PPh$_3$)$_2$Cl$_2$ (9 mg, 0.01 mmol) was stirred for 2 h at 65° C. under nitrogen atmosphere. The mixture was diluted with EtOAc/water and the organic layer was separated, washed with water, brine, dried, filtered and concentrated. The residue was purified by reverse phase C18 column chromatography to give the desired compound as a yellow solid (35 mg, 58%). ESI-MS m/z: 421.05 [M+H]$^+$.

Step 3. Synthesis of 4-((5-(4-cyclohexylphenyl)pyridine)-3-sulfonamido)-3-methoxybenzoic acid 4-((5-(4-cyclohexylphenyl)pyridine)-3-sulfonamido)-3-methoxybenzoic acid was prepared analogous to step 2 in the synthesis of Example 403. ESI-MS m/z: 467.30 [M+H]$^+$, $^1$H NMR (400 MHz, DMSO-d$_6$) δ 9.10 (d, J=2.2 Hz, 1H), 8.84 (d, J=2.2 Hz, 1H), 8.33 (t, J=2.2 Hz, 1H), 7.66-7.60 (m, 2H), 7.56-7.50 (m, 1H), 3.58 (s, 3H), 7.45-7.37 (m, 4H), 2.59 (d, J=11.2 Hz, 1H), 1.79-1.75 (m, 5H), 1.56-1.12 (m, 5H).

Example 434: 3-methoxy-4-((5-((3-(trifluoromethoxy)phenyl)ethynyl)pyridine)-3-sulfonamido)benzoic acid

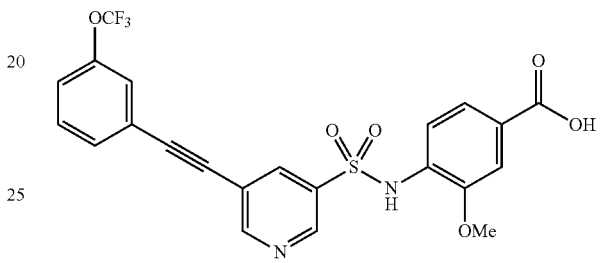

Step 1. Synthesis of methyl 3-methoxy-4-((5-((3-(trifluoromethoxy)phenyl)ethynyl)-pyridine)-3-sulfonamido)benzoate

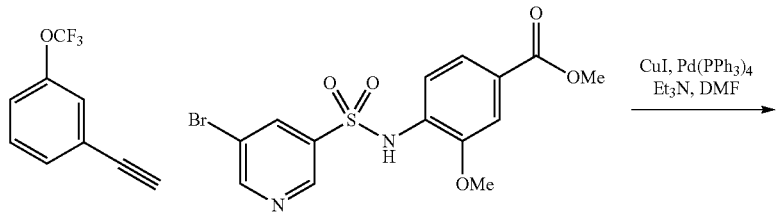

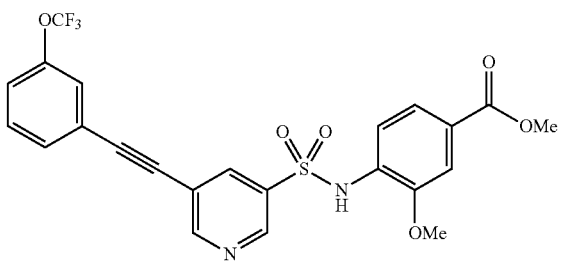

A solution of 1-ethynyl-3-(trifluoromethoxy)benzene (28 mg, 0.15 mmol), methyl 4-(5-bromopyridine-3-sulfonamido)-3-methoxybenzoate (50 mg, 0.12 mmol), CuI (10 mg, 0.05 mmol), Pd(PPh₃)₄ (30 mg, 0.03 mmol) and Et₃N (126 mg, 1.25 mmol) in DMF (2 mL) was stirred overnight at 45° C. The mixture was diluted with EtOAc/water and the organic layer was separated, washed with water, brine, dried, filtered and concentrated. The residue was purified by reverse phase C18 column chromatography to give methyl 3-methoxy-4-((5-((3-(trifluoromethoxy)phenyl)ethynyl)-pyridine)-3-sulfonamido)benzoate as a yellow solid (38 mg, 60%). ESI-MS m/z: 506.95 [M+H]⁺.

Step 2. Synthesis of 3-methoxy-4-((5-((3-(trifluoromethoxy)phenyl)ethynyl)pyridine)-3-sulfonamido) benzoic acid 3-methoxy-4-((5-((3-(trifluoromethoxy)phenyl)ethynyl) pyridine)-3-sulfonamido)benzoic acid was prepared analogous to step 2 in the synthesis of Example 403. ESI-MS m/z: 493.10 [M+H]⁺. ¹HNMR (400 MHz, DMSO-d₆) δ 9.00 (d, J=2.0 Hz, 1H), 8.89 (d, J=2.3 Hz, 1H), 8.34 (t, J=2.1 Hz, 1H), 7.70-7.67 (m, 2H), 7.61 (d, J=8.0 Hz, 1H), 7.54-7.49 (m, 2H), 7.43-7.31 (m, 2H), 3.63 (s, 3H).

Example 435, 437, 438, 472 are prepared analogous to the synthesis of Example 433 where 5-bromopyridine-3-sulfonyl chloride in step 1 is replaced with corresponding substituted phenylsulfonyl chloride.

Example 469, 470 are prepared analogous to the synthesis of Example 433 where 5-bromopyridine-3-sulfonyl chloride is replaced with corresponding substituted bromophenylsulfonyl chloride. 4-cyclohexylphenylboronic acid in step 2 is replaced with 2-(4-((1r,4r)-4-ethylcyclohexyl)phenyl)-4,4,5,5-tetramethyl-1,3,2-dioxaborolane and (4-(trans-4-Pentylcyclohexyl)phenyl)boronic acid respectively.

Example 449: (E)-3-methoxy-4-((2-(4-(3-methoxy-prop-1-en-1-yl)phenyl)thiazole)-5-sulfonamido)benzoic acid

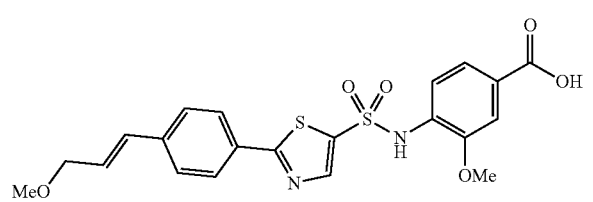 [SMILES: COC/C=C/c1ccc(-c2ncc(S(=O)(=O)Nc3ccc(C(=O)O)cc3OC)s2)cc1]

Synthesis of 2-(4-bromophenyl)thiazole-5-sulfonyl chloride

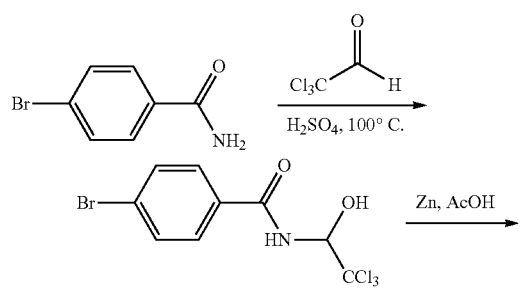

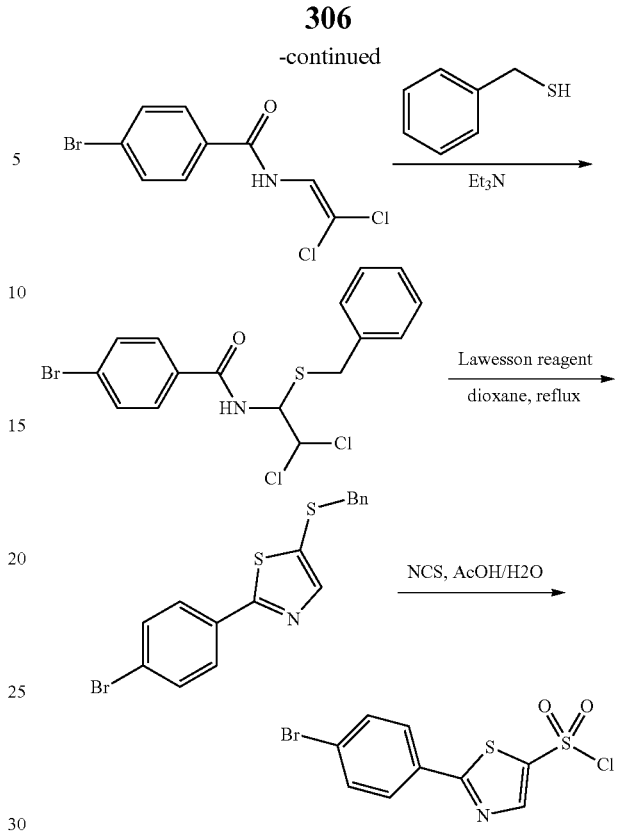

2-(4-bromophenyl)thiazole-5-sulfonyl chloride is prepared according to reported procedures for the regioisomer. (Demydchuk, Bogdan A. et al. Synthetic Communications, 2012, 42(19), 2866-2875. Note: The wrong regioisomer is assigned in the original paper.)

Step 1. Synthesis of 4-bromo-N-(2,2,2-trichloro-1-hydroxyethyl)benzamide

A solution of 4-bromobenzamide (20 g, 100 mmol) and chloral (16.2 g, 110 mmol) in toluene (200 mL) was stirred for overnight at 100° C. The resulting mixture was concentrated and purified by reverse flash chromatography to give 4-bromo-N-(2,2,2-trichloro-1-hydroxyethyl)benzamide as a white solid (21 g, 60%).

Step 2. Synthesis of 4-bromo-N-(2,2-dichlorovinyl)benzamide

A solution of 4-bromo-N-(2,2,2-trichloro-1-hydroxyethyl)benzamide (21 g, 60 mmol), Zn (7.9 g, 120 mmol) in AcOH (200 mL) was stirred for overnight at room temperature. The resulting mixture was filtered through celite and the filtrate was concentrated. The mixture was purified by reverse flash chromatography to give 4-bromo-N-(2,2-dichlorovinyl)benzamide as a white solid (10 g, 55%).

Step 3. Synthesis of N-(1-(benzylthio)-2,2-dichloroethyl)-4-bromobenzamide

A solution of 4-bromo-N-(2,2-dichlorovinyl)benzamide (10 g, 34 mmol), benzyl mercaptan (4.2 g, 34 mmol) and TEA (3.43 g, 34 mmol) in 2-propanol (100 mL) was stirred for 24 h at room temperature. The resulting mixture was concentrated and the residue was purified by reverse flash chromatography to N-(1-(benzylthio)-2,2-dichloroethyl)-4-bromobenzamide as a white solid (12 g, 80%).

Step 4. Synthesis of 5-(benzylthio)-2-(4-bromophenyl)thiazole

A solution of N-(1-(benzylthio)-2,2-dichloroethyl)-4-bromobenzamide (12 g, 28 mmol), Lawesson reagent (11.6 g, 28 mmol) in dioxane (100 mL) was stirred for overnight at 110° C. The mixture was acidified with HCl (1N, aq). The mixture was diluted with EtOAc/water and the organic layer was separated, washed with water, brine, dried, filtered and concentrated. The residue was purified by reverse flash chromatography to give 5-(benzylthio)-2-(4-bromophenyl)thiazole as a white solid (8 g, 69%).

Step 5. Synthesis of 2-(4-bromophenyl)thiazole-5-sulfonyl chloride

A solution of 5-(benzylthio)-2-(4-bromophenyl)thiazole (6 g, 16.6 mmol) in H₂O (100 mL) and AcOH (400 mL) was stirred for 10 min at 0° C. NCS (8.85 g, 66.2 mmol) was added in three portions at 0° C. The resulting mixture was stirred for overnight at room temperature. The precipitated solids were collected by filtration after H₂O (100 mL) was added. The solids was azeotroped with THF to give 2-(4-bromophenyl)thiazole-5-sulfonyl chloride as a white solid (4.0351 g, 71%). ESI-MS m/z: 339.90 [M+H]⁺. ¹H NMR (400 MHz, DMSO-d₆) δ 7.95-7.77 (m, 3H), 7.75-7.61 (m, 2H).

Step 6. Synthesis of methyl 4-((2-(4-bromophenyl)thiazole)-5-sulfonamido)-3-methoxybenzoate

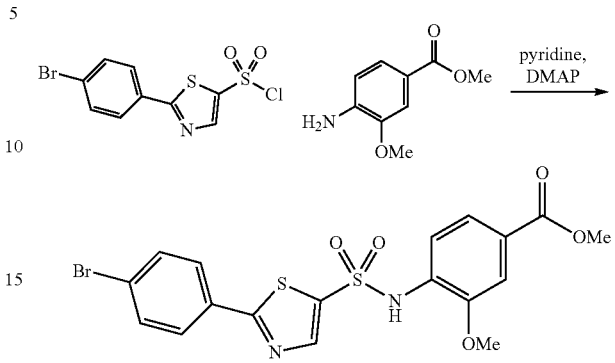

To 2-(4-bromophenyl)thiazole-5-sulfonyl chloride (0.5 g, 1.477 mmol) in pyridine (1.477 ml) was added DMAP (0.018 g, 0.148 mmol) and methyl 4-amino-3-methoxybenzoate (0.535 g, 2.95 mmol) respectively and the resulting mixture was stirred at rt for 2 h. The mixture was diluted with DCM and HCl (1M). The organic layer was separated, dried over Na₂SO₄, filtered, and concentrated. The residue was purified by CombiFlash to give methyl 4-((2-(4-bromophenyl)thiazole)-5-sulfonamido)-3-methoxybenzoate (330 mg, 46%) as a white crystal.

Step 7. Synthesis of (E)-3-methoxy-4-((2-(4-(3-methoxyprop-1-en-1-yl)phenyl)thiazole)-5-sulfonamido)benzoic acid

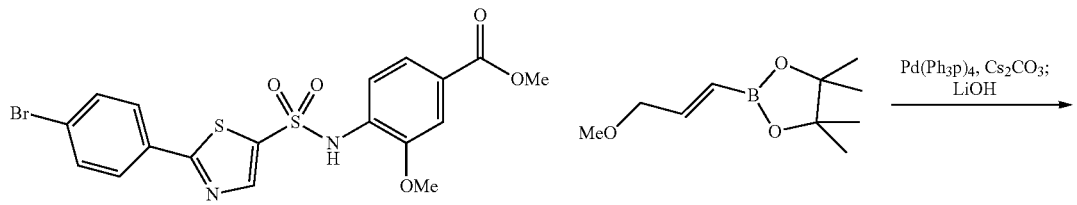

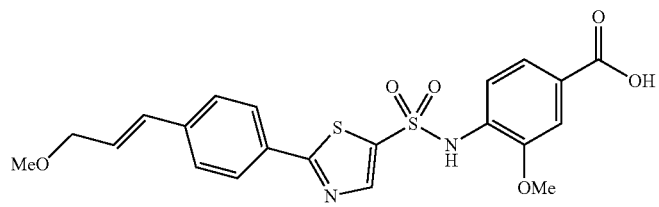

To a mixture of cesium carbonate (23.66 mg, 0.073 mmol), methyl 4-((2-(4-bromophenyl)thiazole)-4-sulfonamido)-3-methoxybenzoate (27 mg, 0.056 mmol) and (E)-2-(3-methoxyprop-1-en-1-yl)-4,4,5,5-tetramethyl-1,3,2-dioxaborolane (13.3 mg, 0.067 mmol) in Toluene (0.8 ml) and MeOH (0.200 ml) was added Pd(Ph3p)4 (6.46 mg, 5.59 µmol). The resulting mixture was stirred at 100° C. in microwave reactor for 45 min. To the mixture was added LiOH (1M) (447 µl, 0.447 mmol) and the resulting mixture was stirred at 100° C. in microwave reactor for 30 min. The mixture was diluted with EtOAc/1N HCl, the organic layer was separated, washed with water, brine, dried, filtered and concentrated. The residue was purified by HPLC to give (E)-3-methoxy-4-((2-(4-(3-methoxyprop-1-en-1-yl)phenyl)thiazole)-5-sulfonamido)benzoic acid (10 mg, 0.022 mmol, 38.9% yield). ESI-MS m/z: 459.1 [M−H]⁻; ¹H NMR (400 MHz, Chloroform-d) δ 8.01 (s, 1H), 7.81 (d, J=8.1 Hz, 2H), 7.75-7.64 (m, 3H), 7.47 (d, J=1.5 Hz, 1H), 7.41 (d, J=8.2 Hz, 2H), 6.60 (d, J=16.0 Hz, 1H), 6.36 (dt, J=16.0, 5.7 Hz, 1H), 4.09 (dd, J=5.7, 1.6 Hz, 2H), 3.84 (s, 3H), 3.39 (s, 3H).

Examples 427 and 450 are prepared analogous to the synthesis of Example 449 where (E)-2-(3-methoxyprop-1-en-1-yl)-4,4,5,5-tetramethyl-1,3,2-dioxaborolane in step 7 is replaced with (5,6,7,8-tetrahydronaphthalen-2-yl)boronic acid and 2-(1-cyclopropylvinyl)-4,4,5,5-tetramethyl-1,3,2-dioxaborolane respectively.

Example 451: 3-methoxy-4-((2-(4-(4-phenylcyclohexyl)phenyl)thiazole)-5-sulfonamido)benzoic acid

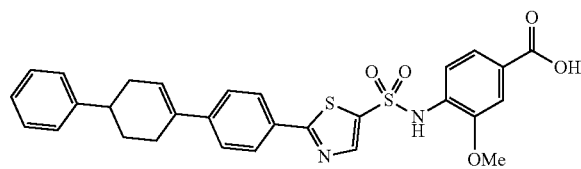 [SMILES: COc1cc(C(=O)O)ccc1NS(=O)(=O)c1cnc(-c2ccc(C3=CCC(c4ccccc4)CC3)cc2)s1]

Step 1. Synthesis of methyl 3-methoxy-4-((2-(2',3',4',5'-tetrahydro-[1,1':4',1''-terphenyl]-4-yl)thiazole)-5-sulfonamido)benzoate

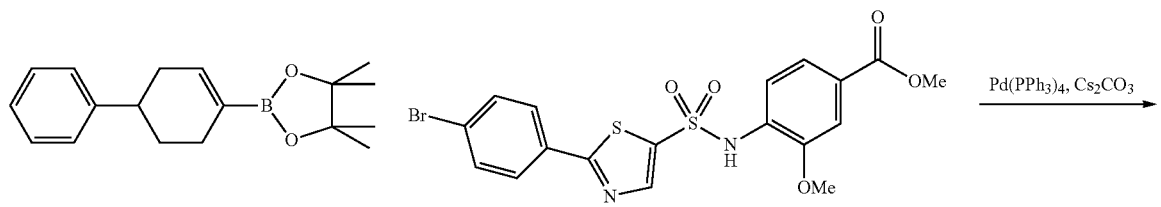

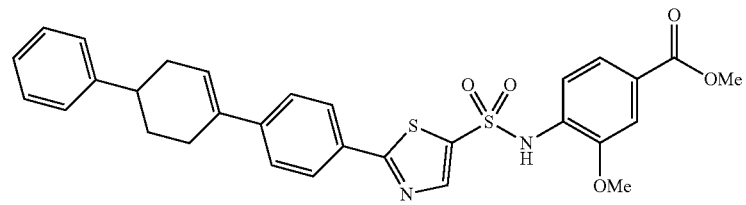

To 4,4,5,5-tetramethyl-2-(1,2,3,6-tetrahydro-[1,1'-biphenyl]-4-yl)-1,3,2-dioxaborolane (28.2 mg, 0.099 mmol), methyl 4-((2-(4-bromophenyl) thiazole)-5-sulfonamido)-3-methoxybenzoate (40 mg, 0.083 mmol), cesium carbonate (35.1 mg, 0.108 mmol) in toluene (0.8 ml)/MeOH (0.200 ml) was added cesium carbonate (35.1 mg, 0.108 mmol), Pd(PPh$_3$)$_4$ (7.65 mg, 6.62 μmol) and the mixture was stirred at 100° C. in microwave reactor for 30 min, The mixture was diluted with EtOAc/1N HCl, and the organic layer was separated, washed with water, brine, dried, filtered and concentrated. The residue was purified by column chromatography eluting with 0-60% EtOAc/cyclohexane to give methyl 3-methoxy-4-((2-(2',3',4',5'-tetrahydro-[1,1':4',1"-terphenyl]-4-yl) thiazole)-5-sulfonamido)benzoate (21 mg, 0.037 mmol, 45.3% yield).

Step 2. Synthesis of 3-methoxy-4-((2-(2',3',4',5'-tetrahydro-[1,1':4',1"-terphenyl]-4-yl)thiazole)-5-sulfonamido)benzoic acid

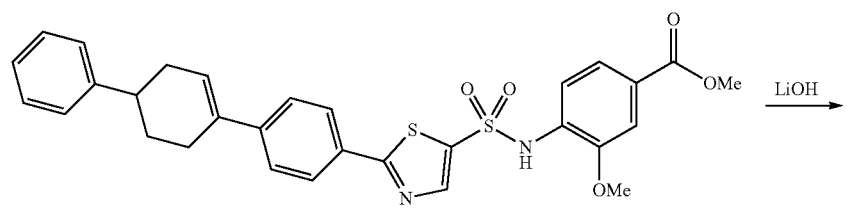

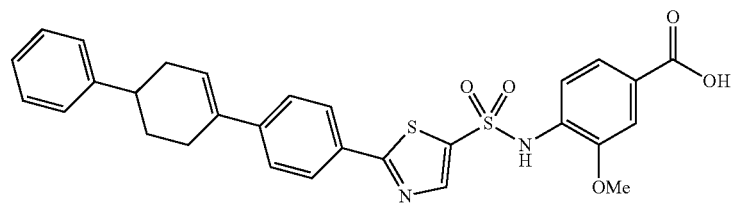

To a solution of methyl 3-methoxy-4-((2-(2',3',4',5'-tetrahydro-[1,1':4',1"-terphenyl]-4-yl)thiazole)-5-sulfonamido)benzoate in THF (1 ml) was added LiOH (1 N, 143 μl, 0.143 mmol), the resulting mixture was stirred at 120° C. in microwave reactor for 30 min. The mixture was diluted with EtOAc/1N HCl, the organic layer was separated, washed with water, brine, dried, filtered and concentrated. The residue was purified by column chromatography eluting with 0-60% EtOAc/cyclohexane to give 3-methoxy-4-((2-(2',3',4',5'-tetrahydro-[1,1':4',1"-terphenyl]-4-yl)thiazole)-5-sulfonamido)benzoic acid (6.5 mg, 0.012 mmol, 83% yield). ESI-MS m/z: 545.1 [M−H]⁻.

Example 452: 3-methoxy-4-((2-(4-(4-phenylcyclohexyl)phenyl)thiazole)-5-sulfonamido)benzoic acid

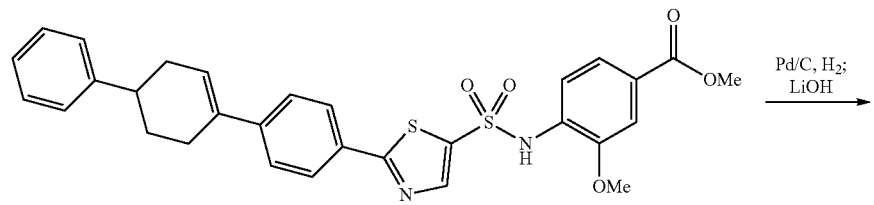

-continued

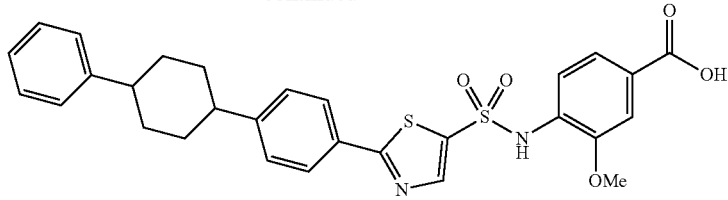

To methyl 3-methoxy-4-((2-(2',3',4',5'-tetrahydro-[1,1':4',1''-terphenyl]-4-yl)thiazole)-5-sulfonamido)benzoate (13 mg, 0.023 mmol), Pd—C (4.93 mg, 4.64 µmol) was added tetrahydrofuran (1 ml) and the resulting mixture was stirred at 60° C. for 14 h under 60 PSI $H_2$ atmosphere. Another portion of Pd—C (15 mg) in MeOH (0.5 ml) was added and the resulting mixture was stirred at 60° C. for 2 days under 60 PSI $H_2$ atmosphere. The mixture was filtered through celite and concentrated.

The residue was dissolved in THF (1 ml) and LiOH (1N, 232 µl, 0.232 mmol) was added, the resulting mixture was stirred at 120° C. in microwave reactor for 30 min. The mixture was diluted with EtOAc/1N HCl, the organic layer was separated, washed with water, brine, dried, filtered and concentrated. The residue was purified by column chromatography eluting with 0-60% EtOAc/cyclohexane to 3-methoxy-4-((2-(4-(4-phenylcyclohexyl)phenyl) thiazole)-5-sulfonamido)benzoic acid (8 mg, 0.015 mmol, 62.9% yield). ESI-MS m/z: 547.1 [M−H]⁻.

Example 453: is prepared analogous to the synthesis of Example 449 where (4-(4,4-dimethylcyclohexyl)phenyl)boronic acid is used in Suzuki coupling step.

Example 454: 4-((2-(4,4-dimethylcyclohex-1-en-1-yl)thiazole)-4-sulfonamido)-3-methoxybenzoic acid

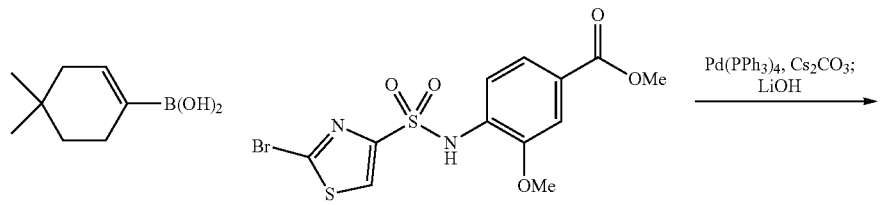

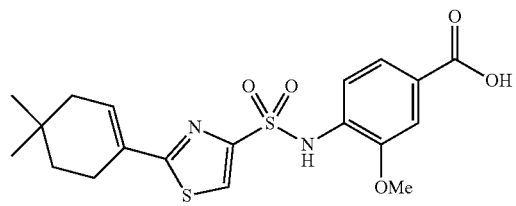

A mixture of (4,4-dimethylcyclohex-1-en-1-yl)boronic acid (22.69 mg, 0.147 mmol), methyl 4-((2-bromothiazole)-4-sulfonamido)-3-methoxybenzoate (50 mg, 0.123 mmol), Pd(PPh$_3$)$_4$ (14.19 mg, 0.012 mmol), cesium carbonate (52.0 mg, 0.160 mmol) in toluene (1.4 ml)/MeOH (0.350 ml) was stirred at 120° C. in microwave reactor for 30 min.

To the mixture was added LiOH (1N, 737 μl, 0.737 mmol) and the mixture was stirred at 120° C. in microwave reactor for 30 min. The mixture was diluted with EtOAc/HCl (1N) and the organic layer was separated, washed with water, brine, dried, filtered and concentrated. The residue was purified by column chromatography on silica gel eluting with 0 to 10% MeOH/DCM to give 4-((2-(4,4-dimethylcyclohex-1-en-1-yl) thiazole)-4-sulfonamido)-3-methoxybenzoic acid (18 mg, 0.043 mmol, 34.7% yield). ESI-MS m/z: 545.1 [M−H]⁻.

Example 457: 4-((2-(4,4-dimethylcyclohexyl)thiazole)-4-sulfonamido)-3-methoxybenzoic acid To 4-((2-(4,4-dimethylcyclohex-1-en-1-yl)thiazole)-4-sulfonamido)-3-methoxybenzoic acid (10 mg, 0.024 mmol) and Pd—C (10.07 mg, 9.47 μmol) was added MeOH (1 ml) and the resulting mixture was stirred under 50 PSI H$_2$ at 70° C. for 1 day. The mixture was filtered and concentrated to give 4-((2-(4,4-dimethylcyclohexyl)thiazole)-4-sulfonamido)-3-methoxybenzoic acid (10.4 mg). ESI-MS m/z: 523.1 [M−H]⁻.

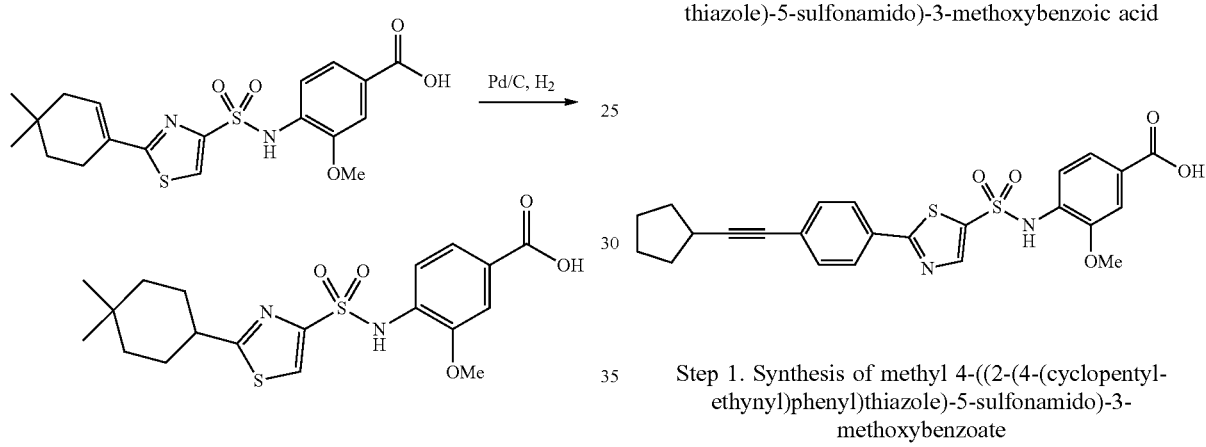

Example 455: 4-((2-(4-(cyclopentylethynyl)phenyl)thiazole)-5-sulfonamido)-3-methoxybenzoic acid

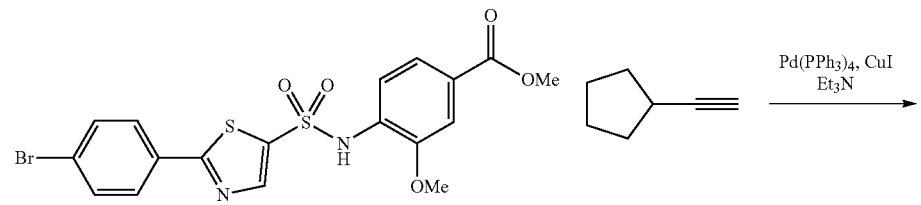

Step 1. Synthesis of methyl 4-((2-(4-(cyclopentylethynyl)phenyl)thiazole)-5-sulfonamido)-3-methoxybenzoate

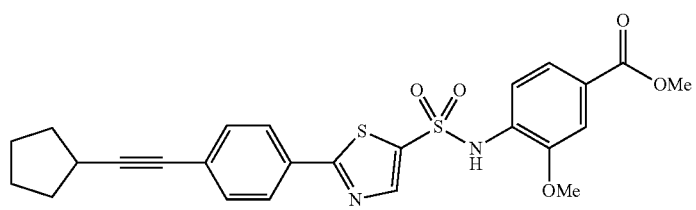

To methyl 4-((2-(4-bromophenyl)thiazole)-5-sulfonamido)-3-methoxybenzoate (36.5 mg, 0.081 mmol), ethynylcyclopentane (11.50 mg, 0.122 mmol), copper(I) iodide (3.10 mg, 0.016 mmol) and Pd(PPh$_3$)$_4$ (9.41 mg, 8.14 µmol) in DMF (1 ml) was added TEA (227 µl, 1.628 mmol) and the resulting mixture was stirred at 100° C. for 1.5 h in a microwave reactor. The mixture was diluted with EtOAc/HCl (1N), and the organic layer was separated, washed with water, brine, dried, filtered and concentrated.

To the residue was added THF (1 ml), water (0.5 ml) and LiOH (1N, 651 µl, 0.651 mmol), the resulting mixture was stirred at 120° C. in microwave reactor for 30 min. The mixture was diluted with EtOAc/HCl (1N) and the organic layer was separated, washed with water, brine, dried, filtered and concentrated. The residue was purified via column chromatography on silica gel eluting with 0-50% EtOAc/cyclohexane to give methyl 4-((2-(4-(cyclopentylethynyl)phenyl)-thiazole)-5-sulfonamido)-3-methoxybenzoate. (14 mg, 0.028 mmol, 38.9% yield). ESI-MS m/z: 495.1 [M−H]⁻.

Step 2. Synthesis of 4-((2-(4-(cyclopentylethynyl)phenyl)thiazole)-5-sulfonamido)-3-methoxybenzoic acid To methyl 4-((2-(4-(cyclopentylethynyl)phenyl)-thiazole)-5-sulfonamido)-3-methoxybenzoate (14 mg, 0.028 mmol) in tetrahydrofuran (1 ml) was added LiOH (1N, 282 µl, 0.282 mmol) and the resulting mixture was stirred at 100° C. for 30 min in microwave reactor. To the mixture was added MeOH (0.3 ml) and stirred at 140° C. for 10 h in microwave reactor. The mixture was diluted with EtOAc/HCl (1N) and the organic layer was separated, washed with water, brine, dried, filtered and concentrated give 4-((2-(4-(cyclopentylethynyl)phenyl)thiazole)-5-sulfonamido)-3-methoxybenzoic acid (15 mg). ESI-MS m/z: 481.1 [M−H]⁻; ¹H NMR (400 MHz, Methanol-d4) δ 8.14 (s, 1H), 7.82-7.74 (m, 2H), 7.69 (dd, J=8.3, 1.7 Hz, 1H), 7.63 (d, J=8.3 Hz, 1H), 7.51 (d, J=1.8 Hz, 1H), 7.48-7.41 (m, 2H), 3.81 (s, 3H), 2.84 (p, J=7.5 Hz, 1H), 2.11-1.92 (m, 2H), 1.90-1.51 (m, 6H).

Example 456: 4-((2-(4-(4,4-dimethylcyclohexyl)phenyl)benzo[d]thiazole)-5-sulfonamido)-3-methoxybenzoic acid

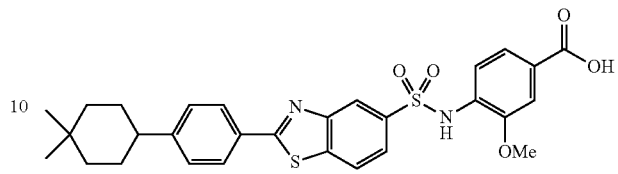

Step 1. Synthesis of methyl 4-((2-chlorobenzo[d]thiazole)-5-sulfonamido)-3-methoxybenzoate

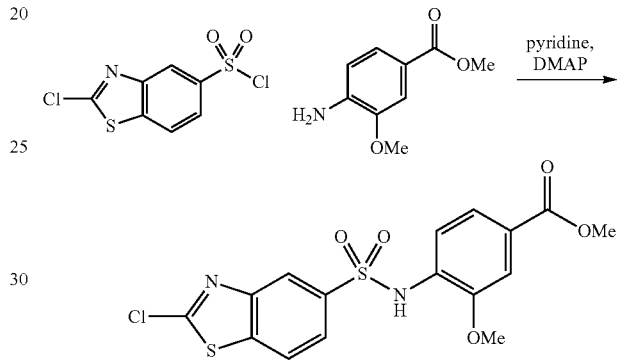

To a mixture of 2-chlorobenzo[d]thiazole-5-sulfonyl chloride (200 mg, 0.746 mmol), methyl 4-amino-3-methoxybenzoate (203 mg, 1.119 mmol) in DCM (3 ml) was added pyridine (241 µl, 2.98 mmol) and DMAP (9.11 mg, 0.075 mmol). The resulting mixture was stirred at RT for 3 h, then concentrated, the residue was purified by column chromatography on silica gel eluting with 0-40% EtOAc/Cyclohexane to give methyl 4-((2-chlorobenzo[d]thiazole)-5-sulfonamido)-3-methoxybenzoate (195 mg, 63%). 1H NMR (500 MHZ, Chloroform-d) δ 8.39 (dd, J=1.6, 0.8 Hz, 1H), 7.92-7.76 (m, 2H), 7.57 (d, J=1.1 Hz, 2H), 7.42 (s, 1H), 7.39 (t, J=1.1 Hz, 1H), 3.83 (s, 3H), 3.76 (s, 3H).

Step 2. Synthesis of 4-((2-(4-(4,4-dimethylcyclohexyl)phenyl)benzo[d]thiazole)-5-sulfonamido)-3-methoxybenzoic acid

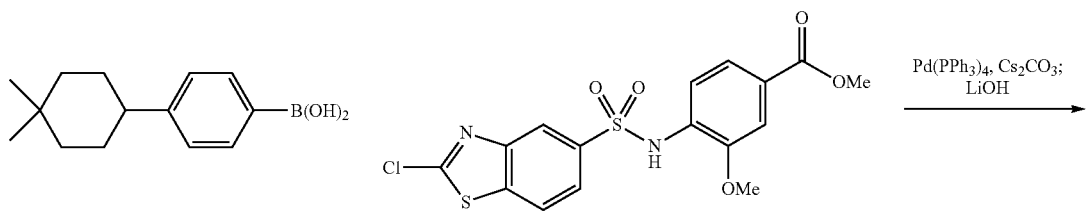

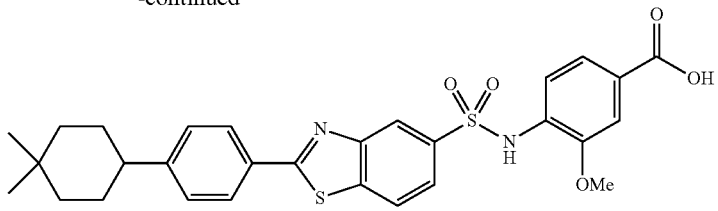

A mixture of (4-(4,4-dimethylcyclohexyl)phenyl)boronic acid (23.61 mg, 0.102 mmol), methyl 4-((2-chlorobenzo[d]thiazole)-5-sulfonamido)-3-methoxybenzoate (35 mg, 0.085 mmol), Pd(PPh$_3$)$_4$ (9.80 mg, 8.48 μmol), cesium carbonate (35.9 mg, 0.110 mmol) in toluene (0.8 ml)/MeOH (0.200 ml) was stirred at 120° C. in microwave reactor for 30 min. To the mixture was added LiOH (509 μl, 0.509 mmol) and the resulting mixture was stirred at 100° C. in microwave reactor for 45 min. The mixture was diluted with EtOAc/HCl (1N) and the organic layer was separated, washed with water, brine, dried, filtered and concentrated. The residue was purified by column chromatography on silica gel eluting with 0-50% to give 4-((2-(4-(4,4-dimethylcyclohexyl)phenyl)benzo[d]thiazole)-5-sulfonamido)-3-methoxybenzoic acid (22 mg, 0.040 mmol, 47.1% yield). ESI-MS m/z: 549.1 [M−H]$^-$; 1H NMR (500 MHz, Methanol-d$_4$) δ 8.49 (d, J=1.8 Hz, 1H), 8.08-7.92 (m, 3H), 7.79 (dd, J=8.5, 1.8 Hz, 1H), 7.61 (d, J=1.7 Hz, 2H), 7.44-7.36 (m, 2H), 3.75 (s, 3H), 2.51 (tt, J=11.8, 4.0 Hz, 1H), 1.79-1.57 (m, 4H), 1.57-1.46 (m, 2H), 1.37 (td, J=13.0, 4.2 Hz, 2H), 1.00 (s, 3H), 0.97 (s, 3H).

Example 323 and Example 363 are prepared analogous to the synthesis of Example 456 wherein (4-fluorophenyl)boronic acid, (4-cyclohexylphenyl)boronic acid is used in the step 2 Suzuki coupling respectively.

Example 458 and Example 460 are prepared analogous to the synthesis of Example 359 where (4-(4,4-dimethylcyclohexyl)phenyl)boronic acid or 4,4,5,5-tetramethyl-2-(4-((1r,4r)-4-(trifluoromethyl)cyclohexyl)phenyl)-1,3,2-dioxaborolane is used in the Suzuki coupling step respectively.

Example 459: 4-((2-(6-(4,4-dimethylcyclohex-1-en-1-yl)naphthalen-2-yl)thiazole)-4-sulfonamido)-3-methoxybenzoic acid

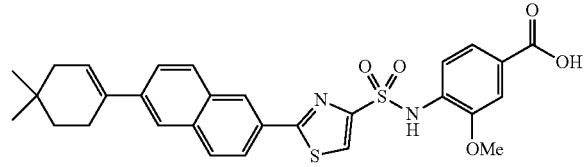 [SMILES: COc1cc(C(=O)O)ccc1NS(=O)(=O)c1csc(-c2ccc3cc(C4=CCC(C)(C)CC4)ccc3c2)n1]

Step 1. Synthesis of 2-bromo-6-(4,4-dimethylcyclohex-1-en-1-yl)naphthalene

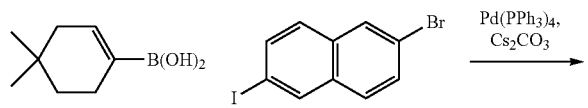

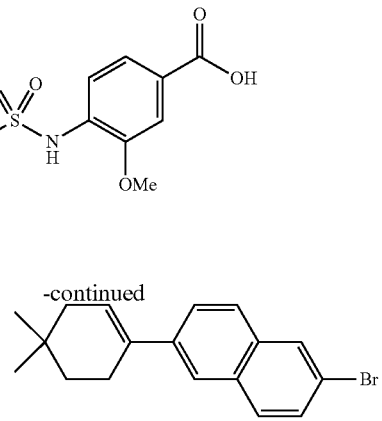

A mixture of (4,4-dimethylcyclohex-1-en-1-yl) boronic acid (100 mg, 0.649 mmol), 2-bromo-6-iodonaphthalene (216 mg, 0.649 mmol), Pd(PPh$_3$) 4 (37.5 mg, 0.032 mmol), cesium carbonate (275 mg, 0.844 mmol) in toluene (3 ml)/MeOH (0.750 ml) was stirred at 100° C. in microwave reactor for 45 min. The mixture was diluted with EtOAc/water and the organic layer was separated, washed with water, brine, dried, filtered and concentrated. The residue was purified by column chromatography on silica gel eluting with 0-30% EtOAc/cyclohexane to give 2-bromo-6-(4,4-dimethylcyclohex-1-en-1-yl) naphthalene (160 mg, 0.508 mmol, 78% yield).

Step 2. Synthesis of 2-(6-(4,4-dimethylcyclohex-1-en-1-yl)naphthalen-2-yl)-4,4,5,5-tetramethyl-1,3,2-dioxaborolane

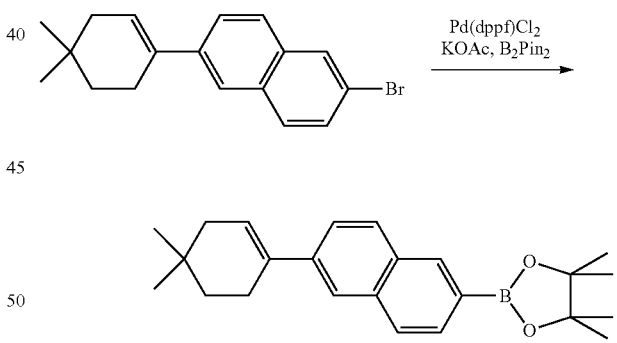

To a mixture of potassium acetate (145 mg, 1.475 mmol), 2-bromo-6-(4,4-dimethylcyclohex-1-en-1-yl) naphthalene (155 mg, 0.492 mmol), 4,4,4',4',5,5,5',5'-octamethyl-2,2'-bi(1,3,2-dioxaborolane) (187 mg, 0.738 mmol) and Pd(dppf)Cl$_2$ (17.99 mg, 0.025 mmol) was added Dioxane (3 ml) and the resulting mixture was stirred at 125° C. in microwave reactor for 3 h, and then 110° C. for 14 h at oil bath. The mixture was diluted with EtOAc/water, the organic layer was separated, washed with water, brine, dried, filtered and concentrated. The residue was purified by column chromatography on silica gel eluting with 0-60% EtOAc/cyclohexane to give 2-(6-(4,4-dimethylcyclohex-1-en-1-yl) naphthalen-2-yl)-4,4,5,5-tetramethyl-1,3,2-dioxaborolane (118 mg, 0.326 mmol, 66.2% yield).

Step 3. Synthesis of 4-((2-(6-(4,4-dimethylcyclohex-1-en-1-yl)naphthalen-2-yl)thiazole)-4-sulfonamido)-3-methoxybenzoic acid

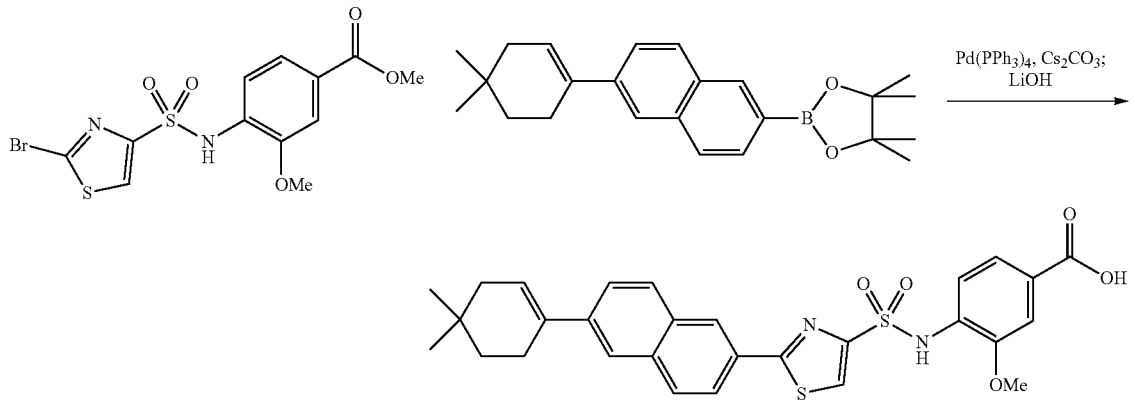

4-((2-(6-(4,4-dimethylcyclohex-1-en-1-547.1yl)naphthalen-2-yl)thiazole)-4-sulfonamido)-3-methoxybenzoic acid is prepared analogous to the synthesis of Example 403. ESI-MS m/z: 547.1 [M−H]⁻.

Example 477: 4-((4″-(tert-butyl)-2-fluoro-2″,3″,4″,5″-tetrahydro-[1,1′:4′,1″-terphenyl])-3-sulfonamido)-3-methoxybenzoic acid

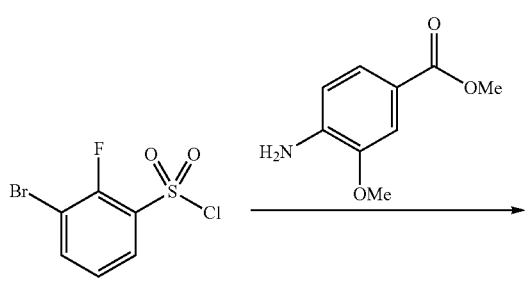

Synthesis of methyl 4-((4′-chloro-2-fluoro-[1,1′-biphenyl])-3-sulfonamido)-3-methoxybenzoate

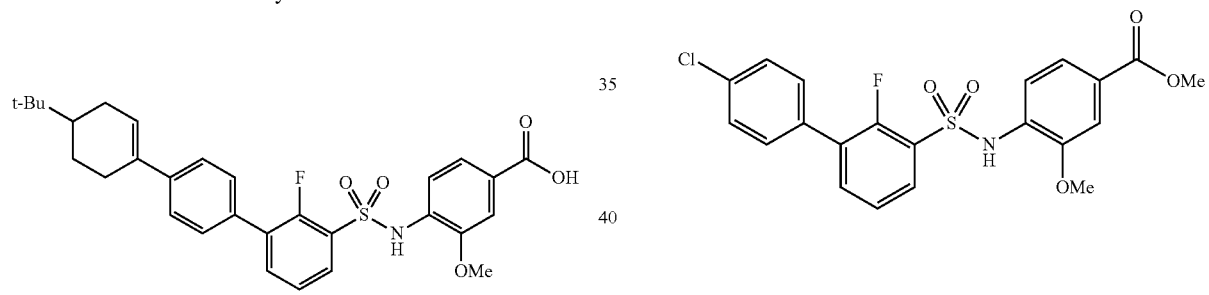

Step 1. Synthesis of methyl 4-((3-bromo-2-fluorophenyl)sulfonamido)-3-methoxybenzoate Methyl 4-((3-bromo-2-fluorophenyl)sulfonamido)-3-methoxybenzoate is prepared analogous to the synthesis of methyl 4-((5-bromopyridine)-3-sulfonamido)-3-methoxybenzoate as in Example 433.

Step 2. Synthesis of methyl 4-((4′-chloro-2-fluoro-[1,1′-biphenyl])-3-sulfonamido)-3-methoxybenzoate A solution of methyl 4-(3-bromo-2-fluorobenzenesulfonamido)-3-methoxybenzoate 1 (2 g, 4.78 mmol), (4-chlorophenyl)boronic acid (900 mg, 5.7 mmol), Pd(dppf)Cl₂ (700 mg, 0.96 mmol) and K₃PO₄ (3.04 g, 14.3 mmol) in 1,4-dioxane (20 mL) was stirred for overnight at 80° C. under nitrogen atmosphere. The mixture was diluted with EtOAc/water and the organic layer was separated, washed with water, brine, dried, filtered and concentrated. The residue was purified by reverse flash chromatography to give methyl 4-((4′-chloro-2-fluoro-[1,1′-biphenyl])-3-sulfonamido)-3-methoxybenzoate as a yellow solid (800 mg, 37%). ESI-MS m/z: 450.88 [M+H]⁺.

Step 3. Synthesis of methyl 4-((4"-(tert-butyl)-2-fluoro-2",3",4",5"-tetrahydro-[1,1':4',1"-terphenyl])-3-sulfonamido)-3-methoxybenzoate

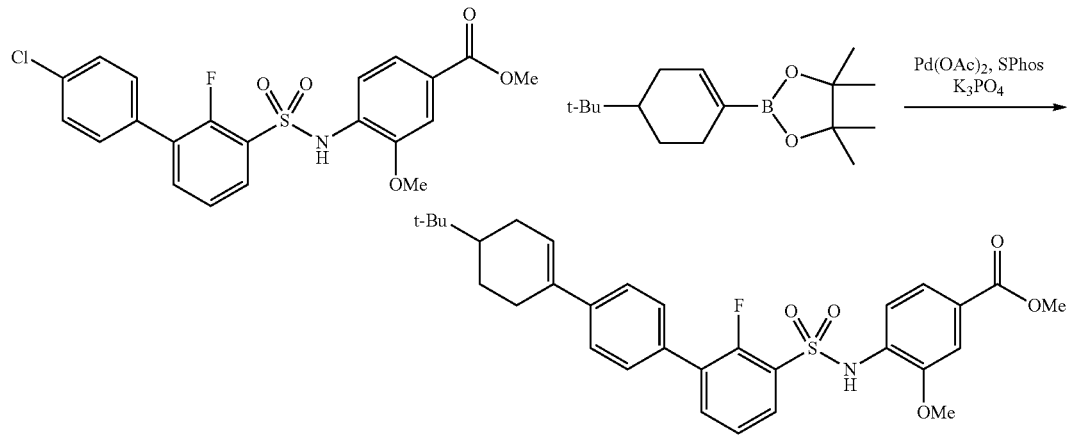

A mixture of methyl 4-{4'-chloro-2-fluoro-[1,1'-biphenyl]-3-sulfonamido}-3-methoxybenzoate (300 mg, 0.667 mmol), 4-tert-butylcyclohex-1-en-1-ylboronic acid (182 mg, 1.00 mmol), SPhos Pd G1 (90 mg, 0.13 mmol), Pd(OAc)$_2$ (30 mg, 0.13 mmol), K$_3$PO$_4$ (424 mg, 2.00 mmol) in THF (5 mL) and H$_2$O (5 mL) was stirred with microwave radiation for 30 min at 110° C. The mixture was diluted with EtOAc/water and the organic layer was separated, washed with water, brine, dried, filtered and concentrated. The residue was purified by reverse flash chromatography to give methyl 4-((4"-(tert-butyl)-2-fluoro-2",3",4",5"-tetrahydro-[1,1':4',1"-terphenyl])-3-sulfonamido)-3-methoxybenzoate as a yellow solid (240 mg, 65%). ESI-MS m/z: 538.68 [M+H]$^+$.

Step 4. Synthesis of 4-((4"-(tert-butyl)-2-fluoro-2",3",4",5"-tetrahydro-[1,1':4',1"-terphenyl])-3-sulfonamido)-3-methoxybenzoic acid 4-((4"-(tert-butyl)-2-fluoro-2",3",4",5"-tetrahydro-[1,1': 4',1"-terphenyl])-3-sulfonamido)-3-methoxybenzoic acid is prepared from methyl 4-((4"-(tert-butyl)-2-fluoro-2",3",4", 5"-tetrahydro-[1,1':4',1"-terphenyl])-3-sulfonamido)-3-methoxybenzoate analogous to step 2 in the synthesis of Example 403.

Example 478: 4-((4'-((1r,4r)-4-(tert-butyl)cyclohexyl)-2-fluoro-[1,1'-biphenyl])-3-sulfonamido)-3-methoxybenzoic acid and Example 479: 4-((4'-((1s,4s)-4-(tert-butyl)cyclohexyl)-2-fluoro-[1,1'-biphenyl])-3-sulfonamido)-3-methoxybenzoic acid Example 478

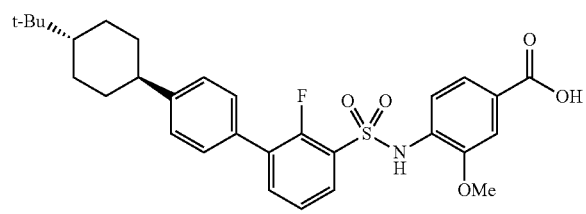 [SMILES: COc1cc(C(=O)O)ccc1NS(=O)(=O)c1cccc(-c2ccc(C3=CCC(C(C)(C)C)CC3)cc2)c1F]

Example 479

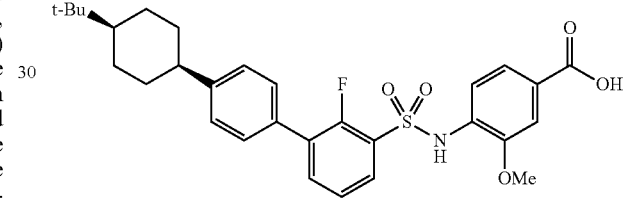

Step 1. Synthesis of methyl 4-((4'-(4-(tert-butyl)cyclohexyl)-2-fluoro-[1,1'-biphenyl])-3-sulfonamido)-3-methoxybenzoate

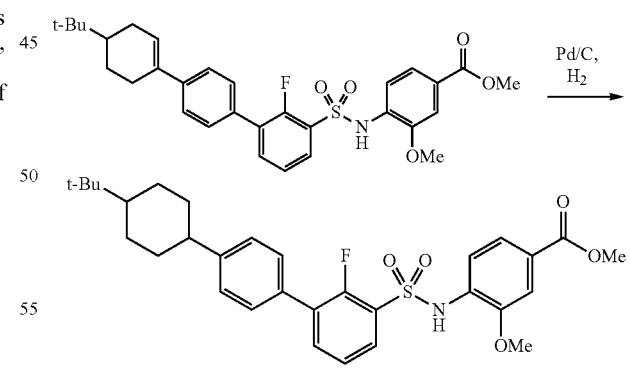

A solution of the methyl 4-((4"-(tert-butyl)-2-fluoro-2", 3",4",5"-tetrahydro-[1,1':4',1"-terphenyl])-3-sulfonamido)-3-methoxybenzoate (200 mg, 0.45 mmol), Pd/C (25 mg, 0.22 mmol) in methanol (10 mL) was stirred for 6 h at room temperature under H$_2$ atmosphere. The mixture was filtered through celite and the filtrate was concentrated. The residue was purified to give the methyl 4-((4'-(4-(tert-butyl)cyclohexyl)-2-fluoro-[1,1'-biphenyl])-3-sulfonamido)-3- methoxybenzoate as a black oil (200 mg crude) and used in the next step directly without further purification. ESI-MS m/z: 554.23 [M+H]⁺.

Step 2. Synthesis of 4-((4'-((1r,4r)-4-(tert-butyl)cyclohexyl)-2-fluoro-[1,1'-biphenyl])-3-sulfonamido)-3-methoxybenzoic acid and 4-((4'-((1s,4s)-4-(tert-butyl)cyclohexyl)-2-fluoro-[1,1'-biphenyl])-3-sulfonamido)-3-methoxybenzoic acid A solution of methyl 4-((4'-(4-(tert-butyl)cyclohexyl)-2-fluoro-[1,1'-biphenyl])-3-sulfonamido)-3-methoxybenzoate (250 mg, 0.45 mmol), LiOH (300 mg, 12.53 mmol) in MeOH (8 mL) and H₂O (4 mL) was stirred for overnight at room temperature. The mixture was acidified to pH 5 with HCl (aq.). The mixture was diluted with EtOAc/water and the organic layer was separated, washed with water, brine, dried, filtered and concentrated. The residue was purified by reverse flash chromatography to give two desired compounds.
4-((4'-((1r,4r)-4-(tert-butyl)cyclohexyl)-2-fluoro-[1,1'-biphenyl])-3-sulfonamido)-3-methoxybenzoic acid (45.3 mg) was obtained as a white solid. ESI-MS m/z: 538.20 [M–H]⁻. ¹H NMR (400 MHz, Chloroform-d) δ 7.95-7.87 (m, 1H), 7.70 (s, 1H), 7.68-7.61 (m, 2H), 7.55 (d, J=8.4 Hz, 1H), 7.50 (d, J=1.7 Hz, 1H), 7.46-7.39 (m, 2H), 7.35-7.28 (m, 3H), 3.87 (s, 3H), 2.52 (t, J=12.2 Hz, 1H), 2.05-1.90 (m, 4H), 1.52 (d, J=12.2 Hz, 1H), 1.46 (d, J=12.4 Hz, 1H), 1.30-1.16 (m, 2H), 1.16-1.06 (m, 1H), 0.92 (s, 9H). 4-((4'-((1s,4s)-4-(tert-butyl)cyclohexyl)-2-fluoro-[1,1'-biphenyl])-3-sulfonamido)-3-methoxybenzoic acid (60.6 mg) was obtained as a white solid. ESI-MS m/z: 538.15 [M–H]⁻. ¹H NMR (400 MHz, Chloroform-d) δ 7.96-7.87 (m, 1H), 7.73-7.63 (m, 3H), 7.56 (d, J=8.4 Hz, 1H), 7.51 (d, J=1.7 Hz, 1H), 7.49-7.40 (m, 4H), 7.32 (d, J=7.8 Hz, 1H), 3.87 (s, 3H), 3.10 (s, 1H), 2.33-2.25 (m, 2H), 1.83 (s, 2H), 1.30-1.13 (m, 3H), 0.83 (s, 9H).

Example 474: 4-((2-fluoro-4'-((1s,4s)-4-(trifluoromethyl)cyclohexyl)-[1,1'-biphenyl])-3-sulfonamido)-3-methoxybenzoic acid and Example 475: 4-((2-fluoro-4'-((1r,4r)-4-(trifluoromethyl)cyclohexyl)-[1,1'-biphenyl])-3-sulfonamido)-3-methoxybenzoic acid Example 474

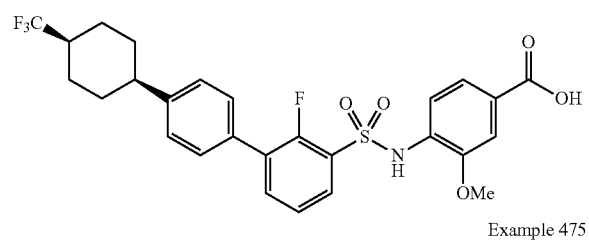

Example 475

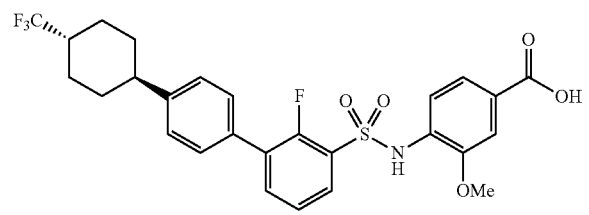

Example 474 and Example 475 are prepared analogous to the synthesis of Example 478 and Example 479 wherein (4-(trifluoromethyl)cyclohex-1-en-1-yl)boronic acid is used in the Suzuki coupling step.

Example 473 and Example 476 are prepared analogous to the synthesis of Example 477 wherein 2-(4,4-difluorocyclohex-1-en-1-yl)-4,4,5,5-tetramethyl-1,3,2-dioxaborolane and 2-(4,4-dimethylcyclohex-1-en-1-yl)-4,4,5,5-tetramethyl-1,3,2-dioxaborolane is used in the Suzuki coupling step respectively.

Example 461: 3-methoxy-4-((2-phenyloxazole)-4-sulfonamido)benzoic acid

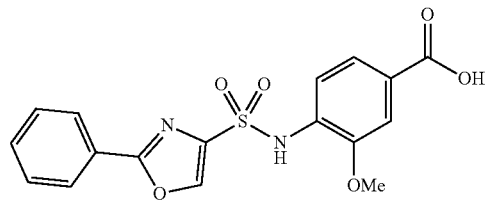 [SMILES: COc1cc(C(=O)O)ccc1NS(=O)(=O)c1coc(-c2ccccc2)n1]

2-phenyloxazole-4-sulfonyl chloride is synthesized according to literature procedure (Trujillo, John I. et al, Synlett, 2015, 26(12), 1764-1768).

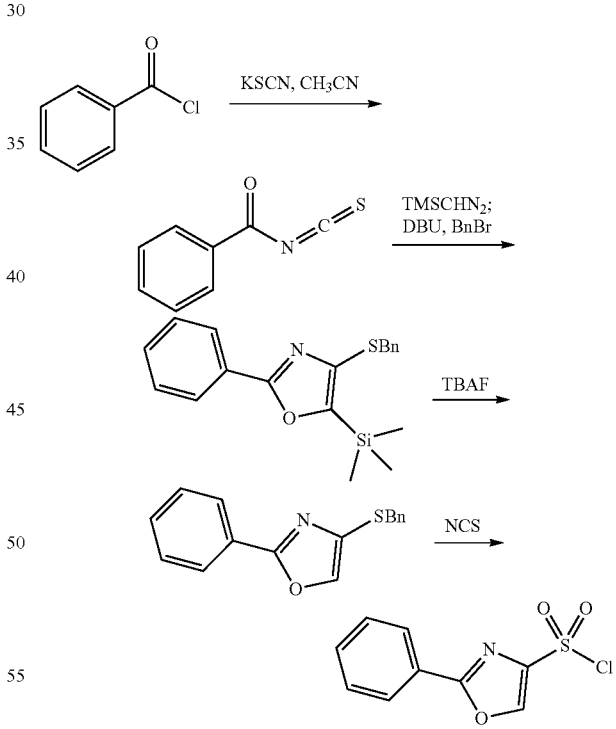

Step 1. Synthesis of benzoyl isothiocyanate

A solution of benzoyl chloride (2 g, 14.2 mmol) and potassium thiocyanate (1.38 g, 14.2 mmol) in acetonitrile (30 mL) was stirred for overnight at room temperature. The resulting mixture was concentrated to give benzoyl isothiocyanate as white solid (2.5 g crude) and used in the next step directly without further purification.

Step 2. Synthesis of 4-(benzylthio)-2-phenyl-5-(trimethylsilyl)oxazole

TMSCHN$_2$ (2.10 g, 18.3 mmol) was added dropwise at 0° C. to the solution of benzoyl isothiocyanate (2 g crude) in CH$_2$Cl$_2$ (100 mL) The mixture was stirred for 1 h at 0° C. DBU (3.44 g, 22.5 mmol) and BnBr (2.09 g, 12.2 mmol) was added dropwise at 0° C. The mixture was stirred for overnight at room temperature. The solution was diluted with DCM/water and the organic layer was separated, dried and concentrated to give 4-(benzylthio)-2-phenyl-5-(trimethylsilyl)oxazole as a black oil (3 g crude). This material was used in the next step directly without further purification.

Step 3. Synthesis of 4-(benzylthio)-2-phenyloxazole

A solution of 4-(benzylthio)-2-phenyl-5-(trimethylsilyl)oxazole (3 g crude) and 3 mL TBAF (1 M in THF) in THF (30 mL) was stirred for 30 min at room temperature. The mixture was diluted with EtOAc/water and the organic layer was separated, dried and concentrated. The residue was purified by reverse phase C18 column chromatography to give the 4-(benzylthio)-2-phenyloxazole as a white solid (650 mg).

Step 4. Synthesis of 2-phenyloxazole-4-sulfonyl chloride

A solution of 4-(benzylthio)-2-phenyloxazole (500 mg, 1.85 mmol) in AcOH (4 mL) and H$_2$O (1 mL) was stirred for 10 min at 0° C. NCS (998 mg, 1.49 mmol) was added in three portions. The mixture was stirred for 2 h at room temperature. The mixture was diluted with EtOAc/water and the organic layer was separated, dried and concentrated to give 2-phenyloxazole-4-sulfonyl chloride as a black oil (850 mg crude). This material was used in the next step directly without further purification.

Step 5. Synthesis of methyl 3-methoxy-4-((2-phenyloxazole)-4-sulfonamido)benzoate

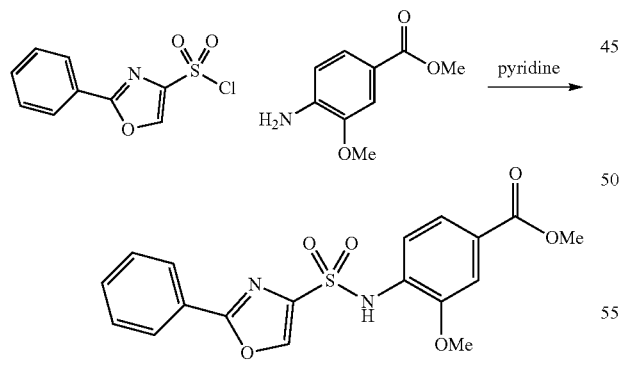

A solution of methyl 4-amino-3-methoxybenzoate (446 mg, 2.4 mmol) and pyridine (26 mg, 0.33 mmol) in CH$_2$Cl$_2$ (5 mL) was treated for 10 min at room temperature under nitrogen atmosphere. 2-phenyloxazole-4-sulfonyl chloride (400 mg crude) in CH$_2$Cl$_2$ (2 mL) was added dropwise. The mixture was stirred for 3 h at room temperature. The solution was diluted with DCM/water and the organic layer was separated, dried and concentrated. The residue was purified by reverse phase C18 column chromatography to give methyl 3-methoxy-4-((2-phenyloxazole)-4-sulfonamido)benzoate (80 mg) as a yellow oil. ESI-MS m/z: 389.00 [M+H]$^+$.

Step 6. Synthesis of 3-methoxy-4-((2-phenyloxazole)-4-sulfonamido)benzoic acid

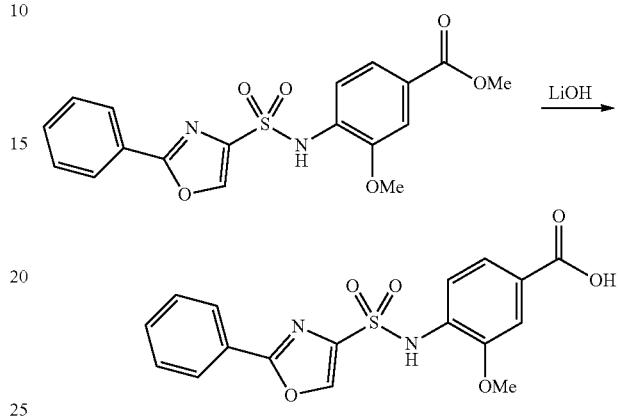

A solution of methyl 3-methoxy-4-((2-phenyloxazole)-4-sulfonamido)benzoate (80 mg, 0.2 mmol), LiOH (49 mg, 2.0 mmol) in 1,4-dioxane (4 mL) and water (2 mL) was stirred for 8 h. The mixture was adjusted pH=5 with 1M HCl, and extracted with EtOAc, the organic layer was separated, dried, and concentrated. The residue was purified by reverse phase C18 column chromatography to give 3-methoxy-4-((2-phenyloxazole)-4-sulfonamido)benzoic acid as a yellow solid (20.6 mg, 27%). ESI-MS m/z: 375.00 [M+H]$^+$ 1H NMR (400 MHz, DMSO-d$_6$) δ 12.92 (s, 1H), 10.22 (s, 1H), 8.87 (s, 1H), 8.02-7.95 (m, 2H), 7.66-7.50 (m, 4H), 7.50-7.43 (m, 2H), 3.70 (s, 3H).

Examples 413, 414, 415, 416, 417, 418, 465, are prepared analogous to the synthesis of Example 461 where benzoyl chloride is replaced with corresponding substituted benzoyl chloride.

Example 466: 4-((2-(4-isopropylphenyl)oxazole)-4-sulfonamido)-3-methoxybenzoic acid

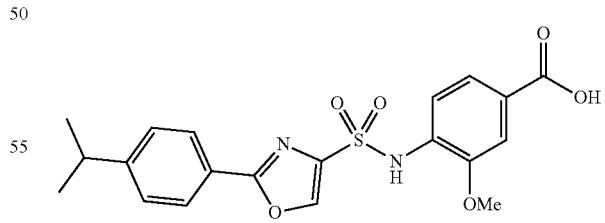

Synthesis of 2-(4-iodophenyl)oxazole-4-sulfonyl chloride 2-(4-iodophenyl)oxazole-4-sulfonyl chloride is synthesized in a similar way as 2-phenyloxazole-4-sulfonyl chloride in Example 461.

Step 2. Synthesis of methyl 3-methoxy-4-((2-(4-(prop-1-en-2-yl)phenyl)oxazole)-4-sulfonamido)benzoate

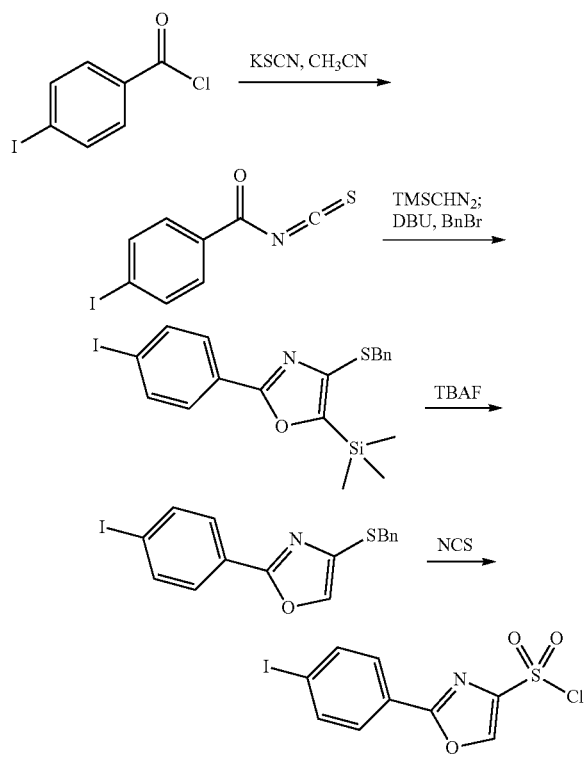

Step 1. Synthesis of methyl 4-((2-iodooxazole)-4-sulfonamido)-3-methoxybenzoate

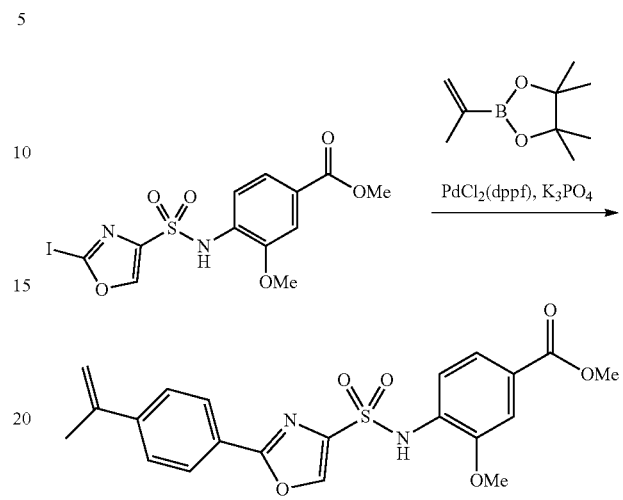

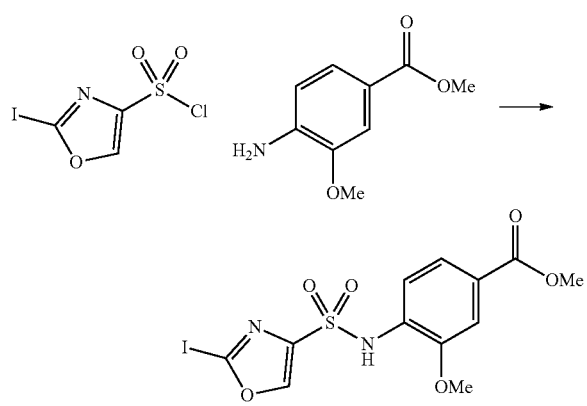

A solution of methyl 4-amino-3-methoxybenzoate (2 g, 8.34 mmol) and pyridine (107.0 mg, 1.36 mmol) in DCM (20 mL) was stirred for 10 min at room temperature under nitrogen atmosphere. 2-(4-iodophenyl)-1,3-oxazole-4-sulfonyl chloride (4.9 g crude) in CH$_2$Cl$_2$ (10 mL) was added dropwise. The mixture was stirred for 3 h at room temperature. The mixture was diluted with DCM/water and the organic layer was separated, dried and concentrated. The residue was purified by reverse phase C18 column chromatography to give methyl 4-((2-iodooxazole)-4-sulfonamido)-3-methoxybenzoate (2.7 g) as a yellow oil. ESI-MS m/z: 515.00 [M+H]$^+$.

A solution of methyl 4-((2-iodooxazole)-4-sulfonamido)-3-methoxybenzoate (300 mg, 0.58 mmol), prop-1-en-2-ylboronic acid (60 mg, 0.69 mmol), Pd(dppf)Cl$_2$ (32 mg, 0.04 mmol) and K$_3$PO$_4$ (85 mg, 0.39 mmol) in 1,4-dioxane (2 mL) for overnight at 80° C. under nitrogen atmosphere. The mixture was diluted with EtOAc/water and the organic layer was separated, dried and concentrated. The residue was purified by reverse phase C18 column chromatography to give methyl 3-methoxy-4-((2-(4-(prop-1-en-2-yl)phenyl)oxazole)-4-sulfonamido)benzoate (190 mg, 75%) as a yellow oil.

Step 3. Synthesis of methyl 4-((2-(4-isopropylphenyl)oxazole)-4-sulfonamido)-3-methoxybenzoate

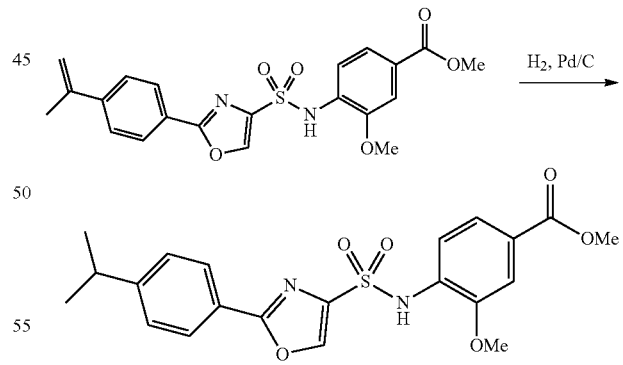

A solution of methyl 3-methoxy-4-((2-(4-(prop-1-en-2-yl)phenyl)oxazole)-4-sulfonamido)benzoate (190 mg, 0.427 mmol), Pd/C (22 mg, 0.21 mmol) in methanol (10 mL) was for 6 h at room temperature under H$_2$ atmosphere. The mixture was filtered through celite, and the filtrate was concentrated to give Synthesis of methyl 4-((2-(4-isopropylphenyl)oxazole)-4-sulfonamido)-3-methoxybenzoate as a black oil (150 mg crude) and used in the next step directly without further purification.

Step 4. Synthesis of 4-((2-(4-isopropylphenyl)oxazole)-4-sulfonamido)-3-methoxybenzoic acid 4-((2-(4-isopropylphenyl)oxazole)-4-sulfonamido)-3-methoxybenzoic acid is prepared similarly to step 6 in Example 461. ESI-MS m/z: 415.05 [M−H]⁻. ¹H NMR (400 MHz, DMSO-d₆) δ 10.23-10.15 (s, 1H), 8.84-8.78 (s, 1H), 7.93-7.88 (d, J=8.1 Hz, 2H), 7.51 (s, 1H), 7.50-7.39 (d, J=8.2 Hz, 4H), 3.70 (s, 3H), 3.00-2.96 (m, 1H), 1.25-1.22 (d, J=6.8 Hz, 6H).

Example 419, 420, 464, 467, 468 are prepared analogous to the synthesis of Example 466 where prop-1-en-2-ylboronic acid is replaced with the corresponding boronic acid.

Synthesis of 2-bromothiazole-4-sulfonyl chloride

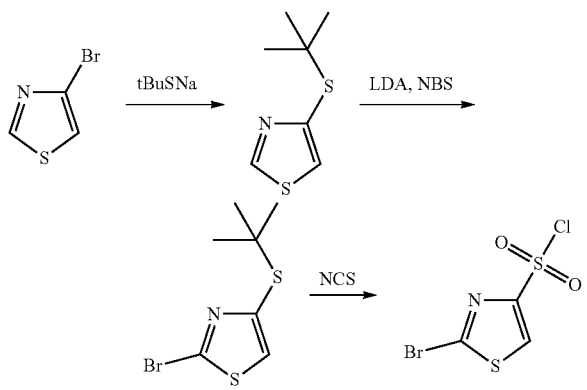

Step 1. Synthesis of 4-(tert-butylthio)thiazole

A mixture of 4-bromo-1,3-thiazole (1 g, 6.10 mmol) and (tert-butylsulfanyl)sodium (1.37 g, 12.19 mmol) in DMF was stirred for 2 h at 140° C. under nitrogen atmosphere. The resulting mixture was diluted with water (30 mL) and extracted with CH₂Cl₂ (3×30 mL). The combined organic layers were washed with brine, dried over anhydrous Na₂SO₄, filtered and concentrated. The residue was purified by reverse flash chromatography to give 4-(tert-butylthio)thiazole as a white solid (420 mg, 40%). ¹H NMR (500 MHz, Chloroform-d) δ 8.82 (t, J=1.8 Hz, 1H), 7.45 (d, J=2.0 Hz, 1H), 1.34 (d, J=1.3 Hz, 10H).

Step 2. Synthesis of 2-bromo-4-(tert-butylthio)thiazole

A solution of LDA (1.0 M, 2.3 ml) is added dropwise to a solution of 4-(tert-butylsulfanyl)-1,3-thiazole (200 mg, 1.15 mmol) in THF (40 ml) at −78° C. under nitrogen. After stirring at −78° C. for 10 minutes, solid NBS (247 mg, 1.39 mmol) is added in portions. The resulting mixture is stirred at −78° C. for 20 minutes and warmed to room temperature over a 1 hour period. The resulting mixture was quenched with NH₄Cl solution, extracted with CH₂Cl₂ (3×30 mL). The organic layers was combined, washed with brine, dried over anhydrous Na₂SO₄, filtered and concentrated. The residue was purified by reverse flash chromatography to give 2-bromo-4-(tert-butylthio)thiazole as a yellow oil (50 mg, 17%). ESI-MS m/z: 252 [M+H]⁺; ¹H NMR (500 MHz, Chloroform-d) δ 7.14 (s, 1H), 1.30 (s, 10H).

Step 3. Synthesis of 2-bromothiazole-4-sulfonyl chloride

To a solution of 2-bromo-4-(tert-butylsulfanyl)-1,3-thiazole (50 mg, 0.20 mmol) in acetic (0.4 ml) and water (0.1 ml) at 0° C. was added NCS (79 mg, 0.60 mmol) in three portions. The reaction was stirred for 15 min at 0° C. and then ambient temperature for 2 hours. The mixture was diluted with EtOAc/water, and the organic layer was separated, washed with water, brine, dried, filtered and concentrated to give 2-bromothiazole-4-sulfonyl chloride as crude product. ESI-MS m/z: 262 [M+H]⁺.

Example 524: 4-((2-(4-(4,4-dimethylcyclohexyl)-2-(trifluoromethyl)phenyl)thiazole)-4-sulfonamido)-2-fluoro-5-methoxybenzoic acid

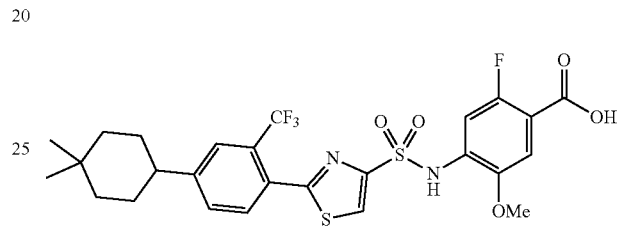

Step 1. Synthesis of methyl 4-((2-(4-chloro-2-(trifluoromethyl)phenyl)thiazole)-4-sulfonamido)-2-fluoro-5-methoxybenzoate

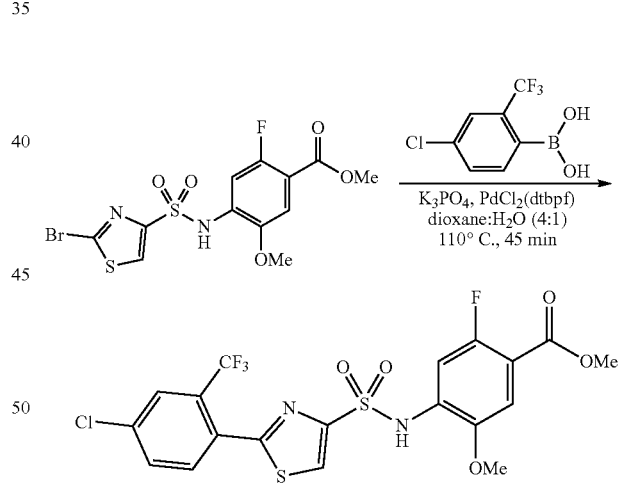

To a mixture of methyl 4-((2-bromothiazole)-4-sulfonamido)-2-fluoro-5-methoxybenzoate (120 mg, 0.282 mmol), (4-chloro-2-(trifluoromethyl)phenyl)boronic acid (63.3 mg, 0.282 mmol), and PdCl₂(dtbpf) (27.6 mg, 0.042 mmol) and K₃PO₄ (180 mg, 0.847 mmol) was added Dioxane (2.258 ml)/Water (0.564 ml). The reaction was heated at 110° C. for 45 minutes under microwave condition. Crude was filtered through silica and washed with ethyl acetate and concentrated to afford methyl 4-((2-(4-chloro-2-(trifluoromethyl)phenyl)thiazole)-4-sulfonamido)-2-fluoro-5-methoxybenzoate, which was directly use in next step. ESI-MS m/z: 525.0 [M+H]⁺.

Step 2. Synthesis of methyl 4-((2-(4-chloro-2-(trifluoromethyl)phenyl)thiazole)-4-sulfonamido)-2-fluoro-5-methoxybenzoate

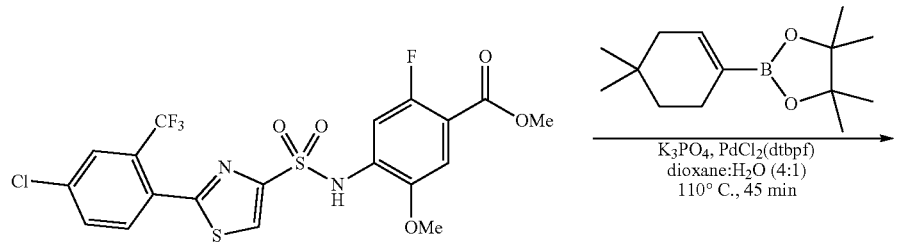

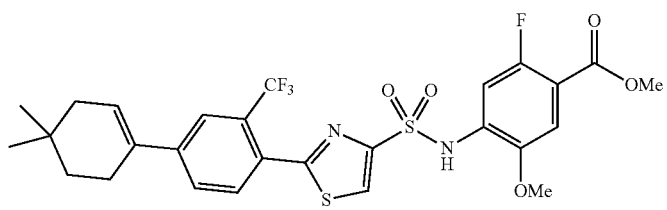

To a mixture of methyl 4-((2-(4-chloro-2-(trifluoromethyl)phenyl)thiazole)-4-sulfonamido)-2-fluoro-5-methoxybenzoate (0.148 g, 0.282 mmol), 2-(4,4-dimethylcyclohex-1-en-1-yl)-4,4,5,5-tetramethyl-1,3,2-dioxaborolane (0.080 g, 0.338 mmol), PdCl₂(dtbpf) (0.028 g, 0.042 mmol) and K₃PO₄ (0.180 g, 0.846 mmol), were added Dioxane (2.256 ml)/Water (0.564 ml). The reaction was heated at 110° C. for 45 minutes under microwave condition. Crude was filtered through silica and washed with ethyl acetate and concentrated to afford methyl 4-((2-(4',4'-dimethyl-3-(trifluoromethyl)-2',3',4',5'-tetrahydro-[1,1'-biphenyl]-4-yl)thiazole)-4-sulfonamido)-2-fluoro-5-methoxybenzoate which was directly used in next step. ESI-MS m/z: 599.1 [M+H]⁺.

Step 3. Synthesis of 4-((2-(4',4'-dimethyl-3-(trifluoromethyl)-2',3',4',5'-tetrahydro-[1,1'-biphenyl]-4-yl)thiazole)-4-sulfonamido)-2-fluoro-5-methoxybenzoic acid

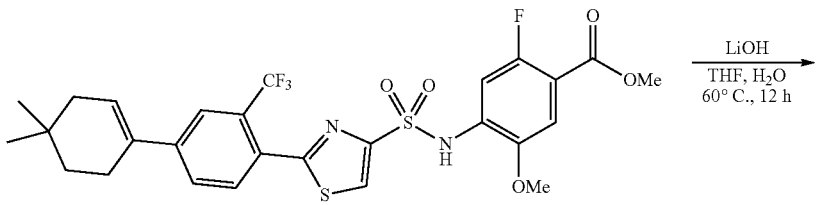

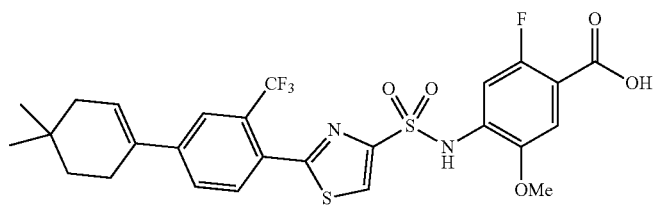

To a solution of methyl 4-((2-(4',4'-dimethyl-3-(trifluoromethyl)-2',3',4',5'-tetrahydro-[1,1'-biphenyl]-4-yl)thiazole)-4-sulfonamido)-2-fluoro-5-methoxybenzoate (0.169 g, 0.282 mmol) in THF (5.64 mL) was added lithium hydroxide (1M in water) (5.6 mL, 5.6 mmol) and the resulting mixture was heated at 60° C. for 12 h. Then reaction mixture was allowed to cool to room temperature and quenched with 1N HCl and extracted with EtOAc (×2). Combined organic layers was washed with brine and dried over Na$_2$SO$_4$, filtered, and concentrated. The crude was purified through reversed phase flash column chromatography eluting with water/acetonitrile (10% acetonitrile→90% acetonitrile) to provide 4-((2-(4',4'-dimethyl-3-(trifluoromethyl)-2',3',4',5'-tetrahydro-[1,1'-biphenyl]-4-yl)thiazole)-4-sulfonamido)-2-fluoro-5-methoxybenzoic acid (38 mg, 0.065 mmol, 23% yield) as white solid. ESI-MS m/z: 585.1 [M+H]$^+$; $^1$H NMR (500 MHz, DMSO-d$_6$) δ 13.14 (br, 1H), 10.34 (s, 1H), 8.66 (s, 1H), 7.89-7.82 (m, 2H), 7.72 (d, J=8.0 Hz, 1H), 7.37 (d, J=12.1 Hz, 1H), 7.32 (d, J=6.6 Hz, 1H), 6.43-6.38 (m, 1H), 3.75 (s, 3H), 2.48-2.40 (m, 2H), 2.07-1.99 (m, 2H), 1.52 (t, J=6.4 Hz, 2H), 0.95 (s, 6H).

Step 4. Synthesis of 4-((2-(4-(4,4-dimethylcyclohexyl)-2-(trifluoromethyl)phenyl)thiazole)-4-sulfonamido)-3-methoxybenzoic acid

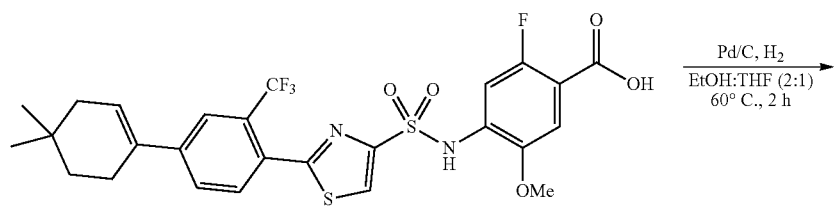

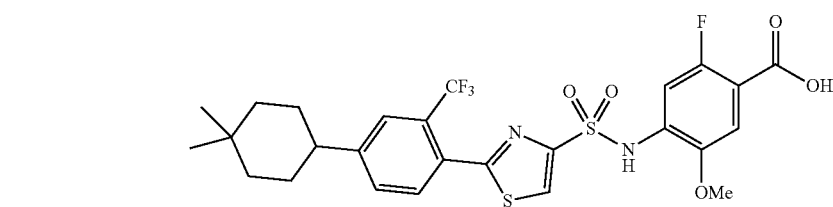

4-((2-(4',4'-dimethyl-3-(trifluoromethyl)-2',3',4',5'-tetrahydro-[1,1'-biphenyl]-4-yl)thiazole)-4-sulfonamido)-2-fluoro-5-methoxybenzoic acid (31 mg, 0.053 mmol) was dissolved in Ethanol (1.178 ml)/THF (0.589 ml). 5% Pd on carbon (56.4 mg, 0.027 mmol) was added and the reaction was heated at 60° C. for 2 h under hydrogen balloon. After 2 h, reaction mixture was filtered through silica then concentrated and purified in reversed phase flash column chromatography eluting with water/acetonitrile (30% acetonitrile→100% acetonitrile) to isolate 4-((2-(4-(4,4-dimethylcyclohexyl)-2-(trifluoromethyl)phenyl)thiazole)-4-sulfonamido)-3-methoxybenzoic acid (16.5 mg, 53%) as white solid. ESI-MS m/z: 587.1 [M+H]$^+$; 1H NMR (400 MHz, DMSO-d$_6$) δ 13.13 (br, 1H), 10.32 (s, 1H), 8.65 (s, 1H), 7.79-7.65 (m, 3H), 7.37 (d, J=12.1 Hz, 1H), 7.32 (d, J=6.6 Hz, 1H), 3.75 (s, 3H), 2.71-2.56 (m, 1H), 1.73-1.58 (m, 4H), 1.53-1.41 (m, 2H), 1.40-1.28 (m, 2H), 0.99 (s, 3H), 0.95 (s, 3H).

Example 670: 4-((2-(4-((1r,4r)-4-ethylcyclohexyl)phenyl)benzo[d]oxazole)-5-sulfonamido)-2-fluoro-5-methoxybenzoic acid

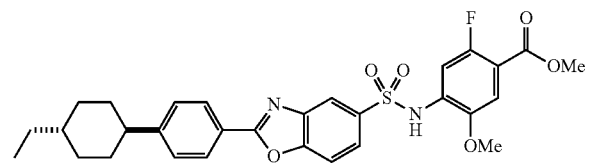

Step 1. Synthesis of -nitrobenzo[d]oxazole-2(3H)-thione

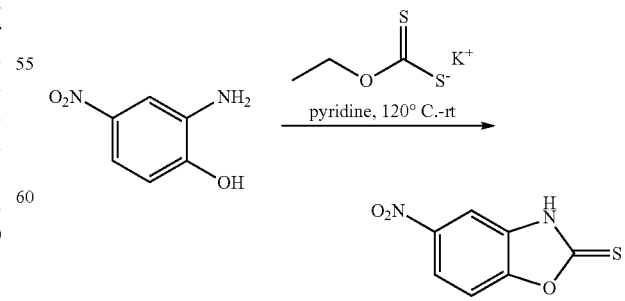

To a solution of 2-amino-4-nitrophenol (10.0 g, 65 mmol, 1.0 eq) in pyridine (60 mL) was added potassium O-ethyl carbonodithioate (12.5 g, 78 mmol, 1.2 eq). The mixture was heated to 120° C. for 6 h. Then the mixture was cooled to room temperature for 16 h. The mixture was concentrated. H$_2$O (100 mL) was added and extracted by DCM (50 mL×3), washed with brine (20 mL×3), dried over Na$_2$SO$_4$, filtered and concentrated. The crude was purified by silica gel column chromatography (Petroleum ether:EtOAc=30:1) to afford 5-nitrobenzo[d]oxazole-2(3H)-thione (6.0 g, 47.2%) as a brown solid. $^1$H NMR (300 MHz, DMSO-d$_6$): δ 8.20-8.17 (m, 1H), 7.94 (s, 1H), 7.73 (d, J=7.8 Hz, 1H) ppm. LCMS: 197.0 ([M+H]$^+$).

Step 2. Synthesis of
2-chloro-5-nitrobenzo[d]oxazole

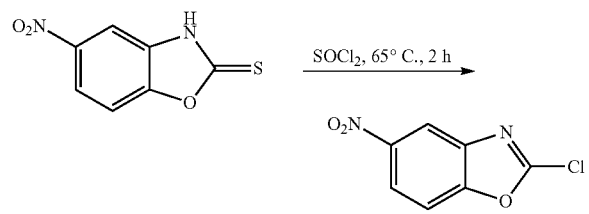

To a solution of 5-nitrobenzo[d]oxazole-2(3H)-thione ((6.0 g, 30 mmol, 1.0 eq) in SOCl$_2$ (30 mL) and the mixture was heated to 65° C. for 2 h. The mixture was concentrated. H$_2$O (50 mL) was added and extracted by EtOAc (30 mL×3), washed with brine (15 mL×3), dried over Na$_2$SO$_4$, filtered and concentrated. The crude was purified by silica gel column chromatography (Petroleum ether:EtOAc=50:1) to afford 2-chloro-5-nitrobenzo[d]oxazole (4.0 g, 66.6%) as a brown solid. $^1$H NMR (300 MHz, CDCl$_3$): δ 8.59 (s, 1H), 8.37-8.34 (m, 1H), 7.65 (d, J=8.7 Hz, 1H) ppm. LCMS: 198.9 ([M+H]$^+$).

Step 3. Synthesis of 2-(4-((1r,4r)-4-ethylcyclohexyl)
phenyl)-5-nitrobenzo[d]oxazole

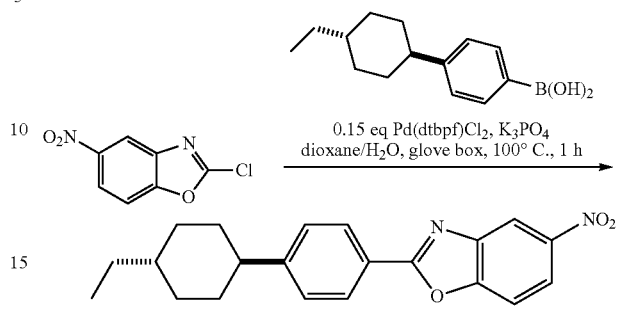

To a solution of 2-chloro-5-nitrobenzo[d]oxazole (700 mg, 3.5 mmol, 1.0 eq), (4-((1r,4r)-4-ethylcyclohexyl)phenyl) boronic acid (1.2 g, 5.3 mmol, 1.5 eq) and K$_3$PO$_4$ (2.2 g, 10.5 mmol, 3.0 eq) in dioxane:water (3.0 mL: 0.75 mL) was added Pd(dtbpf)Cl$_2$ (342 mg, 0.53 mmol, 0.15 eq). The mixture was stirred in glove box at 100° C. for 1 h. After completion of the reaction, the mixture was concentrated. The crude was purified by silica gel column chromatography (Petroleum ether:EtOAc=80:1) to afford 2-(4-((1r,4r)-4-ethylcyclohexyl)phenyl)-5-nitrobenzo[d]oxazole (700 mg, 56.9%) as a yellow solid. H NMR (300 MHz, DMSO-d$_6$): δ 8.65 (s, 1H), 8.35-8.31 (m, 1H), 8.15 (d, J=6.9 Hz, 2H), 8.03 (d, J=9.3 Hz, 1H), 7.51 (d, J=7.5 Hz, 2H), 2.64-2.59 (m, 1H), 1.87-1.83 (m, 4H), 1.54-1.42 (m, 2H), 1.23 (s, 3H), 1.11-1.03 (m, 2H), 0.89 (s, 3H) ppm. LCMS: 351.1 ([M+H]$^+$).

Step 4. Synthesis of 2-(4-((1r,4r)-4-ethylcyclohexyl)
phenyl)benzo[d]oxazol-5-amine

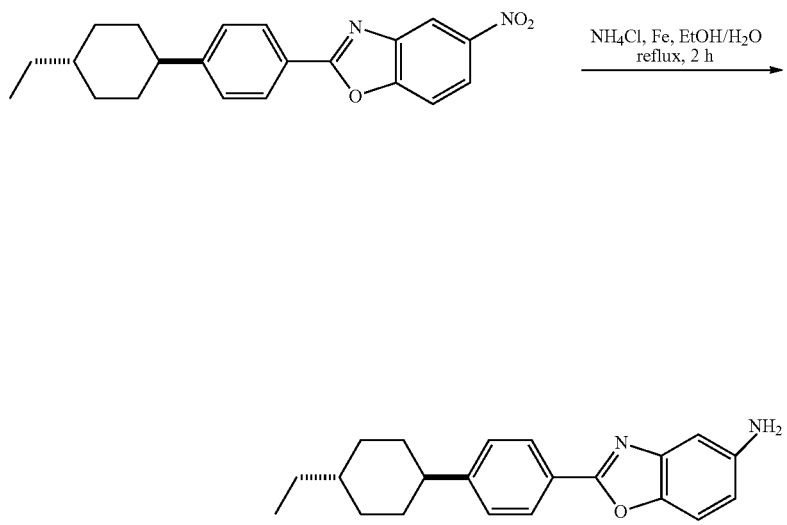

To a solution of 2-(4-((1r,4r)-4-ethylcyclohexyl)phenyl)-5-nitrobenzo[d]oxazole (700 mg, 2.0 mmol, 1.0 eq) and NH₄Cl (535 mg, 10.0 mmol, 5.0 eq) in EtOH:water (14.0 mL: 2.8 mL) was added Fe (560 mg, 10.0 mmol, 5.0 eq). The mixture was stirred at reflux for 2 h. After completion of the reaction, the mixture was filtered through a Celite pad, the solid was washed with MeOH (5 mL×5) and the filtrate was concentrated to give the crude product. The crude was purified by silica gel column chromatography (Petroleum ether:EtOAc=30:1) to afford 2-(4-((1r,4r)-4-ethylcyclohexyl)phenyl)benzo[d]oxazol-5-amine (600 mg, 93.7%) as a yellow solid.

$^1$H NMR (300 MHz, DMSO-$d_6$): δ 8.05-8.03 (m, 2H), 7.45-7.38 (m, 3H), 6.85 (d, J=2.1 Hz, 1H), 6.67-6.63 (m, 1H), 5.09 (s, 2H), 2.60-2.56 (m, 1H), 1.86-1.83 (m, 4H), 1.53-1.39 (m, 2H), 1.29-1.21 (m, 3H), 1.10-0.99 (m, 2H), 0.91-0.85 (m, 3H) ppm. LCMS: 321.1 ([M+H]$^+$).

Step 5. Synthesis of 2-(4-((1r,4r)-4-ethylcyclohexyl)phenyl)benzo[d]oxazole-5-sulfonyl chloride

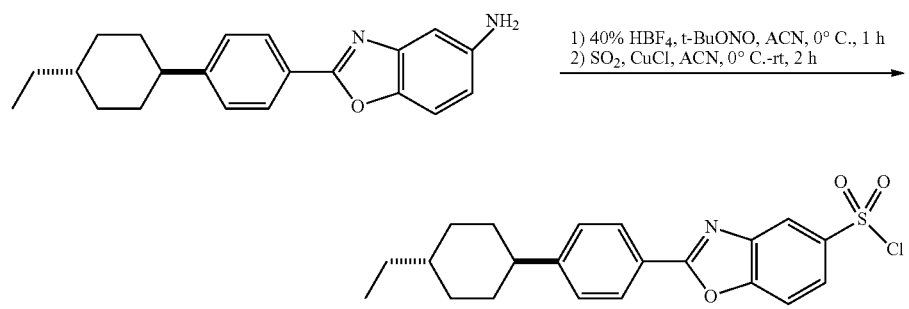

Step 5a: To a solution of 2-(4-((1r,4r)-4-ethylcyclohexyl)phenyl)benzo[d]oxazol-5-amine (500 mg, 1.6 mmol, 1.0 eq) in ACN (8.0 mL) was added HBF₄ (40% wt solution in water, 527 mg, 2.4 mmol, 1.5 eq) dropwise at 0° C. under N₂ atmosphere. Tert-butyl nitrite (185 mg, 1.8 mmol, 1.1 eq) was added by dropwise at 0° C. Then the reaction mixture was stirred at this temperature for 1 h.

Step 5b: SO₂ (g) was bubbled into a solution of CuCl (475 mg, 4.8 mmol, 3.0 eq) in ACN (7.0 mL) at 0° C. for 0.5 h. Then the solution (from step 5a) was added dropwise at 0° C. Then the reaction mixture was stirred at room temperature for 2 h. The mixture was concentrated. Water (10 mL) was added and extracted by DCM (10 mL×3), washed with brine (5 mL×3), dried over Na₂SO₄, filtered and concentrated. The crude was purified by silica gel chromatography (Petroleum ether:EtOAc=30:1) to afford 2-(4-((1r,4r)-4-ethylcyclohexyl)phenyl)benzo[d]oxazole-5-sulfonyl chloride (170 mg, 26.3%) as a yellow solid. $^1$H NMR (400 MHz, DMSO-$d_6$): δ 8.13 (d, J=8.0 Hz, 2H), 7.91 (s, 1H), 7.69 (s, 2H), 7.47 (d, J=8.0 Hz, 2H), 2.62-2.59 (m, 1H), 2.02-1.97 (m, 1H), 1.87-1.85 (m, 4H), 1.54-1.45 (m, 2H), 1.29-1.28 (m, 2H), 1.10-1.05 (m, 2H), 0.91-0.88 (m, 3H) ppm. LCMS: 404.0 ([M+H]$^+$).

Step 6 Synthesis of methyl 4-((2-(4-((1r,4r)-4-ethylcyclohexyl)phenyl)benzo[d]oxazole)-5-sulfonamido)-2-fluoro-5-methoxybenzoate

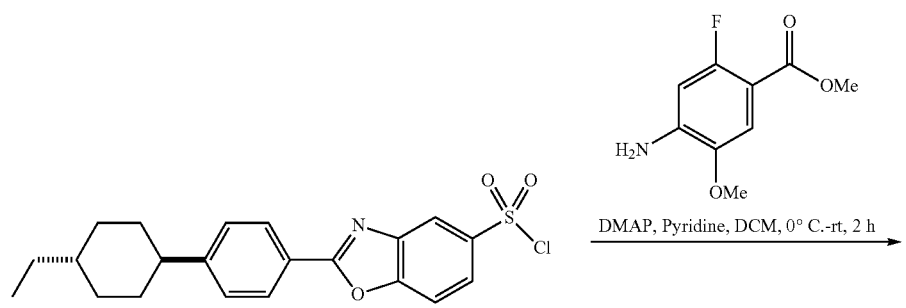

-continued

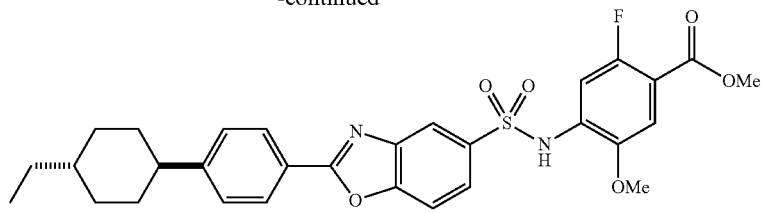

To a solution of methyl 4-amino-2-fluoro-5-methoxybenzoate (100 mg, 0.50 mmol, 1.0 eq), dried pyridine (119 mg, 1.5 mmol, 3.0 eq) and DMAP (12 mg, 0.1 mmol, 0.2 eq) in DCM (2 mL) was added dropwise 2-(4-((1r,4r)-4-ethylcyclohexyl)phenyl)benzo[d]oxazole-5-sulfonyl chloride (200 mg, 0.50 mmol, 1.0 eq) in DCM (0.3 mL) at 0° C. The reaction was stirred at room temperature for 2 h. The mixture was concentrated and the crude was purified by silica gel column chromatography (Petroleum ether:EtOAc=10:1) to afford methyl 4-((2-(4-((1r,4r)-4-ethylcyclohexyl)phenyl)benzo[d]oxazole)-5-sulfonamido)-2-fluoro-5-methoxybenzoate (180 mg, 63.6%) as a pink solid. LCMS: 567.0 ([M+H]$^+$).

Step 7

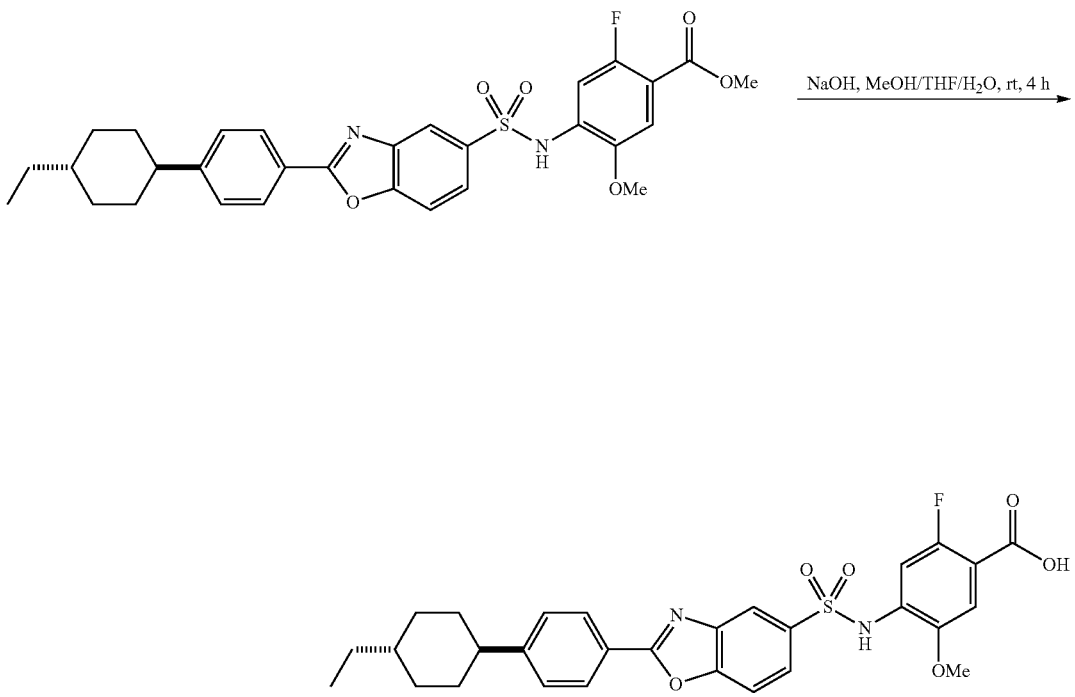

To a solution of methyl 4-((2-(4-((1r,4r)-4-ethylcyclohexyl)phenyl)benzo[d]oxazole)-5-sulfonamido)-2-fluoro-5-methoxybenzoate (160 mg, 0.28 mmol, 1.0 eq) in THF:MeOH:H₂O (2.0 mL: 2.0 mL: 2.0 mL) was added NaOH (90 mg, 2.24 mmol, 8.0 eq). The mixture was stirred at room temperature for 4 h. After completion, the mixture was concentrated, H₂O (4.0 mL) was added. The slurry was extracted with a mixture of DCM:MeOH=10:1 (2.0 mL×3). The aqueous phase was adjusted to pH=1-2 with HCl (2.5 mL, 2 N) at 0° C. and then extracted with DCM:MeOH=10:1 (3 mL×3), washed with brine (2 mL×3), dried over Na₂SO₄, filtered and concentrated. The crude was purified Prep-HPLC (Waters XBridge Prep C18 OBD, (CH₃CN:H₂O=80-95-100-9 min-40 mL, 0.1% CF₃COOH as additive) to afford 4-((2-(4-((1r,4r)-4-ethylcyclohexyl)phenyl)benzo[d]oxazole)-5-sulfonamido)-2-fluoro-5-methoxybenzoic acid (31.7 mg, 20.6%) as a white solid. ¹H NMR (300 MHz, DMSO-d₆): δ 13.13 (s, 1H), 10.30 (s, 1H), 8.26 (d, J=1.5 Hz, 1H), 8.14-8.11 (m, 2H), 8.00-7.91 (m, 2H), 7.49 (d, J=8.4 Hz, 2H), 7.27-7.18 (m, 2H), 3.66 (s, 3H), 2.63-2.54 (m, 1H), 1.87-1.83 (m, 4H), 1.54-1.43 (m, 2H), 1.28-1.24 (m, 3H), 1.11-1.00 (m, 2H), 0.92-0.87 (m, 3H) ppm. LCMS: 553.0 ([M+H]⁺).

Example 685: 2-fluoro-5-methoxy-4-((1-(4-((1s,4s)-4-(trifluoromethyl)cyclohexyl)phenyl)-1H-pyrazole)-4-sulfonamido)benzoic acid and Example 686: 2-fluoro-5-methoxy-4-((1-(4-((1r,4r)-4-(trifluoromethyl)cyclohexyl)phenyl)-1H-pyrazole)-4-sulfonamido)benzoic acid Example 685
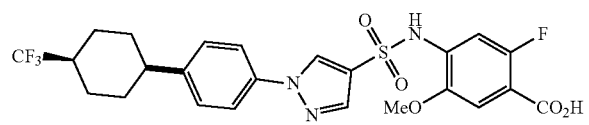

Example 686
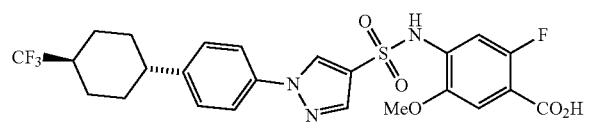

Step 1. Synthesis of methyl 4-((1-(4-chlorophenyl)-1H-pyrazole)-4-sulfonamido)-2-fluoro-5-methoxybenzoate

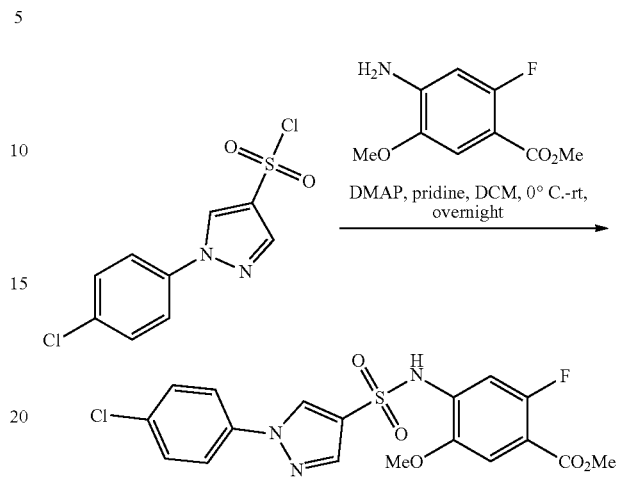

To a solution of methyl 4-amino-2-fluoro-5-methoxybenzoate (287 mg, 1.44 mmol, 1.0 eq), pyridine (341 mg, 4.32 mmol, 3.0 eq) and DMAP (35 mg, 0.3 mmol, 0.2 eq) in DCM (4 mL) was added dropwise 1-(4-chlorophenyl)-1H-pyrazole-4-sulfonyl chloride (400 mg, 1.44 mmol, 1.0 eq) in DCM (4 mL) at 0° C. The reaction was stirred at room temperature for overnight. The mixture was concentrated and the crude was purified by Prep-TLC (Petroleum ether:EtOAc=7:3) to afford methyl 4-((1-(4-chlorophenyl)-1H-pyrazole)-4-sulfonamido)-2-fluoro-5-methoxybenzoate (200 mg, 31.6%) as a yellow solid. ¹H NMR (300 MHz, DMSO-d₆): δ 10.15 (s, 1H), 9.23 (s, 1H), 8.12 (s, 1H), 7.93-7.90 (m, 2H), 7.61-7.58 (m, 2H), 7.34-7.29 (m, 2H), 3.81 (s, 3H), 3.75 (s, 3H). LCMS: 440.0, 442.0 ([M+H]⁺).

Step 2. Synthesis of methyl 2-fluoro-5-methoxy-4-((1-(4'-(trifluoromethyl)-2',3',4',5'-tetrahydro-[1,1'-biphenyl]-4-yl)-1H-pyrazole)-4-sulfonamido)benzoate

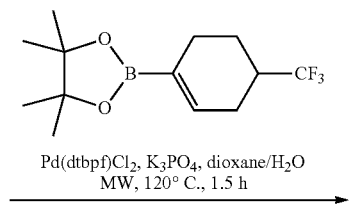

Pd(dtbpf)Cl₂, K₃PO₄, dioxane/H₂O
MW, 120° C., 1.5 h

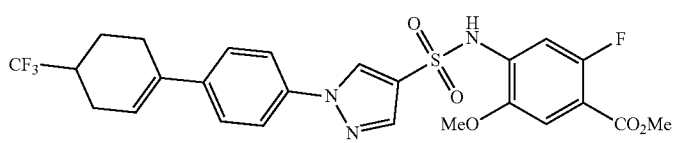

To a solution of methyl 4-((1-(4-chlorophenyl)-1H-pyrazole)-4-sulfonamido)-2-fluoro-5-methoxybenzoate (70 mg, 0.16 mmol, 1.0 eq), 4,4,5,5-tetramethyl-2-(4-(trifluoromethyl)cyclohex-1-en-1-yl)-1,3,2-dioxaborolane (65 mg, 0.24 mmol, 1.5 eq) and K$_3$PO$_4$ (102 mg, 0.48 mmol, 3.0 eq) in dioxane:water (1.6 mL:0.4 mL) was added Pd(dtbpf)Cl$_2$ (15.5 mg, 0.024 mmol, 0.15 eq). The sealed vial was irradiated in the microwave on a Biotage Synthesis at 120° C. for 1.5 h. After completion, the mixture was concentrated. H$_2$O (2 mL) was added and extracted by EtOAc (3 mL×3), washed with brine (2 mL×1), dried over Na$_2$SO$_4$, filtered and concentrated. The crude was purified by Prep-TLC (Petroleum ether:EtOAc=2:1) to afford methyl 2-fluoro-5-methoxy-4-((1-(4'-(trifluoromethyl)-2',3',4',5'-tetrahydro-[1,1'-biphenyl]-4-yl)-1H-pyrazole)-4-sulfonamido)benzoate (45 mg, 50.8%) as a white solid. $^1$H NMR (400 MHz, DMSO-d$_6$): δ 10.11 (s, 1H), 9.19 (s, 1H), 8.09 (s, 1H), 7.85-7.83 (m, 2H), 7.58-7.56 (m, 2H), 7.33-7.30 (m, 2H), 6.25 (s, 1H), 3.81 (s, 3H), 3.75 (s, 3H), 2.59-2.55 (m, 3H), 2.27-2.19 (m, 2H), 2.11-2.08 (m, 1H), 1.62-1.57 (m, 1H). LCMS: 554.2 ([M+H]$^+$).

Step 3. Synthesis of methyl 2-fluoro-5-methoxy-4-((1-(4-(4-(trifluoromethyl)cyclohexyl)phenyl)-1H-pyrazole)-4-sulfonamido)benzoate

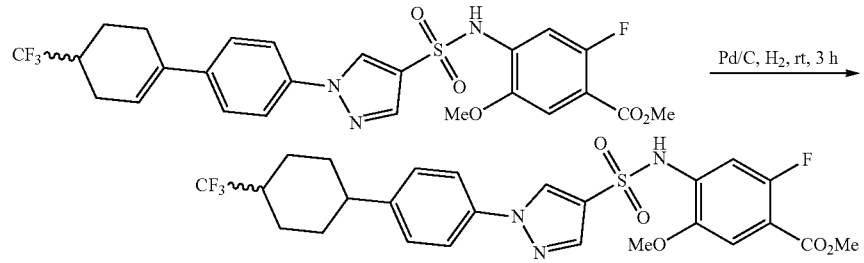

To a solution of methyl 2-fluoro-5-methoxy-4-((1-(4'-(trifluoromethyl)-2',3',4',5'-tetrahydro-[1,1'-biphenyl]-4-yl)-1H-pyrazole)-4-sulfonamido)benzoate (45 mg, 0.08 mmol, 1.0 eq) in MeOH (2 mL) was added Pd/C (22.5 mg, 50% wt). The flask was purged with H$_2$ (3×) then filled with H$_2$ (atmospheric pressure). The reaction mixture was stirred at room temperature 3 h. The mixture was filtered, and the filtrate was concentrated to afford methyl 2-fluoro-5-methoxy-4-((1-(4-(4-(trifluoromethyl)cyclohexyl)phenyl)-1H-pyrazole)-4-sulfonamido)benzoate (45 mg, 99.6%) as a white solid. The crude was used for next step without any further purification. LCMS: 556.2 ([M+H]$^+$).

Step 4. Synthesis of 2-fluoro-5-methoxy-4-((1-(4-((1s,4s)-4-(trifluoromethyl)cyclohexyl)phenyl)-1H-pyrazole)-4-sulfonamido)benzoic acid and 2-fluoro-5-methoxy-4-((1-(4-((1r,4r)-4-(trifluoromethyl)cyclohexyl)phenyl)-1H-pyrazole)-4-sulfonamido)benzoic acid

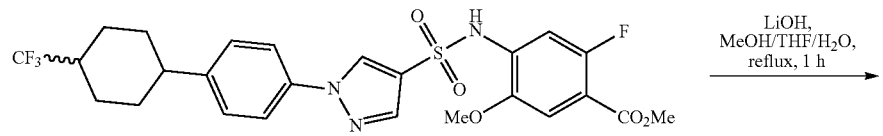

-continued

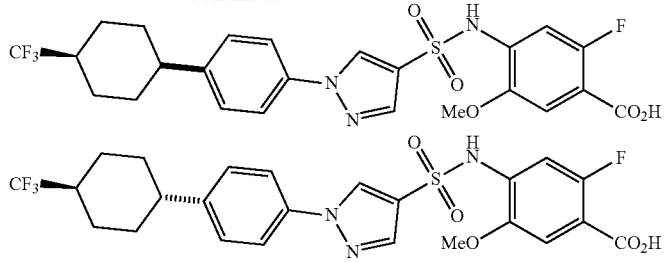

To a solution of methyl 2-fluoro-5-methoxy-4-((1-(4-(4-(trifluoromethyl)cyclohexyl)phenyl)-1H-pyrazole)-4-sulfonamido)benzoate (45 mg, 0.08 mmol, 1 eq) in THF:MeOH:H₂O (1.0 mL:1.0 mL:1.0 mL) was added LiOH (27 mg, 0.64 mmol, 8 eq). The reaction mixture was stirred at 100° C. for 1 h. After completion, the mixture was concentrated. H₂O (2.0 mL) was added. The slurry was extracted with a mixture of DCM:MeOH=10:1 (2.0 mL×3). The aqueous phase was adjusted to pH=1-2 with HCl (2.0 mL, 2 N) and extracted with DCM:MeOH=10:1 (2.0 mL×3), washed with brine (1 mL×1), dried over Na₂SO₄, filtered and concentrated. The crude was purified Prep-HPLC (Waters XBridge Prep C18 OBD, (CH₃CN:H₂O=60-74-100-8 min-40 mL, 0.1% HCOOH as additive) to afford two desired compounds as white solid.

2-fluoro-5-methoxy-4-((1-(4-((1s,4s)-4-(trifluoromethyl)cyclohexyl)phenyl)-1H-pyrazole)-4-sulfonamido)benzoic acid (8.8 mg) $^1$H NMR (300 MHz, DMSO-$d_6$): δ 13.07 (s, 1H), 10.07 (s, 1H), 9.10 (s, 1H), 8.05 (s, 1H), 7.81-7.78 (m, 2H), 7.42-7.39 (m, 2H), 7.31-7.23 (m, 2H), 3.73 (s, 3H), 2.82 (s, 1H), 2.54 (s, 1H), 1.87-1.74 (m, 8H). LCMS: 540.1 ([M−H]⁺).

2-fluoro-5-methoxy-4-((1-(4-((1r,4r)-4-(trifluoromethyl)cyclohexyl)phenyl)-1H-pyrazole)-4-sulfonamido)benzoic acid (3.3 mg) $^1$H NMR (300 MHz, DMSO-$d_6$): δ 13.03 (s, 1H), 10.04 (s, 1H), 9.09 (s, 1H), 8.04 (s, 1H), 7.80-7.77 (m, 2H), 7.39-7.36 (m, 2H), 7.30-7.22 (m, 2H), 3.73 (s, 3H), 2.64-2.60 (m, 1H), 2.37-2.31 (m, 1H), 1.99-1.87 (m, 4H), 1.57-1.39 (m, 4H). LCMS: 540.1 ([M−H]⁺).

The following examples were prepared using procedures similar to those described above:

| Example # | Structure | LC-MS [M + H]⁺ unless otherwise noted | $^1$H-NMR |
|---|---|---|---|
| 405 | 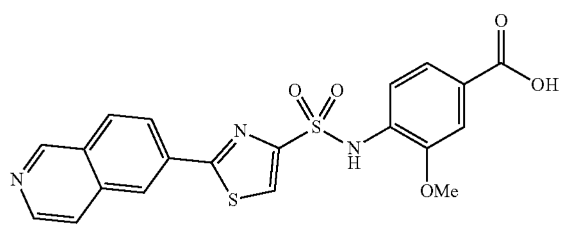 [SMILES: COc1cc(C(=O)O)ccc1NS(=O)(=O)c1csc(-c2ccc3cnccc3c2)n1] | 442.0 | $^1$H NMR (400 MHz, DMSO-d6) δ 12.87 (s, 1H), 10.13 (s, 1H), 9.41 (s, 1H), 8.64-8.56 (m, 2H), 8.50 (s, 1H), 8.30 (d, J = 8.6 Hz, 1H), 8.25-8.15 (m, 1H), 8.00 (d, J = 5.8 Hz, 1H), 7.60-7.50 (m, 2H), 7.44 (d, J = 1.6 Hz, 1H), 3.65 (s, 3H). |
| 406 | 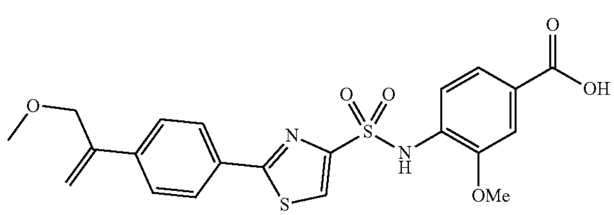 [SMILES: C=C(COC)c1ccc(-c2nc(S(=O)(=O)Nc3ccc(C(=O)O)cc3OC)cs2)cc1] | 459.1 [M − H]⁻ | 1H NMR (400 MHz, Chloroform-d) δ 8.02 (s, 1H), 7.83 (d, J = 8.5 Hz, 1H), 7.76-7.62 (m, 4H), 7.56-7.49 (m, 2H), 7.47 (d, J = 1.6 Hz, 1H), 5.61 (d, J = 1.0 Hz, 1H), 5.39 (t, J = 1.2 Hz, 1H), 4.31 (d, J = 1.2 Hz, 2H), 3.84 (s, 4H), 3.35 (s, 3H). |
| 411 | 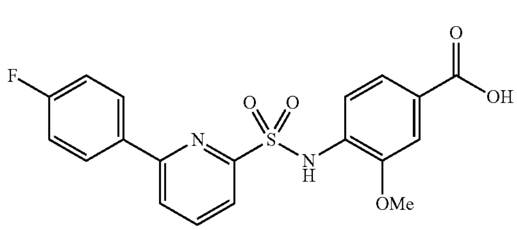 [SMILES: COc1cc(C(=O)O)ccc1NS(=O)(=O)c1cccc(-c2ccc(F)cc2)n1] | 403.10 | $^1$H NMR (400 MHz, DMSO-d6) δ 9.98 (s, 1H), 8.22 (d, J = 8.0 Hz, 1H), 8.13 (t, J = 7.8 Hz, 1H), 8.10-8.00 (m, 2H), 7.86 (d, J = 7.6 Hz, 1H), 7.60-7.49 (m, 2H), 7.39 (d, J = 1.7 Hz, 1H), 7.32 (t, J = 8.7 Hz, 2H), 3.61 (s, 3H). |

-continued

| Example # | Structure | LC-MS [M + H]+ unless otherwise noted | 1H-NMR |
|---|---|---|---|
| 412 | 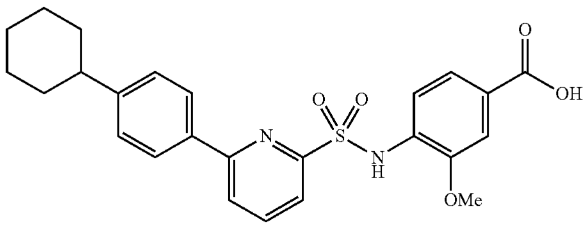 [SMILES: COc1cc(C(=O)O)ccc1NS(=O)(=O)c1cccc(-c2ccc(C3CCCCC3)cc2)n1] | 467.15 | 1H NMR (400 MHz, DMSO-d6) δ 12.90 (s, 1H), 9.93 (s, 1H), 8.20-8.15 (m, 1H), 8.11 (t, J = 7.8 Hz, 1H), 7.90-7.81 (m, 3H), 7.60 (d, J = 8.3 Hz, 1H), 7.59-7.50 (m, 1H), 7.41 (d, J = 1.8 Hz, 1H), 7.35-7.29 (m, 2H), 3.62 (s, 3H), 2.57 (d, J = 9.7 Hz, 1H), 1.85-1.77 (m, 4H), 1.76-1.68 (m, 1H), 1.51-1.35 (m, 4H), 1.38-1.22 (m, 2H) |
| 413 | 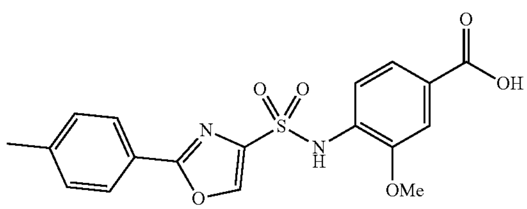 [SMILES: COc1cc(C(=O)O)ccc1NS(=O)(=O)c1coc(-c2ccc(C)cc2)n1] | 389.05 | 1H NMR (400 MHz, DMSO-d6) δ 12.94 (s, 1H), 10.20 (s, 1H), 8.83 (s, 1H), 7.91-7.84 (m, 2H), 7.57-7.50 (m, 1H), 7.50-7.42 (m, 2H), 7.39 (d, J = 8.0 Hz, 2H), 3.70 (s, 3H), 2.39 (s, 3H). |
| 414 | 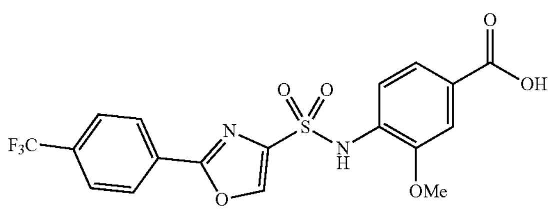 | 443.05 | 1H NMR (400 MHz, DMSO-d6) δ 12.98 (s, 1H), 10.27 (s, 1H), 8.96 (s, 1H), 8.19 (d, J = 8.2 Hz, 2H), 7.96 (d, J = 8.3 Hz, 2H), 7.59-7.50 (m, 1H), 7.50-7.43 (m, 2H), 3.70 (s, 3H). |
| 415 | 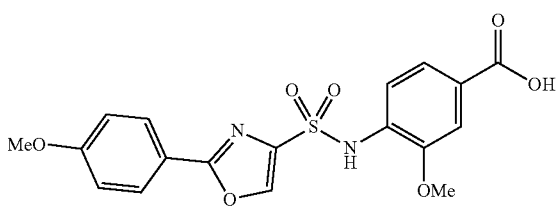 [SMILES: COc1ccc(-c2nc(S(=O)(=O)Nc3ccc(C(=O)O)cc3OC)co2)cc1] | 405.05 | 1H NMR (400 MHz, DMSO-d6) δ 10.18 (s, 1H), 8.80 (s, 1H), 7.96-7.90 (m, 2H), 7.59-7.50 (m, 1H), 7.51-7.43 (m, 2H), 7.17-7.10 (m, 2H), 3.85 (s, 3H), 3.71 (s, 3H). |
| 416 | 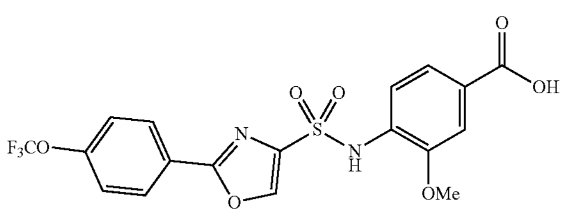 [SMILES: COc1cc(C(=O)O)ccc1NS(=O)(=O)c1coc(-c2ccc(OC(F)(F)F)cc2)n1] | 459.10 | 1H NMR (400 MHz, DMSO-d6) δ 12.95 (s, 1H), 10.26 (s, 1H), 8.92 (s, 1H), 8.16-8.08 (m, 2H), 7.63-7.57 (m, 2H), 7.59-7.50 (m, 1H), 7.51-7.44 (m, 2H), 3.71 (s, 3H). |
| 417 | 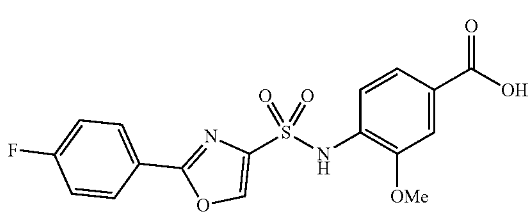 | 390.95 | 1H NMR (400 MHz, DMSO-d6) δ 12.91 (s, 1H), 10.21 (s, 1H), 8.87 (s, 1H), 8.08-7.99 (m, 2H), 7.59-7.50 (m, 1H), 7.50-7.38 (m, 4H), 3.71 (s, 3H). |

-continued

| Example # | Structure | LC-MS [M + H]+ unless otherwise noted | 1H-NMR |
|---|---|---|---|
| 418 | 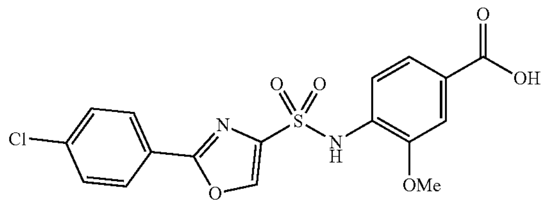 [SMILES: COc1cc(C(=O)O)ccc1NS(=O)(=O)c1coc(-c2ccc(Cl)cc2)n1] | 406.95 | 1H NMR (400 MHz, DMSO-d6) δ 12.93 (s, 1H), 10.23 (s, 1H), 8.88 (s, 1H), 8.03-7.95 (m, 2H), 7.70-7.62 (m, 2H), 7.59-7.50 (m, 1H), 7.50-7.42 (m, 2H), 3.70 (s, 3H). |
| 419 | 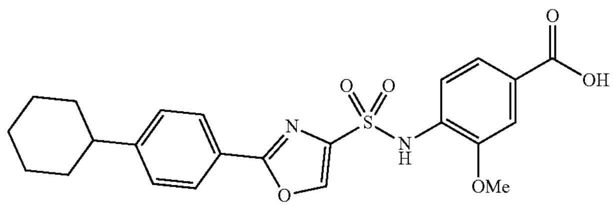 [SMILES: COc1cc(C(=O)O)ccc1NS(=O)(=O)c1coc(-c2ccc(C3CCCCC3)cc2)n1] | [M − H]− 455.10 | 1H NMR (400 MHz, DMSO-d6) δ 10.19 (s, 1H), 8.82 (s, 1H), 7.93-7.86 (d, J = 8.3 Hz, 2H), 7.55-7.35 (m, 5H), 3.70 (s, 3H), 2.60 (s, 1H), 2.08 (s, 1H), 1.85-1.76 (d, J = 9.9 Hz, 5H), 1.76-1.69 (d, J = 12.2 Hz, 2H), 1.49-1.32 (m, 4H). |
| 420 | 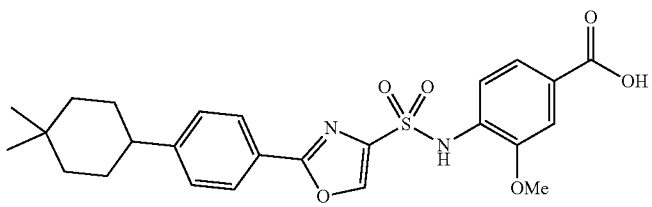 [SMILES: COc1cc(C(=O)O)ccc1NS(=O)(=O)c1coc(-c2ccc(C3CCC(C)(C)CC3)cc2)n1] | [M − H]− 483.10 | 1H NMR (400 MHz, DMSO-d6) δ 10.18 (s, 1H), 8.81 (s, 1H), 7.93-7.86 (d, J = 8.3 Hz, 2H), 7.55-7.39 (m, 5H), 3.71 (s, 3H), 2.70-2.64 (m, 1H), 1.69-1.57 (d, J = 3.1 Hz, 2H), 1.50-1.43 (d, J = 12.9 Hz, 2H), 1.40-1.27 (m, 2H), 1.02-0.92 (d, J = 12.8 Hz, 6H). |
| 426 | 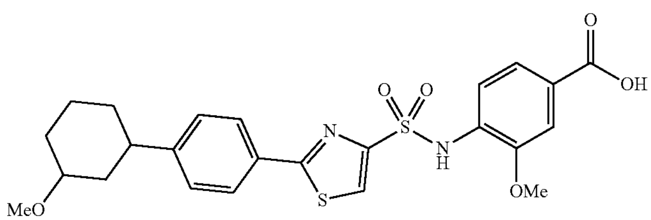 [SMILES: COc1cc(C(=O)O)ccc1NS(=O)(=O)c1csc(-c2ccc(C3CCCC(OC)C3)cc2)n1] | 503.1 | 1H NMR (400 MHz, DMSO-d6) δ 8.31 (s, 1H), 7.84 (d, J = 8.0 Hz, 2H), 7.50 (s, 2H), 7.42 (d, J = 7.8 Hz, 3H), 3.67 (s, 3H), 3.26 (s, 3H), 3.30-3.19 (m, 1H), 2.66-2.62 (m, 1H), 2.14 (d, J = 11.9 Hz, 1H), 2.06 (d, J = 12.2 Hz, 1H), 1.88-1.80 (m, 1H), 1.74 (d, J = 11.0 Hz, 1H), 1.47-1.22 (m, 3H), 1.19-1.05 (m, 1H). |
| 427 | 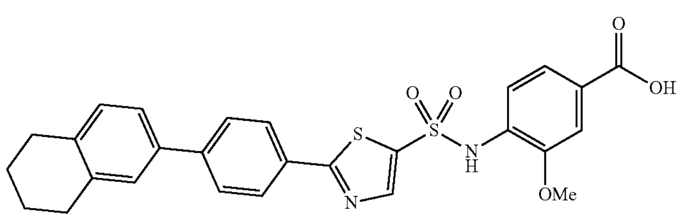 | 519.1 [M − H]− | |
| 428 | 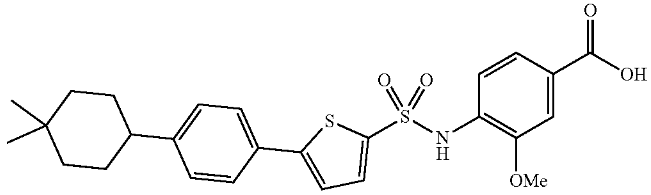 | [M − H]− 498.10 | 1H NMR (400 MHz, DMSO-d6) δ 12.90 (s, 1H), 10.09 (s, 1H), 7.55-7.62 (m, 2H), 7.47-7.55 (m, 2H), 7.40-7.47 (m, 3H), 7.36-7.36 (m, 2H), 3.69 (s, 3H), 2.39-2.47 (m, 1H), 1.55-1.65 (m, 4H), 1.46 (d, J = 12.7 Hz, 2H), 1.22-1.38 (m, 2H), 0, .96 (d, J = 12.3 Hz, 6H). |

| Example # | Structure | LC-MS [M + H]+ unless otherwise noted | ¹H-NMR |
|---|---|---|---|
| 429 | 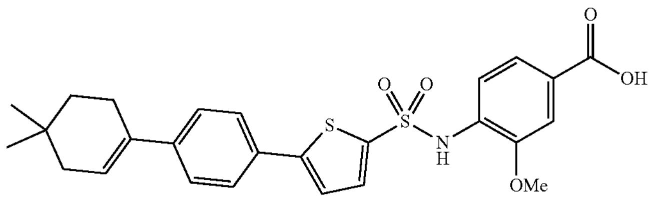 [SMILES: COc1cc(C(=O)O)ccc1NS(=O)(=O)c1ccc(-c2ccc(C3=CCC(C)(C)CC3)cc2)s1] | [M − H]⁻ 496.10 | 1H NMR (400 MHz, DMSO-d6) δ 7.63 (d, J = 8.4 Hz, 2H), 7.47-7.57 (m, 5H), 7.41-7.47 (m, 2H), 6.22 (s, 1H), 3.70 (s, 3H), 2.39 (s, 2H), 2.00 (d, J = 3.6 Hz, 2H), 1.49 (t, J = 6.4 Hz, 2H), 0.94 (s, 6H). |
| 430 | 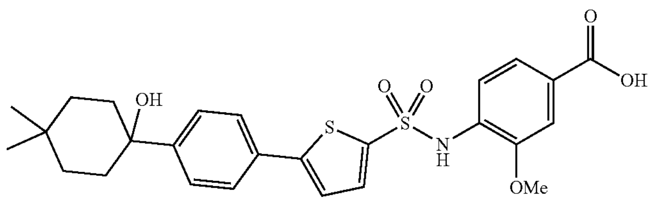 [SMILES: COc1cc(C(=O)O)ccc1NS(=O)(=O)c1ccc(-c2ccc(C3(O)CCC(C)(C)CC3)cc2)s1] | [M − H]⁻ 514.15 | ¹H NMR (400 MHz, DMSO-d6) δ 7.90-7.42 (m, 4H), 7.40 (d, J = 15.3 Hz, 5H), 4.74 (s, 1H), 3.69 (s, 3H), 1.83 (d, J = 12.6 Hz, 2H), 1.69 (t, J = 13.0 Hz, 2H), 1.48 (d, J = 13.2 Hz, 2H), 1.29-1.06 (m, 2H), 0.96 (d, J = 10.1 Hz, 6H). |
| 433 | 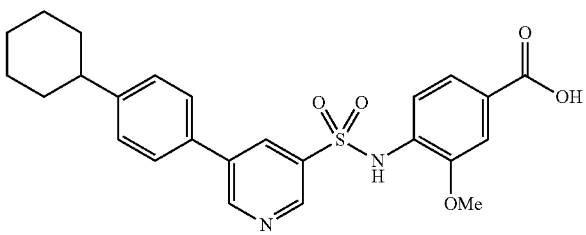 [SMILES: COc1cc(C(=O)O)ccc1NS(=O)(=O)c1cncc(-c2ccc(C3CCCCC3)cc2)c1] | 467.30 | ¹H NMR (400 MHz, DMSO-d6) δ 9.10 (d, J = 2.2 Hz, 1H), 8.84 (d, J = 2.2 Hz, 1H), 8.33 (t, J = 2.2 Hz, 1H), 7.66-7.60 (m, 2H), 7.56-7.50 (m, 1H), 3.58 (s, 3H), 7.45-131 (m, 4H), 2.59 (d, J = 11.2 Hz, 1H), 1.79-1.75 (m, 5H), 1.56-1.12 (m, 5H). |
| 434 | 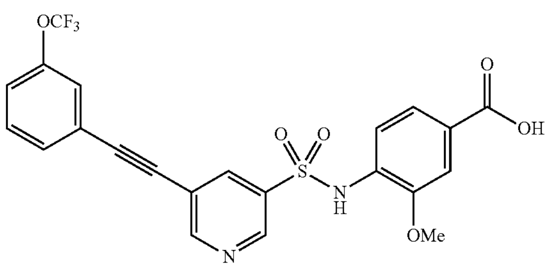 [SMILES: COc1cc(C(=O)O)ccc1NS(=O)(=O)c1cncc(C#Cc2cccc(OC(F)(F)F)c2)c1] | 493.10 | ¹H NMR (400 MHz, DMSO-d6) δ 9.00 (d, J = 2.0 Hz, 1H), 8.89 (d, J = 2.3 Hz, 1H), 8.34 (t, J = 2.1 Hz, 1H), 7.70-7.67 (m, 2H), 7.61 (d, J = 8.0 Hz, 1H), 7.54-7.49 (m, 2H), 7.43-7.31 (m, 2H), 3.63 (s, 3H). |
| 435 | 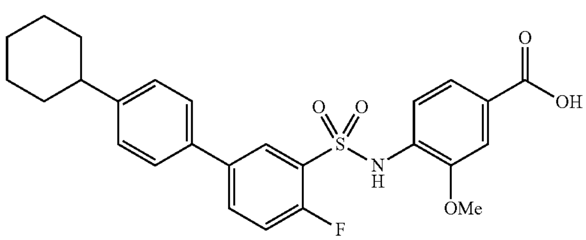 [SMILES: COc1cc(C(=O)O)ccc1NS(=O)(=O)c1cc(-c2ccc(C3CCCCC3)cc2)ccc1F] | [M − H]⁻ 482.10 | ¹H NMR (400 MHz, DMSO-d6) δ 12.93 (s, 1H), 10.18 (s, 1H), 7.97-7.86 (m, 2H), 7.55-7.46 (m, 4H), 7.44-7.36 (m, 2H), 7.36-7.29 (m, 2H), 3.63 (s, 3H), 2.54 (s, 1H), 1.80 (d, J = 10.2 Hz, 4H), 1.71 (d, J = 12.6 Hz, 1H), 1.49-1.31 (m, 4H), 1.31-1.21 (m, 1H). |
| 436 | 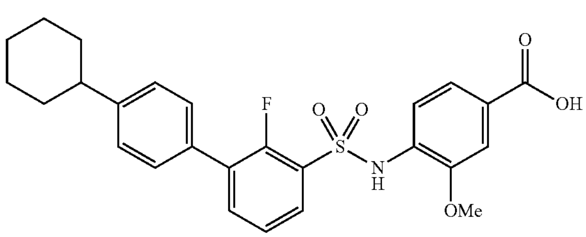 [SMILES: COc1cc(C(=O)O)ccc1NS(=O)(=O)c1cccc(-c2ccc(C3CCCCC3)cc2)c1F] | [M − H]⁻ 482.10 | ¹H NMR (400 MHz, DMSO-d6) δ 12.96 (s, 1H), 10.08 (s, 1H), 7.80-7.72 (m, 1H), 7.70-7.62 (m, 1H), 7.54-7.48 (m, 1H), 7.48-7.41 (m, 2H), 7.40-7.30 (m, 5H), 3.58 (s, 3H), 2.57 (s, 1H), 1.82 (s, 4H), 1.72 (d, J = 12.7 Hz, 1H), 1.52-1.42 (m, 2H), 1.41 (s, 1H), 1.37-1.22 (m, 1H). |

-continued

| Example # | Structure | LC-MS [M + H]+ unless otherwise noted | 1H-NMR |
|---|---|---|---|
| 437 | 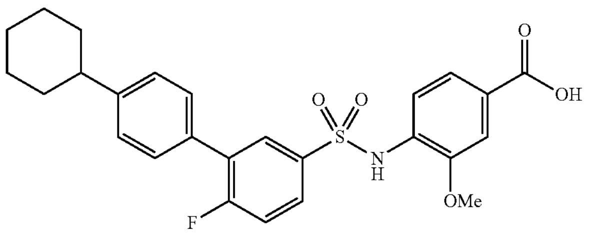 [SMILES: COc1cc(C(=O)O)ccc1NS(=O)(=O)c1ccc(F)c(-c2ccc(C3CCCCC3)cc2)c1] | [M − H]− 482.10 | 1H NMR (400 MHz, DMSO-d6) δ 7.93-7.87 (m, 1H), 7.82-7.75 (m, 1H), 7.54-7.45 (m, 2H), 7.45-7.33 (m, 6H), 3.63 (s, 3H), 2.58 (d, J = 11.1 Hz, 1H), 1.82 (d, J = 9.7 Hz, 5H), 1.72 (d, J = 12.7 Hz, 1H), 1.45-1.39 (m, 4H), 1.26 (d, J = 11.8 Hz, 1H). |
| 438 | 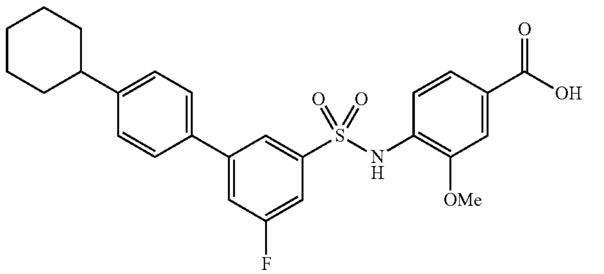 [SMILES: COc1cc(C(=O)O)ccc1NS(=O)(=O)c1cc(F)cc(-c2ccc(C3CCCCC3)cc2)c1] | [M − H]− 482.10 | 1H NMR (400 MHz, DMSO-d6) δ 12.94 (s, 1H), 10.08 (s, 1H), 7.88 (d, J = 1.6 Hz, 1H), 7.85-7.80 (m, 1H), 7.62-7.52 (m, 3H), 7.52-7.50 (m, 1H), 7.45-7.40 (m, 2H), 7.36 (d, J = 8.1 Hz, 2H), 3.64 (s, 3H), 2.57 (d, J = 11.0 Hz, 1H), 1.81 (d, J = 10.5 Hz, 4H), 1.72 (d, J = 12.9 Hz, 1H), 1.49-1.42 (m, 3H), 1.39-1.28 (m, 1H), 1.25 (d, J = 11.4 Hz, 1H). |
| 449 | 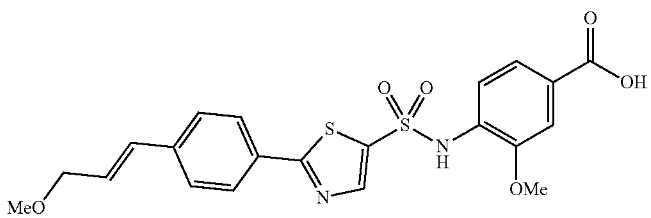 [SMILES: COC/C=C/c1ccc(-c2ncc(S(=O)(=O)Nc3ccc(C(=O)O)cc3OC)s2)cc1] | 459.1 [M − H]− | 1H NMR (400 MHz, Chloroform-d) δ 8.01 (s, 1H), 7.81 (d, J = 8.1 Hz, 2H), 7.75-7.64 (m, 3H), 7.47 (d, J = 1.5 Hz, 1H), 7.41 (d, J = 8.2 Hz, 2H), 6.60 (d, J = 16.0 Hz, 1H), 6.36 (dt, J = 16.0, 5.7 Hz, 1H), 4.09 (dd, J = 5.7, 1.6 Hz, 2H), 3.84 (s, 3H), 3.39 (s, 3H). |
| 450 | 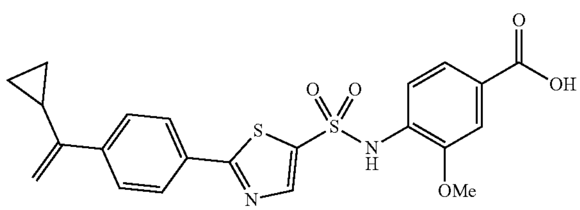 [SMILES: C=C(c1ccc(-c2ncc(S(=O)(=O)Nc3ccc(C(=O)O)cc3OC)s2)cc1)C1CC1] | 455.1 [M − H]− | 1H NMR (400 MHz, Methanol-d4) δ 8.14 (s, 1H), 7.84 (d, J = 8.5 Hz, 2H), 7.73-7.58 (m, 4H), 7.52 (d, J = 1.7 Hz, 1H), 7.42 (s, 1H), 5.39 (s, 1H), 5.04 (t, J = 1.1 Hz, 1H), 3.81 (s, 3H), 1.77-1.55 (m, 1H), 0.98-0.79 (m, 2H), 0.75-0.46 (m, 2H). |
| 451 | 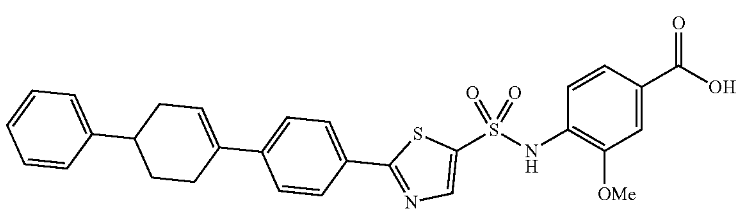 [SMILES: COc1cc(C(=O)O)ccc1NS(=O)(=O)c1cnc(-c2ccc(C3=CCC(c4ccccc4)CC3)cc2)s1] | 545.1 [M − H]− | |
| 452 | 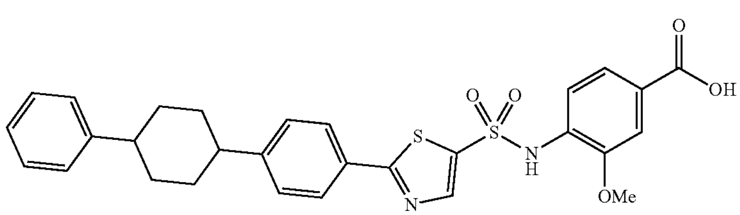 [SMILES: COc1cc(C(=O)O)ccc1NS(=O)(=O)c1cnc(-c2ccc(C3CCC(c4ccccc4)CC3)cc2)s1] | 547.1 [M − H]− | |

-continued

| Example # | Structure | LC-MS [M + H]+ unless otherwise noted | 1H-NMR |
|---|---|---|---|
| 453 | 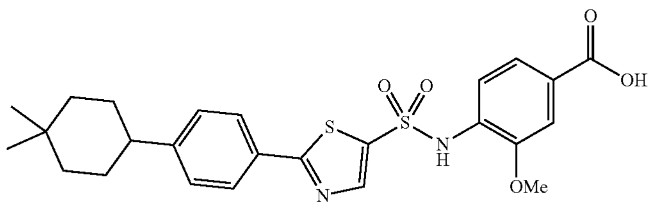 [SMILES: COc1cc(C(=O)O)ccc1NS(=O)(=O)c1cnc(-c2ccc(C3CCC(C)(C)CC3)cc2)s1] | 500.1 [M − H]− | 1H NMR (500 MHz, Methanol-d4) δ 8.10 (s, 1H), 7.87-7.77 (m, 2H), 7.73-7.61 (m, 3H), 7.55 (d, J = 1.8 Hz, 1H), 7.42-7.20 (m, 2H), 3.79 (s, 3H), 2.57-2.44 (m, 1H), 1.77-1.62 (m, 4H), 1.54 (dt, J = 13.4, 2.4 Hz, 2H), 1.39 (td, J = 12.8, 5.1 Hz, 2H), 1.02 (s, 3H), 0.99 (s, 3H). |
| 454 | 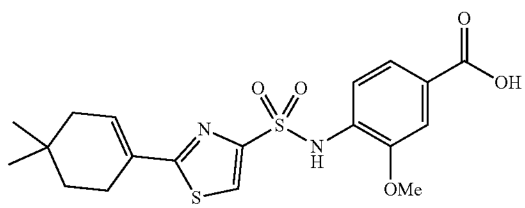 [SMILES: COc1cc(C(=O)O)ccc1NS(=O)(=O)c1csc(C2=CCC(C)(C)CC2)n1] | 421.2 [M − H]− | |
| 455 | 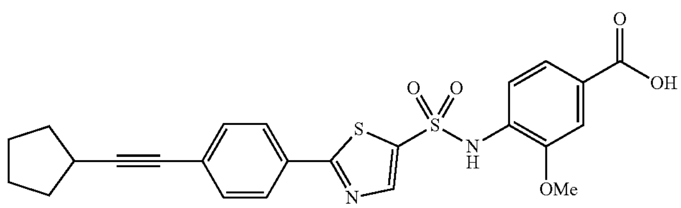 [SMILES: COc1cc(C(=O)O)ccc1NS(=O)(=O)c1cnc(-c2ccc(C#CC3CCCC3)cc2)s1] | 481.1 [M − H]− | 1H NMR (400 MHz, Methanol-d4) δ 8.14 (s, 1H), 7.82-7.74 (m, 2H), 7.69 (dd, J = 8.3, 1.7 Hz, 1H), 7.63 (d, J = 8.3 Hz, 1H), 7.51 (d, J = 1.8 Hz, 1H), 7.48-7.41 (m, 2H), 3.81 (s, 3H), 2.84 (p, J = 7.5 Hz, 1H), 2.11-1.92 (m, 2H), 1.90-1.51 (m, 6H). |
| 456 | 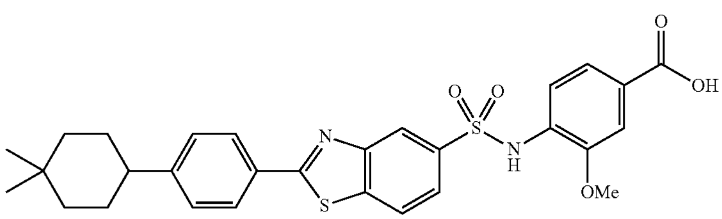 [SMILES: COc1cc(C(=O)O)ccc1NS(=O)(=O)c1ccc2sc(-c3ccc(C4CCC(C)(C)CC4)cc3)nc2c1] | 549.1 [M − H]− | 1H NMR (500 MHz, Methanol-d4) δ 8.49 (d, J = 1.8 Hz, 1H), 8.08-7.92 (m, 3H), 7.79 (dd, J = 8.5, 1.8 Hz, 1H), 7.61 (d, J = 1.7 Hz, 2H), 7.44-7.36 (m, 2H), 3.75 (s, 3H), 2.51 (tt, J = 11.8, 4.0 Hz, 1H), 1.79-1.57 (m, 4H), 1.57-1.46 (m, 2H), 1.37 (td, J = 13.0, 4.2 Hz, 2H), 1.00 (s, 3H), 0.97 (s, 3H). |
| 457 | 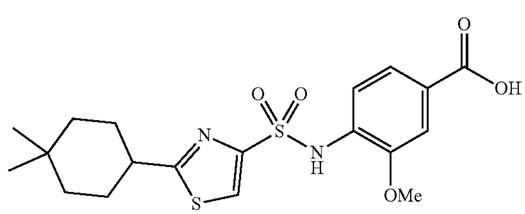 [SMILES: COc1cc(C(=O)O)ccc1NS(=O)(=O)c1csc(C2CCC(C)(C)CC2)n1] | 523.1 [M − H]− | |
| 458 | 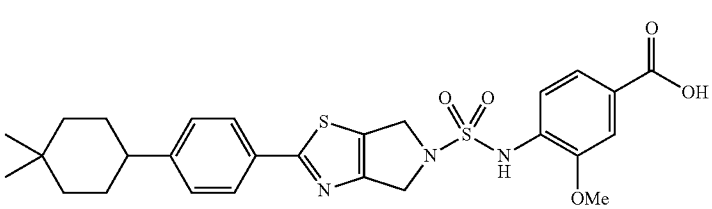 [SMILES: COc1cc(C(=O)O)ccc1NS(=O)(=O)N1Cc2nc(-c3ccc(C4CCC(C)(C)CC4)cc3)sc2C1] | 540.2 [M − H]− | 1H NMR (500 MHz, Chloroform-d) δ 7.75 (d, J = 8.2 Hz, 2H), 7.64 (dd, J = 8.3, 1.7 Hz, 1H), 7.57 (d, J = 8.4 Hz, 1H), 7.48 (d, J = 1.8 Hz, 1H), 7.29-7.24 (m, 2H), 4.69 (dd, J = 4.4, 2.6 Hz, 2H), 4.60 (dd, J = 4.4, 2.6 Hz, 2H), 3.87 (s, 3H), 3.86 (s, 3H), |

| Example # | Structure | LC-MS [M + H]+ unless otherwise noted | 1H-NMR |
|---|---|---|---|
| | | | 2.47-2.38 (m, 1H), 1.72-1.55 (m, 4H), 1.52-1.45 (m, 2H), 1.37-1.26 (m, 2H), 0.96 (s, 3H), 0.94 (s, 3H). |
| 459 | 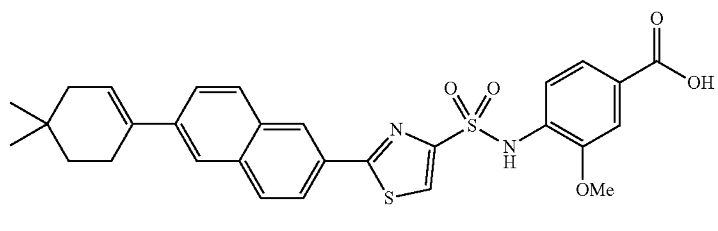 [SMILES: COc1cc(C(=O)O)ccc1NS(=O)(=O)c1csc(-c2ccc3cc(C4=CCC(C)(C)CC4)ccc3c2)n1] | 547.1 [M − H]− | |
| 460 | 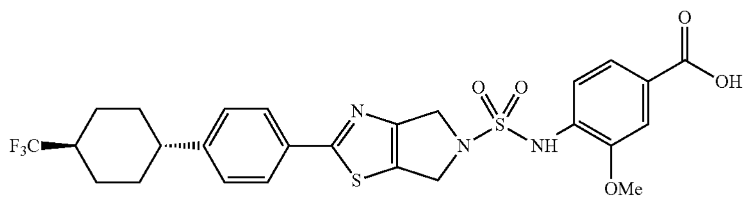 [SMILES: COc1cc(C(=O)O)ccc1NS(=O)(=O)N1Cc2nc(-c3ccc([C@H]4CC[C@H](C(F)(F)F)CC4)cc3)sc2C1] | 580.1 [M − H]− | |
| 461 | 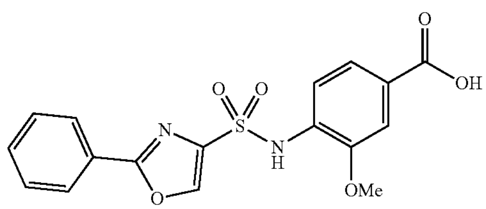 [SMILES: COc1cc(C(=O)O)ccc1NS(=O)(=O)c1coc(-c2ccccc2)n1] | 375.00 | 1H NMR (400 MHz, DMSO-d6) δ 12.92 (s, 1H), 10.22 (s, 1H), 8.87 (s, 1H), 8.02-7.95 (m, 2H), 7.66-7.50 (m, 4H), 7.50-7.43 (m, 2H), 3.70 (s, 3H). |
| 462 | 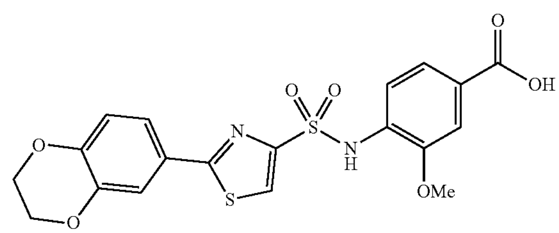 [SMILES: COc1cc(C(=O)O)ccc1NS(=O)(=O)c1csc(-c2ccc3c(c2)OCCO3)n1] | 449.15 | 1H NMR (400 MHz, DMSO-d6) δ 10.01 (s, 1H), 8.30 (s, 1H), 7.52 (d, J = 2.4 Hz, 2H), 7.45-7.35 (m, 3H), 7.00 (d, J = 8.3 Hz, 1H), 4.36-4.27 (m, 4H), 3.68 (s, 3H). |
| 463 | 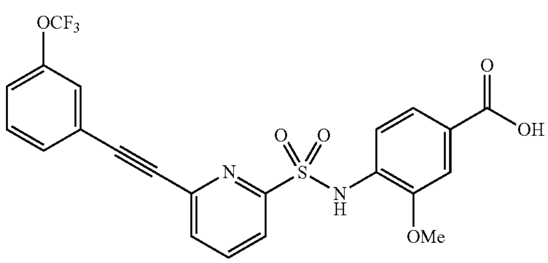 [SMILES: COc1cc(C(=O)O)ccc1NS(=O)(=O)c1cccc(C#Cc2cccc(OC(F)(F)F)c2)n1] | 493.10 | 1H NMR (400 MHz, DMSO-d6) δ 12.87 (s, 1H), 10.18 (s, 1H), 8.14 (t, J = 7.8 Hz, 1H), 7.98-7.87 (m, 2H), 7.74-7.67 (m, 2H), 7.63 (t, J = 7.9 Hz, 1H), 7.58-7.47 (m, 2H), 7.42 (d, J = 1.8 Hz, 1H), 7.37 (d, J = 8.2 Hz, 1H), 3.62 (s, 3H). |
| 464 | 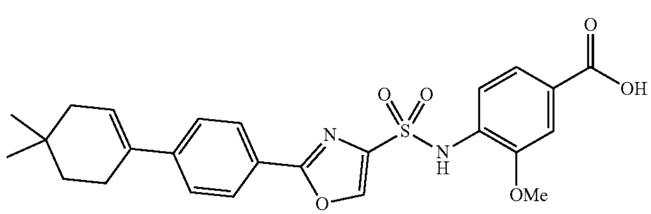 | 481.10 [M − H]− | 1H NMR (400 MHz, DMSO-d6) δ 10.21 (s, 1H), 8.82 (s, 1H), 7.95-7.88 (d, J = 8.5 Hz, 2H), 7.67-7.60 (d, J = 8.4 Hz, 2H), 7.56-7.50 (d, J = 8.2 Hz, 1H), 7.49-7.39 (d, J = 12.5 Hz, 2H), 6.33 (s, 0H), 3.70 (s, 3H), 2.32 (s, 1H), 2.02 (s, 2H), 1.54-1.46 (t, J = 6.4, 6.4 Hz, 2H), 0.94 (s, 6H). |

| Example # | Structure | LC-MS [M + H]+ unless otherwise noted | 1H-NMR |
|---|---|---|---|
| 465 | 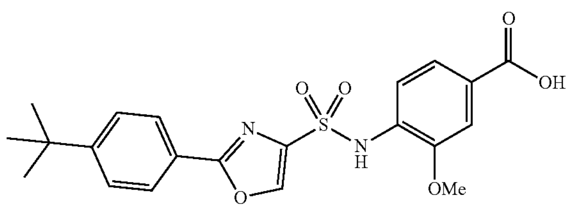 [SMILES: COc1cc(C(=O)O)ccc1NS(=O)(=O)c1coc(-c2ccc(C(C)(C)C)cc2)n1] | [M − H]− 429.05 | 1H NMR (400 MHz, DMSO-d6) δ 8.45 (s, 1H), 8.26 (s, 1H), 7.89-7.83 (m, 2H), 7.59-7.51 (m, 2H), 7.33-7.29 (d, J = 1.9 Hz, 1H), 7.27-7.22 (m, 1H), 7.11-7.06 (d, J = 8.2 Hz, 1H), 3.66 (s, 3H), 1.29 (s, 9H). |
| 466 | 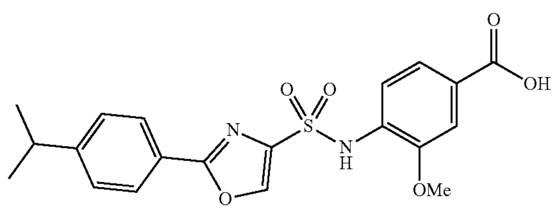 [SMILES: COc1cc(C(=O)O)ccc1NS(=O)(=O)c1coc(-c2ccc(C(C)C)cc2)n1] | 503.10 | 1H NMR (400 MHz, DMSO-d6) δ 8.31 (s, 1H), 7.84 (d, J = 8.0 Hz, 2H), 7.50 (s, 2H), 7.42 (d, J = 7.8 Hz, 3H), 3.67 (s, 3H), 3.26 (s, 3H), 3.30-3.19 (m, 1H), 2.66-2.62 (m, 1H), 2.14 (d, J = 11.9 Hz, 1H), 2.06 (d, J = 12.2 Hz, 1H), 1.88-1.80 (m, 1H), 1.74 (d, J = 11.0 Hz, 1H), 1.47-1.22 (m, 3H), 1.19-1.05 (m, 1H). |
| 467 | 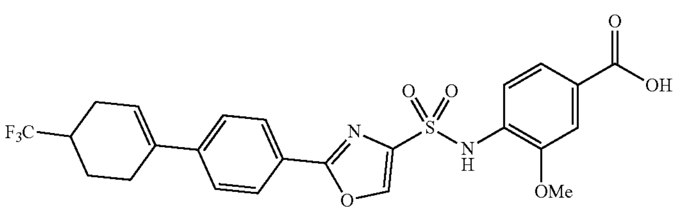 [SMILES: COc1cc(C(=O)O)ccc1NS(=O)(=O)c1coc(-c2ccc(C3=CCC(C(F)(F)F)CC3)cc2)n1] | [M − H]− 415.05 | 1H NMR (400 MHz, DMSO-d6) δ 10.23-10.15 (s, 1H), 8.84-8.78 (s, 1H), 7.93-7.88 (d, J = 8.1 Hz, 2H), 7.51 (s, 1H), 7.50-7.39 (d, J = 8.2 Hz, 4H), 3.70 (s, 3H), 3.00-2.96 (m, 1H), 1.25-1.22 (d, J = 6.8 Hz, 6H). |
| 468 | 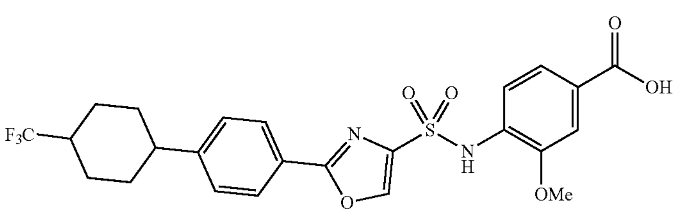 [SMILES: COc1cc(C(=O)O)ccc1NS(=O)(=O)c1coc(-c2ccc(C3CCC(C(F)(F)F)CC3)cc2)n1] | [M − H]− 523.10 | 1H NMR (400 MHz, Chloroform-d) δ 8.21 (s, 1H), 7.99-7.92 (d, J = 8.1 Hz, 2H), 7.76-7.67 (m, 3H), 7.56-7.51 (d, J = 1.8 Hz, 1H), 7.39-7.31 (m, 2H), 3.92 (s, 3H), 2.79 (s, 1H), 2.18-1.86 (m, 4H), 1.74 (s, 2H), 1.64 (s, 1H), 1.56-1.45 (t, J = 10.2, 10.2 Hz, 1H) |
| 469 | 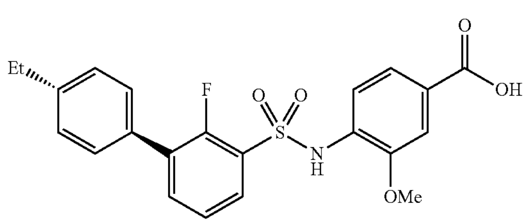 | [M − H]− 510.10 | 1H NMR (400 MHz, Chloroform-d) δ 7.94-7.88 (m, 1H), 7.73-7.62 (m, 3H), 7.59-7.53 (d, J = 8.4 Hz, 1H), 7.52-7.47 (d, J = 1.8 Hz, 1H), 7.45-7.39 (m, 2H), 7.35-7.29 (m, 3H), 3.85 (s, 3H), 2.62-2.46 (m, 1H), 2.01-1.89 (m, 5H), 1.55-1.45 (m, 2H), 1.35-1.25 (m, 2H), 1.14-1.01 (m, 2H), 0.98-0.90 (d, J = 7.4 Hz, 2H). |

| Example # | Structure | LC-MS [M + H]+ unless otherwise noted | 1H-NMR |
|---|---|---|---|
| 470 | 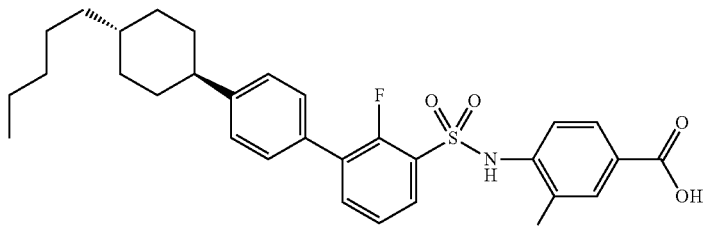 | [M − H]− 552.10 | 1H NMR (400 MHz, Chloroform-d) δ 7.95-7.87 (m, 1H), 7.73-7.62 (m, 3H), 7.58-7.53 (d, J = 8.4 Hz, 1H), 7.53-7.47 (d, J = 1.7 Hz, 1H), 7.45-7.39 (m, 2H), 7.34-7.29 (m, 3H), 3.85 (s, 3H), 2.59-2.48 (m, 1H), 2.05-1.82 (m, 4H), 1.56-1.41 (m, 2H), 1.41-1.22 (m, 9H), 1.16-1.02 (m, 2H), 0.96-0.89 (t, J = 7.0, 7.0 Hz, 3H). |
| 471 | 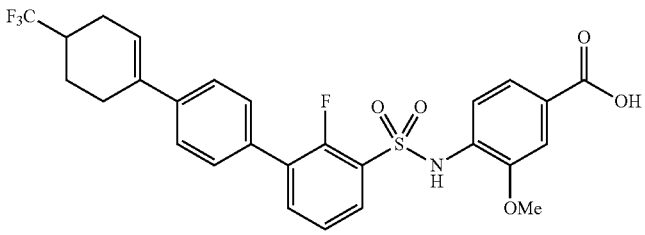 [SMILES: COc1cc(C(=O)O)ccc1NS(=O)(=O)c1cccc(-c2ccc(C3=CCC(C(F)(F)F)CC3)cc2)c1F] | [M − H]− 548.00 | 1H NMR (400 MHz, Chloroform-d) δ 7.89-7.96 (m, 1H), 7.63-7.73 (m, 3H), 7.56 (d, J = 8.5 Hz, 2H), 7.50 (d, J = 1.7 Hz, 1H), 7.47 (s, 3H), 7.33 (d, J = 7.8 Hz, 1H), 6.19 (s, 1H), 3.86 (s, 3H), 2.49-2.67 (m, 3H), 2.36 (d, J = 14.0 Hz, 2H), 2.23 (d, J = 13.0 Hz, 1H), 1.76-1.71 (m, 1H). |
| 472 | 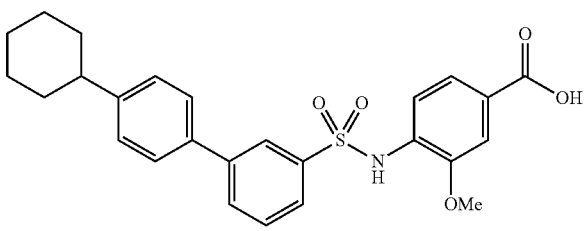 [SMILES: COc1cc(C(=O)O)ccc1NS(=O)(=O)c1cccc(-c2ccc(C3CCCCC3)cc2)c1] | 466.05 | 1H NMR (400 MHz, DMSO-d6) δ 8.03 (t, J = 1.9 Hz, 1H), 7.92-7.88 (m, 1H), 7.79-7.72 (m, 1H), 7.62 (t, J = 7.8 Hz, 1H), 7.47-7.56 (m, 3H), 7.30-7.44 (m, 4H), 3.62 (s, 3H), 2.57 (d, J = 10.5 Hz, 1H), 1.82 (d, J = 9.9 Hz, 4H), 1.72 (d, J = 12.6 Hz, 1H), 1.35-1.56 (m, 4H), 1.18-1.32 (m, 1H) |
| 473 | 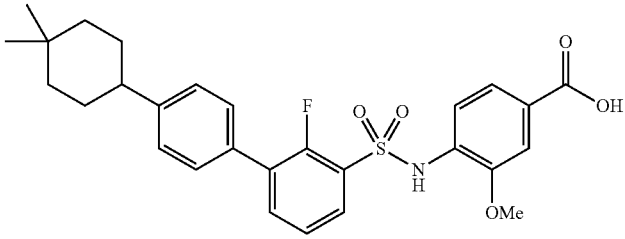 [SMILES: COc1cc(C(=O)O)ccc1NS(=O)(=O)c1cccc(-c2ccc(C3CCC(C)(C)CC3)cc2)c1F] | [M + 18] 529.15 | 1H NMR (400 MHz, Chloroform-d) δ 7.92-8.00 (m, 1H), 7.72 (s, 1H), 7.70-7.61 (m, 2H), 7.56 (d, J = 8.5 Hz, 1H), 7.51 (d, J = 1.7 Hz, 1H), 7.43 (m, 2H), 7.38-7.28 (m, 3H), 3.87 (s, 3H), 2.49 (m, 1H), 1.80-1.60 (m, 4H), 1.59-1.49 (m, 2H), 1.40-1.35 (m, 2H), 1.00 (d, J = 8.1 Hz, 6H). |
| 474 | 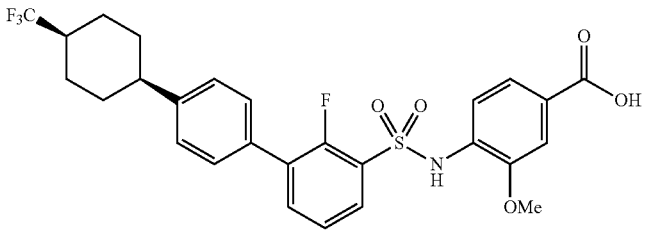 [SMILES: COc1cc(C(=O)O)ccc1NS(=O)(=O)c1cccc(-c2ccc([C@H]3CC[C@@H](C(F)(F)F)CC3)cc2)c1F] | [M − H]− 550.05 | 1H NMR (400 MHz, Chloroform-d) δ 7.93-7.98 (m, 1H), 7.62-7.75 (m, 3H), 7.55 (d, J = 8.5 Hz, 1H), 7.51 (d, J = 1.7 Hz, 1H), 7.46-7.42 (m, 2H), 3.87 (s, 3H), 7.20-7.34 (m, 3H), 2.58 (d, J = 11.3 Hz, 1H), 2.02-2.25 (m, 5H), 1.41-1.65 (m, 4H). |

| Example # | Structure | LC-MS [M + H]+ unless otherwise noted | 1H-NMR |
|---|---|---|---|
| 475 | (structure) | [M − H]− 550.20 | 1H NMR (400 MHz, Chloroform-d) δ 7.93-7.99 (m, 1H), 7.71 (s, 1H), 7.66-7.71 (m, 2H), 7.55 (d, J = 8.5 Hz, 1H), 7.51 (d, J = 1.8 Hz, 1H), 7.44-7.50 (m, 2H), 7.27-7.38 (m, 3H), 3.87 (s, 3H), 2.78 (t, J = 8.3 Hz, 1H), 2.40-2.30 (m, 1H), 1.98-2.03 (m, 3H), 1.79-1.82 (m, 4H). |
| 476 | (structure) | [M − H]− 518.05 | 1H NMR (400 MHz, Chloroform-d) δ 7.93 (t, J = 1.1 Hz, 1H), 7.62-7.73 (m, 3H), 7.55 (d, J = 8.4 Hz, 1H), 7.51 (d, J = 1.7 Hz, 1H), 7.39-7.48 (m, 2H), 7.30-7.37 (m, 3H), 3.87 (s, 3H), 2.69 (s, 1H), 2.26 (t, J = 9.8 Hz, 2H), 1.83-2.03 (m, 5H). |
| 477 | (structure) | [M − H]− 536.15 | 1H NMR (400 MHz, Chloroform-d) δ 7.95-7.87 (m, 1H), 7.74-7.61 (m, 3H), 7.59-7.53 (d, J = 8.4 Hz, 1H), 7.51-7.42 (m, 5H), 7.34-7.30 (d, J = 7.8 Hz, 1H), 6.28-6.22 (m, 1H), 3.85 (s, 3H), 2.61-2.44 (m, 2H), 2.34-2.25 (d, J = 18.4 Hz, 1H), 2.08-1.97 (m, 2H), 1.44-1.25 (m, 2H), 0.95 (s, 9H). |
| 478 | (structure) | [M − H]− 538.20 | 1H NMR (400 MHz, Chloroform-d) δ 7.95-7.87 (m, 1H), 7.70 (s, 1H), 7.68-7.61 (m, 2H), 7.55 (d, J = 8.4 Hz, 1H), 7.50 (d, J = 1.7 Hz, 1H), 7.46-7.39 (m, 2H), 7.35-7.28 (m, 3H), 3.87 (s, 3H), 2.52 (t, J = 12.2 Hz, 1H), 2.05-1.90 (m, 4H), 1.52 (d, J = 12.2 Hz, 1H), 1.46 (d, J = 12.4 Hz, 1H), 1.30-1.16 (m, 2H), 1.16-1.06 (m, 1H), 0.92 (s, 9H). |
| 479 | (structure) | [M − H]− 538.15 | 1H NMR (400 MHz, Chloroform-d) δ 7.96-7.87 (m, 1H), 7.73-7.63 (m, 3H), 7.56 (d, J = 8.4 Hz, 1H), 7.51 (d, J = 1.7 Hz, 1H), 7.49-7.40 (m, 4H), 7.32 (d, J = 7.8 Hz, 1H), 3.87 (s, 3H), 3.10 (s, 1H), 2.33-2.25 (m, 2H), 1.83 (s, 2H), 1.30-1.13 (m, 3H), 0.83 (s, 9H). |

| Example # | Structure | LC-MS [M + H]+ unless otherwise noted | 1H-NMR |
|---|---|---|---|
| 480 | 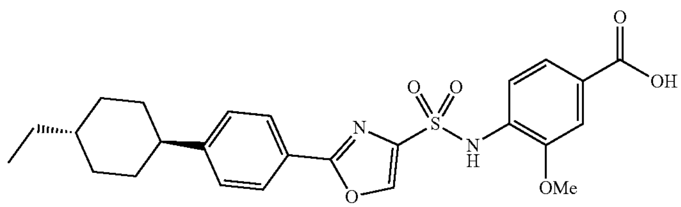 [SMILES: CC[C@H]1CC[C@H](c2ccc(-c3nc(S(=O)(=O)Nc4ccc(C(=O)O)cc4OC)co3)cc2)CC1] | [M − H]− 521.05 | 1H NMR (400 MHz, Chloroform-d) δ 8.21 (s, 1H), 8.01-7.93 (m, 2H), 7.77-7.67 (m, 3H), 7.57-7.52 (d, J = 1.7 Hz, 1H), 7.50-7.45 (m, 2H), 6.22 (s, 1H),3.9O (s, 3H), 2.61-2.47 (m, 3H), 2.44-2.30 (d, J = 14.4 Hz, 2H), 2.26-2.18 (m, 1H), 1.79-1.65 (m, 1H). |
| 481 | 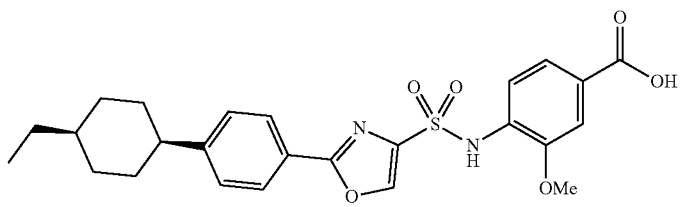 [SMILES: CC[C@H]1CC[C@@H](c2ccc(-c3nc(S(=O)(=O)Nc4ccc(C(=O)O)cc4OC)co3)cc2)CC1] | 485.15 | 1H NMR (400 MHz, DMSO-d6) δ 12.80 (s, 1H), 10.20 (s, 1H), 8.80 (s, 1H), 7.93-7.84 (m, 2H), 7.62-7.19 (m, 5H), 3.71 (s, 3H), 2.66 (t, J = 10.2 Hz, 1H), 1.74-1.51 (m, 9H), 1.48-1.33 (m, 2H), 0.89 (t, J = 7.4 Hz, 3H). |
| 482 | 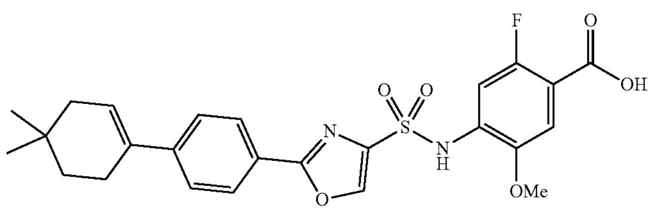 [SMILES: COc1cc(C(=O)O)c(F)cc1NS(=O)(=O)c1coc(-c2ccc(C3=CCC(C)(C)CC3)cc2)n1] | 501.15 | 1H NMR (400 MHz, DMSO-d6) δ 13.20 (s, 1H), 10.53 (s, 1H), 8.99 (s, 1H), 7.95-7.88 (m, 2H), 7.76-7.61 (m, 2H), 7.38-7.31 (m, 2H), 6.32 (t, J = 2.9 Hz, 1H), 3.72 (s, 3H), 2.43 (d, J = 2.1 Hz, 2H), 2.03 (q, J = 2.3 Hz, 2H), 1.51 (t, J = 6.4 Hz, 2H), 0.95 (s, 6H). |
| 483 | 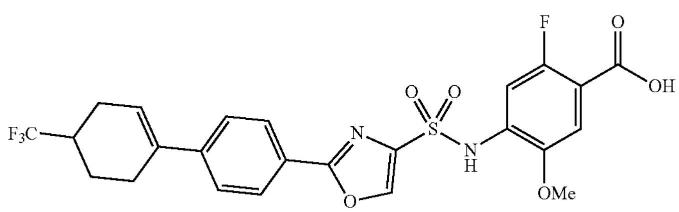 [SMILES: COc1cc(C(=O)O)c(F)cc1NS(=O)(=O)c1coc(-c2ccc(C3=CCC(C(F)(F)F)CC3)cc2)n1] | [M − H]− 538.95 | 1H NMR (400 MHz, DMSO-d6) δ 8.35 (s, 1H), 7.93-7.86 (m, 2H), 7.63-7.57 (m, 2H), 7.03 (d, J = 7.8 Hz, 1H), 6.95 (d, J = 14.8 Hz, 1H), 6.33 (d, J = 4.6 Hz, 1H), 3.64 (s, 3H), 2.57-2.50 (m, 3H), 2.45 (s, 1H), 2.30-2.18 (m, 1H), 2.14-2.06 (m, 1H), 1.67-1.52 (m, 1H). |
| 484 | 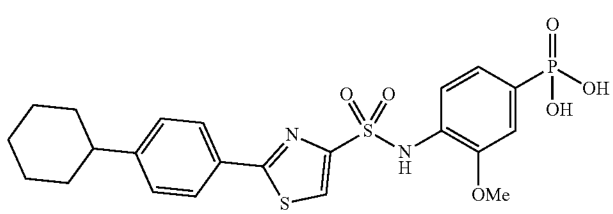 [SMILES: COc1cc(P(=O)(O)O)ccc1NS(=O)(=O)c1csc(-c2ccc(C3CCCCC3)cc2)n1] | 509.10 | 1H NMR (400 MHz, DMSO-d6) δ 8.19 (s, 1H), 7.83 (d, J = 7.9 Hz, 2H), 7.39 (d, J = 8.0 Hz, 2H), 7.27-7.21 (m, 1H), 7.20-7.10 (m, 2H), 3.43 (s, 3H), 2.59-2.53 (m, 1H), 1.84-1.66 (m, 5H), 1.49-1.23 (m, 5H). |
| 485 | 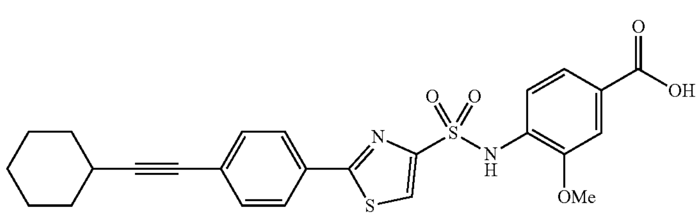 [SMILES: COc1cc(C(=O)O)ccc1NS(=O)(=O)c1csc(-c2ccc(C#CC3CCCCC3)cc2)n1] | [M − H]− 495.10 | 1H NMR (400 MHz, DMSO-d6) δ 12.97 (s, 1H), 10.43 (s, 1H), 8.24 (s, 1H), 7.99-7.88 (m, 2H), 7.55 (m, 1H), 7.53-7.47 (m, 2H), 7.46-7.41 (m, 2H), 3.68 (s, 3H), 2.69 (m, 1H), 1.93-1.76 (m, 2H), 1.68 (d, J = 8.0 Hz, 2H), 1.58-1.42 (m, 3H), 1.42-1.25 (m, 3H). |

| Example # | Structure | LC-MS [M + H]+ unless otherwise noted | 1H-NMR |
|---|---|---|---|
| 486 | 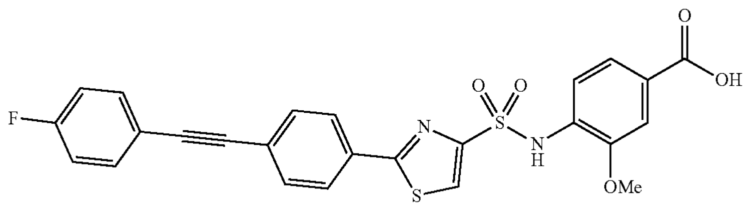 [SMILES: COc1cc(C(=O)O)ccc1NS(=O)(=O)c1csc(-c2ccc(C#Cc3ccc(F)cc3)cc2)n1] | 509.00 | 1H NMR (400 MHz, DMSO-d6) δ 12.85 (s, 1H), 10.46 (s, 1H), 8.22 (s, 1H), 8.06-7.99 (m, 2H), 7.73-7.62 (m, 4H), 7.56-7.50 (m, 1H), 7.42 (d, J = 8.4 Hz, 2H), 7.36-7.26 (m, 2H), 3.69 (s, 3H). |
| 487 | 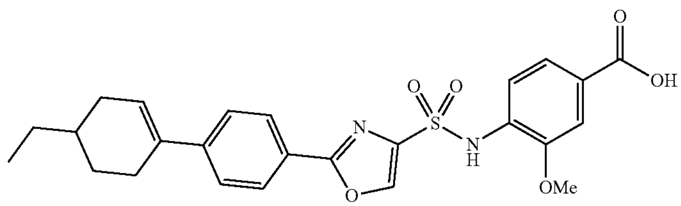 [SMILES: CCC1CC=C(c2ccc(-c3nc(S(=O)(=O)Nc4ccc(C(=O)O)cc4OC)co3)cc2)CC1] | 483.02 | 1H NMR (400 MHz, DMSO-d6) δ 12.96 (s, 1H), 10.19 (s, 1H), 8.84 (s, 1H), 7.95-7.88 (m, 2H), 7.62 (d, J = 8.4 Hz, 2H), 7.58-7.50 (m, 1H), 7.50-7.42 (m, 2H), 6.35 (s, 1H), 3.33 (s, 2H), 2.45-2.33 (m, 3H), 1.89 (s, 2H), 1.47 (s, 1H), 1.39-1.22 (m, 3H), 0.93 (t, J = 7.4 Hz, 3H). |
| 488 | 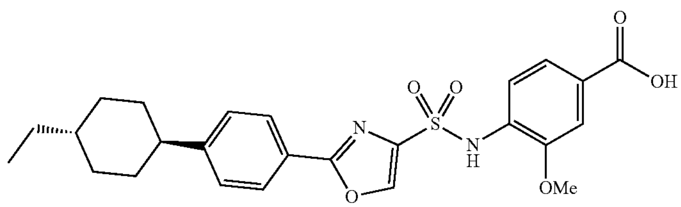 | 485.10 | 1H NMR (400 MHz, DMSO-d6) δ 12.69 (s, 1H), 10.19 (s, 1H), 8.83 (d, J = 4.0 Hz, 1H), 8.01-7.81 (m, 2H), 7.56-7.49 (m, 1H), 7.50-7.37 (m, 4H), 3.71 (s, 3H), 3.32 (s, 1H), 2.69-2.53 (m, 1H), 1.85 (d, J = 11.5 Hz, 4H), 1.59-1.36 (m, 2H), 1.31-1.15 (m, 3H), 1.05 (d, J = 11.7 Hz, 2H), 0.90 (t, J = 7.2 Hz, 3H). |
| 489 | 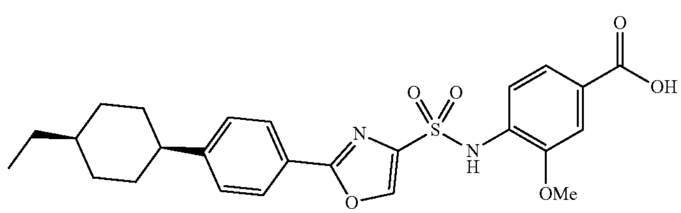 [SMILES: CC[C@H]1CC[C@@H](c2ccc(-c3nc(S(=O)(=O)Nc4ccc(C(=O)O)cc4OC)co3)cc2)CC1] | 485.15 | 1H NMR (400 MHz, DMSO-d6) δ 12.80 (s, 1H), 10.20 (s, 1H), 8.80 (s, 1H), 7.93-7.84 (m, 2H), 7.62-7.19 (m, 5H), 3.71 (s, 3H), 2.66 (t, J = 10.2 Hz, 1H), 1.74-1.51 (m, 9H), 1.48-1.33 (m, 2H), 0.89 (t, J = 7.4 Hz, 3H). |
| 490 | 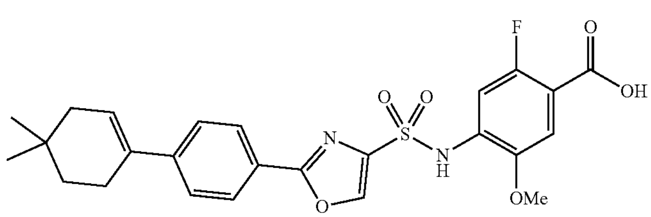 | 501.15 | 1H NMR (400 MHz, DMSO-d6) δ 13.20 (s, 1H), 10.53 (s, 1H), 8.99 (s, 1H), 7.95-7.88 (m, 2H), 7.76-7.61 (m, 2H), 7.38-7.31 (m, 2H), 6.32 (t, J = 2.9 Hz, 1H), 3.72 (s, 3H), 2.43 (d, J = 2.1 Hz, 2H), 2.03 (q, J = 2.3 Hz, 2H), 1.51 (t, J = 6.4 Hz, 2H), 0.95 (s, 6H). |
| 491 | 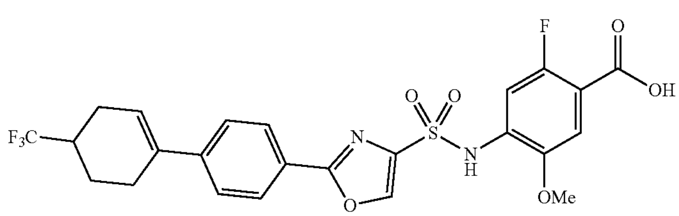 [SMILES: COc1cc(C(=O)O)c(F)cc1NS(=O)(=O)c1coc(-c2ccc(C3=CCC(C(F)(F)F)CC3)cc2)n1] | [M − H]− 538.95 | 1H NMR (400 MHz, DMSO-d6) δ 8.35 (s, 1H), 7.93-7.86 (m, 2H), 7.63-7.57 (m, 2H), 7.03 (d, J = 7.8 Hz, 1H), 6.95 (d, J = 14.8 Hz, 1H), 6.33 (d, J = 4.6 Hz, 1H), 3.64 (s, 3H), 2.57-2.50 (m, 3H), 2.45 (s, 1H), 2.30-2.18 (m, 1H), 2.14-2.06 (m, 1H), 1.67-1.52 (m, 1H). |

-continued

| Example # | Structure | LC-MS [M + H]+ unless otherwise noted | 1H-NMR |
|---|---|---|---|
| 492 | 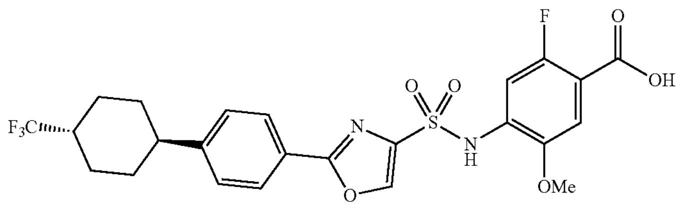 [SMILES: COc1cc(C(=O)O)c(F)cc1NS(=O)(=O)c1coc(-c2ccc([C@H]3CC[C@H](C(F)(F)F)CC3)cc2)n1] | 543.00 | 1H NMR (400 MHz, DMSO-d6) δ 8.67 (s, 1H), 8.14 (s, 1H), 7.89 (d, J = 8.2 Hz, 2H), 7.43 (d, J = 8.2 Hz, 2H), 7.16 (s, 1H), 3.68 (s, 3H), 1.94 (m, J = 27.2, 12.4 Hz, 4H), 2.71-2.57 (m, 2H), 2.42-2.28 (m, 1H). 1.63-1.56 (m, 1H), 1.46 (d, J = 10.7 Hz, 2H). |
| 493 | 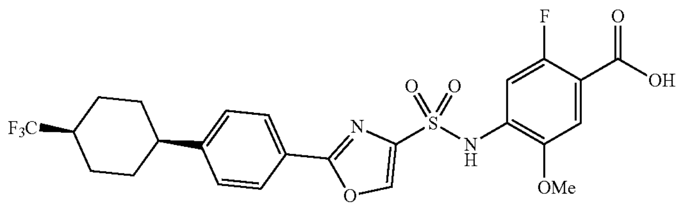 [SMILES: COc1cc(C(=O)O)c(F)cc1NS(=O)(=O)c1coc(-c2ccc([C@H]3CC[C@@H](C(F)(F)F)CC3)cc2)n1] | 542.95 | 1H NMR (400 MHz, DMSO-d6) 13.45 (s, 1H), δ 10.53 (s, 1H), 8.94 (s, 1H), 7.91 (d, J = 8.3 Hz, 2H), 7.48 (d, J = 8.2 Hz, 2H), 7.31 (s, 2H), 3.71 (s, 3H), 2.85 (s, 1H), 2.08-1.63 (m, 9H). |
| 494 | 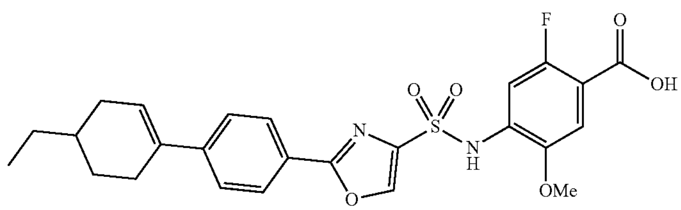 [SMILES: CCC1CC=C(c2ccc(-c3nc(S(=O)(=O)Nc4cc(F)c(C(=O)O)cc4OC)co3)cc2)CC1] | 501.15 | 1H NMR (400 MHz, DMSO-d6) δ 10.50 (s, 1H), 8.94 (s, 1H), 7.98-7.83 (m, 2H), 7.62 (d, J = 8.4 Hz, 2H), 7.42-7.17 (m, 2H), 6.35 (s, 1H), 3.71 (s, 3H), 2.45 (s, 3H), 1.91 (d, J = 13.7 Hz, 2H), 1.47 (s, 1H), 1.36-1.18 (m, 3H), 0.93 (t, J = 7.4 Hz, 3H). |
| 495 | 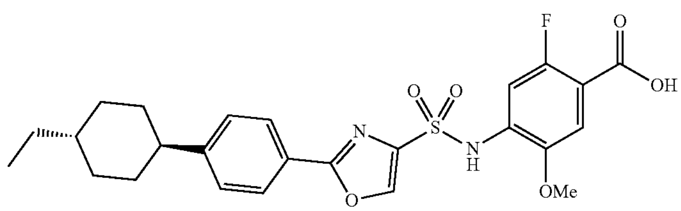 [SMILES: CC[C@H]1CC[C@H](c2ccc(-c3nc(S(=O)(=O)Nc4cc(F)c(C(=O)O)cc4OC)co3)cc2)CC1] | 503.20 | 1H NMR (400 MHz, DMSO-d6) δ 8.90 (s, 1H), 7.92-7.78 (m, 2H), 7.43 (d, J = 8.2 Hz, 2H), 7.30 (d, J = 9.4 Hz, 2H), 3.71 (s, 3H), 2.58 (d, J = 3.4 Hz, 1H), 2.02-1.70 (m, 4H), 1.57-1.40 (m, 2H), 1.25-1.31 (m, 3H), 1.06-1.14 (m, 2H), 0.89 (t, J = 7.2 Hz, 3H). |
| 496 | 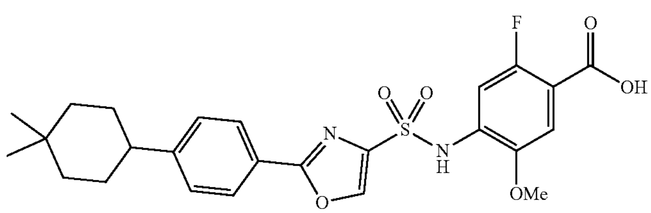 | 503.20 | 1H NMR (400 MHz, DMSO-d6) δ 13.19 (s, 1H), 10.50 (s, 1H), 8.97 (s, 1H), 7.92-7.85 (m, 2H), 7.50-7.44 (m, 2H), 7.39-7.29 (m, 2H), 3.72 (s, 3H), 2.54 (s, 1H), 1.68-1.57 (m, 4H), 1.47 (d, J = 12.8 Hz, 2H), 1.39-1.26 (m, 2H), 0.96 (d, J = 12.7 Hz, 6H). |
| 497 | 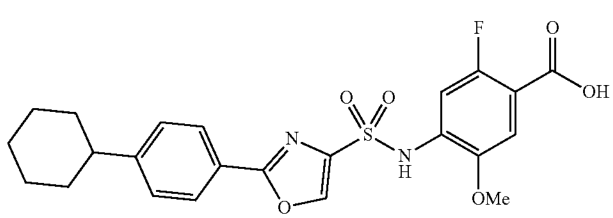 [SMILES: COc1cc(C(=O)O)c(F)cc1NS(=O)(=O)c1coc(-c2ccc(C3CCCCC3)cc2)n1] | [M − H]− 472.85 | 1H NMR (400 MHz, DMSO-d6) δ 13.00 (s, 1H), 8.85 (s, 1H), 7.88 (d, J = 8.3 Hz, 2H), 7.43 (d, J = 8.3 Hz, 2H), 7.27 (d, J = 9.4 Hz, 2H), 3.70 (s, 3H), 1.86-1.62 (m, 5H), 1.52-1.13 (m, 6H). |

-continued

| Example # | Structure | LC-MS [M + H]+ unless otherwise noted | 1H-NMR |
|---|---|---|---|
| 498 | 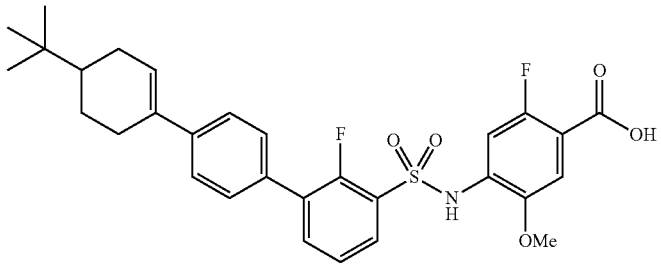 [SMILES: COc1cc(C(=O)O)c(F)cc1NS(=O)(=O)c1cccc(-c2ccc(C3=CCC(C(C)(C)C)CC3)cc2)c1F] | [M − H]− 554.25 | 1H NMR (400 MHz, DMSO-d6) δ 13.20 (s, 1H), 10.40 (s, 1H), 7.86-7.72 (m, 2H), 7.55 (d, J = 8.4 Hz, 2H), 7.52-7.46 (m, 2H), 7.42 (t, J = 7.8 Hz, 1H), 7.30 (d, J = 6.6 Hz, 1H), 7.18 (d, J = 11.6 Hz, 1H), 6.32-6.26 (m, 1H), 3.61 (s, 3H), 2.41 (s, 1H), 2.27 (s, 1H), 2.23 (s, 1H), 1.98 (d, J = 9.5 Hz, 2H), 1.40-1.13 (m, 2H), 0.91 (s, 9H). |
| 499 | 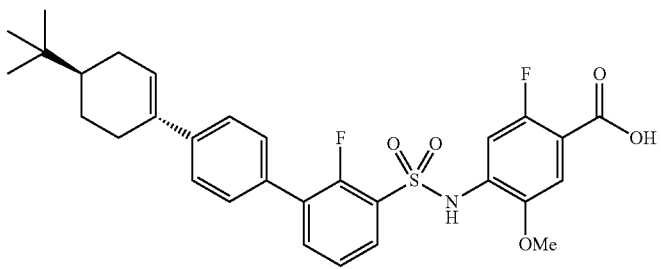 | [M − H]− 556.25 | 1H NMR (400 MHz, Chloroform-d) δ 8.00-7.92 (m, 1H), 7.76 (s, 1H), 7.71-7.63 (m, 1H), 7.46-7.40 (m, 2H), 7.39-7.25 (m, 5H), 3.87 (s, 3H), 2.59-2.44 (m, 1H), 2.05-1.90 (m, 4H), 1.52 (d, J = 12.2 Hz, 1H), 1.46 (d, J = 12.3 Hz, 1H), 1.30-1.20 (m, 1H), 1.20-1.06 (m, 2H), 0.92 (s, 9H). |
| 500 | 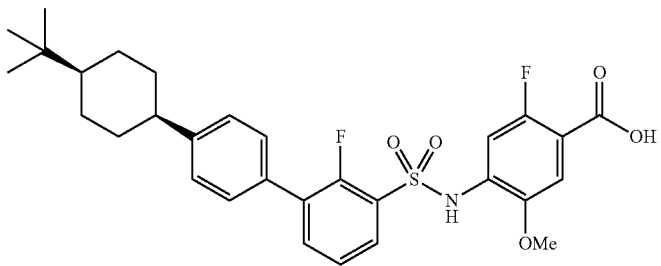 [SMILES: COc1cc(C(=O)O)c(F)cc1NS(=O)(=O)c1cccc(-c2ccc([C@H]3CC[C@@H](C(C)(C)C)CC3)cc2)c1F] | [M − H]− 556.30 | 1H NMR (400 MHz, Chloroform-d) δ 7.96 (t, J = 6.9 Hz, 1H), 7.78-7.69 (m, 2H), 7.52-7.41 (m, 4H), 7.40-7.31 (m, 3H), 3.87 (s, 3H), 3.10 (s, 1H), 2.29 (d, J = 13.8 Hz, 2H), 1.82 (d, J = 14.6 Hz, 2H), 1.64 (d, J = 10.9 Hz, 2H), 1.29-1.13 (m, 3H), 0.83 (s, 9H). |
| 501 | 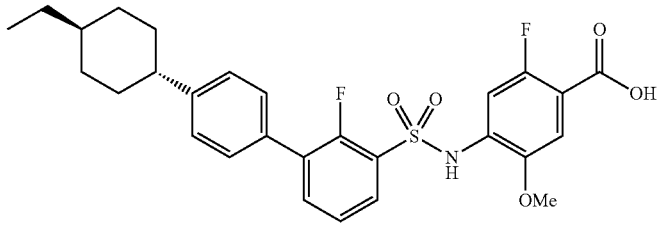 [SMILES: CC[C@H]1CC[C@H](c2ccc(-c3cccc(S(=O)(=O)Nc4cc(F)c(C(=O)O)cc4OC)c3F)cc2)CC1] | 530.10 | 1H NMR (400 MHz, DMSO-d6) δ 13.00 (s, 1H), 10.43 (s, 1H), 7.88-7.69 (m, 2H), 7.47-7.23 (m, 5H), 7.15 (d, J = 11.6 Hz, 2H), 3.61 (s, 3H), 1.85 (d, J = 11.6 Hz, 4H), 1.56-1.18 (m, 6H), 1.09-1.03 (m, 2H), 0.90 (t, J = 7.2 Hz, 3H). |
| 502 | 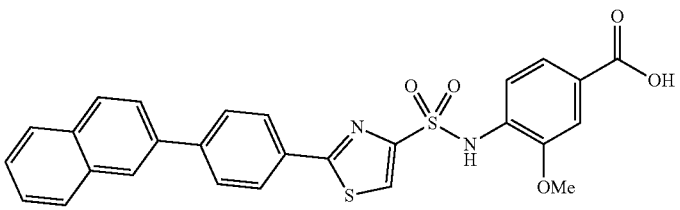 [SMILES: COc1cc(C(=O)O)ccc1NS(=O)(=O)c1csc(-c2ccc(-c3ccc4ccccc4c3)cc2)n1] | 517.20 | 1H NMR (400 MHz, DMSO-d6) δ 10.10 (s, 1H), 8.41 (s, 1H), 8.35 (d, J = 1.7 Hz, 1H), 8.10-8.00 (m, 6H), 8.00-7.90 (m, 2H), 7.62-7.53 (m, 4H), 7.45 (s, 1H), 3.69 (s, 3H). |

| Example # | Structure | LC-MS [M + H]+ unless otherwise noted | 1H-NMR |
|---|---|---|---|
| 503 | 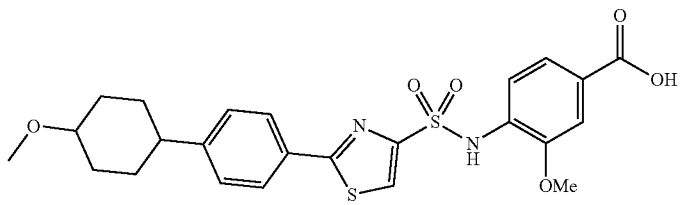 [SMILES: COc1cc(C(=O)O)ccc1NS(=O)(=O)c1csc(-c2ccc(C3CCC(OC)CC3)cc2)n1] | 503.4 [M + H]+ | 1H NMR (500 MHz, Methanol-d4) δ 8.15 (s, 1H), 7.86-7.78 (m, 2H), 7.65-7.57 (m, 2H), 7.50 (d, J = 1.7 Hz, 1H), 7.37-7.30 (m, 2H), 3.74 (s, 3H), 3.58-3.54 (m, 1H), 3.36 (s, 3H), 2.70-2.58 (m, 1H), 2.12-2.04 (m, 2H), 1.86-1.73 (m, 2H), 1.66-1.55 (m, 4H). |
| 504 | 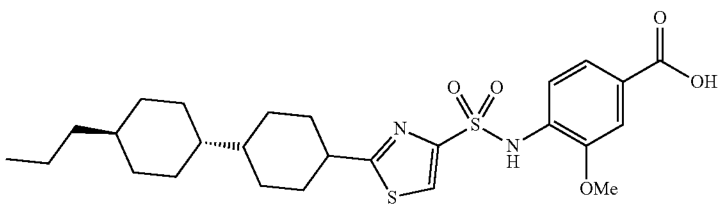 [SMILES: CCC[C@H]1CC[C@H](C2CCC(c3nc(S(=O)(=O)Nc4ccc(C(=O)O)cc4OC)cs3)CC2)CC1] | 521.5 [M + H]+ | 1H NMR (400 MHz, DMSO-d6) δ 9.80 (br, 1H), 8.28 (s, 1H), 7.51-7.36 (m, 3H), 3.74 (s, 3H), 3.30-3.22 (m, 1H), 2.06-1.93 (m, 2H), 1.82-1.02 (m, 16H), 1.00-0.67 (m, 8H). |
| 505 | 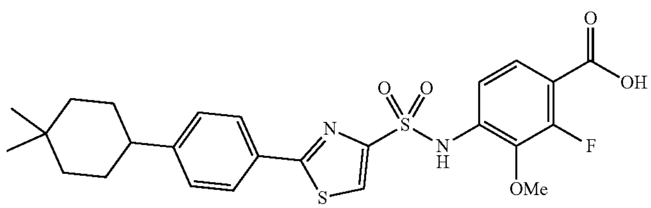 [SMILES: COc1c(NS(=O)(=O)c2csc(-c3ccc(C4CCC(C)(C)CC4)cc3)n2)ccc(C(=O)O)c1F] | 519.4 [M + H]+ | 1H NMR (400 MHz, DMSO-d6) δ 13.16 (br, 1H), 10.61 (s, 1H), 8.48 (s, 1H), 7.87-7.77 (m, 2H), 7.57-7.51 (dd, J = m, 1H), 7.48-7.36 (m, 3H), 3.69 (s, 3H), 2.50-2.46 (m, 1H), 1.66-1.57 (m, 4H), 1.51-1.41 (m, 2H), 1.39-1.26 (m, 2H), 0.98 (s, 3H), 0.94 (s, 3H). |
| 506 | 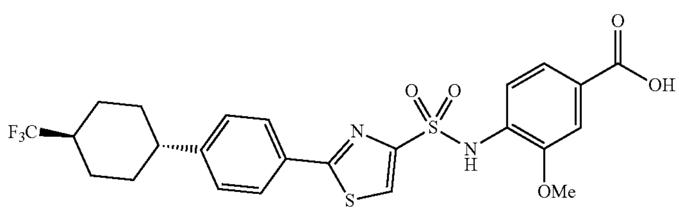 [SMILES: COc1cc(C(=O)O)ccc1NS(=O)(=O)c1csc(-c2ccc([C@H]3CC[C@H](C(F)(F)F)CC3)cc2)n1] | 541.3 [M + H]+ | 1H NMR (400 MHz, DMSO-d6) δ 10.03 (s, 1H), 8.35 (s, 1H), 7.84 (d, J = 8.1 Hz, 2H), 7.56-7.47 (m, 2H), 7.44-7.37 (m, 3H), 3.67 (s, 3H), 2.69-2.56 (m, 1H), 2.43-2.28 (m, 1H), 2.02-1.86 (m, 4H), 1.55 (qd, J = 12.6, 2.9 Hz, 2H), 1.42 (qd, J = 12.4, 3.1 Hz, 2H). |
| 507 | 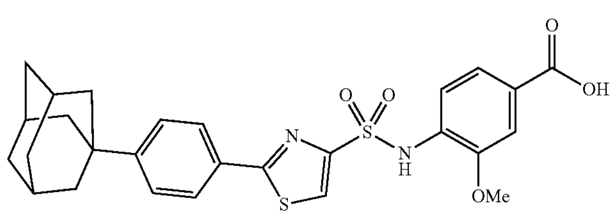 [SMILES: COc1cc(C(=O)O)ccc1NS(=O)(=O)c1csc(-c2ccc(C34CC5CC(CC(C5)C3)C4)cc2)n1] | 525.4 [M + H]+ | 1H NMR (400 MHz, Methanol-d4) δ 8.15 (s, 1H), 7.87-7.81 (m, 2H), 7.64-7.57 (m, 2H), 7.53-7.46 (m, 3H), 3.73 (s, 3H), 2.16-1.77 (m, 21H). |
| 508 | 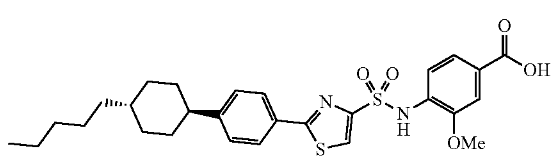 [SMILES: CCCCC[C@H]1CC[C@H](c2ccc(-c3nc(S(=O)(=O)Nc4ccc(C(=O)O)cc4OC)cs3)cc2)CC1] | 543.2 [M + H]+ | 1H NMR (500 MHz, DMSO-d6) δ 12.93 (br, 1H), 10.03 (br, 1H), 8.34 (s, 1H), 7.85-7.80 (m, 2H), 7.55-7.48 (m, 2H), 7.42 (d, J = 1.6 Hz, 1H), 7.41-7.36 (m, 2H), 3.67 (s, 3H), 2.58-2.51 (m, 1H), 1.87-1.77 (m, 4H), 1.45 (qd, J = 13.1, 12.6, 3.6 Hz, |

-continued

| Example # | Structure | LC-MS [M + H]+ unless otherwise noted | 1H-NMR |
|---|---|---|---|
| | | | 2H), 1.36-1.16 (m, 8H), 1.10-0.96 (m, 2H), 0.87 (t, J = 7.1 Hz, 3H). |
| 509 | 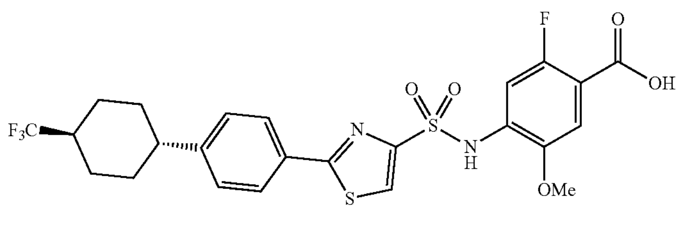 [SMILES: COc1cc(C(=O)O)c(F)cc1NS(=O)(=O)c1csc(-c2ccc([C@H]3CC[C@H](C(F)(F)F)CC3)cc2)n1] | 559.3 [M + H]+ | 1H NMR (400 MHz, Chloroform-d) δ 8.09 (s, 1H), 7.82 (d, J = 8.0 Hz, 2H), 7.72 (s, 1H), 7.57 (d, J = 12.0 Hz, 1H), 7.36 (d, J = 6.1 Hz, 1H), 7.30-7.24 (m, 2H), 3.86 (s, 3H), 2.65-2.49 (m, 1H), 2.19-1.94 (m, 5H), 1.58-1.40 (m, 4H). |
| 510 | 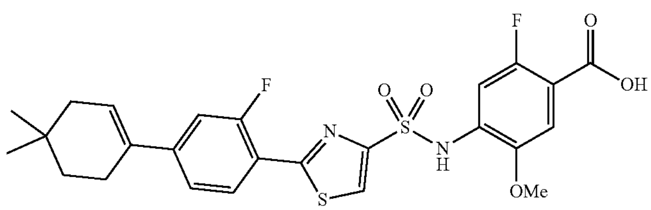 [SMILES: COc1cc(C(=O)O)c(F)cc1NS(=O)(=O)c1csc(-c2ccc(C3=CCC(C)(C)CC3)cc2F)n1] | 535.2 [M + H]+ | 1H NMR (500 MHz, DMSO-d6) δ 13.17 (br, 1H), 10.40 (s, 1H), 8.55 (s, 1H), 8.00 (t, J = 8.1 Hz, 1H), 7.54-7.48 (m, 2H), 7.41 (d, J = 12.0 Hz, 1H), 7.30 (d, J = 6.6 Hz, 1H), 6.41 (t, J = 3.9 Hz, 1H), 3.68 (s, 3H), 2.44-2.38 (m, 2H), 2.05-1.98 (m, 2H), 1.50 (t, J = 6.4 Hz, 2H), 0.94 (s, 6H). |
| 511 | 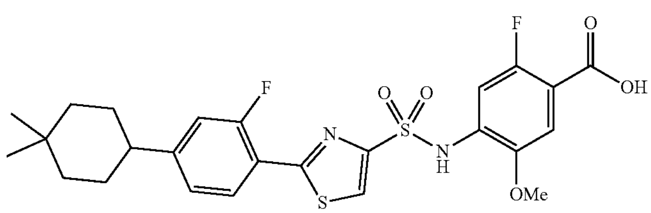 [SMILES: COc1cc(C(=O)O)c(F)cc1NS(=O)(=O)c1csc(-c2ccc(C3CCC(C)(C)CC3)cc2F)n1] | 537.2 [M + H]+ | 1H NMR (500 MHz, DMSO-d6) δ 13.16 (br, 1H), 10.40 (s, 1H), 8.54 (s, 1H), 7.97 (t, J = 8.1 Hz, 1H), 7.45-7.35 (m, 2H), 7.35-7.27 (m, 2H), 3.69 (s, 3H), 2.57-2.50 (m, 1H), 1.68-1.58 (m, 4H), 1.49-1.41 (m, 2H), 1.37-1.27 (m, 2H), 0.98 (s, 3H), 0.94 (s, 3H). |
| 512 | 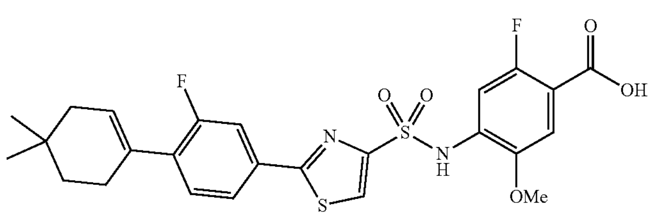 | 535.2 [M + H]+ | 1H NMR (400 MHz, DMSO-d6) δ 13.17 (br, 1H), 10.40 (s, 1H), 8.51 (s, 1H), 7.71 (dd, J = 8.1, 1.9 Hz, 1H), 7.65 (dd, J = 11.8, 1.8 Hz, 1H), 7.49 (t, J = 8.0 Hz, 1H), 7.39 (d, J = 12.2 Hz, 1H), 7.30 (d, J = 6.7 Hz, 1H), 6.02-5.97 (m, 1H), 3.68 (s, 3H), 2.40-2.32 (m, 2H), 2.02-1.94 (m, 2H), 1.48 (t, J = 6.4 Hz, 2H), 0.96 (s, 6H). |
| 513 | 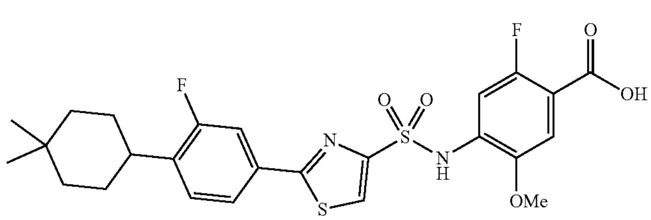 [SMILES: COc1cc(C(=O)O)c(F)cc1NS(=O)(=O)c1csc(-c2ccc(C3CCC(C)(C)CC3)c(F)c2)n1] | 537.2 [M + H]+ | 1H NMR (400 MHz, DMSO-d6) δ 13.16 (br, 1H), 10.39 (s, 1H), 8.50 (s, 1H), 7.70 (dd, J = 8.1, 1.8 Hz, 1H), 7.62 (dd, J = 11.1, 1.8 Hz, 1H), 7.56 (t, J = 7.8 Hz, 1H), 7.41 (d, J = 12.2 Hz, 1H), 7.30 (d, J = 6.6 Hz, 1H), 3.69 (s, 3H), 2.80-2.70 (m, 1H), 1.76-1.53 (m, 4H), |

| Example # | Structure | LC-MS [M + H]+ unless otherwise noted | 1H-NMR |
|---|---|---|---|
| | | | 1.51-1.41 (m, 2H), 1.40-1.26 (m, 2H), 0.98 (s, 3H), 0.95 (s, 3H). |
| 514 | 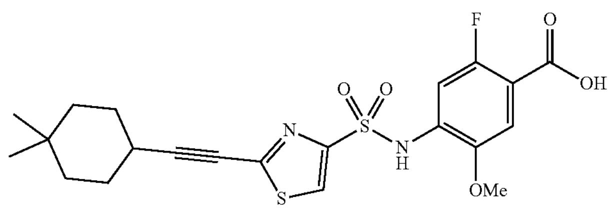 [SMILES: COc1cc(C(=O)O)c(F)cc1NS(=O)(=O)c1csc(C#CC2CCC(C)(C)CC2)n1] | 467.2 [M + H]+ | 1H NMR (400 MHz, DMSO-d6) δ 13.18 (br, 1H), 10.42 (s, 1H), 8.44 (s, 1H), 7.31 (d, J = 6.6 Hz, 1H), 7.22 (d, J = 12.0 Hz, 1H), 3.71 (s, 3H), 2.74-2.63 (m, 1H), 1.83-1.71 (m, 2H), 1.64-1.51 (m, 2H), 1.44-1.34 (m, 2H), 1.27-1.15 (m, 2H), 0.90 (s, 3H), 0.89 (s, 3H). |
| 515 | 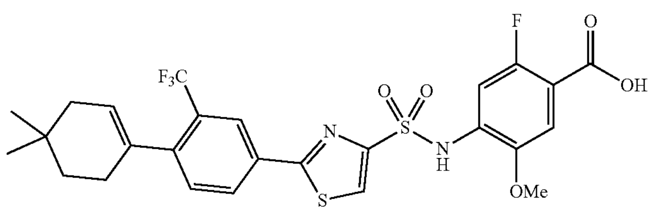 [SMILES: COc1cc(C(=O)O)c(F)cc1NS(=O)(=O)c1csc(-c2ccc(C3=CCC(C)(C)CC3)c(C(F)(F)F)c2)n1] | 585.2 [M + H]+ | 1H NMR (400 MHz, Chloroform-d) δ 8.17-8.11 (m, 2H), 7.94 (dd, J = 8.0, 1.9 Hz, 1H), 7.76 (s, 1H), 7.54 (d, J = 12.0 Hz, 1H), 7.37 (d, J = 6.2 Hz, 1H), 7.30 (d, J = 8.0 Hz, 1H), 5.58-5.52 (m, 1H), 3.88 (s, 3H), 2.29-2.20 (m, 2H), 1.98-1.93 (m, 2H), 1.51 (t, J = 6.3 Hz, 2H), 1.00 (s, 6H). |
| 516 | 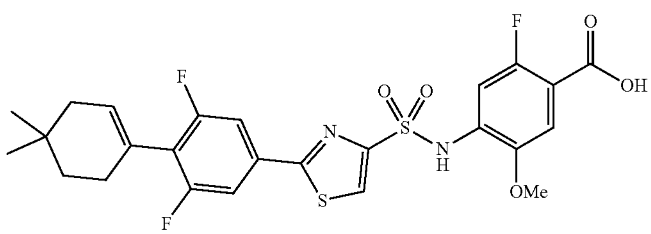 [SMILES: COc1cc(C(=O)O)c(F)cc1NS(=O)(=O)c1csc(-c2cc(F)c(C3=CCC(C)(C)CC3)c(F)c2)n1] | 553.1 [M + H]+ | 1H NMR (400 MHz, DMSO-d6) δ 13.19 (br, 1H), 10.41 (s, 1H), 8.57 (s, 1H), 7.61 (d, J = 7.3 Hz, 2H), 7.43-7.36 (m, 2H), 7.34-7.28 (m, 1H), 5.81-5.76 (m, 1H), 3.68 (m, 3H), 2.29-2.21 (m, 2H), 2.00-1.95 (m, 2H), 1.48 (t, J = 6.3 Hz, 2H), 0.98 (s, 6H). |
| 517 | 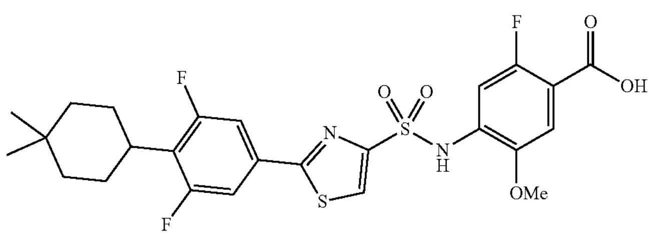 [SMILES: COc1cc(C(=O)O)c(F)cc1NS(=O)(=O)c1csc(-c2cc(F)c(C3CCC(C)(C)CC3)c(F)c2)n1] | 555.2 [M + H]+ | 1H NMR (400 MHz, Chloroform-d) δ 8.14 (s, 1H), 7.73 (s, 1H), 7.51 (d, J = 11.8 Hz, 1H), 7.40-7.33 (m, 3H), 3.89 (s, 3H), 2.98-2.85 (m, 1H), 2.10-1.95 (m, 2H), 1.59-1.20 (m, 6H), 1.01 (s, 3H), 0.98 (s, 3H). |
| 518 | 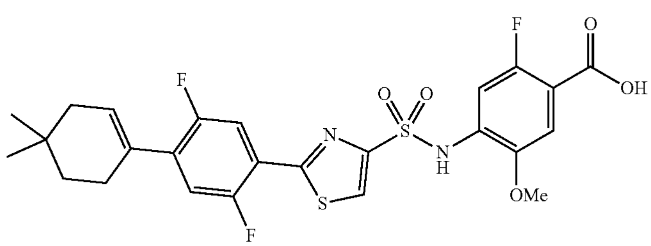 [SMILES: COc1cc(C(=O)O)c(F)cc1NS(=O)(=O)c1csc(-c2cc(F)c(C3=CCC(C)(C)CC3)cc2F)n1] | 553.1 [M + H]+ | 1H NMR (400 MHz, DMSO-d6) δ 10.42 (s, 1H), 8.60 (s, 1H), 7.72-7.64 (m, 1H), 7.53-7.45 (m, 1H), 7.45-7.39 (m, 1H), 7.33-7.28 (m, 1H), 6.14-6.09 (m, 1H), 3.68 (m, 3H), 2.42-2.33 (m, 2H), 2.03-1.96 (m, 2H), 1.48 (t, J = 6.3 Hz, 2H), 0.96 (s, 6H). |

-continued

| Example # | Structure | LC-MS [M + H]+ unless otherwise noted | 1H-NMR |
|---|---|---|---|
| 519 | 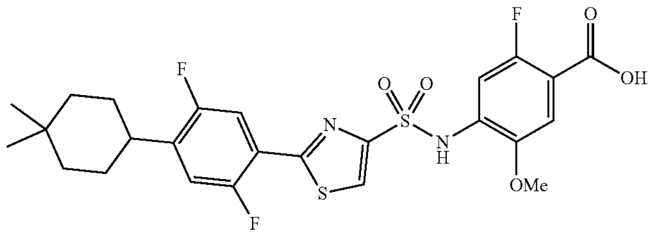 [SMILES: COc1cc(C(=O)O)c(F)cc1NS(=O)(=O)c1csc(-c2cc(F)c(C3CCC(C)(C)CC3)cc2F)n1] | 555.2 [M + H]+ | 1H NMR (400 MHz, DMSO-d6) δ 13.17 (br, 1H), 10.42 (s, 1H), 8.60 (s, 1H), 7.67 (dd, J = 10.4, 5.9 Hz, 1H), 7.57 (dd, J = 11.8, 5.9 Hz, 1H), 7.43 (d, J = 12.1 Hz, 1H), 7.31 (d, J = 6.6 Hz, 1H), 3.68 (s, 3H), 2.80-2.68 (m, 1H), 1.75-1.54 (m, 4H), 1.51-1.41 (m, 2H), 1.40-1.27 (m, 2H), 0.99 (s, 3H), 0.94 (s, 3H). |
| 520 | 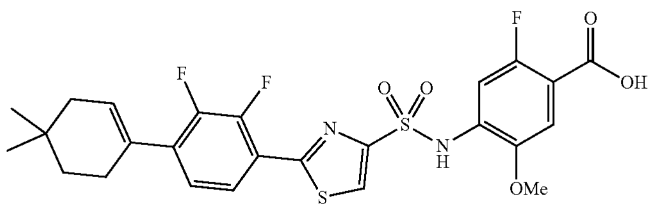 [SMILES: COc1cc(C(=O)O)c(F)cc1NS(=O)(=O)c1csc(-c2ccc(C3=CCC(C)(C)CC3)c(F)c2F)n1] | 553.1 [M + H]+ | 1H NMR (400 MHz, DMSO-d6) δ 13.20 (br, 1H), 10.44 (s, 1H), 8.63 (s, 1H), 7.83-7.74 (m, 1H), 7.44-7.33 (m, 2H), 7.31 (d, J = 6.6 Hz, 1H), 6.12-6.05 (m, 1H), 3.68 (s, 3H), 2.42-2.34 (m, 2H), 2.04-1.97 (m, 2H), 1.49 (t, J = 6.4 Hz, 2H), 0.96 (s, 6H). |
| 521 | 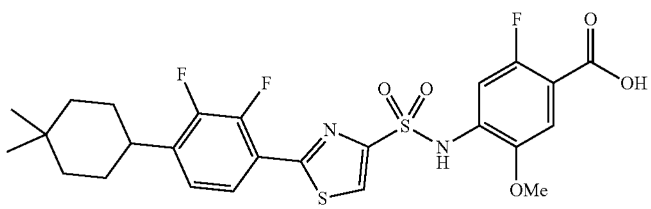 [SMILES: COc1cc(C(=O)O)c(F)cc1NS(=O)(=O)c1csc(-c2ccc(C3CCC(C)(C)CC3)c(F)c2F)n1] | 555.2 [M + H]+ | 1H NMR (400 MHz, DMSO-d6) δ 10.44 (s, 1H), 8.61 (s, 1H), 7.79 (t, J = 7.6 Hz, 1H), 7.47-7.37 (m, 2H), 7.30 (d, J = 6.6 Hz, 1H), 3.69 (s, 3H), 2.85-2.74 (m, 1H), 1.77-1.55 (m, 4H), 1.52-1.41 (m, 2H), 1.41-1.28 (m, 2H), 0.99 (s, 3H), 0.95 (s, 3H). |
| 522 | 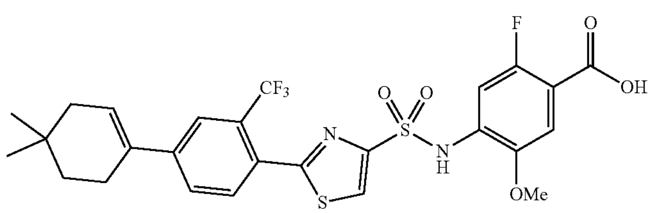 | 585.1 [M + H]+ | 1H NMR (500 MHz, DMSO-d6) δ 13.14 (br, 1H), 10.34 (s, 1H), 8.66 (s, 1H), 7.89-7.82 (m, 2H), 7.72 (d, J = 8.0 Hz, 1H), 7.37 (d, J = 12.1 Hz, 1H), 7.32 (d, J = 6.6 Hz, 1H), 6.43-6.38 (m, 1H), 3.75 (s, 3H), 2.48-2.40 (m, 2H), 2.07-1.99 (m, 2H), 1.52 (t, J = 6.4 Hz, 2H), 0.95 (s, 6H). |
| 523 | 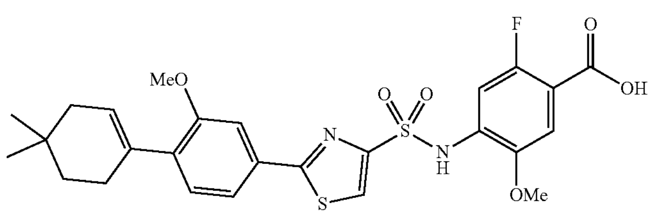 | 547.2 [M + H]+ | 1H NMR (400 MHz, DMSO-d6) δ 13.18 (br, 1H), 10.38 (s, 1H), 8.50 (s, 1H), 7.49 (d, J = 12.1 Hz, 1H), 7.45 (dd, J = 7.8, 1.7 Hz, 1H), 7.39-7.35 (m, 1H), 7.32 (d, J = 6.6 Hz, 1H), 7.23 (d, J = 7.8 Hz, 1H), 5.74-5.68 (m, 1H), 3.82 (s, 3H), 3.70 (s, 3H), 2.36-2.28 (m, 2H), 1.98-1.90 (m, 2H), 1.43 (t, J = 6.4 Hz, 2H), 0.96 (s, 6H). |

| Example # | Structure | LC-MS [M + H]+ unless otherwise noted | ¹H-NMR |
|---|---|---|---|
| 524 | 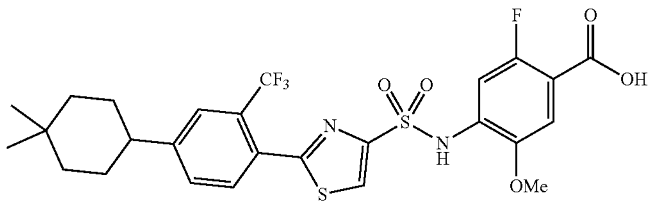 [SMILES: COc1cc(C(=O)O)c(F)cc1NS(=O)(=O)c1csc(-c2ccc(C3CCC(C)(C)CC3)cc2C(F)(F)F)n1] | 587.1 [M + H]+ | ¹H NMR (400 MHz, DMSO-d₆) δ 13.13 (br, 1H), 10.32 (s, 1H), 8.65 (s, 1H), 7.79-7.65 (m, 3H), 7.37 (d, J = 12.1 Hz, 1H), 7.32 (d, J = 6.6 Hz, 1H), 3.75 (s, 3H), 2.71-2.56 (m, 1H), 1.73-1.58 (m, 4H), 1.53-1.41 (m, 2H), 1.40-1.28 (m, 2H), 0.99 (s, 3H), 0.95 (s, 3H). |
| 525 | 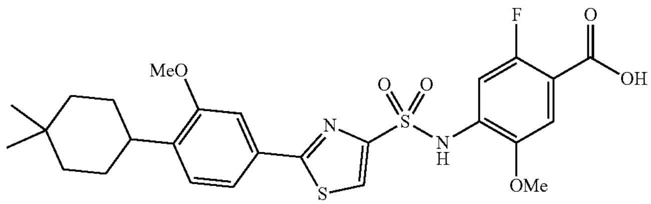 [SMILES: COc1cc(C(=O)O)c(F)cc1NS(=O)(=O)c1csc(-c2ccc(C3CCC(C)(C)CC3)c(OC)c2)n1] | 549.2 [M + H]+ | ¹H NMR (500 MHz, DMSO-d₆) δ 13.18 (br, 1H), 10.37 (s, 1H), 8.48 (s, 1H), 7.50 (d, J = 12.2 Hz, 1H), 7.45 (dd, J = 7.9, 1.7 Hz, 1H), 7.41-7.29 (m, 3H), 3.85 (s, 3H), 3.70 (s, 3H), 2.87-2.77 (m, 1H), 1.65-1.50 (m, 4H), 1.48-1.40 (m, 2H), 1.37-1.26 (m, 2H), 0.97 (s, 3H), 0.94 (s, 3H). |
| 526 | 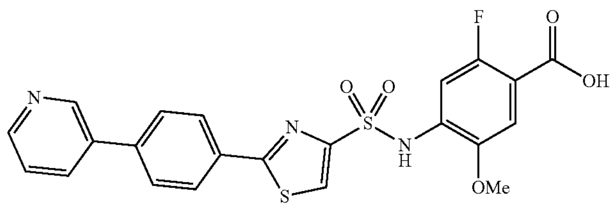 [SMILES: COc1cc(C(=O)O)c(F)cc1NS(=O)(=O)c1csc(-c2ccc(-c3cccnc3)cc2)n1] | 486.1 [M + H]+ | ¹H NMR (500 MHz, DMSO-d6) δ 13.17 (br, 1H), 10.42 (br, 1H), 8.99 (d, J = 2.4 Hz, 1H), 8.62 (dd, J = 4.7, 1.6 Hz, 1H), 8.52 (s, 1H), 8.18 (dt, J = 8.2, 1.9 Hz, 1H), 8.07-8.01 (m, 2H), 7.97-7.91 (m, 2H), 7.53 (dd, J = 8.0, 4.7 Hz, 1H), 7.43 (d, J = 12.2 Hz, 1H), 7.31 (d, J = 6.6 Hz, 1H), 3.70 (s, 3H). |
| 527 | 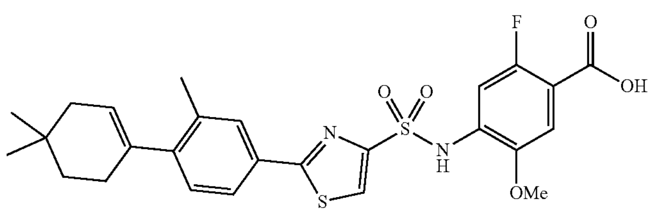 [SMILES: COc1cc(C(=O)O)c(F)cc1NS(=O)(=O)c1csc(-c2ccc(C3=CCC(C)(C)CC3)c(C)c2)n1] | 531.2 [M + H]+ | ¹H NMR (500 MHz, DMSO-d₆) δ 13.17 (br, 1H), 10.35 (s, 1H), 8.46 (s, 1H), 7.71-7.68 (m, 1H), 7.66 (dd, J = 7.9, 2.0 Hz, 1H), 7.42 (d, J = 12.1 Hz, 1H), 7.31 (d, J = 6.6 Hz, 1H), 7.20 (d, J = 7.9 Hz, 1H), 5.53-5.48 (m, 1H), 3.69 (s, 3H), 2.31 (s, 3H), 2.23-2.15 (m, 2H), 1.97-1.89 (m, 2H), 1.48 (t, J = 6.3 Hz, 2H), 0.99 (s, 6H). |
| 528 | 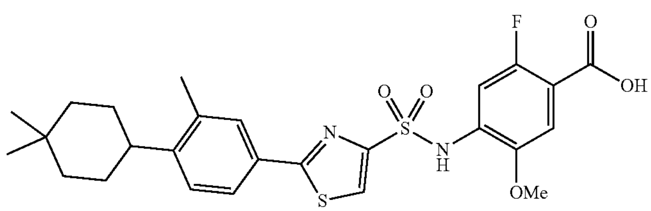 [SMILES: COc1cc(C(=O)O)c(F)cc1NS(=O)(=O)c1csc(-c2ccc(C3CCC(C)(C)CC3)c(C)c2)n1] | 533.2 [M + H]+ | ¹H NMR (500 MHz, Chloroform-d) δ 8.07 (s, 1H), 7.72 (s, 1H), 7.69-7.64 (m, 2H), 7.57 (d, J = 12.4 Hz, 1H), 7.36 (d, J = 6.0 Hz, 1H), 7.31 (d, J = 8.8 Hz, 1H), 3.87 (s, 3H), 2.69-2.57 (m, 1H), 2.37 (s, 3H), 1.67-1.30 (m, 8H), 1.00 (s, 3H), 0.97 (s, 3H). |

-continued

| Example # | Structure | LC-MS [M + H]+ unless otherwise noted | 1H-NMR |
|---|---|---|---|
| 529 | 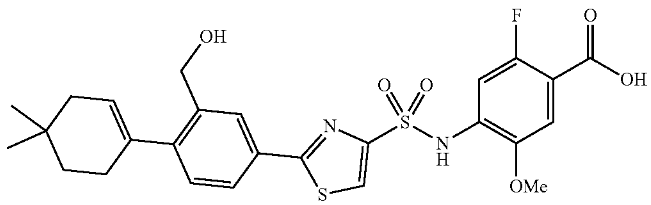 [SMILES: COc1cc(C(=O)O)c(F)cc1NS(=O)(=O)c1csc(-c2ccc(C3=CCC(C)(C)CC3)c(CO)c2)n1] | 547.2 [M + H]+ | 1H NMR (400 MHz, DMSO-d6) δ 10.42 (br, 1H), 8.44 (s, 1H), 8.05 (d, J = 2.0 Hz, 1H), 7.73 (dd, J = 8.0, 2.0 Hz, 1H), 7.34 (d, J = 12.1 Hz, 1H), 7.29 (d, J = 6.7 Hz, 1H), 7.23 (d, J = 8.0 Hz, 1H), 5.54-5.47 (m, 1H), 5.34-5.26 (m, 1H), 4.53 (d, J = 3.9 Hz, 2H), 3.69 (s, 3H), 2.25-2.15 (m, 2H), 1.97-1.89 (m, 2H), 1.47 (t, J = 6.3 Hz, 2H), 0.98 (s, 6H). |
| 530 | 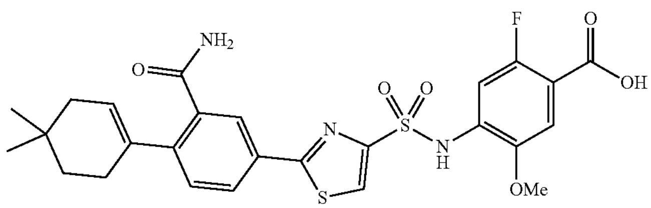 [SMILES: COc1cc(C(=O)O)c(F)cc1NS(=O)(=O)c1csc(-c2ccc(C3=CCC(C)(C)CC3)c(C(N)=O)c2)n1] | 560.1 [M + H]+ | 1H NMR (400 MHz, DMSO-d6) δ 10.43 (br, 1H), 8.49 (s, 1H), 7.89-7.83 (m, 2H), 7.77 (s, 1H), 7.48 (s, 1H), 7.42-7.26 (m, 3H), 5.68-5.63 (m, 1H), 3.69 (s, 3H), 2.38-2.24 (m, 2H), 1.96-1.84 (m, 2H), 1.43 (t, J = 6.4 Hz, 2H), 0.95 (s, 6H). |
| 531 | 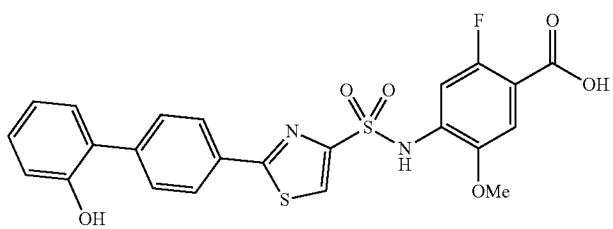 [SMILES: COc1cc(C(=O)O)c(F)cc1NS(=O)(=O)c1csc(-c2ccc(-c3ccccc3O)cc2)n1] | 501.0 [M + H]+ | 1H NMR (400 MHz, DMSO-d6) δ 10.40 (br, 1H), 9.73 (s, 1H), 8.49 (s, 1H), 7.96-7.88 (m, 2H), 7.79-7.67 (m, 2H), 7.42 (d, J = 12.1 Hz, 1H), 7.37-7.26 (m, 2H), 7.21 (td, J = 7.7, 1.7 Hz, 1H), 6.97 (d, J = 8.0 Hz, 1H), 6.93-6.88 (m, 1H), 3.70 (s, 3H). |
| 532 | 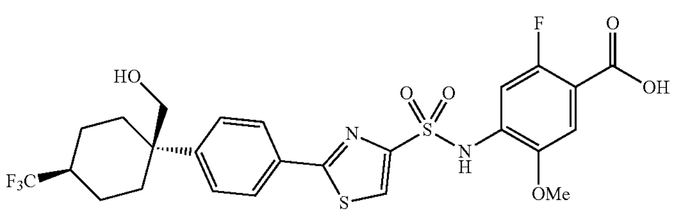 [SMILES: COc1cc(C(=O)O)c(F)cc1NS(=O)(=O)c1csc(-c2ccc([C@]3(CO)CC[C@@H](C(F)(F)F)CC3)cc2)n1] | 589.2 [M + H]+ | 1H NMR (400 MHz, DMSO-d6) δ 10.38 (br, 1H), 8.46 (s, 1H), 7.83 (d, J = 8.3 Hz, 2H), 7.54 (d, J = 8.3 Hz, 2H), 7.43 (d, J = 12.2 Hz, 1H), 7.30 (d, J = 6.7 Hz, 1H), 4.61 (t, J = 5.2 Hz, 1H), 3.70 (s, 3H), 3.64 (d, J = 5.1 Hz, 2H), 2.38-2.25 (m, 1H), 2.23-2.16 (m, 2H), 1.84-1.69 (m, 2H), 1.64-1.51 (m, 4H). |
| 533 | 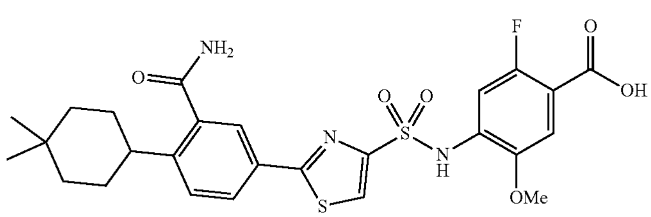 [SMILES: COc1cc(C(=O)O)c(F)cc1NS(=O)(=O)c1csc(-c2ccc(C3CCC(C)(C)CC3)c(C(N)=O)c2)n1] | 562.2 [M + H]+ | 1H NMR (400 MHz, DMSO-d6) δ 13.15 (br, 1H), 10.41 (s, 1H), 8.49 (s, 1H), 7.94 (s, 1H), 7.87 (dd, J = 8.2, 2.1 Hz, 1H), 7.79 (d, J = 2.0 Hz, 1H), 7.59 (d, J = 8.2 Hz, 1H), 7.52 (s, 1H), 7.40-7.27 (m, 2H), 3.70 (s, 3H), 2.92-2.76 (m, 1H), 1.73-1.54 (m, 4H), 1.52-1.37 (m, 2H), 1.33-1.14 (m, 2H), 0.99 (s 3H), 0.93 (s, 3H). |

| Example # | Structure | LC-MS [M + H]+ unless otherwise noted | 1H-NMR |
|---|---|---|---|
| 534 | 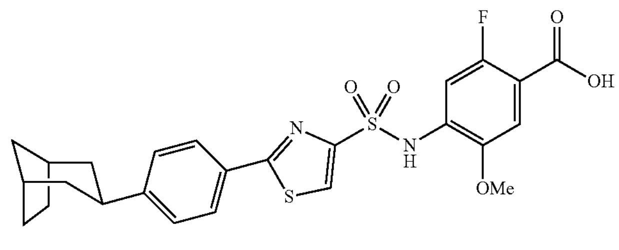 [SMILES: COc1cc(C(=O)O)c(F)cc1NS(=O)(=O)c1csc(-c2ccc(C3CC4CCC(C4)C3)cc2)n1] | 517.1 [M + H]+ | 1H NMR (500 MHz, DMSO-d6) δ 13.18 (br, 1H), 10.36 (s, 1H), 8.46 (s, 1H), 7.83-7.78 (m, 2H), 7.45-7.39 (m, 3H), 7.31 (d, J = 6.6 Hz, 1H), 3.69 (s, 3H), 2.92 (tt, J = 11.7, 5.4 Hz, 1H), 2.30-2.25 (m, 2H), 1.74-1.43 (m, 10H). |
| 535 | 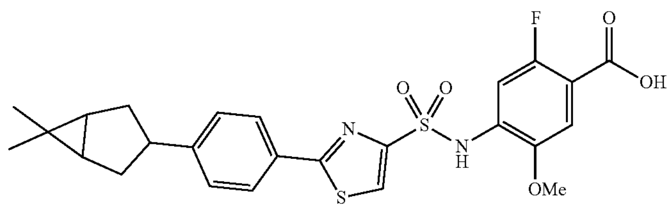 [SMILES: COc1cc(C(=O)O)c(F)cc1NS(=O)(=O)c1csc(-c2ccc(C3CC4C(C3)C4(C)C)cc2)n1] | 517.1 [M + H]+ | 1H NMR (400 MHz, DMSO-d6) δ 13.19 (br, 1H), 10.36 (s, 1H), 8.47 (s, 1H), 7.84-7.77 (m, 2H), 7.44-7.34 (m, 3H), 7.31 (d, J = 6.6 Hz, 1H), 3.69 (s, 3H), 3.14 (p, J = 8.4 Hz, 1H), 2.14-2.03 (m, 2H), 1.95-1.83 (m, 2H), 1.30-1.21 (m, 2H), 1.06 (s, 3H), 0.99 (s, 3H). |
| 536 | 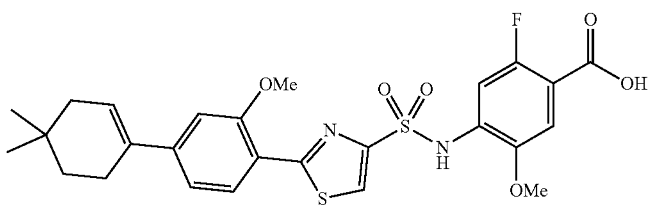 [SMILES: COc1cc(C(=O)O)c(F)cc1NS(=O)(=O)c1csc(-c2ccc(C3=CCC(C)(C)CC3)cc2OC)n1] | 547.2 [M + H]+ | 1H NMR (400 MHz, DMSO-d6) δ 13.17 (br, 1H), 10.28 (s, 1H), 8.46 (s, 1H), 8.03 (d, J = 8.3 Hz, 1H), 7.44 (d, J = 12.2 Hz, 1H), 7.30 (d, J = 6.6 Hz, 1H), 7.27-7.18 (m, 2H), 6.39-6.31 (m, 1H), 4.06 (s, 3H), 3.68 (s, 3H), 2.49-2.39 (m, 2H), 2.05-1.99 (m, 2H), 1.51 (t, J = 6.4 Hz, 2H), 0.95 (s, 6H). |
| 537 | 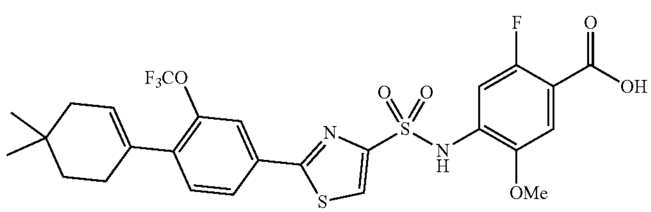 [SMILES: COc1cc(C(=O)O)c(F)cc1NS(=O)(=O)c1csc(-c2ccc(C3=CCC(C)(C)CC3)c(OC(F)(F)F)c2)n1] | 601.2 [M + H]+ | 1H NMR (500 MHz, DMSO-d6) δ 13.17 (br, 1H), 10.42 (s, 1H), 8.55 (s, 1H), 7.89 (dd, J = 8.1, 1.8 Hz, 1H), 7.79-7.75 (m, 1H), 7.53 (d, J = 8.0 Hz, 1H), 7.42 (d, J = 12.0 Hz, 1H), 7.31 (d, J = 6.5 Hz, 1H), 5.83-5.78 (m, 1H), 3.68 (s, 3H), 2.33-2.27 (m, 2H), 2.01-1.93 (m, 2H), 1.47 (t, J = 6.3 Hz, 2H), 0.97 (s, 6H). |
| 538 | 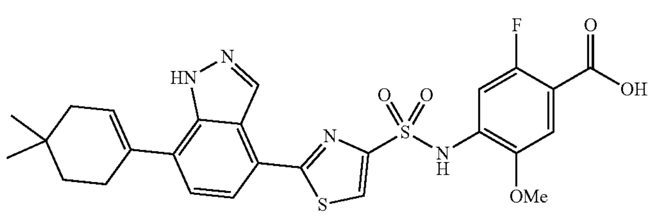 [SMILES: COc1cc(C(=O)O)c(F)cc1NS(=O)(=O)c1csc(-c2ccc(C3=CCC(C)(C)CC3)c3[nH]ncc23)n1] | 557.1 [M + H]+ | 1H NMR (500 MHz, DMSO-d6) δ 13.33 (s, 1H), 13.15 (br, 1H), 10.51 (s, 1H), 8.60 (s, 1H), 8.54 (s, 1H), 7.69 (d, J = 7.5 Hz, 1H), 7.42 (d, J = 12.1 Hz, 1H), 7.34 (d, J = 7.5 Hz, 1H), 7.29 (d, J = 6.6 Hz, 1H), 6.24 (s, 1H), 3.67 (s, 3H), 2.53-2.50 (m, 2H), 2.12-2.06 (m, 2H), 1.55 (t, J = 6.3 Hz, 2H), 1.01 (s, 6H). |

-continued

| Example # | Structure | LC-MS [M + H]+ unless otherwise noted | 1H-NMR |
|---|---|---|---|
| 539 | 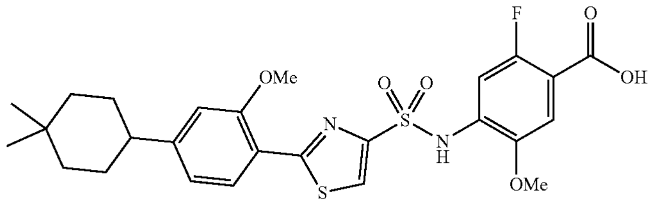 [SMILES: COc1cc(C(=O)O)c(F)cc1NS(=O)(=O)c1csc(-c2ccc(C3CCC(C)(C)CC3)cc2OC)n1] | 549.2 [M + H]+ | 1H NMR (500 MHz, DMSO-d6) δ 13.16 (br, 1H), 10.28 (s, 1H), 8.45 (s, 1H), 8.01 (d, J = 8.1 Hz, 1H), 7.45 (d, J = 12.2 Hz, 1H), 7.30 (d, J = 6.6 Hz, 1H), 7.13 (d, J = 1.5 Hz, 1H), 7.05 (dd, J = 8.2, 1.6 Hz, 1H), 4.03 (s, 3H), 3.69 (s, 3H), 1.70-1.61 (m, 4H), 1.51-1.43 (m, 2H), 1.37-1.28 (m, 2H), 1.00 (s, 3H), 0.95 (s, 3H). |
| 540 | 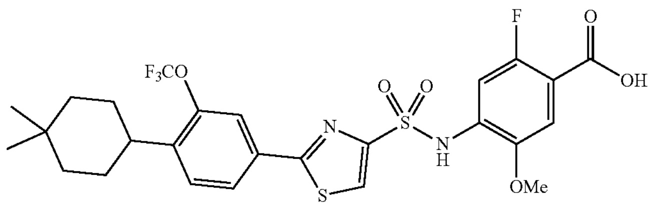 | 603.2 [M + H]+ | 1H NMR (500 MHz, DMSO-d6) δ 13.17 (br, 1H), 10.41 (s, 1H), 8.54 (s, 1H), 7.88 (dd, J = 8.1, 1.9 Hz, 1H), 7.76-7.69 (m, 2H), 7.43 (d, J = 12.0 Hz, 1H), 7.31 (d, J = 6.6 Hz, 1H), 3.68 (s, 3H), 2.77 (tt, J = 12.2, 3.5 Hz, 1H), 1.67 (qd, J = 13.0, 3.2 Hz, 2H), 1.57-1.45 (m, 4H), 1.37-1.28 (m, 2H), 1.00 (s, 3H), 0.95 (s, 3H). |
| 541 | 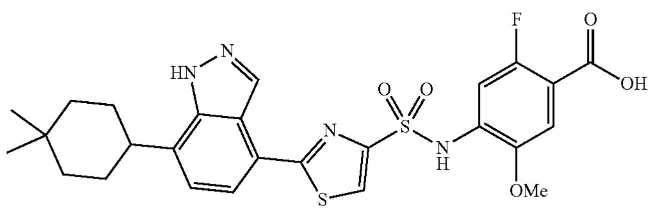 [SMILES: COc1cc(C(=O)O)c(F)cc1NS(=O)(=O)c1csc(-c2ccc(C3CCC(C)(C)CC3)c3[nH]ncc23)n1] | 559.3 [M + H]+ | 1H NMR (400 MHz, DMSO-d6) δ 13.49 (s, 1H), 13.15 (br, 1H), 10.51 (s, 1H), 8.55 (s, 2H), 7.67 (d, J = 7.4 Hz, 1H), 7.43 (d, J = 12.1 Hz, 1H), 7.35 (d, J = 7.5 Hz, 1H), 7.29 (d, J = 6.6 Hz, 1H), 3.68 (s, 3H), 3.10-2.97 (m, 1H), 1.83-1.62 (m, 4H), 1.58-1.36 (m, 4H), 1.01 (s, 3H), 0.99 (s, 3H). |
| 542 | 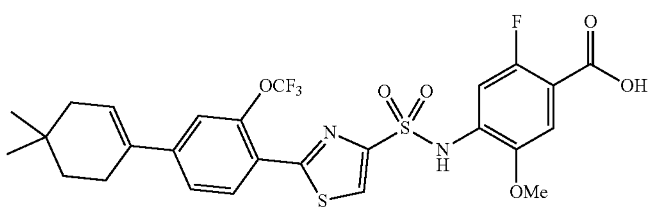 [SMILES: COc1cc(C(=O)O)c(F)cc1NS(=O)(=O)c1csc(-c2ccc(C3=CCC(C)(C)CC3)cc2OC(F)(F)F)n1] | 601.2 [M + H]+ | 1H NMR (500 MHz, DMSO-d6) δ 13.19 (br, 1H), 10.41 (s, 1H), 8.58 (s, 1H), 8.09 (d, J = 8.4 Hz, 1H), 7.68 (dd, J = 8.4, 1.8 Hz, 1H), 7.55-7.51 (m, 1H), 7.39 (d, J = 12.0 Hz, 1H), 7.30 (d, J = 6.7 Hz, 1H), 6.44-6.39 (m, 1H), 3.66 (s, 3H), 2.46-2.38 (m, 2H), 2.06-2.00 (m, 2H), 1.51 (t, J = 6.4 Hz, 2H), 0.95 (s, 6H). |
| 543 | 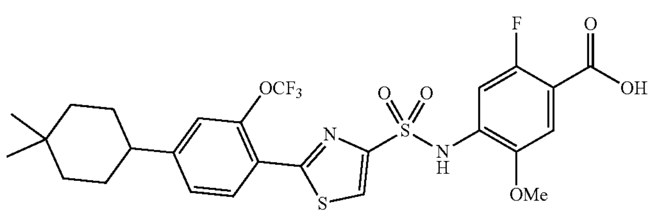 [SMILES: COc1cc(C(=O)O)c(F)cc1NS(=O)(=O)c1csc(-c2ccc(C3CCC(C)(C)CC3)cc2OC(F)(F)F)n1] | 603.1 [M + H]+ | 1H NMR (400 MHz, DMSO-d6) δ 13.20 (br, 1H), 10.40 (s, 1H), 8.57 (s, 1H), 8.06 (d, J = 8.2 Hz, 1H), 7.52 (dd, J = 8.3, 1.7 Hz, 1H), 7.46-7.42 (m, 1H), 7.40 (d, J = 12.1 Hz, 1H), 7.30 (d, J = 6.6 Hz, 1H), 3.68 (s, 3H), 2.64-2.53 (m, 1H), 1.72-1.54 (m, |

-continued

| Example # | Structure | LC-MS [M + H]+ unless otherwise noted | 1H-NMR |
|---|---|---|---|
| | | | 4H), 1.51-1.41 (m, 2H), 1.38-1.27 (m, 2H), 0.98 (s, 3H), 0.94 (s, 3H). |
| 544 | 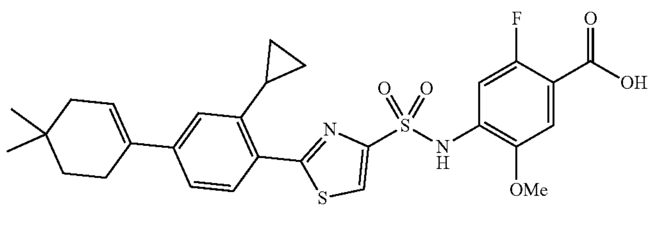 [SMILES: COc1cc(C(=O)O)c(F)cc1NS(=O)(=O)c1csc(-c2ccc(C3=CCC(C)(C)CC3)cc2C2CC2)n1] | 557.2 [M + H]+ | 1H NMR (500 MHz, DMSO-d6) δ 13.16 (br, 1H), 10.34 (s, 1H), 8.59 (s, 1H), 7.71 (d, J = 8.2 Hz, 1H), 7.43 (d, J = 12.3 Hz, 1H), 7.39 (dd, J = 8.3, 1.9 Hz, 1H), 7.31 (d, J = 6.6 Hz, 1H), 7.17 (d, J = 1.9 Hz, 1H), 6.26-6.22 (m, 1H), 3.71 (s, 3H), 2.43-2.37 (m, 2H), 2.30-2.23 (m, 1H), 2.01-1.97 (m, 2H), 1.48 (t, J = 6.4 Hz, 2H), 0.94 (s, 6H), 0.86-0.78 (m, 2H), 0.73-0.68 (m, 2H). |
| 545 | 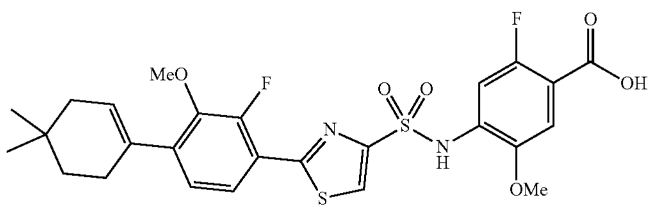 [SMILES: COc1cc(C(=O)O)c(F)cc1NS(=O)(=O)c1csc(-c2ccc(C3=CCC(C)(C)CC3)c(OC)c2F)n1] | 565.2 [M + H]+ | 1H NMR (500 MHz, DMSO-d6) δ 13.16 (br, 1H), 10.41 (s, 1H), 8.58 (s, 1H), 7.74-7.68 (m, 1H), 7.40 (d, J = 12.0 Hz, 1H), 7.30 (d, J = 6.5 Hz, 1H), 7.18 (d, J = 8.3 Hz, 1H), 5.89-5.84 (m, 1H), 3.81 (s, 3H), 3.69 (s, 3H), 2.39-2.32 (m, 2H), 2.01-1.94 (m, 2H), 1.47 (t, J = 6.4 Hz, 2H), 0.98 (s, 6H). |
| 546 | 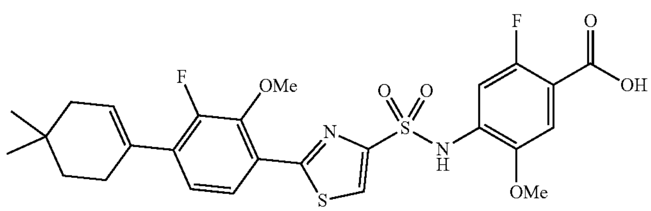 [SMILES: COc1cc(C(=O)O)c(F)cc1NS(=O)(=O)c1csc(-c2ccc(C3=CCC(C)(C)CC3)c(F)c2OC)n1] | 565.1 [M + H]+ | 1H NMR (500 MHz, DMSO-d6) δ 13.16 (br, 1H), 10.35 (s, 1H), 8.54 (s, 1H), 7.83 (dd, J = 8.4, 1.3 Hz, 1H), 7.42 (d, J = 12.1 Hz, 1H), 7.30 (d, J = 6.6 Hz, 1H), 7.23 (dd, J = 8.4, 7.1 Hz, 1H), 6.03-5.98 (m, 1H), 4.02 (d, J = 1.6 Hz, 3H), 3.69 (s, 3H), 2.41-2.36 (m, 2H), 2.02-1.98 (m, 2H), 1.48 (t, J = 6.4 Hz, 2H), 0.97 (s, 6H). |
| 547 | 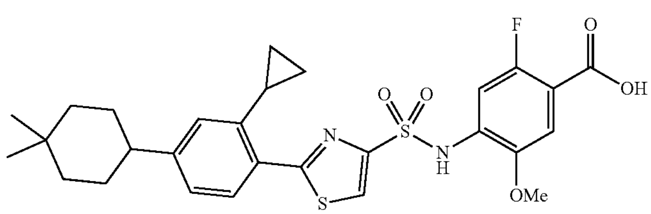 [SMILES: COc1cc(C(=O)O)c(F)cc1NS(=O)(=O)c1csc(-c2ccc(C3CCC(C)(C)CC3)cc2C2CC2)n1] | 559.2 [M + H]+ | 1H NMR (400 MHz, DMSO-d6) δ 13.15 (s, 1H), 10.32 (s, 1H), 8.58 (s, 1H), 7.64 (d, J = 8.0 Hz, 1H), 7.43 (d, J = 12.2 Hz, 1H), 7.31 (d, J = 6.7 Hz, 1H), 7.22 (dd, J = 8.0, 1.8 Hz, 1H), 7.01 (d, J = 1.7 Hz, 1H), 3.72 (s, 3H), 2.48-2.38 (m, 1H), 2.27-2.17 (m, 1H), 1.69-1.18 (m, 8H), 0.97 (s, 3H), 0.94 (s, 3H), 0.84-0.78 (m, 2H), 0.71-0.63 (m, 2H). |

-continued

| Example # | Structure | LC-MS [M + H]+ unless otherwise noted | 1H-NMR |
|---|---|---|---|
| 548 | 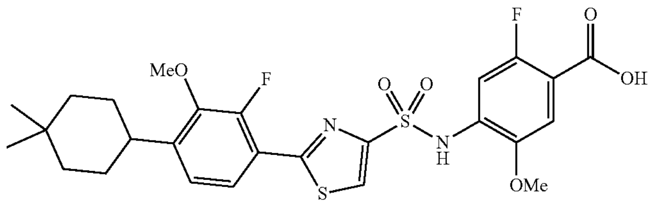 [SMILES: COc1cc(C(=O)O)c(F)cc1NS(=O)(=O)c1csc(-c2ccc(C3CCC(C)(C)CC3)c(OC)c2F)n1] | 567.2 [M + H]+ | 1H NMR (400 MHz, Chloroform-d) δ 8.20 (s, 1H), 7.83 (dd, J = 8.4, 6.9 Hz, 1H), 7.71 (s, 1H), 7.60 (d, J = 12.0 Hz, 1H), 7.36 (d, J = 6.2 Hz, 1H), 7.11 (dd, J = 8.4, 1.4 Hz, 1H), 3.93 (d, J = 1.4 Hz, 3H), 3.87 (s, 3H), 2.86 (tt, J = 11.0, 5.0 Hz, 1H), 1.76-1.31 (m, 8H), 1.00 (s, 3H), 0.97 (s, 3H) |
| 549 | 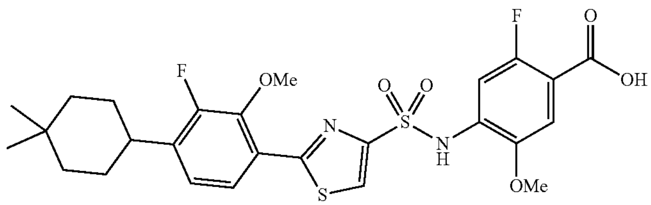 [SMILES: COc1cc(C(=O)O)c(F)cc1NS(=O)(=O)c1csc(-c2ccc(C3CCC(C)(C)CC3)c(F)c2OC)n1] | 567.2 [M + H]+ | 1H NMR (400 MHz, DMSO-d6) δ 13.17 (s, 1H), 10.36 (s, 1H), 8.54 (s, 1H), 7.83 (d, J = 8.3 Hz, 1H), 7.44 (d, J = 12.2 Hz, 1H), 7.34-7.26 (m, 2H), 4.02 (d, J = 1.7 Hz, 2H), 3.70 (s, 2H), 2.80-2.70 (m, 1H), 1.76-1.56 (m, 4H), 1.52-1.52 (m, 2H), 1.41-1.29 (m, 2H), 0.99 (s, 3H), 0.95 (s, 3H). |
| 550 | 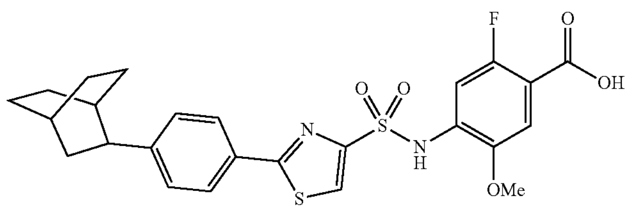 [SMILES: COc1cc(C(=O)O)c(F)cc1NS(=O)(=O)c1csc(-c2ccc(C3CC4CCC3CC4)cc2)n1] | 517.1 [M + H]+ | 1H NMR (500 MHz, DMSO-d6) δ 13.15 (br, 1H), 10.37 (s, 1H), 8.47 (s, 1H), 7.85 (d, J = 8.3 Hz, 2H), 7.46 (d, J = 8.2 Hz, 2H), 7.41 (d, J = 12.1 Hz, 1H), 7.30 (d, J = 6.6 Hz, 1H), 3.69 (s, 3H), 3.04 (t, J = 9.1 Hz, 1H), 2.00-1.89 (m, 1H), 1.81-1.43 (m, 10H), 1.36-1.27 (m, 1H). |
| 551 | 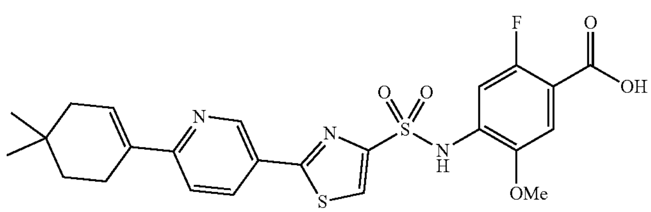 [SMILES: COc1cc(C(=O)O)c(F)cc1NS(=O)(=O)c1csc(-c2ccc(C3=CCC(C)(C)CC3)nc2)n1] | 518.2 [M + H]+ | 1H NMR (400 MHz, DMSO-d6) δ 13.18 (br, 1H), 10.42 (s, 1H), 9.02 (d, J = 2.4 Hz, 1H), 8.54 (s, 1H), 8.19 (dd, J = 8.4, 2.4 Hz, 1H), 7.69 (d, J = 8.5 Hz, 1H), 7.42 (d, J = 12.1 Hz, 1H), 7.31 (d, J = 6.6 Hz, 1H), 6.90-6.83 (m, 1H), 3.69 (s, 3H), 2.55-2.50 (m, 2H), 2.08-2.03 (m, 2H), 1.50 (t, J = 6.4 Hz, 2H), 0.95 (s, 6H). |
| 552 | 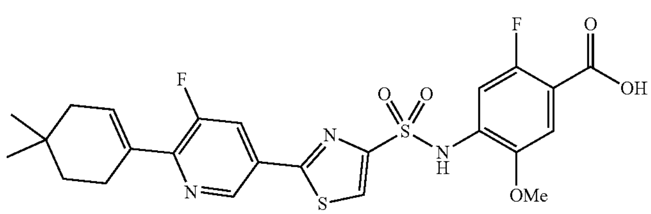 | 536.2 [M + H]+ | 1H NMR (400 MHz, DMSO-d6) δ 13.19 (br, 1H), 10.44 (s, 1H), 8.92-8.88 (m, 1H), 8.59 (s, 1H), 8.10 (dd, J = 12.2, 1.9 Hz, 1H), 7.41 (d, J = 12.1 Hz, 1H), 7.31 (d, J = 6.6 Hz, 1H), 6.63-6.58 (m, 1H), 3.68 (s, 3H), 2.56-2.51 (m, 2H), 2.10-2.03 (m, 2H), 1.50 (t, J = 6.4 Hz, 2H), 0.96 (s, 6H). |

-continued

| Example # | Structure | LC-MS [M + H]+ unless otherwise noted | 1H-NMR |
|---|---|---|---|
| 553 | 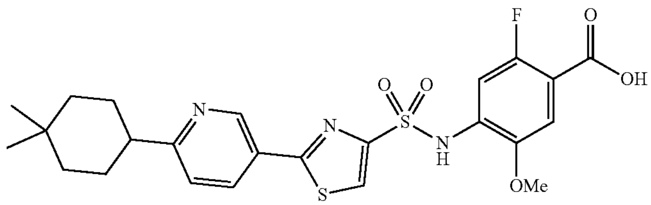 [SMILES: COc1cc(C(=O)O)c(F)cc1NS(=O)(=O)c1csc(-c2ccc(C3CCC(C)(C)CC3)nc2)n1] | 520.2 [M + H]+ | 1H NMR (500 MHz, DMSO-d6) δ 13.14 (br, 1H), 10.42 (s, 1H), 9.00 (d, J = 2.3 Hz, 1H), 8.52 (s, 1H), 8.17 (dd, J = 8.2, 2.4 Hz, 1H), 7.48 (d, J = 8.2 Hz, 1H), 7.40 (d, J = 12.2 Hz, 1H), 7.30 (d, J = 6.7 Hz, 1H), 3.69 (s, 3H), 2.71-2.61 (m, 1H), 1.78-1.66 (m, 4H), 1.51-1.43 (m, 2H), 1.37-1.28 (m, 2H), 0.96 (s, 3H), 0.95 (s, 3H). |
| 554 | 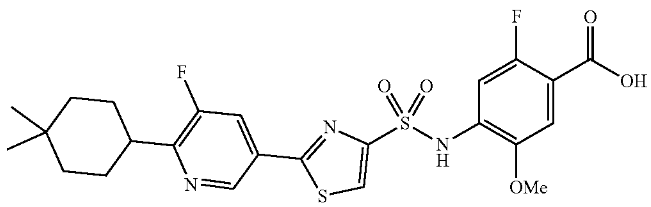 [SMILES: COc1cc(C(=O)O)c(F)cc1NS(=O)(=O)c1csc(-c2cnc(C3CCC(C)(C)CC3)c(F)c2)n1] | 538.2 [M + H]+ | 1H NMR (500 MHz, DMSO-d6) δ 13.17 (br, 1H), 10.44 (s, 1H), 8.92-8.89 (m, 1H), 8.58 (s, 1H), 8.06 (dd, J = 10.5, 1.9 Hz, 1H), 7.40 (d, J = 12.1 Hz, 1H), 7.31 (d, J = 6.6 Hz, 1H), 3.69 (s, 3H), 3.00-2.91 (m, 1H), 1.81 (qd, J = 13.4, 3.5 Hz, 2H), 1.66-1.57 (m, 2H), 1.53-1.44 (m, 2H), 1.35 (td, J = 13.4, 3.9 Hz, 2H), 0.96 (s, 3H), 0.95 (s, 3H). |
| 555 | 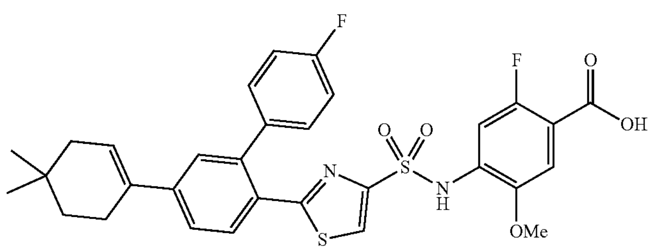 [SMILES: COc1cc(C(=O)O)c(F)cc1NS(=O)(=O)c1csc(-c2ccc(C3=CCC(C)(C)CC3)cc2-c2ccc(F)cc2)n1] | 611.4 [M + H]+ | 1H NMR (400 MHz, DMSO-d6) δ 13.17 (br, 1H), 10.29 (s, 1H), 8.31 (s, 1H), 7.87 (d, J = 8.3 Hz, 1H), 7.62 (dd, J = 8.4, 1.9 Hz, 1H), 7.38 (d, J = 1.9 Hz, 1H), 7.35-7.26 (m, 4H), 7.24-7.15 (m, 2H), 6.36-6.31 (m, 1H), 3.71 (s, 3H), 2.48-2.37 (m, 2H), 2.04-1.97 (m, 2H), 1.49 (t, J = 6.4 Hz, 2H), 0.94 (s, 6H). |
| 556 | 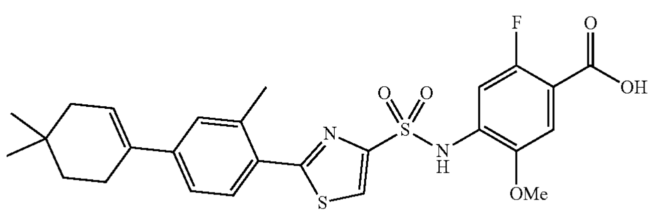 [SMILES: COc1cc(C(=O)O)c(F)cc1NS(=O)(=O)c1csc(-c2ccc(C3=CCC(C)(C)CC3)cc2C)n1] | 531.2 [M + H]+ | 1H NMR (400 MHz, DMSO-d6) δ 13.15 (br, 1H), 10.33 (s, 1H), 8.55 (s, 1H), 7.69 (d, J = 8.1 Hz, 1H), 7.50-7.42 (m, 2H), 7.40 (dd, J = 8.2, 2.0 Hz, 1H), 7.31 (d, J = 6.6 Hz, 1H), 6.30-6.19 (m, 1H), 3.72 (s, 3H), 2.44 (s, 3H), 2.43-2.36 (m, 2H), 2.03-1.96 (m, 2H), 1.49 (t, J = 6.4 Hz, 2H), 0.94 (s, 6H). |
| 557 | 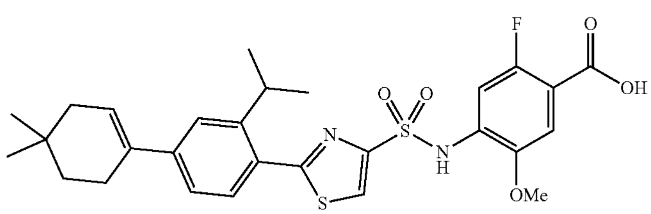 [SMILES: COc1cc(C(=O)O)c(F)cc1NS(=O)(=O)c1csc(-c2ccc(C3=CCC(C)(C)CC3)cc2C(C)C)n1] | 559.3 [M + H]+ | 1H NMR (400 MHz, DMSO-d6) δ 13.12 (br, 1H), 10.32 (s, 1H), 8.59 (s, 1H), 7.52-7.47 (m, 2H), 7.42-7.31 (m, 3H), 6.27-6.22 (m, 1H), 3.74 (s, 3H), 3.51-3.38 (m, 1H), 2.45-2.36 (m, 2H), 2.05-1.96 (m, 2H), 1.50 (t, J = 6.4 Hz, 2H), 1.04 (d, J = 6.8 Hz, 6H), 0.95 (s, 6H). |

| Example # | Structure | LC-MS [M + H]+ unless otherwise noted | 1H-NMR |
|---|---|---|---|
| 558 | 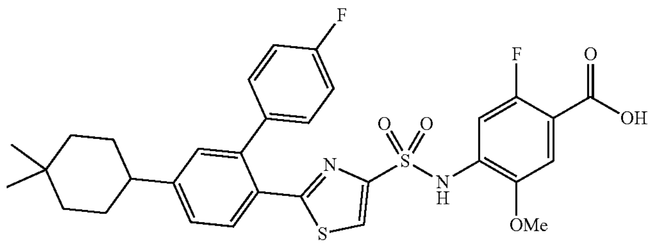 [SMILES: COc1cc(C(=O)O)c(F)cc1NS(=O)(=O)c1csc(-c2ccc(C3CCC(C)(C)CC3)cc2-c2ccc(F)cc2)n1] | 613.4 [M + H]+ | 1H NMR (400 MHz, DMSO-d6) δ 13.17 (br, 1H), 10.27 (s, 1H), 8.33 (s, 1H), 7.80 (d, J = 8.1 Hz, 1H), 7.46 (dd, J = 8.2, 1.9 Hz, 1H), 7.36-7.23 (m, 5H), 7.21-7.11 (m, 2H), 3.73 (s, 3H), 2.59-2.49 (m, 1H), 1.71-1.58 (m, 4H), 1.51-1.41 (m, 2H), 1.39-1.26 (m, 2H), 1.23 (s, 1H), 0.97 (s, 3H), 0.94 (s, 3H). |
| 559 | 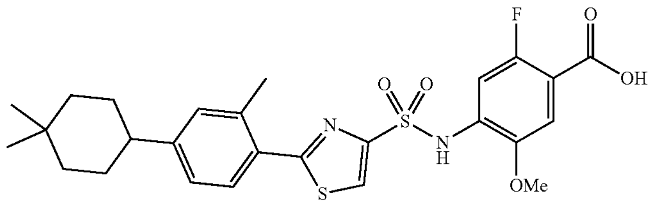 [SMILES: COc1cc(C(=O)O)c(F)cc1NS(=O)(=O)c1csc(-c2ccc(C3CCC(C)(C)CC3)cc2C)n1] | 533.2 [M + H]+ | 1H NMR (400 MHz, DMSO-d6) δ 13.15 (br, 1H), 10.32 (s, 1H), 8.55 (s, 1H), 7.64 (d, J = 8.0 Hz, 1H), 7.47 (d, J = 12.2 Hz, 1H), 7.31 (d, J = 6.6 Hz, 1H), 7.29-7.26 (m, 1H), 7.25-7.20 (m, 1H), 3.73 (s, 3H), 2.48-2.42 (m, 1H), 2.41 (s, 3H), 1.66-1.56 (m, 4H), 1.50-1.40 (m, 2H), 1.39-1.26 (m, 2H), 0.98 (s, 3H), 0.94 (s, 3H). |
| 560 | 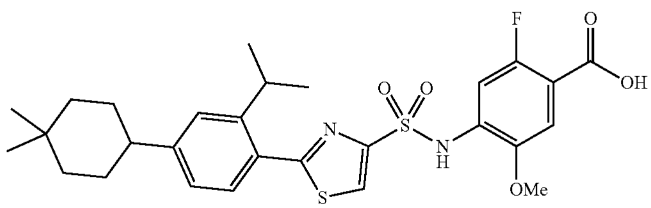 [SMILES: COc1cc(C(=O)O)c(F)cc1NS(=O)(=O)c1csc(-c2ccc(C3CCC(C)(C)CC3)cc2C(C)C)n1] | 561.3 [M + H]+ | 1H NMR (400 MHz, DMSO-d6) δ 13.14 (br, 1H), 10.31 (s, 1H), 8.58 (s, 1H), 7.50-7.29 (m, 4H), 7.21 (dd, J = 8.1, 1.8 Hz, 1H), 3.74 (s, 3H), 3.43-3.33 (m, 1H), 2.48-2.40 (m, 1H), 1.69-1.17 (m, 8H), 1.03 (d, J = 6.8 Hz, 6H), 0.98 (s, 3H), 0.95 (s, 3H) |
| 561 | 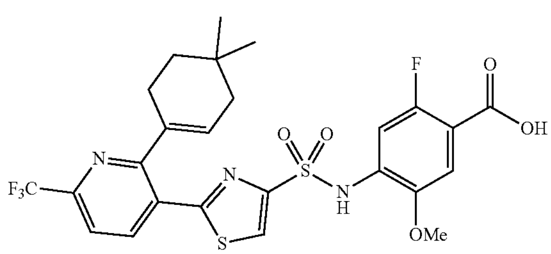 [SMILES: COc1cc(C(=O)O)c(F)cc1NS(=O)(=O)c1csc(-c2ccc(C(F)(F)F)nc2C2=CCC(C)(C)CC2)n1] | 586.2 [M + H]+ | 1H NMR (400 MHz, DMSO-d6) δ 13.19 (br, 1H), 10.43 (s, 1H), 8.65 (s, 1H), 8.40 (d, J = 8.1 Hz, 1H), 7.96 (d, J = 8.2 Hz, 1H), 7.32 (dd, J = 9.3, 2.7 Hz, 2H), 5.71-5.65 (m, 1H), 3.71 (s, 3H), 2.28-2.20 (m, 2H), 1.78-1.70 (m, 2H), 1.40 (t, J = 6.3 Hz, 2H), 0.89 (s, 6H). |
| 562 | 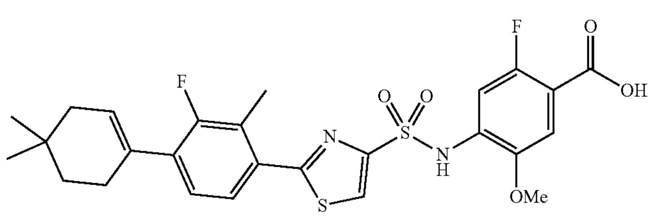 [SMILES: COc1cc(C(=O)O)c(F)cc1NS(=O)(=O)c1csc(-c2ccc(C3=CCC(C)(C)CC3)c(F)c2C)n1] | 549.1 [M + H]+ | 1H NMR (400 MHz, DMSO-d6) δ 13.16 (br, 1H), 10.38 (s, 1H), 8.59 (s, 1H), 7.50 (d, J = 8.1 Hz, 1H), 7.44 (d, J = 12.2 Hz, 1H), 7.31 (d, J = 6.6 Hz, 1H), 7.27 (t, J = 7.9 Hz, 1H), 5.94-5.88 (m, 1H), 3.72 (s, 3H), 2.37-2.31 (m, 2H), 2.31 (d, J = 2.7 Hz, 3H), 2.01-1.95 (m, 2H), 1.47 (t, J = 6.4 Hz, 2H), 0.96 (s, 6H). |

-continued

| Example # | Structure | LC-MS [M + H]+ unless otherwise noted | 1H-NMR |
|---|---|---|---|
| 563 | 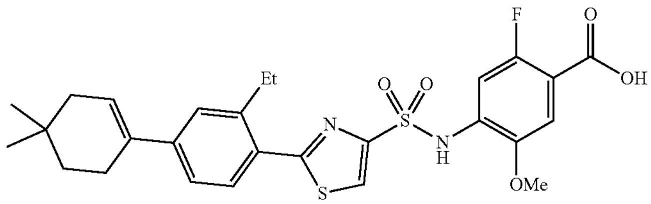 [SMILES: CCc1cc(C2=CCC(C)(C)CC2)ccc1-c1nc(S(=O)(=O)Nc2cc(F)c(C(=O)O)cc2OC)cs1] | 545.2 [M + H]+ | 1H NMR (500 MHz, DMSO-d6) δ 13.14 (br, 1H), 10.32 (s, 1H), 8.57 (s, 1H), 7.60 (d, J = 8.1 Hz, 1H), 7.47-7.35 (m, 3H), 7.32 (d, J = 6.6 Hz, 1H), 6.28-6.23 (m, 1H), 3.73 (s, 3H), 2.80 (q, J =7.4 Hz, 2H), 2.44-2.37 (m, 2H), 2.03-1.98 (m, 2H), 1.49 (t, J = 6.4 Hz, 2H), 0.95 (t, J = 7.5 Hz, 3H), 0.94 (s, 6H). |
| 564 | 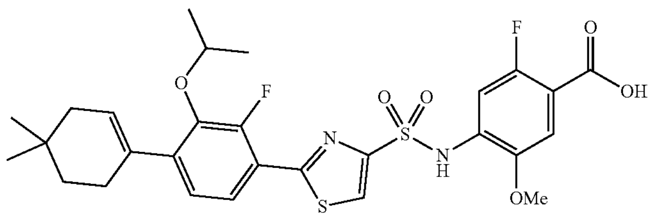 [SMILES: COc1cc(C(=O)O)c(F)cc1NS(=O)(=O)c1csc(-c2ccc(C3=CCC(C)(C)CC3)c(OC(C)C)c2F)n1] | 593.3 [M + H]+ | 1H NMR (500 MHz, DMSO-d6) δ 13.17 (br, 1H), 10.41 (s, 1H), 8.59 (s, 1H), 7.70 (dd, J = 8.3, 6.9 Hz, 1H), 7.42 (d, J = 12.1Hz, 1H), 7.31 (d, J = 6.7 Hz, 1H), 7.17 (dd, J = 8.3, 1.1 Hz, 1H), 5.89-5.84 (m, 1H), 4.29 (sept, J = 6.1 Hz, 1H), 3.69 (s, 3H), 2.40-2.33 (m, 2H), 2.01-1.93 (m, 2H), 1.46 (t, J = 6.3 Hz, 2H), 1.21 (d, J = 6.1 Hz, 6H), 0.97 (s, 6H). |
| 565 | 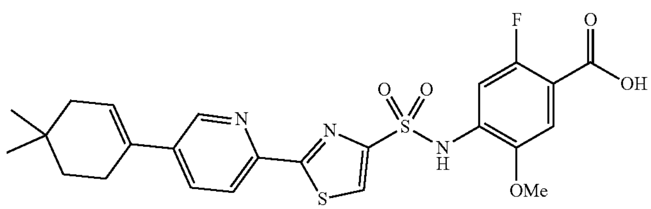 [SMILES: COc1cc(C(=O)O)c(F)cc1NS(=O)(=O)c1csc(-c2ccc(C3=CCC(C)(C)CC3)cn2)n1] | 518.2 [M + H]+ | 1H NMR (500 MHz, DMSO-d6) δ 13.04 (br, 1H), 10.39 (br, 1H), 8.76 (d, J = 2.3 Hz, 1H), 8.48 (s, 1H), 8.05 (dd, J = 8.3, 2.3 Hz, 1H), 7.94 (d, J = 8.3 Hz, 1H), 7.37 (d, J = 12.3 Hz, 1H), 7.28 (d, J = 6.6 Hz, 1H), 6.44-6.37 (m, 1H), 3.67 (s, 3H), 2.47-2.40 (m, 2H), 2.06-1.99 (m, 2H), 1.51 (t, J = 6.4 Hz, 2H), 0.95 (s, 6H). |
| 566 | 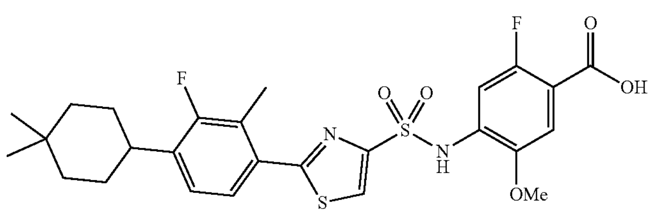 [SMILES: COc1cc(C(=O)O)c(F)cc1NS(=O)(=O)c1csc(-c2ccc(C3CCC(C)(C)CC3)c(F)c2C)n1] | 551.2 [M + H]+ | 1H NMR (500 MHz, DMSO-d6) δ 13.16 (br, 1H), 10.37 (s, 1H), 8.58 (s, 1H), 7.49 (d, J = 8.1 Hz, 1H), 7.44 (d, J = 12.2 Hz, 1H), 7.36 (t, J = 7.8 Hz, 1H), 7.31 (d, J = 6.6 Hz, 1H), 3.72 (s, 3H), 2.75 (tt, J = 12.0, 3.8 Hz, 1H), 2.30 (d, J = 2.6 Hz, 3H), 1.72-1.55 (m, 4H), 1.51-1.42 (m, 2H), 1.34 (td, J = 13.3, 4.0 Hz, 2H), 0.98 (s, 3H), 0.95 (s, 3H). |
| 567 | 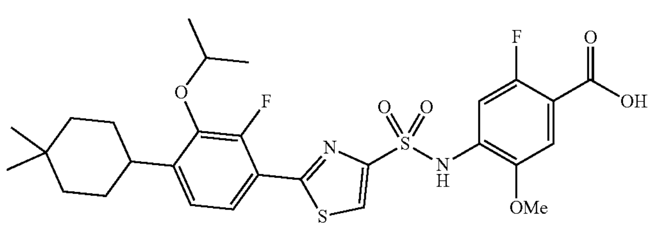 [SMILES: COc1cc(C(=O)O)c(F)cc1NS(=O)(=O)c1csc(-c2ccc(C3CCC(C)(C)CC3)c(OC(C)C)c2F)n1] | 595.3 [M + H]+ | 1H NMR (500 MHz, DMSO-d6) δ 13.14 (br, 1H), 10.41 (s, 1H), 8.57 (s, 1H), 7.71 (dd, J = 8.3, 6.9 Hz, 1H), 7.42 (d, J = 12.2 Hz, 1H), 7.36 (d, J = 8.4 Hz, 1H), 7.30 (d, J = 6.6 Hz, 1H), 4.36 (hept, J = 6.1 Hz, 1H), 3.70 (s, 3H), 2.93-2.84 (m, 1H), 1.68- |

| Example # | Structure | LC-MS [M + H]+ unless otherwise noted | 1H-NMR |
|---|---|---|---|
| | | | 1.56 (m, 2H), 1.54-1.44 (m, 4H), 1.35-1.29 (m, 2H), 1.29 (d, J = 6.2 Hz, 6H), 1.01 (s, 3H), 0.95 (s, 3H). |
| 568 | 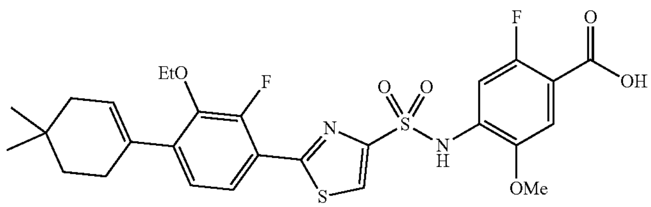 [SMILES: CCOc1c(C2=CCC(C)(C)CC2)ccc(-c2nc(S(=O)(=O)Nc3cc(F)c(C(=O)O)cc3OC)cs2)c1F] | 579.4 [M + H]+ | 1H NMR (500 MHz, DMSO-d6) δ 13.17 (br, 1H), 10.41 (s, 1H), 8.59 (s, 1H), 7.70 (dd, J = 8.3, 6.9 Hz, 1H), 7.41 (d, J = 12.0 Hz, 1H), 7.31 (d, J = 6.6 Hz, 1H), 7.17 (dd, J = 8.2, 1.2 Hz, 1H), 5.88-5.83 (m, 1H), 4.01 (q, J = 7.0 Hz, 2H), 3.69 (s, 3H), 2.39-2.33 (m, 2H), 2.00-1.94 (m, 2H), 1.47 (t, J = 6.3 Hz, 2H), 1.28 (t, J = 7.0 Hz, 3H), 0.98 (s, 6H). |
| 569 | 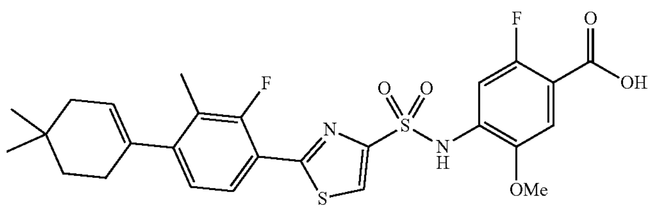 [SMILES: COc1cc(C(=O)O)c(F)cc1NS(=O)(=O)c1csc(-c2ccc(C3=CCC(C)(C)CC3)c(C)c2F)n1] | 549.2 [M + H]+ | 1H NMR (500 MHz, DMSO-d6) δ 13.16 (br, 1H), 10.39 (s, 1H), 8.56 (s, 1H), 7.84 (t, J = 7.8 Hz, 1H), 7.41 (d, J = 12.1 Hz, 1H), 7.30 (d, J = 6.6 Hz, 1H), 7.14 (d, J = 8.2 Hz, 1H), 5.58-5.54 (m, 1H), 3.68 (s, 3H), 2.24 (d, J = 2.6 Hz, 3H), 2.22-2.17 (m, 2H), 1.99-1.93 (m, 2H), 1.49 (t, J = 6.3 Hz, 2H), 0.99 (s, 6H). |
| 570 | 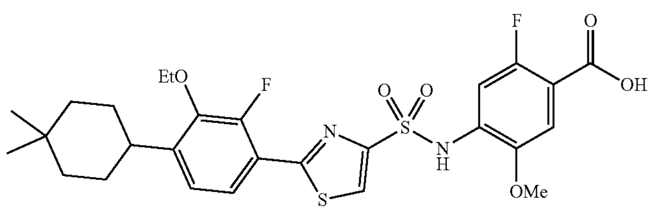 [SMILES: CCOc1c(C2CCC(C)(C)CC2)ccc(-c2nc(S(=O)(=O)Nc3cc(F)c(C(=O)O)cc3OC)cs2)c1F] | 581.3 [M + H]+ | 1H NMR (400 MHz, DMSO-d6) δ 13.18 (br, 1H), 10.41 (s, 1H), 8.59 (s, 1H), 7.71 (dd, J = 8.3, 7.0 Hz, 1H), 7.43 (d, J = 12.1Hz, 1H), 7.34 (d, J = 8.3 Hz, 1H), 7.31 (d, J = 6.6 Hz, 1H), 4.08 (q, J = 7.0 Hz, 2H), 3.70 (s, 3H), 2.93-2.78 (m, 1H), 1.71-1.43 (m, 6H), 1.35 (t, J = 7.0 Hz, 3H), 1.35-1.27 (m, 2H), 1.00 (s, 3H), 0.95 (s, 3H). |
| 571 | 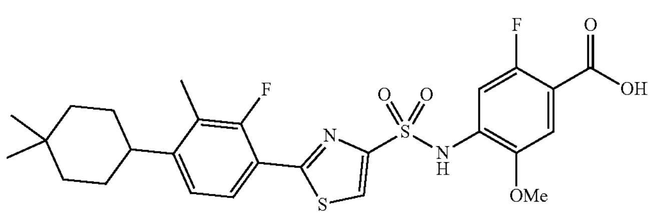 | 551.2 [M + H]+ | 1H NMR (400 MHz, DMSO-d6) δ 13.18 (br, 1H), 10.39 (s, 1H), 8.55 (s, 1H), 7.86 (t, J = 8.0 Hz, 1H), 7.43 (d, J = 12.1 Hz, 1H), 7.35 (d, J = 8.4 Hz, 1H), 7.31 (d, J = 6.6 Hz, 1H), 3.69 (s, 3H), 2.76-2.64 (m, 1H), 2.27 (d, J = 2.5 Hz, 3H), 1.69-1.32 (m, 8H), 1.00 (s, 3H), 0.96 (s, 3H). |

-continued

| Example # | Structure | LC-MS [M + H]+ unless otherwise noted | 1H-NMR |
|---|---|---|---|
| 572 | 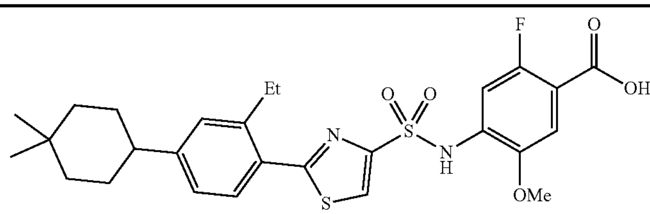 | 547.2 [M + H]+ | 1H NMR (400 MHz, DMSO-d6) δ 13.14 (br, 1H), 10.30 (s, 1H), 8.57 (s, 1H), 7.54 (d, J = 7.9 Hz, 1H), 7.42 (d, J = 12.2 Hz, 1H), 7.32 (d, J = 6.6 Hz, 1H), 7.28-7.19 (m, 2H), 3.73 (s, 3H), 2.76 (q, J = 7.4 Hz, 2H), 2.55-2.38 (m, 1H), 1.66-1.56 (m, 4H), 1.50-1.41 (m, 2H), 1.38-1.25 (m, 2H), 0.98 (s, 3H), 0.94 (s, 3H), 0.96-0.89 (m, 6H), 0.93 (t, J = 7.4 Hz, 3H). |
| 573 | 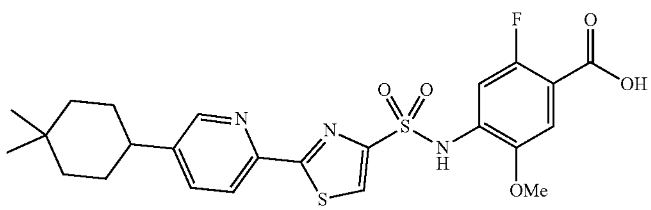 [SMILES: COc1cc(C(=O)O)c(F)cc1NS(=O)(=O)c1csc(-c2ccc(C3CCC(C)(C)CC3)cn2)n1] | 520.2 [M + H]+ | 1H NMR (400 MHz, Chloroform-d) δ 8.46 (d, J = 2.1 Hz, 1H), 8.17 (s, 1H), 8.05 (dd, J = 8.2, 0.8 Hz, 1H), 7.72-7.69 (m, 1H), 7.67 (dd, J = 8.2, 2.2 Hz, 1H), 7.59 (d, J = 12.0 Hz, 1H), 7.36 (d, J = 6.2 Hz, 1H), 3.86 (s, 3H), 2.51 (tt, J = 11.8, 4.1 Hz, 1H), 1.76-1.49 (m, 6H), 1.36 (td, J = 13.1, 4.4 Hz, 2H), 0.98 (s, 3H), 0.98 (s, 3H). |
| 574 | 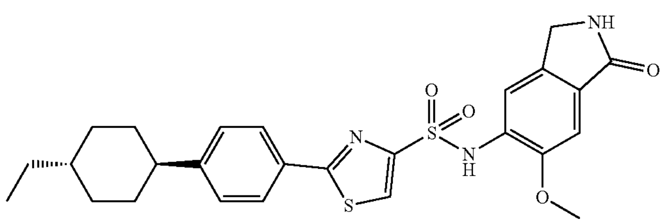 [SMILES: CC[C@H]1CC[C@H](c2ccc(-c3nc(S(=O)(=O)Nc4cc5c(cc4OC)C(=O)NC5)cs3)cc2)CC1] | 512.3 [M + H]+ | 1H NMR (400 MHz, DMSO-d6) δ 9.95 (s, 1H), 8.48 (s, 1H), 8.28 (s, 1H), 7.86-7.78 (m, 2H), 7.57 (s, 1H), 7.43-7.34 (m, 2H), 7.14 (s, 1H), 4.28 (s, 2H), 3.63 (s, 3H), 2.59-2.51 (m, 1H), 1.89-1.79 (m, 4H), 1.52-0.95 (m, 7H), 0.89 (t, J = 7.0 Hz, 3H). |
| 575 | 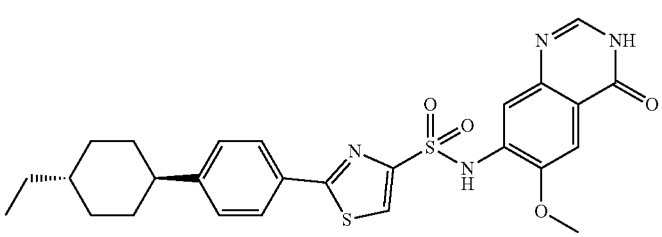 [SMILES: CC[C@H]1CC[C@H](c2ccc(-c3nc(S(=O)(=O)Nc4cc5nc[nH]c(=O)c5cc4OC)cs3)cc2)CC1] | 525.4 [M + H]+ | 1H NMR (500 MHz, DMSO-d6) δ 12.16 (s, 1H), 10.27 (s, 1H), 8.45 (s, 1H), 7.99 (s, 1H), 7.83 (d, J = 8.2 Hz, 2H), 7.74 (s, 1H), 7.45 (s, 1H), 7.38 (d, J = 8.1 Hz, 2H), 3.79 (s, 3H), 2.61-2.49 (m, 1H), 1.88-1.77 (m, 4H), 1.51-0.96 (m, 7H), 0.89 (t, J = 7.3 Hz, 3H). |
| 576 | 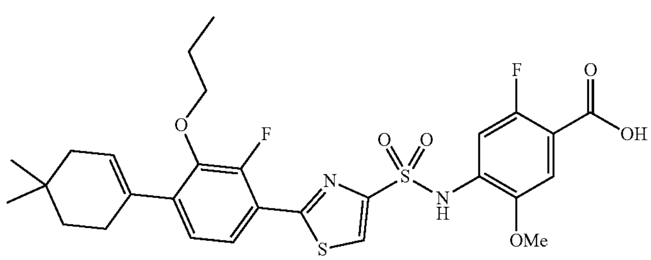 [SMILES: CCCOc1c(C2=CCC(C)(C)CC2)ccc(-c2nc(S(=O)(=O)Nc3cc(F)c(C(=O)O)cc3OC)cs2)c1F] | 593.2 [M + H]+ | 1H NMR (400 MHz, DMSO-d6) δ 13.17 (br, 1H), 10.41 (s, 1H), 8.59 (s, 1H), 7.70 (dd, J = 8.3, 7.0 Hz, 1H), 7.41 (d, J = 12.1Hz, 1H), 7.31 (d, J = 6.6 Hz, 1H), 7.17 (dd, J = 8.3, 1.2 Hz, 1H), 5.89-5.82 (m, 1H), 3.91 (t, J = 6.4 Hz, 2H), 3.69 (s, 3H), 2.40-2.33 (m, 2H), 2.00-1.93 (m, 2H), 1.69 (h, J = 7.1 Hz, 2H), 1.46 (t, |

| Example # | Structure | LC-MS [M + H]+ unless otherwise noted | 1H-NMR |
|---|---|---|---|
| | | | J = 6.3 Hz, 2H), 0.97 (s, 6H), 0.97 (t, J = 7.4 Hz, 3H). |
| 577 | 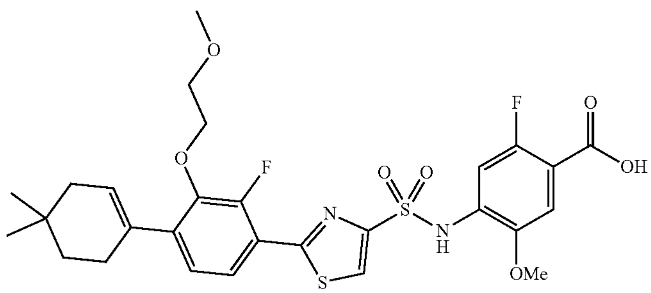 [SMILES: COCCOc1c(C2=CCC(C)(C)CC2)ccc(-c2nc(S(=O)(=O)Nc3cc(F)c(C(=O)O)cc3OC)cs2)c1F] | 609.2 [M + H]+ | 1H NMR (400 MHz, DMSO-d6) δ 13.15 (s, 1H), 10.41 (s, 1H), 8.59 (s, 1H), 7.70 (dd, J = 8.3, 6.9 Hz, 1H), 7.41 (d, J = 12.1 Hz, 1H), 7.31 (d, J = 6.6 Hz, 1H), 7.17 (dd, J = 8.3, 1.2 Hz, 1H), 5.90-5.84 (m, 1H), 4.09 (dd, J = 5.5, 3.5 Hz, 2H), 3.69 (s, 3H), 3.63-3.56 (m, 2H), 3.27 (s, 3H), 2.41-2.33 (m, 2H), 2.00-1.93 (m, 2H), 1.46 (t, J = 6.3 Hz, 2H), 0.97 (s, 6H). |
| 578 | 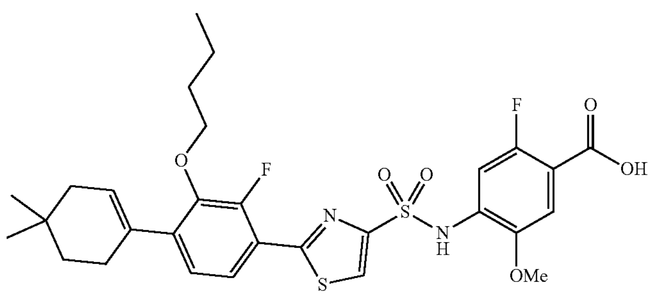 | 607.5 [M + H]+ | 1H NMR (500 MHz, DMSO-d6) δ 13.18 (br, 1H), 10.40 (s, 1H), 8.59 (s, 1H), 7.70 (dd, J = 8.3, 6.9 Hz, 1H), 7.41 (d, J = 12.0 Hz, 1H), 7.31 (d, J = 6.6 Hz, 1H), 7.17 (d, J = 8.3 Hz, 1H), 5.87-5.83 (m, 1H), 3.95 (t, J = 6.4 Hz, 2H), 3.69 (s, 3H), 2.39-2.32 (m, 2H), 2.00-1.93 (m, 2H), 1.69-1.61 (m, 2H), 1.46 (t, J = 5.6 Hz, 2H), 1.47-1.38 (m, 2H), 0.97 (s, 6H), 0.91 (t, J = 7.4 Hz, 3H). |
| 579 | 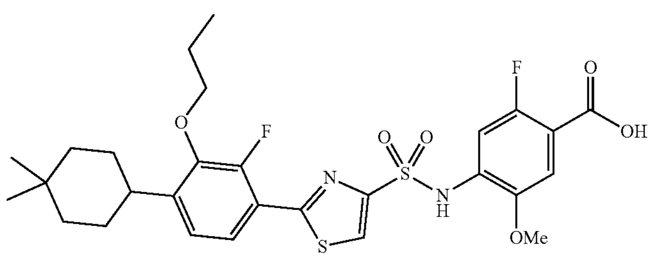 | 595.3 [M + H]+ | 1H NMR (500 MHz, DMSO-d6) δ 13.16 (br, 1H), 10.40 (s, 1H), 8.57 (s, 1H), 7.71 (dd, J = 8.4, 7.0 Hz, 1H), 7.42 (d, J = 12.1 Hz, 1H), 7.34 (d, J = 8.4 Hz, 1H), 7.30 (d, J = 6.5 Hz, 1H), 3.99 (t, J = 6.4 Hz, 2H), 3.70 (s, 3H), 2.92-2.83 (m, 1H), 1.76 (h, J = 7.1 Hz, 2H), 1.63 (td, J = 12.8, 3.3 Hz, 2H), 1.58-1.44 (m, 4H), 1.38-1.28 (m, 2H), 1.03 (t, J = 7.4 Hz, 3H), 1.00 (s, 3H), 0.95 (s, 3H). |
| 580 | 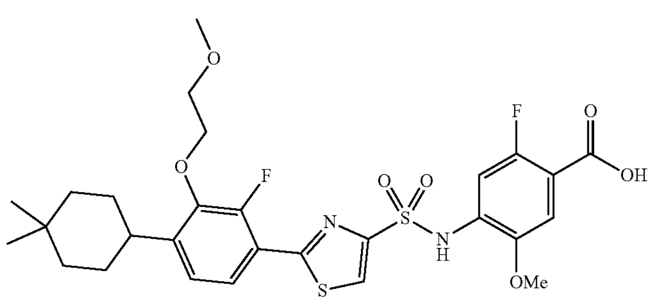 [SMILES: COCCOc1c(C2CCC(C)(C)CC2)ccc(-c2nc(S(=O)(=O)Nc3cc(F)c(C(=O)O)cc3OC)cs2)c1F] | 611.3 [M + H]+ | 1H NMR (500 MHz, DMSO-d6) δ 13.14 (br, 1H), 10.40 (s, 1H), 8.57 (s, 1H), 7.72 (dd, J = 8.4, 6.9 Hz, 1H), 7.42 (d, J = 12.1 Hz, 1H), 7.34 (d, J = 8.2 Hz, 1H), 7.30 (d, J = 6.6 Hz, 1H), 4.18-4.13 (m, 2H), 3.70 (s, 3H), 3.65-3.60 (m, 2H), 3.32 (s, 3H), 2.97 (tt, J = 12.1, 3.7 Hz, 1H), 1.70-1.41 (m, 6H), 1.37-1.27 (m, 2H), 1.00 (s, 3H), 0.95 (s, 3H). |

| Example # | Structure | LC-MS [M + H]+ unless otherwise noted | 1H-NMR |
|---|---|---|---|
| 581 | 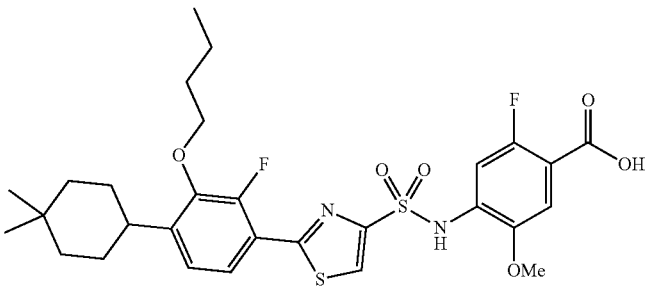 | 609.3 [M + H]+ | 1H NMR (500 MHz, DMSO-d6) δ 13.13 (br, 1H), 10.40 (s, 1H), 8.57 (s, 1H), 7.71 (dd, J = 8.4, 6.9 Hz, 1H), 7.42 (d, J = 12.1 Hz, 1H), 7.34 (d, J = 8.7 Hz, 1H), 7.30 (d, J = 6.6 Hz, 1H), 4.02 (t, J = 6.3 Hz, 2H), 3.70 (s, 3H), 2.85 (tt, J = 12.2, 3.6 Hz, 1H), 1.79-1.42 (m, 10H), 1.31 (td, J = 13.3, 3.8 Hz, 2H), 1.00 (s, 3H), 0.95 (t, J = 7.5 Hz, 3H), 0.95 (s, 3H). |
| 582 | 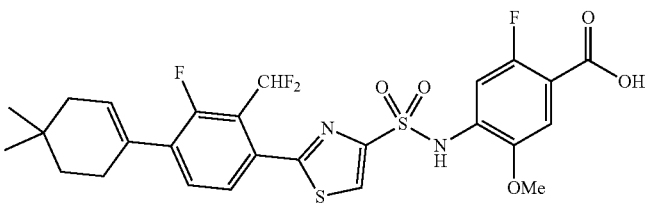 [SMILES: COc1cc(C(=O)O)c(F)cc1NS(=O)(=O)c1csc(-c2ccc(C3=CCC(C)(C)CC3)c(F)c2C(F)F)n1] | 585.2 [M + H]+ | 1H NMR (500 MHz, DMSO-d6) δ 13.16 (br, 1H), 10.47 (s, 1H), 8.64 (s, 1H), 7.68-7.60 (m, 2H), 7.57-7.29 (m, 3H), 6.01-5.96 (m, 1H), 3.70 (s, 3H), 2.42-2.32 (m, 2H), 2.04-1.96 (m, 2H), 1.49 (t, J = 6.4 Hz, 2H), 0.97 (s, 6H). |
| 583 | 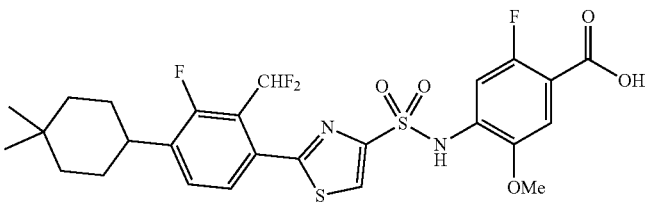 [SMILES: COc1cc(C(=O)O)c(F)cc1NS(=O)(=O)c1csc(-c2ccc(C3CCC(C)(C)CC3)c(F)c2C(F)F)n1] | 587.2 [M + H]+ | 1H NMR (500 MHz, DMSO-d6) δ 13.16 (br, 1H), 10.46 (s, 1H), 8.63 (s, 1H), 7.75 (t, J = 7.7 Hz, 1H), 7.62 (d, J = 8.1 Hz, 1H), 7.55-7.29 (m, 3H), 3.70 (s, 3H), 2.88-2.77 (m, 1H), 1.80-1.55 (m, 4H), 1.52-1.44 (m, 2H), 1.40-1.32 (m, 2H), 0.99 (s, 3H), 0.95 (s, 3H). |
| 584 | 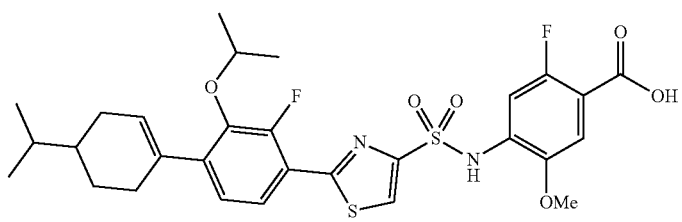 | 607.3 [M + H]+ | 1H NMR (500 MHz, DMSO-d6) δ 13.17 (br, 1H), 10.40 (s, 1H), 8.59 (s, 1H), 7.70 (dd, J = 8.3, 6.9 Hz, 1H), 7.41 (d, J = 12.1 Hz, 1H), 7.31 (d, J = 6.6 Hz, 1H), 7.16 (dd, J = 8.3, 1.2 Hz, 1H), 5.99-5.91 (m, 1H), 4.27 (hept, J = 6.1 Hz, 1H), 3.69 (s, 3H), 2.43-2.37 (m, 1H), 2.27-2.18 (m, 1H), 1.96-1.82 (m, 2H), 1.52 (h, J = 6.6 Hz, 1H), 1.41-1.24 (m, 3H), 1.22 (t, J = 6.1 Hz, 6H), 0.93-0.88 (m, 6H). |

-continued

| Example # | Structure | LC-MS [M + H]+ unless otherwise noted | 1H-NMR |
|---|---|---|---|
| 585 | 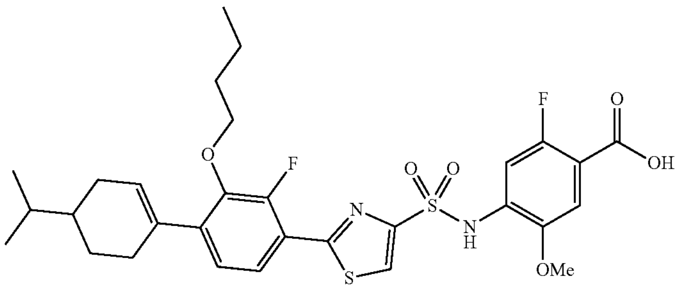 [SMILES: CCCCOc1c(C2=CCC(C(C)C)CC2)ccc(-c2nc(S(=O)(=O)Nc3cc(F)c(C(=O)O)cc3OC)cs2)c1F] | 621.3 [M + H]+ | 1H NMR (500 MHz, DMSO-d6) δ 13.18 (br, 1H), 10.40 (s, 1H), 8.59 (s, 1H), 7.69 (dd, J = 8.3, 6.9 Hz, 1H), 7.41 (d, J = 12.0 Hz, 1H), 7.31 (d, J = 6.6 Hz, 1H), 7.16 (dd, J = 8.2, 1.2 Hz, 1H), 5.95-5.90 (m, 1H), 3.95 (t, J = 6.3 Hz, 2H), 3.69 (s, 3H), 2.40-2.34 (m, 1H), 2.26-2.17 (m, 1H), 1.95-1.82 (m, 2H), 1.68-1.61 (m, 2H), 1.58-1.26 (m, 6H), 0.95-0.88 (m, 9H). |
| 586 | 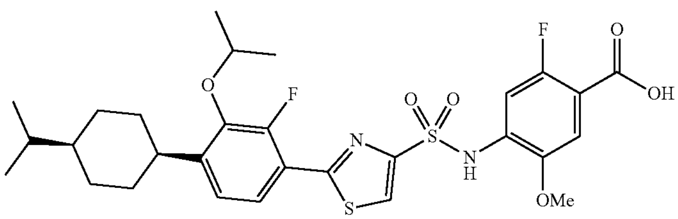 [SMILES: COc1cc(C(=O)O)c(F)cc1NS(=O)(=O)c1csc(-c2ccc([C@H]3CC[C@@H](C(C)C)CC3)c(OC(C)C)c2F)n1] | 609.4 [M + H]+ | 1H NMR (500 MHz, DMSO-d6) δ 13.09 (br, 1H), 10.42 (s, 1H), 8.52 (s, 1H), 7.71 (dd, J = 8.3, 6.9 Hz, 1H), 7.39 (d, J = 12.5 Hz, 1H), 7.32 (d, J = 8.4 Hz, 1H), 7.30-7.20 (m, 1H), 4.37 (sept, J = 6.1 Hz, 1H), 3.70 (s, 3H), 3.06-2.98 (m, 1H), 2.00-1.81 (m, 3H), 1.64-1.39 (m, 6H), 1.29 (d, J = 6.1 Hz, 6H), 1.26-1.20 (m, 1H), 0.92 (d, J = 6.5 Hz, 6H). |
| 587 | 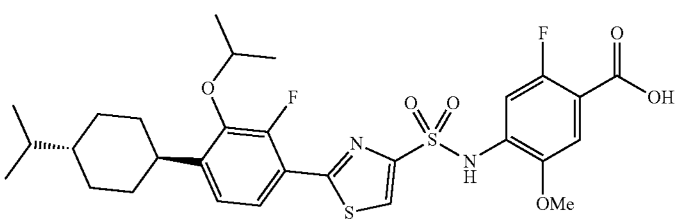 [SMILES: COc1cc(C(=O)O)c(F)cc1NS(=O)(=O)c1csc(-c2ccc([C@H]3CC[C@H](C(C)C)CC3)c(OC(C)C)c2F)n1] | 609.6 [M + H]+ | 1H NMR (400 MHz, DMSO-d6) δ 13.12 (br, 1H), 10.39 (s, 1H), 8.56 (s, 1H), 7.75-7.65 (m, 1H), 7.42 (d, J = 12.1 Hz, 1H), 7.33-7.24 (m, 2H), 4.36 (hept, J = 6.1 Hz, 1H), 3.70 (s, 3H), 2.97-2.87 (m, 1H), 1.84-1.69 (m, 4H), 1.52-1.37 (m, 3H), 1.29 (d, J = 6.1 Hz, 6H), 1.22-1.03 (m, 3H), 0.88 (d, J = 6.7 Hz, 6H). |
| 588 | 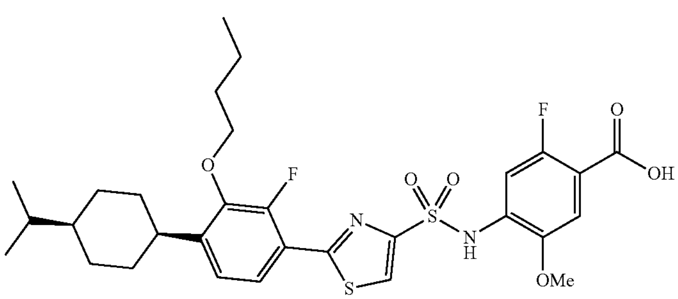 [SMILES: CCCCOc1c(F)c(-c2nc(S(=O)(=O)Nc3cc(F)c(C(=O)O)cc3OC)cs2)ccc1[C@H]1CC[C@@H](C(C)C)CC1] | 623.5 [M + H]+ | 1H NMR (400 MHz, DMSO-d6) δ 13.03 (br, 1H), 10.42 (br, 1H), 8.51 (s, 1H), 7.72 (t, J = 7.6 Hz, 1H), 7.38 (d, J = 12.6 Hz, 1H), 7.31 (d, J = 8.4 Hz, 1H), 7.29-7.21 (m, 1H), 4.02 (t, J = 6.3 Hz, 2H), 3.69 (s, 3H), 3.04-2.93 (m, 1H), 1.98-1.42 (m, 13H), 1.27-1.19 (m, 1H), 0.96 (t, J = 7.4 Hz, 3H), 0.91 (d, J = 6.5 Hz, 6H). |

-continued

| Example # | Structure | LC-MS [M + H]+ unless otherwise noted | 1H-NMR |
|---|---|---|---|
| 589 | 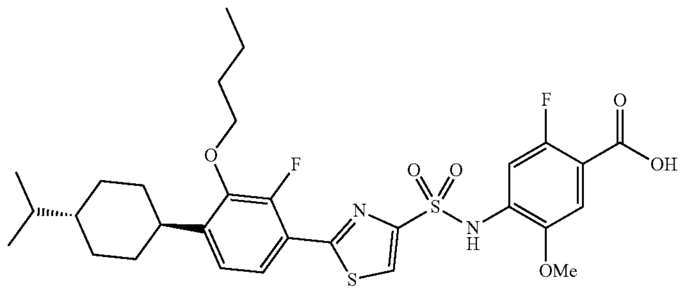 [SMILES: CCCCOc1c(F)c(-c2nc(S(=O)(=O)Nc3cc(F)c(C(=O)O)cc3OC)cs2)ccc1[C@H]1CC[C@H](C(C)C)CC1] | 623.3 [M + H]+ | 1H NMR (500 MHz, DMSO-d6) δ 12.48 (br, 1H), 10.41 (br, 1H), 8.34 (br, 1H), 7.73 (t, J = 7.7 Hz, 1H), 7.29 (br, 1H), 7.25 (d, J = 8.4 Hz, 1H), 7.17 (br, 1H), 4.02 (t, J = 6.3 Hz, 2H), 3.67 (s, 3H), 2.92-2.83 (m, 1H), 1.85-1.68 (m, 6H), 1.56-1.41 (m, 5H), 1.21-1.06 (m, 3H), 0.95 (t, J = 7.4 Hz, 3H), 0.88 (d, J = 6.8 Hz, 6H). |
| 590 | 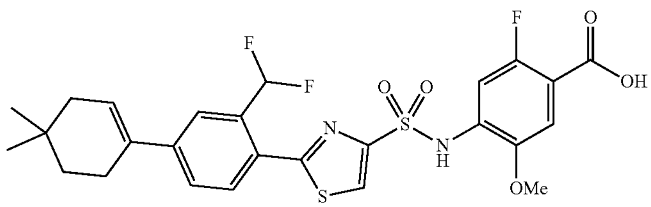 | 567.2 [M + H]+ | 1H NMR (500 MHz, DMSO-d6) δ 13.16 (br, 1H), 10.43 (s, 1H), 8.62 (s, 1H), 7.84 (d, J = 8.3 Hz, 1H), 7.80 (d, J = 1.9 Hz, 1H), 7.74 (dd, J = 8.2, 1.9 Hz, 1H), 7.61-7.35 (m, 2H), 7.32 (d, J = 6.6 Hz, 1H), 6.39-6.33 (m, 1H), 3.71 (s, 3H), 2.46-2.40 (m, 2H), 2.06-2.00 (m, 2H), 1.51 (t, J = 6.4 Hz, 2H), 0.95 (s, 6H). |
| 591 | 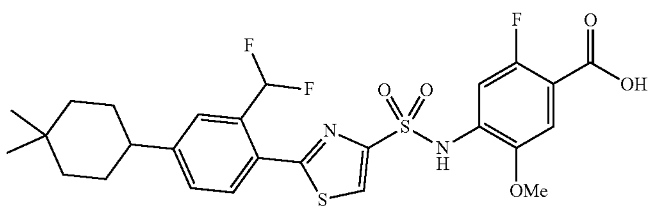 [SMILES: COc1cc(C(=O)O)c(F)cc1NS(=O)(=O)c1csc(-c2ccc(C3CCC(C)(C)CC3)cc2C(F)F)n1] | 569.3 [M + H]+ | 1H NMR (500 MHz, DMSO-d6) δ 13.15 (br, 1H), 10.41 (s, 1H), 8.61 (s, 1H), 7.80 (d, J = 8.0 Hz, 1H), 7.67 (d, J = 1.8 Hz, 1H), 7.61 (dd, J = 8.2, 1.9 Hz, 1H), 7.56-7.30 (m, 3H), 3.72 (s, 3H), 2.65-2.54 (m, 1H), 1.69-1.58 (m, 4H), 1.54-1.42 (m, 2H), 1.39-1.28 (m, 2H), 0.98 (s, 3H), 0.95 (s, 3H). |
| 592 | 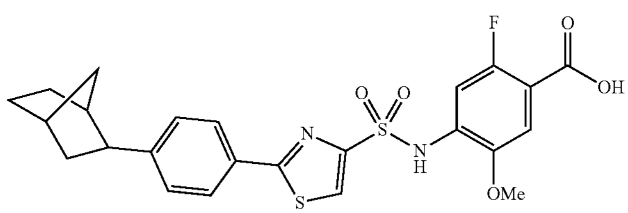 [SMILES: COc1cc(C(=O)O)c(F)cc1NS(=O)(=O)c1csc(-c2ccc(C3CC4CCC3C4)cc2)n1] | 503.2 [M + H]+ | 1H NMR (400 MHz, DMSO-d6) δ 13.16 (br, 1H), 10.37 (s, 1H), 8.46 (s, 1H), 7.85-7.78 (m, 2H), 7.44-7.35 (m, 3H), 7.30 (d, J = 6.6 Hz, 1H), 3.69 (s, 3H), 2.80 (dd, J = 9.0, 5.6 Hz, 1H), 2.37-2.27 (m, 2H), 1.81-1.72 (m, 2H), 1.65-1.13 (m, 7H) |
| 593 | 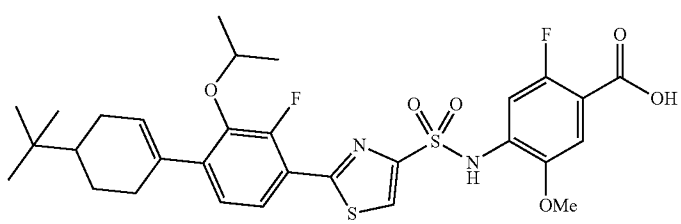 [SMILES: COc1cc(C(=O)O)c(F)cc1NS(=O)(=O)c1csc(-c2ccc(C3=CCC(C(C)(C)C)CC3)c(OC(C)C)c2F)n1] | 621.3 [M + H]+ | 1H NMR (400 MHz, DMSO-d6) δ 13.10 (br, 1H), 10.40 (s, 1H), 8.58 (s, 1H), 7.69 (dd, J = 8.2, 6.9 Hz, 1H), 7.41 (d, J = 12.1 Hz, 1H), 7.30 (d, J = 6.6 Hz, 1H), 7.16 (d, J = 8.3 Hz, 1H), 6.00-5.93 (m, 1H), 4.27 (hept, J = 6.1 Hz, 1H), 3.69 (s, 3H), 2.46-2.15 (m, 4H), 2.00-1.88 (m, 2H), 1.37-1.25 (m, 1H), 1.22 (t, J = 6.0 Hz, 6H), 0.90 (s, 9H). |

-continued

| Example # | Structure | LC-MS [M + H]+ unless otherwise noted | 1H-NMR |
|---|---|---|---|
| 594 | 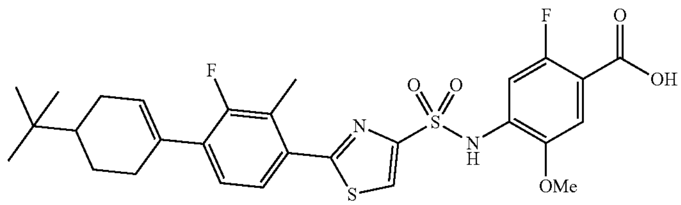 [SMILES: COc1cc(C(=O)O)c(F)cc1NS(=O)(=O)c1csc(-c2ccc(C3=CCC(C(C)(C)C)CC3)c(F)c2C)n1] | 577.4 [M + H]+ | 1H NMR (400 MHz, DMSO-d6) δ 13.10 (br, 1H), 10.38 (s, 1H), 8.58 (s, 1H), 7.50 (d, J = 8.1 Hz, 1H), 7.43 (d, J = 12.2 Hz, 1H), 7.31 (d, J = 6.6 Hz, 1H), 7.27 (t, J = 7.9 Hz, 1H), 6.06-5.98 (m, 1H), 3.72 (s, 3H), 2.45-2.16 (m, 3H), 2.31 (d, J = 2.6 Hz, 3H), 2.02-1.87 (m, 2H), 1.41-1.17 (m, 2H), 0.89 (s, 9H). |
| 595 | 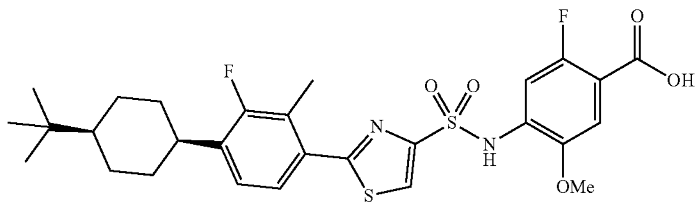 [SMILES: COc1cc(C(=O)O)c(F)cc1NS(=O)(=O)c1csc(-c2ccc([C@H]3CC[C@@H](C(C)(C)C)CC3)c(F)c2C)n1] | 579.5 [M + H]+ | 1H NMR (400 MHz, DMSO-d6) δ 13.09 (br, 1H), 10.37 (br, 1H), 8.56 (s, 1H), 7.51 (d, J = 8.2 Hz, 1H), 7.48-7.38 (m, 2H), 7.30 (d, J = 6.6 Hz, 1H), 3.72 (s, 3H), 3.29-3.19 (m, 1H), 2.30 (d, J = 2.5 Hz, 3H), 2.10-1.99 (m, 2H), 1.87-1.72 (m, 2H), 1.65-1.54 (m, 2H), 1.27-1.05 (m, 3H), 0.82 (s, 9H). |
| 596 | 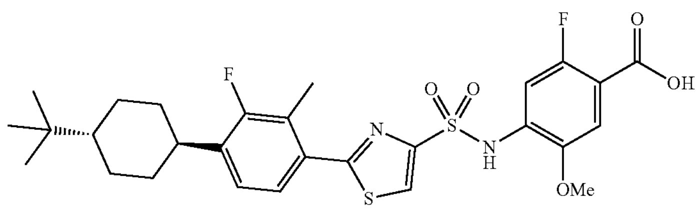 [SMILES: COc1cc(C(=O)O)c(F)cc1NS(=O)(=O)c1csc(-c2ccc([C@H]3CC[C@H](C(C)(C)C)CC3)c(F)c2C)n1] | 579.5 [M + H]+ | 1H NMR (400 MHz, DMSO-d6) δ 12.87 (br, 1H), 10.39 (br, 1H), 8.48 (s, 1H), 7.48 (d, J = 8.1 Hz, 1H), 7.40 (d, J = 12.7 Hz, 1H), 7.34-7.18 (m, 2H), 3.70 (s, 3H), 2.83-2.72 (m, 1H), 2.31 (d, J = 2.5 Hz, 3H), 1.93-0.99 (m, 9H), 0.87 (s, 9H). |
| 597 | 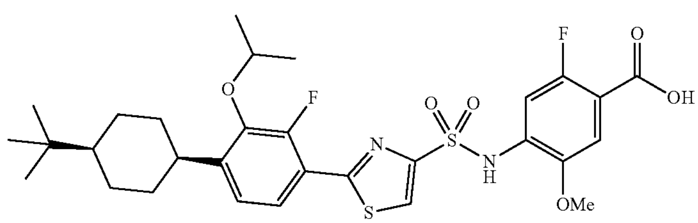 [SMILES: COc1cc(C(=O)O)c(F)cc1NS(=O)(=O)c1csc(-c2ccc([C@H]3CC[C@@H](C(C)(C)C)CC3)c(OC(C)C)c2F)n1] | 623.3 [M + H]+ | 1H NMR (400 MHz, DMSO-d6) δ 13.10 (br, 1H), 10.39 (s, 1H), 8.56 (s, 1H), 7.70 (t, J = 7.7 Hz, 1H), 7.42 (d, J = 12.2 Hz, 1H), 7.33-7.23 (m, 2H), 4.36 (hept, J = 6.1 Hz, 1H), 3.70 (s, 3H), 2.98-2.85 (m, 1H), 1.89-1.72 (m, 4H), 1.52-1.35 (m, 2H), 1.29 (d, J = 6.1 Hz, 6H), 1.18-1.05 (m, 3H), 0.87 (s, 9H). |
| 598 | 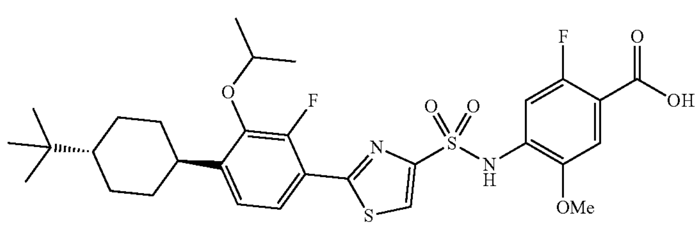 [SMILES: COc1cc(C(=O)O)c(F)cc1NS(=O)(=O)c1csc(-c2ccc([C@H]3CC[C@H](C(C)(C)C)CC3)c(OC(C)C)c2F)n1] | 623.3 [M + H]+ | 1H NMR (400 MHz, DMSO-d6) δ 13.10 (br, 1H), 10.4 (br, 1H), 8.53 (s, 1H), 7.70 (t, J = 7.7 Hz, 1H), 7.42-7.34 (m, 2H), 7.27 (d, J = 6.8 Hz, 1H), 4.45 (hept, J = 6.1 Hz, 1H), 3.69 (s, 3H), 2.58-2.52 (m, 1H), 2.04-1.96 (m, 2H), 1.78-1.64 (m, 2H), 1.62-1.53 (m, 2H), 1.27 (d, J = 6.4 Hz, 6H), 1.33-1.08 (m, 3H), 0.84 (s, 9H). |

-continued

| Example # | Structure | LC-MS [M + H]+ unless otherwise noted | ¹H-NMR |
|---|---|---|---|
| 599 | 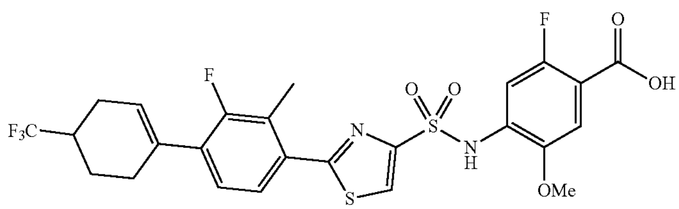 [SMILES: COc1cc(C(=O)O)c(F)cc1NS(=O)(=O)c1csc(-c2ccc(C3=CCC(C(F)(F)F)CC3)c(F)c2C)n1] | 589.3 [M + H]+ | ¹H NMR (400 MHz, DMSO-d$_6$) δ 13.16 (br, 1H), 10.39 (s, 1H), 8.60 (s, 1H), 7.53 (d, J = 8.1 Hz, 1H), 7.43 (d, J = 12.1 Hz, 1H), 7.34-7.26 (m, 2H), 6.04-5.97 (m, 1H), 3.72 (s, 3H), 2.73-1.99 (m, 6H), 2.32 (d, J = 2.7 Hz, 3H), 1.59 (qd, J = 12.0, 5.2 Hz, 1H). |
| 600 | 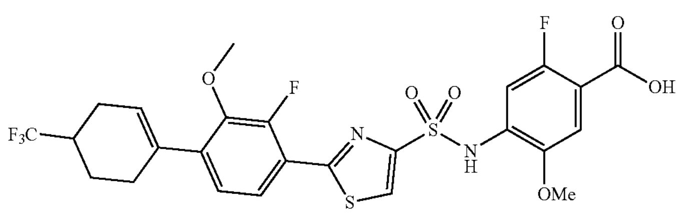 [SMILES: COc1cc(C(=O)O)c(F)cc1NS(=O)(=O)c1csc(-c2ccc(C3=CCC(C(F)(F)F)CC3)c(OC)c2F)n1] | 605.2 [M + H]+ | ¹H NMR (400 MHz, DMSO-d$_6$) δ 13.15 (br, 1H), 10.41 (s, 1H), 8.59 (s, 1H), 7.72 (dd, J = 8.3, 7.0 Hz, 1H), 7.40 (d, J = 12.1 Hz, 1H), 7.30 (d, J = 6.6 Hz, 1H), 7.19 (dd, J = 8.4, 1.3 Hz, 1H), 5.99-5.93 (m, 1H), 3.84 (d, J = 1.1 Hz, 3H), 3.69 (s, 3H), 2.74-1.98 (m, 6H), 1.60 (qd, J = 12.1, 5.2 Hz, 1H). |
| 601 | 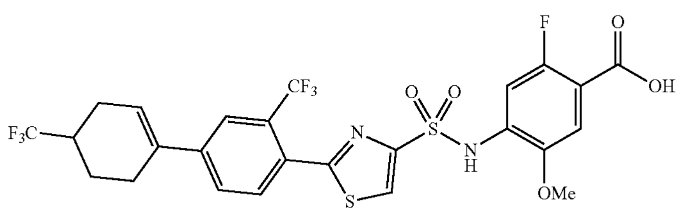 | 625.3 [M + H]+ | ¹H NMR (400 MHz, DMSO-d$_6$) δ 13.12 (br, 1H), 10.34 (s, 1H), 8.66 (s, 1H), 7.90-7.82 (m, 2H), 7.75 (d, J = 8.1 Hz, 1H), 7.36 (d, J = 12.2 Hz, 1H), 7.31 (d, J = 6.6 Hz, 1H), 6.48-6.40 (m, 1H), 3.74 (s, 3H), 2.70-2.06 (m, 6H), 1.69-1.54 (m, 1H). |
| 602 | 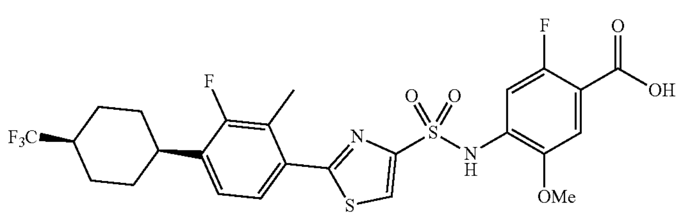 [SMILES: COc1cc(C(=O)O)c(F)cc1NS(=O)(=O)c1csc(-c2ccc([C@H]3CC[C@@H](C(F)(F)F)CC3)c(F)c2C)n1] | 591.2 [M + H]+ | ¹H NMR (400 MHz, DMSO-d$_6$) δ 13.15 (br, 1H), 10.37 (s, 1H), 8.58 (s, 1H), 7.50 (d, J = 8.1 Hz, 1H), 7.43 (d, J = 12.2 Hz, 1H), 7.33-7.25 (m, 2H), 3.72 (s, 3H), 3.05-2.92 (m, 1H), 2.62-2.51 (m, 1H), 2.30 (d, J = 2.6 Hz, 3H), 1.97-1.63 (m, 8H). |
| 603 | 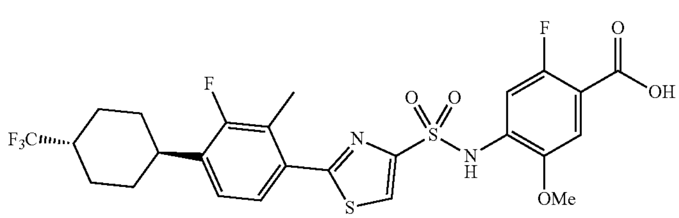 [SMILES: COc1cc(C(=O)O)c(F)cc1NS(=O)(=O)c1csc(-c2ccc([C@H]3CC[C@H](C(F)(F)F)CC3)c(F)c2C)n1] | 591.3 [M + H]+ | ¹H NMR (400 MHz, DMSO-d$_6$) δ 13.09 (br, 1H), 10.38 (br, 1H), 8.55 (s, 1H), 7.51 (d, J = 8.1 Hz, 1H), 7.42 (d, J = 12.3 Hz, 1H), 7.33-7.25 (m, 2H), 3.71 (s, 3H), 2.94-2.81 (m, 1H), 2.44-2.33 (m, 1H), 2.31 (d, J = 2.5 Hz, 3H), 2.04-1.93 (m, 2H), 1.93-1.84 (m, 2H), 1.67-1.53 (m, 2H), 1.52-1.38 (m, 2H). |

-continued

| Example # | Structure | LC-MS [M + H]+ unless otherwise noted | 1H-NMR |
|---|---|---|---|
| 604 | 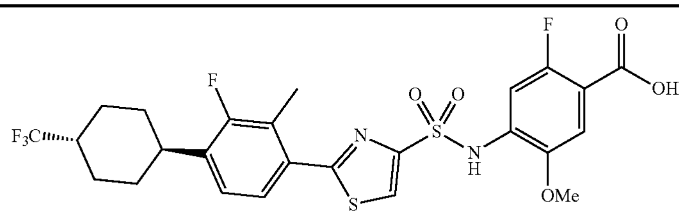 | 607.3 [M + H]+ | 1H NMR (400 MHz, DMSO-d$_6$) δ 13.10 (br, 1H), 10.43 (br, 1H), 8.55 (s, 1H), 7.77-7.69 (m, 1H), 7.38 (d, J = 12.3 Hz, 1H), 7.28 (d, J = 6.7 Hz, 1H), 7.23 (d, J = 8.4 Hz, 1H), 3.91 (d, J = 1.3 Hz, 3H), 3.69 (s, 3H), 3.03 (pent, J = 7.2 Hz, 1H), 2.64-2.53 (m, 1H), 2.01-1.59 (m, 8H). |
| 605 | 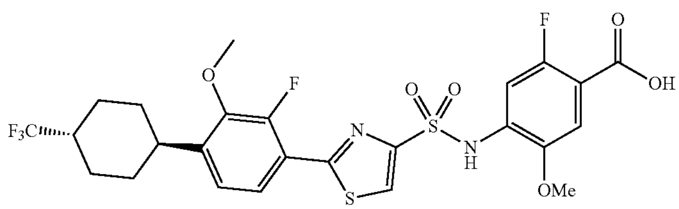 [SMILES: COc1cc(C(=O)O)c(F)cc1NS(=O)(=O)c1csc(-c2ccc([C@H]3CC[C@H](C(F)(F)F)CC3)c(OC)c2F)n1] | 607.3 [M + H]+ | 1H NMR (400 MHz, DMSO-d$_6$) δ 13.12 (br, 1H), 10.40 (s, 1H), 8.57 (s, 1H), 7.78-7.69 (m, 1H), 7.42 (d, J = 12.2 Hz, 1H), 7.32-7.23 (m, 2H), 3.90 (d, J = 1.2 Hz, 3H), 3.69 (s, 3H), 3.01-2.89 (m, 1H), 2.44-2.33 (m, 1H), 2.02-1.93 (m, 2H), 1.87-1.78 (m, 2H), 1.65-1.37 (m, 4H). |
| 606 | 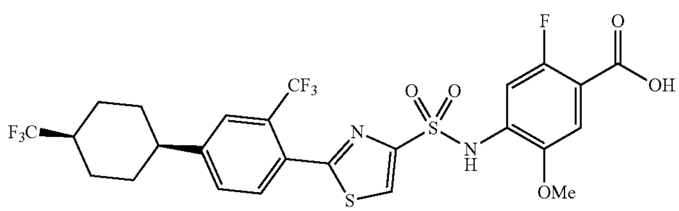 [SMILES: COc1cc(C(=O)O)c(F)cc1NS(=O)(=O)c1csc(-c2ccc([C@H]3CC[C@@H](C(F)(F)F)CC3)cc2C(F)(F)F)n1] | 627.3 [M + H]+ | 1H NMR (400 MHz, DMSO-d$_6$) δ 13.01 (br, 1H), 10.30 (br, 1H), 8.60 (s, 1H), 7.77-7.66 (m, 3H), 7.38-7.22 (m, 2H), 3.73 (s, 3H), 3.01-1.90 (m, 1H), 2.61-2.52 (m, 1H), 1.89-1.71 (m, 8H). |
| 607 | 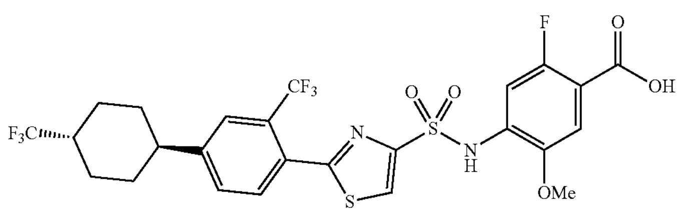 [SMILES: COc1cc(C(=O)O)c(F)cc1NS(=O)(=O)c1csc(-c2ccc([C@H]3CC[C@H](C(F)(F)F)CC3)cc2C(F)(F)F)n1] | 627.3 [M + H]+ | 1H NMR (400 MHz, DMSO-d$_6$) δ 12.86 (br, 1H), 10.32 (br, 1H), 8.57 (br, 1H), 7.80-7.64 (m, 3H), 7.38-7.16 (m, 2H), 3.73 (s, 3H), 2.84-2.70 (m, 1H), 2.43-2.33 (m, 1H), 2.03-2.86 (m, 4H), 1.68-1.36 (m, 4H). |
| 608 | 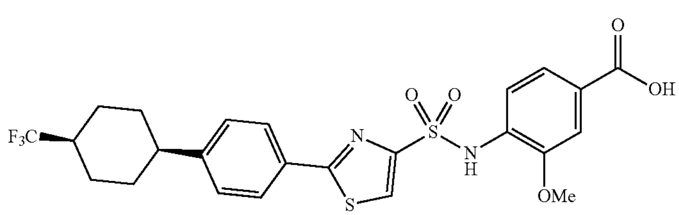 | 541.11 | 1H NMR (400 MHz, Chloroform-d) δ 8.03 (s, 1H), 7.81 (d, J = 8.4 Hz, 2H), 7.73-7.69 (m, 3H), 7.49 (d, J = 1.6 Hz, 1H), 7.30 (d, J = 8.4 Hz, 2H), 3.87 (s, 3H), 2.74 (dt, J = 9.3, 4.9 Hz, 1H), 2.32 (ddd, J = 20.8, 10.7, 5.6 Hz, 1H), 2.01-1.88 (m, 4H), 1.83-1.67 (m, 4H). |
| 609 | 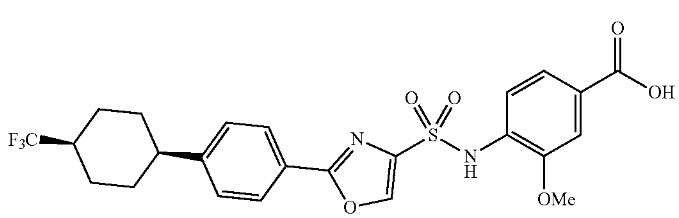 [SMILES: COc1cc(C(=O)O)ccc1NS(=O)(=O)c1coc(-c2ccc([C@H]3CC[C@@H](C(F)(F)F)CC3)cc2)n1] | 525.13 | 1H NMR (500 MHz, Chloroform-d) δ 8.19 (s, 1H), 7.93 (d, J = 8.4 Hz, 2H), 7.76-7.63 (m, 3H), 7.52 (d, J = 1.7 Hz, 1H), 7.33 (d, J = 8.4 Hz, 2H), 3.89 (s, 3H), 2.74 (dt, J = 9.8, 5.1 Hz, 1H), 2.32 (dp, J = 10.5, 5.3 Hz, 1H), 2.00-1.85 (m, 4H), 1.83-1.65 (m, 4H). |

-continued

| Example # | Structure | LC-MS [M + H]+ unless otherwise noted | 1H-NMR |
|---|---|---|---|
| 610 | 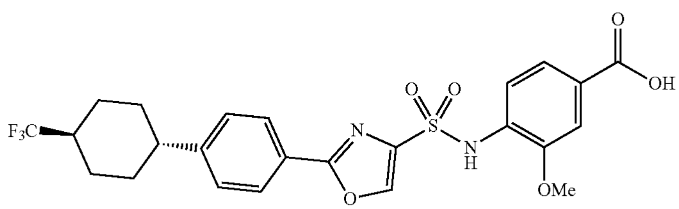 | 525.13 | 1H NMR (500 MHz, Chloroform-d) δ 8.19 (s, 1H), 7.93 (d, J = 8.3 Hz, 2H), 7.74-7.64 (m, 3H), 7.51 (d, J = 1.7 Hz, 1H), 7.29 (d, J = 8.4 Hz, 2H), 3.90 (s, 3H), 2.57 (m, 1H), 2.18-1.93 (m, 5H), 1.56-1.42 (m, 4H). |
| 611 | 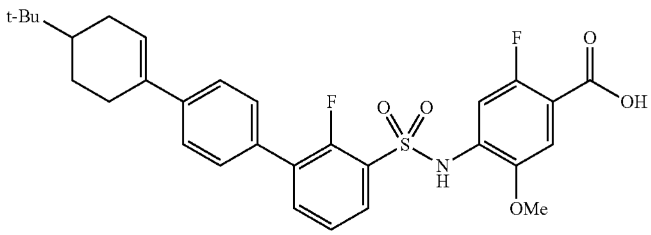 [SMILES: COc1cc(C(=O)O)c(F)cc1NS(=O)(=O)c1cccc(-c2ccc(C3=CCC(C(C)(C)C)CC3)cc2)c1F] | [M − H]− 554.25 | 1H NMR (400 MHz, DMSO-d6) δ 13.20 (s, 1H), 10.40 (s, 1H), 7.86-7.72 (m, 2H), 7.55 (d, J = 8.4 Hz, 2H), 7.52-7.46 (m, 2H), 7.42 (t, J = 7.8 Hz, 1H), 7.30 (d, J = 6.6 Hz, 1H), 7.18 (d, J = 11.6 Hz, 1H), 6.32-6.26 (m, 1H), 3.61 (s, 3H), 2.41 (s, 1H), 2.27 (s, 1H), 2.23 (s, 1H), 1.98 (d, J = 9.5 Hz, 2H), 1.40-1.13 (m, 2H), 0.91 (s, 9H). |
| 612 | 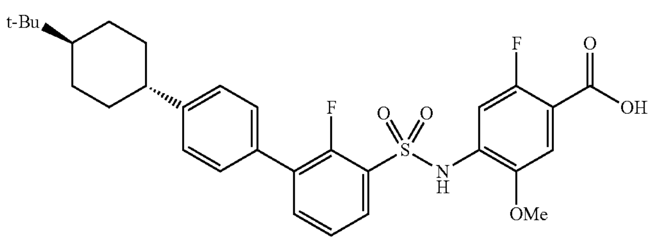 [SMILES: COc1cc(C(=O)O)c(F)cc1NS(=O)(=O)c1cccc(-c2ccc([C@H]3CC[C@H](C(C)(C)C)CC3)cc2)c1F] | [M − H]− 556.25 | 1H NMR (400 MHz, Chloroform-d) δ 8.00-7.92 (m, 1H), 7.76 (s, 1H), 7.71-7.63 (m, 1H), 7.46-7.40 (m, 2H), 7.39-7.25 (m, 5H), 3.87 (s, 3H), 2.59-2.44 (m, 1H), 2.05-1.90 (m, 4H), 1.52 (d, J = 12.2 Hz, 1H), 1.46 (d, J = 12.3 Hz, 1H), 1.30-1.20 (m, 1H), 1.20-1.06 (m, 2H), 0.92 (s, 9H). |
| 613 | 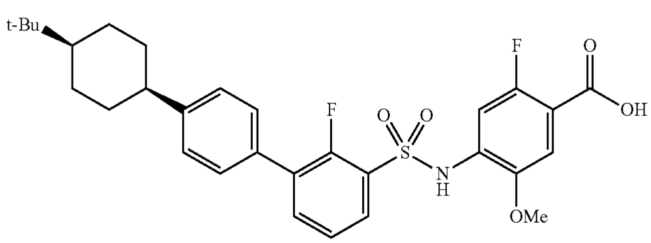 [SMILES: COc1cc(C(=O)O)c(F)cc1NS(=O)(=O)c1cccc(-c2ccc([C@H]3CC[C@@H](C(C)(C)C)CC3)cc2)c1F] | [M − H]− 556.30 | 1H NMR (400 MHz, Chloroform-d) δ 7.96 (t, J = 6.9 Hz, 1H), 7.78-7.69 (m, 2H), 7.52-7.41 (m, 4H), 7.40-7.31 (m, 3H), 3.87 (s, 3H), 3.10 (s, 1H), 2.29 (d, J = 13.8 Hz, 2H), 1.82 (d, J = 14.6 Hz, 2H), 1.64 (d, J = 10.9 Hz, 2H), 1.29-1.13 (m, 3H), 0.83 (s, 9H). |
| 614 | 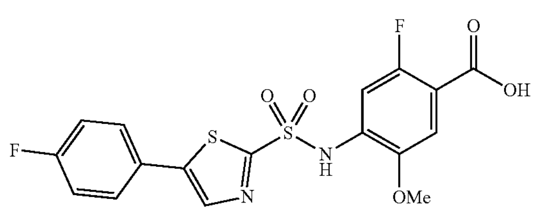 [SMILES: COc1cc(C(=O)O)c(F)cc1NS(=O)(=O)c1ncc(-c2ccc(F)cc2)s1] | 427.0 | 1H NMR (300 MHz, DMSO-d6): δ 12.9 (s, 1H), 11.1 (s, 1H), 8.37 (s, 1H), 7.91-7.78 (m, 2H), 7.46-7.21 (m, 4H), 3.74 (s, 3H). |

-continued

| Example # | Structure | LC-MS [M + H]+ unless otherwise noted | 1H-NMR |
|---|---|---|---|
| 615 | 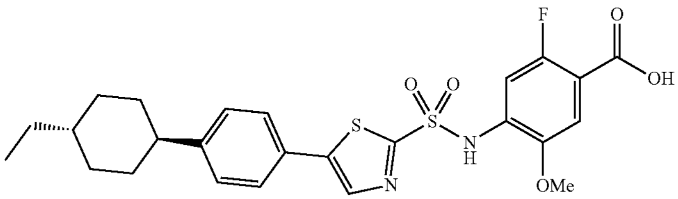 [SMILES: CC[C@H]1CC[C@H](c2ccc(-c3cnc(S(=O)(=O)Nc4cc(F)c(C(=O)O)cc4OC)s3)cc2)CC1] | 519.0 | 1H NMR (300 MHz, DMSO-d6): δ 13.26 (s, 1H), 10.90 (s, 1H), 8.41 (s, 1H), 7.69-7.64 (m, 2H), 7.42-7.30 (m, 4H), 3.69 (s, 3H), 1.82 (t, 4H), 1.50-1.38 (m, 2H), 1.29-1.14 (m, 4H), 1.09-0.95 (m, 2H), 0.88 (t, 3H). |
| 616 | 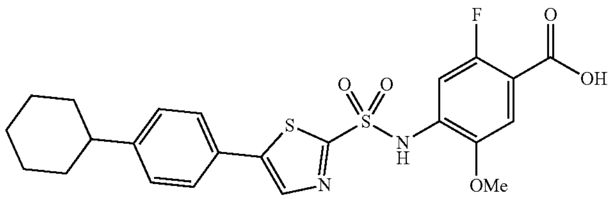 [SMILES: COc1cc(C(=O)O)c(F)cc1NS(=O)(=O)c1ncc(-c2ccc(C3CCCCC3)cc2)s1] | 491.0 | 1H NMR (300 MHz, DMSO-d6): δ 13.21 (s, 1H), 10.92 (s, 1H), 8.41 (s, 1H), 7.70-7.62 (m, 2H), 7.43-7.28 (m, 4H), 3.69 (s, 3H), 2.54 (t, 1H), 1.84-1.65 (m, 5H), 1.48-1.24 (m, 5H) |
| 617 | 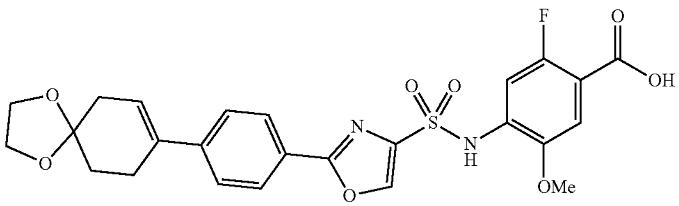 [SMILES: COc1cc(C(=O)O)c(F)cc1NS(=O)(=O)c1coc(-c2ccc(C3=CCC4(CC3)OCCO4)cc2)n1] | 531.12 | 1H NMR (400 MHz, Methanol-d4) δ 8.36 (s, 1H), 7.95 (d, J = 8.0 Hz, 2H), 7.52 (d, J = 8.0 Hz, 2H), 7.43 (d, J = 11.9 Hz, 1H), 7.39 (d, J = 6.3 Hz, 1H), 6.17-6.12 (m, 1H), 4.05 (s, 4H), 3.86 (s, 3H), 2.74-2.61 (m, 2H), 2.55-2.45 (m, 2H), 1.95 (t, J = 6.5 Hz, 2H). |
| 618 | 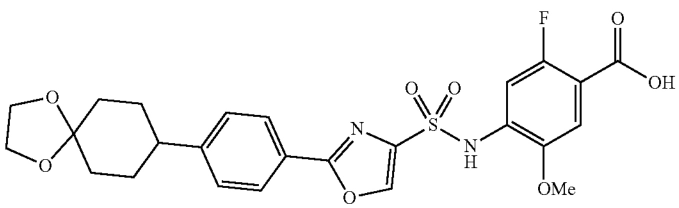 [SMILES: COc1cc(C(=O)O)c(F)cc1NS(=O)(=O)c1coc(-c2ccc(C3CCC4(CC3)OCCO4)cc2)n1] | 533.14 | 1H NMR (400 MHz, Chloroform-d) δ 8.25 (s, 1H), 7.92 (d, J = 8.0 Hz, 2H), 7.47 (d, J = 11.9 Hz, 1H), 7.38 (d, J = 6.4 Hz, 1H), 7.33 (d, J = 8.0 Hz, 2H), 3.99 (s, 4H), 3.88 (s, 3H), 2.56-2.48 (m, 1H), 2.27-2.11 (m, 2H), 2.00-1.62 (m, 6H). |
| 619 | 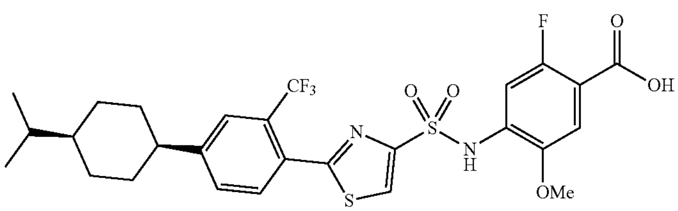 [SMILES: COc1cc(C(=O)O)c(F)cc1NS(=O)(=O)c1csc(-c2ccc([C@H]3CC[C@@H](C(C)C)CC3)cc2C(F)(F)F)n1] | 601.15 | 1H NMR (400 MHz, DMSO-d6) δ 13.15 (s, 1H), 10.33 (s, 1H), 8.67 (s, 1H), 7.80-7.66 (m, 3H), 7.38 (d, J = 12.1 Hz, 1H), 7.33 (d, J = 6.6 Hz, 1H), 3.76 (s, 3H), 2.84 (td, J = 9.2, 8.6, 4.3 Hz, 1H), 1.88-1.60 (m, 8H), 1.59-1.45 (m, 2H), 0.89 (d, J = 6.6 Hz, 6H). |
| 620 | 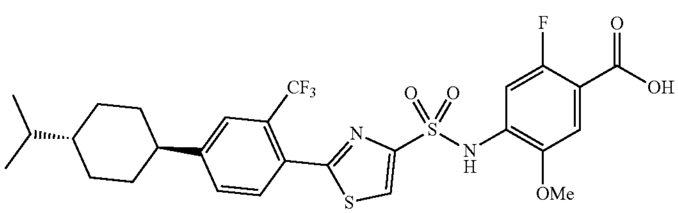 [SMILES: COc1cc(C(=O)O)c(F)cc1NS(=O)(=O)c1csc(-c2ccc([C@H]3CC[C@H](C(C)C)CC3)cc2C(F)(F)F)n1] | 601.15 | 1H NMR (400 MHz, DMSO-d6) δ 13.14 (s, 1H), 10.33 (s, 1H), 8.67 (s, 1H), 7.77-7.64 (m, 3H), 7.38 (d, J = 12.1 Hz, 1H), 7.33 (d, J = 6.6 Hz, 1H), 3.76 (s, 3H), 2.67 (tt, J = 12.0, 3.4 Hz, 1H), 1.89 (d, J = 12.5 Hz, 2H), 1.80 (d, J = 9.4 Hz, 2H), 1.56-1.40 (m, 3H), 1.19-1.10 (m, 3H), 0.89 (d, J = 6.8 Hz, 6H). |

| Example # | Structure | LC-MS [M + H]+ unless otherwise noted | 1H-NMR |
|---|---|---|---|
| 621 | 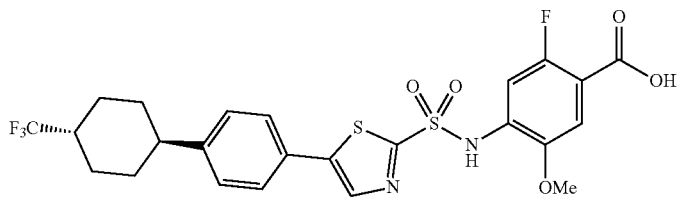 [SMILES: COc1cc(C(=O)O)c(F)cc1NS(=O)(=O)c1ncc(-c2ccc([C@H]3CC[C@H](C(F)(F)F)CC3)cc2)s1] | 559.10 | 1H NMR (400 MHz, DMSO-d6) δ 13.22 (s, 1H), 10.91 (s, 1H), 8.43 (s, 1H), 7.70 (s, 2H), 7.35 (s, 4H), 3.70 (s, 3H), 2.35 (m, 1H), 2.04-1.80 (m, 4H), 1.60-1.32 (m, 5H). |
| 622 | 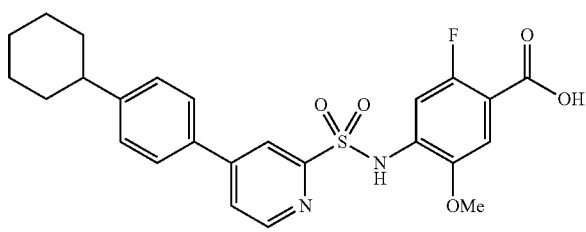 [SMILES: COc1cc(C(=O)O)c(F)cc1NS(=O)(=O)c1cc(-c2ccc(C3CCCCC3)cc2)ccn1] | 485.1 | 1H NMR (300 MHz, DMSO-d6) δ 12.88 (s, 1H), 10.32 (s, 1H), 8.72 (d, 1H), 8.21 (s, 1H), 7.95 (d, 1H), 7.75 (d, 2H), 7.42 (d, 2H), 7.35 (d, 1H), 7.27 (d, 1H), 3.69 (s, 3H), 2.54 (t, 1H), 1.81 (d, 4H), 1.71 (d, 1H), 1.51-1.32 (m, 5H). |
| 623 | 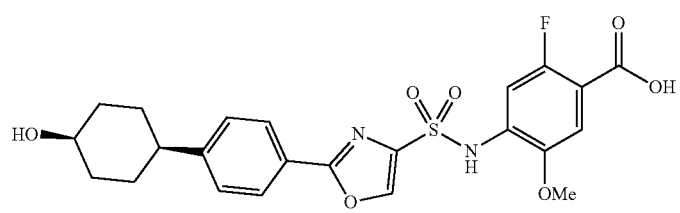 [SMILES: COc1cc(C(=O)O)c(F)cc1NS(=O)(=O)c1coc(-c2ccc([C@H]3CC[C@@H](O)CC3)cc2)n1] | 491.13 | 1H NMR (400 MHz, Methanol-d4) δ 8.58 (s, 1H), 7.93 (d, J = 8.0 Hz, 2H), 7.47 (d, J = 12.0 Hz, 1H), 7.41 (d, J = 6.4 Hz, 1H), 7.39 (d, J = 8.2 Hz, 2H), 3.82 (s, 3H), 3.63 (td, J = 10.7, 5.3 Hz, 1H), 2.59 (ddd, J = 12.2, 8.6, 3.5 Hz, 1H), 2.08 (d, J = 12.2 Hz, 2H), 1.91 (d, J = 13.1 Hz, 2H), 1.67-1.52 (m, 2H), 1.50-1.37 (m, 2H). |
| 624 | 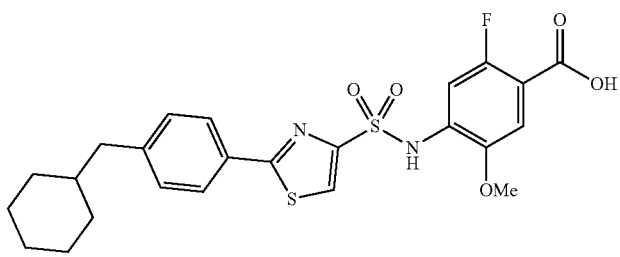 [SMILES: COc1cc(C(=O)O)c(F)cc1NS(=O)(=O)c1csc(-c2ccc(CC3CCCCC3)cc2)n1] | 503.0 [M − H]− | 1H NMR (300 MHz, DMSO-d6) δ 12.9 (s, 1H), 10.4 (s, 1H), 8.34 (s, 1H), 7.13-8.09 (m, 1H), 7.82-7.79 (m, 2H), 7.34-7.25 (m, 4H), 4.25-4.23 (m, 1H), 3.69 (s, 3H), 1.70-1.59 (m, 5H), 1.30-1.09 (m, 5H), 0.97-0.83 (m, 4H). |
| 625 | 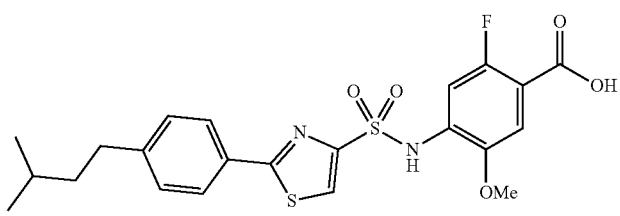 [SMILES: COc1cc(C(=O)O)c(F)cc1NS(=O)(=O)c1csc(-c2ccc(CCC(C)C)cc2)n1] | 479.1 | 1H NMR (400 MHz, CDCl3): δ 8.08 (s, 1H), 7.80 (s, 1H), 7.78 (s, 1H), 7.72 (s, 1H), 7.56 (d, J = 12.0 Hz, 1H), 131 (d, J = 6.4 Hz, 1H), 7.24 (s, 1H), 3.86 (s, 3H), 2.65 (t, J = 8.0 Hz, 2H), 1.62-1.55 (m, 1H), 1.53-1.48 (m, 2H), 0.94 (s, 3H), 0.93 (s, 3H). |

-continued

| Example # | Structure | LC-MS [M + H]+ unless otherwise noted | 1H-NMR |
|---|---|---|---|
| 626 | 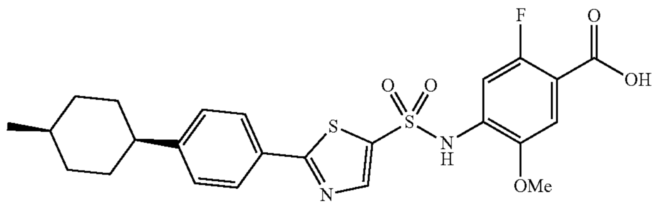 [SMILES: COc1cc(C(=O)O)c(F)cc1NS(=O)(=O)c1cnc(-c2ccc([C@H]3CC[C@@H](C)CC3)cc2)s1] | 505.1 | 1H NMR (300 MHz, DMSO-d6) δ 13.12 (s, 1H), 10.66 (s, 1H), 8.25 (s, 1H), 7.90-7.87 (m, 2H), 7.43-7.40 (m, 2H), 7.31 (d, J = 6.0 Hz, 1H), 7.22 (d, J = 11.4 Hz, 1H), 3.67 (s, 3H), 2.64-2.61 (m, 1H), 1.91 (s, 1H), 1.75-1.58 (m, 6H), 1.50-1.47 (m, 2H), 1.00 (d, J = 7.2 Hz, 3H). |
| 627 | 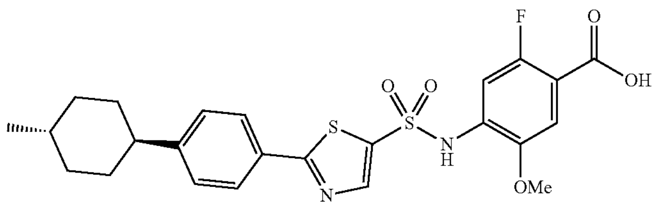 [SMILES: COc1cc(C(=O)O)c(F)cc1NS(=O)(=O)c1cnc(-c2ccc([C@H]3CC[C@H](C)CC3)cc2)s1] | 505.1 | 1H NMR (300 MHz, DMSO-d6) δ 13.01 (s, 1H), 10.67 (s, 1H), 8.22 (s, 1H), 7.88-7.86 (m, 2H), 7.39-7.36 (m, 2H), 7.29 (d, J = 6.3 Hz, 1H), 7.20 (d, J = 12.0 Hz, 1H), 3.67 (s, 3H),1.76 (s, 4H), 1.53-1.40 (m, 3H), 1.23 (s, 1H), 1.12-1.00 (m, 2H), 0.91 (d, J = 6.3 Hz, 3H). |
| 628 | 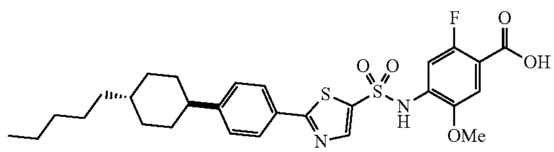 | 559.1 [M − H]− | 1H NMR (300 MHz, DMSO-d6): δ 1.25 (s, 1H), 10.66 (s, 1H), 8.29 (s, 1H), 7.88 (d, J = 8.2 Hz, 2H), 7.38 (d, J = 8.2 Hz, 2H), 7.33 (d, J =6.6 Hz, 1H), 7.25 (d, J = 11.6 Hz, 1H), 7.37 (s, 3H), 3.33 (s, 3H), 1.82-1.80 (m, 4H), 1.46 (q, J = 9.3 Hz, 2H), 1.19-1.17 (m, 10H), 1.05 (q, J = 8.3 Hz, 2H), 0.87 (t, J = 6.9 Hz, 3H). |
| 629 | 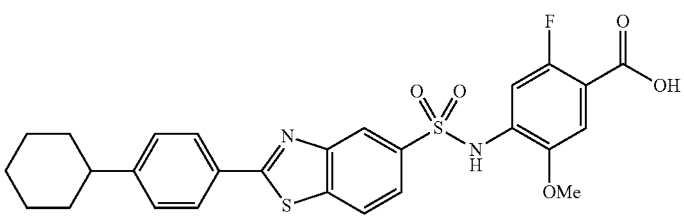 [SMILES: COc1cc(C(=O)O)c(F)cc1NS(=O)(=O)c1ccc2sc(-c3ccc(C4CCCCC4)cc3)nc2c1] | 539.0 [M − H]− | 1H NMR (400 MHz, DMSO): δ 12.64 (s, 1H), 10.61 (s, 1H), 8.41 (s, 1H), 8.32 (d, 1H), 8.03 (d, 2H), 7.87 (d, 1H), 7.44 (d, 2H), 7.21 (d, 1H), 7.13 (d, 1H), 3.65 (s, 3H), 2.60 (m, 1H), 1.86-1.67 (m, 5H), 1.51-1.31 (m, 5H). |
| 630 | 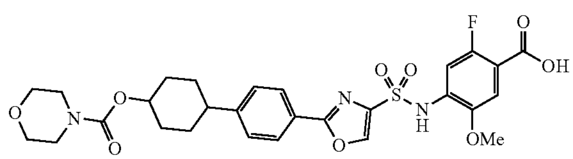 [SMILES: COc1cc(C(=O)O)c(F)cc1NS(=O)(=O)c1coc(-c2ccc(C3CCC(OC(=O)N4CCOCC4)CC3)cc2)n1] | 604.18 | 1H NMR (400 MHz, Chloroform-d) δ 8.26 (s, 1H), 7.92 (d, J = 8.0 Hz,, 2H), 7.80 (s, 1H), 7.47 (d, J = 11.7 Hz, 1H), 7.38 (d, J = 6.2 Hz, 1H, 7.29 (d, J = 8.0 Hz, 2H), 4.71 (tt, J = 10.6, 4.3 Hz, 1H), 3.87 (s, 3H), 3.76 (ddt, J = 7.5, 5.8, 2.1 Hz, 1H), 3.69 (dt, J = 12.0, 4.8 Hz, 4H), 3.48 (t, J = 4.9 Hz, 4H), 2.57 (tt, J = 11.9, 3.4 Hz, 1H), 2.17 (dd, J = 12.2, 3.9 Hz, 2H), 1.94 (dd, J = 9.5, 6.5 Hz, 2H), 1.68-1.41 (m, 4H). |

| Example # | Structure | LC-MS [M + H]+ unless otherwise noted | 1H-NMR |
|---|---|---|---|
| 631 | 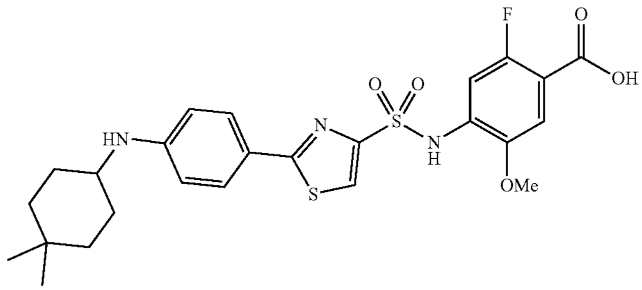 [SMILES: COc1cc(C(=O)O)c(F)cc1NS(=O)(=O)c1csc(-c2ccc(NC3CCC(C)(C)CC3)cc2)n1] | 532.1 [M − H]− | |
| 632 | 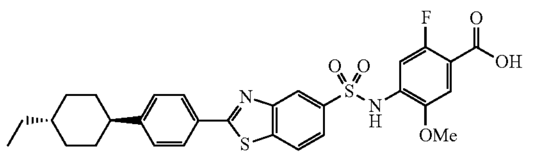 [SMILES: CC[C@H]1CC[C@H](c2ccc(-c3nc4cc(S(=O)(=O)Nc5cc(F)c(C(=O)O)cc5OC)ccc4s3)cc2)CC1] | 569.2 | 1H NMR (400 MHz, DMSO): δ 13.04 (s, 1H), 10.35 (s, 1H), 8.45 (s, 1H), 8.36 (d, 1H), 8.03 (d, 2H), 7.90 (d, 1H), 7.45 (d, 2H), 7.30-7.18 (m, 2H), 3.66 (s, 3H), 2.57 (t, 1H), 1.85 (d, 4H), 1.47 (q, 2H), 1.28-1.20 (m, 3H), 1.05 (q, 2H), 0.89 (t, 3H). |
| 633 | 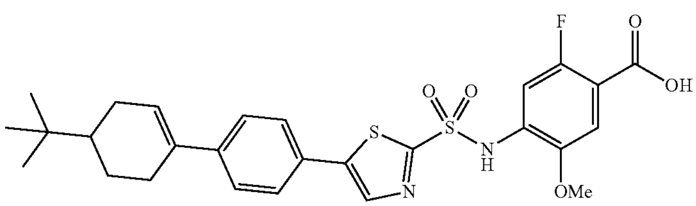 [SMILES: COc1cc(C(=O)O)c(F)cc1NS(=O)(=O)c1ncc(-c2ccc(C3=CCC(C(C)(C)C)CC3)cc2)s1] | 545.1 | |
| 634 | 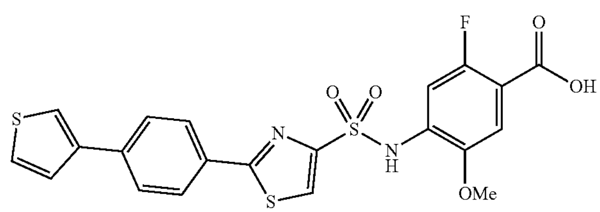 [SMILES: COc1cc(C(=O)O)c(F)cc1NS(=O)(=O)c1csc(-c2ccc(-c3ccsc3)cc2)n1] | 491.0 | 1H NMR (300 MHz, DMSO-d6) δ 13.15 (s, 1H), 10.40 (s, 1H), 8.50 (s, 1H), 8.06 (s, 1H), 7.93 (dd, 4H), 7.71-7.63 (m, 2H), 7.42 (d, 1H), 7.35 (d, 1H), 3.69 (s, 3H). |
| 635 | 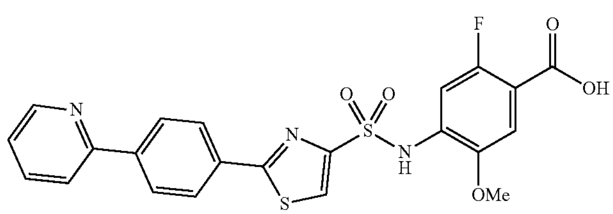 [SMILES: COc1cc(C(=O)O)c(F)cc1NS(=O)(=O)c1csc(-c2ccc(-c3ccccn3)cc2)n1] | 486.10 | 1H NMR (300 MHz, DMSO-d6): 12.92 (s, 1H), 10.33 (s, 1H), 8.71 (s, 1H), 8.45 (s, 1H), 8.27 (d, 2H), 8.11-8.00 (m, 3H), 7.94 (t, 1H), 7.46-7.32 (m, 2H), 7.27 (s, 1H), 3.69 (s, 3H). |
| 636 | 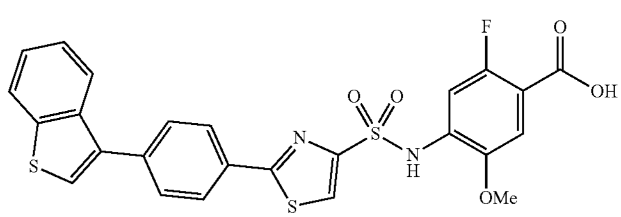 [SMILES: COc1cc(C(=O)O)c(F)cc1NS(=O)(=O)c1csc(-c2ccc(-c3csc4ccccc34)cc2)n1] | 538.9 [M − H]− | 1H NMR (400 MHz, DMSO-d6) δ 13.16 (s, 1H), 10.43 (s, 1H), 8.53 (s, 1H), 8.13-8.09 (m, 3H), 8.01-7.93 (m, 2H), 7.84-7.78 (d, 2H), 7.51-7.40 (m, 3H), 7.35-7.30 (d, 1H), 3.89 (s, 3H). |

| Example # | Structure | LC-MS [M + H]+ unless otherwise noted | 1H-NMR |
|---|---|---|---|
| 637 | 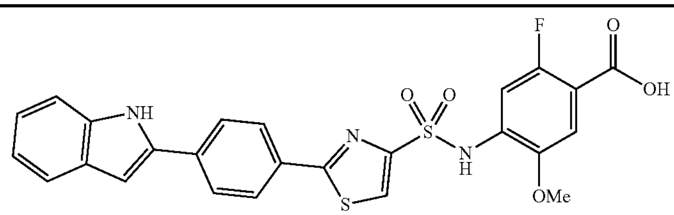 | 521.8 [M − H]− | 1H NMR (400 MHz, DMSO-d6) δ 13.06 (s, 1H), 11.69 (s, 1H), 10.41 (s, 1H), 8.47 (s, 1H) 8.06-7.95 (m, 3H), 7.60-7.52 (d, 1H), 7.48-7.38 (m, 2H), 7.32-7.28 (d, 1H), 7.16-6.91 (m, 3H), 3.71 (s, 3H). |
| 638 | 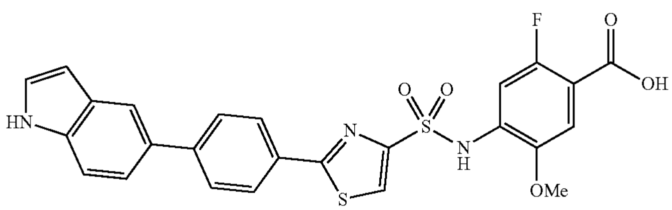 [SMILES: COc1cc(C(=O)O)c(F)cc1NS(=O)(=O)c1csc(-c2ccc(-c3ccc4[nH]ccc4c3)cc2)n1] | 521.9 [M − H]− | 1H NMR (400 MHz, DMSO-d6): δ 13.18 (s, 1H), 11.21 (s, 1H), 10.39 (s, 1H), 8.50 (s, 1H), 7.99-7.92 (t, 3H), 7.88-7.83 (d, 2H), 7.49 (s, 2H), 7.45-7.38 (m, 2H), 7.34-7.30 (d, 1H), 6.51 (t, 1H), 3.70 (s, 3H). |
| 639 | 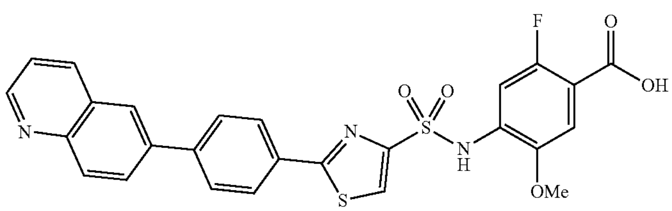 [SMILES: COc1cc(C(=O)O)c(F)cc1NS(=O)(=O)c1csc(-c2ccc(-c3ccc4ncccc4c3)cc2)n1] | 536.0 | 1H NMR (400 MHz, DMSO-d6) δ 12.99 (s, 1H), 10.45 (s, 1H), 8.93-8.92 (m, 1H), 8.49-8.46 (m, 2H), 8.42 (s, 1H), 8.20-8.18 (m, 1H), 8.14-8.12 (m, 1H), 8.07 (q, J = 8.5 Hz, 4H), 7.59 (dd, J1 = 4.2 Hz, J2 = 12.4 Hz, 1H), 7.43 (d, J = 12.4 Hz, 1H), 7.30 (J = 6.6 Hz, 1H), 3.71 (s, 3H). |
| 640 | 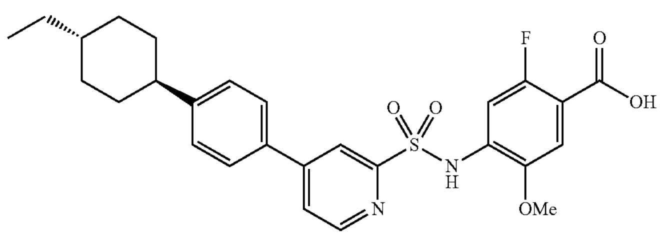 [SMILES: CC[C@H]1CC[C@H](c2ccc(-c3ccnc(S(=O)(=O)Nc4cc(F)c(C(=O)O)cc4OC)c3)cc2)CC1] | 511.1 [M − H]− | 1H NMR (300 MHz, DMSO-d6) δ 12.88 (s, 1H), 10.32 (s, 1H), 8.72 (d, 1H), 8.21 (s, 1H), 7.95 (d, 1H), 7.75 (d, 2H), 7.42 (d, 2H), 7.35 (d, 1H), 7.27 (d, 1H), 3.69 (s, 3H), 2.54 (t, 1H), 1.81 (d, 4H), 1.48 (dd, 2H), 1.28-1.23 (m, 3H), 1.13-0.96 (m, 2H), 0.89 (t, 3H) ppm. |
| 641 | 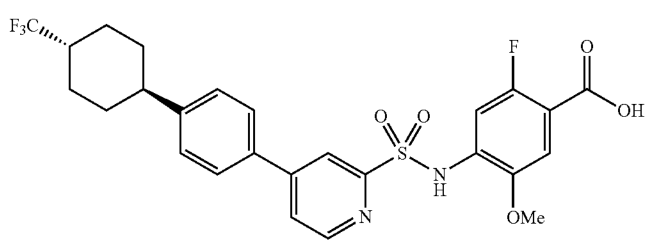 [SMILES: COc1cc(C(=O)O)c(F)cc1NS(=O)(=O)c1cc(-c2ccc([C@H]3CC[C@H](C(F)(F)F)CC3)cc2)ccn1] | 551.1 [M − H]− | 1H NMR (300 MHz, DMSO-d6) δ 8.72 (d, 1H), 8.21 (s, 1H), 7.95 (d, 1H), 7.75 (d, 2H), 7.42 (d, 2H), 7.35 (d, 1H), 7.27 (d, 1H), 3.69 (s, 3H), 2.64 (t, 1H), 2.45-2.28 (m, 1H), 2.05-1.81 (m, 4H), 1.68-1.36 (m, 4H). |
| 642 | 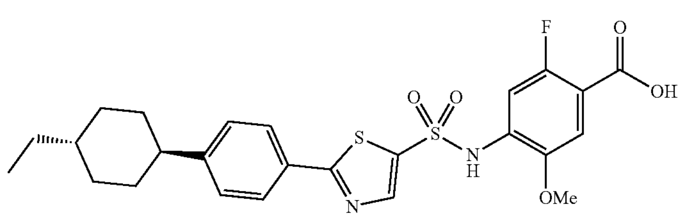 [SMILES: CC[C@H]1CC[C@H](c2ccc(-c3ncc(S(=O)(=O)Nc4cc(F)c(C(=O)O)cc4OC)s3)cc2)CC1] | 519.1 | 1H NMR (300 MHz, DMSO-d6) δ 13.33 (s, 1H), 10.66 (s, 1H), 8.29 (s, 1H), 7.88 (d, J = 7.7 Hz, 2H), 7.39-7.33 (m, 3H), 7.26 (d, J = 11.8 Hz, 1H), 3.67 (s, 3H), 3.17 (s, 1H), 1.88-1.76 (m, 4H), 1.50-1.38 (m, 2H), 1.24-1.15 (m, 4H), 1.05 (t, J = 12.3 Hz, 2H), 0.88 (t, J = 6.6 Hz, 2H). |

-continued

| Example # | Structure | LC-MS [M + H]+ unless otherwise noted | 1H-NMR |
|---|---|---|---|
| 643 | 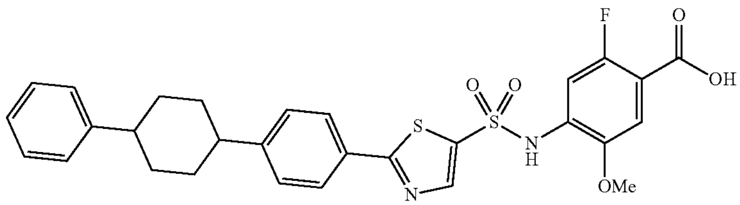 [SMILES: COc1cc(C(=O)O)c(F)cc1NS(=O)(=O)c1cnc(-c2ccc(C3CCC(c4ccccc4)CC3)cc2)s1] | 565.1 [M − H]− | |
| 644 | 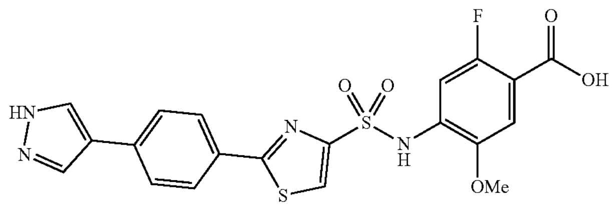 [SMILES: COc1cc(C(=O)O)c(F)cc1NS(=O)(=O)c1csc(-c2ccc(-c3cn[nH]c3)cc2)n1] | 473.0 [M − H]− | 1H NMR (300 MHz, DMSO-d6) δ 13.12 (s, 2H), 10.38 (s, 1H), 8.47 (s, 1H), 8.19 (s, 2H), 7.90-7.87 (m, 2H), 7.79-7.77 (m, 2H), 7.46 (d, J = 12.3 Hz, 1H), 7.31 (d, J =5.7 Hz, 1H), 3.70 (s, 3H). |
| 645 | 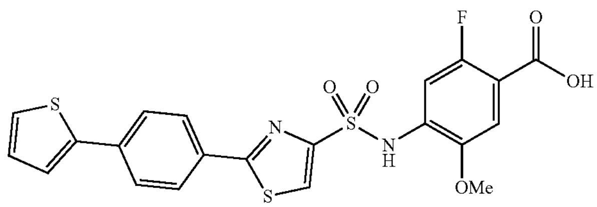 [SMILES: COc1cc(C(=O)O)c(F)cc1NS(=O)(=O)c1csc(-c2ccc(-c3cccs3)cc2)n1] | 489.0 [M − H]− | 1H NMR (400 MHz, DMSO-d6): δ 13.14 (s, 1H), 10.40 (s, 1H), 8.49 (s, 1H), 7.96-7.94 (m, 2H), 7.84-7.82 (m, 2H), 7.68-7.65 (m, 2H), 7.41 (d, J = 12.0 Hz, 1H), 7.30 (d, J = 6.4 Hz, 1H), 7.20-7.18 (m, 1H), 3.69 (s, 3H). |
| 646 | 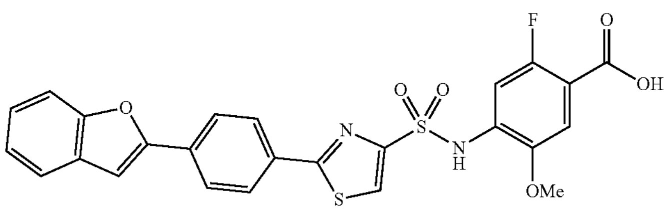 [SMILES: COc1cc(C(=O)O)c(F)cc1NS(=O)(=O)c1csc(-c2ccc(-c3cc4ccccc4o3)cc2)n1] | 522.9 [M − H]− | 1H NMR (300 MHz, DMSO-d6): δ 13.18 (s, 1H), 10.47 (s, 1H), 8.55 (s, 1H), 8.07 (dd, 4H), 7.74-7.60 (m, 3H), 7.47-7.25 (m, 4H), 3.69 (s, 3H). |
| 647 | 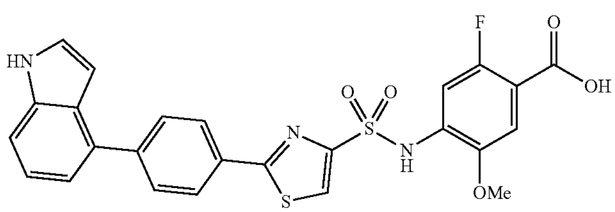 [SMILES: COc1cc(C(=O)O)c(F)cc1NS(=O)(=O)c1csc(-c2ccc(-c3cccc4[nH]ccc34)cc2)n1] | 522.0 [M − H]− | 1H NMR (400 MHz, DMSO-d6) δ 13.06 (s, 1H), 11.34 (s, 1H), 10.42 (s, 1H), 8.48 (s, 1H), 8.03 (d, J = 8.4 Hz, 2H), 7.85 (d, J = 8.4 Hz, 2H), 7.48-7.44 (m, 2H), 7.39 (d, J = 12.3 Hz, 1H), 7.35-7.28 (m, 1H), 7.23-7.17 (m, 2H), 6.62 (m, 1H), 3.71 (s, 3H). |
| 648 | 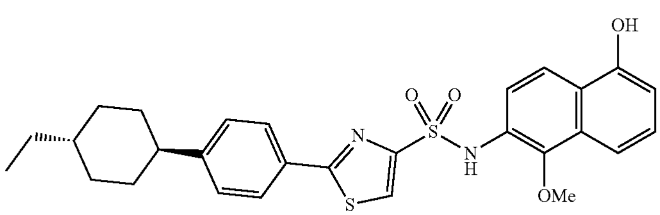 [SMILES: CC[C@H]1CC[C@H](c2ccc(-c3nc(S(=O)(=O)Nc4ccc5c(O)cccc5c4OC)cs3)cc2)CC1] | 523.1 | |
| 649 | 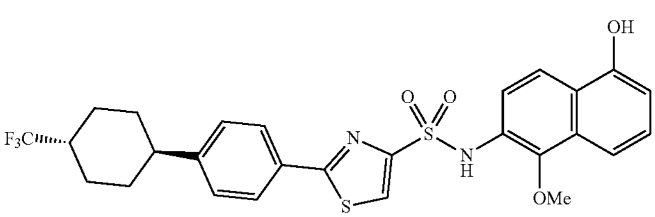 [SMILES: COc1c(NS(=O)(=O)c2csc(-c3ccc([C@H]4CC[C@H](C(F)(F)F)CC4)cc3)n2)ccc2c(O)cccc12] | 561.0 [M − H]− | |

-continued
| Example # | Structure | LC-MS [M + H]+ unless otherwise noted | 1H-NMR |
|---|---|---|---|
| 650 | 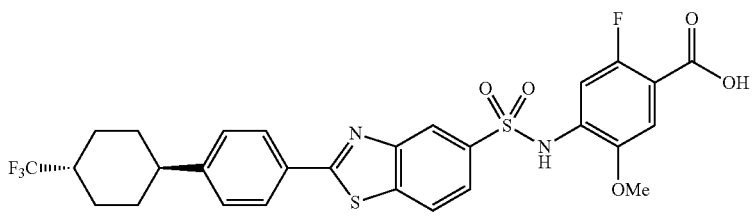 | 609.1 | 1H NMR (400 MHz, DMSO): 12.82 (s, 1H), 10.46 (s, 1H), 8.45 (s, 1H), 8.33 (d, 1H), 8.05 (d, 2H), 7.90 (d, 1H), 7.45 (d, 2H), 7.25-7.10 (m, 2H), 3.66 (s, 3H), 2.66 (t, 1H), 2.42-2.32 (m, 1H), 2.04-1.85 (m, 4H), 1.66-1.51 (m, 2H), 1.50-1.38 (m, 2H). |
| 651 | 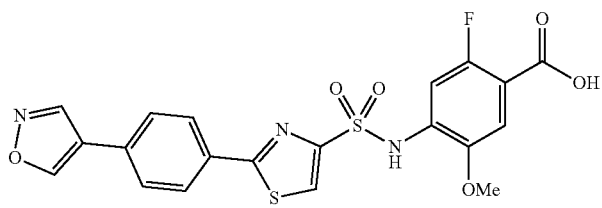 [SMILES: COc1cc(C(=O)O)c(F)cc1NS(=O)(=O)c1csc(-c2ccc(-c3cnoc3)cc2)n1] | 474.0 [M − H]− | |
| 652 | 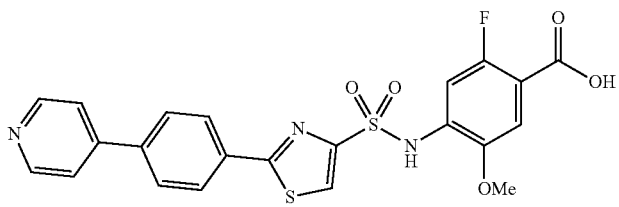 [SMILES: COc1cc(C(=O)O)c(F)cc1NS(=O)(=O)c1csc(-c2ccc(-c3ccncc3)cc2)n1] | 486.05 | 1H NMR (300 MHz, DMSO-d6): 13.15 (s, 1H), 10.40 (s, 1H), 8.69 (s, 2H), 8.50 (s, 1H), 8.06 (dd, 4H), 7.81 (s, 2H), 7.42 (d, 1H), 7.35 (d, 1H), 3.69 (s, 3H). |
| 653 | 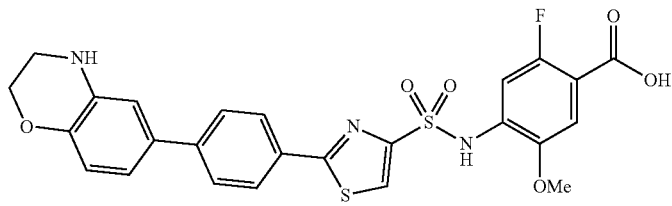 [SMILES: COc1cc(C(=O)O)c(F)cc1NS(=O)(=O)c1csc(-c2ccc(-c3ccc4c(c3)NCCO4)cc2)n1] | 542.0 | |
| 654 | 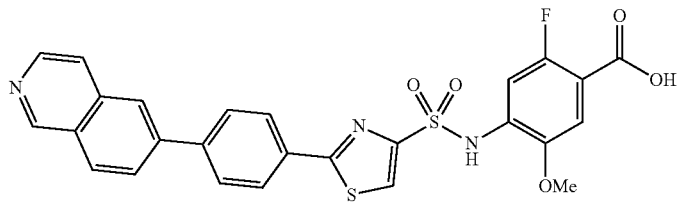 [SMILES: COc1cc(C(=O)O)c(F)cc1NS(=O)(=O)c1csc(-c2ccc(-c3ccc4cnccc4c3)cc2)n1] | 536.0 | |
| 655 | 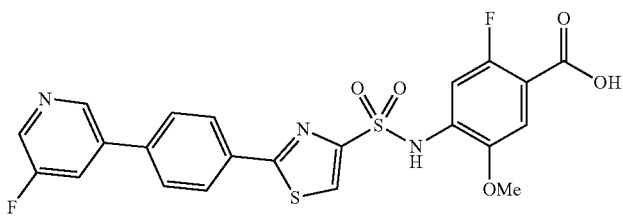 [SMILES: COc1cc(C(=O)O)c(F)cc1NS(=O)(=O)c1csc(-c2ccc(-c3cncc(F)c3)cc2)n1] | 504.0 [M − H]− | 1H NMR (300 MHz, DMSO-d6): 13.18 (s, 1H), 10.47 (s, 1H), 8.90 (s, 1H), 8.64 (s, 1H), 8.56, (s, 1H), 8.20 (d, 1H), 8.03 (dd, 4H), 7.46 (d, 1H), 7.32 (d, 1H), 3.69 (s, 3H). |

-continued

| Example # | Structure | LC-MS [M + H]+ unless otherwise noted | 1H-NMR |
|---|---|---|---|
| 656 | 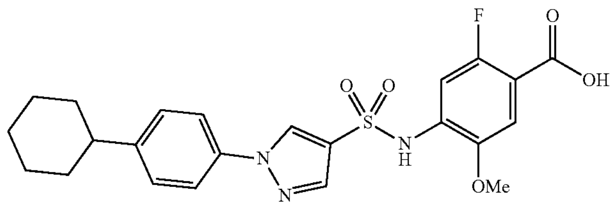 [SMILES: COc1cc(C(=O)O)c(F)cc1NS(=O)(=O)c1cnn(-c2ccc(C3CCCCC3)cc2)c1] | 472.0 [M − H]− | |
| 657 | 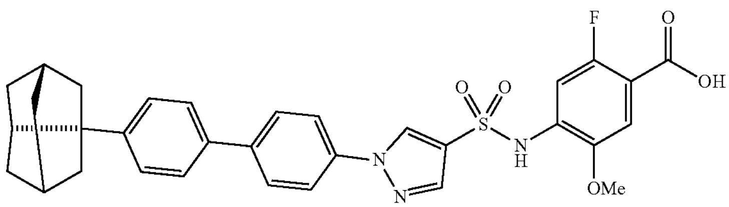 [SMILES: COc1cc(C(=O)O)c(F)cc1NS(=O)(=O)c1cnn(-c2ccc(-c3ccc(C45CC6C[C@H](C[C@H]4C6)C5)cc3)cc2)c1] | 600.1 [M − H]− | |
| 658 | 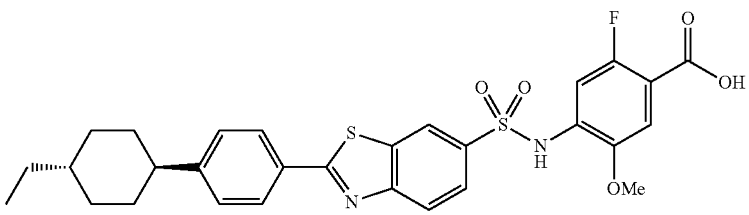 [SMILES: CC[C@H]1CC[C@H](c2ccc(-c3nc4ccc(S(=O)(=O)Nc5cc(F)c(C(=O)O)cc5OC)cc4s3)cc2)CC1] | 566.8 [M − H]− | |
| 659 | 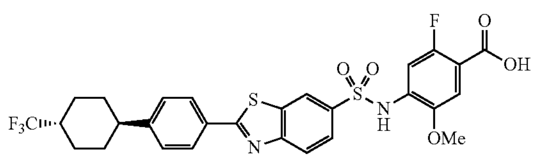 [SMILES: COc1cc(C(=O)O)c(F)cc1NS(=O)(=O)c1ccc2nc(-c3ccc([C@H]4CC[C@H](C(F)(F)F)CC4)cc3)sc2c1] | 608.9 | |
| 660 | 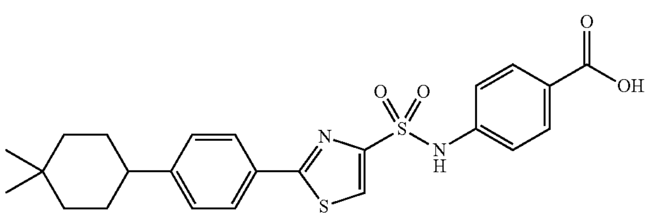 [SMILES: CC1(C)CCC(c2ccc(-c3nc(S(=O)(=O)Nc4ccc(C(=O)O)cc4)cs3)cc2)CC1] | 468.9 [M − H]− | |
| 661 | 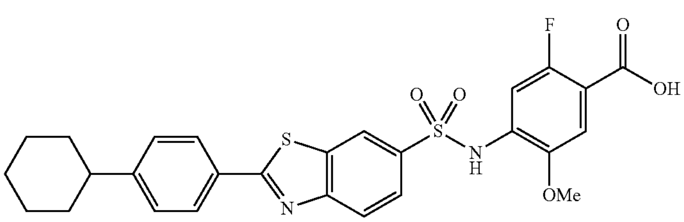 [SMILES: COc1cc(C(=O)O)c(F)cc1NS(=O)(=O)c1ccc2nc(-c3ccc(C4CCCCC4)cc3)sc2c1] | 538.8 [M − H]− | |
| 662 | 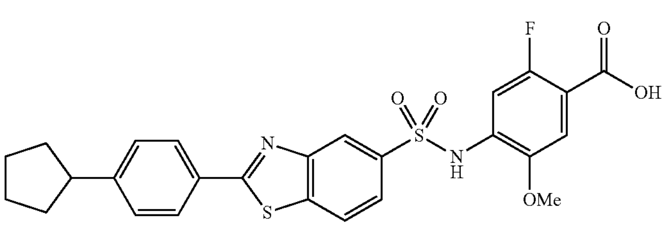 [SMILES: COc1cc(C(=O)O)c(F)cc1NS(=O)(=O)c1ccc2sc(-c3ccc(C4CCCC4)cc3)nc2c1] | 527.0 | |

-continued
| Example # | Structure | LC-MS [M + H]+ unless otherwise noted | 1H-NMR |
|---|---|---|---|
| 663 | 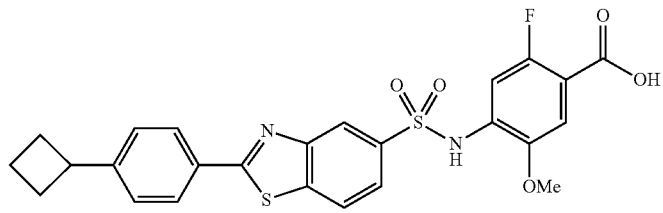 [SMILES: COc1cc(C(=O)O)c(F)cc1NS(=O)(=O)c1ccc2sc(-c3ccc(C4CCC4)cc3)nc2c1] | 513.0 | |
| 664 | 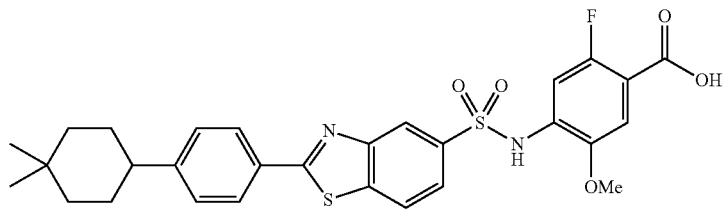 | 566.9 [M − H]− | |
| 665 | 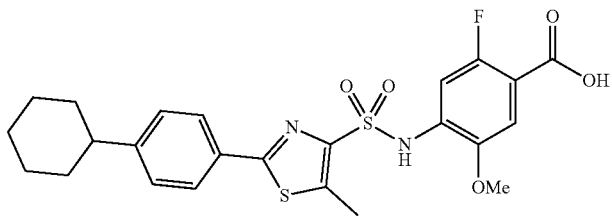 [SMILES: COc1cc(C(=O)O)c(F)cc1NS(=O)(=O)c1nc(-c2ccc(C3CCCCC3)cc2)sc1C] | 505.0 | |
| 666 | 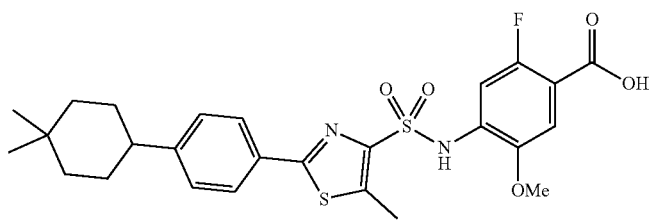 [SMILES: COc1cc(C(=O)O)c(F)cc1NS(=O)(=O)c1nc(-c2ccc(C3CCC(C)(C)CC3)cc2)sc1C] | 533.2 | |
| 667 | 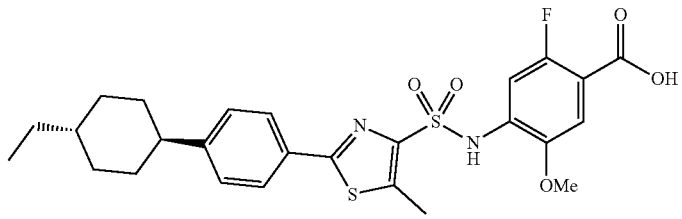 [SMILES: CC[C@H]1CC[C@H](c2ccc(-c3nc(S(=O)(=O)Nc4cc(F)c(C(=O)O)cc4OC)c(C)s3)cc2)CC1] | 532.8 | |
| 668 | 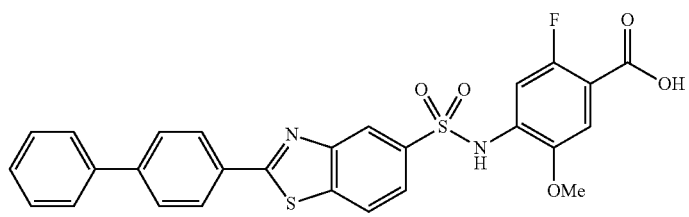 [SMILES: COc1cc(C(=O)O)c(F)cc1NS(=O)(=O)c1ccc2sc(-c3ccc(-c4ccccc4)cc3)nc2c1] | 533.0 | |

| Example # | Structure | LC-MS [M + H]+ unless otherwise noted | 1H-NMR |
|---|---|---|---|
| 669 | 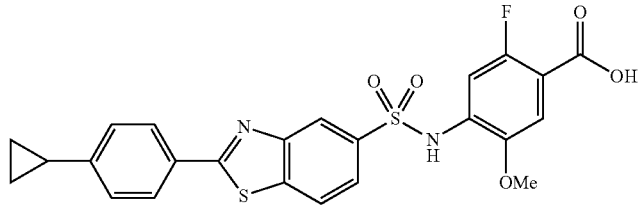 [SMILES: COc1cc(C(=O)O)c(F)cc1NS(=O)(=O)c1ccc2sc(-c3ccc(C4CC4)cc3)nc2c1] | 498.9 | |
| 670 | 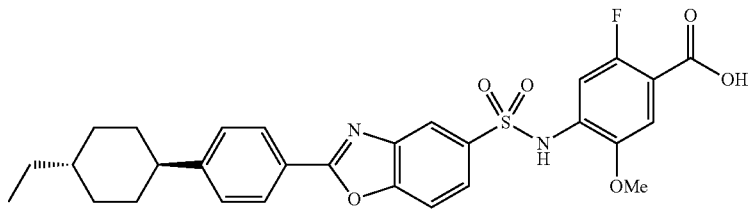 [SMILES: CC[C@H]1CC[C@H](c2ccc(-c3nc4cc(S(=O)(=O)Nc5cc(F)c(C(=O)O)cc5OC)ccc4o3)cc2)CC1] | 553.0 | |
| 671 | 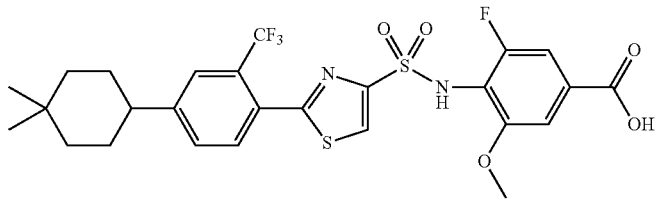 [SMILES: COc1cc(C(=O)O)cc(F)c1NS(=O)(=O)c1csc(-c2ccc(C3CCC(C)(C)CC3)cc2C(F)(F)F)n1] | 587.0 | |
| 672 | 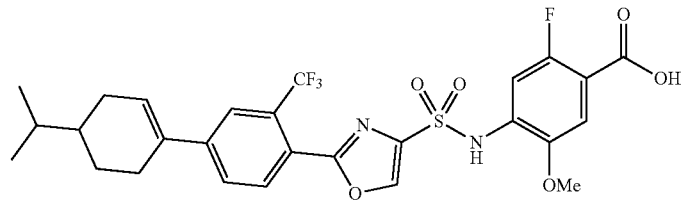 [SMILES: COc1cc(C(=O)O)c(F)cc1NS(=O)(=O)c1coc(-c2ccc(C3=CCC(C(C)C)CC3)cc2C(F)(F)F)n1] | 583.15 | 1H NMR (400 MHz, Methanol-d4) δ 8.52 (s, 1H), 7.89 (d, J = 8.2 Hz, 1H), 7.81 (s, 1H), 7.70 (dd, J = 8.2, 1.8 Hz, 1H), 7.47 (d, J = 11.9 Hz, 1H), 7.41 (d, J = 6.3 Hz, 1H), 66.37 (s, 1H), 3.86 (s, 3H), 2.59-2.42 (m, 2H), 2.41-2.27 (m, 1H), 2.01-1.92 (m, 2H), 1.63-1.50 (m, 1H), 1.42-1.35 (m, 2H), 0.96 (dd, J = 6.8, 5.1 Hz, 6H). |
| 673 | 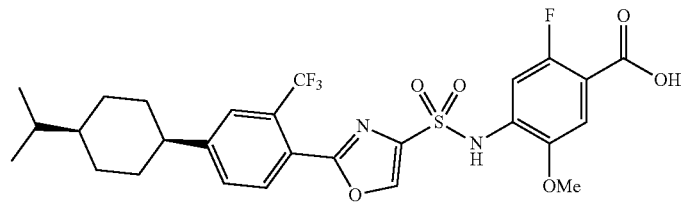 [SMILES: COc1cc(C(=O)O)c(F)cc1NS(=O)(=O)c1coc(-c2ccc([C@H]3CC[C@@H](C(C)C)CC3)cc2C(F)(F)F)n1] | 585.16 | 1H NMR (400 MHz, Methanol-d4) δ 8.49 (s, 1H), 7.87 (d, J = 8.1 Hz, 1H), 7.69 (s, 1H), 7.60 (d, J = 8.5 Hz, 1H), 7.47 (d, J = 11.8 Hz, 1H), 7.41 (d, J = 6.2 Hz, 1H), 3.86 (s, 3H), 2.88-2.76 (m, 1H), 1.84-1.67 (m, 6H), 1.64-1.49 (m, 2H), 1.34-1.20 (m, 2H), 0.92 (d, J = 6.6 Hz, 6H). |

| Example # | Structure | LC-MS [M + H]+ unless otherwise noted | 1H-NMR |
|---|---|---|---|
| 674 | 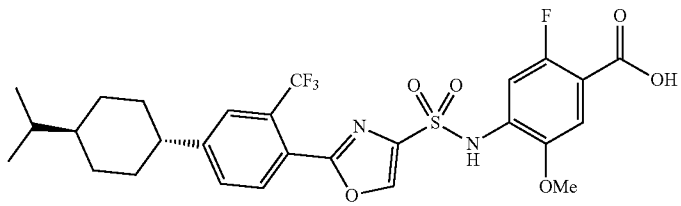 [SMILES: COc1cc(C(=O)O)c(F)cc1NS(=O)(=O)c1coc(-c2ccc([C@H]3CC[C@H](C(C)C)CC3)cc2C(F)(F)F)n1] | 585.16 | 1H NMR (400 MHz, Methanol-d4) δ 8.49 (s, 1H), 7.86 (d, J = 8.1 Hz, 1H), 7.66 (s, 1H), 7.55 (s, 1H), 7.46 (d, J = 11.8 Hz, 1H), 7.41 (d, J = 6.2 Hz, 1H), 3.86 (s, 3H), 2.62 (ddd, J = 12.2, 9.0, 3.6 Hz, 1H), 2.04-1.83 (m, 4H), 1.57-1.40 (m, 3H), 1.25-1.11 (m, 3H), 0.92 (d, J = 6.8 Hz, 6H). |
| 675 | 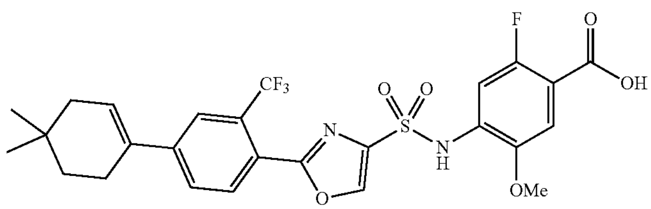 | 569.14 | 1H NMR (400 MHz, Methanol-d4) δ 8.51 (s, 1H), 7.90 (d, J = 8.2 Hz, 1H), 7.83 (d, J = 1.8 Hz, 1H), 7.71 (dd, J = 8.2, 1.9 Hz, 1H), 7.47 (d, J = 11.9 Hz, 1H), 7.41 (d, J = 6.3 Hz, 1H), 6.34-6.28 (m, 1H), 3.86 (s, 3H), 2.51-2.40 (m, 2H), 2.11-2.05 (m, 2H), 1.59 (t, J = 6.4 Hz, 2H), 1.00 (s, 6H). |
| 676 | 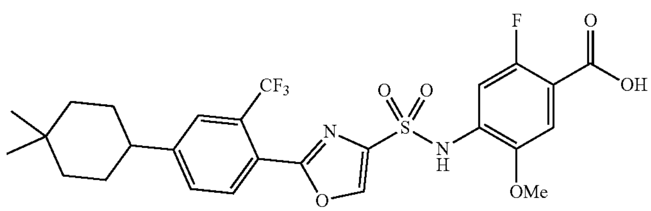 | 571.14 | 1H NMR (400 MHz, Methanol-d4) δ 8.54 (s, 1H), 7.87 (d, J = 8.0 Hz, 1H), 7.67 (s, 1H), 7.59 (dd, J = 7.9, 1.7, 1H), 7.47 (d, J = 11.9 Hz, 1H), 7.41 (d, J = 6.4 Hz, 1H), 3.86 (s, 3H), 2.59 (ddt, J = 11.7, 8.3, 4.2 Hz, 1H), 1.80-1.61 (m, 4H), 1.59-1.48 (m, 2H), 1.48-1.33 (m, 2H), 1.02 (s, 3H), 0.98 (s, 3H). |
| 677 | 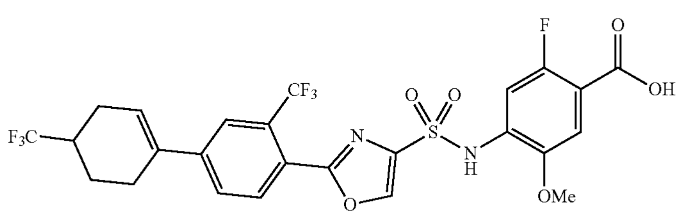 | 609.09 | 1H NMR (400 MHz, Methanol-d4) δ 8.51 (s, 1H), 7.93 (d, J = 8.2 Hz, 1H), 7.82 (d, J = 1.9 Hz, 1H), 7.71 (dd, J = 8.3, 1.9 Hz, 1H), 7.47 (d, J = 11.8 Hz, 1H), 7.41 (d, J = 6.3 Hz, 1H), 6.33 (s, 1H), 3.86 (s, 3H), 2.71-2.50 (m, 3H), 2.50-2.30 (m, 2H), 2.28-2.18 (m, 1H), 1.73 (ddt, J = 18.8, 12.2, 6.3 Hz, 1H). |
| 678 | 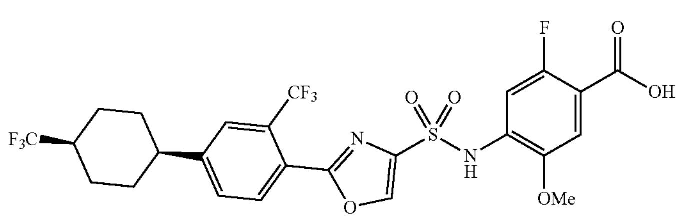 | 611.11 | 1H NMR (400 MHz, Acetonitrile-d3) δ 8.55 (s, 1H), 7.88 (d, J = 8.1 Hz, 1H), 7.78 (d, J = 1.8 Hz, 1H), 7.70 (dd, J = 8.1, 1.8 Hz, 1H), 7.48-7.30 (m, 2H), 3.85 (s, 3H), 3.01-2.88 (m, 1H), 2.46 (tq, J = 10.6, 5.3 Hz, 1H), 1.96-1.63 (m, 8H). |

| Example # | Structure | LC-MS [M + H]+ unless otherwise noted | 1H-NMR |
|---|---|---|---|
| 679 | 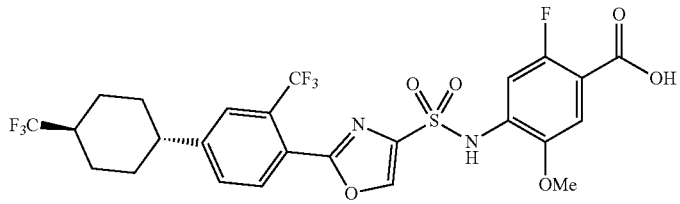 [SMILES: COc1cc(C(=O)O)c(F)cc1NS(=O)(=O)c1coc(-c2ccc([C@H]3CC[C@H](C(F)(F)F)CC3)cc2C(F)(F)F)n1] | 611.11 | 1H NMR (400 MHz, Methanol-d4) δ 8.71 (s, 1H), 7.90 (d, J = 7.9 Hz, 1H), 7.77 (s, 1H), 7.69 (d, J = 8.0 Hz, 1H), 7.47 (d, J = 11.9 Hz, 1H), 7.42 (d, J = 6.1 Hz, 1H), 3.84 (s, 3H), 2.81-2.72 (m, 1H), 2.38-2.18 (m, 1H), 2.15-1.99 (m, 4H), 1.70-1.47 (m, 4H). |
| 680 | 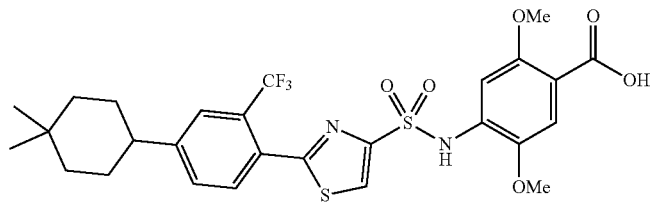 | 599.2 | |
| 681 | 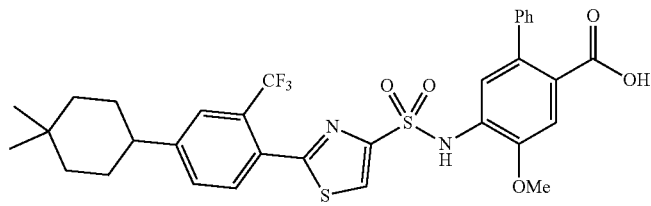 [SMILES: COc1cc(C(=O)O)c(-c2ccccc2)cc1NS(=O)(=O)c1csc(-c2ccc(C3CCC(C)(C)CC3)cc2C(F)(F)F)n1] | 645.1 | |
| 682 | 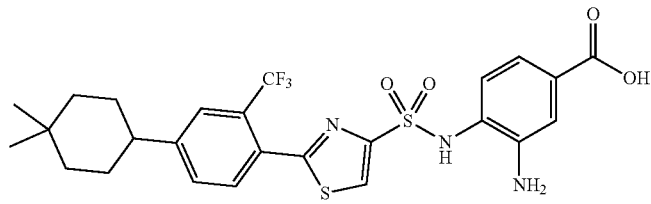 | [M − H]− 566.0 | |
| 683 | 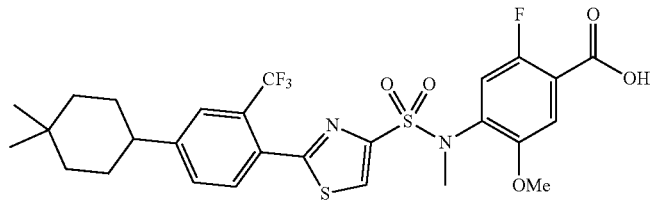 [SMILES: COc1cc(C(=O)O)c(F)cc1N(C)S(=O)(=O)c1csc(-c2ccc(C3CCC(C)(C)CC3)cc2C(F)(F)F)n1] | 601.1 | |
| 684 | 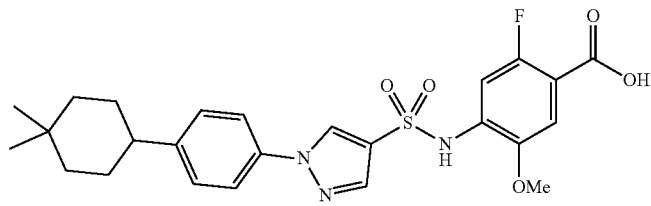 [SMILES: COc1cc(C(=O)O)c(F)cc1NS(=O)(=O)c1cnn(-c2ccc(C3CCC(C)(C)CC3)cc2)c1] | [M − H]− 500.10 | |

| Example # | Structure | LC-MS [M + H]+ unless otherwise noted | 1H-NMR |
|---|---|---|---|
| 685 | 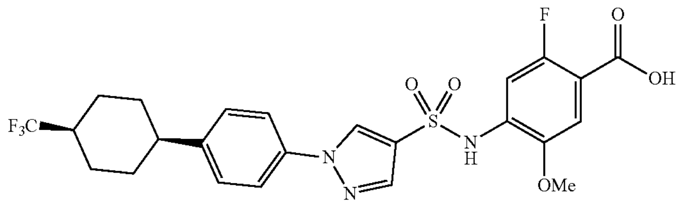 [SMILES: COc1cc(C(=O)O)c(F)cc1NS(=O)(=O)c1cnn(-c2ccc([C@H]3CC[C@@H](C(F)(F)F)CC3)cc2)c1] | [M − H]− 540.10 | |
| 686 | 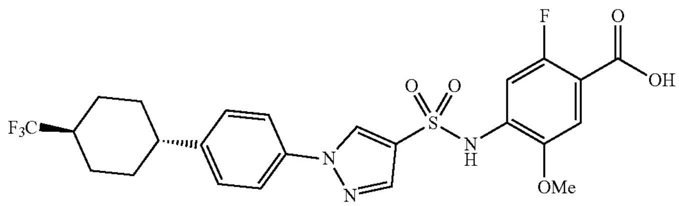 [SMILES: COc1cc(C(=O)O)c(F)cc1NS(=O)(=O)c1cnn(-c2ccc([C@H]3CC[C@H](C(F)(F)F)CC3)cc2)c1] | [M − H]− 540.10 | |
| 687 | 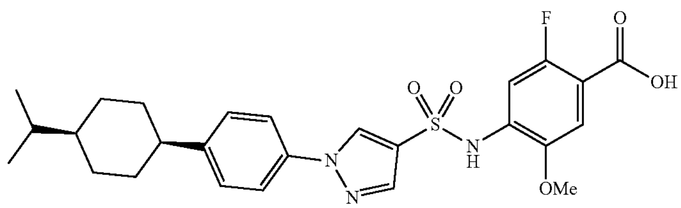 [SMILES: COc1cc(C(=O)O)c(F)cc1NS(=O)(=O)c1cnn(-c2ccc([C@H]3CC[C@@H](C(C)C)CC3)cc2)c1] | 516.20 | |
| 688 | 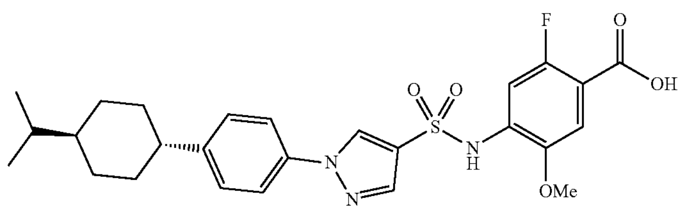 [SMILES: COc1cc(C(=O)O)c(F)cc1NS(=O)(=O)c1cnn(-c2ccc([C@H]3CC[C@H](C(C)C)CC3)cc2)c1] | 516.20 | |
| 689 | 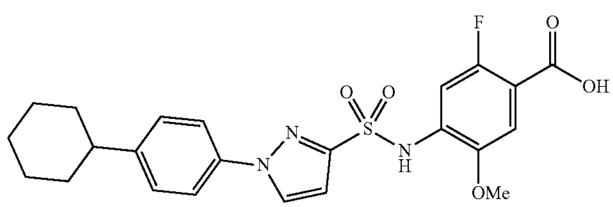 [SMILES: COc1cc(C(=O)O)c(F)cc1NS(=O)(=O)c1ccn(-c2ccc(C3CCCCC3)cc2)n1] | 474.0 | |
| 690 | 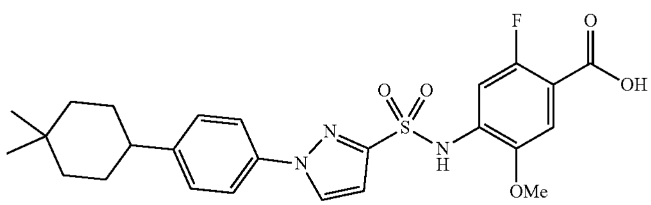 [SMILES: COc1cc(C(=O)O)c(F)cc1NS(=O)(=O)c1ccn(-c2ccc(C3CCC(C)(C)CC3)cc2)n1] | 502.0 | |
| 691 | 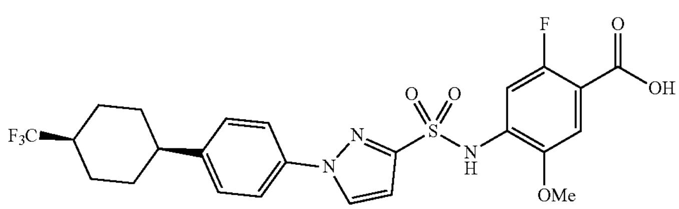 [SMILES: COc1cc(C(=O)O)c(F)cc1NS(=O)(=O)c1ccn(-c2ccc([C@H]3CC[C@@H](C(F)(F)F)CC3)cc2)n1] | 542.0 | |

-continued

| Example # | Structure | LC-MS [M + H]+ unless otherwise noted | ¹H-NMR |
|---|---|---|---|
| 692 | 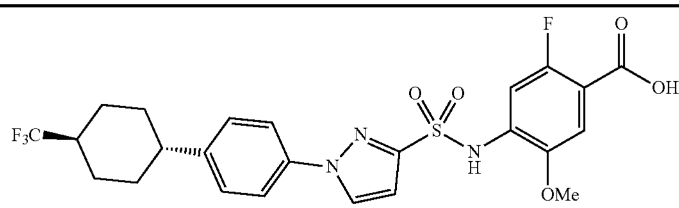 | 542.0 | |
| 693 | 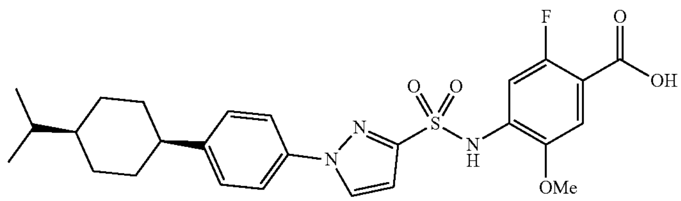 [SMILES: COc1cc(C(=O)O)c(F)cc1NS(=O)(=O)c1ccn(-c2ccc([C@H]3CC[C@@H](C(C)C)CC3)cc2)n1] | 516.2 | |
| 694 | 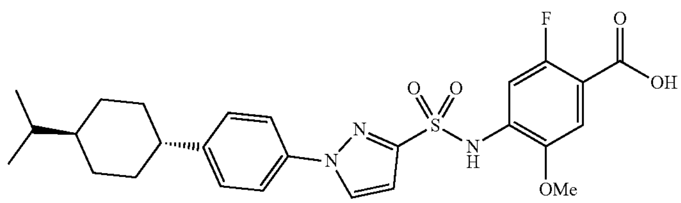 [SMILES: COc1cc(C(=O)O)c(F)cc1NS(=O)(=O)c1ccn(-c2ccc([C@H]3CC[C@H](C(C)C)CC3)cc2)n1] | 516.2 | |
| 695 | 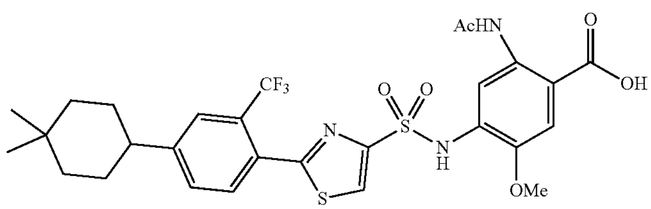 [SMILES: COc1cc(C(=O)O)c(NC(C)=O)cc1NS(=O)(=O)c1csc(-c2ccc(C3CCC(C)(C)CC3)cc2C(F)(F)F)n1] | [M − H]⁻ 624.1 | |
| 696 | 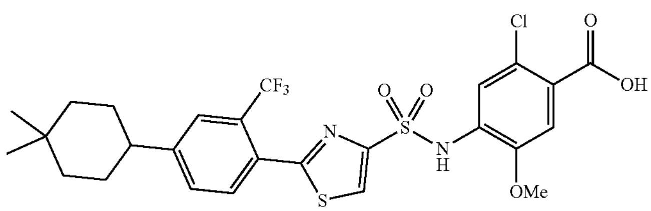 | 603.1 | |
| 697 | 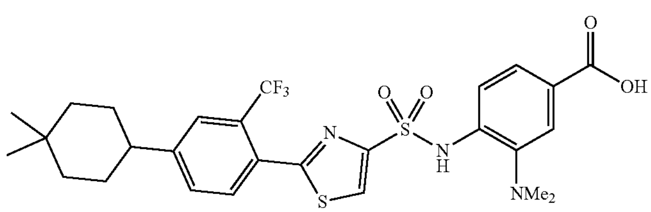 [SMILES: CN(C)c1cc(C(=O)O)ccc1NS(=O)(=O)c1csc(-c2ccc(C3CCC(C)(C)CC3)cc2C(F)(F)F)n1] | 582.1 | |
| 698 | 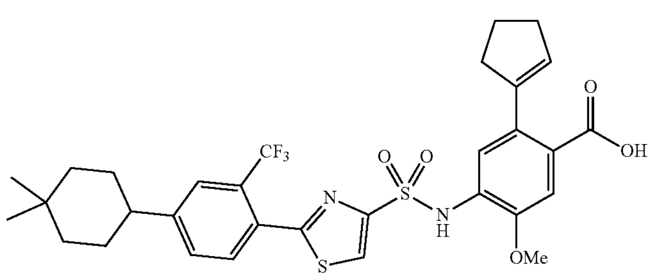 [SMILES: COc1cc(C(=O)O)c(C2=CCCC2)cc1NS(=O)(=O)c1csc(-c2ccc(C3CCC(C)(C)CC3)cc2C(F)(F)F)n1] | 635.2 | |

-continued

| Example # | Structure | LC-MS [M + H]+ unless otherwise noted | 1H-NMR |
|---|---|---|---|
| 699 | 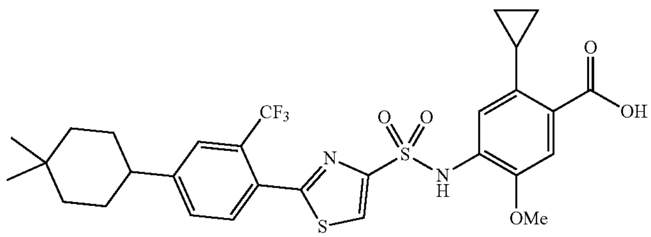 [SMILES: COc1cc(C(=O)O)c(C2CC2)cc1NS(=O)(=O)c1csc(-c2ccc(C3CCC(C)(C)CC3)cc2C(F)(F)F)n1] | 609.3 | |
| 700 | 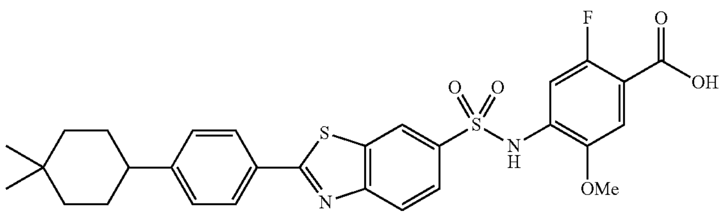 [SMILES: COc1cc(C(=O)O)c(F)cc1NS(=O)(=O)c1ccc2nc(-c3ccc(C4CCC(C)(C)CC4)cc3)sc2c1] | 569.20 | |
| 701 | 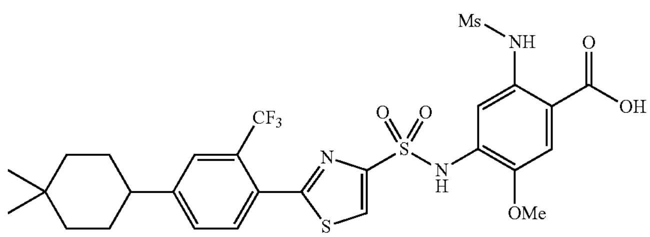 [SMILES: COc1cc(C(=O)O)c(NS(C)(=O)=O)cc1NS(=O)(=O)c1csc(-c2ccc(C3CCC(C)(C)CC3)cc2C(F)(F)F)n1] | [M − H]− 660.05 | |
| 702 | 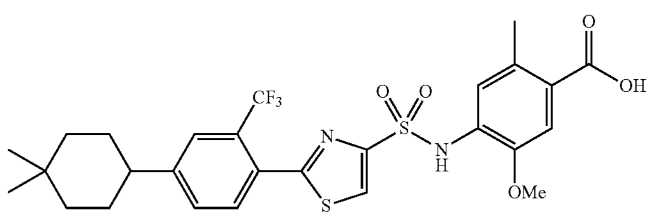 [SMILES: COc1cc(C(=O)O)c(C)cc1NS(=O)(=O)c1csc(-c2ccc(C3CCC(C)(C)CC3)cc2C(F)(F)F)n1] | 583.10 | |
| 703 | 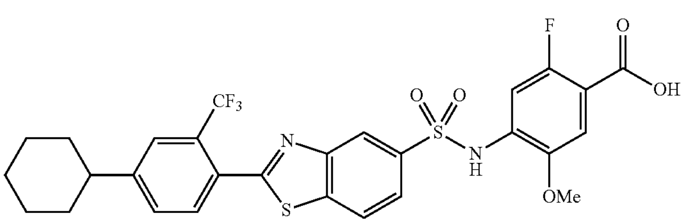 [SMILES: COc1cc(C(=O)O)c(F)cc1NS(=O)(=O)c1ccc2sc(-c3ccc(C4CCCCC4)cc3C(F)(F)F)nc2c1] | 609.10 | |
| 704 | 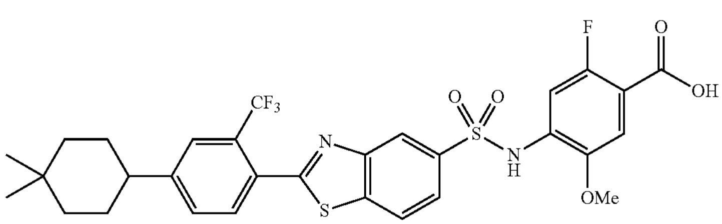 [SMILES: COc1cc(C(=O)O)c(F)cc1NS(=O)(=O)c1ccc2sc(-c3ccc(C4CCC(C)(C)CC4)cc3C(F)(F)F)nc2c1] | [M − H]− 635.10 | |

-continued

| Example # | Structure | LC-MS [M + H]+ unless otherwise noted | ¹H-NMR |
|---|---|---|---|
| 705 | 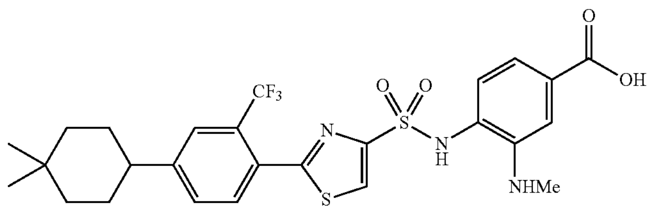 [SMILES: CNc1cc(C(=O)O)ccc1NS(=O)(=O)c1csc(-c2ccc(C3CCC(C)(C)CC3)cc2C(F)(F)F)n1] | 568.16 | |
| 706 | 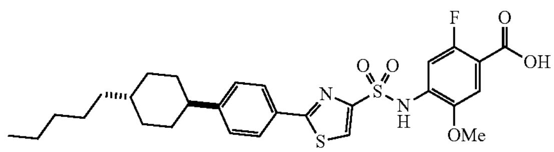 | 561.30 | |
| 707 | 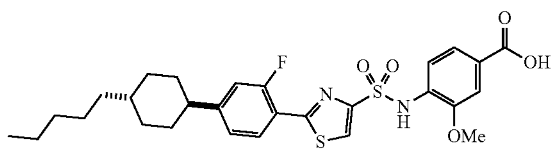 | 561.31 | |
| 708 | 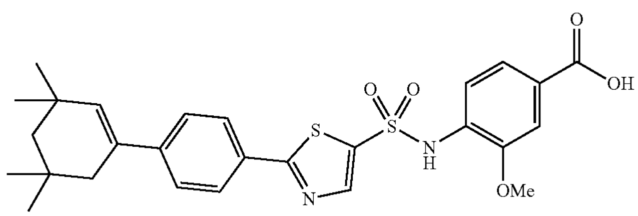 [SMILES: COc1cc(C(=O)O)ccc1NS(=O)(=O)c1cnc(-c2ccc(C3=CC(C)(C)CC(C)(C)C3)cc2)s1] | 528.21 | |
| 709 | 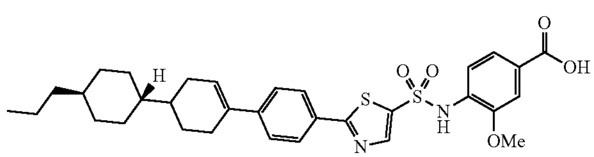 [SMILES: CCC[C@H]1CC[C@H](C2CC=C(c3ccc(-c4ncc(S(=O)(=O)Nc5ccc(C(=O)O)cc5OC)s4)cc3)CC2)CC1] | 594.26 [M − H]− | |
| 710 | 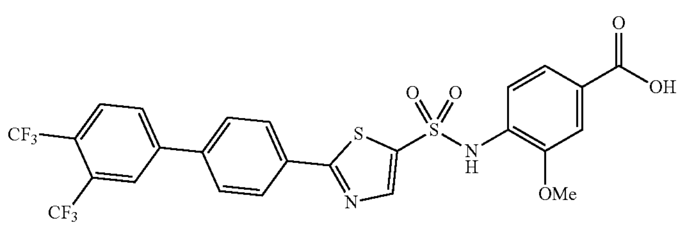 [SMILES: COc1cc(C(=O)O)ccc1NS(=O)(=O)c1cnc(-c2ccc(-c3ccc(C(F)(F)F)c(C(F)(F)F)c3)cc2)s1] | 603.18 | ¹H NMR (500 MHz, Acetone-d₆) δ 8.32 (s, 1H), 8.29-8.25 (m, 2H), 8.18-8.13 (m, 3H), 8.02-7.99 (m, 2H), 7.72-7.70 (m, 2H), 7.55 (t, J = 1.0 Hz, 1H), 3.82 (s, 3H). |
| 711 | 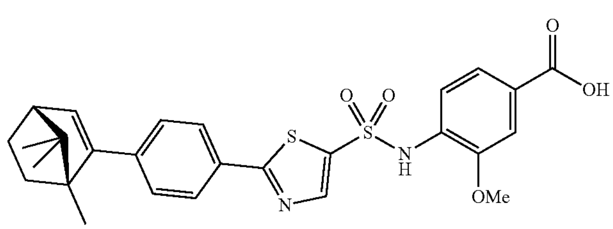 [SMILES: COc1cc(C(=O)O)ccc1NS(=O)(=O)c1cnc(-c2ccc(C3=C[C@H]4CC[C@]3(C)C4(C)C)cc2)s1] | 525.25 | |

-continued

| Example # | Structure | LC-MS [M + H]+ unless otherwise noted | 1H-NMR |
|---|---|---|---|
| 712 | F3C-[cyclohexyl]-[phenyl]-[thiazole]-SO2NH-[phenyl(OMe)]-COOH | 539.15 [M − H]− | 1H NMR (400 MHz, Acetone-d6) δ 8.20 (s, 1H), 7.93 (d, J = 8.4 Hz, 2H), 7.74-7.65 (m, 2H), 7.54 (s, 1H), 7.48-7.42 (m, 2H), 3.81 (s, 3H), 2.92-2.83 (m, 6H), 2.54-2.41 (m, 1H), 2.02-1.80 (m, 8H). |
| 713 | CF3-[cyclohexyl]-[phenyl]-[thiazole]-SO2NH-[phenyl(OMe)]-COOH | 541.15 | 1H NMR (400 MHz, Acetone-d6) δ 8.19-8.16 (m, 1H), 7.91 (d, J = 8.2 Hz, 2H), 7.72-7.63 (m, 2H), 7.53 (d, J = 1.6 Hz, 1H), 7.41 (d, J = 8.2Hz, 2H), 3.81 (s, 3H), 2.74-2.63 (m, 1H), 2.38-2.25 (m, 1H), 1.70-1.43 (m, 8H). |
| 714 | CF3F2C-[phenyl]-[phenyl]-[thiazole]-SO2NH-[phenyl(OMe)]-COOH | 585.13 | 1H NMR (500 MHz, Acetone-d6) δ 8.27 (s, 1H), 8.15-8.11 (m, 2H), 8.01 (d, J = 8.2 Hz, 2H), 7.94-7.89 (m, 2H), 7.83 (d, J = 8.3 Hz, 2H), 7.72-7.70 (m, 2H), 7.57-7.54 (m, 1H), 3.83 (s, 3H). |
| 715 | propyl-[cyclohexyl]-[phenyl]-[thiazole]-SO2NH-[phenyl(F)(OMe)]-COOH | 533.27 | 1H NMR (400 MHz, Acetone-d6) δ 8.43 (s, 1H), 7.87 (d, J = 8.4 Hz, 2H), 7.58 (d, J = 12.2 Hz, 1H), 7.43-7.36 (m, 3H), 3.85 (s, 3H), 2.63-2.52 (m, 1H), 1.92-1.84 (m, 4H), 1.59-1.45 (m, 2H), 1.44-1.27 (m, 3H), 1.27-1.18 (m, 2H), 1.16-1.02 (m, 2H), 0.90 (t, J = 7.3 Hz, 3H). |
| 716 | CF3-[cyclohexenyl]-[phenyl]-[thiazole]-SO2NH-[phenyl(OMe)]-COOH | 539.10 | 1H NMR (400 MHz, Chloroform-d) δ 8.00 (s, 1H), 7.83-7.78 (m, 2H), 7.70 (d, J = 8.4 Hz, 1H), 7.66 (dd, J = 8.5, 1.7 Hz, 1H), 7.46 (d, J = 1.7 Hz, 1H), 7.42-7.38 (m, 2H), 6.19-6.13 (m, 1H), 3.84 (s, 3H), 2.63-2.22 (m, 5H), 2.21-2.13 (m, 1H), 1.74-1.59 (m, 1H). |
| 717 | tBu-[cyclohexenyl]-[phenyl]-[thiazole]-SO2NH-[phenyl(F)(OMe)]-COOH | 543.22 [M − H]− | |

-continued
| Example # | Structure | LC-MS [M + H]+ unless otherwise noted | 1H-NMR |
|---|---|---|---|
| 718 | 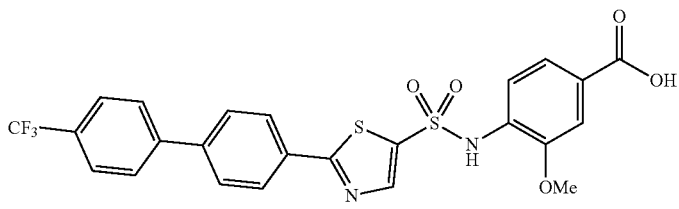 [SMILES: COc1cc(C(=O)O)ccc1NS(=O)(=O)c1cnc(-c2ccc(-c3ccc(C(F)(F)F)cc3)cc2)s1] | 535.08 | 1H NMR (400 MHz, DMSO-d6) δ 12.99 (s, 1H), 10.44 (s, 1H), 8.25 (s, 1H), 8.14-8.08 (m, 2H), 7.98 (d, J = 8.2 Hz, 3H), 7.95-7.89 (m, 2H), 7.86 (d, J = 8.2 Hz, 2H), 7.56 (dd, J = 8.3, 1.8 Hz, 1H), 7.49-7.42 (m, 2H), 3.68 (s, 3H). |
| 719 | 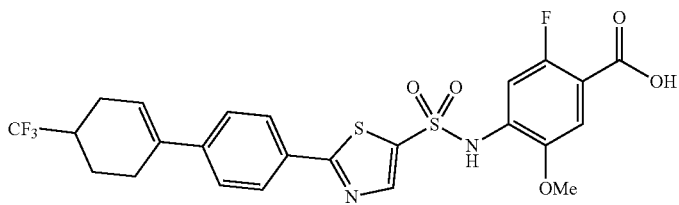 [SMILES: COc1cc(C(=O)O)c(F)cc1NS(=O)(=O)c1cnc(-c2ccc(C3=CCC(C(F)(F)F)CC3)cc2)s1] | 557.11 | |
| 720 | 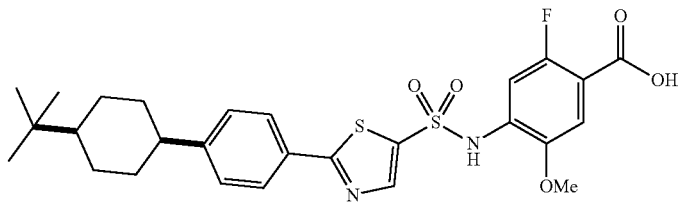 | 547.26 | |
| 721 | 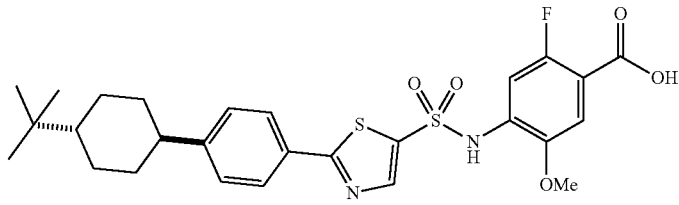 | 547.24 | |
| 722 | 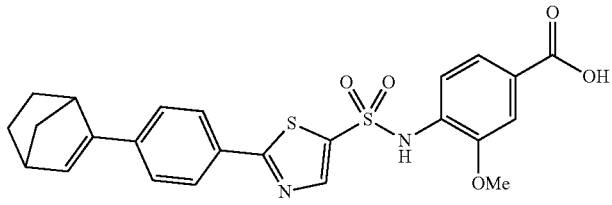 [SMILES: COc1cc(C(=O)O)ccc1NS(=O)(=O)c1cnc(-c2ccc(C3=CC4CCC3C4)cc2)s1] | 481.14 [M − H]− | |
| 723 | 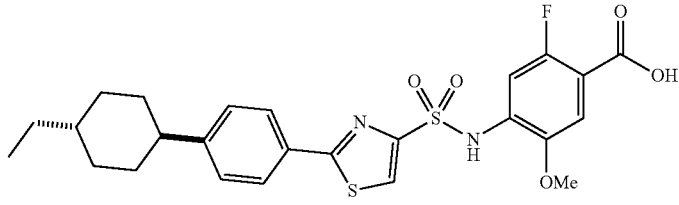 | 519.16 | 1H NMR (400 MHz, Acetone-d6) δ 8.43 (s, 1H), 7.87 (d, J = 8.1 Hz, 2H), 7.59 (d, J = 12.2 Hz, 1H), 7.48-7.18 (m, 3H), 3.86 (s, 3H), 2.63-2.51 (m, 1H), 1.93-1.86 (m, 4H), 1.59-1.45 (m, 2H), 1.32-1.20 (m, 3H), 1.15-1.02 (m, 2H), 0.91 (t, J = 7.1 Hz, 3H). |

-continued

| Example # | Structure | LC-MS [M + H]+ unless otherwise noted | 1H-NMR |
|---|---|---|---|
| 724 | 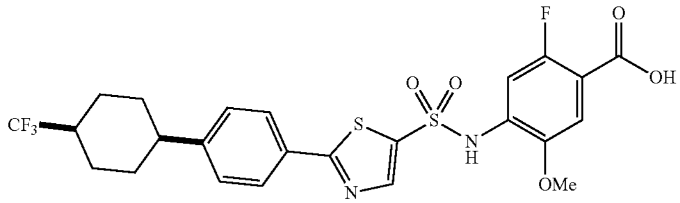 | 559.25 | |
| 725 | 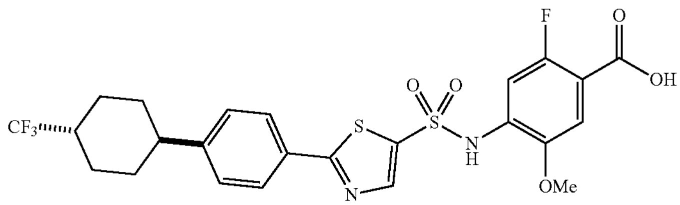 | 559.24 | |
| 726 | 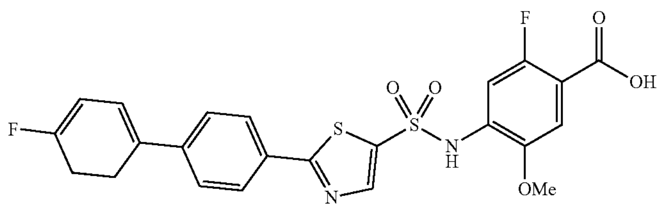 [SMILES: COc1cc(C(=O)O)c(F)cc1NS(=O)(=O)c1cnc(-c2ccc(C3=CC=C(F)CC3)cc2)s1] | 505.10 | |
| 727 | 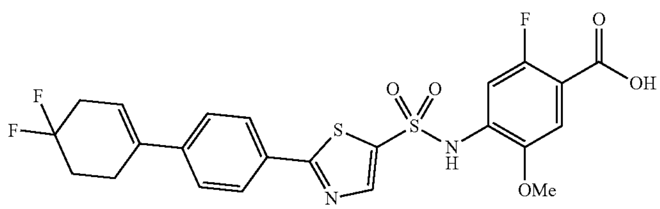 [SMILES: COc1cc(C(=O)O)c(F)cc1NS(=O)(=O)c1cnc(-c2ccc(C3=CCC(F)(F)CC3)cc2)s1] | 525.10 | |
| 728 | 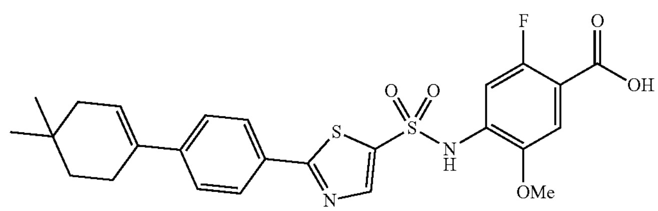 [SMILES: COc1cc(C(=O)O)c(F)cc1NS(=O)(=O)c1cnc(-c2ccc(C3=CCC(C)(C)CC3)cc2)s1] | 517.10 | |
| 729 | 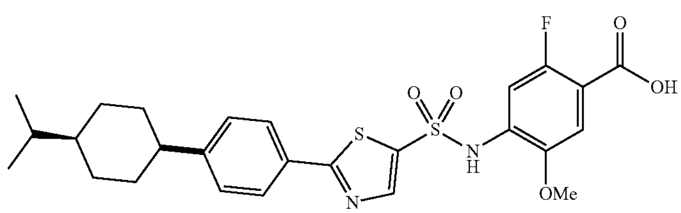 | 533.26 | |
| 730 | 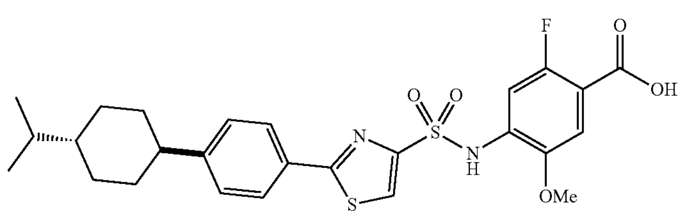 | 533.29 | |

-continued

| Example # | Structure | LC-MS [M + H]+ unless otherwise noted | 1H-NMR |
|---|---|---|---|
| 731 | 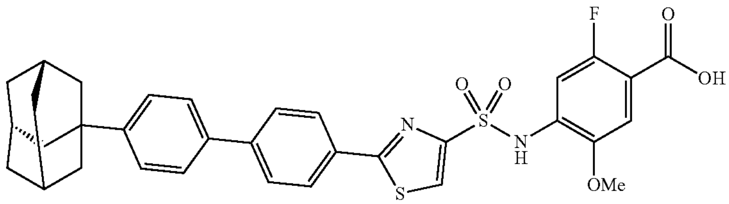 [SMILES: COc1cc(C(=O)O)c(F)cc1NS(=O)(=O)c1csc(-c2ccc(-c3ccc(C45CC6C[C@H](C4)C[C@H](C6)C5)cc3)cc2)n1] | 617.23 [M − H]− | |
| 732 | 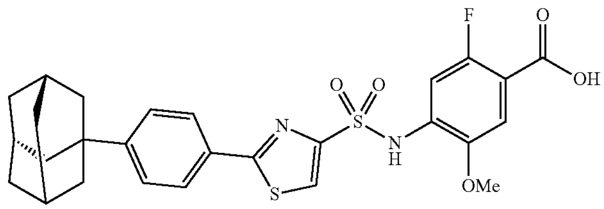 [SMILES: COc1cc(C(=O)O)c(F)cc1NS(=O)(=O)c1csc(-c2ccc(C34CC5C[C@H](C3)C[C@H](C5)C4)cc2)n1] | 543.24 | |
| 733 | 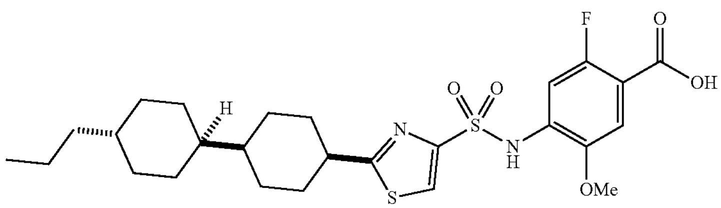 | 537.25 [M − H]− | |
| 734 | 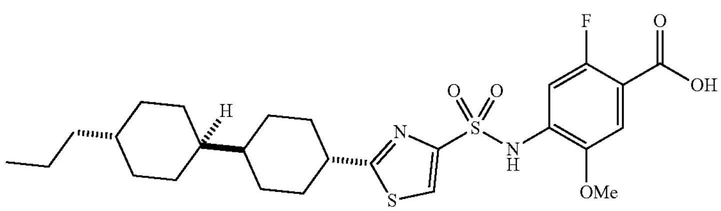 | 537.23 [M − H]− | |
| 735 | 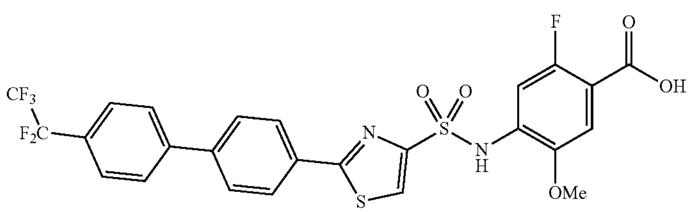 [SMILES: COc1cc(C(=O)O)c(F)cc1NS(=O)(=O)c1csc(-c2ccc(-c3ccc(C(F)(F)C(F)(F)F)cc3)cc2)n1] | 601.04 [M − H]− | |
| 736 | 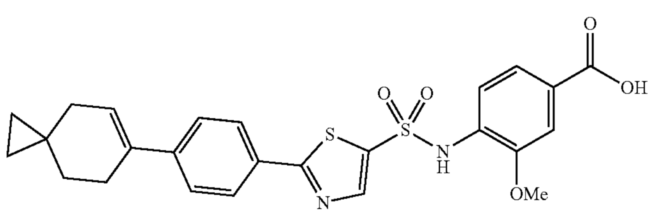 | 497.14 | |
| 737 | 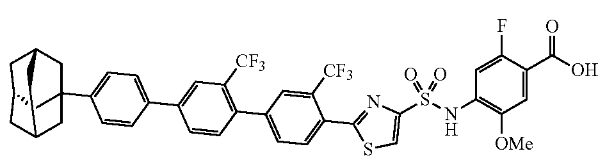 [SMILES: COc1cc(C(=O)O)c(F)cc1NS(=O)(=O)c1csc(-c2ccc(-c3ccc(-c4ccc(C56CC7C[C@H](C5)C[C@H](C7)C6)cc4)cc3C(F)(F)F)cc2C(F)(F)F)n1] | 831.18 | |

-continued

| Example # | Structure | LC-MS [M + H]+ unless otherwise noted | 1H-NMR |
|---|---|---|---|
| 738 | 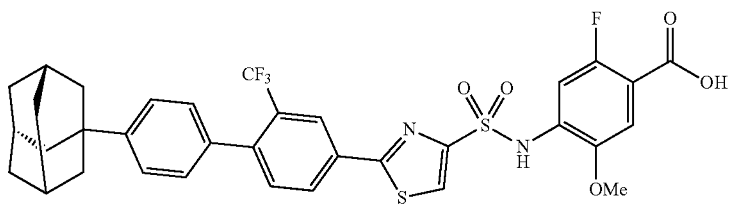 [SMILES: COc1cc(C(=O)O)c(F)cc1NS(=O)(=O)c1csc(-c2ccc(-c3ccc(C45CC6C[C@H](C4)C[C@H](C6)C5)cc3)c(C(F)(F)F)c2)n1] | 687.17 | |
| 739 | 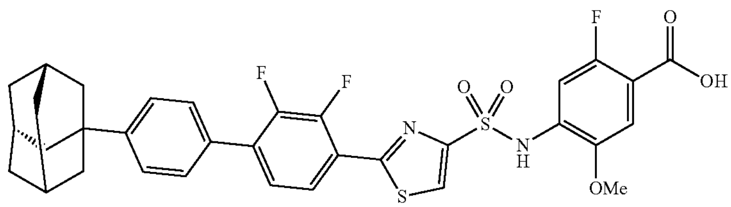 [SMILES: COc1cc(C(=O)O)c(F)cc1NS(=O)(=O)c1csc(-c2ccc(-c3ccc(C45CC6C[C@H](C4)C[C@H](C6)C5)cc3)c(F)c2F)n1] | 655.16 | |
| 740 | 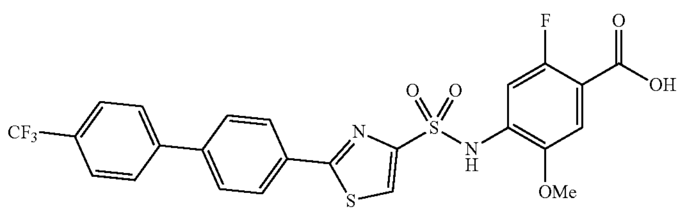 [SMILES: COc1cc(C(=O)O)c(F)cc1NS(=O)(=O)c1csc(-c2ccc(-c3ccc(C(F)(F)F)cc3)cc2)n1] | 551.04 [M − H]− | |
| 741 | 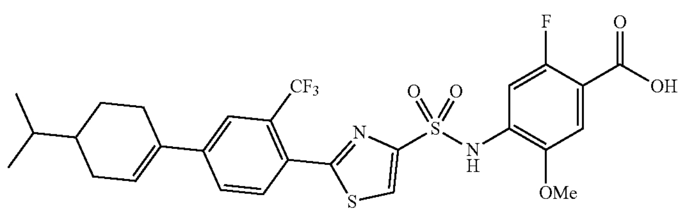 [SMILES: COc1cc(C(=O)O)c(F)cc1NS(=O)(=O)c1csc(-c2ccc(C3=CCC(C(C)C)CC3)cc2C(F)(F)F)n1] | 599.17 | |
| 742 | 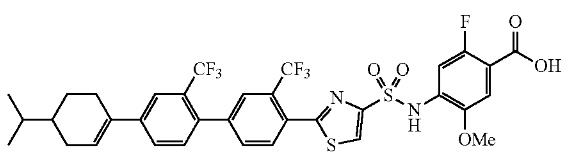 [SMILES: COc1cc(C(=O)O)c(F)cc1NS(=O)(=O)c1csc(-c2ccc(-c3ccc(C4=CCC(C(C)C)CC4)cc3C(F)(F)F)cc2C(F)(F)F)n1] | 743.17 | |
| 743 | 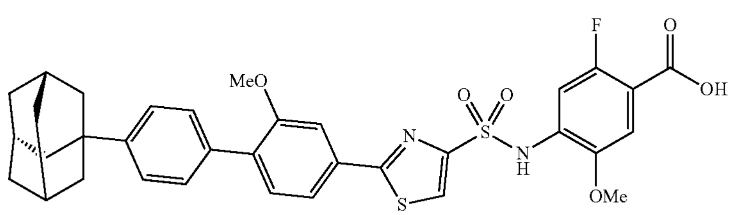 [SMILES: COc1cc(C(=O)O)c(F)cc1NS(=O)(=O)c1csc(-c2ccc(-c3ccc(C45CC6C[C@H](C4)C[C@H](C6)C5)cc3)c(OC)c2)n1] | 649.20 | |
| 744 | 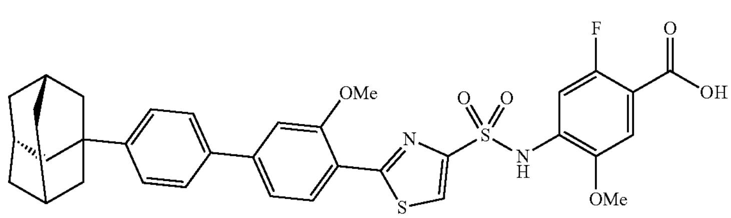 [SMILES: COc1cc(C(=O)O)c(F)cc1NS(=O)(=O)c1csc(-c2ccc(-c3ccc(C45CC6C[C@H](C4)C[C@H](C6)C5)cc3)cc2OC)n1] | 649.19 | |

-continued

| Example # | Structure | LC-MS [M + H]+ unless otherwise noted | ¹H-NMR |
|---|---|---|---|
| 745 | 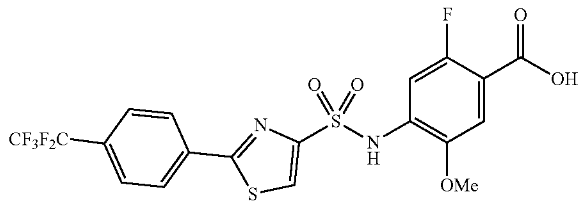 | 527.02 | ¹H NMR (400 MHz, Acetone-d₆) δ 8.58 (d, J = 0.8 Hz, 1H), 8.21 (d, J = 8.1Hz, 2H), 7.87 (d, J = 8.3 Hz, 2H), 7.55 (d, J = 12.0 Hz, 1H), 7.40 (d, J = 6.4 Hz, 1H), 3.85 (s, 3H). |
| 746 | 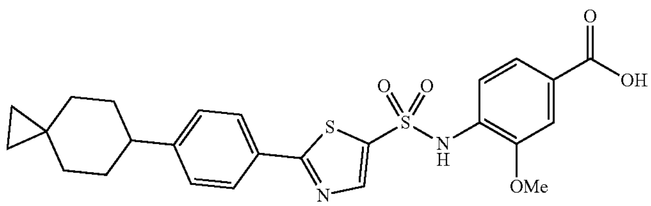 [SMILES: COc1cc(C(=O)O)ccc1NS(=O)(=O)c1cnc(-c2ccc(C3CCC4(CC3)CC4)cc2)s1] | 499.20 | |
| 747 | 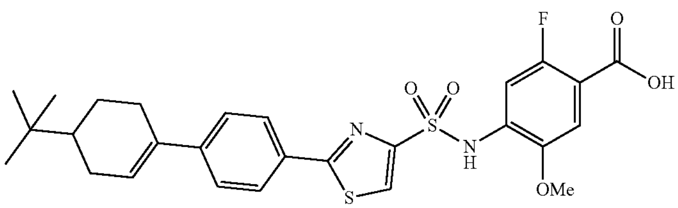 [SMILES: COc1cc(C(=O)O)c(F)cc1NS(=O)(=O)c1csc(-c2ccc(C3=CCC(C(C)(C)C)CC3)cc2)n1] | 545.24 | |
| 748 | 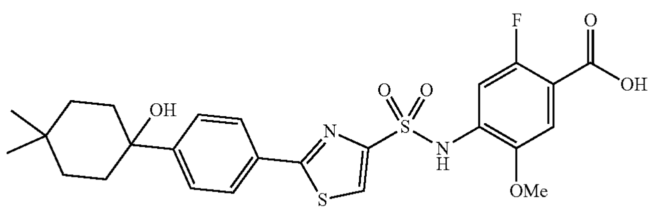 [SMILES: COc1cc(C(=O)O)c(F)cc1NS(=O)(=O)c1csc(-c2ccc(C3(O)CCC(C)(C)CC3)cc2)n1] | 535.17 | |
| 749 | 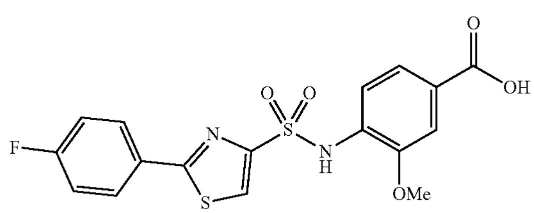 [SMILES: COc1cc(C(=O)O)ccc1NS(=O)(=O)c1csc(-c2ccc(F)cc2)n1] | 409.11 | |
| 750 | 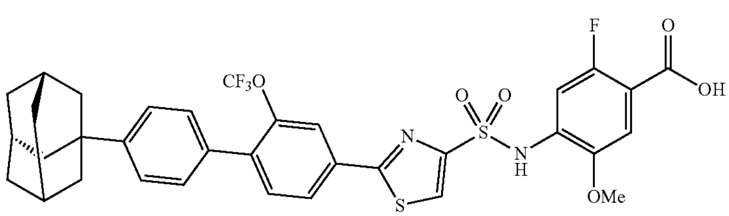 | 703.16 | |
| 753 | 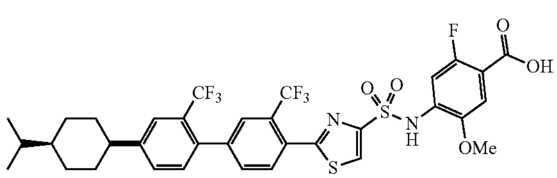 | 745.17 | |

| Example # | Structure | LC-MS [M + H]+ unless otherwise noted | 1H-NMR |
|---|---|---|---|
| 754 | 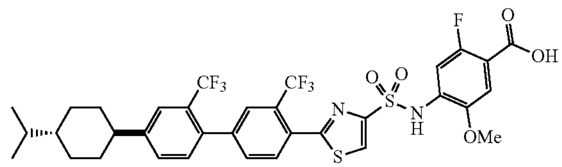 | 745.17 | |
| 755 | 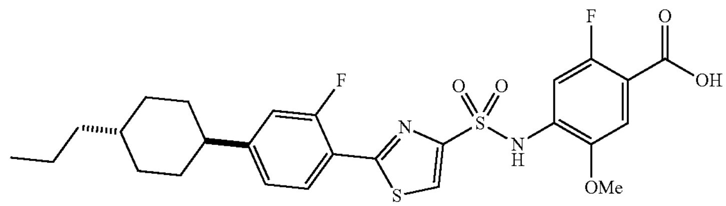 | 551.16 | 1H NMR (400 MHz, Acetone-d6) δ 8.56 (d, J = 0.9 Hz, 1H), 8.10 (t, J = 8.0 Hz, 1H), 7.62 (d, J = 12.1 Hz, 1H), 7.42 (d, J = 6.4 Hz, 1H), 7.33-7.22 (m, 2H), 3.87 (s, 3H), 2.69-2.58 (m, 1H), 1.96-1.86 (m, 4H), 1.62-1.47 (m, 2H), 1.45-1.28 (m, 3H), 1.29-1.19 (m, 2H), 1.18-1.03 (m, 2H), 0.92 (t, J = 7.3 Hz, 2H). |
| 756 | 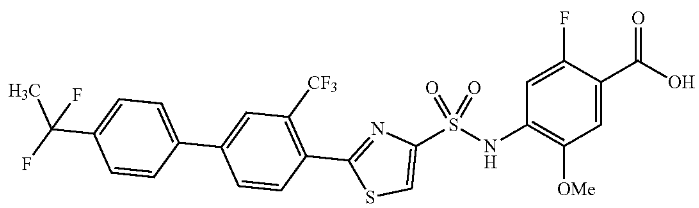 [SMILES: COc1cc(C(=O)O)c(F)cc1NS(=O)(=O)c1csc(-c2ccc(-c3ccc(C(C)(F)F)cc3)cc2C(F)(F)F)n1] | 617.19 | 1H NMR (400 MHz, Acetone-d6) δ 8.69 (s, 1H), 8.21-8.18 (m, 1H), 8.14 (dd, J = 8.0, 1.9 Hz, 1H), 7.95 (d, J = 8.1 Hz, 2H), 7.90 (d, J = 8.0 Hz, 1H), 7.74 (d, J = 8.1Hz, 3H), 7.55 (d, J = 12.1 Hz, 1H), 7.44 (d, J = 6.4 Hz, 1H), 3.89 (s, 3H). |
| 757 | 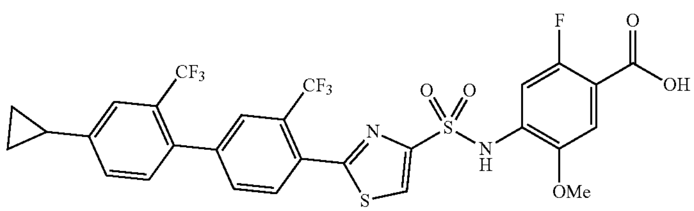 [SMILES: COc1cc(C(=O)O)c(F)cc1NS(=O)(=O)c1csc(-c2ccc(-c3ccc(C4CC4)cc3C(F)(F)F)cc2C(F)(F)F)n1] | 661.08 | 1H NMR (400 MHz, Acetone-d6) δ 8.70 (s, 1H), 7.88-7.83 (m, 2H), 7.76 (dd, J = 8.4, 1.5 Hz, 1H), 7.60 (d, J = 1.8 Hz, 1H), 7.54 (d, J = 12.1 Hz, 1H), 7.49-7.38 (m, 4H), 3.89 (s, 3H), 2.19-2.10 (m, 1H), 1.15-1.07 (m, 2H), 0.89-0.81 (m, 2H). |
| 758 | 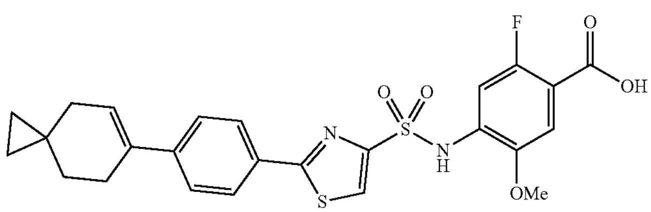 [SMILES: COc1cc(C(=O)O)c(F)cc1NS(=O)(=O)c1csc(-c2ccc(C3=CCC4(CC3)CC4)cc2)n1] | 515.16 | |
| 759 | 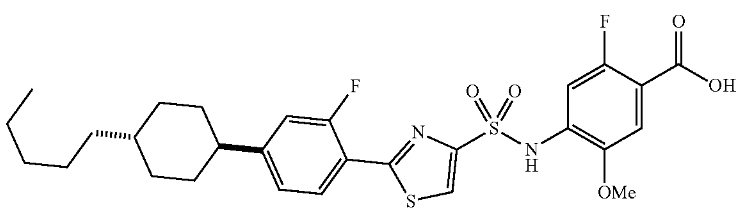 | 577.17 [M − H]− | 1H NMR (400 MHz, Acetone-d6) δ 8.54 (s, 1H), 8.12-8.05 (m, 1H), 7.60 (d, J = 12.1 Hz, 1H), 7.40 (d, J = 6.4 Hz, 1H), 7.31-7.20 (m, 2H), 3.85 (s, 3H), 2.67-2.55 (m, 1H), 1.94-1.84 (m, 4H), 1.59-1.46 (m, 2H), 1.38-1.20 (m, 9H), 1.16-1.02 (m, 2H), 0.89 (t, J = 6.9 Hz, 3H). |

-continued

| Example # | Structure | LC-MS [M + H]+ unless otherwise noted | 1H-NMR |
|---|---|---|---|
| 760 | 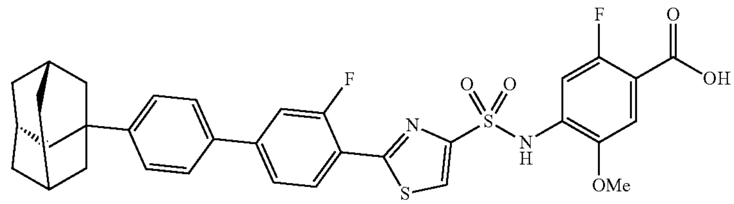 [SMILES: COc1cc(C(=O)O)c(F)cc1NS(=O)(=O)c1csc(-c2ccc(-c3ccc(C45CC6C[C@H](C4)C[C@H](C6)C5)cc3)cc2F)n1] | 637.17 | |
| 761 | 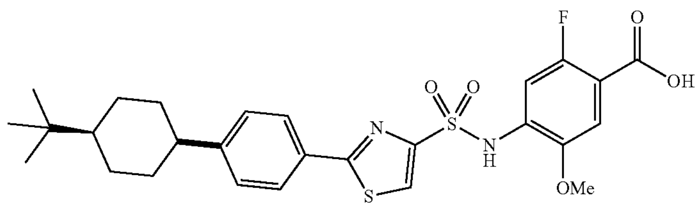 | 547.31 | |
| 762 | 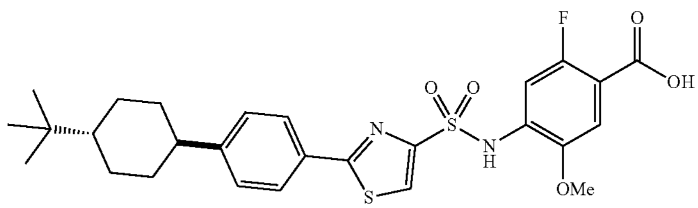 | 547.31 | |
| 763 | 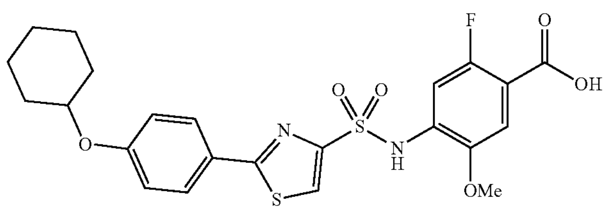 [SMILES: COc1cc(C(=O)O)c(F)cc1NS(=O)(=O)c1csc(-c2ccc(OC3CCCCC3)cc2)n1] | 507.23 | |
| 764 | 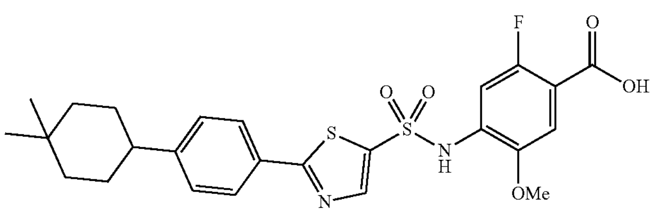 [SMILES: COc1cc(C(=O)O)c(F)cc1NS(=O)(=O)c1cnc(-c2ccc(C3CCC(C)(C)CC3)cc2)s1] | 517.19 [M − H]− | |
| 765 | 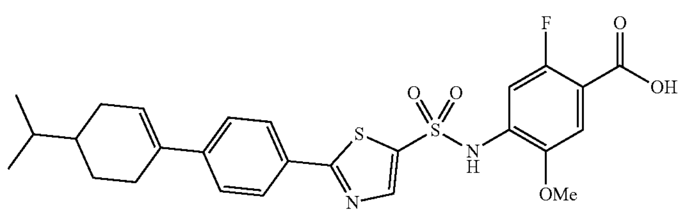 [SMILES: COc1cc(C(=O)O)c(F)cc1NS(=O)(=O)c1cnc(-c2ccc(C3=CCC(C(C)C)CC3)cc2)s1] | 531.20 | |
| 766 | 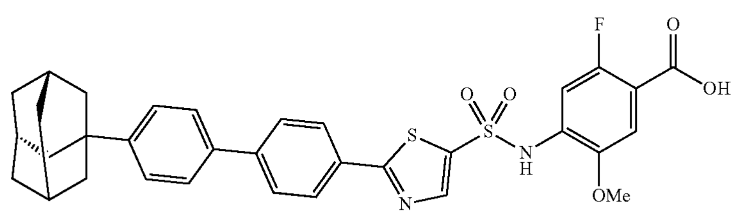 [SMILES: COc1cc(C(=O)O)c(F)cc1NS(=O)(=O)c1cnc(-c2ccc(-c3ccc(C45CC6C[C@H](C4)C[C@H](C6)C5)cc3)cc2)s1] | 617.18 [M − H]− | |

-continued

| Example # | Structure | LC-MS [M + H]+ unless otherwise noted | 1H-NMR |
|---|---|---|---|
| 767 | 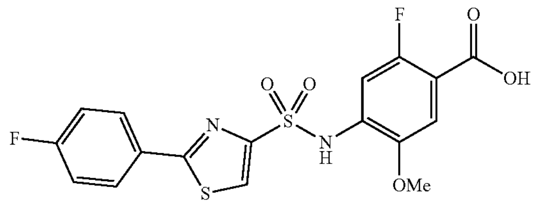 | 427.07 | |
| 768 | 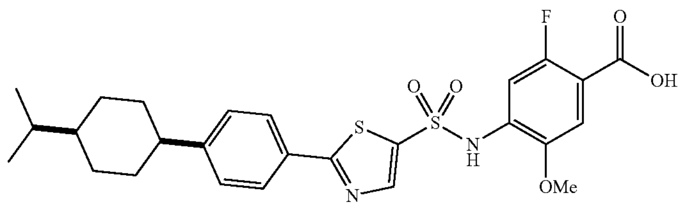 | 531.17 [M − H]− | |
| 769 | 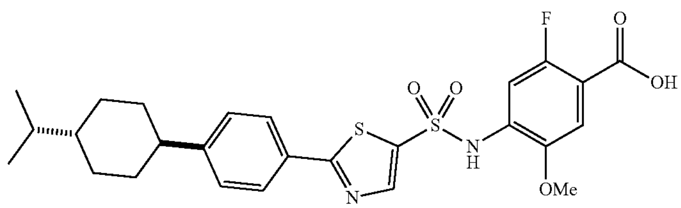 | 533.23 | |
| 770 | 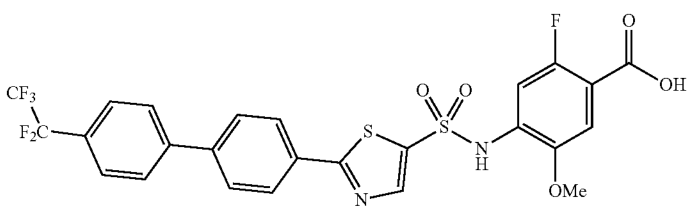 [SMILES: COc1cc(C(=O)O)c(F)cc1NS(=O)(=O)c1cnc(-c2ccc(-c3ccc(C(F)(F)C(F)(F)F)cc3)cc2)s1] | 603.08 | |
| 771 | 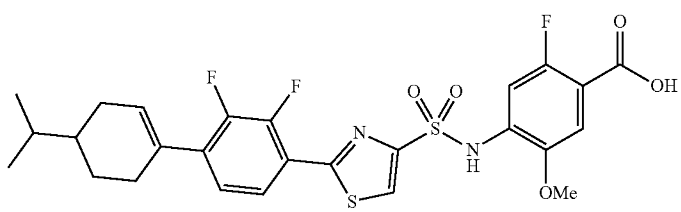 [SMILES: COc1cc(C(=O)O)c(F)cc1NS(=O)(=O)c1csc(-c2ccc(C3=CCC(C(C)C)CC3)c(F)c2F)n1] | 567.18 | |
| 772 | 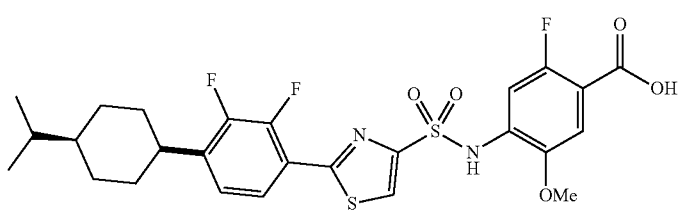 | 569.28 | |
| 773 | 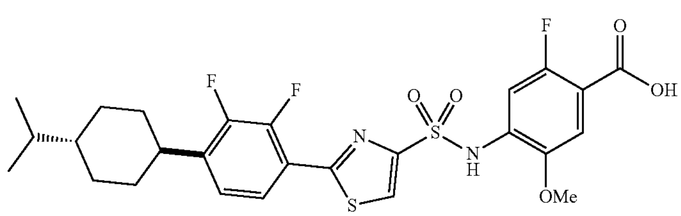 | 569.24 | |

-continued
| Example # | Structure | LC-MS [M + H]+ unless otherwise noted | 1H-NMR |
|---|---|---|---|
| 774 | 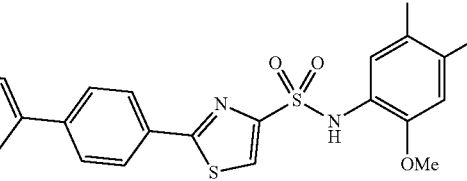 | 529.15 [M − H]− | |
| 775 | 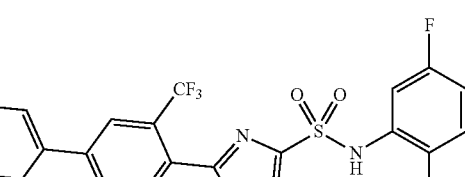 | 687.18 | |
| 776 | 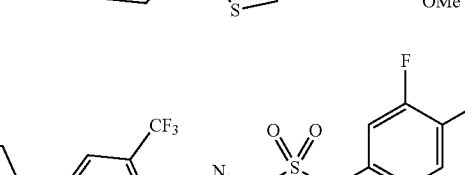 | 613.16 | |
| 777 | 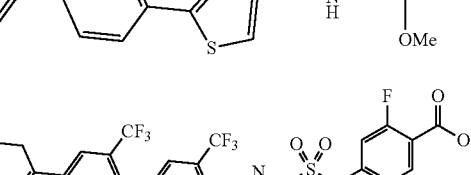 | 457.17 | |
| 778 | 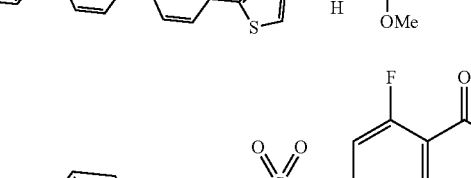 | 517.16 | |
| 779 | 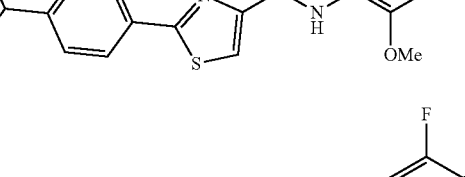 | 535.23 | |
| 780 | 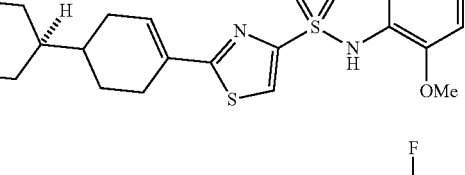 | 613.18 [M − H]− | |

-continued

| Example # | Structure | LC-MS [M + H]+ unless otherwise noted | 1H-NMR |
|---|---|---|---|
| 781 | 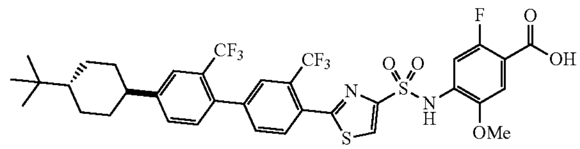 | 757.17 [M − H]− | |
| 782 | 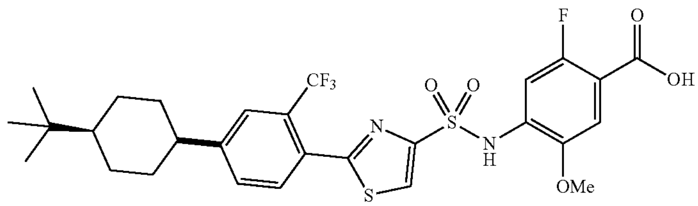 | 613.14 [M − H]− | |
| 783 | 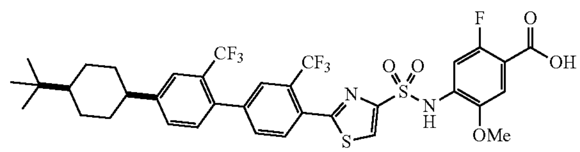 | 757.16 [M − H]− | |
| 784 | 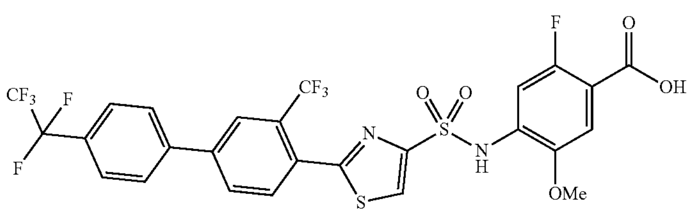 [SMILES: COc1cc(C(=O)O)c(F)cc1NS(=O)(=O)c1csc(-c2ccc(-c3ccc(C(F)(F)C(F)(F)F)cc3)cc2C(F)(F)F)n1] | 671.04 | 1H NMR (400 MHz, Acetone-$d_6$) δ 8.70 (s, 1H), 8.25 (s, 1H), 8.19 (dd, J = 8.0, 1.9 Hz, 1H), 8.10 (d, J = 8.0 Hz, 2H), 7.93 (d, J = 8.0 Hz, 1H), 7.87 (d, J = 8.2 Hz, 2H), 7.55 (d, J = 12.1 Hz, 1H), 7.44 (d, J = 6.5 Hz, 1H), 3.89 (d, J = 0.9 Hz, 3H). |
| 785 | 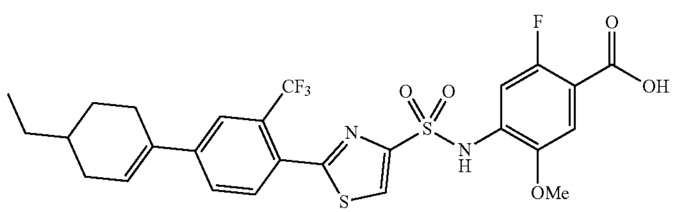 [SMILES: CCC1CC=C(c2ccc(-c3nc(S(=O)(=O)Nc4cc(F)c(C(=O)O)cc4OC)cs3)c(C(F)(F)F)c2)CC1] | 583.11 [M − H]− | |
| 786 | 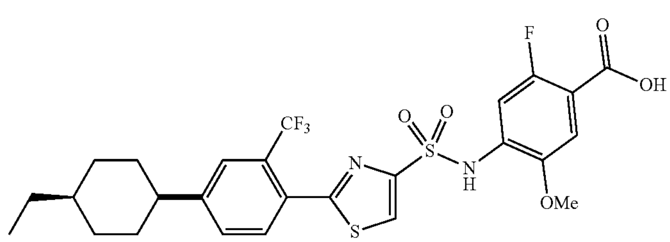 | 587.13 | 1H NMR (400 MHz, Acetone-$d_6$) δ 8.63 (s, 1H), 7.80-7.76 (m, 1H), 7.72 (dd, J = 8.1, 1.8 Hz, 1H), 7.67 (d, J = 8.0 Hz, 1H), 7.53 (d, J = 12.2 Hz, 1H), 7.42 (d, J = 6.5 Hz, 1H), 3.88 (s, 3H), 2.86-2.76 (m, 2H), 1.85-1.57 (m, 9H), 1.55-1.43 (m, 2H), 0.91 (t, J = 7.4 Hz, 3H). |
| 787 | 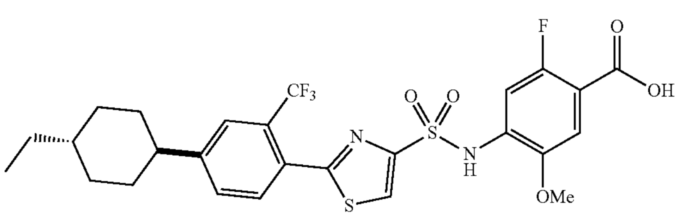 | 585.11 [M − H]− | 1H NMR (400 MHz, Acetone-$d_6$) δ 8.63 (s, 1H), 7.76 (s, 1H), 7.71-7.64 (m, 2H), 7.53 (d, J = 12.3 Hz, 1H), 7.42 (d, J = 6.4 Hz, 1H), 3.88 (s, 3H), 2.77-2.66 (m, 1H), 1.98-1.05 (m, 11H), 0.92 (t, J = 7.1 Hz, 3H). |

| Example # | Structure | LC-MS [M + H]+ unless otherwise noted | 1H-NMR |
|---|---|---|---|
| 788 | 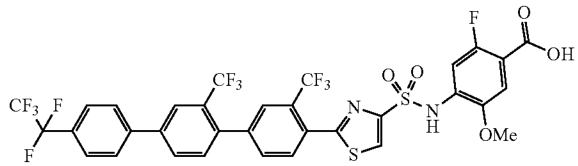 [SMILES: COc1cc(C(=O)O)c(F)cc1NS(=O)(=O)c1csc(-c2ccc(-c3ccc(-c4ccc(C(F)(F)C(F)(F)F)cc4)cc3C(F)(F)F)cc2C(F)(F)F)n1] | 815.05 | |
| 789 | 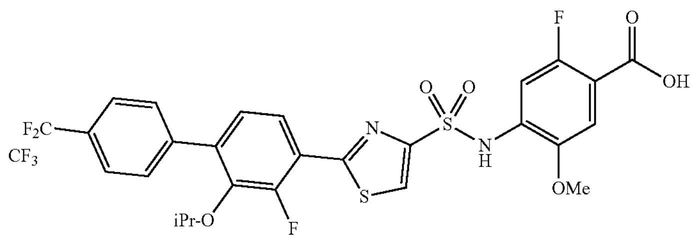 | 677.14 [M − H]− | 1H NMR (500 MHz, Acetone-d6) δ 8.63 (s, 1H), 7.99 (dd, J = 8.4, 6.8 Hz, 1H), 7.94-7.89 (m, 2H), 7.83 (d, J = 8.2 Hz, 2H), 7.61 (d, J = 12.2 Hz, 1H), 7.48 (dd, J = 8.4, 1.5 Hz, 1H), 7.42 (d, J = 6.4 Hz, 1H), 4.20-4.12 (m, 1H), 3.87 (s, 3H), 1.08 (d, J = 6.2 Hz, 6H). |
| 790 | 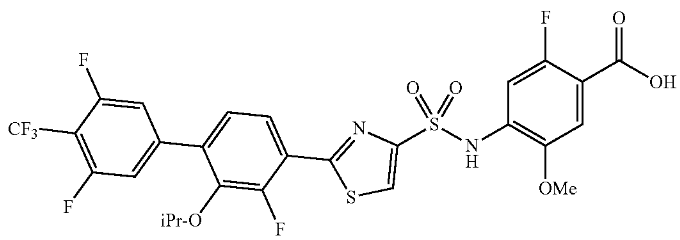 | 665.07 | 1H NMR (500 MHz, Acetone-d6) δ 8.65 (s, 1H), 8.00 (dd, J = 8.4, 6.7 Hz, 1H), 7.64-7.52 (m, 5H), 7.42 (d, J = 6.4 Hz, 1H), 4.35-4.26 (m, 1H), 3.87 (s, 3H), 1.15 (d, J = 6.1 Hz, 6H). |
| 791 | 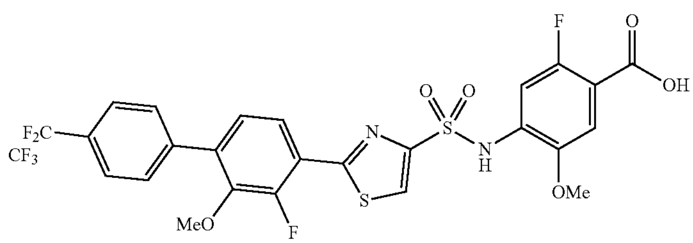 | 649.11 | 1H NMR (400 MHz, Acetone-d6) δ 8.58 (s, 1H), 7.98 (dd, J = 8.4, 6.8 Hz, 1H), 7.88 (d, J = 8.2 Hz, 2H), 7.82 (d, J = 8.3 Hz, 2H), 7.53 (d, J = 12.1 Hz, 1H), 7.45 (dd, J = 8.3, 1.5 Hz, 1H), 7.38 (d, J = 6.5 Hz, 1H), 3.84 (d, J = 1.5 Hz, 3H), 3.83 (s, 4H). |
| 792 | 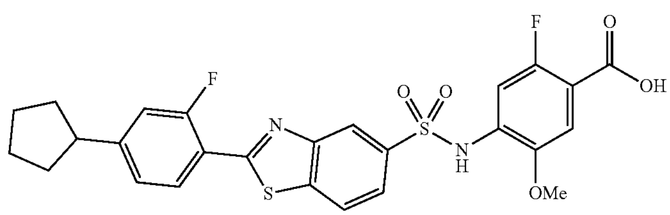 [SMILES: COc1cc(C(=O)O)c(F)cc1NS(=O)(=O)c1ccc2sc(-c3ccc(C4CCCC4)cc3F)nc2c1] | 543.11 | 1H NMR (400 MHz, Acetone-d6) δ 8.54 (d, J = 1.8 Hz, 1H), 8.30 (d, J = 8.5 Hz, 1H), 7.98 (dd, J = 8.5, 1.8 Hz, 1H), 7.87 (dd, J = 8.0, 1.8 Hz, 1H), 7.81 (dd, J = 11.1, 1.8 Hz, 1H), 7.54 (t, J = 7.8 Hz, 1H), 7.42 (d, J = 11.8 Hz, 1H), 7.33 (d, J = 6.4 Hz, 1H), 3.74 (s, 3H), 3.39-3.28 (m, 1H), 2.13-2.07 (m, 2H), 1.95-1.61 (m, 6H). |
| 793 | 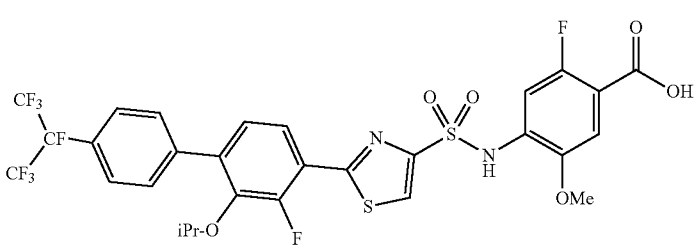 | 727.10 [M − H]− | 1H NMR (400 MHz, Acetone-d6) δ 8.59 (s, 1H), 8.02-7.88 (m, 3H), 7.83 (d, J = 8.3 Hz, 2H), 7.55 (d, J = 12.0 Hz, 1H), 7.47 (dd, J = 8.4, 1.4 Hz, 1H), 7.40 (d, J = 6.5 Hz, 1H), 4.19-4.09 (m, 1H), 3.84 (s, 3H), 1.07 (dd, J = 6.1, 0.8 Hz, 6H). |

-continued

| Example # | Structure | LC-MS [M + H]+ unless otherwise noted | 1H-NMR |
|---|---|---|---|
| 794 | 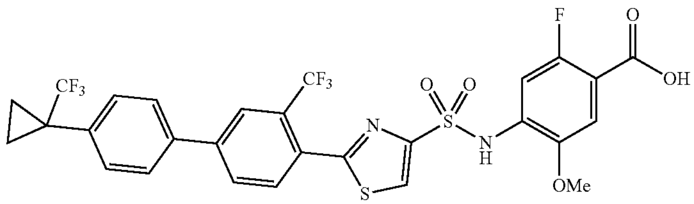 [SMILES: COc1cc(C(=O)O)c(F)cc1NS(=O)(=O)c1csc(-c2ccc(-c3ccc(C4(C(F)(F)F)CC4)cc3)cc2C(F)(F)F)n1] | 661.19 | 1H NMR (400 MHz, Acetone-d6) δ 8.65 (s, 1H), 8.16 (d, J = 1.8 Hz, 1H), 8.10 (dd, J = 8.1, 1.9 Hz, 1H), 7.90-7.79 (m, 3H), 7.67 (d, J = 8.2 Hz, 2H), 7.50 (d, J = 12.0 Hz, 1H), 7.42 (d, J = 6.5 Hz, 1H), 3.86 (s, 3H), 1.44-1.38 (m, 2H), 1.21-1.15 (m, 2H). |
| 795 | 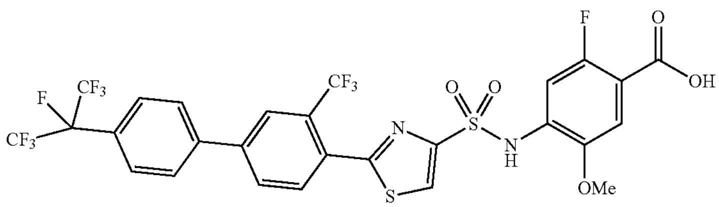 [SMILES: COc1cc(C(=O)O)c(F)cc1NS(=O)(=O)c1csc(-c2ccc(-c3ccc(C(F)(C(F)(F)F)C(F)(F)F)cc3)cc2C(F)(F)F)n1] | 721.08 | 1H NMR (400 MHz, Acetone-d6) δ 11.39 (s, 1H), 8.96 (s, 1H), 8.70 (d, J = 0.9 Hz, 1H), 8.25 (d, J = 1.9 Hz, 1H), 8.19 (dd, J = 8.1, 1.9 Hz, 1H), 8.11 (d, J = 8.5 Hz, 2H), 7.93 (d, J = 8.0 Hz, 1H), 7.88 (d, J = 8.3 Hz, 2H), 7.56 (d, J = 12.1 Hz, 1H), 7.44 (d, J = 6.4 Hz, 1H), 3.89 (s, 3H). |
| 796 | 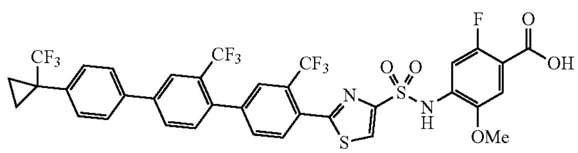 [SMILES: COc1cc(C(=O)O)c(F)cc1NS(=O)(=O)c1csc(-c2ccc(-c3ccc(-c4ccc(C5(C(F)(F)F)CC5)cc4)cc3C(F)(F)F)cc2C(F)(F)F)n1] | 805.58 | 1H NMR (400 MHz, Acetone-d6) δ 8.70 (s, 1H), 8.16 (s, 1H), 8.11 (d, J = 8.1 Hz, 1H), 8.01-7.63 (m, 7H), 7.53 (d, J = 12.2 Hz, 2H), 7.45 (d, J = 6.4 Hz, 1H), 3.90 (s, 3H), 1.48-1.37 (m, 2H), 1.24-1.18 (m, 2H). |
| 797 | 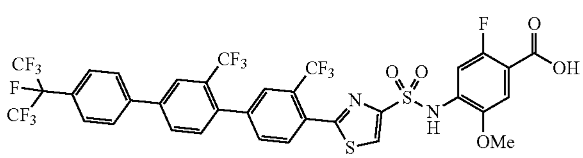 [SMILES: COc1cc(C(=O)O)c(F)cc1NS(=O)(=O)c1csc(-c2ccc(-c3ccc(-c4ccc(C(F)(C(F)(F)F)C(F)(F)F)cc4)cc3C(F)(F)F)cc2C(F)(F)F)n1] | 863.03 [M − H]− | 1H NMR (400 MHz, Acetone-d6) δ 8.70 (s, 1H), 8.25 (s, 1H), 8.19 (d, J = 7.9 Hz, 1H), 8.13 (d, J = 8.3 Hz, 2H), 7.99-7.83 (m, 5H), 7.74 (d, J = 8.0 Hz, 1H), 7.54 (d, J = 12.1 Hz, 1H), 7.45 (d, J = 6.4 Hz, 1H), 3.90 (s, 3H). |
| 798 | 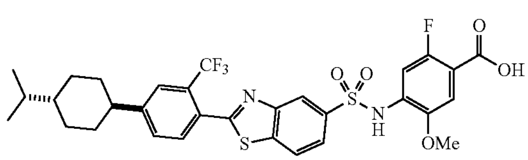 | 649.17 [M − H]− | |
| 799 | 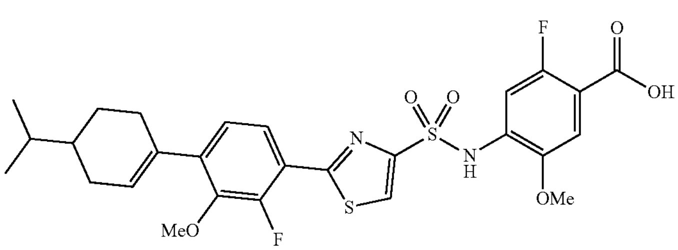 | 577.18 [M − H]− | |

-continued

| Example # | Structure | LC-MS [M + H]+ unless otherwise noted | 1H-NMR |
|---|---|---|---|
| 800 | 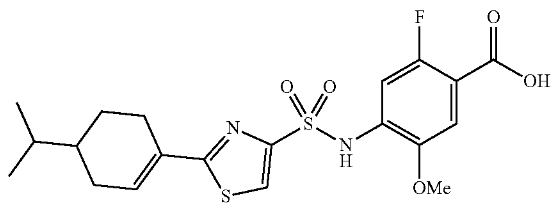 [SMILES: COc1cc(C(=O)O)c(F)cc1NS(=O)(=O)c1csc(C2=CCC(C(C)C)CC2)n1] | 453.22 [M − H]− | |
| 801 | 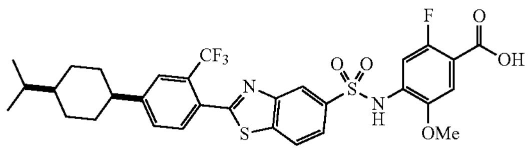 | 648.15 [M − H]− | |
| 802 | 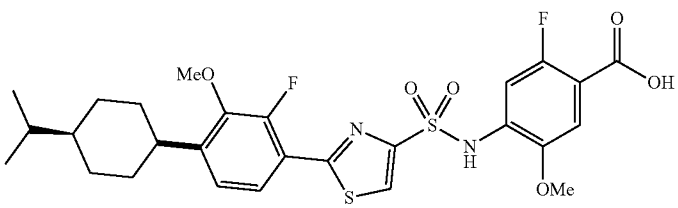 | 579.18 [M − H]− | |
| 803 | 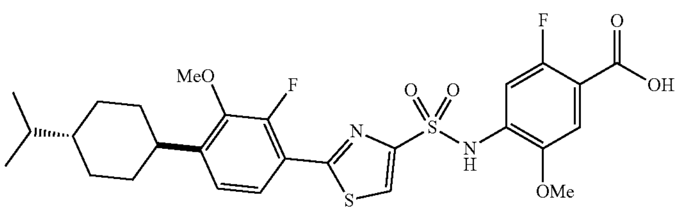 | 579.17 [M − H]− | |
| 804 | 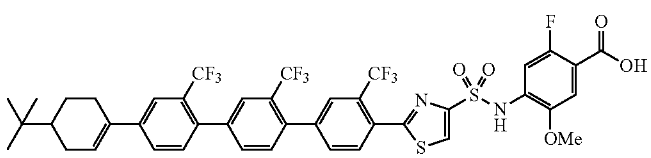 [SMILES: COc1cc(C(=O)O)c(F)cc1NS(=O)(=O)c1csc(-c2ccc(-c3ccc(-c4ccc(C5=CCC(C(C)(C)C)CC5)cc4C(F)(F)F)cc3C(F)(F)F)cc2C(F)(F)F)n1] | 901.18 | |
| 805 | 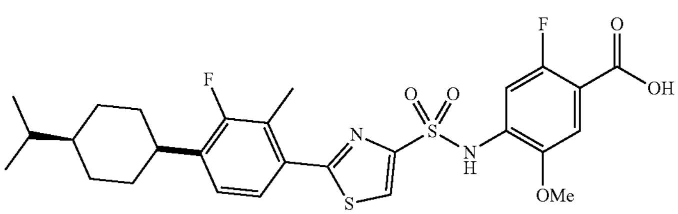 | 563.19 [M − H]− | |
| 806 | 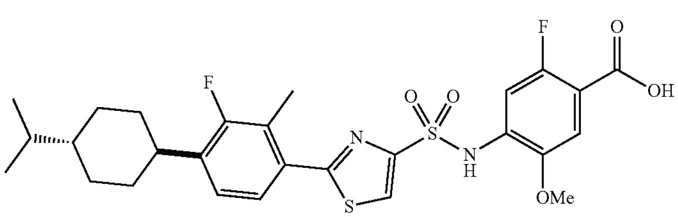 | 563.17 [M − H]− | |

| Example # | Structure | LC-MS [M + H]+ unless otherwise noted | 1H-NMR |
|---|---|---|---|
| 807 | 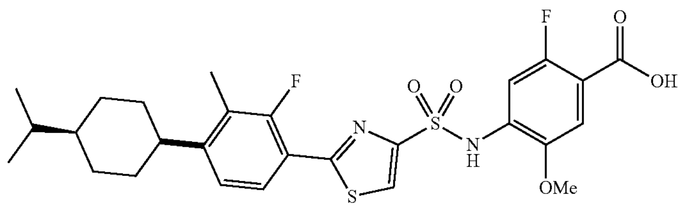 | 563.18 [M − H]− | |
| 808 | 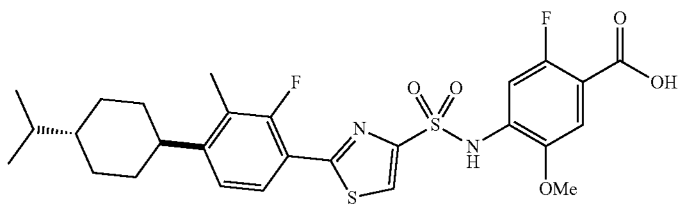 | 563.18 [M − H]− | |
| 809 | 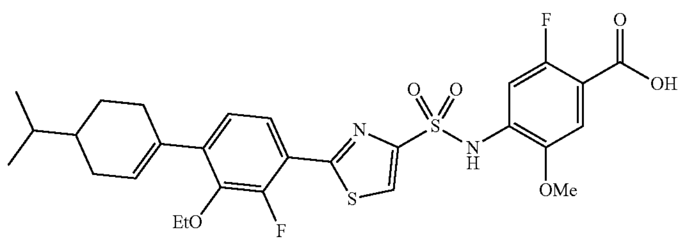 [SMILES: CCOc1c(C2=CCC(C(C)C)CC2)ccc(-c2nc(S(=O)(=O)Nc3cc(F)c(C(=O)O)cc3OC)cs2)c1F] | 591.15 [M − H]− | |
| 810 | 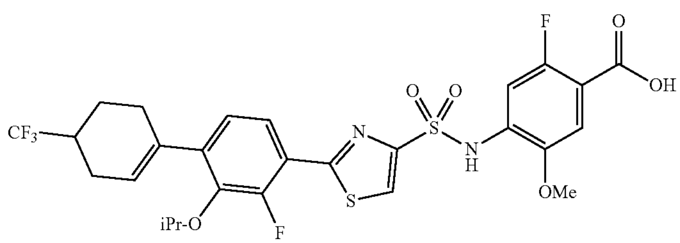 | 631.14 [M − H]− | 1H NMR (400 MHz, Acetone-d6) δ 8.58 (s, 1H), 7.89-7.74 (m, 1H), 7.60 (d, J = 12.2 Hz, 1H), 7.41 (d, J = 6.4 Hz, 1H), 7.15 (dd, J = 8.3, 1.4 Hz, 1H), 6.09-5.94 (m, 1H), 4.50-4.30 (m, 1H), 3.86 (d, J = 0.8 Hz, 3H), 2.63-2.11 (m, 6H), 1.75-1.61 (m, 1H), 1.30-1.23 (m, 6H). |
| 811 | 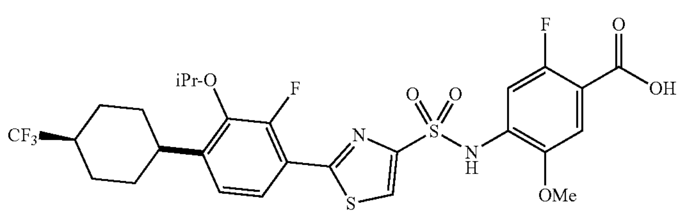 | 633.17 [M − H]− | 1H NMR (400 MHz, Acetone-d6) δ 8.56 (s, 1H), 7.83 (dd, J = 8.4, 6.9 Hz, 1H), 7.58 (d, J = 12.1 Hz, 1H), 7.40 (d, J = 6.4 Hz, 1H), 7.24 (d, J = 1.3 Hz, 1H), 4.58-4.47 (m, 1H), 3.86 (s, 3H), 3.27-3.15 (m, 1H), 2.60-2.47 (m, 1H), 2.11-1.69 (m, 8H), 1.35 (d, J = 6.0 Hz, 6H). |
| 812 | 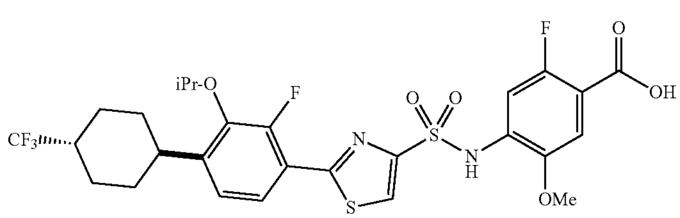 | 633.13 [M − H]− | 1H NMR (400 MHz, Acetone-d6) δ 8.55 (s, 1H), 7.82 (t, J = 7.6 Hz, 1H), 7.60 (d, J = 12.0 Hz, 1H), 7.40 (d, J = 6.2 Hz, 1H), 7.26 (d, J = 8.5 Hz, 1H), 4.57-4.45 (m, 1H), 3.84 (s, 3H), 3.20-3.08 (m, 1H), 2.41-2.29 (m, 1H), 2.11-1.44 (m, 8H), 1.35 (d, J = 6.1 Hz, 6H). |

| Example # | Structure | LC-MS [M + H]+ unless otherwise noted | 1H-NMR |
|---|---|---|---|
| 813 | 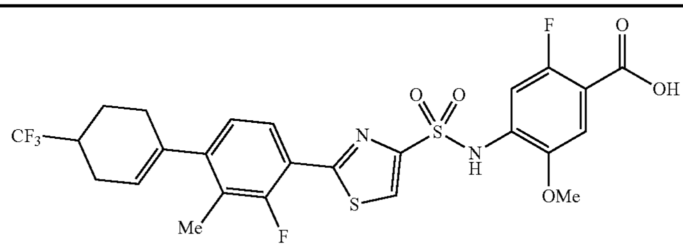 | 587.08 [M − H]− | |
| 814 | 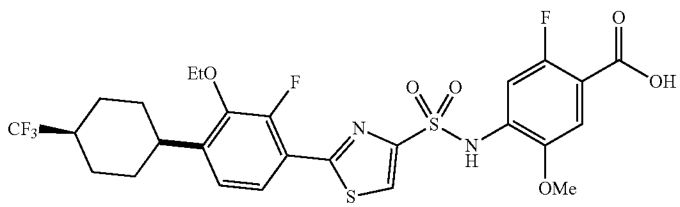 | 619.11 [M − H]− | 1H NMR (400 MHz, Acetone-d6) δ 8.55 (s, 1H), 7.88-7.80 (m, 1H), 7.56 (d, J = 12.1 Hz, 1H), 7.40 (d, J = 6.4 Hz, 1H), 7.24 (dd, J = 8.5, 1.4 Hz, 1H), 4.17 (q, J = 7.1 Hz, 2H), 3.85 (s, 3H), 3.23-3.12 (m, 1H), 2.59-2.47 (m, 1H), 2.10-1.69 (m, 8H), 1.42 (t, J = 7.0 Hz, 3H). |
| 815 | 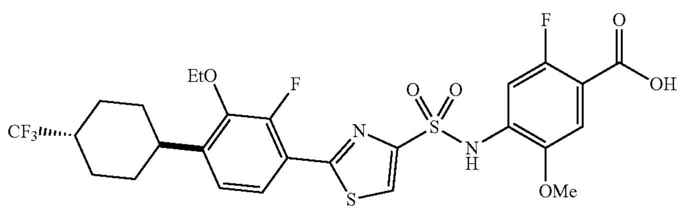 | 619.11 [M − H]− | 1H NMR (400 MHz, Acetone-d6) δ 8.52 (s, 1H), 7.89-7.76 (m, 1H), 7.57 (d, J = 12.2 Hz, 1H), 7.38 (d, J = 6.5 Hz, 1H), 7.24 (d, J = 8.4 Hz, 1H), 4.22-4.12 (m, 2H), 3.83 (s, 3H), 3.15-3.05 (m, 1H), 2.42-2.25 (m, 1H), 2.11-1.47 (m, 8H), 1.42 (t, J = 7.0 Hz, 3H). |
| 816 | 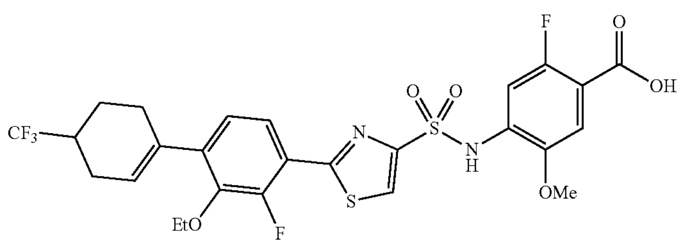 | 617.09 [M − H]− | 1H NMR (400 MHz, Acetone-d6) δ 8.58 (s, 1H), 7.82 (dd, J = 8.3, 6.9 Hz, 1H), 7.60 (d, J = 12.2 Hz, 1H), 7.41 (d, J = 6.5 Hz, 1H), 7.17 (dd, J = 8.3, 1.5 Hz, 1H), 6.05-5.94 (m, 1H), 4.17-4.01 (m, 2H), 3.86 (s, 3H), 3.13-1.95 (m, 6H), 1.77-1.62 (m, 1H), 1.35 (t, J = 7.0 Hz, 3H). |

50

The following examples are prepared using procedures similar to those described above:

| Example # | Structure |
|---|---|
| 407 | 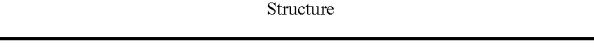 |

|Example #|Structure|
|---|---|
|408|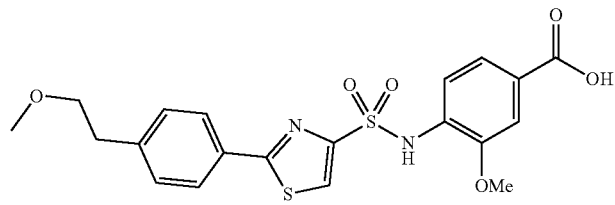 [SMILES: CO/C=C/c1ccc(-c2nc(S(=O)(=O)Nc3ccc(C(=O)O)cc3OC)cs2)cc1]|
|409|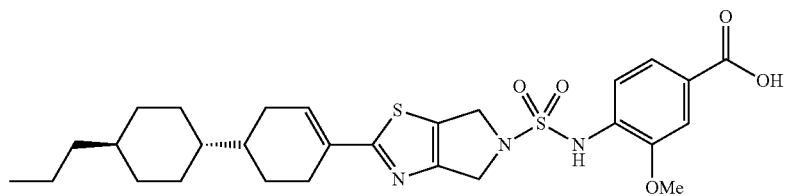 [SMILES: CCC[C@H]1CC[C@H](C2CC=C(c3nc4c(s3)CN(S(=O)(=O)Nc3ccc(C(=O)O)cc3OC)C4)CC2)CC1]|
|410|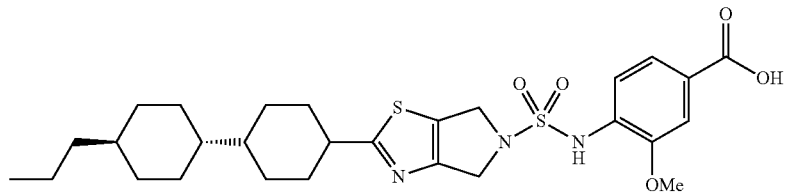 [SMILES: CCC[C@H]1CC[C@H](C2CCC(c3nc4c(s3)CN(S(=O)(=O)Nc3ccc(C(=O)O)cc3OC)C4)CC2)CC1]|
|421|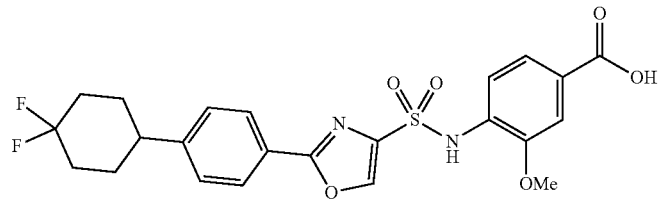 [SMILES: COc1cc(C(=O)O)ccc1NS(=O)(=O)c1coc(-c2ccc(C3CCC(F)(F)CC3)cc2)n1]|
|422|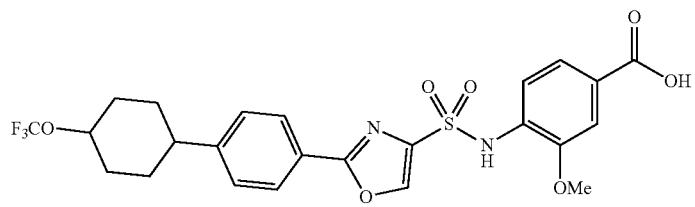|
|423|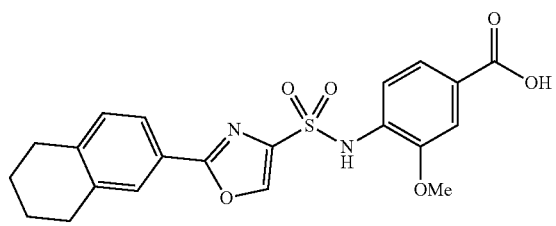 [SMILES: COc1cc(C(=O)O)ccc1NS(=O)(=O)c1coc(-c2ccc3c(c2)CCCC3)n1]|
|424|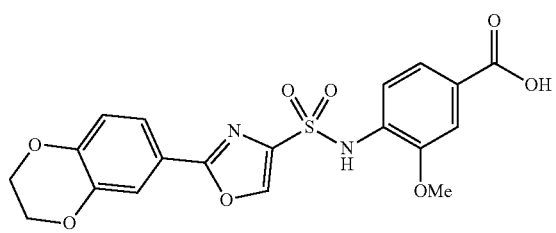|

-continued

| Example # | Structure |
|---|---|
| 425 | 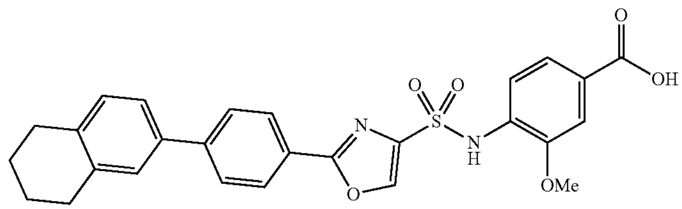 [SMILES: COc1cc(C(=O)O)ccc1NS(=O)(=O)c1coc(-c2ccc(-c3ccc4c(c3)CCCC4)cc2)n1] |
| 431 | 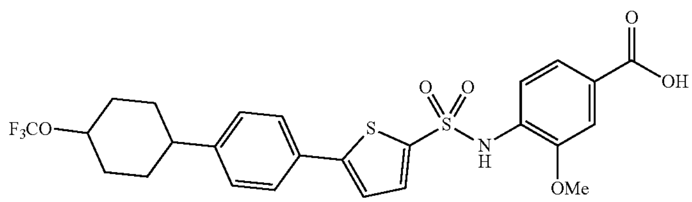 [SMILES: COc1cc(C(=O)O)ccc1NS(=O)(=O)c1ccc(-c2ccc(C3CCC(OC(F)(F)F)CC3)cc2)s1] |
| 432 | 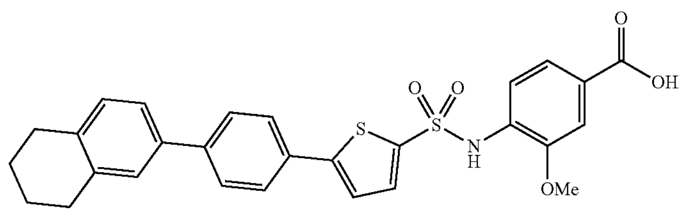 [SMILES: COc1cc(C(=O)O)ccc1NS(=O)(=O)c1ccc(-c2ccc(-c3ccc4c(c3)CCCC4)cc2)s1] |
| 439 | 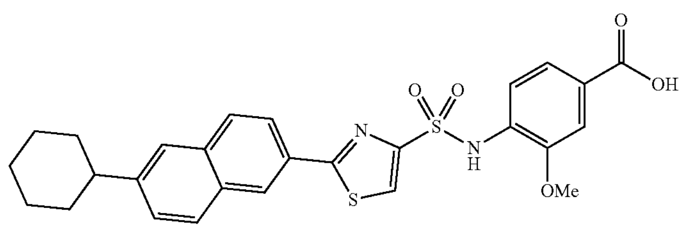 [SMILES: COc1cc(C(=O)O)ccc1NS(=O)(=O)c1csc(-c2ccc3cc(C4CCCCC4)ccc3c2)n1] |
| 440 | 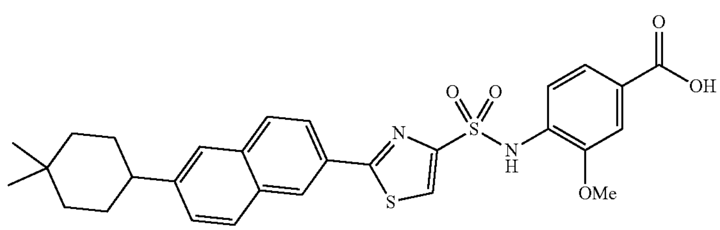 [SMILES: COc1cc(C(=O)O)ccc1NS(=O)(=O)c1csc(-c2ccc3cc(C4CCC(C)(C)CC4)ccc3c2)n1] |
| 441 | 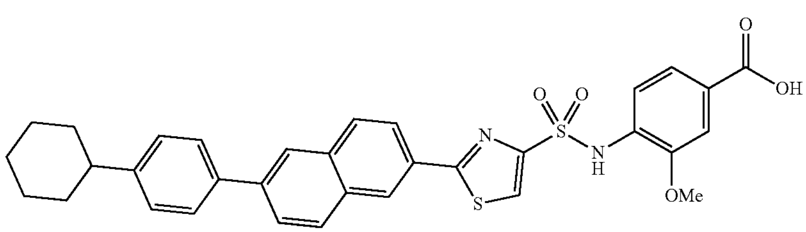 [SMILES: COc1cc(C(=O)O)ccc1NS(=O)(=O)c1csc(-c2ccc3cc(-c4ccc(C5CCCCC5)cc4)ccc3c2)n1] |
| 442 | 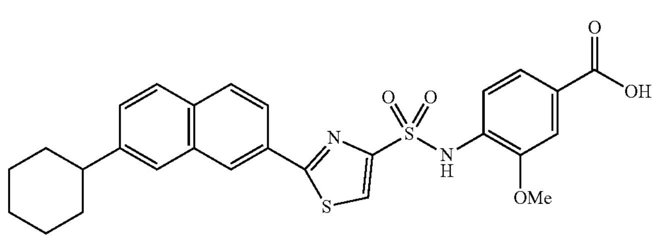 [SMILES: COc1cc(C(=O)O)ccc1NS(=O)(=O)c1csc(-c2ccc3ccc(C4CCCCC4)cc3c2)n1] |

| Example # | Structure |
|---|---|
| 443 | 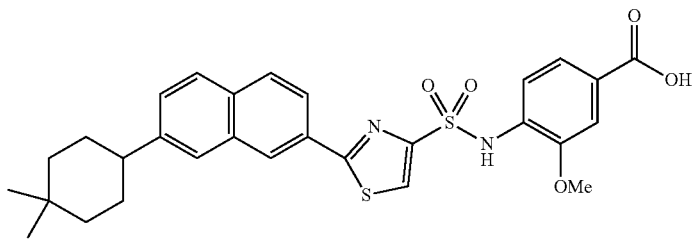 [SMILES: COc1cc(C(=O)O)ccc1NS(=O)(=O)c1csc(-c2ccc3ccc(C4CCC(C)(C)CC4)cc3c2)n1] |
| 444 | 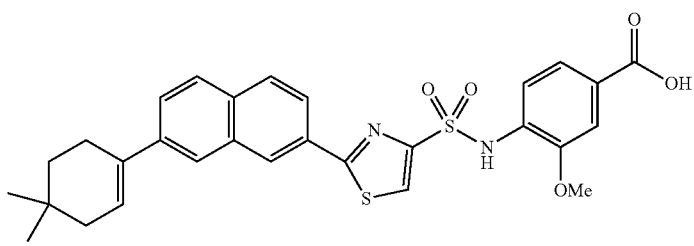 [SMILES: COc1cc(C(=O)O)ccc1NS(=O)(=O)c1csc(-c2ccc3ccc(C4=CCC(C)(C)CC4)cc3c2)n1] |
| 445 | 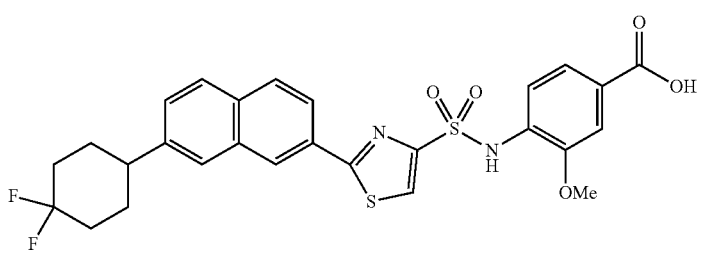 [SMILES: COc1cc(C(=O)O)ccc1NS(=O)(=O)c1csc(-c2ccc3ccc(C4CCC(F)(F)CC4)cc3c2)n1] |
| 446 | 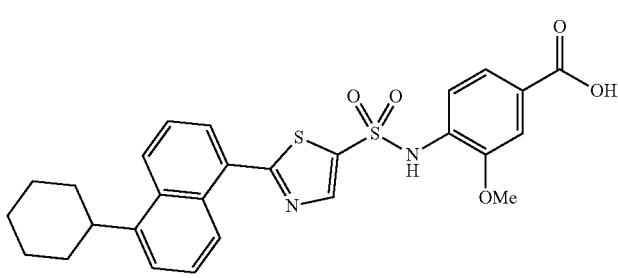 [SMILES: COc1cc(C(=O)O)ccc1NS(=O)(=O)c1cnc(-c2cccc3c(C4CCCCC4)cccc23)s1] |
| 447 | 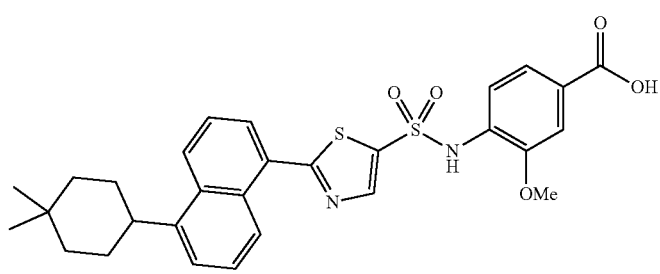 [SMILES: COc1cc(C(=O)O)ccc1NS(=O)(=O)c1cnc(-c2cccc3c(C4CCC(C)(C)CC4)cccc23)s1] |
| 448 | 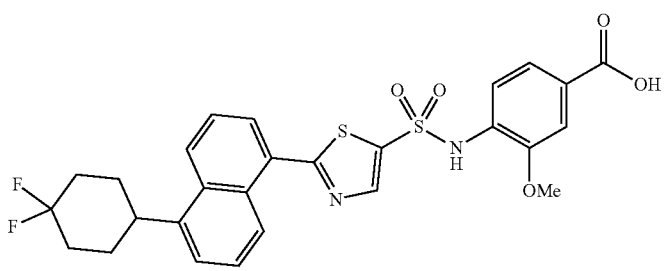 [SMILES: COc1cc(C(=O)O)ccc1NS(=O)(=O)c1cnc(-c2cccc3c(C4CCC(F)(F)CC4)cccc23)s1] |

| Example # | Structure |
|---|---|
| 817 | 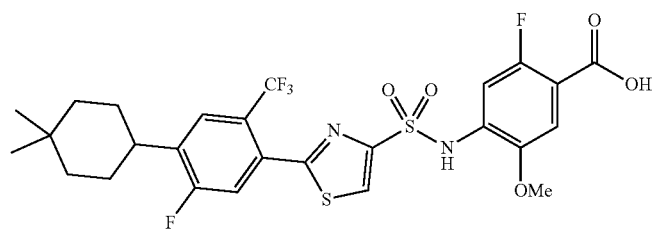 [SMILES: COc1cc(C(=O)O)c(F)cc1NS(=O)(=O)c1csc(-c2cc(F)c(C3CCC(C)(C)CC3)cc2C(F)(F)F)n1] |
| 818 | 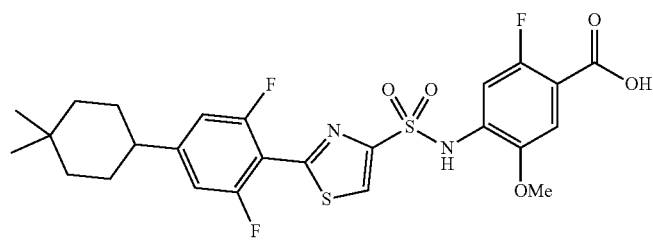 [SMILES: COc1cc(C(=O)O)c(F)cc1NS(=O)(=O)c1csc(-c2c(F)cc(C3CCC(C)(C)CC3)cc2F)n1] |
| 819 | 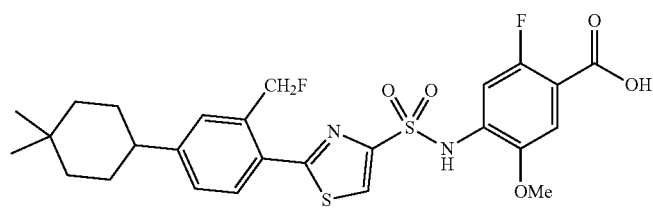 |
| 820 | 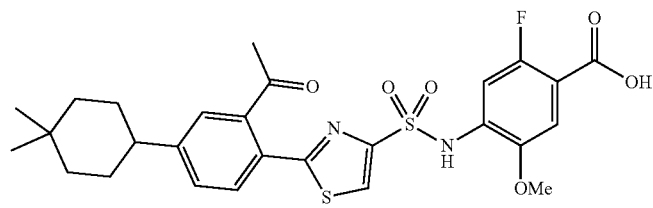 |
| 821 | 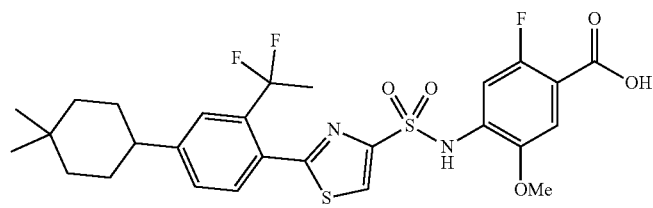 [SMILES: COc1cc(C(=O)O)c(F)cc1NS(=O)(=O)c1csc(-c2ccc(C3CCC(C)(C)CC3)cc2C(C)(F)F)n1] |
| 822 | 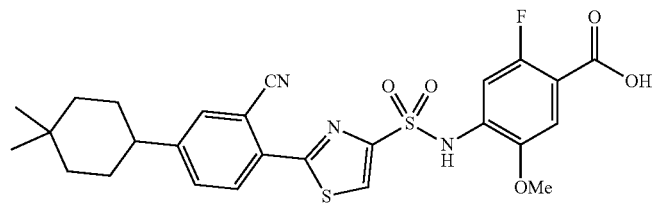 |
| 823 | 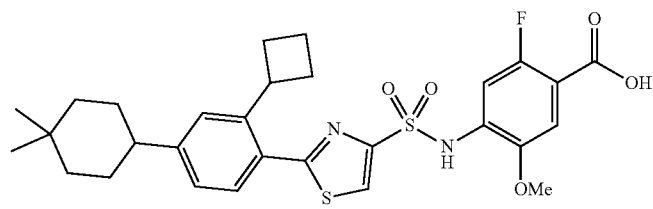 [SMILES: COc1cc(C(=O)O)c(F)cc1NS(=O)(=O)c1csc(-c2ccc(C3CCC(C)(C)CC3)cc2C2CCC2)n1] |

| Example # | Structure |
|---|---|
| 824 | 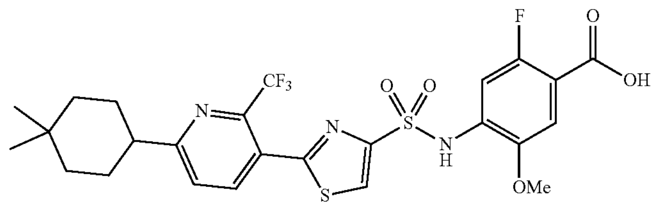 [SMILES: COc1cc(C(=O)O)c(F)cc1NS(=O)(=O)c1csc(-c2ccc(C3CCC(C)(C)CC3)nc2C(F)(F)F)n1] |
| 825 | 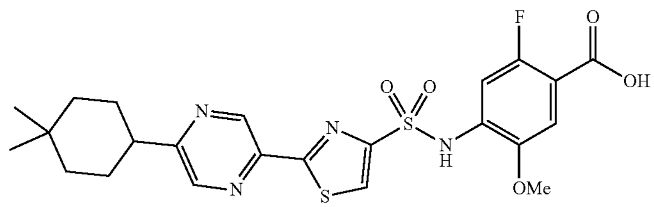 [SMILES: COc1cc(C(=O)O)c(F)cc1NS(=O)(=O)c1csc(-c2cnc(C3CCC(C)(C)CC3)cn2)n1] |
| 826 | 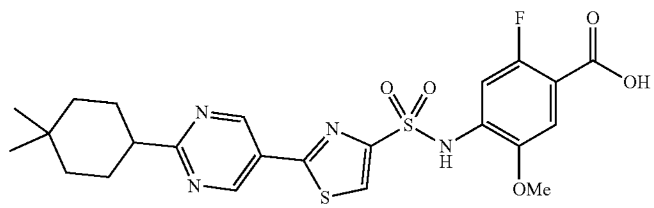 [SMILES: COc1cc(C(=O)O)c(F)cc1NS(=O)(=O)c1csc(-c2cnc(C3CCC(C)(C)CC3)nc2)n1] |
| 827 | 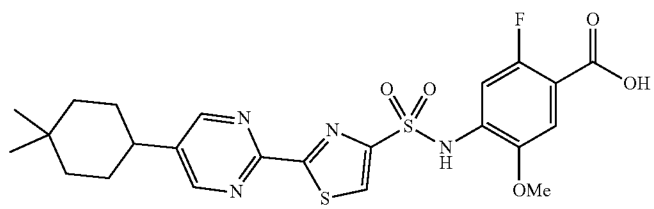 [SMILES: COc1cc(C(=O)O)c(F)cc1NS(=O)(=O)c1csc(-c2ncc(C3CCC(C)(C)CC3)cn2)n1] |
| 828 | 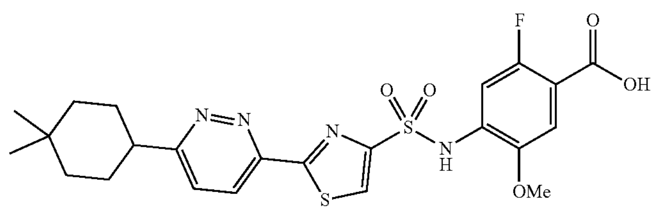 [SMILES: COc1cc(C(=O)O)c(F)cc1NS(=O)(=O)c1csc(-c2ccc(C3CCC(C)(C)CC3)nn2)n1] |
| 829 | 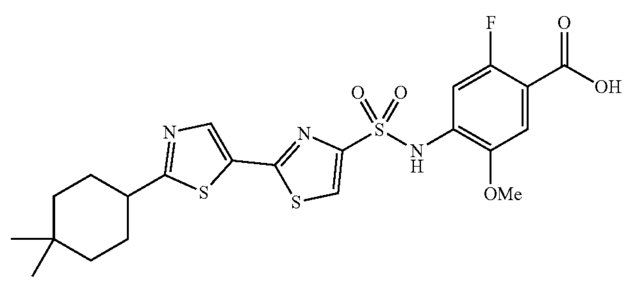 [SMILES: COc1cc(C(=O)O)c(F)cc1NS(=O)(=O)c1csc(-c2cnc(C3CCC(C)(C)CC3)s2)n1] |
| 830 | 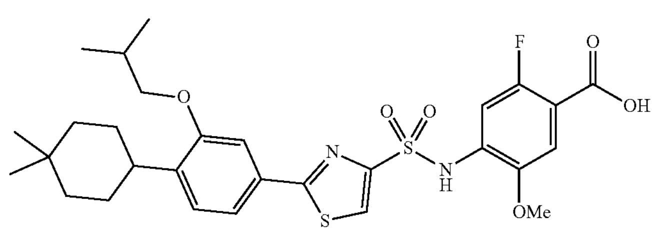 [SMILES: COc1cc(C(=O)O)c(F)cc1NS(=O)(=O)c1csc(-c2ccc(C3CCC(C)(C)CC3)c(OCC(C)C)c2)n1] |

-continued
| Example # | Structure |
|---|---|
| 831 | 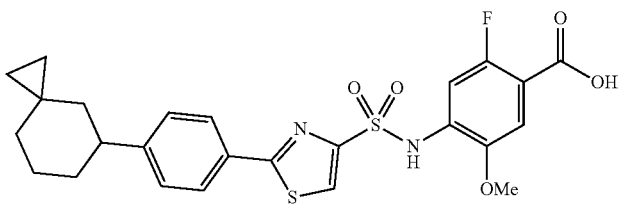 [SMILES: COc1cc(C(=O)O)c(F)cc1NS(=O)(=O)c1csc(-c2ccc(C3CCCC4(CC4)C3)cc2)n1] |
| 832 | 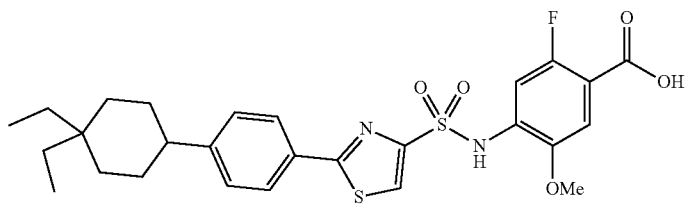 [SMILES: CCC1(CC)CCC(c2ccc(-c3nc(S(=O)(=O)Nc4cc(F)c(C(=O)O)cc4OC)cs3)cc2)CC1] |
| 833 | 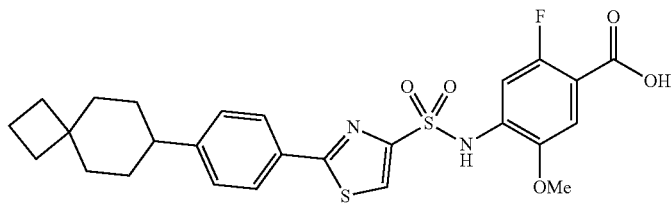 [SMILES: COc1cc(C(=O)O)c(F)cc1NS(=O)(=O)c1csc(-c2ccc(C3CCC4(CCC4)CC3)cc2)n1] |
| 834 | 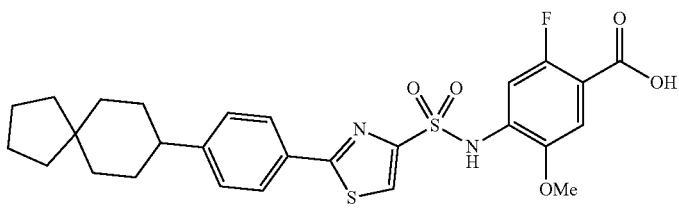 [SMILES: COc1cc(C(=O)O)c(F)cc1NS(=O)(=O)c1csc(-c2ccc(C3CCC4(CCCC4)CC3)cc2)n1] |
| 835 | 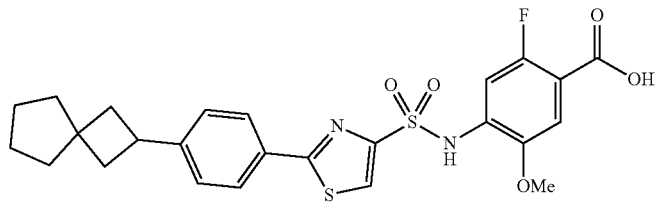 [SMILES: COc1cc(C(=O)O)c(F)cc1NS(=O)(=O)c1csc(-c2ccc(C3CC4(CCCC4)C3)cc2)n1] |
| 836 | 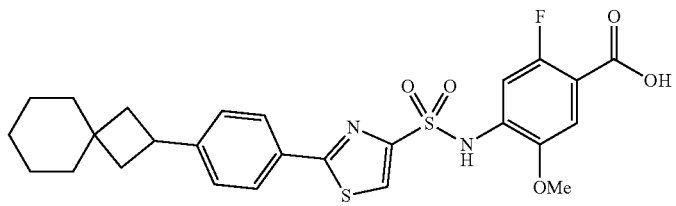 [SMILES: COc1cc(C(=O)O)c(F)cc1NS(=O)(=O)c1csc(-c2ccc(C3CC4(CCCCC4)C3)cc2)n1] |
| 837 | 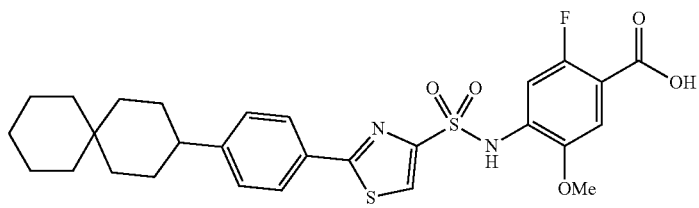 [SMILES: COc1cc(C(=O)O)c(F)cc1NS(=O)(=O)c1csc(-c2ccc(C3CCC4(CCCCC4)CC3)cc2)n1] |

| Example # | Structure |
|---|---|
| 838 | 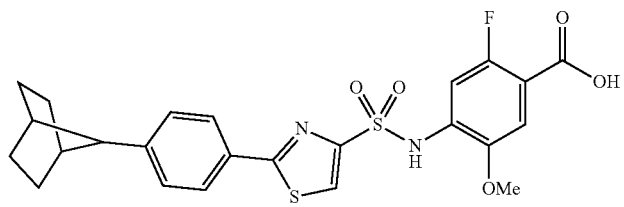 [SMILES: COc1cc(C(=O)O)c(F)cc1NS(=O)(=O)c1csc(-c2ccc(C3C4CCC3CC4)cc2)n1] |
| 839 | 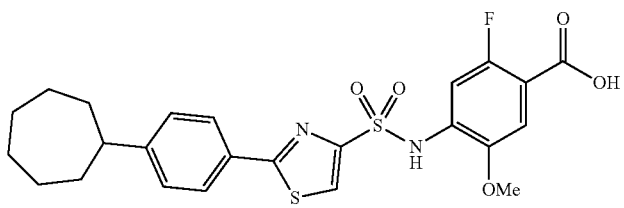 [SMILES: COc1cc(C(=O)O)c(F)cc1NS(=O)(=O)c1csc(-c2ccc(C3CCCCCC3)cc2)n1] |
| 840 | 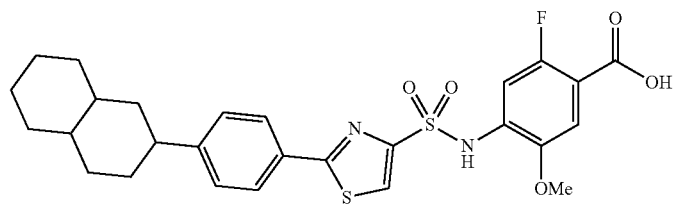 [SMILES: COc1cc(C(=O)O)c(F)cc1NS(=O)(=O)c1csc(-c2ccc(C3CCC4CCCCC4C3)cc2)n1] |
| 841 | 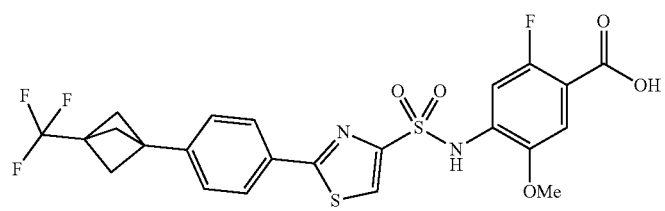 [SMILES: COc1cc(C(=O)O)c(F)cc1NS(=O)(=O)c1csc(-c2ccc(C34CC(C(F)(F)F)(C3)C4)cc2)n1] |
| 842 | 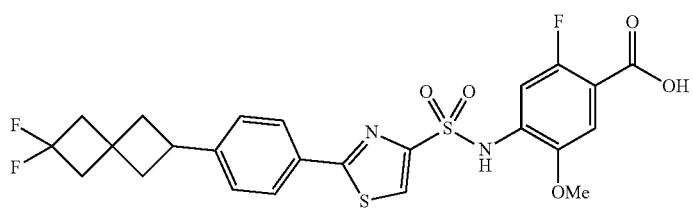 [SMILES: COc1cc(C(=O)O)c(F)cc1NS(=O)(=O)c1csc(-c2ccc(C3CC4(C3)CC(F)(F)C4)cc2)n1] |
| 843 | 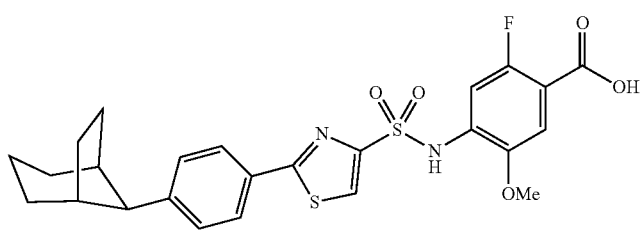 [SMILES: COc1cc(C(=O)O)c(F)cc1NS(=O)(=O)c1csc(-c2ccc(C3C4CCCC3CC4)cc2)n1] |
| 844 | 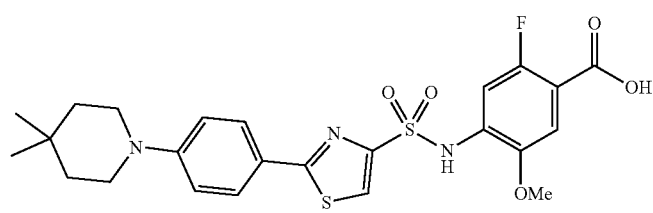 |

| Example # | Structure |
|---|---|
| 845 | 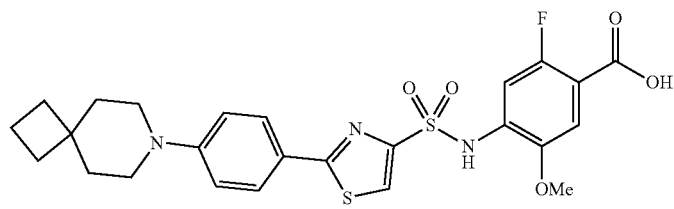 [SMILES: COc1cc(C(=O)O)c(F)cc1NS(=O)(=O)c1csc(-c2ccc(N3CCC4(CCC4)CC3)cc2)n1] |
| 846 | 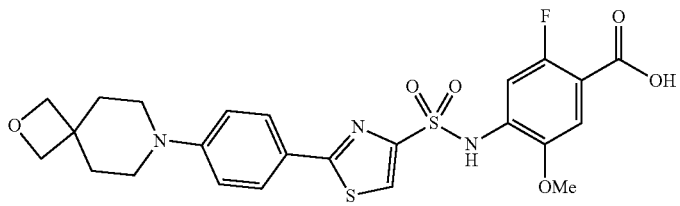 [SMILES: COc1cc(C(=O)O)c(F)cc1NS(=O)(=O)c1csc(-c2ccc(N3CCC4(CC3)COC4)cc2)n1] |
| 847 | 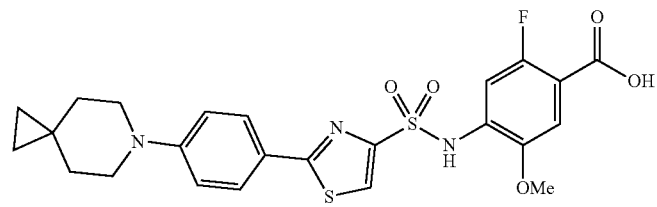 [SMILES: COc1cc(C(=O)O)c(F)cc1NS(=O)(=O)c1csc(-c2ccc(N3CCC4(CC3)CC4)cc2)n1] |
| 848 | 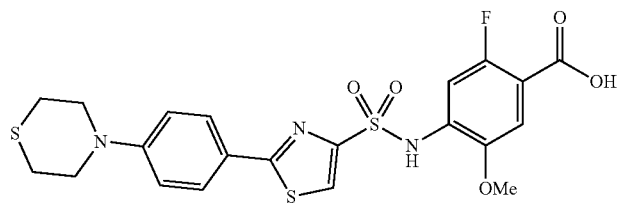 [SMILES: COc1cc(C(=O)O)c(F)cc1NS(=O)(=O)c1csc(-c2ccc(N3CCSCC3)cc2)n1] |
| 849 | 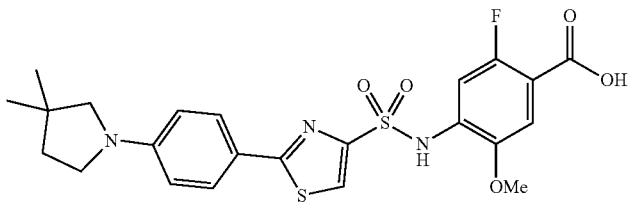 [SMILES: COc1cc(C(=O)O)c(F)cc1NS(=O)(=O)c1csc(-c2ccc(N3CCC(C)(C)C3)cc2)n1] |
| 850 | 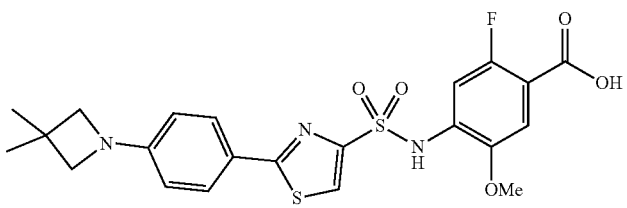 [SMILES: COc1cc(C(=O)O)c(F)cc1NS(=O)(=O)c1csc(-c2ccc(N3CC(C)(C)C3)cc2)n1] |
| 851 | 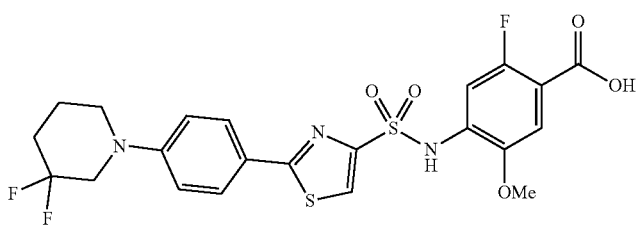 [SMILES: COc1cc(C(=O)O)c(F)cc1NS(=O)(=O)c1csc(-c2ccc(N3CCCC(F)(F)C3)cc2)n1] |

| Example # | Structure |
|---|---|
| 852 | 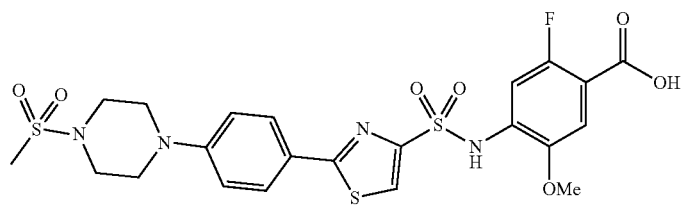 [SMILES: COc1cc(C(=O)O)c(F)cc1NS(=O)(=O)c1csc(-c2ccc(N3CCN(S(C)(=O)=O)CC3)cc2)n1] |
| 853 | 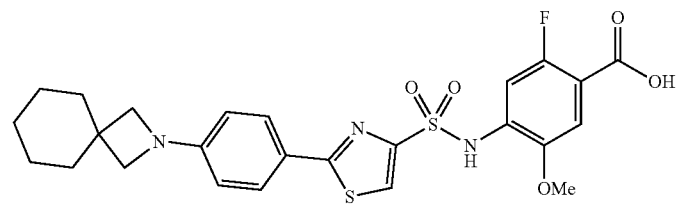 [SMILES: COc1cc(C(=O)O)c(F)cc1NS(=O)(=O)c1csc(-c2ccc(N3CC4(CCCCC4)C3)cc2)n1] |
| 854 | 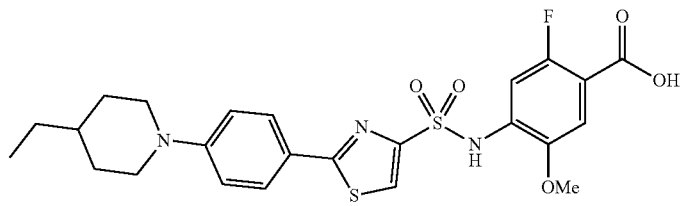 [SMILES: CCC1CCN(c2ccc(-c3nc(S(=O)(=O)Nc4cc(F)c(C(=O)O)cc4OC)cs3)cc2)CC1] |
| 855 | 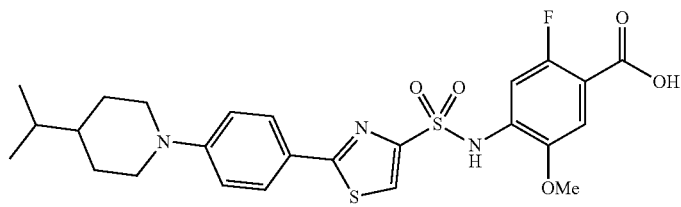 [SMILES: COc1cc(C(=O)O)c(F)cc1NS(=O)(=O)c1csc(-c2ccc(N3CCC(C(C)C)CC3)cc2)n1] |
| 856 | 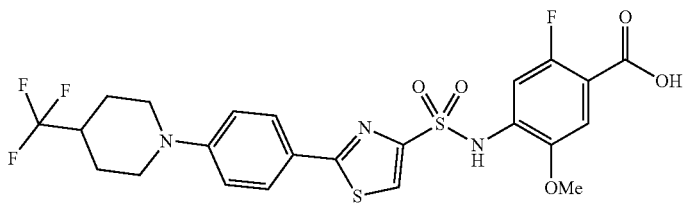 [SMILES: COc1cc(C(=O)O)c(F)cc1NS(=O)(=O)c1csc(-c2ccc(N3CCC(C(F)(F)F)CC3)cc2)n1] |
| 857 | 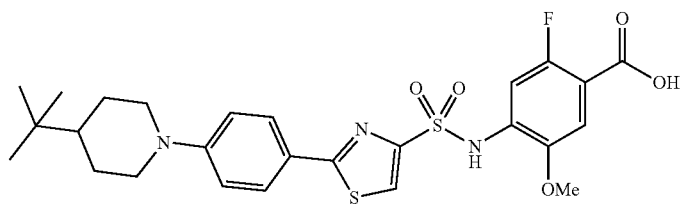 [SMILES: COc1cc(C(=O)O)c(F)cc1NS(=O)(=O)c1csc(-c2ccc(N3CCC(C(C)(C)C)CC3)cc2)n1] |
| 858 | 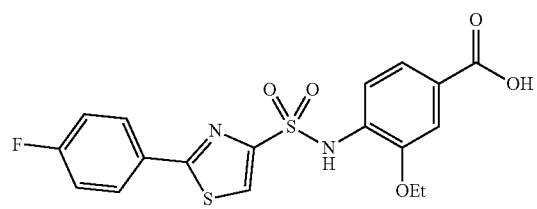 |

| Example # | Structure |
|---|---|
| 859 | 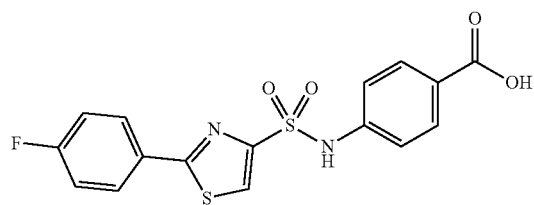 |
| 860 | 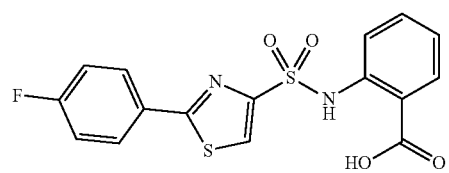 [SMILES: O=C(O)c1ccccc1NS(=O)(=O)c1csc(-c2ccc(F)cc2)n1] |
| 861 | 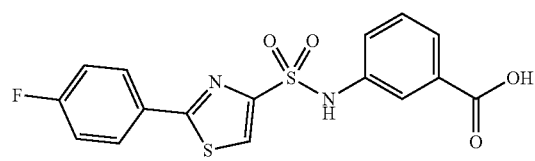 |
| 862 | 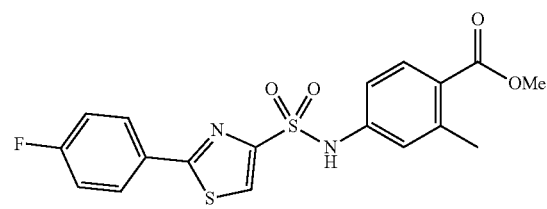 [SMILES: COC(=O)c1ccc(NS(=O)(=O)c2csc(-c3ccc(F)cc3)n2)cc1C] |
| 863 | 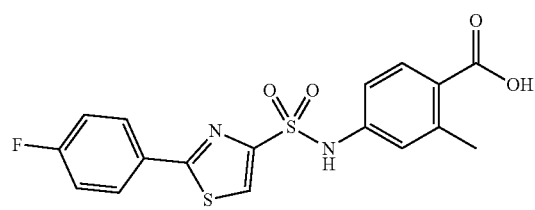 |
| 864 | 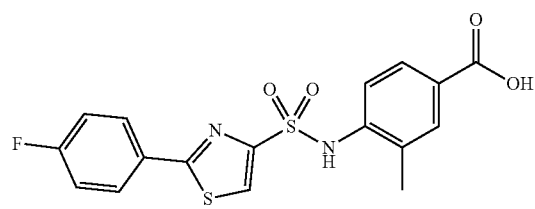 [SMILES: Cc1cc(C(=O)O)ccc1NS(=O)(=O)c1csc(-c2ccc(F)cc2)n1] |
| 865 | 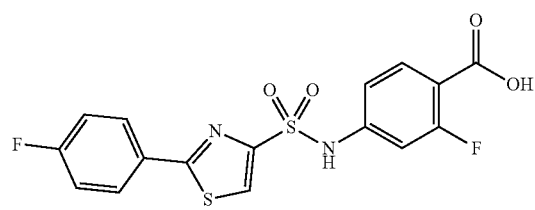 [SMILES: O=C(O)c1ccc(NS(=O)(=O)c2csc(-c3ccc(F)cc3)n2)cc1F] |

| Example # | Structure |
|---|---|
| 866 | 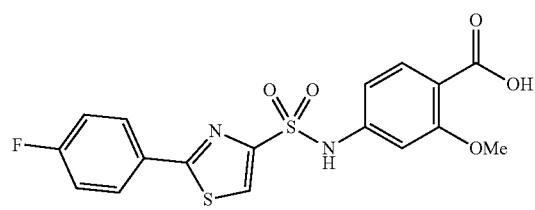 [SMILES: COc1cc(NS(=O)(=O)c2csc(-c3ccc(F)cc3)n2)ccc1C(=O)O] |
| 867 | 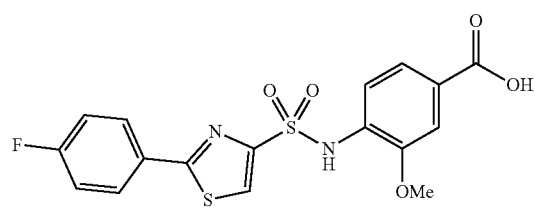 [SMILES: COc1cc(C(=O)O)ccc1NS(=O)(=O)c1csc(-c2ccc(F)cc2)n1] |
| 868 | 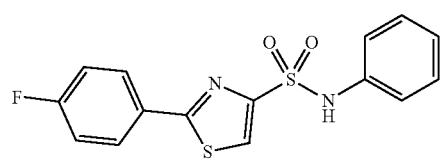 [SMILES: O=S(=O)(Nc1ccccc1)c1csc(-c2ccc(F)cc2)n1] |
| 869 | 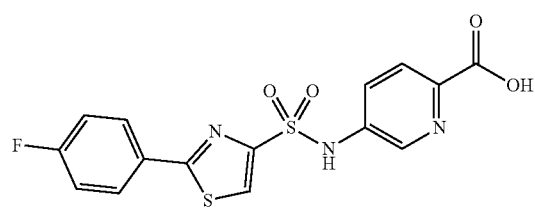 |
| 870 | 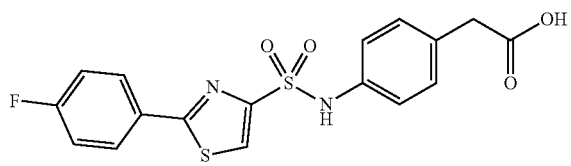 [SMILES: O=C(O)Cc1ccc(NS(=O)(=O)c2csc(-c3ccc(F)cc3)n2)cc1] |
| 871 | 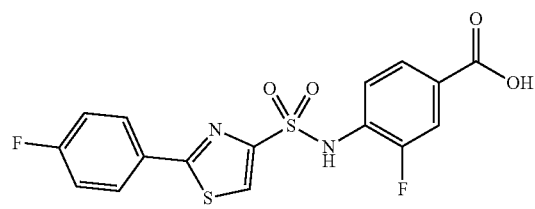 [SMILES: O=C(O)c1ccc(NS(=O)(=O)c2csc(-c3ccc(F)cc3)n2)c(F)c1] |
| 872 | 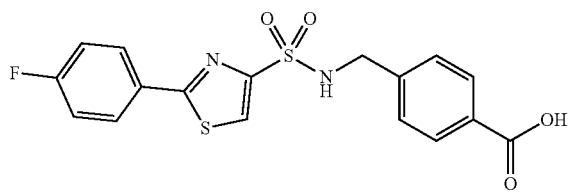 [SMILES: O=C(O)c1ccc(CNS(=O)(=O)c2csc(-c3ccc(F)cc3)n2)cc1] |
| 873 | 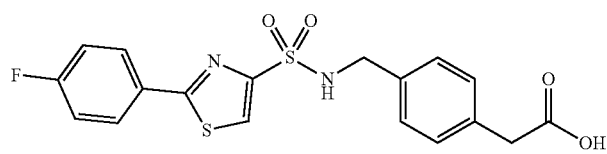 [SMILES: O=C(O)Cc1ccc(CNS(=O)(=O)c2csc(-c3ccc(F)cc3)n2)cc1] |

| Example # | Structure |
|---|---|
| 874 | 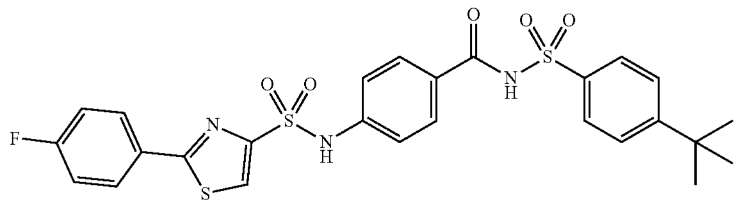 [SMILES: CC(C)(C)c1ccc(S(=O)(=O)NC(=O)c2ccc(NS(=O)(=O)c3csc(-c4ccc(F)cc4)n3)cc2)cc1] |
| 875 | 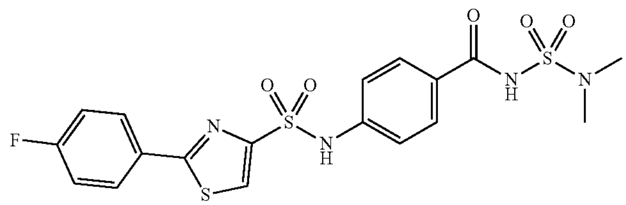 [SMILES: CN(C)S(=O)(=O)NC(=O)c1ccc(NS(=O)(=O)c2csc(-c3ccc(F)cc3)n2)cc1] |
| 876 | 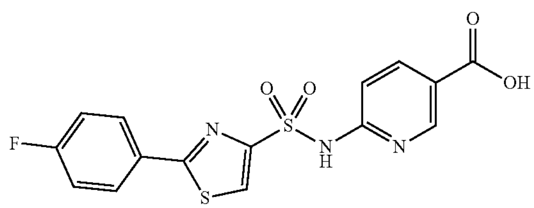 [SMILES: O=C(O)c1ccc(NS(=O)(=O)c2csc(-c3ccc(F)cc3)n2)nc1] |
| 877 | 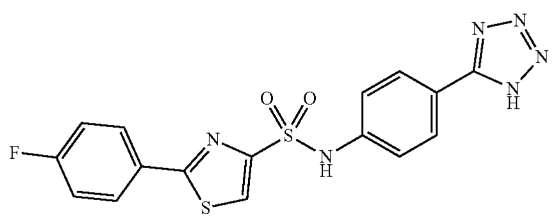 [SMILES: O=S(=O)(Nc1ccc(-c2nnn[nH]2)cc1)c1csc(-c2ccc(F)cc2)n1] |
| 878 | 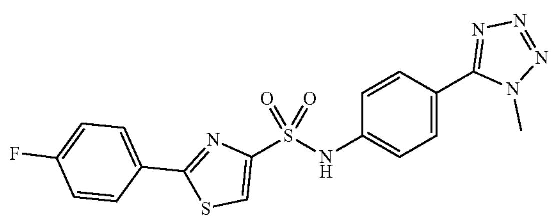 [SMILES: Cn1nnnc1-c1ccc(NS(=O)(=O)c2csc(-c3ccc(F)cc3)n2)cc1] |
| 879 | 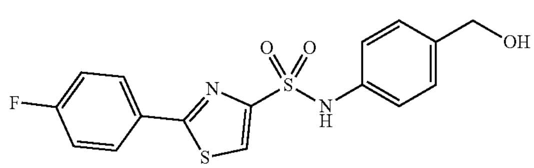 [SMILES: O=S(=O)(Nc1ccc(CO)cc1)c1csc(-c2ccc(F)cc2)n1] |
| 880 | 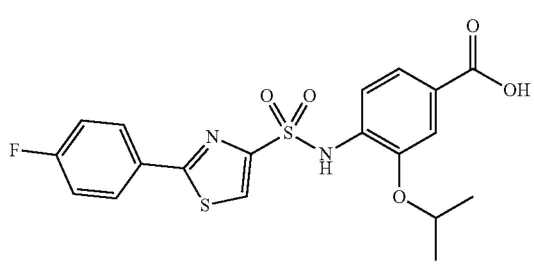 [SMILES: CC(C)Oc1cc(C(=O)O)ccc1NS(=O)(=O)c1csc(-c2ccc(F)cc2)n1] |

-continued
| Example # | Structure |
|---|---|
| 881 | 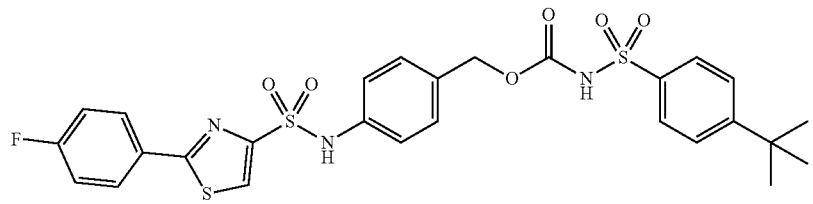 [SMILES: CC(C)(C)c1ccc(S(=O)(=O)NC(=O)OCc2ccc(NS(=O)(=O)c3csc(-c4ccc(F)cc4)n3)cc2)cc1] |
| 882 | 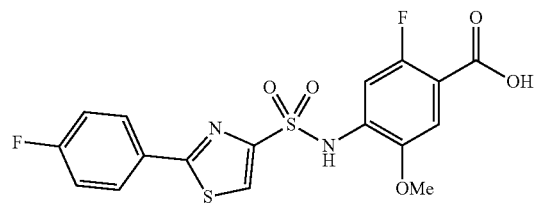 [SMILES: COc1cc(C(=O)O)c(F)cc1NS(=O)(=O)c1csc(-c2ccc(F)cc2)n1] |
| 883 | 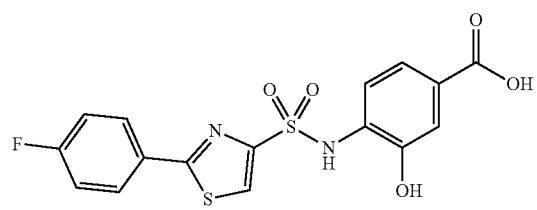 |
| 884 | 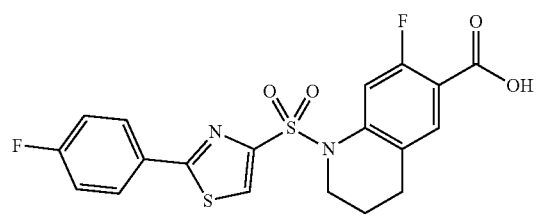 [SMILES: O=C(O)c1cc2c(cc1F)N(S(=O)(=O)c1csc(-c3ccc(F)cc3)n1)CCC2] |
| 885 | 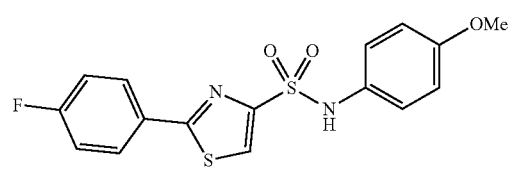 [SMILES: COc1ccc(NS(=O)(=O)c2csc(-c3ccc(F)cc3)n2)cc1] |
| 886 | 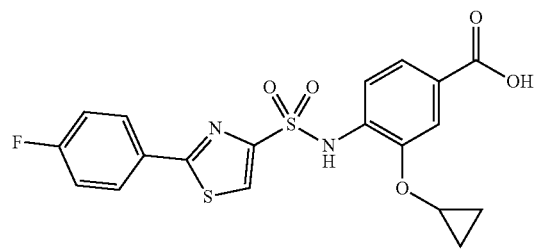 [SMILES: O=C(O)c1ccc(NS(=O)(=O)c2csc(-c3ccc(F)cc3)n2)c(OC2CC2)c1] |
| 887 | 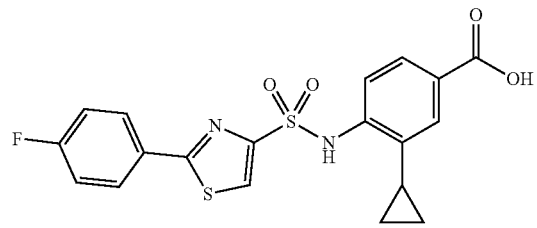 [SMILES: O=C(O)c1ccc(NS(=O)(=O)c2csc(-c3ccc(F)cc3)n2)c(C2CC2)c1] |

-continued

| Example # | Structure |
|---|---|
| 888 | 2-(4-fluorophenyl)-N-(4-carboxy-2-(trifluoromethyl)phenyl)thiazole-4-sulfonamide |
| 889 | 2-(4-fluorophenyl)-N-(4-carboxy-2,6-difluorophenyl)thiazole-4-sulfonamide |
| 890 | 2-(4-fluorophenyl)-N-(6-carboxy-[1,1'-biphenyl]-3-yl)thiazole-4-sulfonamide |
| 891 | 2-(4-fluorophenyl)-N-(4-carboxy-2-(trifluoromethoxy)phenyl)thiazole-4-sulfonamide |
| 892 | 2-(4-fluorophenyl)-N-(4-carboxy-2-(difluoromethoxy)phenyl)thiazole-4-sulfonamide |
| 893 | 2-(4-fluorophenyl)-N-(4-carboxy-2,3-difluorophenyl)thiazole-4-sulfonamide |
| 894 | 2-(4-fluorophenyl)-N-(4-carboxy-2-fluoro-3-methoxyphenyl)thiazole-4-sulfonamide |

-continued
| Example # | Structure |
|---|---|
| 895 | 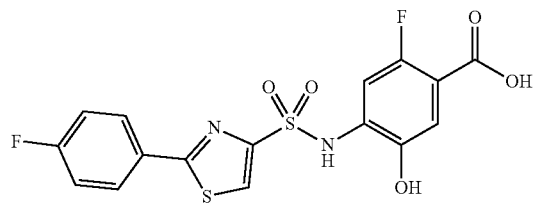 [SMILES: O=C(O)c1cc(O)c(NS(=O)(=O)c2csc(-c3ccc(F)cc3)n2)cc1F] |
| 896 | 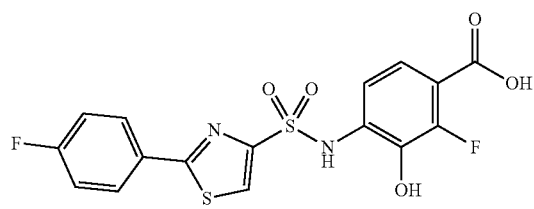 [SMILES: O=C(O)c1ccc(NS(=O)(=O)c2csc(-c3ccc(F)cc3)n2)c(O)c1F] |
| 897 | 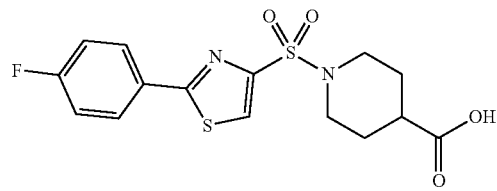 [SMILES: O=C(O)C1CCN(S(=O)(=O)c2csc(-c3ccc(F)cc3)n2)CC1] |
| 898 | 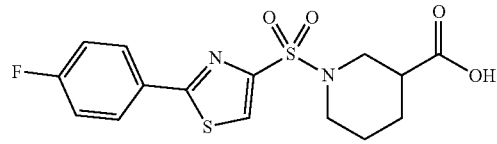 [SMILES: O=C(O)C1CCCN(S(=O)(=O)c2csc(-c3ccc(F)cc3)n2)C1] |
| 899 | 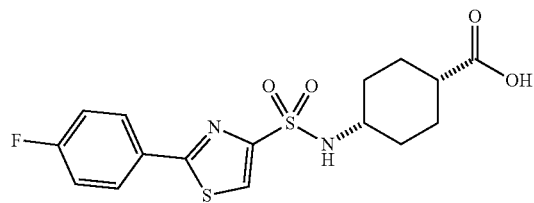 [SMILES: O=C(O)[C@H]1CC[C@@H](NS(=O)(=O)c2csc(-c3ccc(F)cc3)n2)CC1] |
| 900 | 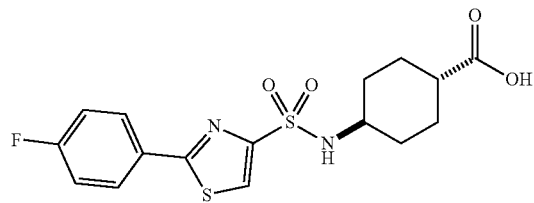 [SMILES: O=C(O)[C@H]1CC[C@H](NS(=O)(=O)c2csc(-c3ccc(F)cc3)n2)CC1] |
| 901 | 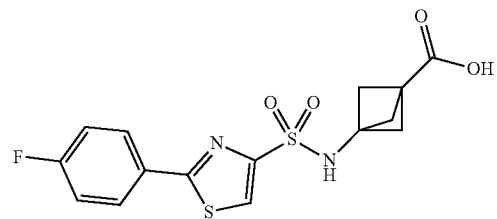 [SMILES: O=C(O)C12CC(NS(=O)(=O)c3csc(-c4ccc(F)cc4)n3)(C1)C2] |

| Example # | Structure |
|---|---|
| 902 | 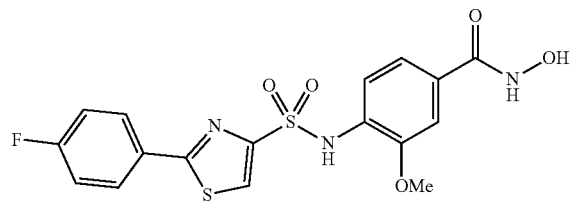 [SMILES: COc1cc(C(=O)NO)ccc1NS(=O)(=O)c1csc(-c2ccc(F)cc2)n1] |
| 903 | 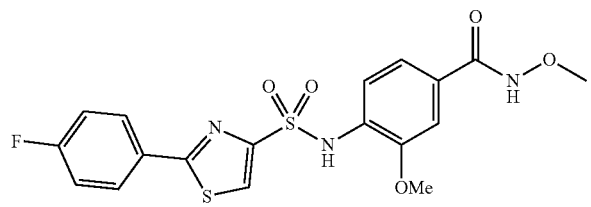 [SMILES: CONC(=O)c1ccc(NS(=O)(=O)c2csc(-c3ccc(F)cc3)n2)c(OC)c1] |
| 904 | 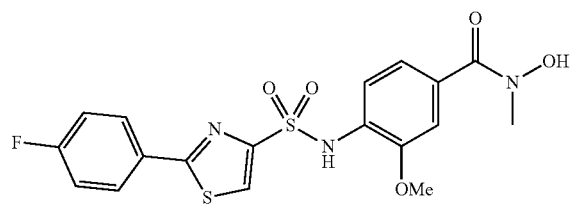 [SMILES: COc1cc(C(=O)N(C)O)ccc1NS(=O)(=O)c1csc(-c2ccc(F)cc2)n1] |
| 905 | 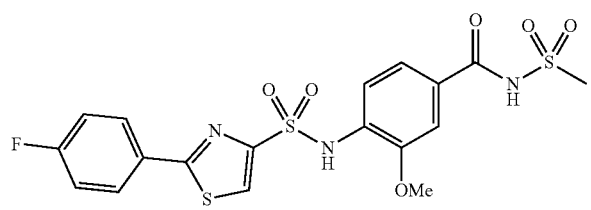 [SMILES: COc1cc(C(=O)NS(C)(=O)=O)ccc1NS(=O)(=O)c1csc(-c2ccc(F)cc2)n1] |
| 906 | 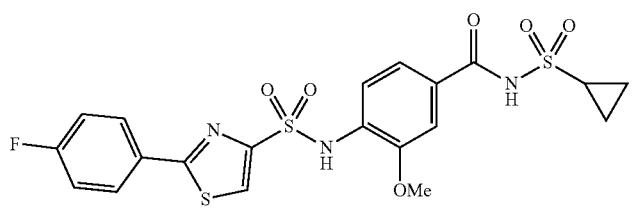 [SMILES: COc1cc(C(=O)NS(=O)(=O)C2CC2)ccc1NS(=O)(=O)c1csc(-c2ccc(F)cc2)n1] |
| 907 | 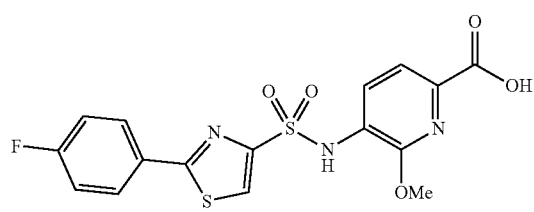 [SMILES: COc1nc(C(=O)O)ccc1NS(=O)(=O)c1csc(-c2ccc(F)cc2)n1] |
| 908 | 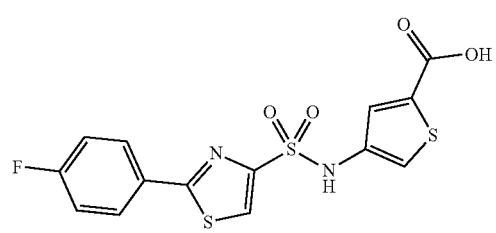 [SMILES: O=C(O)c1cc(NS(=O)(=O)c2csc(-c3ccc(F)cc3)n2)cs1] |

| Example # | Structure |
|---|---|
| 909 | 4-fluorophenyl-thiazole-sulfonamide linked to 3-cyano-4-aminobenzoic acid |
| 910 | 4-fluorophenyl-thiazole-sulfonamide linked to 5-aminothiophene-2-carboxylic acid |
| 911 | 4-fluorophenyl-thiazole-sulfonamide linked to 2-chloro-5-methoxy-4-aminobenzoic acid |
| 912 | 4-fluorophenyl-thiazole-sulfonamide linked to 8-aminoquinoline-5-carboxylic acid |
| 913 | 4-fluorophenyl-thiazole-sulfonamide linked to 2-aminopyrimidine-5-carboxylic acid |
| 914 | 4-fluorophenyl-thiazole-sulfonamide linked to 5-amino-6-methoxypyrazine-2-carboxylic acid |
| 915 | 4-fluorophenyl-thiazole-sulfonamide linked to 6-amino-5-methoxypyridine-3-carboxylic acid |

| Example # | Structure |
|---|---|
| 916 | 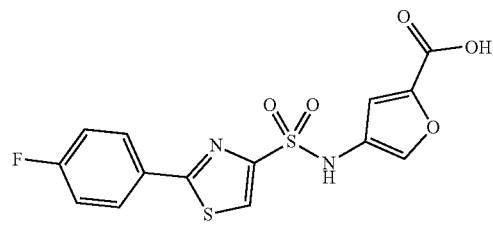 |
| 917 | 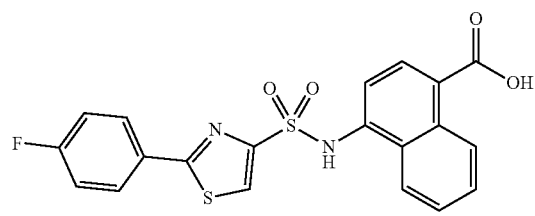 [SMILES: O=C(O)c1ccc(NS(=O)(=O)c2csc(-c3ccc(F)cc3)n2)c2ccccc12] |
| 918 | 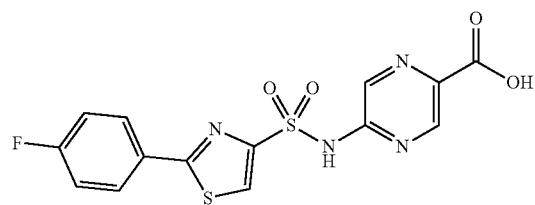 [SMILES: O=C(O)c1cnc(NS(=O)(=O)c2csc(-c3ccc(F)cc3)n2)cn1] |
| 919 | 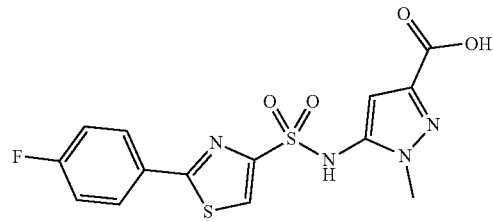 [SMILES: Cn1nc(C(=O)O)cc1NS(=O)(=O)c1csc(-c2ccc(F)cc2)n1] |
| 920 | 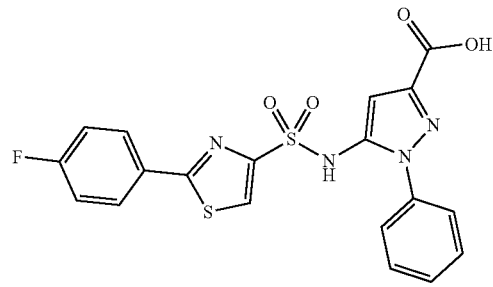 [SMILES: O=C(O)c1cc(NS(=O)(=O)c2csc(-c3ccc(F)cc3)n2)n(-c2ccccc2)n1] |
| 921 | 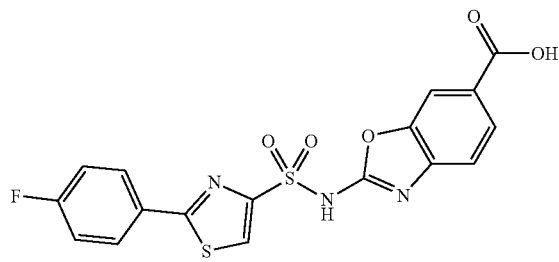 [SMILES: O=C(O)c1ccc2nc(NS(=O)(=O)c3csc(-c4ccc(F)cc4)n3)oc2c1] |

| Example # | Structure |
|---|---|
| 922 | 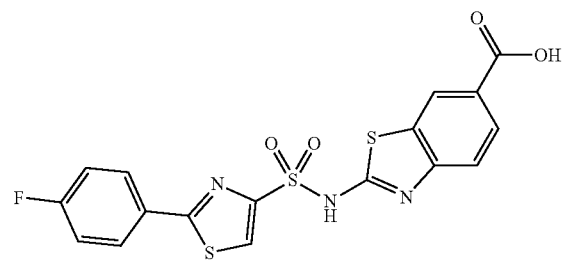 |
| 923 | 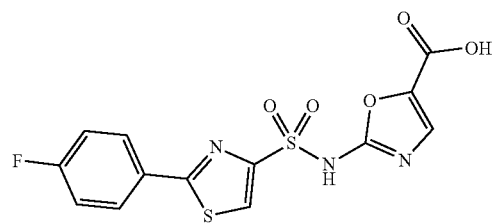 [SMILES: O=C(O)c1cnc(NS(=O)(=O)c2csc(-c3ccc(F)cc3)n2)o1] |
| 924 | 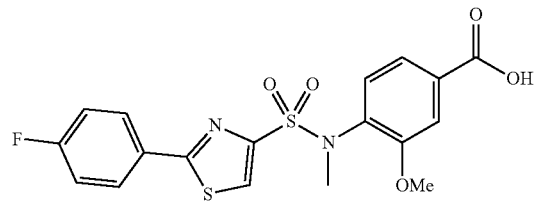 [SMILES: COc1cc(C(=O)O)ccc1N(C)S(=O)(=O)c1csc(-c2ccc(F)cc2)n1] |
| 925 | 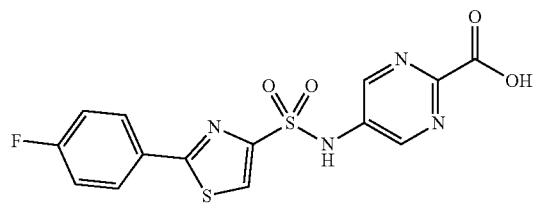 [SMILES: O=C(O)c1ncc(NS(=O)(=O)c2csc(-c3ccc(F)cc3)n2)cn1] |
| 926 | 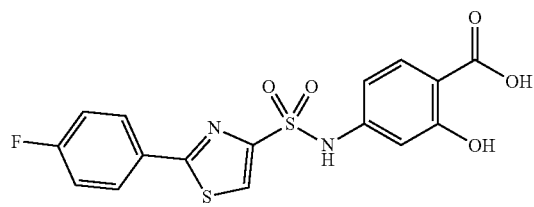 [SMILES: O=C(O)c1ccc(NS(=O)(=O)c2csc(-c3ccc(F)cc3)n2)cc1O] |
| 927 | 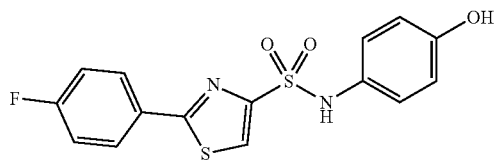 [SMILES: O=S(=O)(Nc1ccc(O)cc1)c1csc(-c2ccc(F)cc2)n1] |
| 928 | 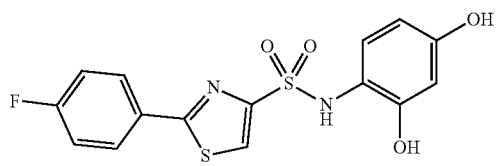 [SMILES: O=S(=O)(Nc1ccc(O)cc1O)c1csc(-c2ccc(F)cc2)n1] |

| Example # | Structure |
|---|---|
| 929 | 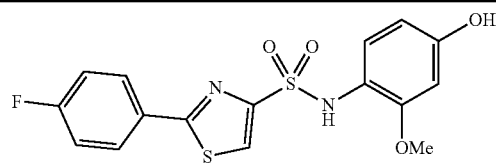 |
| 930 | 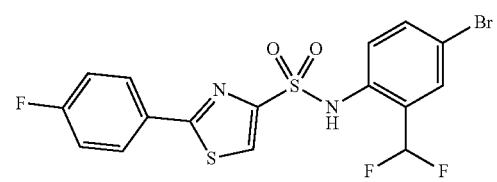 [SMILES: O=S(=O)(Nc1ccc(Br)cc1C(F)F)c1csc(-c2ccc(F)cc2)n1] |
| 931 | 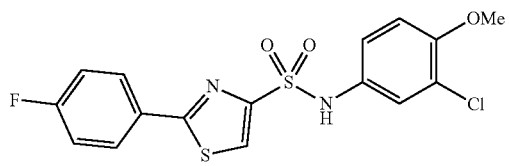 |
| 932 | 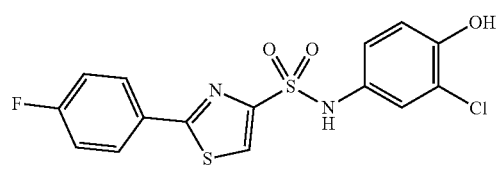 [SMILES: O=S(=O)(Nc1ccc(O)c(Cl)c1)c1csc(-c2ccc(F)cc2)n1] |
| 933 | 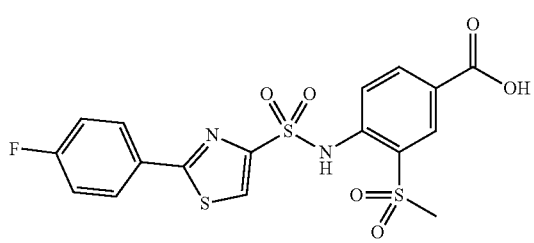 [SMILES: CS(=O)(=O)c1cc(C(=O)O)ccc1NS(=O)(=O)c1csc(-c2ccc(F)cc2)n1] |
| 934 | 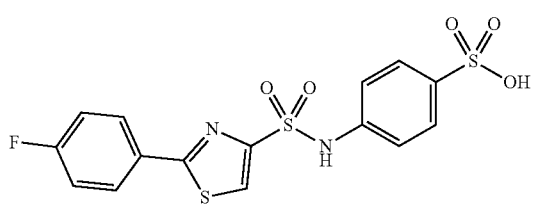 [SMILES: O=S(=O)(O)c1ccc(NS(=O)(=O)c2csc(-c3ccc(F)cc3)n2)cc1] |
| 935 | 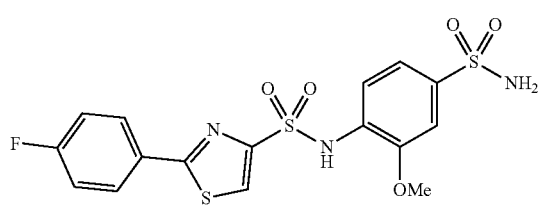 [SMILES: COc1cc(S(N)(=O)=O)ccc1NS(=O)(=O)c1csc(-c2ccc(F)cc2)n1] |
| 936 | 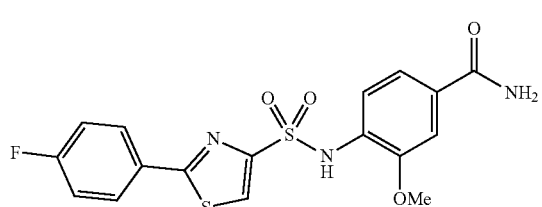 |

| Example # | Structure |
|---|---|
| 937 | 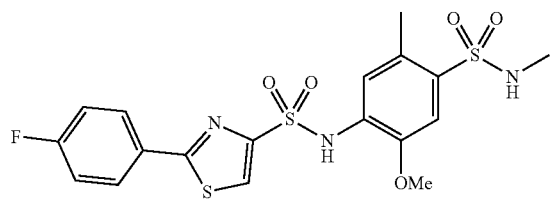 [SMILES: CNS(=O)(=O)c1cc(OC)c(NS(=O)(=O)c2csc(-c3ccc(F)cc3)n2)cc1C] |
| 938 | 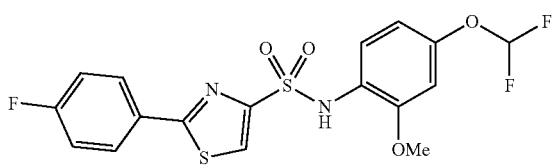 [SMILES: COc1cc(OC(F)F)ccc1NS(=O)(=O)c1csc(-c2ccc(F)cc2)n1] |
| 939 | 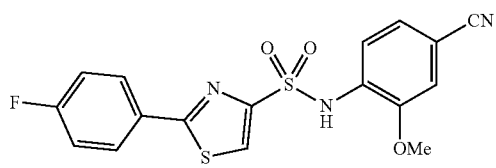 [SMILES: COc1cc(C#N)ccc1NS(=O)(=O)c1csc(-c2ccc(F)cc2)n1] |
| 940 | 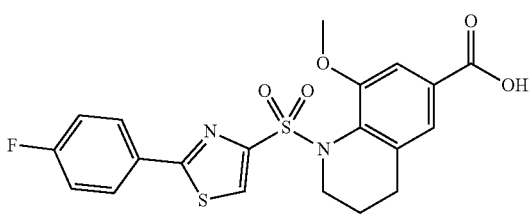 [SMILES: COc1cc(C(=O)O)cc2c1N(S(=O)(=O)c1csc(-c3ccc(F)cc3)n1)CCC2] |
| 941 | 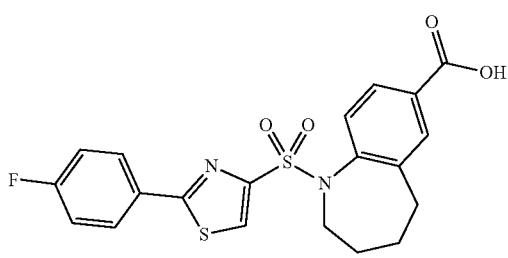 [SMILES: O=C(O)c1ccc2c(c1)CCCCN2S(=O)(=O)c1csc(-c2ccc(F)cc2)n1] |
| 942 | 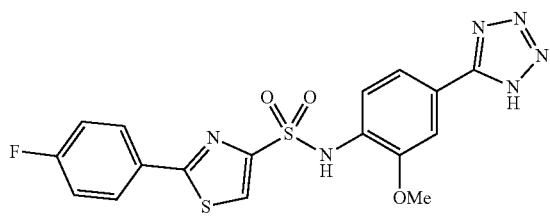 [SMILES: COc1cc(-c2nnn[nH]2)ccc1NS(=O)(=O)c1csc(-c2ccc(F)cc2)n1] |
| 943 | 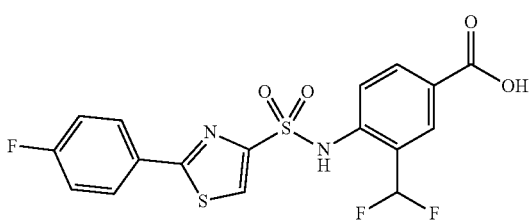 [SMILES: O=C(O)c1ccc(NS(=O)(=O)c2csc(-c3ccc(F)cc3)n2)c(C(F)F)c1] |

-continued

| Example # | Structure |
|---|---|
| 944 | 4-fluorophenyl-thiazole-sulfonamide-naphthalene-CO2H |
| 945 | 4-fluorophenyl-thiazole-sulfonamide-benzothiazole-CO2H |
| 946 | 4-fluorophenyl-thiazole-sulfonamide-(OMe-phenyl)-phenyl-CO2H |
| 947 | 4-fluorophenyl-thiazole-sulfonamide-(OMe-phenyl)-(OMe-phenyl)-CO2H |

Assay

HSD17B13 rapid-fire mass spectrometry assay (RF/MS assay). Recombinant human HSD17B13 was expressed and purified from sf9 cells at Charles River Labs (Saffron Walden, UK). Leukotriene B4 (Catalog #71160-24-2) and 12-oxoleukotriene B4 (Catalog #20140) were purchased from Cayman Chemicals (Ann Arbor, Michigan.). NAD+ (Catalog #N8285), BSA (Catalog #A7030), DMSO (Catalog #D2650), and Tween-20 (Catalog #11332465001) were purchased from Sigma (St. Louis, MO). Formic acid (Catalog #28905) was from ThermoFisher Scientific and 384 deep well PP microplates (Catalog #784261) were from Greiner Bio-One. In a typical $IC_{50}$ assay performed in a 384w PP microplate, test compounds (0-100 μM) were incubated with HSD17B13 (80 nM), LTB4 (10 μM), and NAD$^+$ (0.5 mM) in 10 μL assay buffer (20 mM Tris (pH 7.5), BSA (0.005%), and Tween-20 (0.01%)) at RT for 3 h. The assays were quenched by adding 20 μL of 0.15% aqueous formic acid and the plates were frozen at −80° C. RF/MS analysis was performed at PureHoney Technologies (Billerica, MA) on a RapidFire RF300 system (Agilent Technologies, Inc.) coupled to an API 4000 triple quadrupole mass spectrometer (Sciex) equipped with Agilent RapidFire cartridge type A (C4). The mobile phase was 0.09% formic acid and 0.01% trifluoracetic acid in water (Buffer A) and 0.09% formic acid and 0.01% trifluoracetic acid in 80% aqueous acetonitrile (Buffer B). The RapidFire method conditions were the following: 250 ms aspirate, 3000 ms load/desalt, 4000 ms elute, and 500 ms re-equilibrate. RF-MS/MS was performed in negative polarity (−4500 V), the source temperature was 650° C., and gas 1 and gas 2 settings for nitrogen were set to 50. The curtain gas and collision gas were also nitrogen and were set to 20 and 12, respectively. Leukotriene B4 (335.3) and 12-oxoLeukotriene B4 (333.3) SRM transitions were optimized with Discovery Quant software and extracted ion counts for these analytes were determined.

Data Analysis. HSD17B13 enzyme activity was measured as percent conversion of extracted ion counts and normalized to high and low controls to determine percent residual activity at various concentrations of test compounds. Data were fitted to normalized activity (variable slope) versus concentration fit in GraphPad Prism 7 to determine $IC_{50}$. All experiments were run in duplicates.

By using above method, the inhibition of HSD17B13 was evaluated for the compounds of Formula (I). $IC_{50}$ ranges are as follows: A=$IC_{50}$<0.100 μM; B=0.100 μM<$IC_{50}$<0.500 μM; C=0.500 μM<$IC_{50}$<1 μM; D=1 μM<$IC_{50}$<100 μM; E=$IC_{50}$>100 μM

| Example # | $IC_{50}$ |
|---|---|
| 1 | C |
| 3 | D |
| 4 | D |
| 5 | E |
| 6 | D |
| 7 | D |
| 8 | E |
| 9 | D |
| 10 | D |
| 11 | E |

| Example # | IC$_{50}$ |
|---|---|
| 12 | E |
| 13 | D |
| 14 | D |
| 15 | C |
| 16 | D |
| 17 | E |
| 18 | D |
| 19 | C |
| 20 | D |
| 21 | C |
| 22 | D |
| 23 | A |
| 24 | E |
| 25 | E |
| 26 | D |
| 27 | D |
| 28 | B |
| 29 | D |
| 30 | E |
| 31 | D |
| 32 | D |
| 33 | D |
| 34 | D |
| 35 | D |
| 36 | D |
| 37 | D |
| 38 | D |
| 39 | A |
| 40 | A |
| 41 | D |
| 42 | D |
| 43 | D |
| 44 | D |
| 45 | D |
| 46 | B |
| 47 | D |
| 48 | D |
| 49 | D |
| 50 | B |
| 51 | D |
| 52 | D |
| 53 | D |
| 54 | D |
| 55 | D |
| 56 | C |
| 57 | D |
| 58 | D |
| 59 | B |
| 60 | C |
| 61 | A |
| 62 | A |
| 63 | C |
| 64 | D |
| 65 | E |
| 66 | E |
| 67 | D |
| 68 | E |
| 69 | D |
| 70 | D |
| 71 | D |
| 72 | |
| 73 | D |
| 74 | D |
| 75 | D |
| 76 | C |
| 77 | D |
| 78 | C |
| 79 | D |
| 80 | D |
| 81 | B |
| 82 | D |
| 83 | D |
| 84 | D |
| 85 | B |
| 86 | B |
| 87 | D |

| Example # | IC$_{50}$ |
|---|---|
| 88 | D |
| 89 | D |
| 90 | D |
| 91 | E |
| 92 | D |
| 93 | D |
| 94 | D |
| 95 | B |
| 96 | B |
| 97 | B |
| 98 | B |
| 99 | B |
| 100 | D |
| 101 | D |
| 102 | A |
| 103 | C |
| 104 | D |
| 105 | D |
| 106 | D |
| 107 | C |
| 108 | D |
| 109 | D |
| 110 | D |
| 111 | D |
| 112 | B |
| 113 | D |
| 114 | D |
| 115 | D |
| 116 | D |
| 117 | D |
| 118 | E |
| 119 | D |
| 120 | D |
| 121 | D |
| 122 | D |
| 123 | D |
| 124 | C |
| 125 | C |
| 126 | C |
| 127 | C |
| 128 | B |
| 129 | D |
| 130 | C |
| 131 | D |
| 132 | D |
| 133 | D |
| 134 | C |
| 135 | D |
| 136 | C |
| 137 | D |
| 138 | D |
| 139 | D |
| 140 | C |
| 141 | C |
| 142 | C |
| 143 | D |
| 144 | B |
| 145 | D |
| 146 | B |
| 147 | D |
| 148 | D |
| 149 | C |
| 150 | B |
| 151 | C |
| 152 | B |
| 153 | B |
| 154 | C |
| 155 | D |
| 156 | B |
| 157 | B |
| 158 | B |
| 159 | D |
| 160 | B |
| 161 | B |
| 162 | B |
| 163 | D |

| Example # | IC$_{50}$ |
|---|---|
| 164 | D |
| 165 | D |
| 166 | D |
| 167 | B |
| 168 | B |
| 169 | B |
| 170 | B |
| 171 | A |
| 172 | B |
| 173 | D |
| 174 | A |
| 175 | B |
| 176 | B |
| 177 | B |
| 178 | B |
| 179 | B |
| 180 | B |
| 181 | D |
| 182 | A |
| 183 | D |
| 184 | B |
| 185 | C |
| 186 | A |
| 187 | A |
| 188 | A |
| 189 | A |
| 190 | A |
| 191 | A |
| 192 | D |
| 193 | B |
| 194 | B |
| 195 | A |
| 196 | A |
| 197 | A |
| 198 | C |
| 199 | B |
| 200 | A |
| 201 | A |
| 202 | A |
| 203 | A |
| 204 | A |
| 205 | B |
| 206 | B |
| 207 | C |
| 208 | A |
| 209 | B |
| 210 | A |
| 211 | A |
| 212 | A |
| 213 | B |
| 214 | A |
| 215 | B |
| 216 | B |
| 217 | A |
| 218 | A |
| 219 | B |
| 220 | A |
| 221 | A |
| 222 | A |
| 223 | D |
| 224 | D |
| 225 | A |
| 226 | B |
| 227 | A |
| 228 | A |
| 229 | A |
| 230 | B |
| 231 | A |
| 232 | A |
| 233 | B |
| 234 | B |
| 235 | A |
| 236 | A |
| 237 | B |
| 238 | A |
| 239 | A |

| Example # | IC$_{50}$ |
|---|---|
| 240 | A |
| 241 | A |
| 242 | A |
| 243 | A |
| 244 | C |
| 245 | D |
| 246 | C |
| 247 | B |
| 248 | B |
| 249 | B |
| 250 | B |
| 251 | B |
| 252 | C |
| 253 | B |
| 254 | C |
| 255 | D |
| 256 | D |
| 257 | C |
| 258 | C |
| 259 | D |
| 260 | D |
| 261 | C |
| 262 | D |
| 263 | D |
| 264 | D |
| 265 | D |
| 266 | D |
| 267 | D |
| 268 | B |
| 269 | B |
| 270 | B |
| 271 | B |
| 272 | B |
| 273 | D |
| 274 | C |
| 275 | D |
| 276 | D |
| 277 | D |
| 278 | D |
| 279 | D |
| 280 | B |
| 281 | B |
| 282 | B |
| 283 | B |
| 284 | B |
| 285 | D |
| 286 | C |
| 287 | D |
| 288 | B |
| 289 | C |
| 290 | D |
| 291 | D |
| 292 | D |
| 293 | D |
| 294 | B |
| 295 | D |
| 296 | D |
| 297 | C |
| 298 | D |
| 299 | D |
| 300 | C |
| 301 | C |
| 302 | B |
| 303 | D |
| 304 | C |
| 305 | D |
| 306 | D |
| 307 | C |
| 308 | B |
| 309 | D |
| 310 | D |
| 311 | D |
| 312 | D |
| 313 | D |
| 314 | E |
| 315 | D |

-continued

| Example # | IC$_{50}$ |
|---|---|
| 316 | B |
| 317 | D |
| 318 | D |
| 319 | D |
| 320 | D |
| 321 | D |
| 322 | D |
| 323 | D |
| 324 | B |
| 325 | D |
| 326 | B |
| 327 | D |
| 328 | D |
| 329 | D |
| 330 | B |
| 331 | D |
| 332 | B |
| 333 | B |
| 334 | B |
| 335 | A |
| 336 | A |
| 337 | B |
| 338 | B |
| 339 | C |
| 340 | D |
| 341 | C |
| 342 | C |
| 343 | A |
| 344 | C |
| 345 | B |
| 346 | D |
| 347 | D |
| 348 | A |
| 349 | A |
| 350 | A |
| 351 | A |
| 352 | A |
| 353 | A |
| 354 | A |
| 355 | B |
| 356 | B |
| 357 | B |
| 358 | B |
| 359 | A |
| 360 | D |
| 361 | D |
| 362 | B |
| 363 | B |
| 364 | C |
| 365 | |
| 366 | B |
| 367 | A |
| 368 | B |
| 369 | B |
| 370 | C |
| 371 | B |
| 372 | A |
| 373 | B |
| 374 | B |
| 375 | A |
| 376 | A |
| 377 | D |
| 378 | D |
| 379 | B |
| 380 | B |
| 381 | B |
| 382 | A |
| 383 | A |
| 384 | B |
| 385 | A |
| 386 | B |
| 387 | D |
| 388 | D |
| 389 | D |
| 390 | D |
| 391 | B |

-continued

| Example # | IC$_{50}$ |
|---|---|
| 392 | D |
| 393 | A |
| 394 | D |
| 395 | A |
| 396 | A |
| 397 | A |
| 398 | A |
| 399 | A |
| 400 | D |
| 401 | D |
| 402 | B |
| 403 | C |
| 404 | A |
| 405 | B |
| 406 | B |
| 407 | — |
| 408 | — |
| 409 | — |
| 410 | — |
| 411 | C |
| 412 | B |
| 413 | A |
| 414 | A |
| 415 | A |
| 416 | A |
| 417 | A |
| 418 | A |
| 419 | B |
| 420 | B |
| 421 | — |
| 422 | — |
| 423 | — |
| 424 | — |
| 425 | — |
| 426 | B |
| 427 | B |
| 428 | B |
| 429 | B |
| 430 | B |
| 431 | — |
| 432 | — |
| 433 | C |
| 434 | C |
| 435 | C |
| 436 | A |
| 437 | B |
| 438 | A |
| 439 | — |
| 440 | — |
| 441 | — |
| 442 | — |
| 443 | — |
| 444 | — |
| 445 | — |
| 446 | — |
| 447 | — |
| 448 | — |
| 449 | B |
| 450 | A |
| 451 | B |
| 452 | B |
| 453 | B |
| 454 | B |
| 455 | B |
| 456 | D |
| 457 | C |
| 458 | B |
| 459 | C |
| 460 | D |
| 461 | A |
| 462 | B |
| 463 | B |
| 464 | B |
| 465 | B |
| 466 | A |
| 467 | B |

| Example # | IC$_{50}$ |
|---|---|
| 468 | A |
| 469 | B |
| 470 | B |
| 471 | B |
| 472 | B |
| 473 | B |
| 474 | B |
| 475 | A |
| 476 | B |
| 477 | B |
| 478 | B |
| 479 | B |
| 480 | B |
| 481 | B |
| 482 | A |
| 483 | A |
| 484 | D |
| 485 | B |
| 486 | C |
| 487 | B |
| 488 | B |
| 489 | B |
| 490 | A |
| 491 | A |
| 492 | A |
| 493 | A |
| 494 | A |
| 495 | A |
| 496 | A |
| 497 | B |
| 498 | A |
| 499 | A |
| 500 | A |
| 501 | A |
| 502 | A |
| 503 | B |
| 504 | B |
| 505 | B |
| 506 | A |
| 507 | B |
| 508 | A |
| 509 | A |
| 510 | A |
| 511 | A |
| 512 | A |
| 513 | A |
| 514 | A |
| 515 | A |
| 516 | B |
| 517 | B |
| 518 | B |
| 519 | B |
| 520 | B |
| 521 | B |
| 522 | A |
| 523 | A |
| 524 | A |
| 525 | C |
| 526 | B |
| 527 | B |
| 528 | B |
| 529 | B |
| 530 | C |
| 531 | B |
| 532 | C |
| 533 | C |
| 534 | B |
| 535 | A |
| 536 | A |
| 537 | A |
| 538 | B |
| 539 | A |
| 540 | B |
| 541 | A |
| 542 | A |
| 543 | A |
| 544 | B |
| 545 | A |
| 546 | A |
| 547 | B |
| 548 | A |
| 549 | B |
| 550 | B |
| 551 | B |
| 552 | B |
| 553 | B |
| 554 | B |
| 555 | C |
| 556 | A |
| 557 | B |
| 558 | B |
| 559 | A |
| 560 | B |
| 561 | D |
| 562 | B |
| 563 | A |
| 564 | B |
| 565 | B |
| 566 | A |
| 567 | A |
| 568 | A |
| 569 | A |
| 570 | A |
| 571 | A |
| 572 | A |
| 573 | B |
| 574 | D |
| 575 | D |
| 576 | B |
| 577 | B |
| 578 | B |
| 579 | B |
| 580 | B |
| 581 | B |
| 582 | A |
| 583 | A |
| 584 | A |
| 585 | B |
| 586 | B |
| 587 | A |
| 588 | B |
| 589 | B |
| 590 | A |
| 591 | A |
| 592 | B |
| 593 | A |
| 594 | A |
| 595 | B |
| 596 | A |
| 597 | A |
| 598 | B |
| 599 | A |
| 600 | A |
| 601 | A |
| 602 | A |
| 603 | A |
| 604 | A |
| 605 | A |
| 606 | A |
| 607 | A |
| 608 | B |
| 609 | A |
| 610 | B |
| 611 | A |
| 612 | A |
| 613 | A |
| 614 | A |
| 615 | B |
| 616 | B |
| 617 | A |
| 618 | A |
| 619 | B |

| Example # | IC$_{50}$ |
|---|---|
| 620 | A |
| 621 | B |
| 622 | C |
| 623 | B |
| 624 | B |
| 625 | B |
| 626 | B |
| 627 | A |
| 628 | B |
| 629 | B |
| 630 | A |
| 631 | A |
| 632 | B |
| 633 | B |
| 634 | B |
| 635 | B |
| 636 | B |
| 637 | B |
| 638 | A |
| 639 | A |
| 640 | B |
| 641 | B |
| 642 | B |
| 643 | B |
| 644 | B |
| 645 | B |
| 646 | A |
| 647 | A |
| 648 | D |
| 649 | D |
| 650 | B |
| 651 | B |
| 652 | B |
| 653 | A |
| 654 | B |
| 655 | B |
| 656 | B |
| 657 | C |
| 658 | D |
| 659 | C |
| 660 | B |
| 661 | B |
| 662 | B |
| 663 | B |
| 664 | B |
| 665 | B |
| 666 | B |
| 667 | B |
| 668 | B |
| 669 | B |
| 670 | B |
| 671 | A |
| 672 | A |
| 673 | B |
| 674 | A |
| 675 | A |
| 676 | A |
| 677 | A |
| 678 | A |
| 679 | A |
| 680 | A |
| 681 | D |
| 682 | D |
| 683 | B |
| 684 | B |
| 685 | B |
| 686 | B |
| 687 | B |
| 688 | B |
| 689 | B |
| 690 | B |
| 691 | B |
| 692 | B |
| 693 | B |
| 694 | A |
| 695 | D |
| 696 | C |
| 697 | D |
| 698 | D |
| 699 | D |
| 700 | D |
| 701 | D |
| 702 | D |
| 703 | C |
| 704 | B |
| 705 | D |
| 706 | A |
| 707 | B |
| 708 | B |
| 709 | D |
| 710 | B |
| 711 | B |
| 712 | A |
| 713 | A |
| 714 | B |
| 715 | A |
| 716 | A |
| 717 | A |
| 718 | A |
| 719 | A |
| 720 | B |
| 721 | B |
| 722 | B |
| 723 | A |
| 724 | A |
| 725 | A |
| 726 | B |
| 727 | B |
| 728 | A |
| 729 | B |
| 730 | A |
| 731 | A |
| 732 | B |
| 733 | B |
| 734 | B |
| 735 | B |
| 736 | B |
| 737 | D |
| 738 | B |
| 739 | B |
| 740 | A |
| 741 | A |
| 742 | B |
| 743 | B |
| 744 | B |
| 745 | B |
| 746 | B |
| 747 | A |
| 748 | A |
| 749 | B |
| 750 | B |
| — | — |
| 753 | B |
| 754 | B |
| 755 | A |
| 756 | A |
| 757 | A |
| 758 | B |
| 759 | B |
| 760 | A |
| 761 | B |
| 762 | A |
| 763 | B |
| 764 | A |
| 765 | B |
| 766 | B |
| 767 | B |
| 768 | B |
| 769 | B |
| 770 | A |
| 771 | A |

| Example # | IC$_{50}$ |
|---|---|
| 772 | A |
| 773 | A |
| 774 | A |
| 775 | A |
| 776 | A |
| 777 | B |
| 778 | A |
| 779 | B |
| 780 | A |
| 781 | B |
| 782 | B |
| 783 | B |
| 784 | A |
| 785 | A |
| 786 | B |
| 787 | A |
| 788 | B |
| 789 | A |
| 790 | A |
| 791 | A |
| 792 | B |
| 793 | A |
| 794 | A |
| 795 | A |
| 796 | B |
| 797 | B |
| 798 | B |
| 799 | A |
| 800 | C |
| 801 | C |
| 802 | A |
| 803 | A |
| 804 | D |
| 805 | A |
| 806 | A |
| 807 | A |
| 808 | A |
| 809 | A |
| 810 | A |
| 811 | B |
| 812 | A |
| 813 | A |
| 814 | A |
| 815 | B |
| 816 | A |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by one of Formulas (X-2), (X-3), (X-4), (X-5), (X-6), (X-11) and (X-12), or a pharmaceutically acceptable salt thereof:

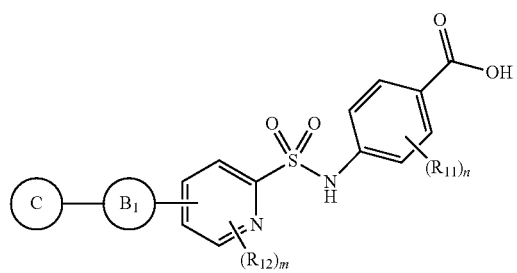

(X-2)

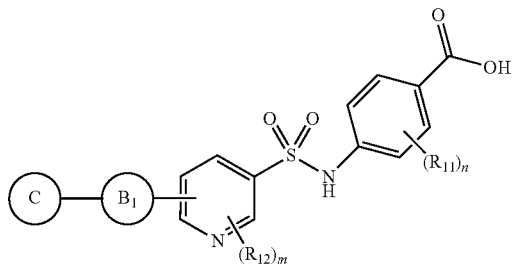

(X-3)

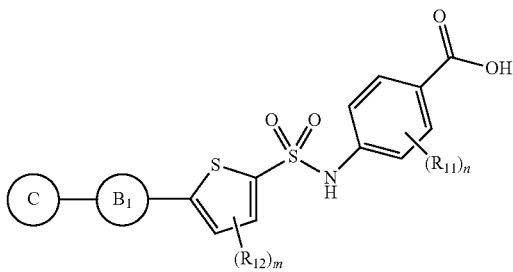

(X-4)

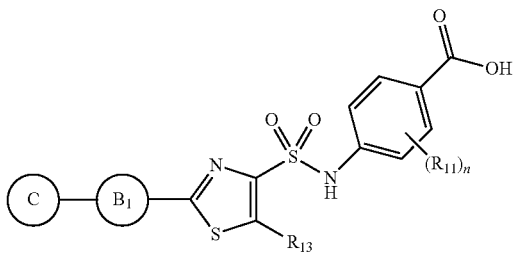

(X-5)

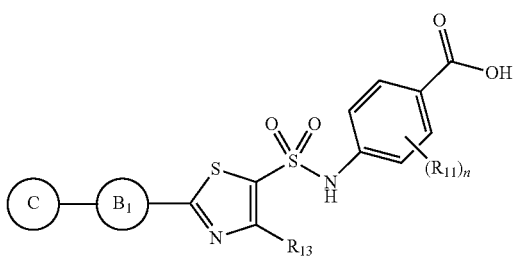

(X-6)

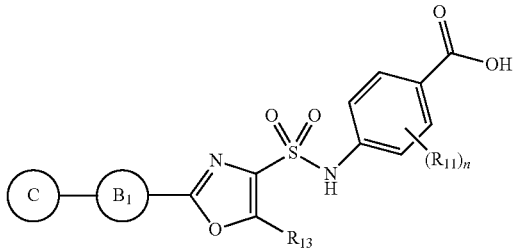

(X-11)

-continued (X-12)

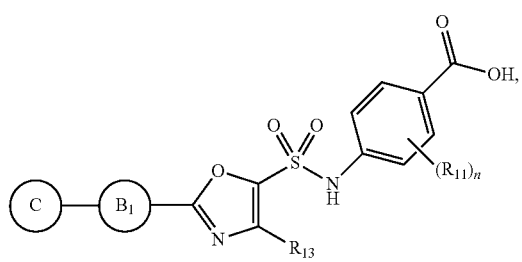

wherein each $R_{11}$ is independently selected from the group consisting of halogen, hydroxy, —$NH_2$, —NHMe, —$NMe_2$, —CN, —$NO_2$, optionally substituted-$C_1$-$C_6$ alkyl, optionally substituted-$C_1$-$C_6$ alkoxyl, optionally substituted-$C_3$-$C_6$ cycloalkyl, optionally substituted-$C_3$-$C_6$ cycloalkenyl, optionally substituted aryl, and optionally substituted heteroaryl; n is 0, 1, 2, or 3; each $R_{12}$ is independently selected from the group consisting of halogen, hydroxy, —$NH_2$, —NHMe, —$NMe_2$, —CN, —$NO_2$, optionally substituted-$C_1$-$C_6$ alkyl, optionally substituted-$C_1$-$C_6$ alkoxyl, optionally substituted-$C_3$-$C_6$ cycloalkyl, optionally substituted-$C_3$-$C_6$ cycloalkenyl, optionally substituted aryl, and optionally substituted heteroaryl; m is 0, 1 or 2; $R_{13}$ is selected from the group consisting of hydrogen, halogen, hydroxy, —$NH_2$, —NHMe, —$NMe_2$, —CN, —$NO_2$, optionally substituted-$C_1$-$C_6$ alkyl, optionally substituted-$C_1$-$C_6$ alkoxyl, optionally substituted $C_3$-$C_6$ cycloalkyl, optionally substituted $C_3$-$C_6$ cycloalkenyl, optionally substituted aryl, and optionally substituted heteroaryl;

(B₁)

is optionally substituted aryl; and (C)

is optionally substituted-$C_3$-$C_{12}$ cycloalkyl, optionally substituted 3- to 12-membered heterocycloalkyl, or optionally substituted-$C_3$-$C_{12}$ cycloalkenyl.

2. The compound of claim 1, represented by one of Formulas (XI-3) to (XI-14) and (XI-17) to (XI-22), or a pharmaceutically acceptable salt thereof:

(XI-1)

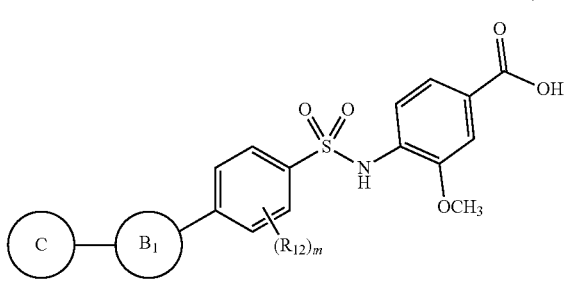

-continued (XI-2)

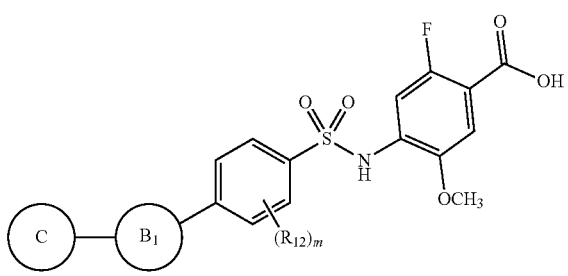

(XI-3)

(XI-4)

(XI-5)

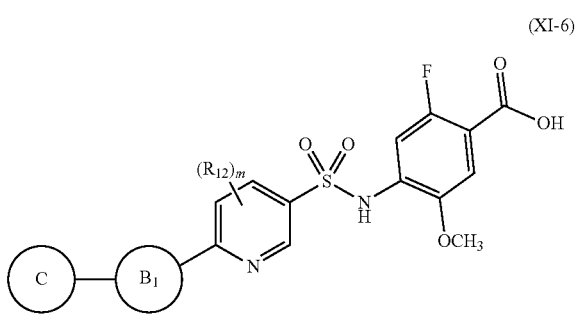

(XI-6)

(XI-7)
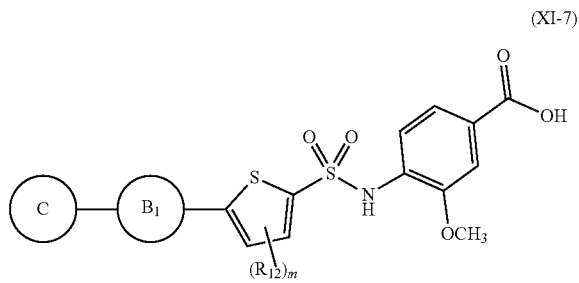
(XI-8)
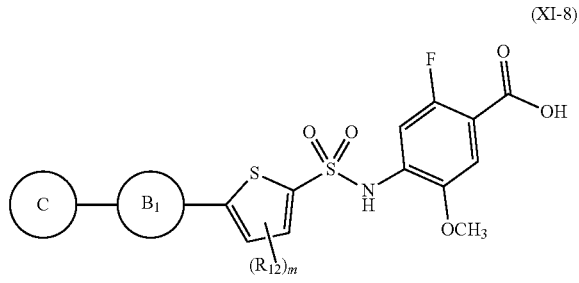
(XI-9)
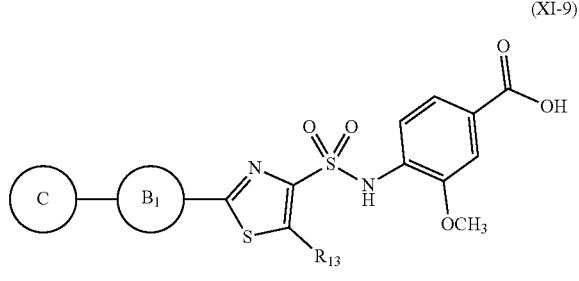
(XI-10)
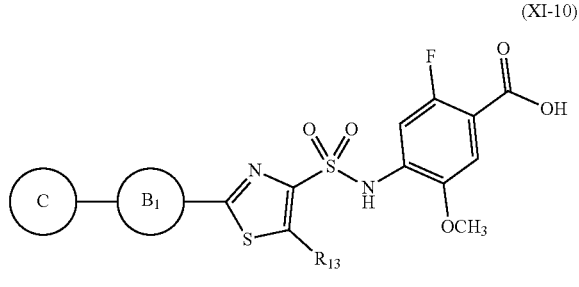
(XI-11)
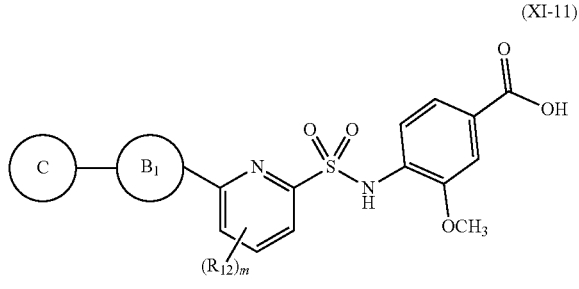
(XI-12)
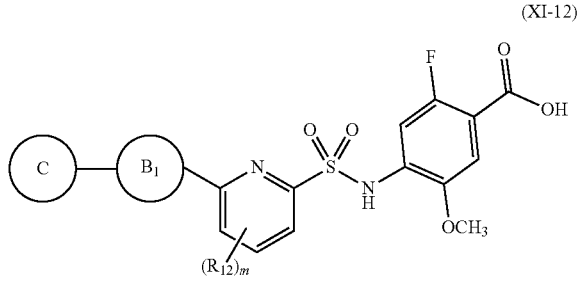
(XI-13)
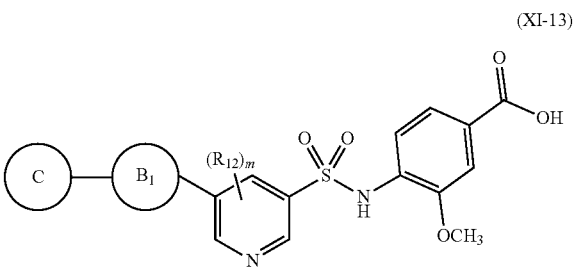
(XI-14)
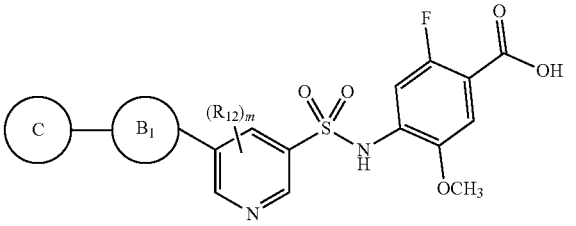
(XI-15)
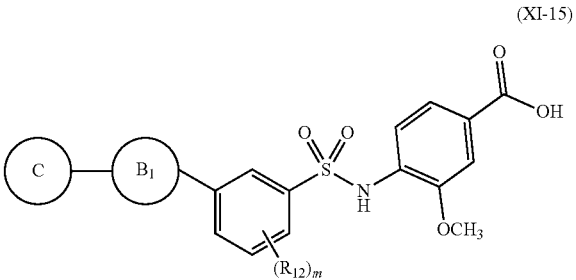
(XI-16)
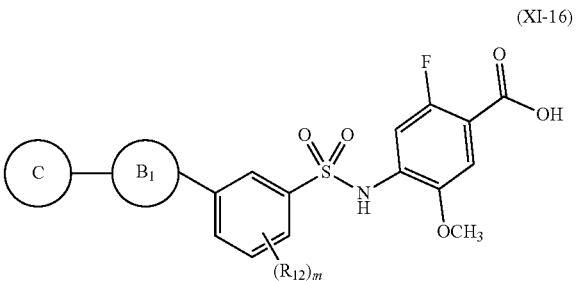
(XI-17)
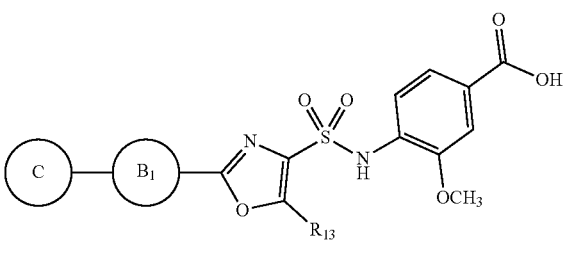
(XI-18)
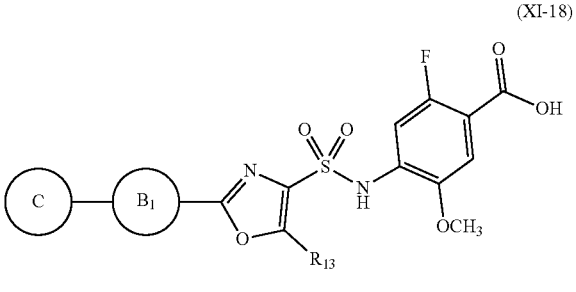

545
-continued (XI-19)
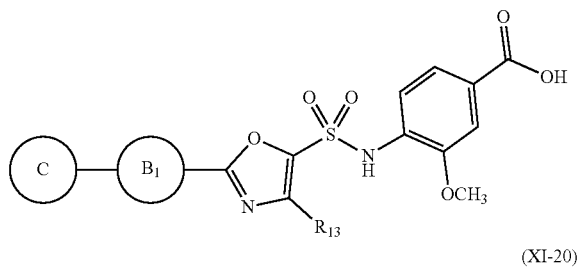

(XI-20)
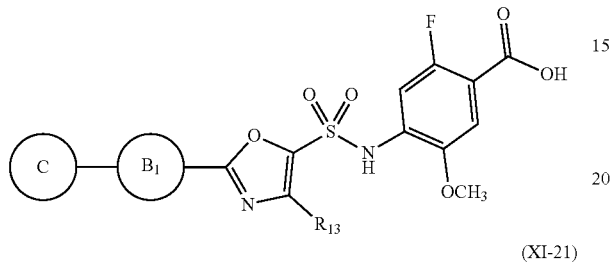

(XI-21)
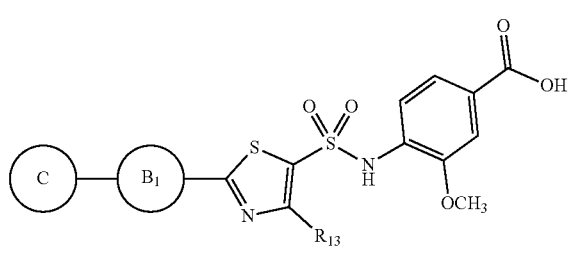

546
-continued (XI-22)
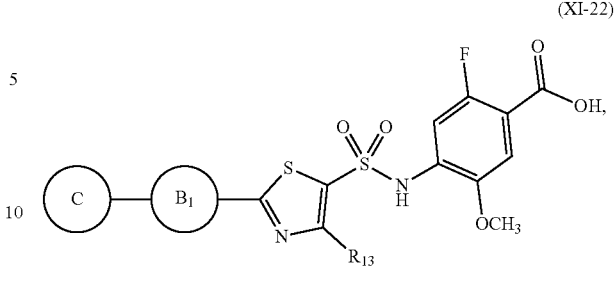

wherein m, $R_{12}$, $R_{13}$, $B_1$ and $C$ are as defined in claim 1.

3. The compound of claim 2, represented by Formula (XI-9) or (XI-10), or a pharmaceutically acceptable salt thereof.

4. The compound of claim 1, represented by Formula (X-5), or a pharmaceutically acceptable salt thereof.

5. The compound of claim 1, selected from the compounds set forth in the table below, or a pharmaceutically acceptable salt thereof:

| Compound # | Structure |
|---|---|
| 281 | 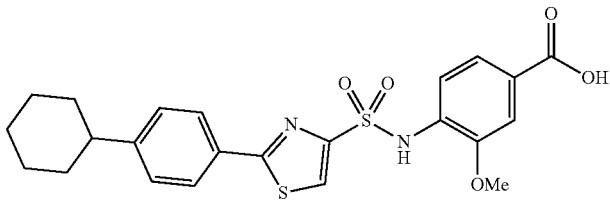 |
| 284 | 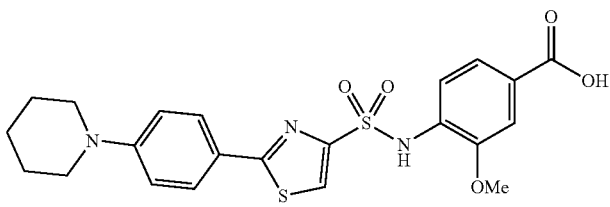 [SMILES: COc1cc(C(=O)O)ccc1NS(=O)(=O)c1csc(-c2ccc(N3CCCCC3)cc2)n1] |
| 300 | 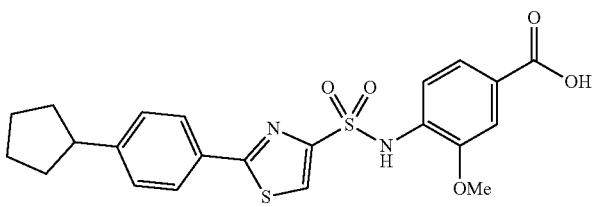 [SMILES: COc1cc(C(=O)O)ccc1NS(=O)(=O)c1csc(-c2ccc(C3CCCC3)cc2)n1] |

-continued
| Compound # | Structure |
|---|---|
| 303 | 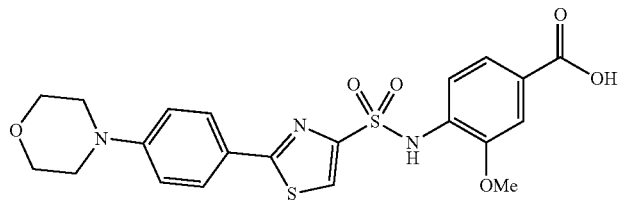 [SMILES: COc1cc(C(=O)O)ccc1NS(=O)(=O)c1csc(-c2ccc(N3CCOCC3)cc2)n1] |
| 336 | 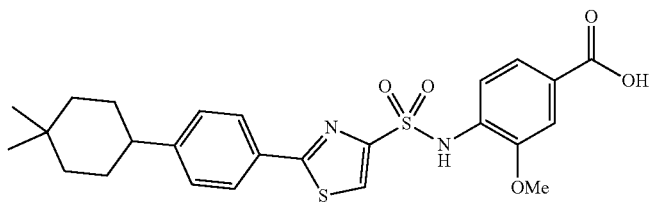 [SMILES: COc1cc(C(=O)O)ccc1NS(=O)(=O)c1csc(-c2ccc(C3CCC(C)(C)CC3)cc2)n1] |
| 340 | 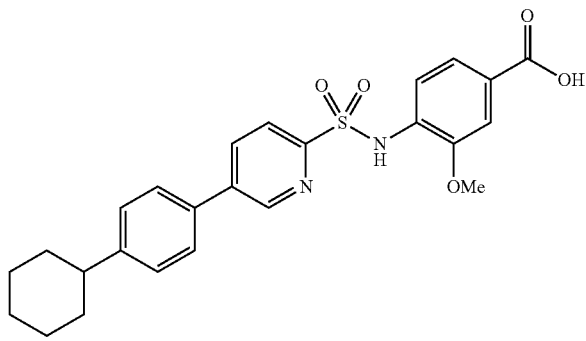 [SMILES: COc1cc(C(=O)O)ccc1NS(=O)(=O)c1ccc(-c2ccc(C3CCCCC3)cc2)cn1] |
| 346 | 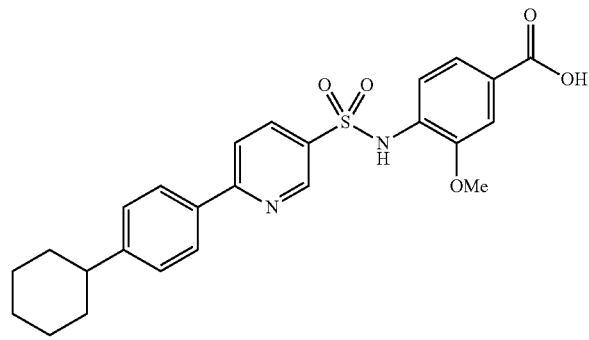 |
| 348 | 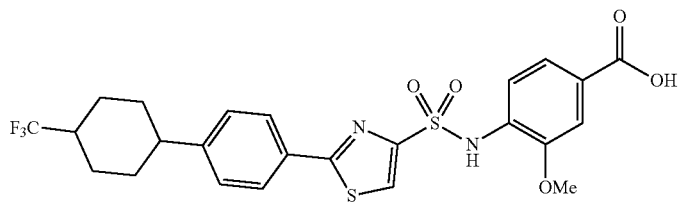 |
| 349 | 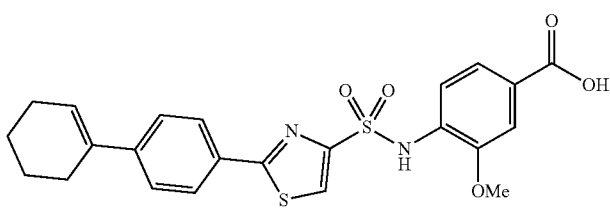 [SMILES: COc1cc(C(=O)O)ccc1NS(=O)(=O)c1csc(-c2ccc(C3=CCCCC3)cc2)n1] |

-continued
| Compound # | Structure |
|---|---|
| 350 | 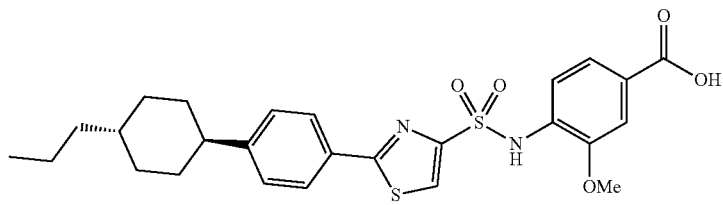 [SMILES: CCC[C@H]1CC[C@H](c2ccc(-c3nc(S(=O)(=O)Nc4ccc(C(=O)O)cc4OC)cs3)cc2)CC1] |
| 351 | 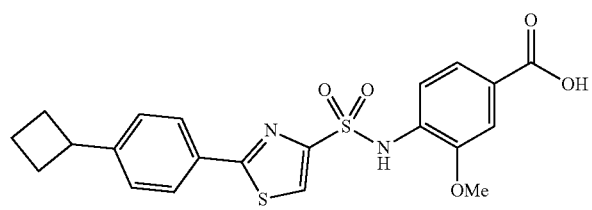 [SMILES: COc1cc(C(=O)O)ccc1NS(=O)(=O)c1csc(-c2ccc(C3CCC3)cc2)n1] |
| 352 | 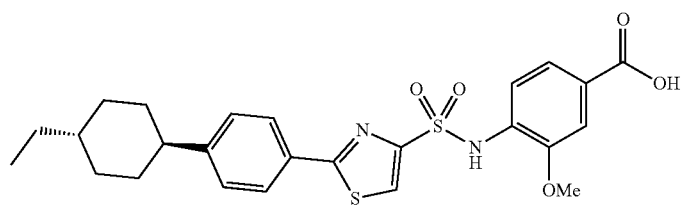 [SMILES: CC[C@H]1CC[C@H](c2ccc(-c3nc(S(=O)(=O)Nc4ccc(C(=O)O)cc4OC)cs3)cc2)CC1] |
| 353 | 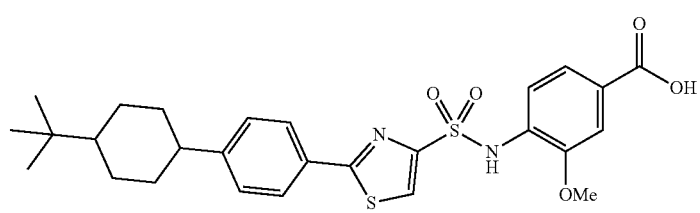 [SMILES: COc1cc(C(=O)O)ccc1NS(=O)(=O)c1csc(-c2ccc(C3CCC(C(C)(C)C)CC3)cc2)n1] |
| 366 | 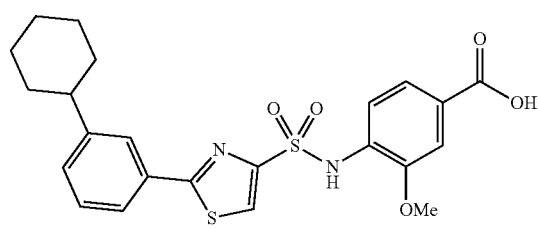 [SMILES: COc1cc(C(=O)O)ccc1NS(=O)(=O)c1csc(-c2cccc(C3CCCCC3)c2)n1] |
| 367 | 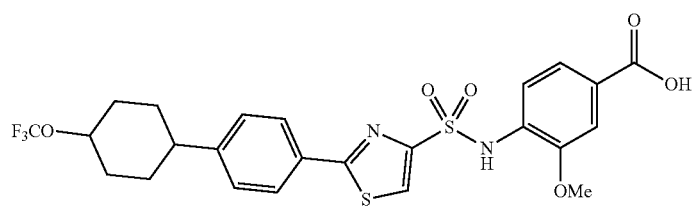 [SMILES: COc1cc(C(=O)O)ccc1NS(=O)(=O)c1csc(-c2ccc(C3CCC(OC(F)(F)F)CC3)cc2)n1] |
| 368 | 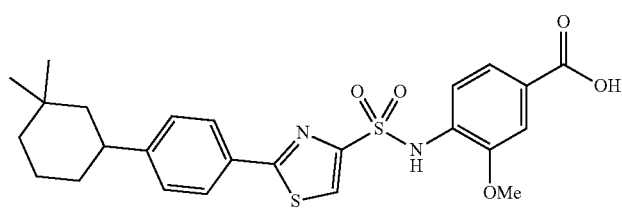 [SMILES: COc1cc(C(=O)O)ccc1NS(=O)(=O)c1csc(-c2ccc(C3CCCC(C)(C)C3)cc2)n1] |

| Compound # | Structure |
|---|---|
| 370 | 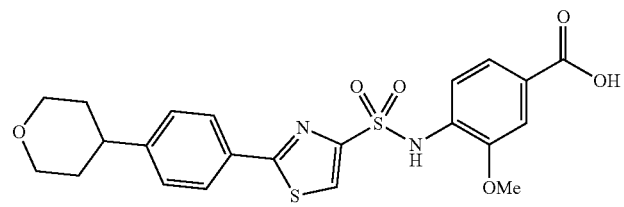 [SMILES: COc1cc(C(=O)O)ccc1NS(=O)(=O)c1csc(-c2ccc(C3CCOCC3)cc2)n1] |
| 371 | 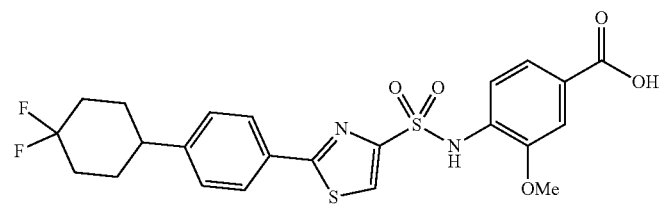 |
| 372 | 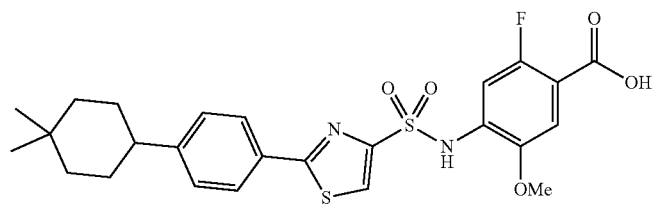 [SMILES: COc1cc(C(=O)O)c(F)cc1NS(=O)(=O)c1csc(-c2ccc(C3CCC(C)(C)CC3)cc2)n1] |
| 374 | 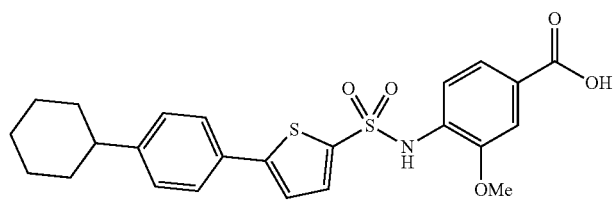 [SMILES: COc1cc(C(=O)O)ccc1NS(=O)(=O)c1ccc(-c2ccc(C3CCCCC3)cc2)s1] |
| 380 | 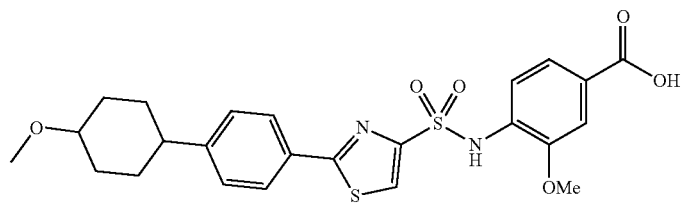 [SMILES: COc1cc(C(=O)O)ccc1NS(=O)(=O)c1csc(-c2ccc(C3CCC(OC)CC3)cc2)n1] |
| 385 | 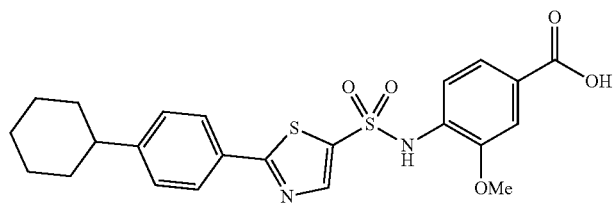 |
| 419 | 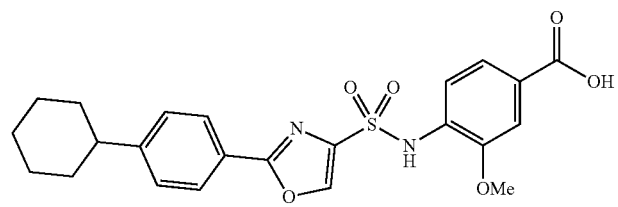 [SMILES: COc1cc(C(=O)O)ccc1NS(=O)(=O)c1coc(-c2ccc(C3CCCCC3)cc2)n1] |

-continued
| Compound # | Structure |
|---|---|
| 420 | 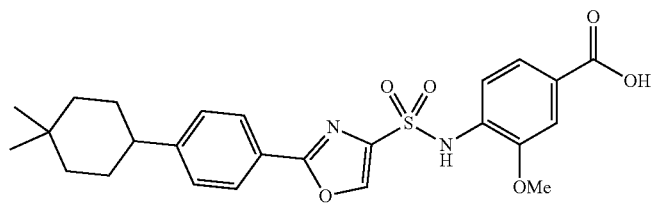 [SMILES: COc1cc(C(=O)O)ccc1NS(=O)(=O)c1coc(-c2ccc(C3CCC(C)(C)CC3)cc2)n1] |
| 421 | 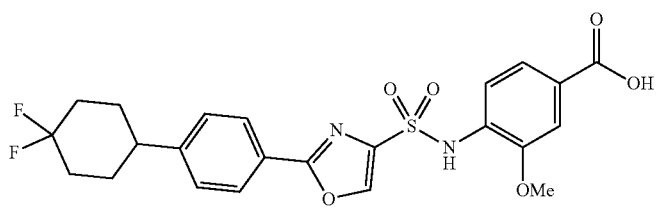 [SMILES: COc1cc(C(=O)O)ccc1NS(=O)(=O)c1coc(-c2ccc(C3CCC(F)(F)CC3)cc2)n1] |
| 422 | 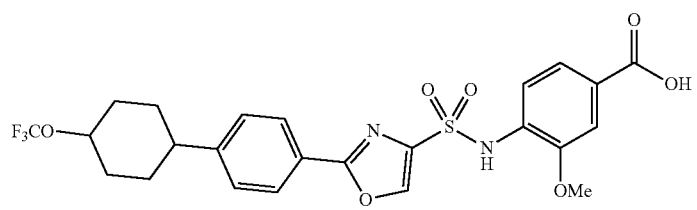 |
| 426 | 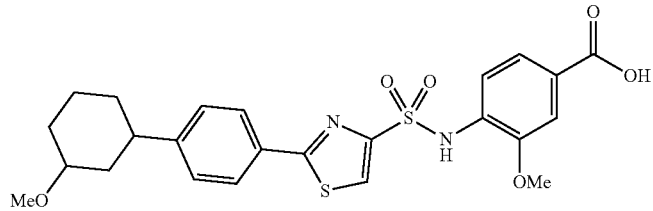 [SMILES: COc1cc(C(=O)O)ccc1NS(=O)(=O)c1csc(-c2ccc(C3CCCC(OC)C3)cc2)n1] |
| 428 | 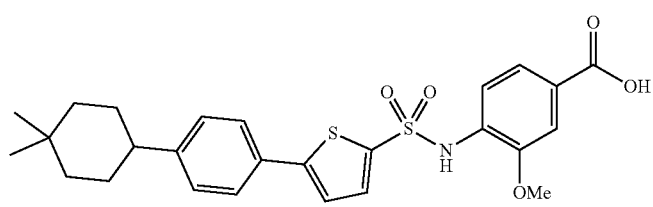 |
| 429 | 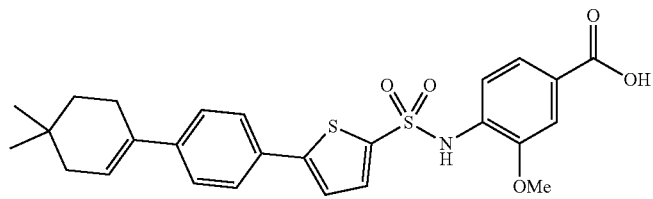 [SMILES: COc1cc(C(=O)O)ccc1NS(=O)(=O)c1ccc(-c2ccc(C3=CCC(C)(C)CC3)cc2)s1] |
| 430 | 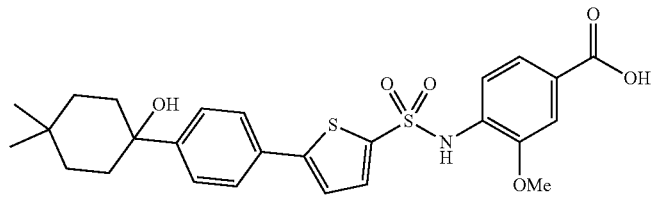 [SMILES: COc1cc(C(=O)O)ccc1NS(=O)(=O)c1ccc(-c2ccc(C3(O)CCC(C)(C)CC3)cc2)s1] |

-continued
| Compound # | Structure |
|---|---|
| 431 | 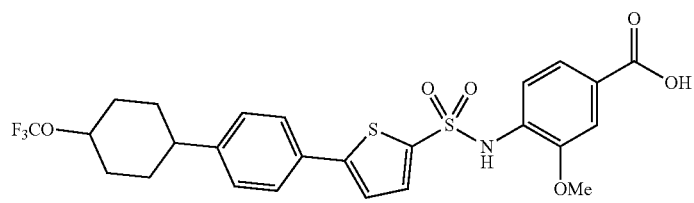 [SMILES: COc1cc(C(=O)O)ccc1NS(=O)(=O)c1ccc(-c2ccc(C3CCC(OC(F)(F)F)CC3)cc2)s1] |
| 433 | 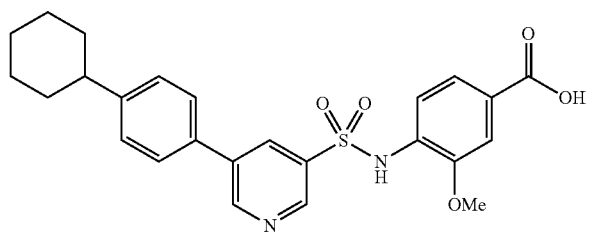 [SMILES: COc1cc(C(=O)O)ccc1NS(=O)(=O)c1cncc(-c2ccc(C3CCCCC3)cc2)c1] |
| 439 | 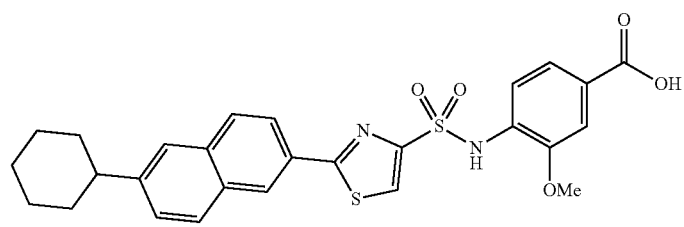 [SMILES: COc1cc(C(=O)O)ccc1NS(=O)(=O)c1csc(-c2ccc3cc(C4CCCCC4)ccc3c2)n1] |
| 440 | 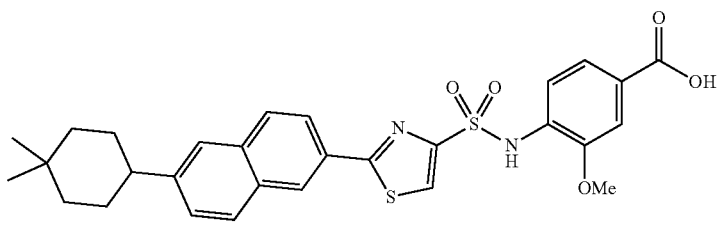 [SMILES: COc1cc(C(=O)O)ccc1NS(=O)(=O)c1csc(-c2ccc3cc(C4CCC(C)(C)CC4)ccc3c2)n1] |
| 442 | 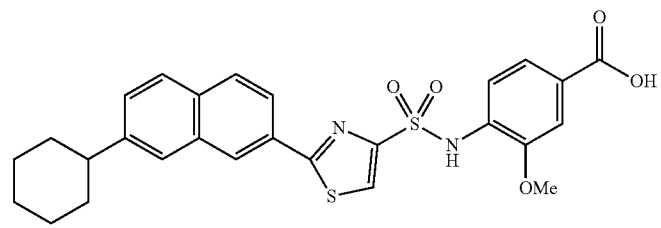 [SMILES: COc1cc(C(=O)O)ccc1NS(=O)(=O)c1csc(-c2ccc3ccc(C4CCCCC4)cc3c2)n1] |
| 443 | 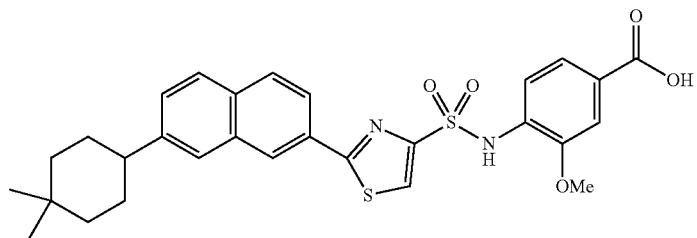 [SMILES: COc1cc(C(=O)O)ccc1NS(=O)(=O)c1csc(-c2ccc3ccc(C4CCC(C)(C)CC4)cc3c2)n1] |

| Compound # | Structure |
|---|---|
| 444 | 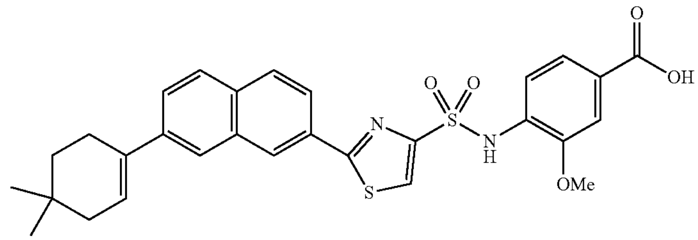 [SMILES: COc1cc(C(=O)O)ccc1NS(=O)(=O)c1csc(-c2ccc3ccc(C4=CCC(C)(C)CC4)cc3c2)n1] |
| 445 | 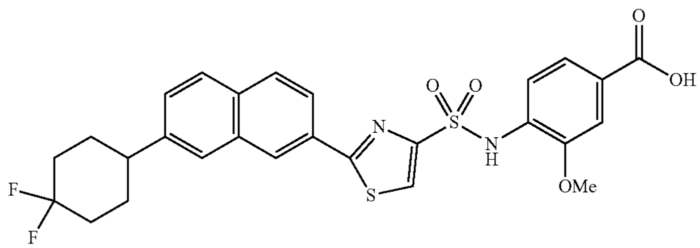 [SMILES: COc1cc(C(=O)O)ccc1NS(=O)(=O)c1csc(-c2ccc3ccc(C4CCC(F)(F)CC4)cc3c2)n1] |
| 446 | 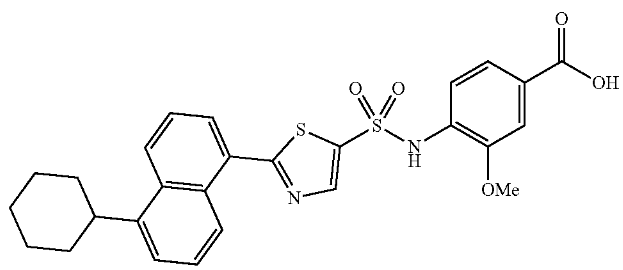 [SMILES: COc1cc(C(=O)O)ccc1NS(=O)(=O)c1cnc(-c2cccc3c(C4CCCCC4)cccc23)s1] |
| 447 | 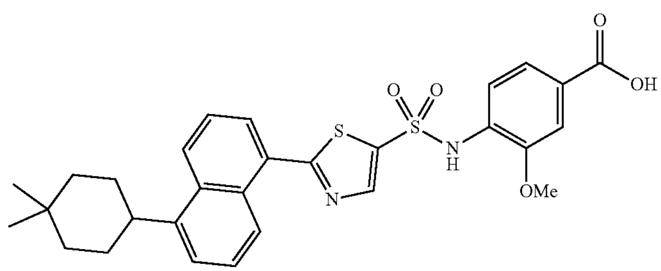 [SMILES: COc1cc(C(=O)O)ccc1NS(=O)(=O)c1cnc(-c2cccc3c(C4CCC(C)(C)CC4)cccc23)s1] |
| 448 | 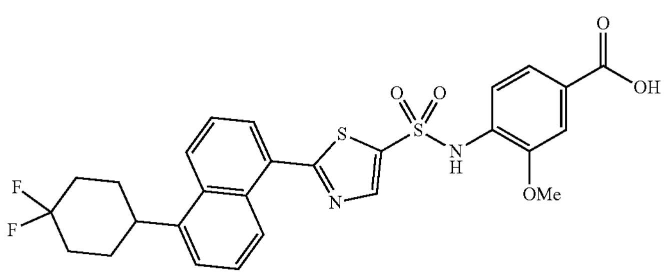 [SMILES: COc1cc(C(=O)O)ccc1NS(=O)(=O)c1cnc(-c2cccc3c(C4CCC(F)(F)CC4)cccc23)s1] |
| 453 | 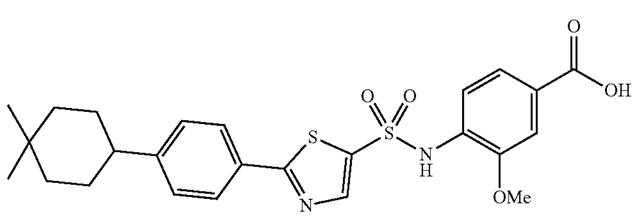 [SMILES: COc1cc(C(=O)O)ccc1NS(=O)(=O)c1cnc(-c2ccc(C3CCC(C)(C)CC3)cc2)s1] |

| Compound # | Structure |
|---|---|
| 459 | 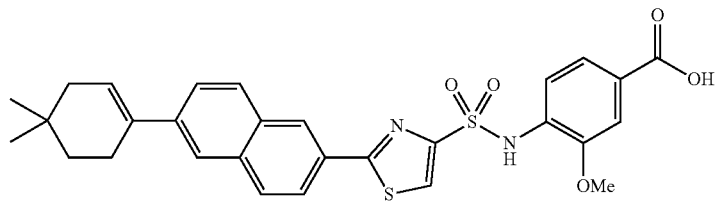 |
| 464 | 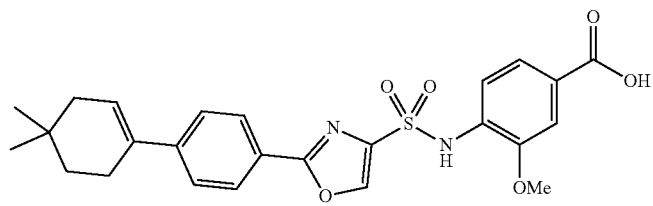 [SMILES: COc1cc(C(=O)O)ccc1NS(=O)(=O)c1coc(-c2ccc(C3=CCC(C)(C)CC3)cc2)n1] |
| 467 | 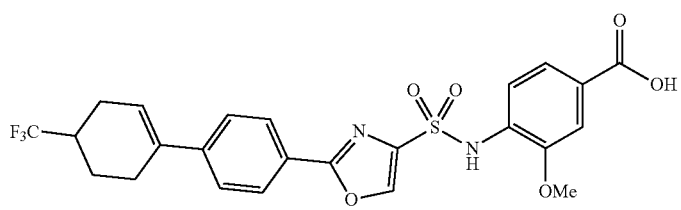 [SMILES: COc1cc(C(=O)O)ccc1NS(=O)(=O)c1coc(-c2ccc(C3=CCC(C(F)(F)F)CC3)cc2)n1] |
| 468 | 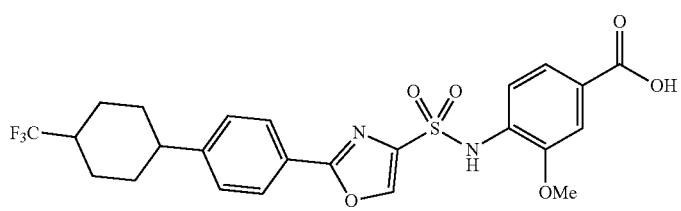 [SMILES: COc1cc(C(=O)O)ccc1NS(=O)(=O)c1coc(-c2ccc(C3CCC(C(F)(F)F)CC3)cc2)n1] |
| 480 | 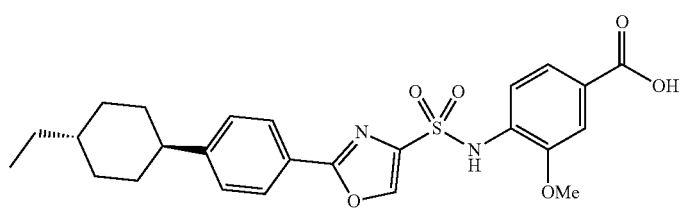 [SMILES: CC[C@H]1CC[C@H](c2ccc(-c3nc(S(=O)(=O)Nc4ccc(C(=O)O)cc4OC)co3)cc2)CC1] |
| 481 | 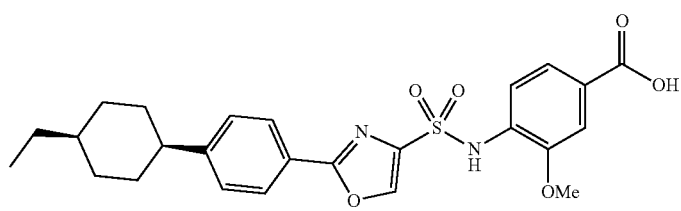 [SMILES: CC[C@H]1CC[C@@H](c2ccc(-c3nc(S(=O)(=O)Nc4ccc(C(=O)O)cc4OC)co3)cc2)CC1] |
| 482 | 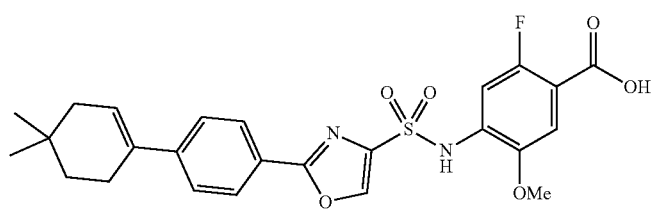 [SMILES: COc1cc(C(=O)O)c(F)cc1NS(=O)(=O)c1coc(-c2ccc(C3=CCC(C)(C)CC3)cc2)n1] |

| Compound # | Structure |
|---|---|
| 483 | 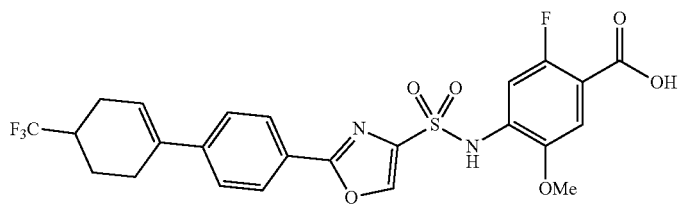 |
| 487 | 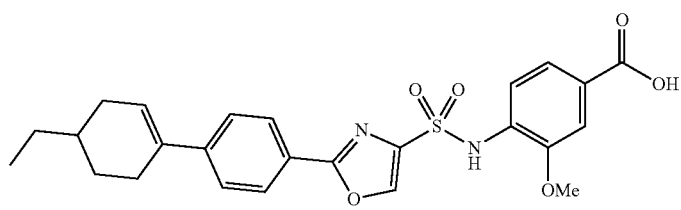 [SMILES: CCC1CC=C(c2ccc(-c3nc(S(=O)(=O)Nc4ccc(C(=O)O)cc4OC)co3)cc2)CC1] |
| 488 | 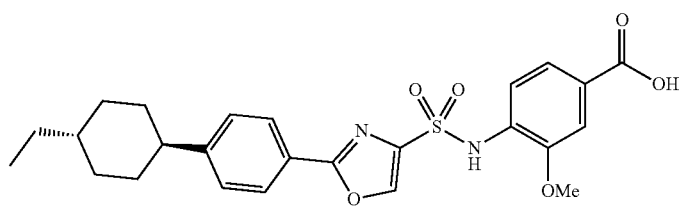 [SMILES: CC[C@H]1CC[C@H](c2ccc(-c3nc(S(=O)(=O)Nc4ccc(C(=O)O)cc4OC)co3)cc2)CC1] |
| 489 | 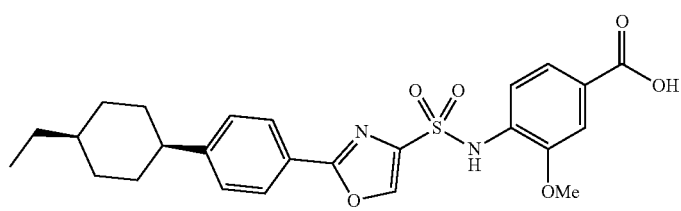 [SMILES: CC[C@H]1CC[C@@H](c2ccc(-c3nc(S(=O)(=O)Nc4ccc(C(=O)O)cc4OC)co3)cc2)CC1] |
| 490 | 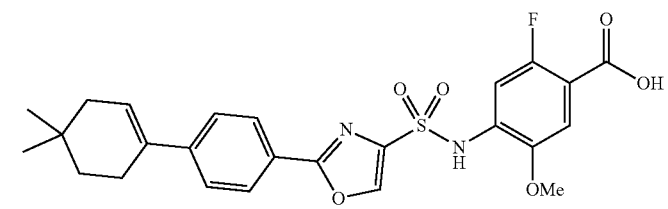 |
| 491 | 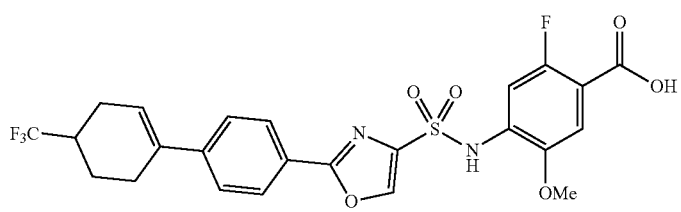 [SMILES: COc1cc(C(=O)O)c(F)cc1NS(=O)(=O)c1coc(-c2ccc(C3=CCC(C(F)(F)F)CC3)cc2)n1] |
| 492 | 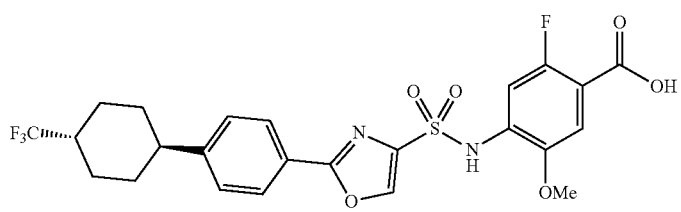 [SMILES: COc1cc(C(=O)O)c(F)cc1NS(=O)(=O)c1coc(-c2ccc([C@H]3CC[C@H](C(F)(F)F)CC3)cc2)n1] |

| Compound # | Structure |
|---|---|
| 493 | 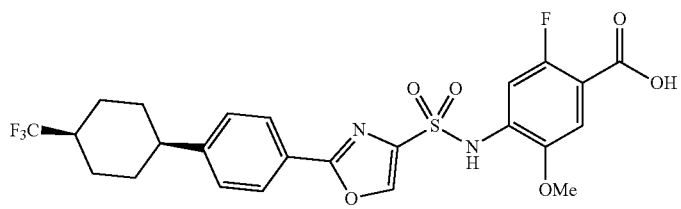 |
| 494 | 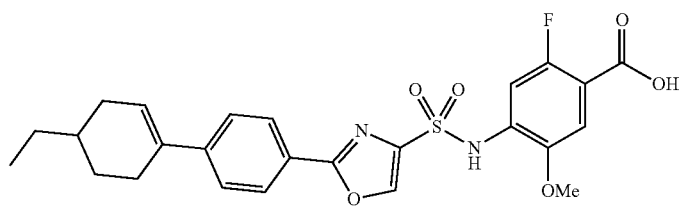 [SMILES: CCC1CC=C(c2ccc(-c3nc(S(=O)(=O)Nc4cc(F)c(C(=O)O)cc4OC)co3)cc2)CC1] |
| 495 | 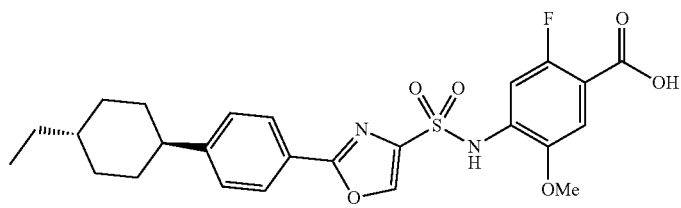 [SMILES: CC[C@H]1CC[C@H](c2ccc(-c3nc(S(=O)(=O)Nc4cc(F)c(C(=O)O)cc4OC)co3)cc2)CC1] |
| 496 | 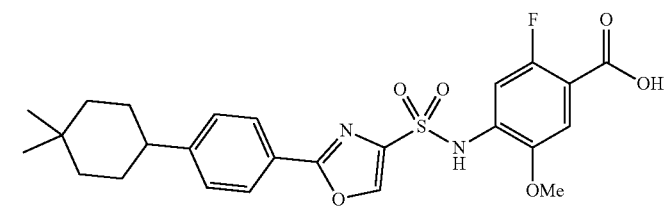 |
| 497 | 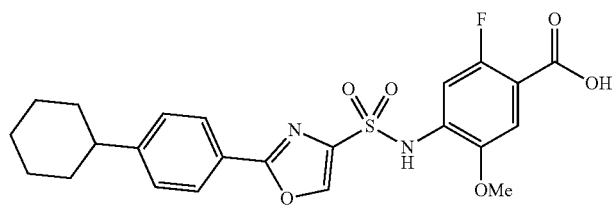 [SMILES: COc1cc(C(=O)O)c(F)cc1NS(=O)(=O)c1coc(-c2ccc(C3CCCCC3)cc2)n1] |
| 503 | 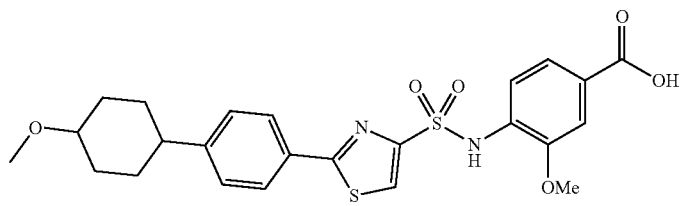 [SMILES: COc1cc(C(=O)O)ccc1NS(=O)(=O)c1csc(-c2ccc(C3CCC(OC)CC3)cc2)n1] |
| 505 | 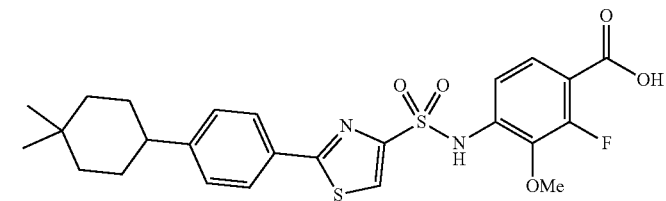 [SMILES: COc1c(NS(=O)(=O)c2csc(-c3ccc(C4CCC(C)(C)CC4)cc3)n2)ccc(C(=O)O)c1F] |

-continued

| Compound # | Structure |
|---|---|
| 506 | 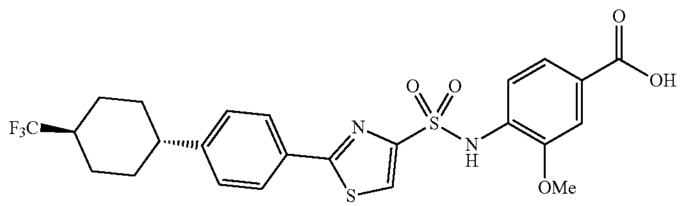 |
| 507 | 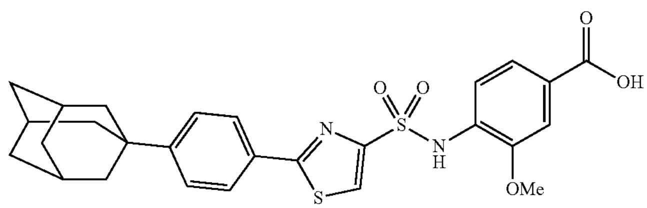 [SMILES: COc1cc(C(=O)O)ccc1NS(=O)(=O)c1csc(-c2ccc(C34CC5CC(CC(C5)C3)C4)cc2)n1] |
| 508 | 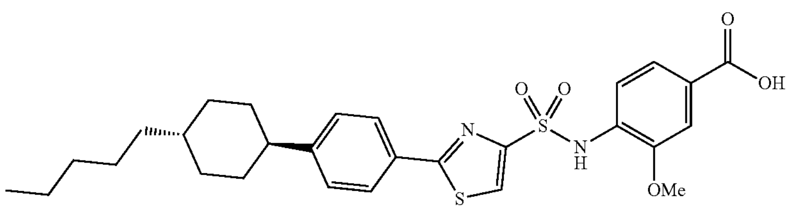 [SMILES: CCCCC[C@H]1CC[C@H](c2ccc(-c3nc(S(=O)(=O)Nc4ccc(C(=O)O)cc4OC)cs3)cc2)CC1] |
| 509 | 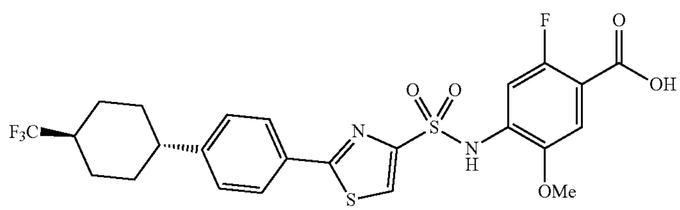 [SMILES: COc1cc(C(=O)O)c(F)cc1NS(=O)(=O)c1csc(-c2ccc([C@H]3CC[C@H](C(F)(F)F)CC3)cc2)n1] |
| 510 | 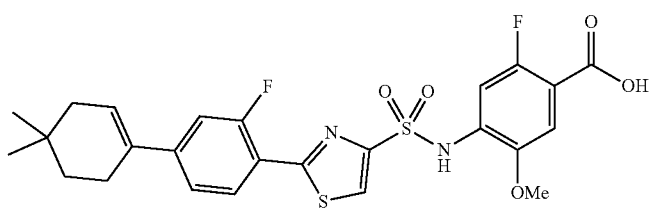 [SMILES: COc1cc(C(=O)O)c(F)cc1NS(=O)(=O)c1csc(-c2ccc(C3=CCC(C)(C)CC3)cc2F)n1] |
| 511 | 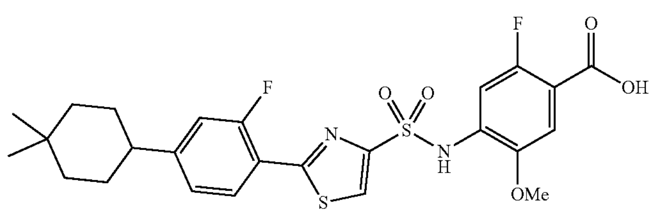 [SMILES: COc1cc(C(=O)O)c(F)cc1NS(=O)(=O)c1csc(-c2ccc(C3CCC(C)(C)CC3)cc2F)n1] |
| 512 | 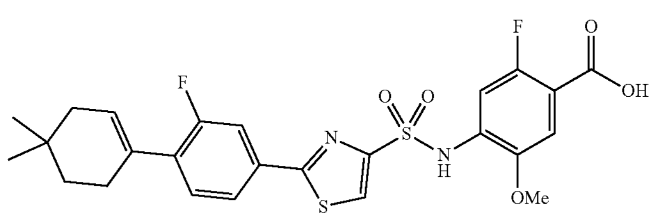 |

| Compound # | Structure |
|---|---|
| 513 | 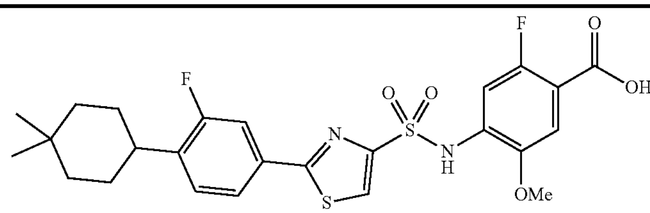 |
| 515 | 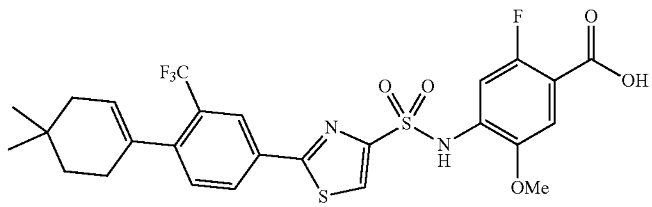 |
| 516 | 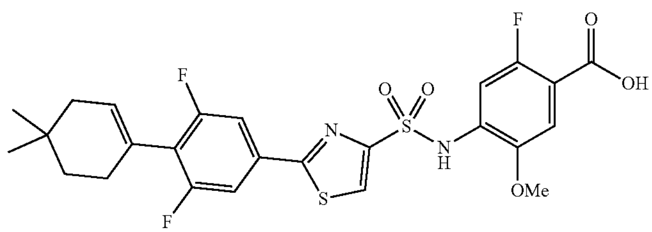 [SMILES: COc1cc(C(=O)O)c(F)cc1NS(=O)(=O)c1csc(-c2cc(F)c(C3=CCC(C)(C)CC3)c(F)c2)n1] |
| 517 | 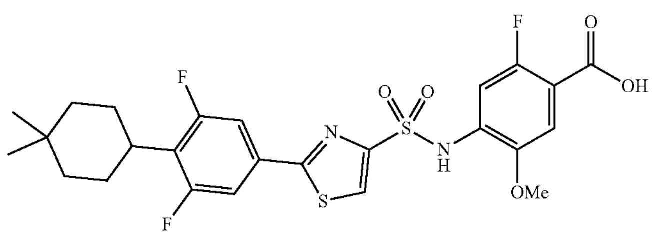 [SMILES: COc1cc(C(=O)O)c(F)cc1NS(=O)(=O)c1csc(-c2cc(F)c(C3CCC(C)(C)CC3)c(F)c2)n1] |
| 518 | 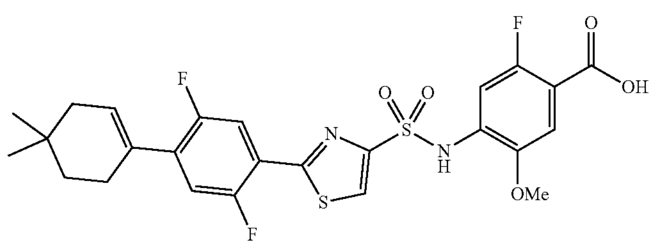 [SMILES: COc1cc(C(=O)O)c(F)cc1NS(=O)(=O)c1csc(-c2cc(F)c(C3=CCC(C)(C)CC3)cc2F)n1] |
| 519 | 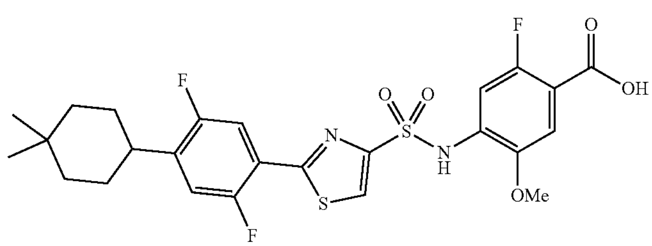 [SMILES: COc1cc(C(=O)O)c(F)cc1NS(=O)(=O)c1csc(-c2cc(F)c(C3CCC(C)(C)CC3)cc2F)n1] |
| 520 | 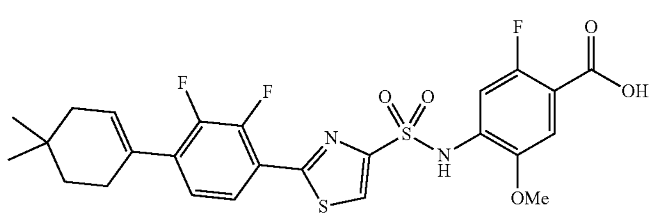 [SMILES: COc1cc(C(=O)O)c(F)cc1NS(=O)(=O)c1csc(-c2ccc(C3=CCC(C)(C)CC3)c(F)c2F)n1] |

-continued
| Compound # | Structure |
|---|---|
| 521 | 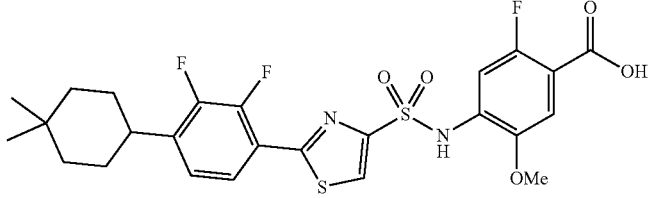 |
| 522 | 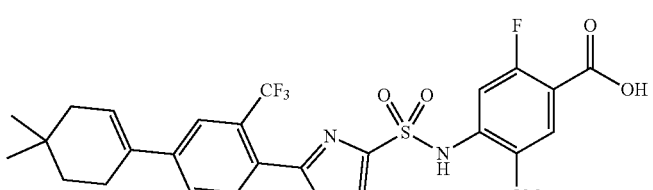 |
| 523 | 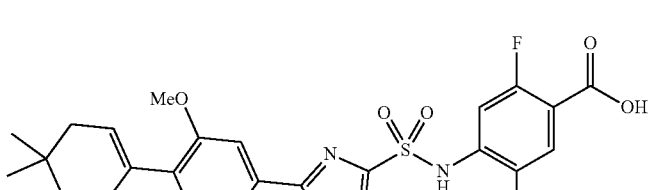 |
| 524 | 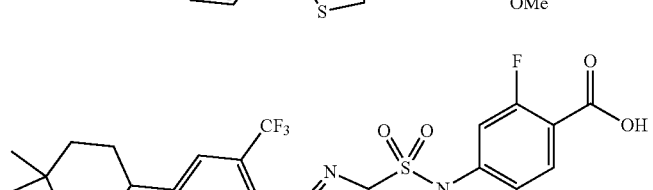 |
| 525 | 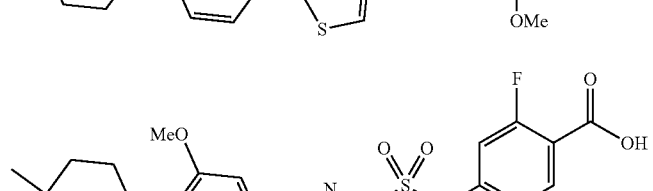 |
| 527 | 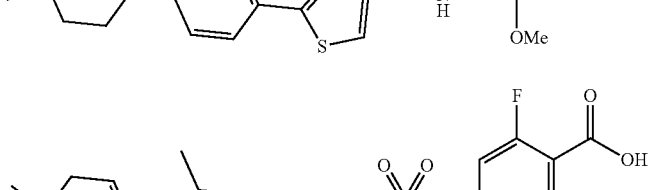 |
| 528 | 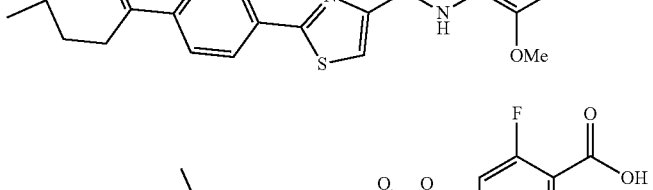 |

-continued
| Compound # | Structure |
|---|---|
| 529 | 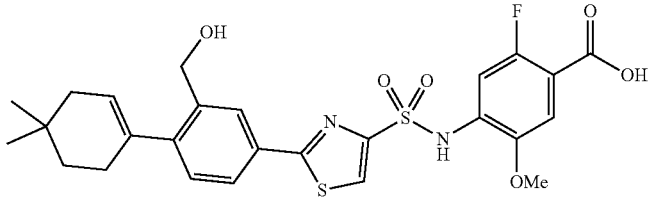 [SMILES: COc1cc(C(=O)O)c(F)cc1NS(=O)(=O)c1csc(-c2ccc(C3=CCC(C)(C)CC3)c(CO)c2)n1] |
| 530 | 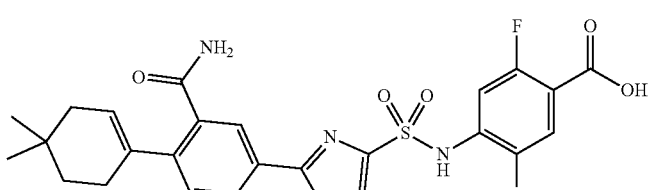 |
| 532 | 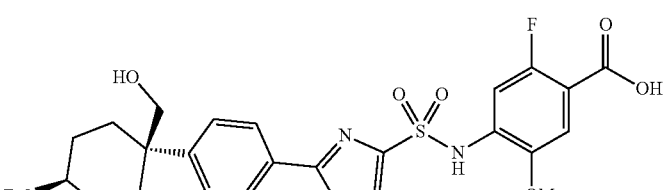 |
| 533 | 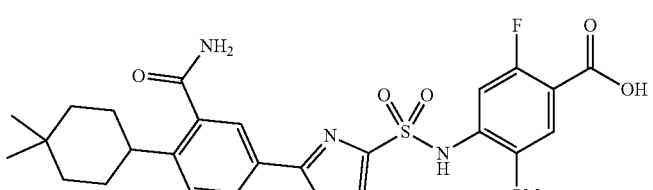 |
| 534 | 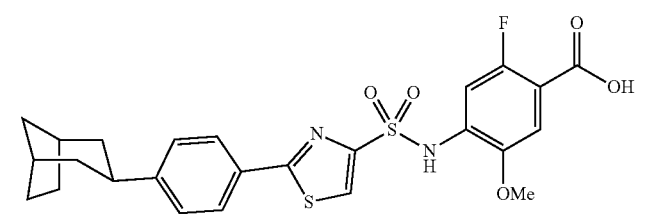 [SMILES: COc1cc(C(=O)O)c(F)cc1NS(=O)(=O)c1csc(-c2ccc(C3CC4CCC(C4)C3)cc2)n1] |
| 535 | 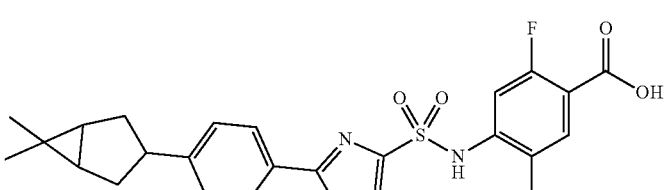 |
| 536 | 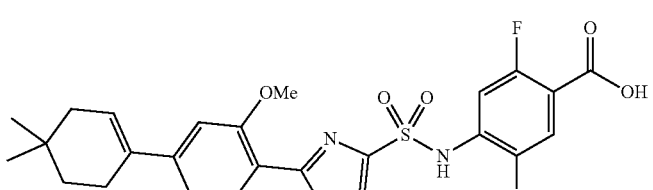 |

-continued

| Compound # | Structure |
|---|---|
| 537 | 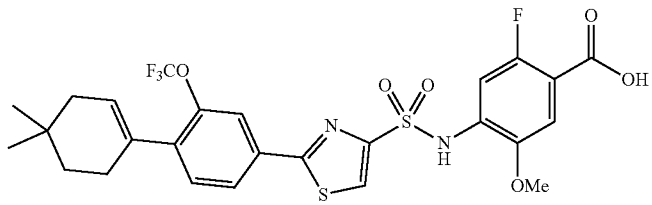 |
| 539 | 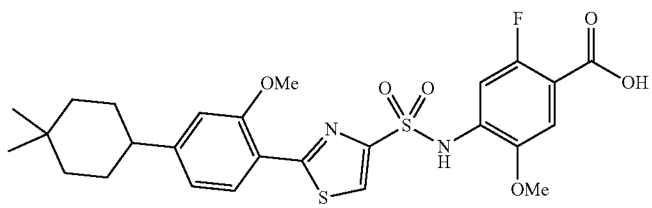 [SMILES: COc1cc(C(=O)O)c(F)cc1NS(=O)(=O)c1csc(-c2ccc(C3CCC(C)(C)CC3)cc2OC)n1] |
| 540 | 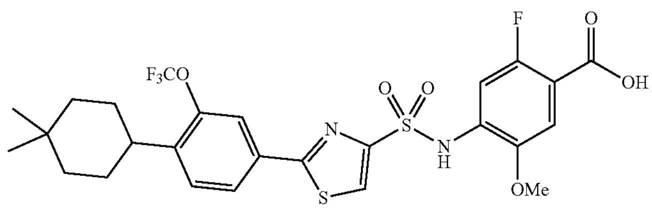 [SMILES: COc1cc(C(=O)O)c(F)cc1NS(=O)(=O)c1csc(-c2ccc(C3CCC(C)(C)CC3)c(OC(F)(F)F)c2)n1] |
| 542 | 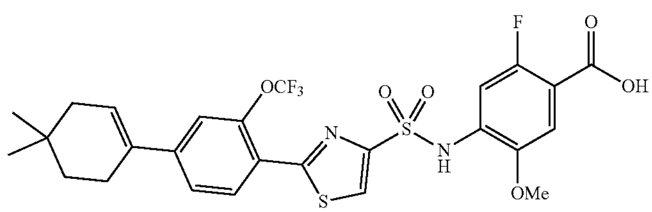 |
| 543 | 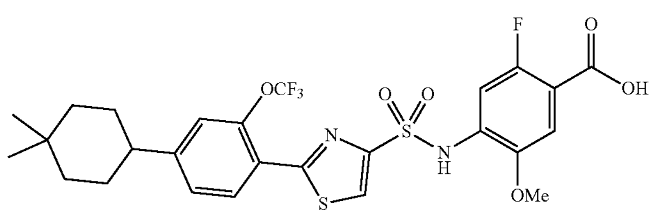 |
| 544 | 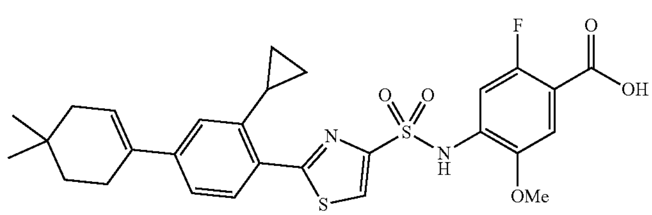 |
| 545 | 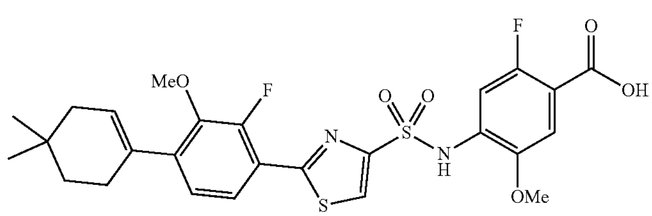 [SMILES: COc1cc(C(=O)O)c(F)cc1NS(=O)(=O)c1csc(-c2ccc(C3=CCC(C)(C)CC3)c(OC)c2F)n1] |

-continued

| Compound # | Structure |
|---|---|
| 546 | 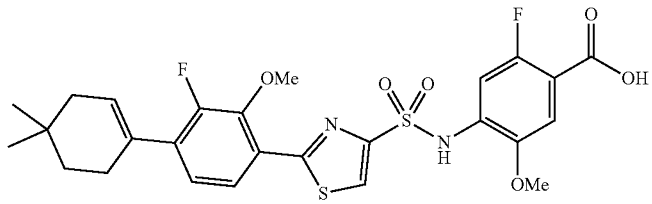 [SMILES: COc1cc(C(=O)O)c(F)cc1NS(=O)(=O)c1csc(-c2ccc(C3=CCC(C)(C)CC3)c(F)c2OC)n1] |
| 547 | 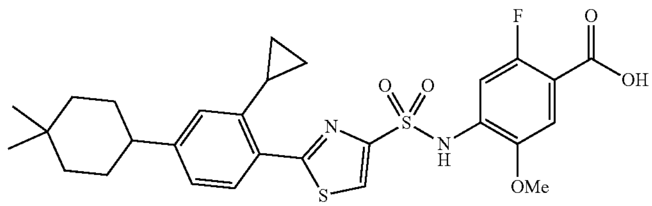 [SMILES: COc1cc(C(=O)O)c(F)cc1NS(=O)(=O)c1csc(-c2ccc(C3CCC(C)(C)CC3)cc2C2CC2)n1] |
| 548 | 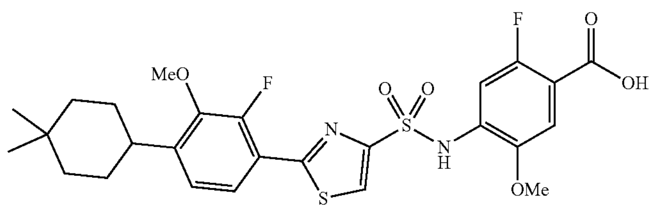 [SMILES: COc1cc(C(=O)O)c(F)cc1NS(=O)(=O)c1csc(-c2ccc(C3CCC(C)(C)CC3)c(OC)c2F)n1] |
| 549 | 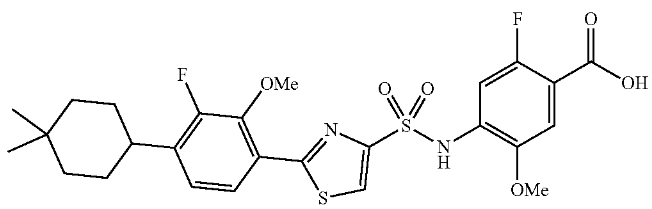 [SMILES: COc1cc(C(=O)O)c(F)cc1NS(=O)(=O)c1csc(-c2ccc(C3CCC(C)(C)CC3)c(F)c2OC)n1] |
| 550 | 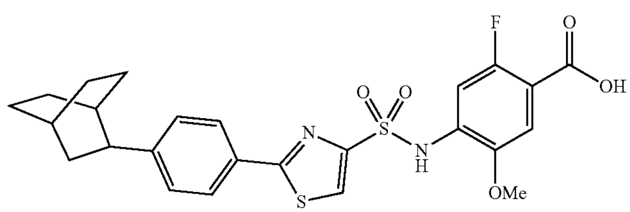 [SMILES: COc1cc(C(=O)O)c(F)cc1NS(=O)(=O)c1csc(-c2ccc(C3CC4CCC3CC4)cc2)n1] |
| 555 | 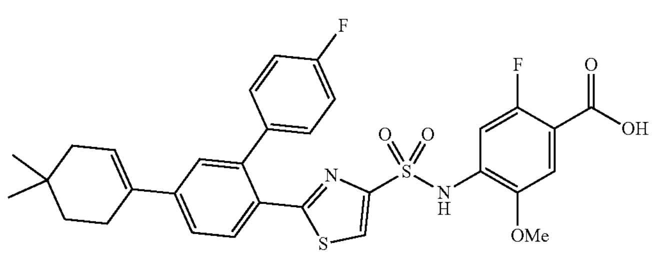 [SMILES: COc1cc(C(=O)O)c(F)cc1NS(=O)(=O)c1csc(-c2ccc(C3=CCC(C)(C)CC3)cc2-c2ccc(F)cc2)n1] |
| 556 | 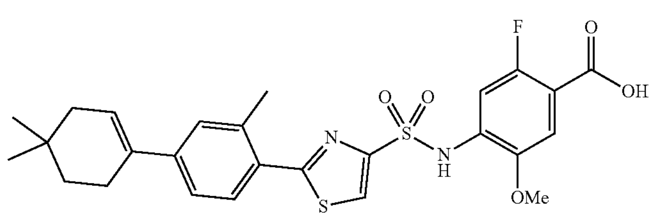 [SMILES: COc1cc(C(=O)O)c(F)cc1NS(=O)(=O)c1csc(-c2ccc(C3=CCC(C)(C)CC3)cc2C)n1] |

US 12,384,753 B2
577                                                                 578
-continued
| Compound # | Structure |
|---|---|
| 557 | 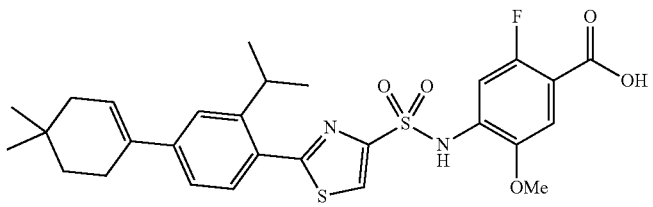 [SMILES: COc1cc(C(=O)O)c(F)cc1NS(=O)(=O)c1csc(-c2ccc(C3=CCC(C)(C)CC3)cc2C(C)C)n1] |
| 558 | 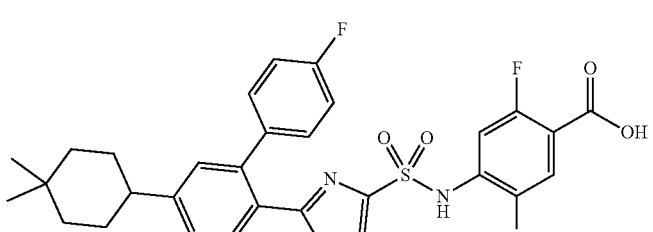 |
| 559 | 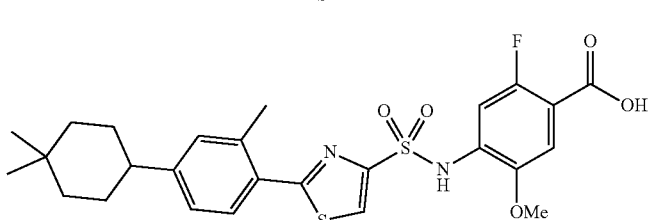 |
| 560 | 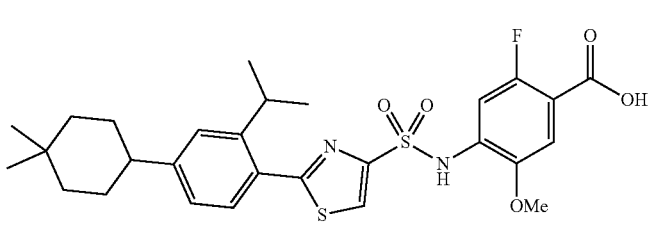 [SMILES: COc1cc(C(=O)O)c(F)cc1NS(=O)(=O)c1csc(-c2ccc(C3CCC(C)(C)CC3)cc2C(C)C)n1] |
| 562 | 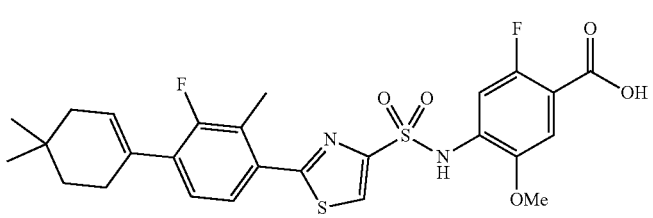 |
| 563 | 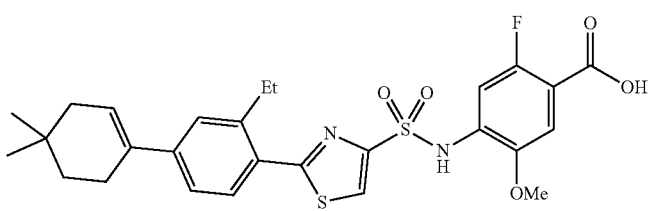 [SMILES: CCc1cc(C2=CCC(C)(C)CC2)ccc1-c1nc(S(=O)(=O)Nc2cc(F)c(C(=O)O)cc2OC)cs1] |
| 564 | 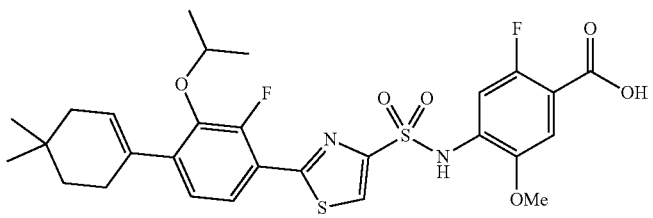 [SMILES: COc1cc(C(=O)O)c(F)cc1NS(=O)(=O)c1csc(-c2ccc(C3=CCC(C)(C)CC3)c(OC(C)C)c2F)n1] |

| Compound # | Structure |
|---|---|
| 566 | 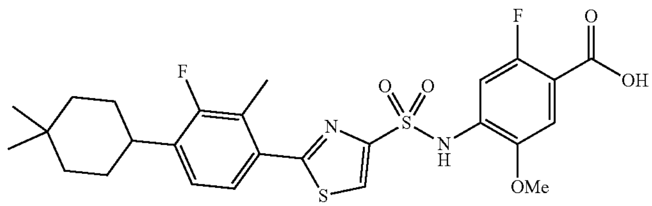 [SMILES: COc1cc(C(=O)O)c(F)cc1NS(=O)(=O)c1csc(-c2ccc(C3CCC(C)(C)CC3)c(F)c2C)n1] |
| 567 | 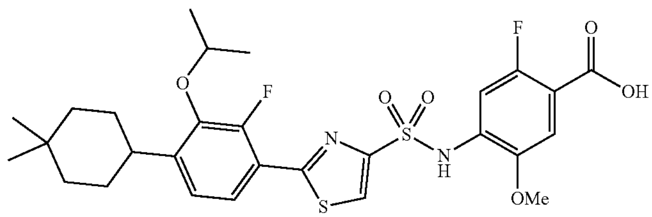 [SMILES: COc1cc(C(=O)O)c(F)cc1NS(=O)(=O)c1csc(-c2ccc(C3CCC(C)(C)CC3)c(OC(C)C)c2F)n1] |
| 568 | 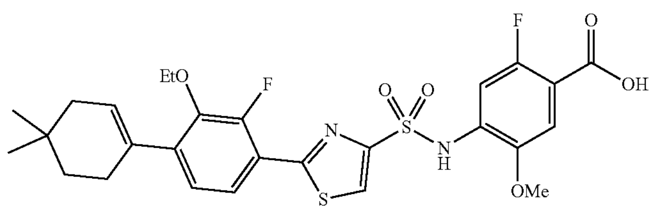 [SMILES: CCOc1c(C2=CCC(C)(C)CC2)ccc(-c2nc(S(=O)(=O)Nc3cc(F)c(C(=O)O)cc3OC)cs2)c1F] |
| 569 | 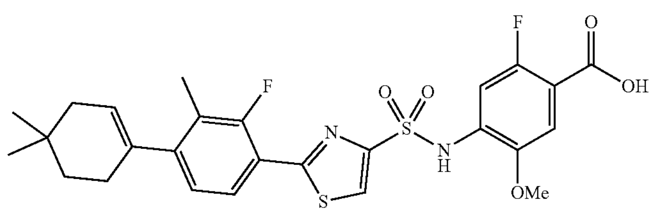 [SMILES: COc1cc(C(=O)O)c(F)cc1NS(=O)(=O)c1csc(-c2ccc(C3=CCC(C)(C)CC3)c(C)c2F)n1] |
| 570 | 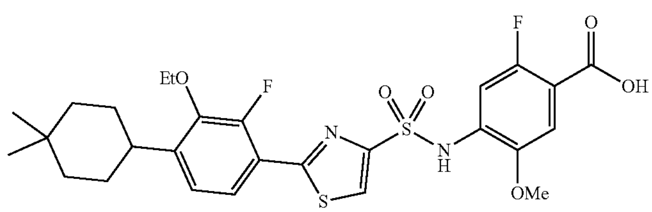 [SMILES: CCOc1c(C2CCC(C)(C)CC2)ccc(-c2nc(S(=O)(=O)Nc3cc(F)c(C(=O)O)cc3OC)cs2)c1F] |
| 571 | 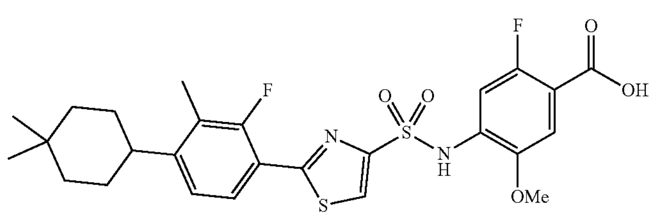 |
| 572 | 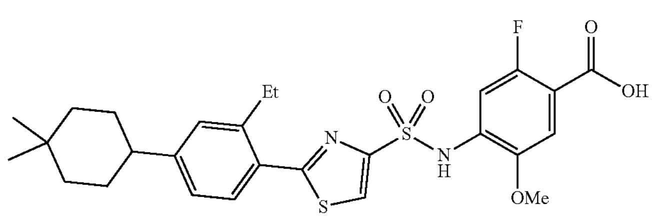 |

| Compound # | Structure |
|---|---|
| 576 | 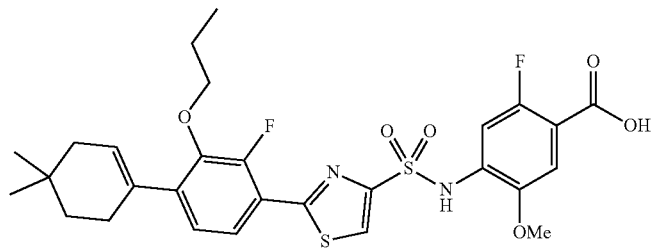 [SMILES: CCCOc1c(C2=CCC(C)(C)CC2)ccc(-c2nc(S(=O)(=O)Nc3cc(F)c(C(=O)O)cc3OC)cs2)c1F] |
| 577 | 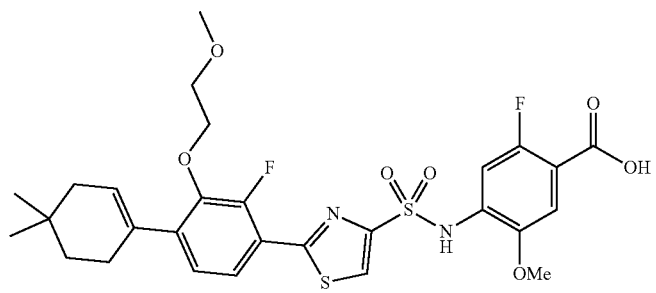 |
| 578 | 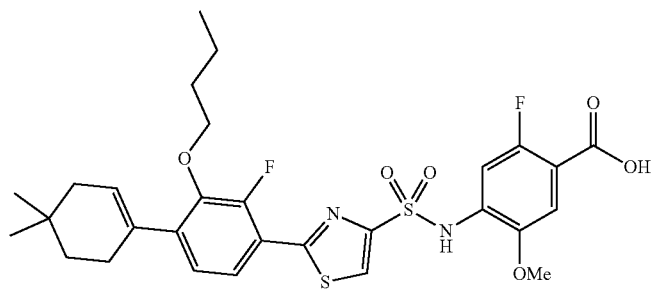 [SMILES: CCCCOc1c(C2=CCC(C)(C)CC2)ccc(-c2nc(S(=O)(=O)Nc3cc(F)c(C(=O)O)cc3OC)cs2)c1F] |
| 579 | 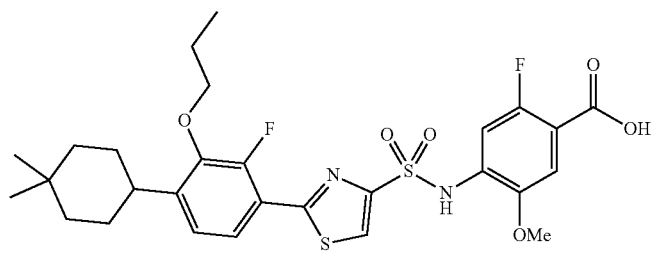 [SMILES: CCCOc1c(C2CCC(C)(C)CC2)ccc(-c2nc(S(=O)(=O)Nc3cc(F)c(C(=O)O)cc3OC)cs2)c1F] |
| 580 | 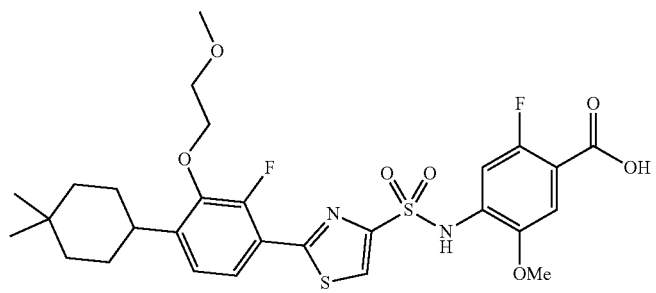 |

| Compound # | Structure |
|---|---|
| 581 | 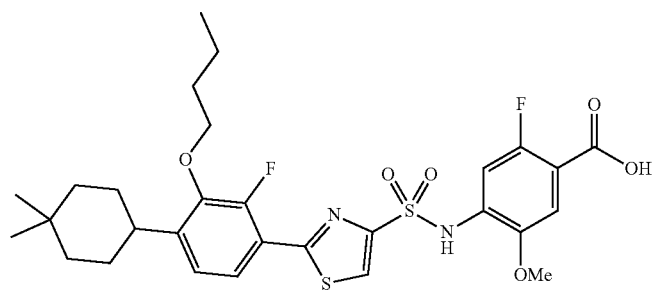 |
| 582 | 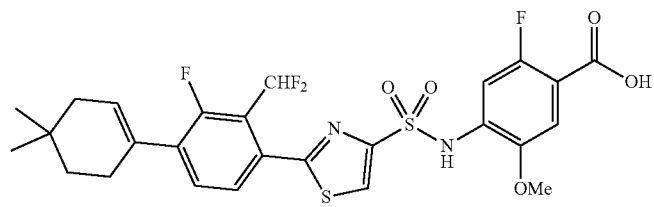 [SMILES: COc1cc(C(=O)O)c(F)cc1NS(=O)(=O)c1csc(-c2ccc(C3=CCC(C)(C)CC3)c(F)c2C(F)F)n1] |
| 583 | 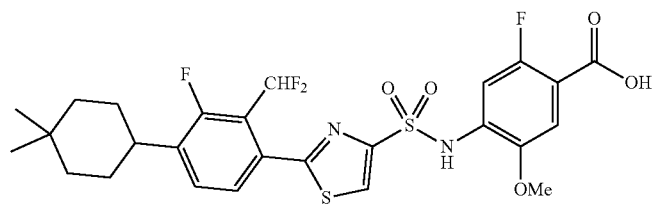 [SMILES: COc1cc(C(=O)O)c(F)cc1NS(=O)(=O)c1csc(-c2ccc(C3CCC(C)(C)CC3)c(F)c2C(F)F)n1] |
| 584 | 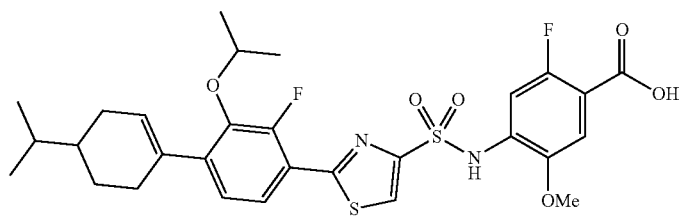 [SMILES: COc1cc(C(=O)O)c(F)cc1NS(=O)(=O)c1csc(-c2ccc(C3=CCC(C(C)C)CC3)c(OC(C)C)c2F)n1] |
| 585 | 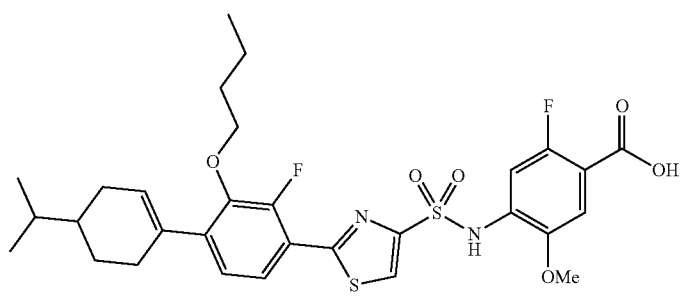 [SMILES: CCCCOc1c(C2=CCC(C(C)C)CC2)ccc(-c2nc(S(=O)(=O)Nc3cc(F)c(C(=O)O)cc3OC)cs2)c1F] |
| 586 | 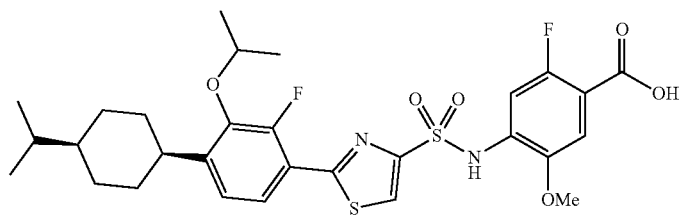 [SMILES: COc1cc(C(=O)O)c(F)cc1NS(=O)(=O)c1csc(-c2ccc([C@H]3CC[C@@H](C(C)C)CC3)c(OC(C)C)c2F)n1] |

| Compound # | Structure |
|---|---|
| 587 | 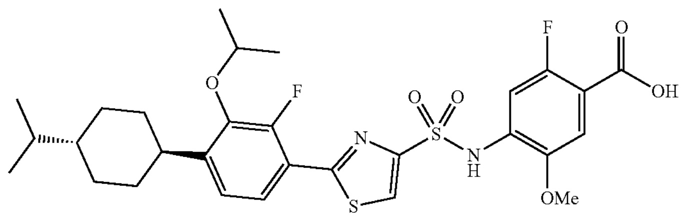 [SMILES: COc1cc(C(=O)O)c(F)cc1NS(=O)(=O)c1csc(-c2ccc([C@H]3CC[C@H](C(C)C)CC3)c(OC(C)C)c2F)n1] |
| 588 | 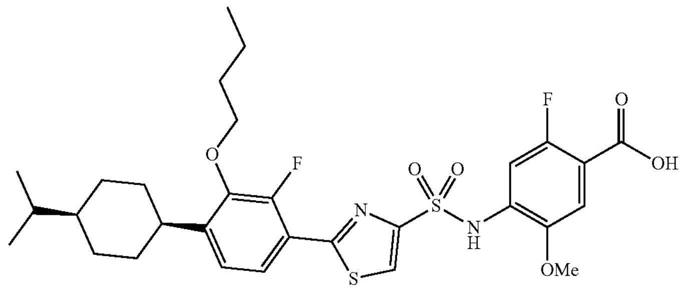 [SMILES: CCCCOc1c(F)c(-c2nc(S(=O)(=O)Nc3cc(F)c(C(=O)O)cc3OC)cs2)ccc1[C@H]1CC[C@@H](C(C)C)CC1] |
| 589 | 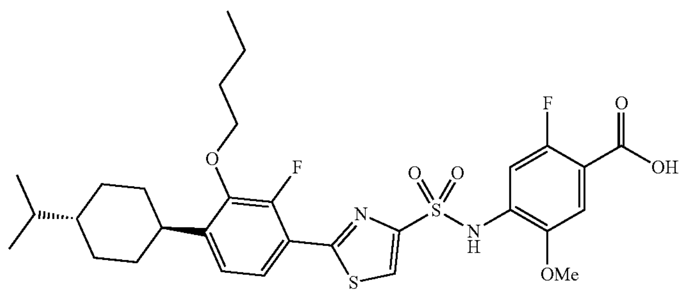 [SMILES: CCCCOc1c(F)c(-c2nc(S(=O)(=O)Nc3cc(F)c(C(=O)O)cc3OC)cs2)ccc1[C@H]1CC[C@H](C(C)C)CC1] |
| 590 | 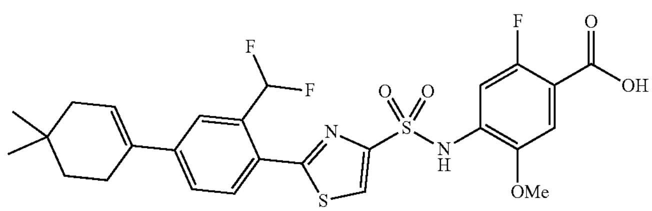 [SMILES: COc1cc(C(=O)O)c(F)cc1NS(=O)(=O)c1csc(-c2ccc(C3=CCC(C)(C)CC3)cc2C(F)F)n1] |
| 591 | 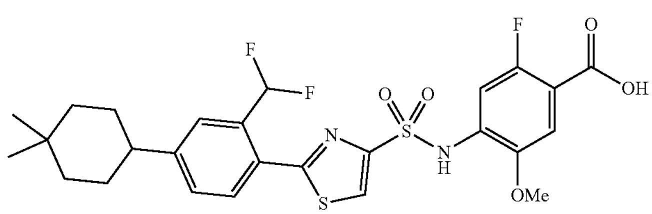 [SMILES: COc1cc(C(=O)O)c(F)cc1NS(=O)(=O)c1csc(-c2ccc(C3CCC(C)(C)CC3)cc2C(F)F)n1] |
| 592 | 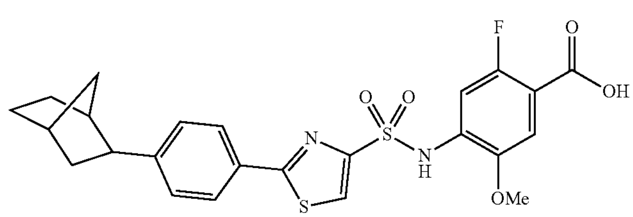 [SMILES: COc1cc(C(=O)O)c(F)cc1NS(=O)(=O)c1csc(-c2ccc(C3CC4CCC3C4)cc2)n1] |

| Compound # | Structure |
|---|---|
| 593 | 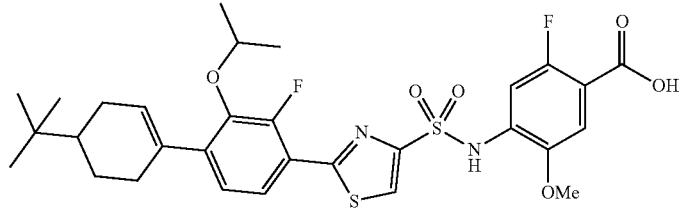 [SMILES: COc1cc(C(=O)O)c(F)cc1NS(=O)(=O)c1csc(-c2ccc(C3=CCC(C(C)(C)C)CC3)c(OC(C)C)c2F)n1] |
| 594 | 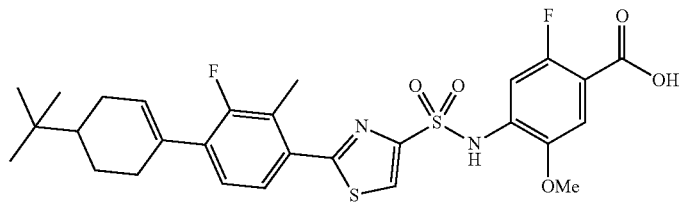 |
| 595 | 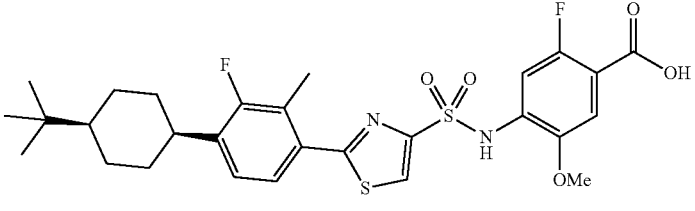 [SMILES: COc1cc(C(=O)O)c(F)cc1NS(=O)(=O)c1csc(-c2ccc([C@H]3CC[C@@H](C(C)(C)C)CC3)c(F)c2C)n1] |
| 596 | 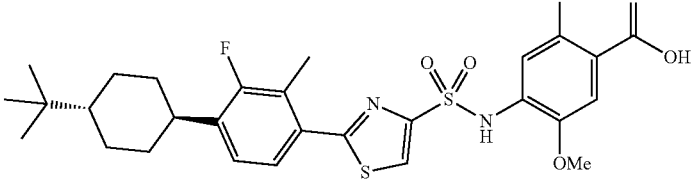 |
| 597 | 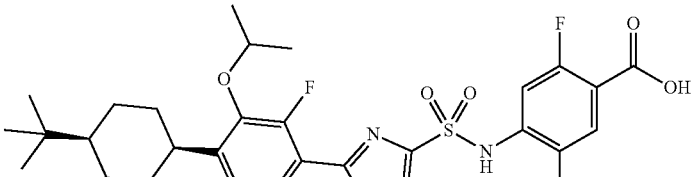 |
| 598 | 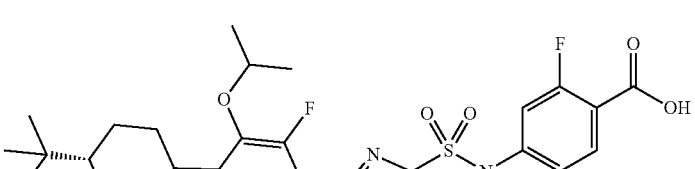 |
| 599 | 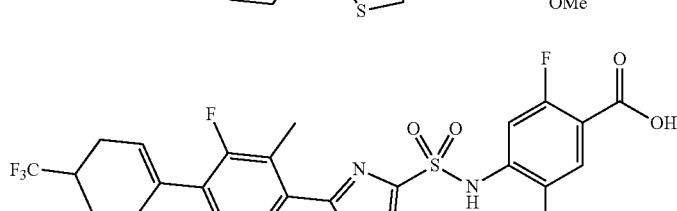 |

-continued

| Compound # | Structure |
|---|---|
| 600 | 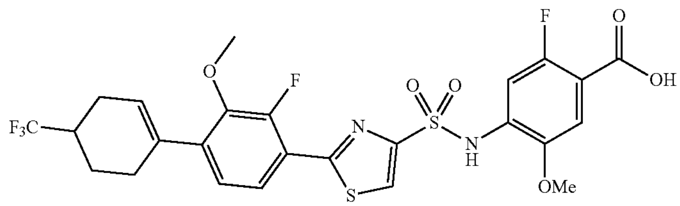 |
| 601 | 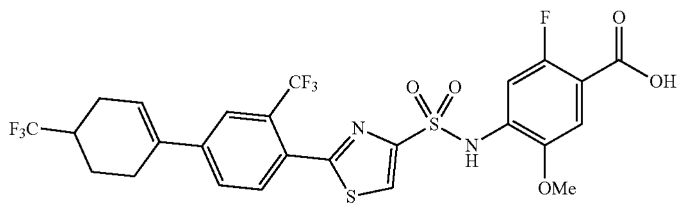 |
| 602 | 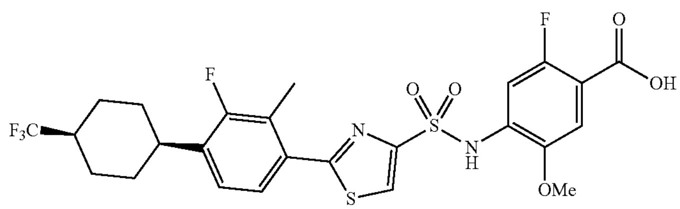 [SMILES: COc1cc(C(=O)O)c(F)cc1NS(=O)(=O)c1csc(-c2ccc([C@H]3CC[C@@H](C(F)(F)F)CC3)c(F)c2C)n1] |
| 603 | 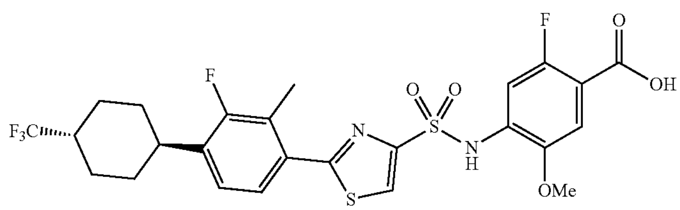 [SMILES: COc1cc(C(=O)O)c(F)cc1NS(=O)(=O)c1csc(-c2ccc([C@H]3CC[C@H](C(F)(F)F)CC3)c(F)c2C)n1] |
| 604 | 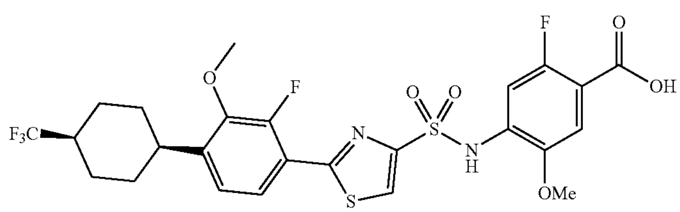 [SMILES: COc1cc(C(=O)O)c(F)cc1NS(=O)(=O)c1csc(-c2ccc([C@H]3CC[C@@H](C(F)(F)F)CC3)c(OC)c2F)n1] |
| 605 | 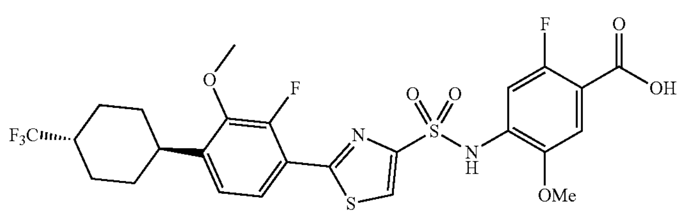 [SMILES: COc1cc(C(=O)O)c(F)cc1NS(=O)(=O)c1csc(-c2ccc([C@H]3CC[C@H](C(F)(F)F)CC3)c(OC)c2F)n1] |
| 606 | 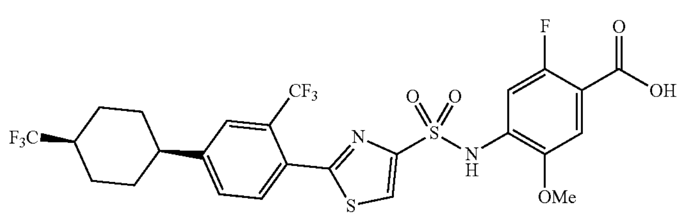 |

-continued

| Compound # | Structure |
|---|---|
| 607 | 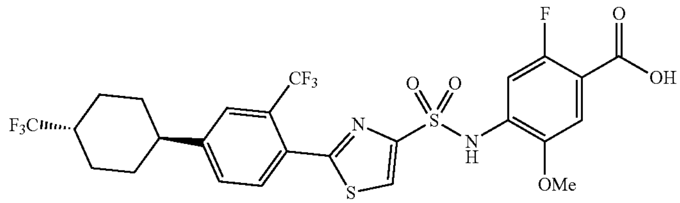 [SMILES: COc1cc(C(=O)O)c(F)cc1NS(=O)(=O)c1csc(-c2ccc([C@H]3CC[C@H](C(F)(F)F)CC3)cc2C(F)(F)F)n1] |
| 608 | 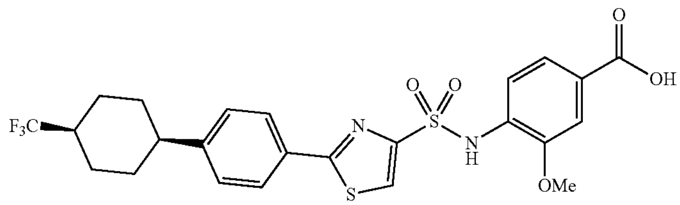 [SMILES: COc1cc(C(=O)O)ccc1NS(=O)(=O)c1csc(-c2ccc([C@H]3CC[C@@H](C(F)(F)F)CC3)cc2)n1] |
| 609 | 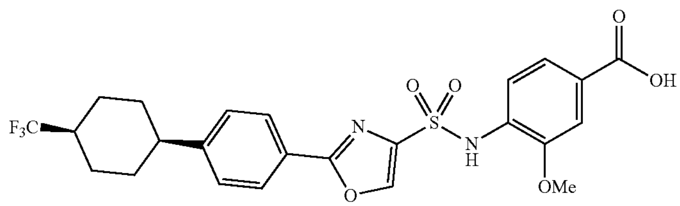 |
| 610 | 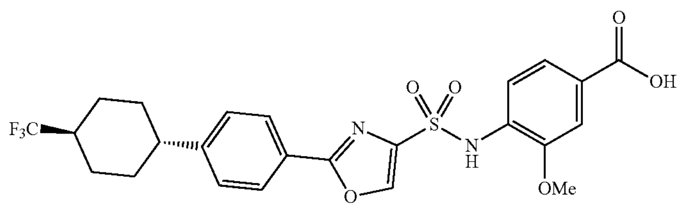 |
| 617 | 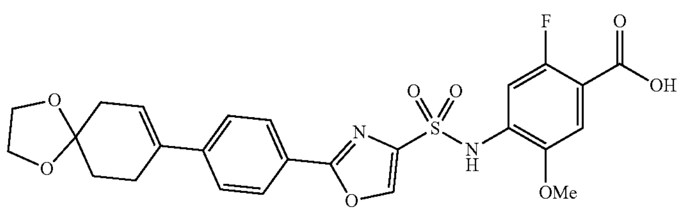 [SMILES: COc1cc(C(=O)O)c(F)cc1NS(=O)(=O)c1coc(-c2ccc(C3=CCC4(CC3)OCCO4)cc2)n1] |
| 618 | 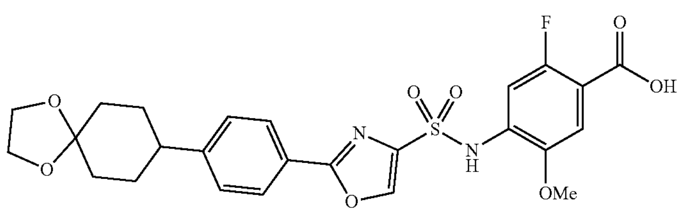 [SMILES: COc1cc(C(=O)O)c(F)cc1NS(=O)(=O)c1coc(-c2ccc(C3CCC4(CC3)OCCO4)cc2)n1] |
| 619 | 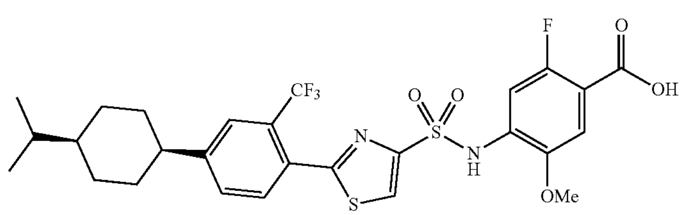 [SMILES: COc1cc(C(=O)O)c(F)cc1NS(=O)(=O)c1csc(-c2ccc([C@H]3CC[C@@H](C(C)C)CC3)cc2C(F)(F)F)n1] |

-continued

| Compound # | Structure |
|---|---|
| 620 | 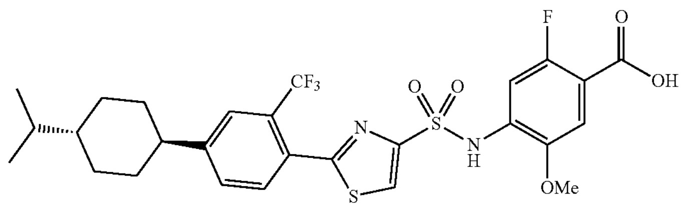 [SMILES: COc1cc(C(=O)O)c(F)cc1NS(=O)(=O)c1csc(-c2ccc([C@H]3CC[C@H](C(C)C)CC3)cc2C(F)(F)F)n1] |
| 622 | 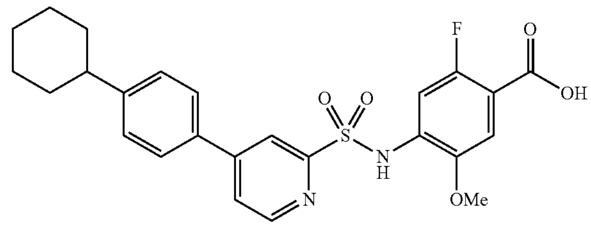 [SMILES: COc1cc(C(=O)O)c(F)cc1NS(=O)(=O)c1cc(-c2ccc(C3CCCCC3)cc2)ccn1] |
| 623 | 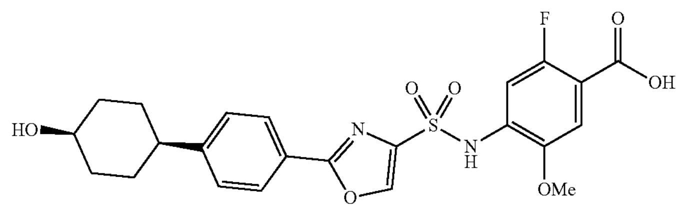 [SMILES: COc1cc(C(=O)O)c(F)cc1NS(=O)(=O)c1coc(-c2ccc([C@H]3CC[C@@H](O)CC3)cc2)n1] |
| 626 | 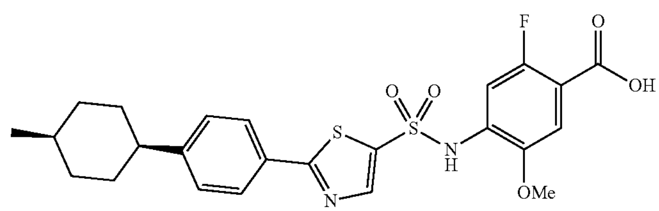 [SMILES: COc1cc(C(=O)O)c(F)cc1NS(=O)(=O)c1cnc(-c2ccc([C@H]3CC[C@@H](C)CC3)cc2)s1] |
| 627 | 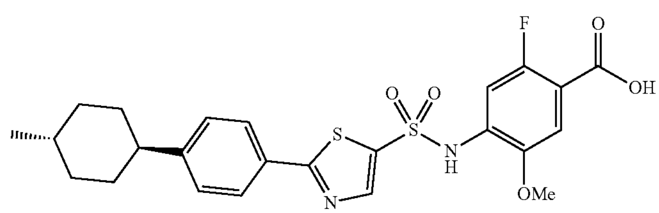 [SMILES: COc1cc(C(=O)O)c(F)cc1NS(=O)(=O)c1cnc(-c2ccc([C@H]3CC[C@H](C)CC3)cc2)s1] |
| 628 | 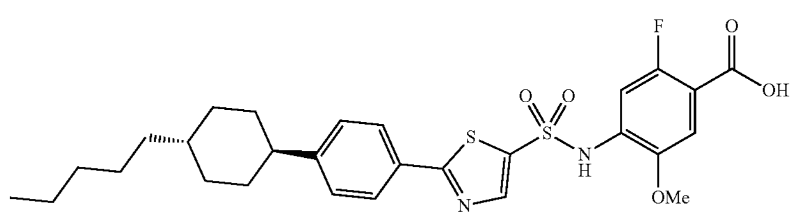 [SMILES: CCCCC[C@H]1CC[C@H](c2ccc(-c3ncc(S(=O)(=O)Nc4cc(F)c(C(=O)O)cc4OC)s3)cc2)CC1] |
| 640 | 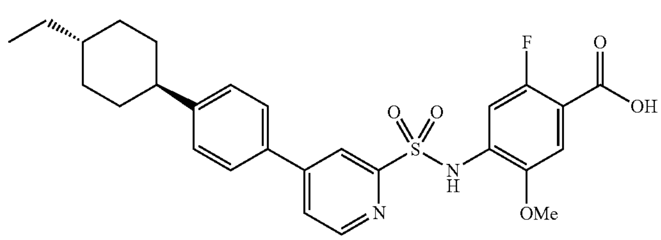 [SMILES: CC[C@H]1CC[C@H](c2ccc(-c3ccnc(S(=O)(=O)Nc4cc(F)c(C(=O)O)cc4OC)c3)cc2)CC1] |

-continued

| Compound # | Structure |
|---|---|
| 641 | (structure) |
| 642 | (structure) |
| 660 | (structure) |
| 665 | (structure) |
| 666 | (structure) |
| 667 | (structure) |
| 671 | (structure) |

| Compound # | Structure |
|---|---|
| 672 | 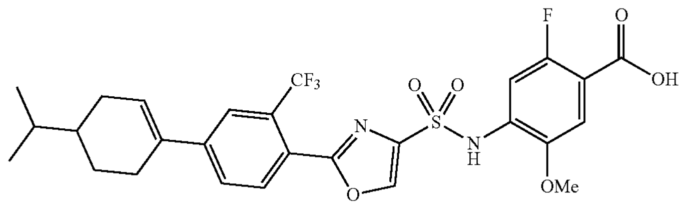 [SMILES: COc1cc(C(=O)O)c(F)cc1NS(=O)(=O)c1coc(-c2ccc(C3=CCC(C(C)C)CC3)cc2C(F)(F)F)n1] |
| 673 | 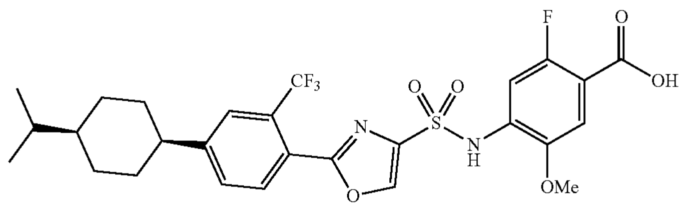 [SMILES: COc1cc(C(=O)O)c(F)cc1NS(=O)(=O)c1coc(-c2ccc([C@H]3CC[C@@H](C(C)C)CC3)cc2C(F)(F)F)n1] |
| 674 | 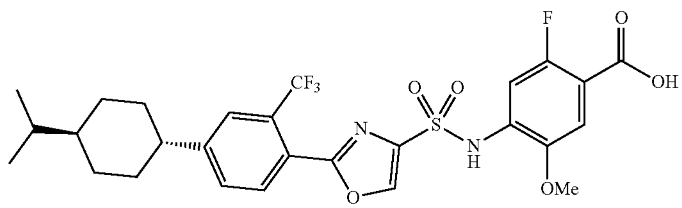 [SMILES: COc1cc(C(=O)O)c(F)cc1NS(=O)(=O)c1coc(-c2ccc([C@H]3CC[C@H](C(C)C)CC3)cc2C(F)(F)F)n1] |
| 675 | 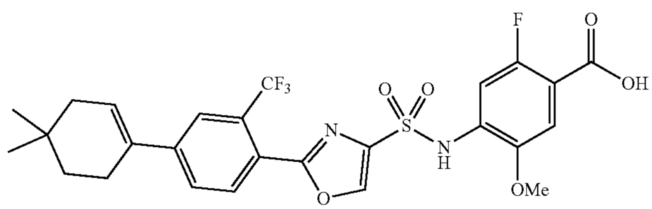 |
| 676 | 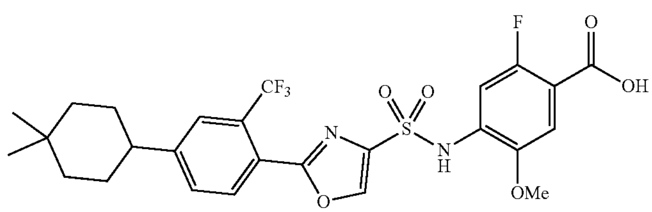 |
| 677 | 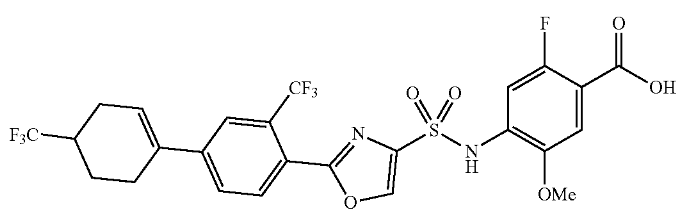 |
| 678 | 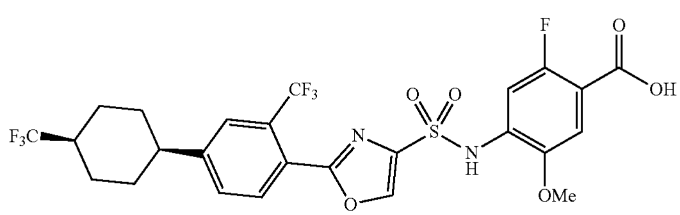 |

-continued

| Compound # | Structure |
|---|---|
| 679 | 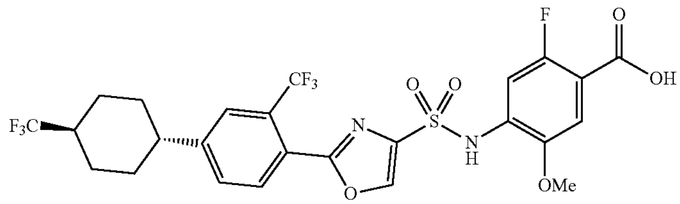 [SMILES: COc1cc(C(=O)O)c(F)cc1NS(=O)(=O)c1coc(-c2ccc([C@H]3CC[C@H](C(F)(F)F)CC3)cc2C(F)(F)F)n1] |
| 680 | 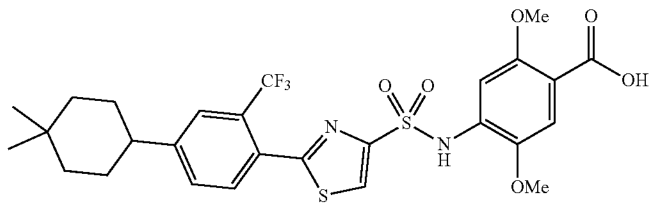 [SMILES: COc1cc(C(=O)O)c(OC)cc1NS(=O)(=O)c1csc(-c2ccc(C3CCC(C)(C)CC3)cc2C(F)(F)F)n1] |
| 681 | 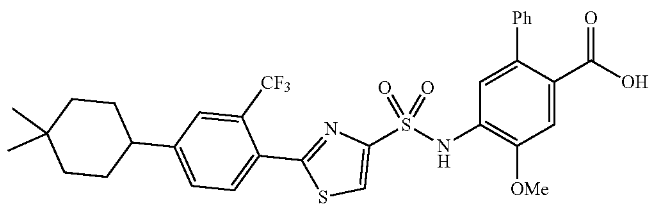 |
| 682 | 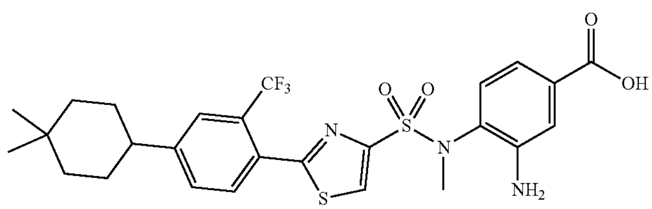 [SMILES: CN(c1ccc(C(=O)O)cc1N)S(=O)(=O)c1csc(-c2ccc(C3CCC(C)(C)CC3)cc2C(F)(F)F)n1] |
| 683 | 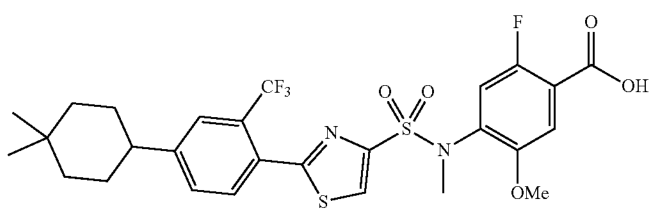 [SMILES: COc1cc(C(=O)O)c(F)cc1N(C)S(=O)(=O)c1csc(-c2ccc(C3CCC(C)(C)CC3)cc2C(F)(F)F)n1] |
| 696 | 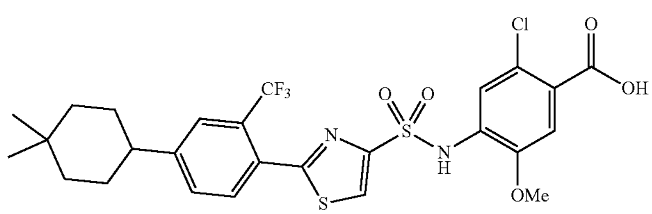 [SMILES: COc1cc(C(=O)O)c(Cl)cc1NS(=O)(=O)c1csc(-c2ccc(C3CCC(C)(C)CC3)cc2C(F)(F)F)n1] |
| 697 | 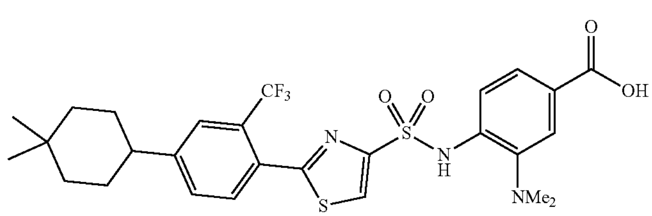 [SMILES: CN(C)c1cc(C(=O)O)ccc1NS(=O)(=O)c1csc(-c2ccc(C3CCC(C)(C)CC3)cc2C(F)(F)F)n1] |

-continued

| Compound # | Structure |
|---|---|
| 698 | 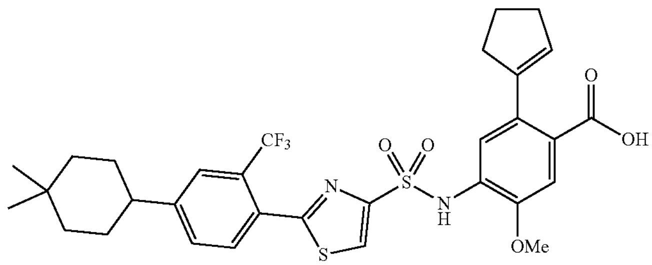 [SMILES: COc1cc(C(=O)O)c(C2=CCCC2)cc1NS(=O)(=O)c1csc(-c2ccc(C3CCC(C)(C)CC3)cc2C(F)(F)F)n1] |
| 699 | 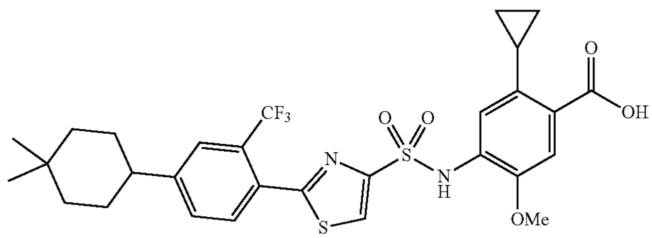 [SMILES: COc1cc(C(=O)O)c(C2CC2)cc1NS(=O)(=O)c1csc(-c2ccc(C3CCC(C)(C)CC3)cc2C(F)(F)F)n1] |
| 702 | 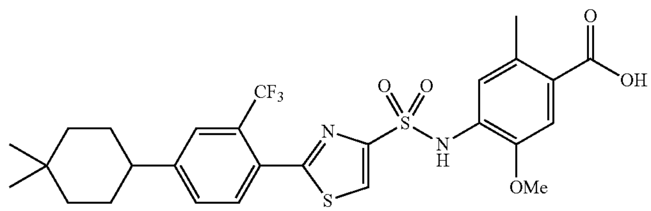 [SMILES: COc1cc(C(=O)O)c(C)cc1NS(=O)(=O)c1csc(-c2ccc(C3CCC(C)(C)CC3)cc2C(F)(F)F)n1] |
| 705 | 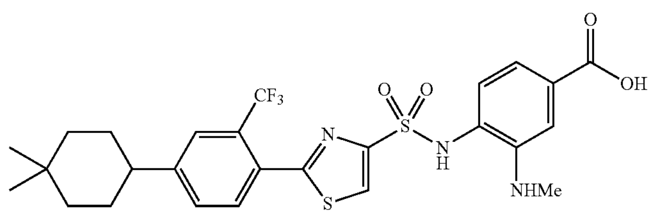 [SMILES: CNc1cc(C(=O)O)ccc1NS(=O)(=O)c1csc(-c2ccc(C3CCC(C)(C)CC3)cc2C(F)(F)F)n1] |
| 706 | 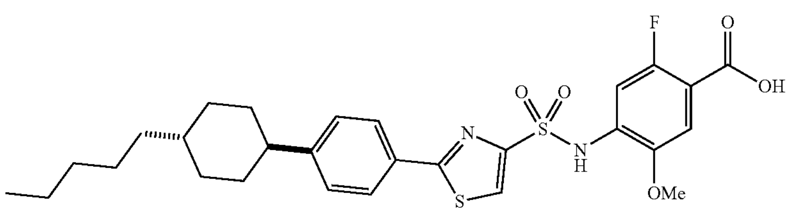 |
| 707 | 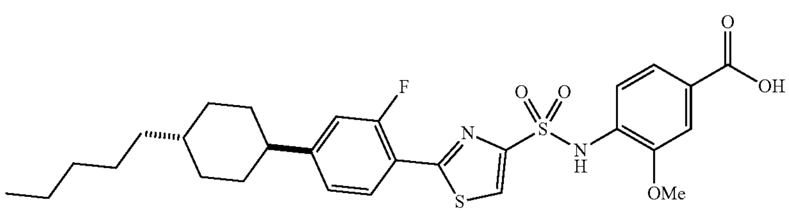 |
| 708 | 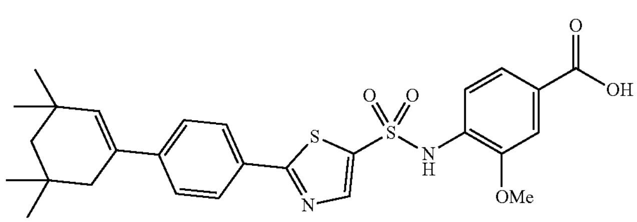 [SMILES: COc1cc(C(=O)O)ccc1NS(=O)(=O)c1cnc(-c2ccc(C3=CC(C)(C)CC(C)(C)C3)cc2)s1] |

-continued

| Compound # | Structure |
|---|---|
| 709 | 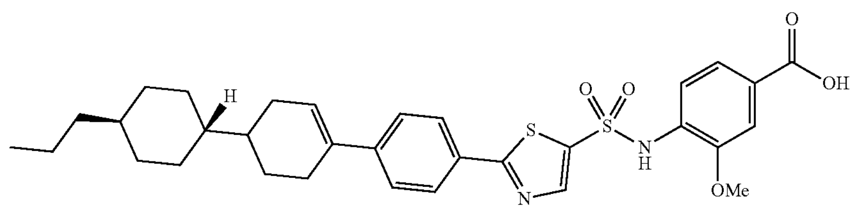 [SMILES: CCC[C@H]1CC[C@H](C2CC=C(c3ccc(-c4ncc(S(=O)(=O)Nc5ccc(C(=O)O)cc5OC)s4)cc3)CC2)CC1] |
| 711 | 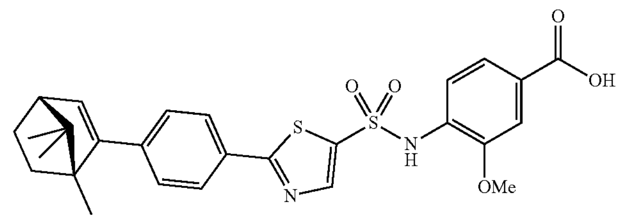 [SMILES: COc1cc(C(=O)O)ccc1NS(=O)(=O)c1cnc(-c2ccc(C3=C[C@H]4CC[C@]3(C)C4(C)C)cc2)s1] |
| 712 | 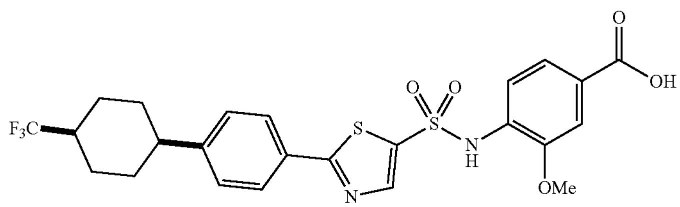 |
| 713 | 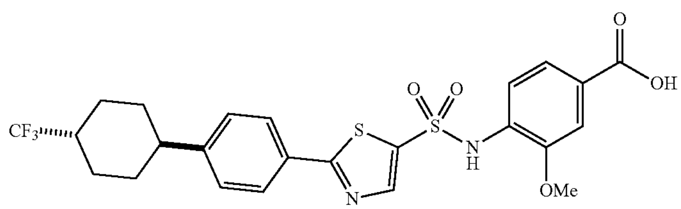 |
| 715 | 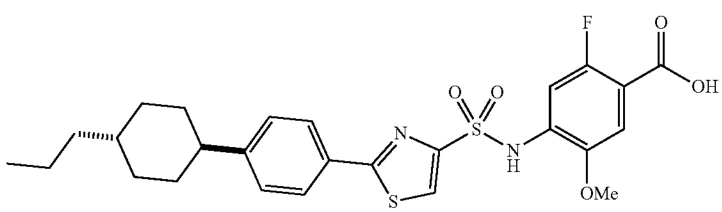 |
| 716 | 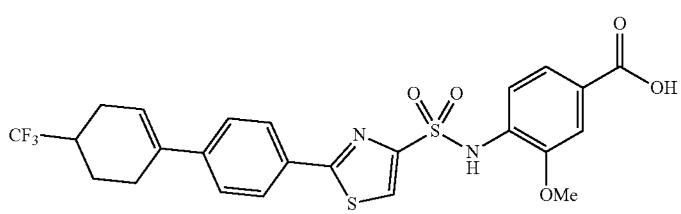 |
| 717 | 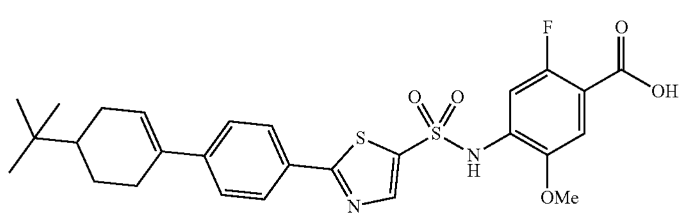 [SMILES: COc1cc(C(=O)O)c(F)cc1NS(=O)(=O)c1cnc(-c2ccc(C3=CCC(C(C)(C)C)CC3)cc2)s1] |

-continued
| Compound # | Structure |
|---|---|
| 719 | 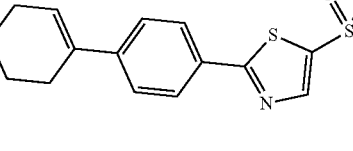 |
| 720 | 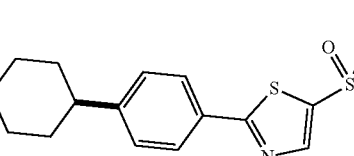 |
| 721 | 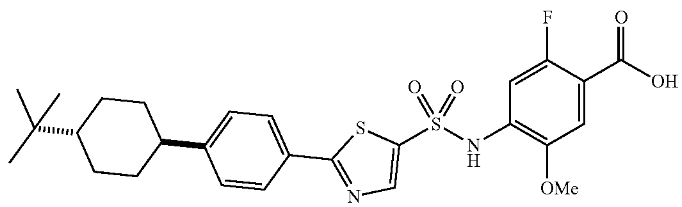 |
| 722 | 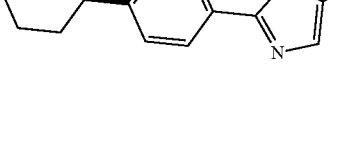 |
| 723 | 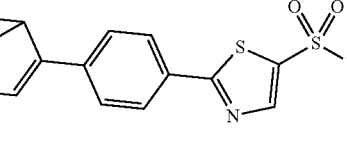 |
| 724 | 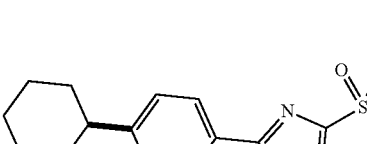 |
| 725 | 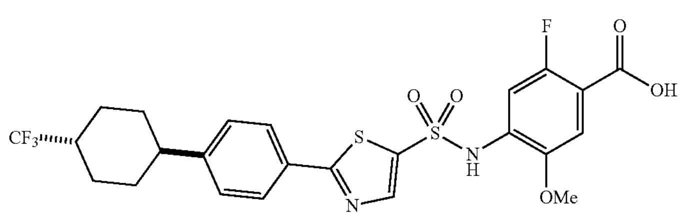 |

-continued

| Compound # | Structure |
|---|---|
| 726 | 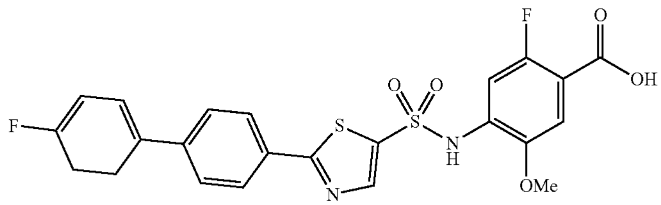 [SMILES: COc1cc(C(=O)O)c(F)cc1NS(=O)(=O)c1cnc(-c2ccc(C3=CC=C(F)CC3)cc2)s1] |
| 727 | 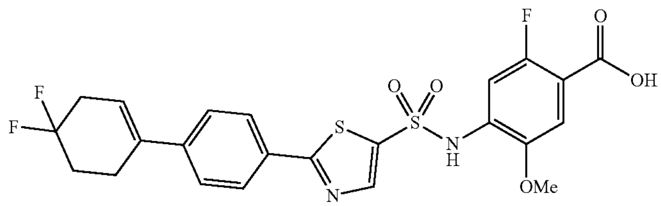 [SMILES: COc1cc(C(=O)O)c(F)cc1NS(=O)(=O)c1cnc(-c2ccc(C3=CCC(F)(F)CC3)cc2)s1] |
| 728 | 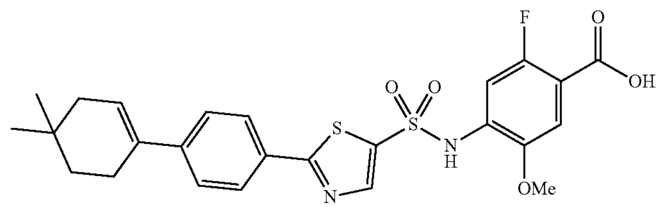 [SMILES: COc1cc(C(=O)O)c(F)cc1NS(=O)(=O)c1cnc(-c2ccc(C3=CCC(C)(C)CC3)cc2)s1] |
| 729 | 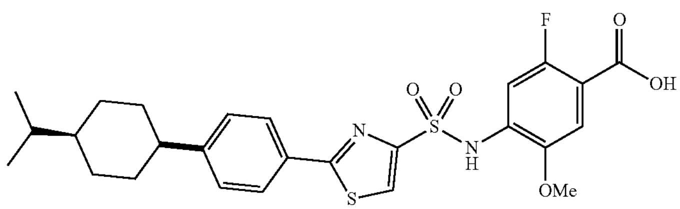 |
| 730 | 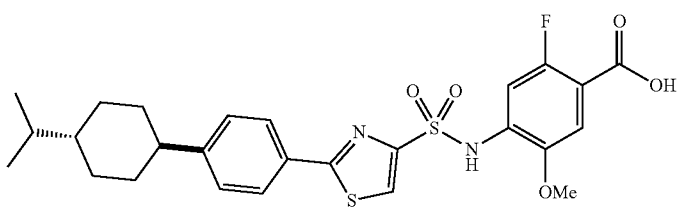 |
| 732 | 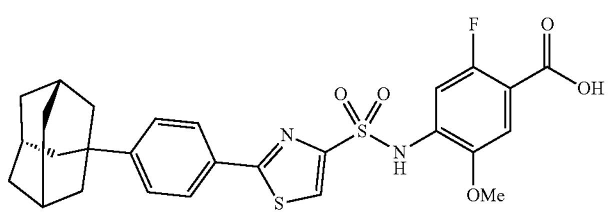 [SMILES: COc1cc(C(=O)O)c(F)cc1NS(=O)(=O)c1csc(-c2ccc(C34CC5C[C@H](C3)C[C@H](C5)C4)cc2)n1] |
| 736 | 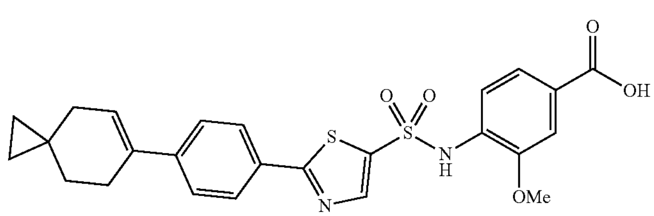 |

-continued

| Compound # | Structure |
|---|---|
| 741 | 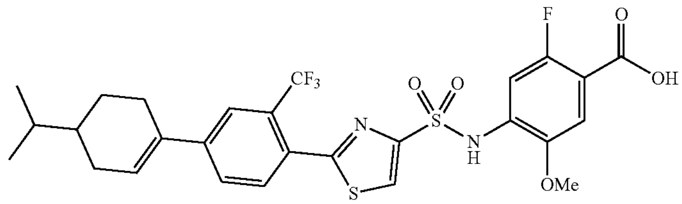 [SMILES: COc1cc(C(=O)O)c(F)cc1NS(=O)(=O)c1csc(-c2ccc(C3=CCC(C(C)C)CC3)cc2C(F)(F)F)n1] |
| 746 | 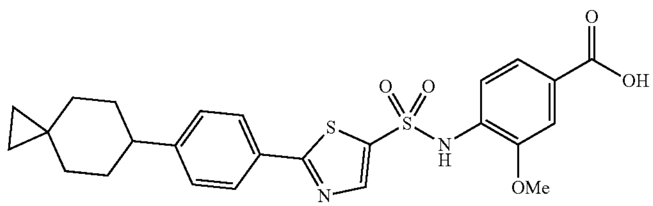 [SMILES: COc1cc(C(=O)O)ccc1NS(=O)(=O)c1cnc(-c2ccc(C3CCC4(CC3)CC4)cc2)s1] |
| 747 | 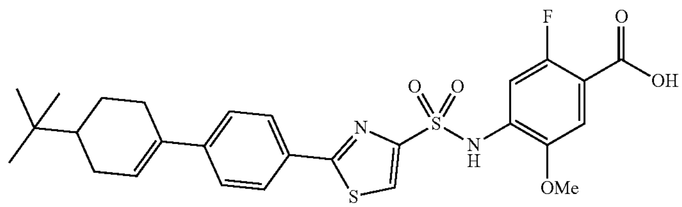 [SMILES: COc1cc(C(=O)O)c(F)cc1NS(=O)(=O)c1csc(-c2ccc(C3=CCC(C(C)(C)C)CC3)cc2)n1] |
| 748 | 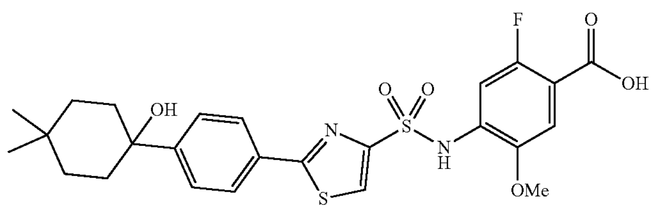 [SMILES: COc1cc(C(=O)O)c(F)cc1NS(=O)(=O)c1csc(-c2ccc(C3(O)CCC(C)(C)CC3)cc2)n1] |
| 755 | 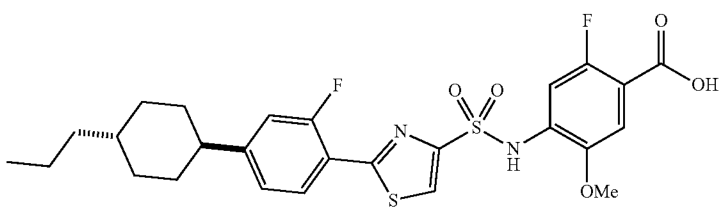 |
| 758 | 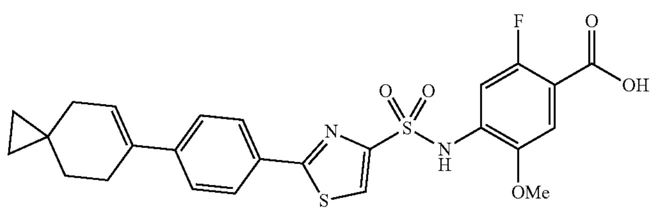 [SMILES: COc1cc(C(=O)O)c(F)cc1NS(=O)(=O)c1csc(-c2ccc(C3=CCC4(CC3)CC4)cc2)n1] |
| 759 | 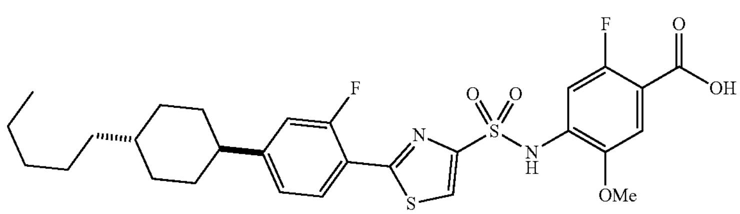 |

| Compound # | Structure |
|---|---|
| 761 | 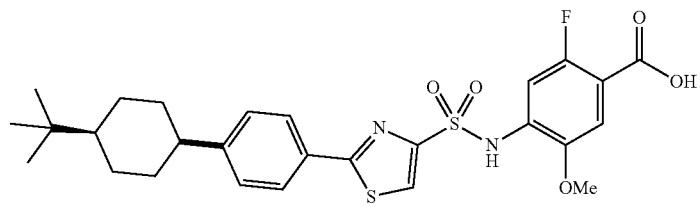 |
| 762 | 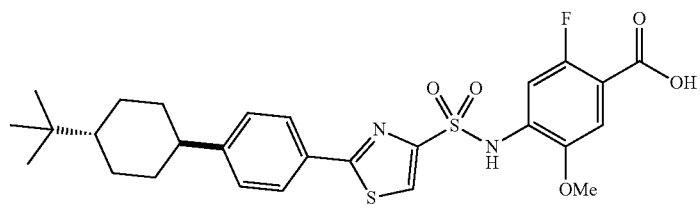 |
| 764 | 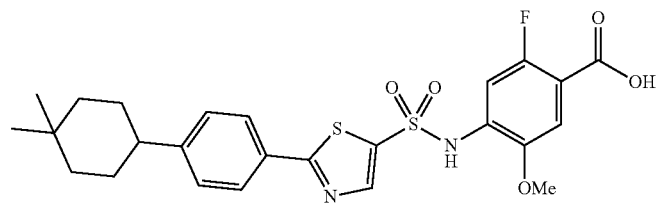 |
| 765 | 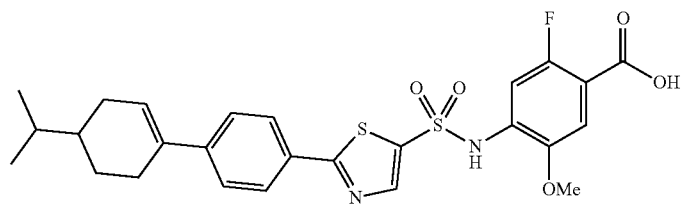 [SMILES: COc1cc(C(=O)O)c(F)cc1NS(=O)(=O)c1cnc(-c2ccc(C3=CCC(C(C)C)CC3)cc2)s1] |
| 768 | 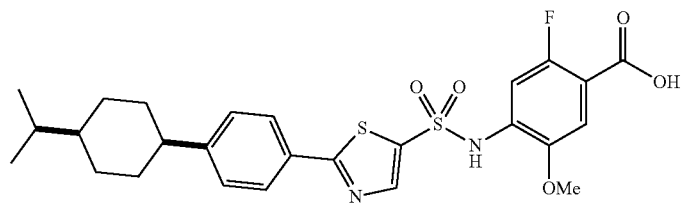 |
| 769 | 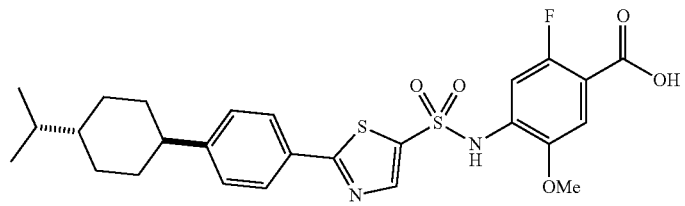 |
| 771 | 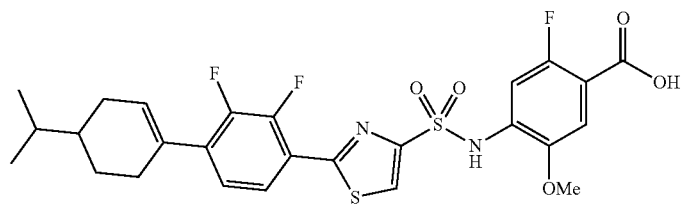 [SMILES: COc1cc(C(=O)O)c(F)cc1NS(=O)(=O)c1csc(-c2ccc(C3=CCC(C(C)C)CC3)c(F)c2F)n1] |

| Compound # | Structure |
|---|---|
| 772 | 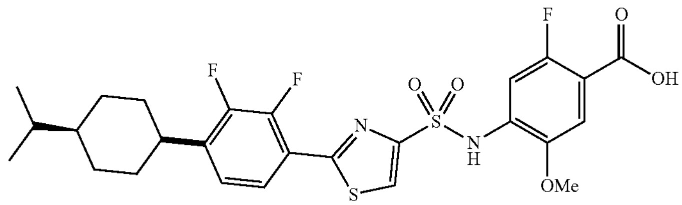 |
| 773 | 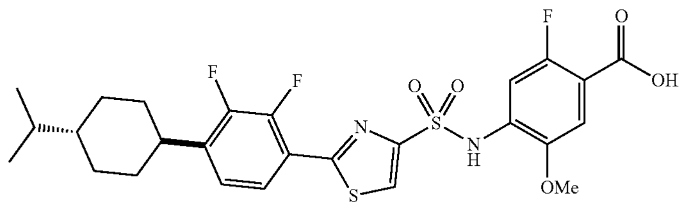 |
| 774 | 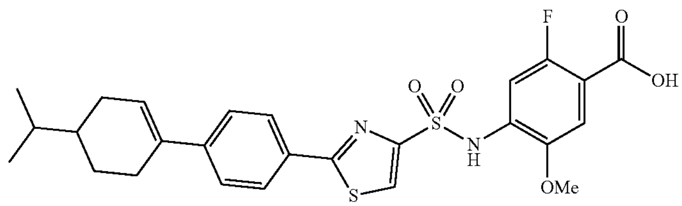 [SMILES: COc1cc(C(=O)O)c(F)cc1NS(=O)(=O)c1csc(-c2ccc(C3=CCC(C(C)C)CC3)cc2)n1] |
| 776 | 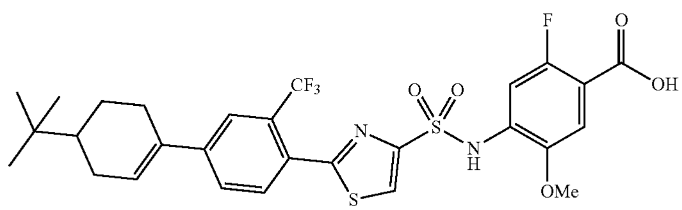 [SMILES: COc1cc(C(=O)O)c(F)cc1NS(=O)(=O)c1csc(-c2ccc(C3=CCC(C(C)(C)C)CC3)cc2C(F)(F)F)n1] |
| 778 | 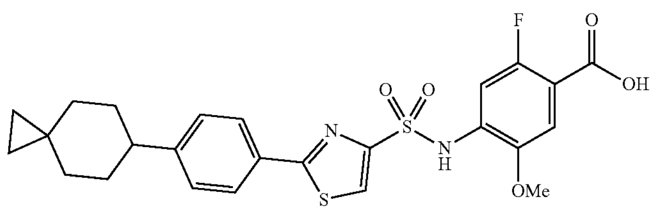 [SMILES: COc1cc(C(=O)O)c(F)cc1NS(=O)(=O)c1csc(-c2ccc(C3CCC4(CC3)CC4)cc2)n1] |
| 780 | 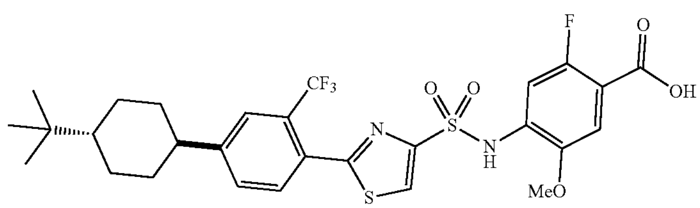 |
| 782 | 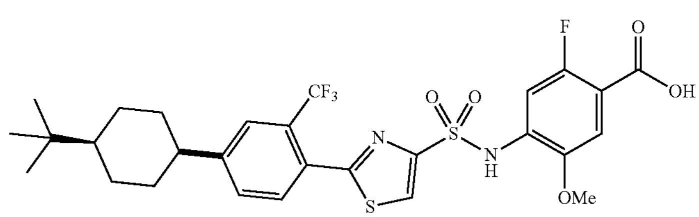 |

| Compound # | Structure |
|---|---|
| 785 | 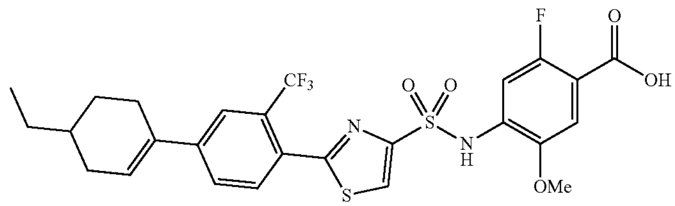 [SMILES: CCC1CC=C(c2ccc(-c3nc(S(=O)(=O)Nc4cc(F)c(C(=O)O)cc4OC)cs3)c(C(F)(F)F)c2)CC1] |
| 786 | 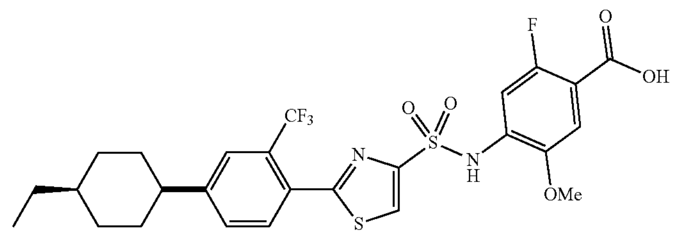 |
| 787 | 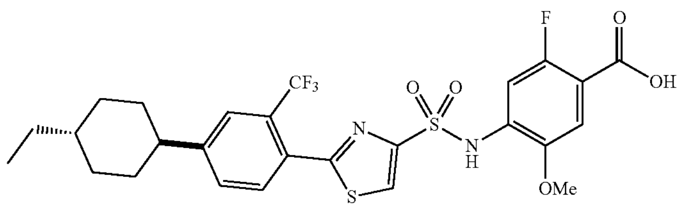 |
| 799 | 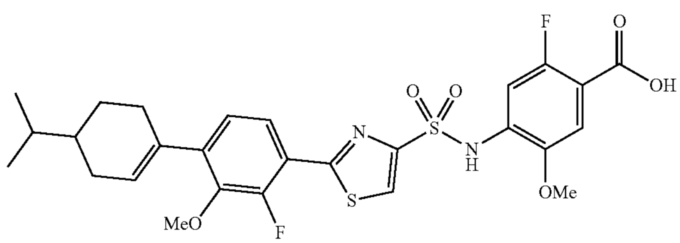 |
| 802 | 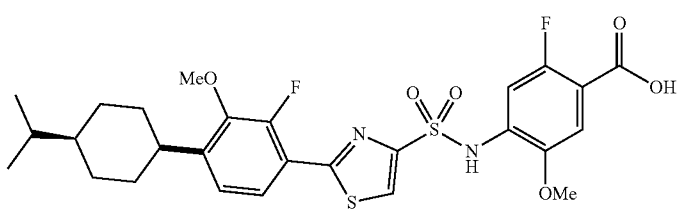 |
| 803 | 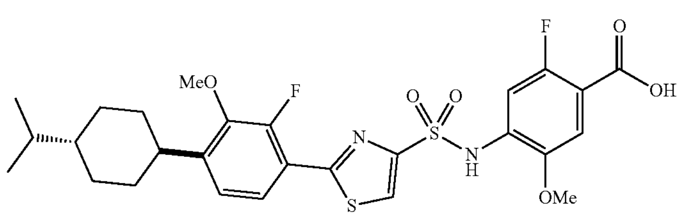 |
| 805 | 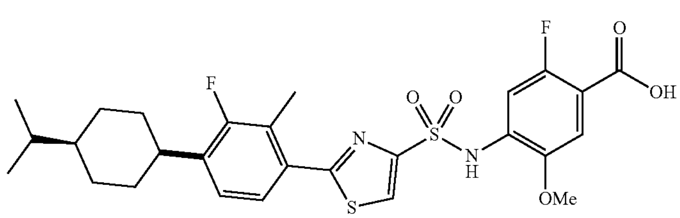 |

-continued

| Compound # | Structure |
|---|---|
| 806 | 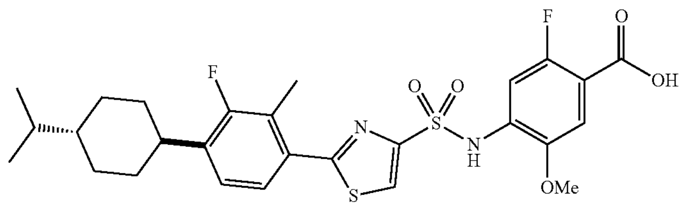 |
| 807 | 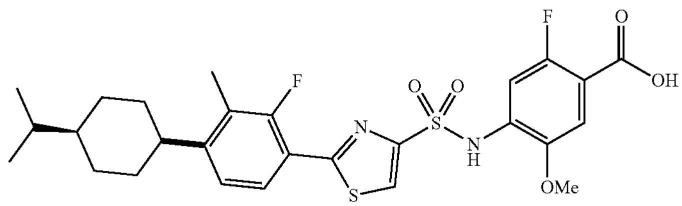 |
| 808 | 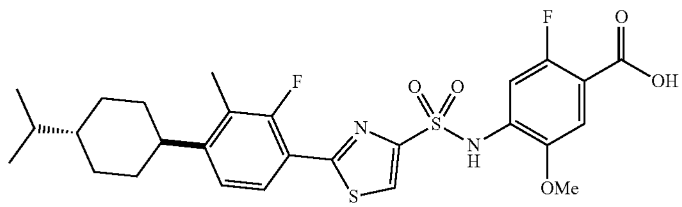 |
| 809 | 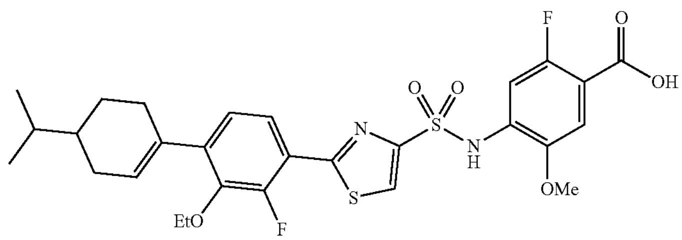 [SMILES: CCOc1c(C2=CCC(C(C)C)CC2)ccc(-c2nc(S(=O)(=O)Nc3cc(F)c(C(=O)O)cc3OC)cs2)c1F] |
| 810 | 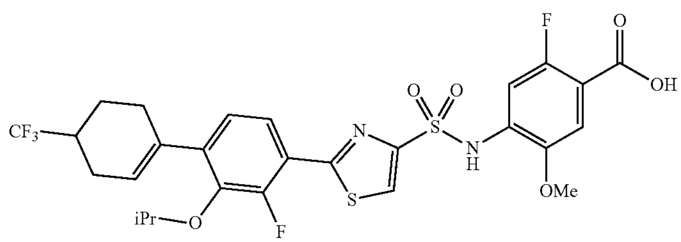 [SMILES: COc1cc(C(=O)O)c(F)cc1NS(=O)(=O)c1csc(-c2ccc(C3=CCC(C(F)(F)F)CC3)c(OC(C)C)c2F)n1] |
| 811 | 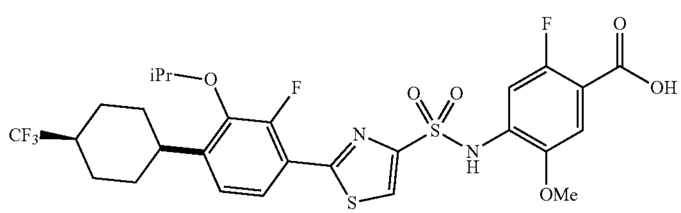 |
| 812 | 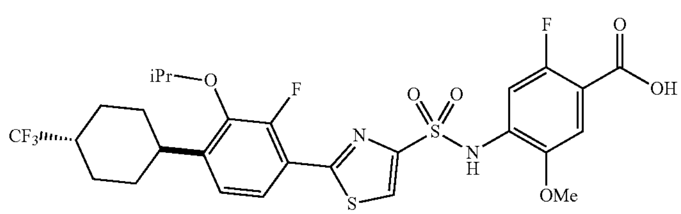 |

| Compound # | Structure |
|---|---|
| 813 | 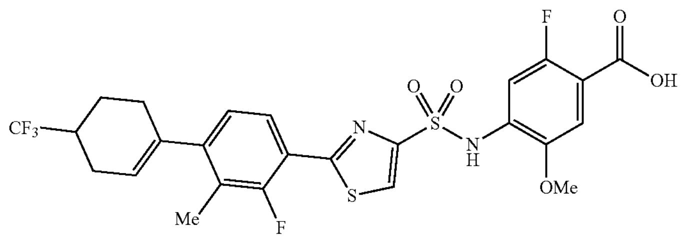 [SMILES: COc1cc(C(=O)O)c(F)cc1NS(=O)(=O)c1csc(-c2ccc(C3=CCC(C(F)(F)F)CC3)c(C)c2F)n1] |
| 814 | 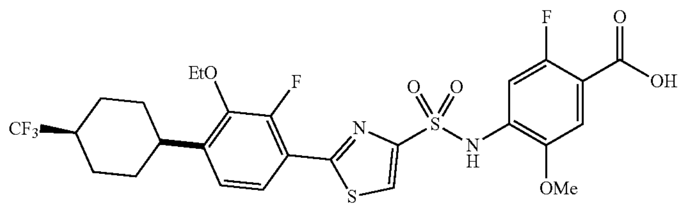 |
| 815 | 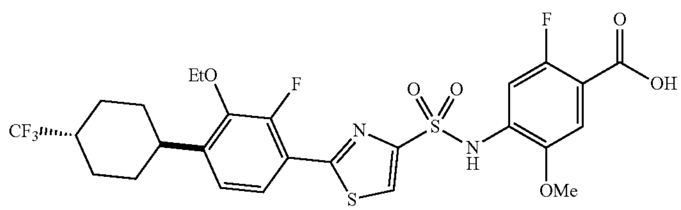 |
| 816 | 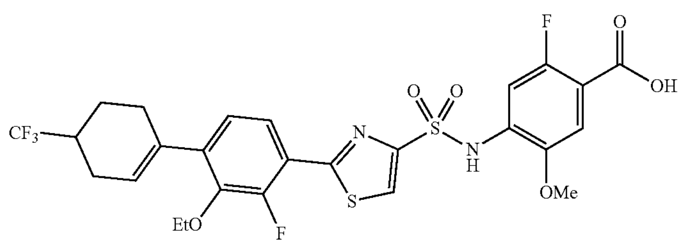 |
| 817 | 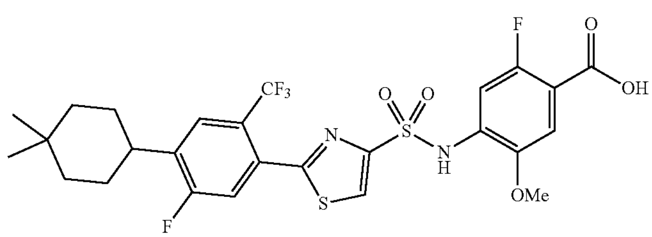 [SMILES: COc1cc(C(=O)O)c(F)cc1NS(=O)(=O)c1csc(-c2cc(F)c(C3CCC(C)(C)CC3)cc2C(F)(F)F)n1] |
| 818 | 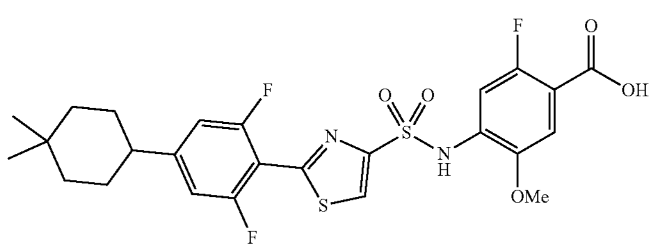 [SMILES: COc1cc(C(=O)O)c(F)cc1NS(=O)(=O)c1csc(-c2c(F)cc(C3CCC(C)(C)CC3)cc2F)n1] |

-continued

| Compound # | Structure |
|---|---|
| 819 | 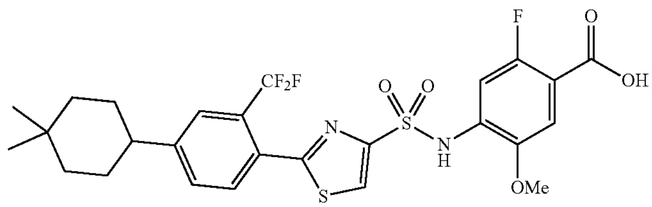 |
| 820 | 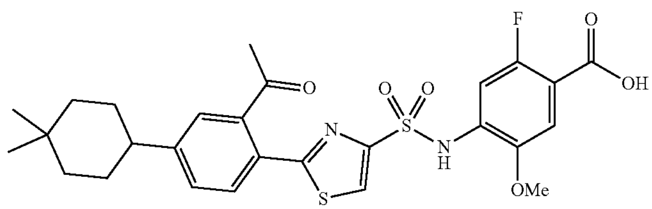 [SMILES: COc1cc(C(=O)O)c(F)cc1NS(=O)(=O)c1csc(-c2ccc(C3CCC(C)(C)CC3)cc2C(C)=O)n1] |
| 821 | 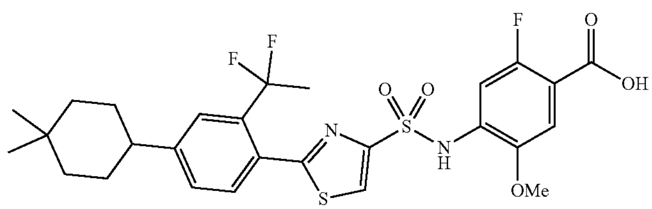 [SMILES: COc1cc(C(=O)O)c(F)cc1NS(=O)(=O)c1csc(-c2ccc(C3CCC(C)(C)CC3)cc2C(C)(F)F)n1] |
| 822 | 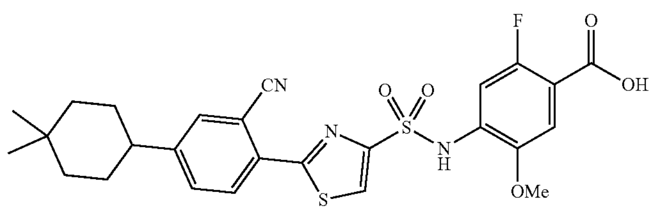 |
| 823 | 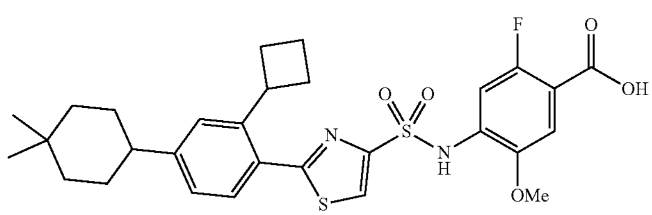 [SMILES: COc1cc(C(=O)O)c(F)cc1NS(=O)(=O)c1csc(-c2ccc(C3CCC(C)(C)CC3)cc2C2CCC2)n1] |
| 830 | 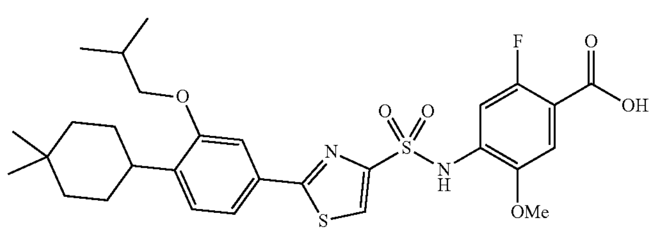 [SMILES: COc1cc(C(=O)O)c(F)cc1NS(=O)(=O)c1csc(-c2ccc(C3CCC(C)(C)CC3)c(OCC(C)C)c2)n1] |
| 831 | 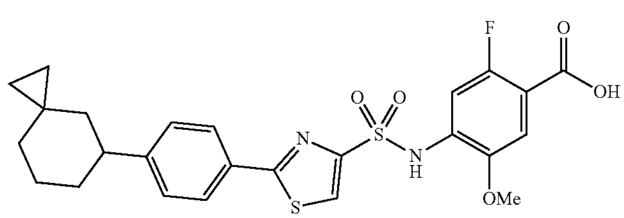 [SMILES: COc1cc(C(=O)O)c(F)cc1NS(=O)(=O)c1csc(-c2ccc(C3CCCC4(CC4)C3)cc2)n1] |

-continued

| Compound # | Structure |
|---|---|
| 832 | 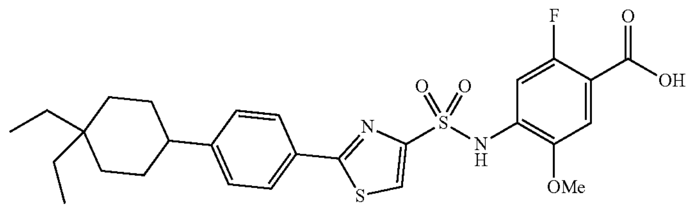 [SMILES: CCC1(CC)CCC(c2ccc(-c3nc(S(=O)(=O)Nc4cc(F)c(C(=O)O)cc4OC)cs3)cc2)CC1] |
| 833 | 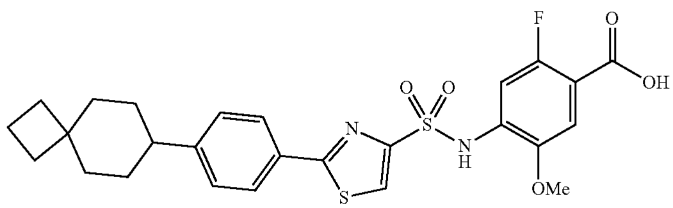 [SMILES: COc1cc(C(=O)O)c(F)cc1NS(=O)(=O)c1csc(-c2ccc(C3CCC4(CCC4)CC3)cc2)n1] |
| 834 | 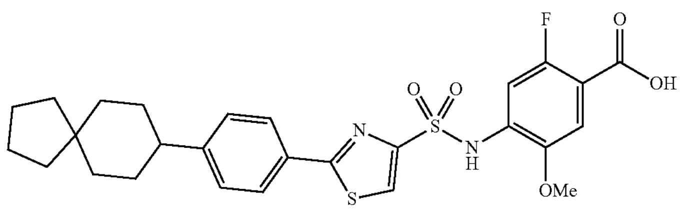 [SMILES: COc1cc(C(=O)O)c(F)cc1NS(=O)(=O)c1csc(-c2ccc(C3CCC4(CCCC4)CC3)cc2)n1] |
| 835 | 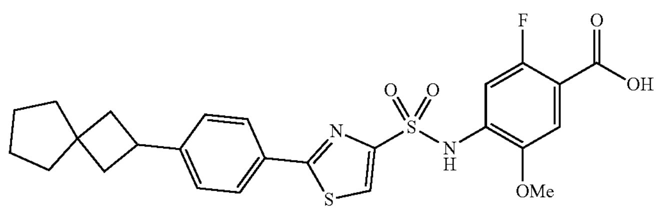 [SMILES: COc1cc(C(=O)O)c(F)cc1NS(=O)(=O)c1csc(-c2ccc(C3CC4(CCCC4)C3)cc2)n1] |
| 836 | 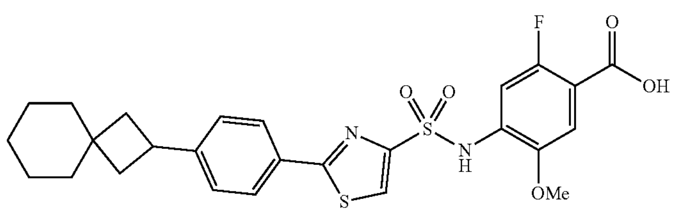 [SMILES: COc1cc(C(=O)O)c(F)cc1NS(=O)(=O)c1csc(-c2ccc(C3CC4(CCCCC4)C3)cc2)n1] |
| 837 | 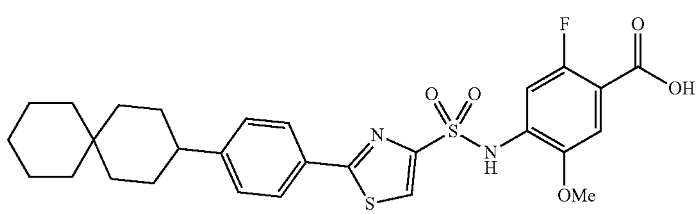 [SMILES: COc1cc(C(=O)O)c(F)cc1NS(=O)(=O)c1csc(-c2ccc(C3CCC4(CCCCC4)CC3)cc2)n1] |
| 838 | 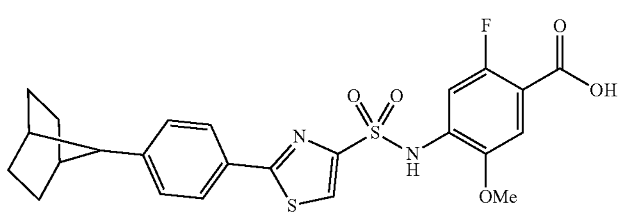 [SMILES: COc1cc(C(=O)O)c(F)cc1NS(=O)(=O)c1csc(-c2ccc(C3C4CCC3CC4)cc2)n1] |

-continued

| Compound # | Structure |
|---|---|
| 839 | 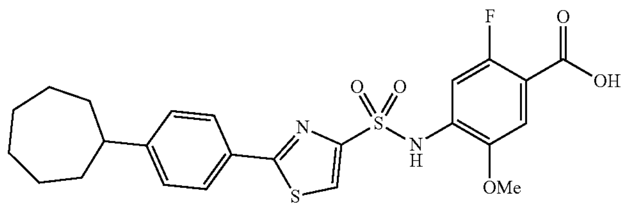 [SMILES: COc1cc(C(=O)O)c(F)cc1NS(=O)(=O)c1csc(-c2ccc(C3CCCCCC3)cc2)n1] |
| 840 | 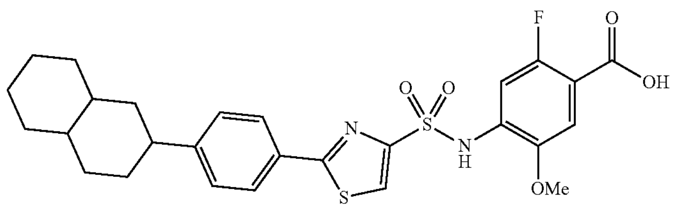 [SMILES: COc1cc(C(=O)O)c(F)cc1NS(=O)(=O)c1csc(-c2ccc(C3CCC4CCCCC4C3)cc2)n1] |
| 841 | 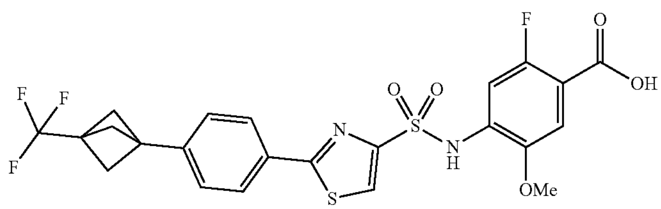 [SMILES: COc1cc(C(=O)O)c(F)cc1NS(=O)(=O)c1csc(-c2ccc(C34CC(C(F)(F)F)(C3)C4)cc2)n1] |
| 842 | 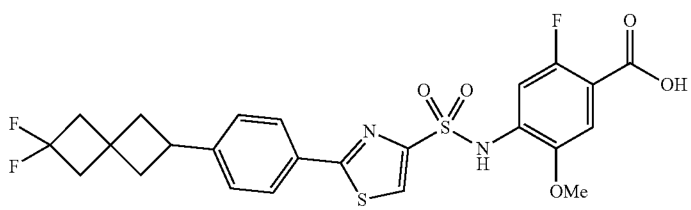 [SMILES: COc1cc(C(=O)O)c(F)cc1NS(=O)(=O)c1csc(-c2ccc(C3CC4(C3)CC(F)(F)C4)cc2)n1] |
| 843 | 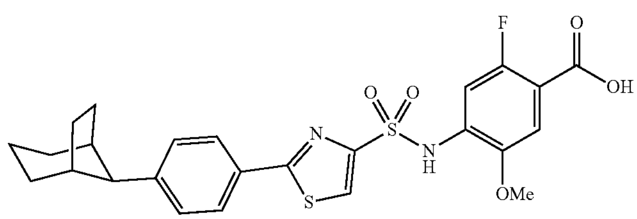 [SMILES: COc1cc(C(=O)O)c(F)cc1NS(=O)(=O)c1csc(-c2ccc(C3C4CCCC3CC4)cc2)n1] |
| 844 | 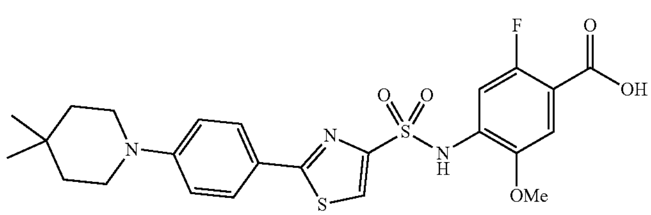 [SMILES: COc1cc(C(=O)O)c(F)cc1NS(=O)(=O)c1csc(-c2ccc(N3CCC(C)(C)CC3)cc2)n1] |
| 845 | 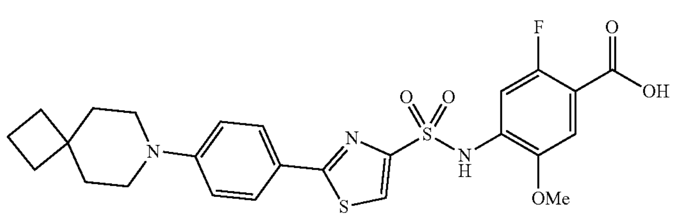 [SMILES: COc1cc(C(=O)O)c(F)cc1NS(=O)(=O)c1csc(-c2ccc(N3CCC4(CCC4)CC3)cc2)n1] |

-continued
| Compound # | Structure |
|---|---|
| 846 | 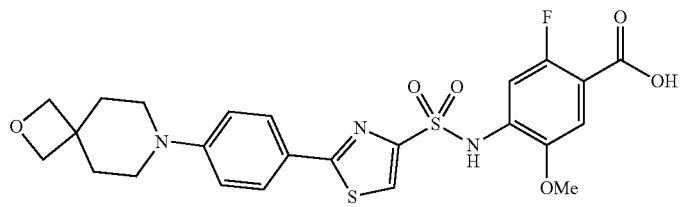 [SMILES: COc1cc(C(=O)O)c(F)cc1NS(=O)(=O)c1csc(-c2ccc(N3CCC4(CC3)COC4)cc2)n1] |
| 847 | 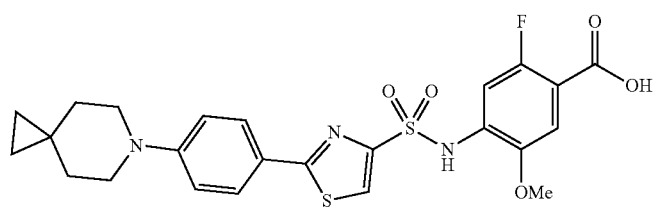 [SMILES: COc1cc(C(=O)O)c(F)cc1NS(=O)(=O)c1csc(-c2ccc(N3CCC4(CC3)CC4)cc2)n1] |
| 848 | 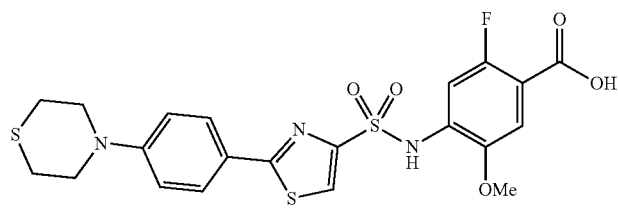 [SMILES: COc1cc(C(=O)O)c(F)cc1NS(=O)(=O)c1csc(-c2ccc(N3CCSCC3)cc2)n1] |
| 849 | 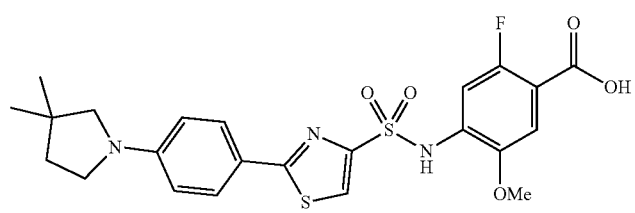 [SMILES: COc1cc(C(=O)O)c(F)cc1NS(=O)(=O)c1csc(-c2ccc(N3CCC(C)(C)C3)cc2)n1] |
| 850 | 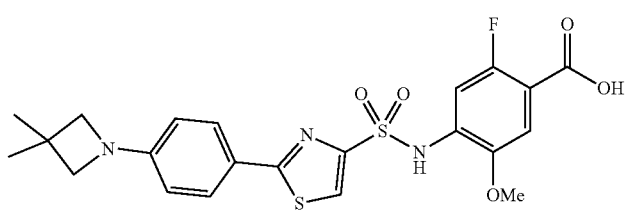 |
| 851 | 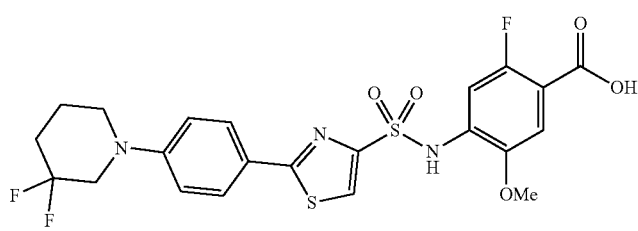 [SMILES: COc1cc(C(=O)O)c(F)cc1NS(=O)(=O)c1csc(-c2ccc(N3CCCC(F)(F)C3)cc2)n1] |
| 852 | 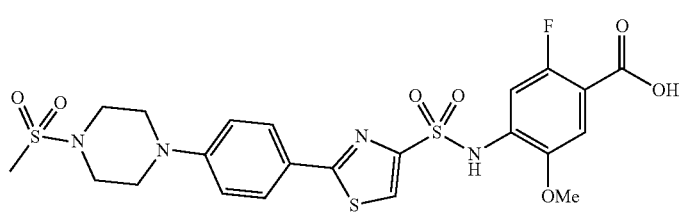 [SMILES: COc1cc(C(=O)O)c(F)cc1NS(=O)(=O)c1csc(-c2ccc(N3CCN(S(C)(=O)=O)CC3)cc2)n1] |

| Compound # | Structure |
|---|---|
| 853 | (structure) |
| 854 | (structure) |
| 855 | (structure) |
| 856 | (structure) |
| 857 | (structure) |

6. A pharmaceutical composition comprising a compound according to claim 1, or a pharmaceutically acceptable salt thereof, and a pharmaceutically acceptable carrier or excipient.

* * * * *

UNITED STATES PATENT AND TRADEMARK OFFICE
CERTIFICATE OF CORRECTION

PATENT NO. : 12,384,753 B2
APPLICATION NO. : 17/891436
DATED : August 12, 2025
INVENTOR(S) : Guoqiang Wang et al.

Page 1 of 2

It is certified that error appears in the above-identified patent and that said Letters Patent is hereby corrected as shown below:

In the Claims

At Column 541

In Claim 2, Lines 55-65 delete " 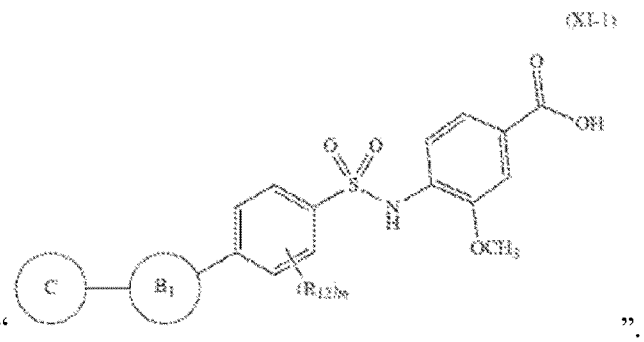 ".

At Column 542

In Claim 2, Lines 1-14 delete " 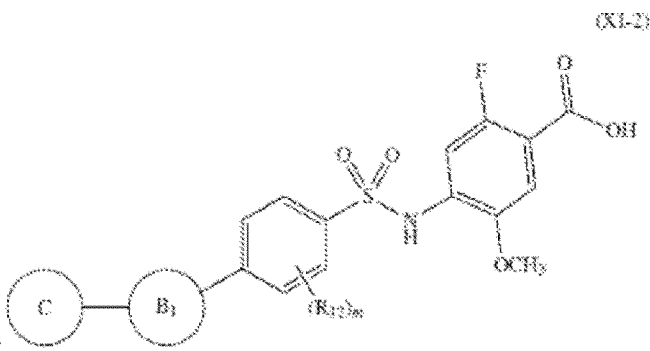 ".

Signed and Sealed this
Thirtieth Day of September, 2025

John A. Squires
*Director of the United States Patent and Trademark Office*

CERTIFICATE OF CORRECTION (continued)
U.S. Pat. No. 12,384,753 B2

Page 2 of 2

At Column 544

In Claim 2, Lines 23-45 delete " 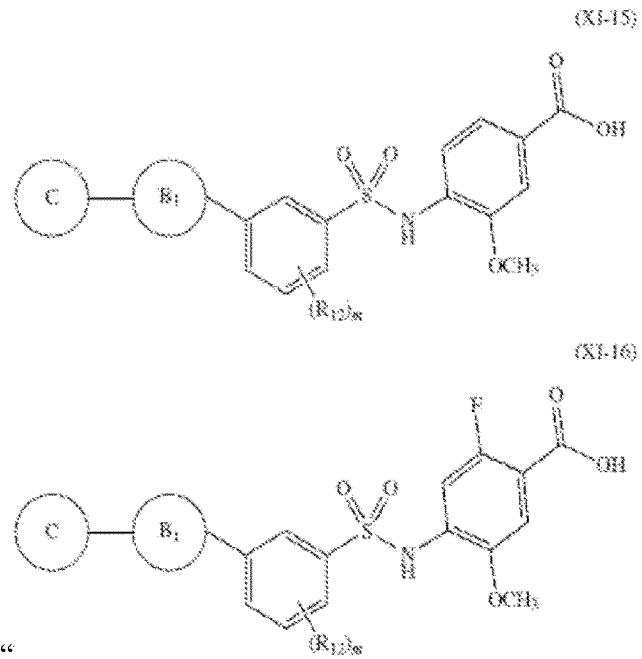 ".